(12) United States Patent
Miyazaki et al.

(10) Patent No.: US 8,158,790 B2
(45) Date of Patent: Apr. 17, 2012

(54) CYCLIC AMINE COMPOUND

(75) Inventors: Shojiro Miyazaki, Tokyo (JP); Yuji Nakamura, Tokyo (JP); Takahiro Nagayama, Tokyo (JP); Taro Tokui, Tokyo (JP); Yasuyuki Ogawa, Kanagawa (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 463 days.

(21) Appl. No.: 12/306,281

(22) PCT Filed: Jun. 22, 2007

(86) PCT No.: PCT/JP2007/062562
§ 371 (c)(1),
(2), (4) Date: Feb. 24, 2009

(87) PCT Pub. No.: WO2007/148774
PCT Pub. Date: Dec. 27, 2007

(65) Prior Publication Data
US 2009/0286807 A1      Nov. 19, 2009

(30) Foreign Application Priority Data

Jun. 23, 2006   (JP) .................. 2006-173633

(51) Int. Cl.
| | |
|---|---|
| *C07D 241/06* | (2006.01) |
| *C07D 241/08* | (2006.01) |
| *C07D 401/04* | (2006.01) |
| *C07D 403/04* | (2006.01) |
| *A61K 31/495* | (2006.01) |
| *A61K 31/496* | (2006.01) |
| *A61P 9/04* | (2006.01) |
| *A61P 9/10* | (2006.01) |
| *A61P 9/12* | (2006.01) |

(52) U.S. Cl. ........ 544/384; 544/392; 544/398; 546/192; 546/264; 546/329; 549/74; 514/252.12; 514/317; 514/357; 514/438

(58) Field of Classification Search .......... None
See application file for complete search history.

(56) References Cited

U.S. PATENT DOCUMENTS
5,559,111 A    9/1996   Göschke

FOREIGN PATENT DOCUMENTS
| | | |
|---|---|---|
| JP | 3240322 B2 | 3/1996 |
| JP | 2000-513740 A | 10/2000 |
| WO | 98/38167 A1 | 9/1998 |
| WO | 2005/051895 A1 | 6/2005 |
| WO | 2005/070870 A2 | 8/2005 |
| WO | 2005/090304 A1 | 9/2005 |

OTHER PUBLICATIONS

Gradman, A.H., et al., "Aliskiren, a Novel Orally Effective Renin Inhibitor, Provides Dose-Dependent Antihypertensive Efficacy and Placebo-Like Tolerability in Hypertensive Patients," Circulation 111(8):1012-1018, Mar. 2005.

Kempf, D.J., et al., "Renin Inhibitors Based on Novel Dipeptide Analogues. Incorporation of the Dehydrohydroxyethylene Isostere at the Scissile Bond," Journal of Medicinal Chemistry 30(11):1978-1983, Nov. 1987.

Rasetti, V., et al., "Bioactive Hydroxyethylene Dipeptide Isosteres With Hydrophobic (P3-P1)-Moieties. A Novel Strategy Towards Small Non-Peptide Renin Inhibitors," Bioorganic & Medicinal Chemistry Letters 6(13):1589-1594, Jul. 1996.

Plummer, M. S., et al., "Design and Synthesis of Renin Inhibitors: Incorporation of Transition-State Isostere Side Chains That Span From the S1 to the S3 Binding Pockets and Examination of P3-Modified Renin Inhibitors," Journal of Medicinal Chemistry 38(15):2893-2905, Jul. 1995.

Supplementary European Search Report mailed Nov. 17, 2010, issued in corresponding European Patent Application No. EP 07 79 0408, filed Jun. 22, 2007, 5 pages.

*Primary Examiner* — Brian J Davis
(74) *Attorney, Agent, or Firm* — Christensen O'Connor Johnson Kindness PLLC

(57) ABSTRACT

The present invention provides an excellent antihypertensive medicament. The medicament of the present invention comprises a compound having the general formula (I) and the like:

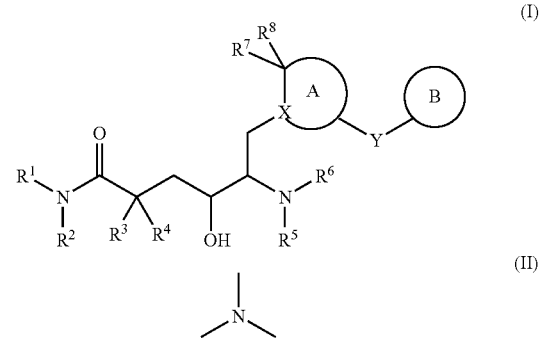

[wherein $R^1$: H, substitutable alkyl, substitutable alkenyl, substitutable cyclic hydrocarbon, substitutable heterocyclyl or the like; $R^2$: H, substitutable alkyl, substitutable alkenyl, substitutable cycloalkyl or the like; $R^3$, $R^4$: H, substitutable alkyl, substitutable alkenyl, substitutable cycloalkyl or the like; $R^5$, $R^6$: H, substitutable alkyl, substitutable cycloalkyl, substitutable alkoxy or the like; $R^7$, $R^8$: H, substitutable alkyl, substitutable cycloalkyl or the like; X: the formula (II) or the like; A: substitutable cyclic hydrocarbon, substitutable heterocyclyl or the like; Y: a single bond, substitutable alkylene, substitutable alkenylene, $-(CH_2)_a-X^1-(CH_2)_b-(X^1$: the formula $-NH-$, $-O-$ or the like; a, b: 0-5) or the like; B: substitutable cyclic hydrocarbon, substitutable heterocyclyl or the like].

28 Claims, No Drawings

CYCLIC AMINE COMPOUND

FIELD OF THE ART

The present invention relates to a novel cyclic amine compound or a pharmacologically acceptable salt thereof having excellent renin inhibitory activity and useful as a medicament [in particular, a medicament for the treatment or prevention (preferably treatment) of hypertension];

a renin inhibitor comprising the cyclic amine compound or a pharmacologically acceptable salt thereof;

a pharmaceutical composition, preferably a pharmaceutical composition for the treatment or prevention of hypertension, comprising the cyclic amine compound or a pharmacologically acceptable salt thereof as an active ingredient;

use of the cyclic amine compound or a pharmacologically acceptable salt thereof for the preparation of a pharmaceutical composition, preferably a pharmaceutical composition for the treatment or prevention of the above disease;

a method for treating or preventing a disease, preferably the above disease, comprising administering a pharmacologically effective amount of the cyclic amine compound or a pharmacologically acceptable salt thereof to a warm-blooded animal (in particular, a human); and a method for preparing the cyclic amine compound or a pharmacologically acceptable salt thereof.

BACKGROUND ART

Hypertension is defined as a symptom with a systolic blood pressure of 140 mmHg or more or a diastolic blood pressure of 90 mmHg or more in the WHO/ISH guidelines. It is reported that there are currently about 40 million patients in Japan and about one billion patients in the world who suffer from hypertension (Dicision Resources, Inc.). Continuous hypertension causes the onset of cerebral hemorrhage, cerebral infarction, aortic aneurysm, nephrosclerosis, myocardial infarction, heart failure or the like, finally resulting in death. A large-scale clinical trial shows that administration of an antihypertensive drug inhibits these diseases. Currently, there are efforts being made to actively lower blood pressure by administration of an antihypertensive drug, exercise, improvement of dietary habit and the like; however, further sufficient blood pressure control is desired.

A main mechanism of hypertension is activation of the renin-angiotensin system (hereinafter sometimes referred to as R-A system). The R-A system is a typical vasopressor system in the living body which increases blood pressure by storing sodium (salinity) in the body to increase circulating blood volume or constrict vascular smooth muscle. In the R-A system, renin converts angiotensinogen to angiotensin I, and angiotensin converting enzyme (hereinafter sometimes referred to as ACE) converts angiotensin I to angiotensin II. Angiotensin II is assumed to act on angiotensin type-1 receptors (hereinafter sometimes referred to as AT1) to cause vasoconstriction, cell proliferation or collagen production and to cause hypertension and subsequent organ failure. Currently, ACE inhibitors inhibiting production of angiotensin II (hereinafter sometimes referred to as ACEI) and angiotensin receptor blockers inhibiting stimuli to AT1 (hereinafter sometimes referred to as ARB) are used as antihypertensive drugs. These drugs are known to have significant hypotensive and organoprotective effects.

Renin is an aspartic protease converting angiotensinogen to angiotensin I and assumed to be a rate-limiting enzyme in the R-A system. Accordingly, renin inhibitors are considered to efficiently inhibit the R-A system and are expected to have the same hypotensive effect as those of ACEI and ARB (Circulation, 2005, vol. 112, p. 1012-18).

There are known some δ-amino-γ-hydroxy-ω-alkanoic acid amide compounds having renin inhibitory activity (see Patent Document 1 or 2, for example). There is also known a δ-amino-γ-hydroxy-ω-alkylalkanoic acid amide compound in which the carbon atom at the 2-position α-position) is substituted with a nitrogen atom (see Patent Document 3 or 4, for example) or in which the carbon atom at the 8-position is substituted with a nitrogen atom (see Patent Document 5, for example). However, there has not been known a δ-amino-γ-hydroxy-ω-alkylalkanoic acid amide compound which has a cyclic group at the 7-position or in which the carbon atom at the 7-position carbon atom is substituted with a nitrogen atom. The compound of the present invention differs greatly in structure from the above known compounds in that the compound has a cyclic group at the 7-position or the carbon atom at the 7-position is substituted with a nitrogen atom.

Patent Document 1: U.S. Pat. No. 5,559,111
Patent Document 2: Japanese Patent No. 3240322
Patent Document 3: WO 2005/070870
Patent Document 4: WO 2005/090304
Patent Document 5: WO 2005/051895

DISCLOSURE OF THE INVENTION

The present inventors have conducted studies on a novel cyclic amine compound for the development of an excellent antihypertensive drug and have found that a cyclic amine compound having a specific structure or a pharmacologically acceptable salt thereof has excellent properties in terms of renin inhibitory activity, solubility, oral absorption, blood concentration, metabolic stability, tissue distribution, bioavailability (hereinafter sometimes referred to as BA), in vitro activity, in vivo activity, a rapid onset of drug effect, a lasting drug effect, physical stability, drug interaction, toxicity and the like and is useful as a medicament [in particular, a medicament for the treatment or prevention (preferably treatment) of hypertension]. The present invention has been completed based on the above finding.

The present invention provides a novel cyclic amine compound or a pharmacologically acceptable salt thereof having excellent renin inhibitory activity and useful as a medicament [in particular, a medicament for the treatment or prevention (preferably treatment) of hypertension];

a renin inhibitor comprising the cyclic amine compound or a pharmacologically acceptable salt thereof;

a pharmaceutical composition, preferably a pharmaceutical composition for the treatment or prevention of hypertension, comprising the cyclic amine compound or a pharmacologically acceptable salt thereof as an active ingredient;

use of the cyclic amine compound or a pharmacologically acceptable salt thereof for the preparation of a pharmaceutical composition, preferably a pharmaceutical composition for the treatment or prevention of the above disease;

a method for treating or preventing a disease, preferably the above disease, comprising administering a pharmacologically effective amount of the cyclic amine compound or a pharmacologically acceptable salt thereof to a warm-blooded animal (in particular, a human); and a method for preparing the cyclic amine compound or a pharmacologically acceptable salt thereof.

The present invention provides:
(1) A compound having the general formula (I) or a pharmacologically acceptable salt thereof:

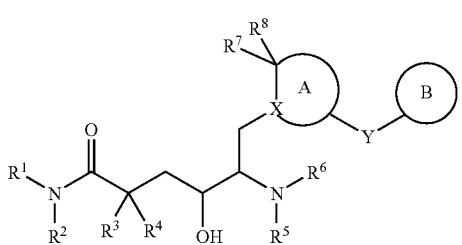

(I)

wherein R¹ represents a hydrogen atom, a $C_1$-$C_8$ alkyl group, a substituted $C_1$-$C_8$ alkyl group, a $C_2$-$C_6$ alkenyl group, a substituted $C_2$-$C_6$ alkenyl group, a $C_2$-$C_6$ alkynyl group, a substituted $C_2$-$C_6$ alkynyl group, a hydroxyl group, a $C_1$-$C_6$ alkoxy group, a substituted $C_1$-$C_6$ alkoxy group, a $C_1$-$C_6$ alkylthio group, a substituted $C_1$-$C_6$ alkylthio group, an amino group, a $C_1$-$C_6$ alkylamino group, a substituted $C_1$-$C_6$ alkylamino group, a di($C_1$-$C_6$ alkyl)amino group (wherein the alkyl groups are the same or different), a substituted di($C_1$-$C_6$ alkyl)amino group (wherein the alkyl groups are the same or different), a formyl group, a ($C_1$-$C_6$ alkyl)carbonyl group, a substituted ($C_1$-$C_6$ alkyl)carbonyl group, a ($C_1$-$C_6$ alkoxy)carbonyl group, a substituted ($C_1$-$C_6$ alkoxy)carbonyl group, a $C_3$-$C_{10}$ cyclic hydrocarbon group, a substituted $C_3$-$C_{10}$ cyclic hydrocarbon group, a 3- to 10-membered heterocyclyl group or a substituted 3- to 10-membered heterocyclyl group, the substituent(s) of each group other than the cyclic hydrocarbon group and the heterocyclyl group in R¹ represent 1 to 3 groups which are the same or different and are selected from Substituent Group α or β, two substituents together may form a $C_1$-$C_5$ alkylene group, and the substituent(s) of the cyclic hydrocarbon group and the heterocyclyl group in R¹ represent 1 to 3 groups which are the same or different and are selected from Substituent Group α; and R² represents a hydrogen atom, a $C_1$-$C_6$ alkyl group, a substituted $C_1$-$C_6$ alkyl group, a $C_2$-$C_6$ alkenyl group, a substituted $C_2$-$C_6$ alkenyl group, a $C_2$-$C_6$ alkynyl group, a substituted $C_2$-$C_6$ alkynyl group, a $C_3$-$C_8$ cycloalkyl group or a substituted $C_3$-$C_8$ cycloalkyl group, and the substituent(s) of each group in R² represent 1 to 3 groups which are the same or different and are selected from Substituent Group α or β, or R¹ and R² together with the nitrogen atom to which they are bonded form a 3- to 10-membered nitrogen-containing heterocyclyl group or a substituted 3- to 10-membered nitrogen-containing heterocyclyl group, and the substituent(s) of the nitrogen-containing heterocyclyl group represent 1 to 3 groups which are the same or different and are selected from Substituent Group α;

R³ represents a hydrogen atom, a $C_1$-$C_6$ alkyl group, a substituted $C_1$-$C_6$ alkyl group, a $C_2$-$C_6$ alkenyl group, a substituted $C_2$-$C_6$ alkenyl group, a $C_2$-$C_6$ alkynyl group, a substituted $C_2$-$C_6$ alkynyl group, a $C_3$-$C_8$ cycloalkyl group, a substituted $C_3$-$C_8$ cycloalkyl group, a hydroxyl group, a $C_1$-$C_6$ alkoxy group, a substituted $C_1$-$C_6$ alkoxy group, a $C_1$-$C_6$ alkylthio group or a substituted $C_1$-$C_6$ alkylthio group, and the substituent(s) of each group in R³ represent 1 to 3 groups which are the same or different and are selected from Substituent Group α; and R⁴ represents a hydrogen atom, a $C_1$-$C_6$ alkyl group, a substituted $C_1$-$C_6$ alkyl group, a $C_2$-$C_6$ alkenyl group, a substituted $C_2$-$C_6$ alkenyl group, a $C_2$-$C_6$ alkynyl group, a substituted $C_2$-$C_6$ alkynyl group, a $C_3$-$C_8$ cycloalkyl group, a substituted $C_3$-$C_8$ cycloalkyl group, a hydroxyl group, a $C_1$-$C_6$ alkoxy group, a substituted $C_1$-$C_6$ alkoxy group, a $C_1$-$C_6$ alkylthio group or a substituted $C_1$-$C_6$ alkylthio group, and the substituent(s) of each group in R⁴ represent 1 to 3 groups which are the same or different and are selected from Substituent Group α, or R³ and R⁴ together form a $C_1$-$C_5$ alkylene group or a substituted $C_1$-$C_5$ alkylene group, and the substituent(s) of the alkylene group represent 1 to 3 groups which are the same or different and are selected from Substituent Group α;

R⁵ represents a hydrogen atom, a $C_1$-$C_6$ alkyl group, a substituted $C_1$-$C_6$ alkyl group, a $C_3$-$C_8$ cycloalkyl group, a substituted $C_3$-$C_8$ cycloalkyl group, a hydroxyl group, a $C_1$-$C_6$ alkoxy group, a substituted $C_1$-$C_6$ alkoxy group, an amino group, a $C_1$-$C_6$ alkylamino group, a substituted $C_1$-$C_6$ alkylamino group, a di($C_1$-$C_6$ alkyl)amino group (wherein the alkyl groups are the same or different) or a substituted di($C_1$-$C_6$ alkyl)amino group (wherein the alkyl groups are the same or different), and the substituent(s) of each group in R⁵ represent 1 to 3 groups which are the same or different and are selected from Substituent Group α;

R⁶ represents a hydrogen atom, a $C_1$-$C_6$ alkyl group, a substituted $C_1$-$C_6$ alkyl group, a $C_3$-$C_8$ cycloalkyl group, a substituted $C_3$-$C_8$ cycloalkyl group, a hydroxyl group, a $C_1$-$C_6$ alkoxy group, a substituted $C_1$-$C_6$ alkoxy group, an amino group, a $C_1$-$C_6$ alkylamino group, a substituted $C_1$-$C_6$ alkylamino group, a di($C_1$-$C_6$ alkyl)amino group (wherein the alkyl groups are the same or different) or a substituted di($C_1$-$C_6$ alkyl)amino group (wherein the alkyl groups are the same or different), and the substituent(s) of each group in R⁶ represent 1 to 3 groups which are the same or different and are selected from Substituent Group α;

R⁷ represents a hydrogen atom, a $C_1$-$C_6$ alkyl group, a substituted $C_1$-$C_6$ alkyl group, a $C_2$-$C_6$ alkenyl group, a substituted $C_2$-$C_6$ alkenyl group, a $C_2$-$C_6$ alkynyl group, a substituted $C_2$-$C_6$ alkynyl group, a $C_3$-$C_8$ cycloalkyl group, a substituted $C_3$-$C_8$ cycloalkyl group, a hydroxyl group, a $C_1$-$C_6$ alkoxy group, a substituted $C_1$-$C_6$ alkoxy group, a $C_1$-$C_6$ alkylthio group or a substituted $C_1$-$C_6$ alkylthio group, and the substituent(s) of each group in R⁷ represent 1 to 3 groups which are the same or different and are selected from Substituent Group α;

R⁸ represents a hydrogen atom, a $C_1$-$C_6$ alkyl group, a substituted $C_1$-$C_6$ alkyl group, a $C_2$-$C_6$ alkenyl group, a substituted $C_2$-$C_6$ alkenyl group, a $C_2$-$C_6$ alkynyl group, a substituted $C_2$-$C_6$ alkynyl group, a $C_3$-$C_8$ cycloalkyl group, a substituted $C_3$-$C_8$ cycloalkyl group, a hydroxyl group, a $C_1$-$C_6$ alkoxy group, a substituted $C_1$-$C_6$ alkoxy group, a $C_1$-$C_6$ alkylthio group or a substituted $C_1$-$C_6$ alkylthio group, and the substituent(s) of each group in R⁸ represent 1 to 3 groups which are the same or different and are selected from Substituent Group α, or R⁷ and R⁸ together form a $C_1$-$C_5$ alkylene group or a substituted $C_1$-$C_5$ alkylene group, and the substituent(s) of the alkylene group represent 1 to 3 groups which are the same or different and are selected from Substituent Group α;

X represents a group having the formula (II), (III) or (IV):

(II)

(III)

(IV)

A represents a 3- to 10-membered nitrogen-containing saturated heterocyclyl group, a substituted 3- to 10-membered nitrogen-containing saturated heterocyclyl group, a 3- to 10-membered nitrogen-containing partially unsaturated heterocyclyl group or a substituted 3- to 10-membered nitrogen-containing partially unsaturated heterocyclyl group when X is a group having the formula (II), and represents a $C_3$-$C_{10}$ saturated cyclic hydrocarbon group, a substituted $C_3$-$C_{10}$ saturated cyclic hydrocarbon group, a $C_3$-$C_{10}$ partially unsaturated cyclic hydrocarbon group, a substituted $C_3$-$C_{10}$ partially unsaturated cyclic hydrocarbon group, a 3- to 10-membered saturated heterocyclyl group, a substituted 3- to 10-membered saturated heterocyclyl group, a 3- to 10-membered partially unsaturated heterocyclyl group or a substituted 3- to 10-membered partially unsaturated heterocyclyl group when X is a group having the formula (III) or (IV), and the substituent(s) of each group in A represent 1 to 3 groups which are the same or different and are selected from Substituent Group α;

Y represents a single bond, a $C_1$-$C_6$ alkylene group, a substituted $C_1$-$C_6$ alkylene group, a $C_2$-$C_6$ alkenylene group, a substituted $C_2$-$C_6$ alkenylene group, a $C_2$-$C_6$ alkynylene group, a substituted $C_2$-$C_6$ alkynylene group or a group having the formula —$(CH_2)_a$—$X^1$—$(CH_2)_b$— [wherein $X^1$ represents a group having the formula —NH—, —$NR^9$— (wherein $R^9$ represents a $C_1$-$C_6$ alkyl group), —O—, —S—, —SO— or —$SO_2$—, a and b independently represent an integer of 0 to 5, and the sum of a and b is 0 to 5], and the substituent(s) of each group in Y represent 1 to 3 groups which are the same or different and are selected from Substituent Group γ; and B represents a $C_3$-$C_{10}$ cyclic hydrocarbon group, a substituted $C_3$-$C_{10}$ cyclic hydrocarbon group, a 3- to 10-membered heterocyclyl group, a substituted 3- to 10-membered heterocyclyl group or a group having the formula (V):

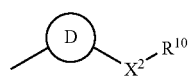
(V)

wherein D represents a $C_3$-$C_{10}$ cyclic hydrocarbon group, a substituted $C_3$-$C_{10}$ cyclic hydrocarbon group, a 3- to 10-membered heterocyclyl group or a substituted 3- to 10-membered heterocyclyl group, and the substituent(s) of each group in D represent 1 to 3 groups which are the same or different and are selected from Substituent Group α, $X^2$ represents a group having the formula —NH—, —$NR^{11}$— (wherein $R^{11}$ represents a $C_1$-$C_6$ alkyl group), —O—, —S—, —SO— or —$SO_2$—, and $R^{10}$ represents a $C_1$-$C_6$ alkyl group, a substituted $C_1$-$C_6$ alkyl group, a $C_2$-$C_6$ alkenyl group, a substituted $C_2$-$C_6$ alkenyl group, a $C_2$-$C_6$ alkynyl group, a substituted $C_2$-$C_6$ alkynyl group, a $C_3$-$C_8$ cycloalkyl group or a substituted $C_3$-$C_8$ cycloalkyl group, and the substituent(s) of each group in $R^{10}$ represent 1 to 3 groups which are the same or different and are selected from Substituent Group δ, and the substituent(s) of each group in B represent 1 to 3 groups which are the same or different and are selected from Substituent Group α, or the carbon atom $C_A$ of the ring A to which Y is bonded, Y and B together represent a group having the formula (VI):

(VI)

wherein E is bonded to A in spiro form and fused with B, E represents a $C_3$-$C_8$ saturated cyclic hydrocarbon group, a substituted $C_3$-$C_8$ saturated cyclic hydrocarbon group, a $C_3$-$C_8$ partially unsaturated cyclic hydrocarbon group, a substituted $C_3$-$C_8$ partially unsaturated cyclic hydrocarbon group, a 3- to 8-membered saturated heterocyclyl group, a substituted 3- to 8-membered saturated heterocyclyl group, a 3- to 8-membered partially unsaturated heterocyclyl group or a substituted 3- to 8-membered partially unsaturated heterocyclyl group, and the substituent(s) of each group in E represent 1 to 3 groups which are the same or different and are selected from Substituent Group α;

Substituent Group α represents the group consisting of a $C_1$-$C_6$ alkyl group, a halogeno $C_1$-$C_6$ alkyl group, a hydroxyl group, a $C_1$-$C_6$ alkoxy group, a halogeno $C_1$-$C_6$ alkoxy group, a mercapto group, a $C_1$-$C_6$ alkylthio group, a $C_1$-$C_6$ alkylsulfinyl group, a $C_1$-$C_6$ alkylsulfonyl group, an amino group, a $C_1$-$C_6$ alkylamino group, a di($C_1$-$C_6$ alkyl)amino group (wherein the alkyl groups are the same or different), a formylamino group, a ($C_1$-$C_6$ alkyl)carbonylamino group, a formyl group, a ($C_1$-$C_6$ alkyl)carbonyl group, a carboxyl group, a ($C_1$-$C_6$ alkoxy)carbonyl group, a carbamoyl group, a ($C_1$-$C_6$ alkylamino)carbonyl group, a di($C_1$-$C_6$ alkyl)aminocarbonyl group (wherein the alkyl groups are the same or different), an aminosulfonyl group, a ($C_1$-$C_6$ alkylamino)sulfonyl group, a di($C_1$-$C_6$ alkyl)aminosulfonyl group (wherein the alkyl groups are the same or different), a cyano group, a nitro group, a halogeno group and an oxo group;

Substituent Group β represents the group consisting of a $C_3$-$C_8$ cycloalkyl group, a substituted $C_3$-$C_8$ cycloalkyl group, a $C_6$-$C_{10}$ aryl group, a substituted $C_6$-$C_{10}$ aryl group, a 3- to 10-membered heterocyclyl group and a substituted 3- to 10-membered heterocyclyl group, and the substituent(s) of each group in Substituent Group β represent 1 to 3 groups which are the same or different and are selected from Substituent Group α;

Substituent Group γ represents the group consisting of a $C_1$-$C_6$ alkyl group, a hydroxyl group, a halogeno group, an oxo group, a hydroxyimino group and a ($C_1$-$C_6$ alkoxy)imino group; and Substituent Group δ represents the group consisting of a hydroxyl group, a $C_1$-$C_6$ alkoxy group, a mercapto group, a $C_1$-$C_6$ alkylthio group, a $C_1$-$C_6$ alkylsulfinyl group, a $C_1$-$C_6$ alkylsulfonyl group, an amino group, a $C_1$-$C_6$ alkylamino group, a di($C_1$-$C_6$ alkyl)amino group (wherein the alkyl groups are the same or different), a ($C_1$-$C_6$ alkyl)carbonylamino group, a ($C_1$-$C_6$ alkyl)sulfonylamino group, an aminocarbonylamino group, a ($C_1$-$C_6$ alkylamino)carbonylamino group, a di($C_1$-$C_6$ alkyl)aminocarbonylamino group (wherein the alkyl groups are the same or different), an aminosulfonylamino group, a ($C_1$-$C_6$ alkylamino)sulfonylamino group and a di($C_1$-$C_6$ alkyl)aminosulfonylamino group (wherein the alkyl groups are the same or different).

A preferred compound having the general formula (I) is:
(2) The compound according to (1), wherein $R^1$ is a $C_1$-$C_8$ alkyl group, a substituted $C_1$-$C_8$ alkyl group, a $C_2$-$C_6$ alkenyl group, a substituted $C_2$-$C_6$ alkenyl group, a $C_2$-$C_6$ alkynyl group, a substituted $C_2$-$C_6$ alkynyl group, a $C_3$-$C_{10}$ cyclic hydrocarbon group, a substituted $C_3$-$C_{10}$ cyclic hydrocarbon group, a 3- to 10-membered heterocyclyl group or a substituted 3- to 10-membered heterocyclyl group, the substituent(s) of each group other than the cyclic hydrocarbon group and the heterocyclyl group in $R^1$ represent 1 to 3 groups which are the same or different and are selected from Substituent Group α1 or β1, and the substituent(s) of the cyclic hydrocarbon group and the heterocyclyl group in $R^1$ represent 1 to 3 groups which are the same or different and are selected from Substituent Group α1, Substituent Group α1 represents the group consisting of a $C_1$-$C_6$ alkyl group, a halogeno $C_1$-$C_6$ alkyl group, a hydroxyl group, a $C_1$-$C_6$ alkoxy group, a halogeno $C_1$-$C_6$ alkoxy group, a mercapto group, a $C_1$-$C_6$ alkylthio group, a $C_1$-$C_6$ alkylsulfinyl group, a $C_1$-$C_6$ alkylsulfonyl group, an amino group, a $C_1$-$C_6$ alkylamino group, a di($C_1$-$C_6$ alkyl)amino group (wherein the alkyl groups are the same or different), a carbamoyl group, a ($C_1$-$C_6$ alkylamino)carbonyl group, a di($C_1$-$C_6$ alkyl)aminocarbonyl group (wherein the alkyl groups are the same or different) and a halogeno group, and Substituent Group β1 represents the group consisting of a $C_3$-$C_8$ cycloalkyl group, a $C_6$-$C_{10}$ aryl group and a 3- to 10-membered heterocyclyl group;

(3) The compound according to (1), wherein $R^1$ is a $C_1$-$C_6$ alkyl group, a substituted $C_1$-$C_6$ alkyl group (wherein the substituent(s) represent 1 to 3 groups which are the same or different and are selected from Substituent Group α2 or β2), a $C_3$-$C_8$ cyclic hydrocarbon group or a substituted $C_3$-$C_8$ cyclic hydrocarbon group (wherein the substituent(s) represent 1 to 3 groups which are the same or different and are selected from Substituent Group α2), Substituent Group α2 represents the group consisting of a $C_1$-$C_6$ alkyl group, a hydroxyl group, a $C_1$-$C_6$ alkoxy group, a carbamoyl group, a ($C_1$-$C_6$ alkylamino)carbonyl group and a di($C_1$-$C_6$ alkyl)aminocarbonyl group (wherein the alkyl groups are the same or different), and Substituent Group β2 represents the group consisting of a $C_3$-$C_8$ cycloalkyl group and a $C_6$-$C_{10}$ aryl group;

(4) The compound according to (1), wherein $R^1$ is a $C_2$-$C_7$ alkyl group or a $C_4$-$C_7$ cycloalkyl group;

(5) The compound according to any one of (1) to (4), wherein $R^2$ is a hydrogen atom, a $C_1$-$C_6$ alkyl group or a $C_3$-$C_8$ cycloalkyl group, or $R^1$ and $R^2$ together with the nitrogen atom to which they are bonded form a 3- to 10-membered nitrogen-containing heterocyclyl group;

(6) The compound according to any one of (1) to (4), wherein $R^2$ is a hydrogen atom;

(7) The compound according to any one of (1) to (6), wherein $R^3$ is a $C_1$-$C_6$ alkyl group, a $C_3$-$C_8$ cycloalkyl group or a $C_1$-$C_6$ alkoxy group, and $R^4$ is a hydrogen atom, a $C_1$-$C_6$ alkyl group or a $C_3$-$C_8$ cycloalkyl group, or $R^3$ and $R^4$ together form a $C_1$-$C_5$ alkylene group;

(8) The compound according to any one of (1) to (6), wherein $R^3$ is a $C_1$-$C_6$ alkyl group, and $R^4$ is a hydrogen atom;

(9) The compound according to any one of (1) to (8), wherein $R^5$ is a hydrogen atom, a $C_1$-$C_6$ alkyl group or a $C_3$-$C_8$ cycloalkyl group, and $R^6$ is a hydrogen atom, a $C_1$-$C_6$ alkyl group or a $C_3$-$C_8$ cycloalkyl group;

(10) The compound according to any one of (1) to (8), wherein $R^5$ and $R^6$ are hydrogen atoms;

(11) The compound according to any one of (1) to (10), wherein $R^7$ is a hydrogen atom, a $C_1$-$C_6$ alkyl group or a $C_3$-$C_8$ cycloalkyl group, and $R^8$ is a hydrogen atom, a $C_1$-$C_6$ alkyl group or a $C_3$-$C_8$ cycloalkyl group, or $R^7$ and $R^8$ together form a $C_2$-$C_4$ alkylene group;

(12) The compound according to any one of (1) to (10), wherein $R^7$ is a $C_1$-$C_4$ alkyl group, and $R^8$ is a $C_1$-$C_4$ alkyl group;

(13) The compound according to any one of (1) to (12), wherein X is a group having the formula (II), A is a 4- to 8-membered nitrogen-containing saturated heterocyclyl group, a substituted 4- to 8-membered nitrogen-containing saturated heterocyclyl group, a 4- to 8-membered nitrogen-containing partially unsaturated heterocyclyl group or a substituted 4- to 8-membered nitrogen-containing partially unsaturated heterocyclyl group, and the substituent(s) of each group in A represent 1 to 3 groups which are the same or different and are selected from Substituent Group α3, and Substituent Group α3 represents the group consisting of a $C_1$-$C_6$ alkyl group, a hydroxyl group, a $C_1$-$C_6$ alkoxy group, an amino group, a $C_1$-$C_6$ alkylamino group, a di($C_1$-$C_6$ alkyl)amino group (wherein the alkyl groups are the same or different), a halogeno group and an oxo group;

(14) The compound according to any one of (1) to (12), wherein X is a group having the formula (II), A is a 5- or 6-membered nitrogen-containing saturated heterocyclyl group or a substituted 5- or 6-membered nitrogen-containing saturated heterocyclyl group (wherein the substituent(s) represent 1 to 3 groups which are the same or different and are selected from Substituent Group α4), and Substituent Group α4 represents the group consisting of a $C_1$-$C_6$ alkyl group, a hydroxyl group, a $C_1$-$C_6$ alkoxy group and an oxo group;

(15) The compound according to any one of (1) to (12), wherein X is a group having the formula (II), and A is a piperazinyl group or a substituted piperazinyl group (wherein the substituent(s) represent 1 to 3 groups which are the same or different and are selected from Substituent Group α4);

(16) The compound according to any one of (1) to (15), wherein Y is a single bond, a $C_1$-$C_6$ alkylene group or a substituted $C_1$-$C_6$ alkylene group (wherein the substituent(s) represent 1 to 3 groups which are the same or different and are selected from Substituent Group γ);

(17) The compound according to any one of (1) to (15), wherein Y is a single bond;

(18) The compound according to any one of (1) to (17), wherein B is a $C_3$-$C_{10}$ cycloalkyl group, a substituted $C_3$-$C_{10}$ cycloalkyl group, a $C_6$-$C_{10}$ aryl group, a substituted $C_6$-$C_{10}$ aryl group, a 5- to 10-membered aromatic heterocyclyl group, a substituted 5- to 10-membered heterocyclyl group or a group having the formula (Va):

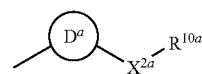

(Va)

wherein $D^a$ represents a $C_3$-$C_{10}$ cycloalkyl group, a substituted $C_3$-$C_{10}$ cycloalkyl group, a $C_6$-$C_{10}$ aryl group, a substituted $C_6$-$C_{10}$ aryl group, a 5- to 10-membered aromatic heterocyclyl group or a substituted 5- to 10-membered heterocyclyl group, and the substituent(s) of each group in $D^a$ represent 1 to 3 groups which are the same or different and are selected from Substituent Group α1, $X^{2a}$ represents a group having the formula —NH—, —O— or —S—, and $R^{10a}$ represents a $C_1$-$C_6$ alkyl group, a substituted $C_1$-$C_6$ alkyl group, a $C_2$-$C_6$ alkenyl group, a substituted $C_2$-$C_6$ alkenyl group, a $C_2$-$C_6$ alkynyl group or a substituted $C_2$-$C_6$ alkynyl group, and the substituent(s) of each group in $R^{10a}$ represent 1 to 3 groups which are the same or different and are selected from Substituent Group δ1, and the substituent(s) of each group in B represent 1 to 3 groups which are the same or different and are selected from Substituent Group α1, and Substituent Group δ1 represents the group consisting of a hydroxyl group, a $C_1$-$C_6$ alkoxy group, a $C_1$-$C_6$ alkylthio group, a $C_1$-$C_6$ alkylsulfinyl group, a $C_1$-$C_6$ alkylsulfonyl group, a $C_1$-$C_6$ alkylamino group and a di($C_1$-$C_6$ alkyl)amino group (wherein the alkyl groups are the same or different);

(19) The compound according to any one of (1) to (17), wherein B is a $C_6$-$C_{10}$ aryl group, a substituted $C_6$-$C_{10}$ aryl group, a 5- or 6-membered aromatic heterocyclyl group, a substituted 5- or 6-membered aromatic heterocyclyl group or a group having the formula (Vb):

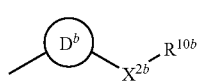

(Vb)

wherein $D^b$ represents a $C_6$-$C_{10}$ aryl group, a substituted $C_6$-$C_{10}$ aryl group, a 5- or 6-membered aromatic heterocyclyl group or a substituted 5- or 6-membered aromatic heterocyclyl group, and the substituent(s) of each group in $D^b$ represent 1 to 3 groups which are the same or different and are selected from Substituent Group α1, $X^{2b}$ represents a group having the formula —O—, and $R^{10b}$ represents a $C_1$-$C_6$ alkyl group, a substituted $C_1$-$C_6$ alkyl group, a substituted $C_2$-$C_6$ alkenyl group or a substituted $C_2$-$C_6$ alkynyl group, and the substituent(s) of each group in $R^{10b}$ represent 1 to 3 groups which are the same or different and are selected from Substituent Group δ2, and the substituent(s) of each group in B represent 1 to 3 groups which are the same or different and are selected from Substituent Group α1, and Substituent Group δ2 represents the group consisting of a hydroxyl group, a $C_1$-$C_6$ alkoxy group, a $C_1$-$C_6$ alkylthio group, a $C_1$-$C_6$ alkylamino group and a di($C_1$-$C_6$ alkyl)amino group (wherein the alkyl groups are the same or different); or

(20) The compound according to any one of (1) to (17), wherein B is a phenyl group, a substituted phenyl group (wherein the substituent(s) represent 1 to 3 groups which are the same or different and are selected from Substituent Group α5) or a group having the formula (Vc):

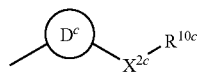

(Vc)

wherein $D^c$ represents a phenyl group or a substituted phenyl group (wherein the substituent(s) represent 1 to 3 groups which are the same or different and are selected from Substituent Group α5), $X^{2c}$ represents a group having the formula —O—, and $R^{10c}$ represents a substituted $C_1$-$C_6$ alkyl group (wherein the substituent(s) represent 1 to 3 groups which are the same or different and are selected from Substituent Group δ3), Substituent Group α5 represents the group consisting of a $C_1$-$C_6$ alkyl group, a halogeno $C_1$-$C_6$ alkyl group, a $C_1$-$C_6$ alkoxy group, a halogeno $C_1$-$C_6$ alkoxy group, an amino group, a $C_1$-$C_6$ alkylamino group, a di($C_1$-$C_6$ alkyl)amino group (wherein the alkyl groups are the same or different) and a halogeno group, and Substituent Group δ3 represents the group consisting of a hydroxyl group, a $C_1$-$C_6$ alkoxy group and a $C_1$-$C_6$ alkylthio group.

Any combination of $R^1$ selected from (2) to (4), $R^2$ selected from (5) or (6), $R^3$ and $R^4$ selected from (7) or (8), $R^5$ and $R^6$ selected from (9) or (10), $R^7$ and $R^8$ selected from (11) or (12), X and A selected from (13) to (15), Y selected from (16) or (17) and B selected from (18) to (20) described above is preferred. For example, the following combinations are preferred:

(21) $R^1$: (2); $R^2$: (5); $R^3$, $R^4$: (7); $R^5$, $R^6$: (9); $R^7$, $R^8$: (11); Y: (16); B: (18);
(22) $R^1$: (3); $R^2$: (6); $R^3$, $R^4$: (8); $R^5$, $R^6$: (10); $R^7$, $R^8$: (12); Y: (17); B: (19);
(23) $R^1$: (4); $R^2$: (6); $R^3$, $R^4$: (8); $R^5$, $R^6$: (10); $R^7$, $R^8$: (12); Y: (17); B: (20); or
(24) A compound selected from the compounds shown in Tables 1 to 3 below.

The present invention also provides:
(25) A pharmaceutical composition comprising the compound according to any one of (1) to (24) or a pharmacologically acceptable salt thereof as an active ingredient;
(26) The pharmaceutical composition according to (25) for the treatment or prevention of a disease which can be treated or prevented by inhibiting renin;
(27) The pharmaceutical composition according to (25) for the treatment or prevention of hypertension;
(28) Use of the compound according to any one of (1) to (24) or a pharmacologically acceptable salt thereof for the preparation of a medicament for the treatment or prevention of a disease;
(29) The use according to (28), wherein the disease is hypertension;
(30) A method for treating or preventing a disease, comprising administering a pharmacologically effective amount of the compound according to any one of (1) to (24) or a pharmacologically acceptable salt thereof to a warm-blooded animal;
(31) The method according to (30), wherein the disease is a disease which can be treated or prevented by inhibiting renin;
(32) The method according to (30), wherein the disease is hypertension; or
(33) The method according to any one of (30) to (32), wherein the warm-blooded animal is a human.

In the general formula (I) of the present invention, the "$C_1$-$C_8$ alkyl group" is a linear or branched alkyl group having 1 to 8 carbon atoms. The group may be a methyl group, an ethyl group, a 1-propyl group, a 2-propyl group, a 1-butyl group, a 2-butyl group, a 2-methyl-1-propyl group, a 2-methyl-2-propyl group, a 1-pentyl group, a 2-pentyl group, a 3-pentyl group, a 3-methyl-1-butyl group, a 2-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 2-ethyl-1-butyl group, a 2,2-dimethyl-1-butyl group, a 2,3-dimethyl-1-butyl group, a 1-heptyl group, a 1-heptyl group or a 1-octyl group, for example, and is preferably a $C_2$-$C_7$ alkyl group, more preferably a $C_3$-$C_6$ alkyl group, still more preferably a $C_4$-$C_6$ alkyl group, and most preferably a 1-butyl group, a 2-methyl-1-propyl group, a 2-methyl-1-butyl group or a 2,2-dimethyl-1-propyl group.

In the general formula (I), the "$C_2$-$C_6$ alkenyl group" is a linear or branched alkenyl group having 2 to 6 carbon atoms and having one or more carbon-carbon double bonds. The group may be a vinyl group, a 2-propenyl group (allyl group), a 2-butenyl group, a 2-pentenyl group, a 3-methyl-2-butenyl group, a 2-hexenyl group or a 3-methyl-2-pentenyl group, for example. The "$C_2$-$C_6$ alkenyl group" in $R^1$ is preferably a $C_3$-$C_6$ alkenyl group, and more preferably a $C_4$-$C_6$ alkenyl group. The "$C_2$-$C_6$ alkenyl group" in $R^2$, $R^3$ and $R^4$ is preferably a $C_2$-$C_4$ alkenyl group, and more preferably a $C_2$-$C_3$ alkenyl group. The "$C_2$-$C_6$ alkenyl group" in $R^{10}$ is preferably a $C_2$-$C_4$ alkenyl group, and more preferably a $C_3$-$C_4$ alkenyl group.

In the general formula (I), the "$C_2$-$C_6$ alkynyl group" is a linear or branched alkynyl group having 2 to 6 carbon atoms and having one or more carbon-carbon triple bonds. The group may be an ethynyl group, a 1-propynyl group, a 2-propynyl group, a 1-butynyl group, a 2-butynyl group, a 1-pentynyl group, a 2-pentynyl group or a 1-hexynyl group, for example. The "$C_2$-$C_6$ alkynyl group" in $R^1$ is preferably a $C_3$-$C_6$ alkynyl group, and more preferably a $C_4$-$C_6$ alkynyl group. The "$C_2$-$C_6$ alkynyl group" in $R^2$, $R^3$ and $R^4$ is preferably a $C_2$-$C_4$ alkynyl group, and more preferably a $C_2$-$C_3$ alkynyl group. The "$C_2$-$C_6$ alkynyl group" in $R^{10}$ is preferably a $C_2$-$C_4$ alkynyl group, and more preferably a $C_3$-$C_4$ alkynyl group.

In the general formula (I), the "$C_1$-$C_6$ alkoxy group" is a hydroxyl group substituted with one $C_1$-$C_6$ alkyl group described below. The group may be a methoxy group, an ethoxy group, a 1-propoxy group, a 2-propoxy group, a 1-butoxy group, a 2-butoxy group, a 2-methyl-1-propoxy group, a 2-methyl-2-propoxy group, a 1-pentyloxy group, a 2-pentyloxy group, a 3-pentyloxy group, a 2-methyl-2-butoxy group, a 3-methyl-2-butoxy group, a 1-hexyloxy group, a 2-hexyloxy group, a 3-hexyloxy group, a 2-methyl-1-pentyloxy group, a 3-methyl-1-pentyloxy group, a 2-ethyl-1-butoxy group, a 2,2-dimethyl-1-butoxy group or a 2,3-dimethyl-1-butoxy group, for example. The "$C_1$-$C_6$ alkoxy group" in $R^1$ is preferably a $C_3$-$C_6$ alkoxy group, and more preferably a $C_4$-$C_6$ alkoxy group. The "$C_1$-$C_6$ alkoxy group" in $R^3$ and $R^4$ is preferably a $C_2$-$C_4$ alkoxy group, and more preferably a $C_2$-$C_3$ alkoxy group. The "$C_1$-$C_6$ alkoxy group" in $R^5$, $R^6$, $R^7$, $R^8$ and Substituent Group α is preferably a $C_1$-$C_4$ alkoxy group, and more preferably a $C_1$-$C_2$ alkoxy group. The "$C_1$-$C_6$ alkoxy group" in Substituent Group δ is preferably a $C_1$-$C_4$ alkoxy group, more preferably a $C_1$-$C_2$ alkoxy group, and most preferably a methoxy group.

In the general formula (I), the "$C_1$-$C_6$ alkylthio group" is a mercapto group substituted with one $C_1$-$C_6$ alkyl group described below. The group may be a methylthio group, an ethylthio group, a 1-propylthio group, a 2-propylthio group, a 1-butylthio group, a 2-butylthio group, a 2-methyl-1-propylthio group, a 2-methyl-2-propylthio group, a 1-pentylthio group, a 2-pentylthio group, a 3-pentylthio group, a 2-methyl-2-butylthio group, a 3-methyl-2-butylthio group, a 1-hexylthio group, a 2-hexylthio group, a 3-hexylthio group, a 2-methyl-1-pentylthio group, a 3-methyl-1-pentylthio group, a 2-ethyl-1-butylthio group, a 2,2-dimethyl-1-butylthio group or a 2,3-dimethyl-1-butylthio group, for example. The "$C_1$-$C_6$ alkylthio group" in $R^1$ is preferably a $C_3$-$C_6$ alkylthio group, and more preferably a $C_4$-$C_6$ alkylthio group. The "$C_1$-$C_6$ alkylthio group" in $R^3$ and $R^4$ is preferably a $C_2$-$C_4$ alkylthio group, and more preferably a $C_2$-$C_3$ alkylthio group. The "$C_1$-$C_6$ alkylthio group" in Substituent Group α is preferably a $C_1$-$C_4$ alkylthio group, and more preferably a $C_1$-$C_2$ alkylthio group. The "$C_1$-$C_6$ alkylthio group" in Substituent Group δ is preferably a $C_1$-$C_4$ alkylthio group, more preferably a $C_1$-$C_2$ alkylthio group, and most preferably a methylthio group.

In the general formula (I), the "$C_1$-$C_6$ alkylamino group" is an amino group substituted with one $C_1$-$C_6$ alkyl group described below. The group may be a methylamino group, an ethylamino group, a 1-propylamino group, a 2-propylamino group, a 1-butylamino group, a 2-butylamino group, a 2-methyl-1-propylamino group, a 2-methyl-2-propylamino group, a 1-pentylamino group, a 2-pentylamino group, a 3-pentylamino group, a 1-hexylamino group, a 2-hexylamino group or a 3-hexylamino group, for example. The "$C_1$-$C_6$ alkylamino group" in $R^1$ is preferably a $C_3$-$C_6$ alkylamino group, and more preferably a $C_4$-$C_6$ alkylamino group. The "$C_1$-$C_6$ alkylamino group" in $R^5$, $R^6$, $R^7$, $R^8$ and Substituent Group α is preferably a $C_1$-$C_4$ alkylamino group, and more preferably a $C_1$-$C_2$ alkylamino group. The "$C_1$-$C_6$ alkylamino group" in Substituent Group δ is preferably a $C_1$-$C_4$ alkylamino group, and more preferably a $C_1$-$C_2$ alkylamino group.

In the general formula (I), the "di($C_1$-$C_6$ alkyl)amino group" is an amino group substituted with two $C_1$-$C_6$ alkyl groups described below which are the same or different. The group may be a dimethylamino group, a methylethylamino group, a methylpropylamino group [such as an N-methyl-N-(1-propyl)amino group], a methylbutylamino group [such as an N-(1-butyl)-N-methylamino group], a methylpentylamino group, a methylhexylamino group, a diethylamino group, an ethylpropylamino group [such as an N-ethyl-N-(1-propyl)amino group], an ethylbutylamino group, a dipropylamino group, a propylbutylamino group, a dibutylamino group, a dipentylamino group or a dihexylamino group, for example. The "di($C_1$-$C_6$ alkyl)amino group" in $R^1$ is preferably a di($C_3$-$C_6$ alkyl)amino group, and more preferably a di($C_4$-$C_6$ alkyl)amino group. The "di($C_1$-$C_6$ alkyl)amino group" in $R^5$, $R^6$, $R^7$, $R^8$ and Substituent Group α is preferably a di($C_1$-$C_4$ alkyl)amino group, and more preferably a di($C_1$-$C_2$ alkyl)amino group. The "di($C_1$-$C_6$ alkyl)amino group" in Substituent Group δ is preferably a di($C_1$-$C_4$ alkyl)amino group, and more preferably a di($C_1$-$C_2$ alkyl)amino group.

In the general formula (I) of the present invention, the "($C_1$-$C_6$ alkyl)carbonyl group" is a carbonyl group substituted with one $C_1$-$C_6$ alkyl group described below. The group may be a methylcarbonyl group, an ethylcarbonyl group, a 1-propylcarbonyl group, a 2-propylcarbonyl group, a 1-butylcarbonyl group, a 2-butylcarbonyl group, a 2-methyl-1-propylcarbonyl group, a 2-methyl-2-propylcarbonyl group, a 1-pentylcarbonyl group, a 2-pentylcarbonyl group, a 3-pentylcarbonyl group, a 2-methyl-2-butylcarbonyl group, a 3-methyl-2-butylcarbonyl group, a 1-hexylcarbonyl group, a 2-hexylcarbonyl group, a 3-hexylcarbonyl group, a 2-methyl-1-pentylcarbonyl group, a 3-methyl-1-pentylcarbonyl group, a 2-ethyl-1-butylcarbonyl group, a 2,2-dimethyl-1-butylcarbonyl group or a 2,3-dimethyl-1-butylcarbonyl group, for example. The "($C_1$-$C_6$ alkyl)carbonyl group" in $R^1$ is preferably a ($C_3$-$C_6$ alkyl)carbonyl group, and more preferably a ($C_4$-$C_6$ alkyl)carbonyl group. The "($C_1$-$C_6$ alkyl)carbonyl group" in $R^7$, $R^8$ and Substituent Group α is preferably a ($C_1$-$C_4$ alkyl)carbonyl group, and more preferably a ($C_1$-$C_2$ alkyl)carbonyl group.

In the general formula (I), the "($C_1$-$C_6$ alkoxy)carbonyl group" is a carbonyl group substituted with one $C_1$-$C_6$ alkoxy group described above. The group may be a methoxycarbonyl group, an ethoxycarbonyl group, a 1-propoxycarbonyl group, a 2-propoxycarbonyl group, a 1-butoxycarbonyl group, a 2-butoxycarbonyl group, a 2-methyl-1-propoxycarbonyl group, a 2-methyl-2-propoxycarbonyl group, a 1-pentyloxycarbonyl group, a 2-pentyloxycarbonyl group, a 3-pentyloxycarbonyl group, a 2-methyl-2-butoxycarbonyl group, a 3-methyl-2-butoxycarbonyl group, a 1-hexyloxycarbonyl group, a 2-hexyloxycarbonyl group, a 3-hexyloxycarbonyl group, a 2-methyl-1-pentyloxycarbonyl group, a 3-methyl-1-pentyloxycarbonyl group, a 2-ethyl-1-butoxycarbonyl group, a 2,2-dimethyl-1-butoxycarbonyl group or a 2,3-dimethyl-1-butoxycarbonyl group, for example. The "($C_1$-$C_6$ alkoxy) carbonyl group" in $R^1$ is preferably a ($C_3$-$C_6$ alkoxy)carbonyl group, and more preferably a ($C_4$-$C_6$ alkoxy)carbonyl group. The "($C_1$-$C_6$ alkoxy)carbonyl group" in $R^7$, $R^8$ and Substituent Group α is preferably a ($C_1$-$C_4$ alkoxy)carbonyl group, and more preferably a ($C_1$-$C_2$ alkoxy)carbonyl group.

In the general formula (I), the "$C_3$-$C_{10}$ cyclic hydrocarbon group" is a monocyclic or bicyclic hydrocarbon group having 3 to 10 carbon atoms and includes a $C_3$-$C_{10}$ saturated cyclic hydrocarbon group ($C_3$-$C_{10}$ cycloalkyl group), a $C_3$-$C_{10}$ partially unsaturated cyclic hydrocarbon group and a $C_6$-$C_{10}$ aromatic hydrocarbon group ($C_6$-$C_{10}$ aryl group). The $C_3$-$C_{10}$ saturated cyclic hydrocarbon group may be a cyclopropyl group, a cyclobutyl group, a cyclopentyl group, a cyclohexyl group, a cycloheptyl group, a cyclooctyl group, a cyclononyl group, a cyclodecyl group, a bicyclo[2,2,1]heptyl group (norbornyl group), a bicyclo[4,2,0]octyl group, a bicyclo[3,2,1] octyl group, a bicyclo[4,3,0]nonyl group, a bicyclo[4,2,1] nonyl group, a bicyclo[3,3,1]nonyl group, a bicyclo[5,3,0] octyl group or a bicyclo[4,4,0]octyl group (perhydronaphthyl group), for example. The $C_3$-$C_{10}$ partially unsaturated cyclic hydrocarbon group is the above $C_3$-$C_{10}$ saturated cyclic hydrocarbon group which is partially oxidized. The group may be a cyclopropenyl group, a cyclobutenyl group, a cyclopentenyl group, a cyclopentanedienyl group, a cyclohexenyl group, a cyclohexanedienyl group, a cycloheptenyl group, a cycloheptanedienyl group, a cyclooctenyl group, a cyclooctanedienyl group, a cyclooctanetrienyl group, a cyclononenyl group, a cyclodecenyl group, an indanyl group or an indenyl group, for example. The $C_6$-$C_{10}$ aromatic hydrocarbon group may be a phenyl group or a naphthyl group, for example. The "$C_3$-$C_{10}$ cyclic hydrocarbon group" in $R^1$ is preferably a $C_3$-$C_8$ cyclic hydrocarbon group, more preferably a $C_3$-$C_8$ cycloalkyl group or a phenyl group, still more preferably a $C_4$-$C_7$ cycloalkyl group, and yet more preferably a $C_5$-$C_6$ cycloalkyl group. The "$C_3$-$C_{10}$ cyclic hydrocarbon group" in B and D is preferably a $C_3$-$C_{10}$ cycloalkyl group or a $C_6$-$C_{10}$ aryl group, more preferably a $C_6$-$C_{10}$ aryl group, and most preferably a phenyl group.

In the general formula (I), the "3- to 10-membered heterocyclyl group" is a monocyclic or bicyclic 3- to 10-membered heterocyclic group containing 1 to 3 atoms selected from the group consisting of a nitrogen atom, an oxygen atom and a sulfur atom and includes a 3- to 10-membered saturated heterocyclyl group, a 3- to 10-membered partially unsaturated heterocyclyl group and a 5- to 10-membered aromatic heterocyclyl group. The 3- to 10-membered saturated heterocyclyl group may be an aziridinyl group, an azetidinyl group, a pyrrolidinyl group, an imidazolidinyl group, a pyrazolidinyl group, an oxazolidinyl group, a thiazolidinyl group, a piperidinyl group, a piperazinyl group, a hexahydropyrimidinyl group, a morpholinyl group, a thiomorpholinyl group, a perhydroazepinyl group, a homopiperazinyl group, a homomorpholinyl group or a decahydroquinolinyl group, for example. The 3- to 10-membered partially unsaturated heterocyclyl group is the above 3- to 10-membered saturated heterocyclyl group which is partially oxidized or the following 5- to 10-membered aromatic heterocyclyl group which is partially reduced. The group may be a pyrrolinyl group, an imidazolinyl group, a pyrazolinyl group, an oxazolinyl group, a thiazolinyl group, a dihydropyridyl group, a tetrahydropyridyl group, a dihydroindolyl group, a dihydrobenzofuranyl group, a dihydrobenzothienyl group, a dihydrobenzimidazolyl group, a dihydrobenzoxazolyl group, a dihydrobenzothiazolyl group, a dihydroquinolyl group, a tetrahydroquinolyl group, a dihydroquinazolinyl group or a tetrahydroquinazolinyl group, for example. The 5- to 10-membered aromatic heterocyclyl group may be a pyrrolyl group, a furyl group, a thienyl group, a pyrazolyl group, an imidazolyl group, an oxazolyl group, an isoxazolyl group, a thiazolyl group, an isothiazolyl group, a triazolyl group, an oxadiazolyl group, a thiadiazolyl group, a pyranyl group, a pyridyl group, a pyridazinyl group, a pyrimidinyl group, a pyrazinyl group, an azepinyl group, an azocinyl group, an azoninyl group, an indolyl group, a benzofuranyl group, a benzothienyl group, a benzimidazolyl group, a benzoxazolyl group, a benzisoxazolyl group, a benzothiazolyl group, a benzisothiazolyl group, a quinolyl group, an isoquinolyl group, a quinoxalinyl group or a quinazolinyl group, for example. The "3- to 10-membered heterocyclyl group" in $R^1$ and Substituent Group β is preferably a 3- to 8-membered heterocyclyl group, more preferably a 3- to 8-membered saturated heterocyclyl group or a 5- or 6-membered aromatic heterocyclyl group, and still more preferably a 4- to 7-membered saturated heterocyclyl group. The "3- to 10-membered heterocyclyl group" in B and D is preferably a 3- to 10-membered saturated heterocyclyl group or a 5- to 10-membered aromatic heterocyclyl group, more preferably a 5- to 10-membered aromatic heterocyclyl group, and still more preferably a 5- or 6-membered aromatic heterocyclyl group.

In the general formula (I), the "$C_1$-$C_6$ alkyl group" or the "$C_1$-$C_6$ alkyl" moiety in each substituent is a linear or branched alkyl group having 1 to 6 carbon atoms. The group may be a methyl group, an ethyl group, a 1-propyl group, a 2-propyl group, a 1-butyl group, a 2-butyl group, a 2-methyl-1-propyl group, a 2-methyl-2-propyl group, a 1-pentyl group, a 2-pentyl group, a 3-pentyl group, a 2-methyl-2-butyl group, a 3-methyl-2-butyl group, a 1-hexyl group, a 2-hexyl group, a 3-hexyl group, a 2-methyl-1-pentyl group, a 3-methyl-1-pentyl group, a 2-ethyl-1-butyl group, a 2,2-dimethyl-1-butyl group or a 2,3-dimethyl-1-butyl group, for example. The "$C_1$-$C_6$ alkyl group" in $R^2$, $R^5$, $R^6$, $R^9$, $R^{11}$, Substituent Group α and Substituent Group γ is preferably a $C_1$-$C_4$ alkyl group, and more preferably a $C_1$-$C_2$ alkyl group. The "$C_1$-$C_6$ alkyl group" in $R^3$ and $R^4$ is preferably a $C_1$-$C_4$ alkyl group, more preferably a $C_1$-$C_3$ alkyl group, and most preferably a methyl group, an ethyl group or a 2-propyl group. The "$C_1$-$C_6$ alkyl group" in $R^7$ is preferably a $C_1$-$C_4$ alkyl group, more preferably a $C_1$-$C_2$ alkyl group, and most preferably a methyl group. The "$C_1$-$C_6$ alkyl group" in $R^{10}$ is preferably a $C_2$-$C_5$ alkyl group, more preferably a $C_2$-$C_4$ alkyl group, still more preferably a $C_3$-$C_4$ alkyl group, and most preferably a 1-propyl group.

In the general formula (I), the "$C_3$-$C_8$ cycloalkyl group" is a cyclic alkyl group having 3 to 8 carbon atoms. The group may be a cyclopropyl group, a cyclobutyl group, a cyclopentyl group, a cyclohexyl group, a cycloheptyl group or a cyclooctyl group, for example, and is preferably a $C_3$-$C_6$ cycloalkyl group, and more preferably a $C_3$-$C_4$ cycloalkyl group.

In the general formula (I), the "3- to 10-membered nitrogen-containing heterocyclyl group" is the above 3- to 10-membered heterocyclyl group containing at least one nitrogen atom. The group is preferably a 3- to 10-membered nitrogen-containing saturated heterocyclyl group or a 5- to 10-membered nitrogen-containing aromatic heterocyclyl group, and more preferably a 4- to 8-membered nitrogen-containing saturated heterocyclyl group.

In the general formula (I), the "$C_1$-$C_5$ alkylene group" is a linear or branched alkylene group having 1 to 5 carbon atoms. The group may be a methylene group, an ethylene group

[—(CH$_2$)$_2$—], a methylmethylene group [—CH(Me)-], a trimethylene group [—(CH$_2$)$_3$—], a methylethylene group [—CH(Me)CH$_2$— or —CH$_2$CH(Me)-], a tetramethylene group [—(CH$_2$)$_4$—], a methyltrimethylene group [—CH(Me)CH$_2$CH$_2$—, —CH$_2$CH(Me)CH$_2$— or —CH$_2$CH$_2$CH(Me)-] or a pentamethylene group [—(CH$_2$)$_5$—], for example, and is preferably a C$_2$-C$_4$ alkylene group, and more preferably a C$_2$-C$_3$ alkylene group.

In the general formula (I), the "3- to 10-membered nitrogen-containing saturated heterocyclyl group" is a 3- to 10-membered saturated heterocyclyl group included in the above 3- to 10-membered heterocyclyl group, which contains at least one nitrogen atom. The group is preferably a 4- to 8-membered nitrogen-containing saturated heterocyclyl group, more preferably a 5- or 6-membered nitrogen-containing saturated heterocyclyl group, still more preferably a pyrrolidinyl group, an imidazolidinyl group, a pyrazolidinyl group, a piperidinyl group, a piperazinyl group, a hexahydropyrimidinyl group, a morpholinyl group or a thiomorpholinyl group, and most preferably a piperazinyl group.

In the general formula (I), the "3- to 10-membered nitrogen-containing partially unsaturated heterocyclyl group" is a 3- to 10-membered partially unsaturated heterocyclyl group included in the above 3- to 10-membered heterocyclyl group, which contains at least one nitrogen atom. The group is preferably a 4- to 8-membered nitrogen-containing partially unsaturated heterocyclyl group, more preferably a 5- or 6-membered nitrogen-containing partially unsaturated heterocyclyl group, and still more preferably a pyrrolinyl group, an imidazolinyl group, a dihydropyridyl group or a tetrahydropyridyl group.

In the general formula (I), the "C$_3$-C$_{10}$ saturated cyclic hydrocarbon group" is a C$_3$-C$_{10}$ saturated cyclic hydrocarbon group (C$_3$-C$_{10}$ cycloalkyl group) included in the above C$_3$-C$_{10}$ cyclic hydrocarbon group. The group is preferably a C$_4$-C$_8$ cycloalkyl group, more preferably a C$_5$-C$_6$ cycloalkyl group, and most preferably a cyclohexyl group.

In the general formula (I), the "C$_3$-C$_{10}$ partially unsaturated cyclic hydrocarbon group" is a C$_3$-C$_{10}$ partially unsaturated cyclic hydrocarbon group included in the above C$_3$-C$_{10}$ cyclic hydrocarbon group. The group is preferably a C$_4$-C$_8$ partially unsaturated cyclic hydrocarbon group, and more preferably a C$_5$-C$_6$ partially unsaturated cyclic hydrocarbon group.

In the general formula (I), the "3- to 10-membered saturated heterocyclyl group" is a 3- to 10-membered saturated heterocyclyl group included in the above 3- to 10-membered heterocyclyl group. The group is preferably a 4- to 8-membered saturated heterocyclyl group, more preferably a 5- or 6-membered saturated heterocyclyl group, and still more preferably a pyrrolidinyl group, an imidazolidinyl group, a pyrazolidinyl group, a piperidinyl group, a piperazinyl group, a hexahydropyrimidinyl group, a morpholinyl group or a thiomorpholinyl group.

In the general formula (I), the "3- to 10-membered partially unsaturated heterocyclyl group" is a 3- to 10-membered partially unsaturated heterocyclyl group included in the above 3- to 10-membered heterocyclyl group. The group is preferably a 4- to 8-membered partially unsaturated heterocyclyl group, more preferably a 5- or 6-membered partially unsaturated heterocyclyl group, and still more preferably a pyrrolinyl group, a imidazolinyl group, a dihydropyridyl group or a tetrahydropyridyl group.

In the general formula (I), the "C$_1$-C$_6$ alkylene group" is a linear or branched alkylene group having 1 to 6 carbon atoms. The group may be a methylene group, an ethylene group [—(CH$_2$)$_2$—], a methylmethylene group [—CH(Me)-], a trimethylene group [—(CH$_2$)$_3$—], a methylethylene group [—CH(Me)CH$_2$— or —CH$_2$CH(Me)-], a tetramethylene group [—(CH$_2$)$_4$—], a methyltrimethylene group [—CH(Me)CH$_2$CH$_2$—, —CH$_2$CH(Me)CH$_2$— or —CH$_2$CH$_2$CH(Me)-], a pentamethylene group [—(CH$_2$)$_5$—] or a hexamethylene group [—(CH$_2$)$_6$—], for example, and is preferably a C$_1$-C$_4$ alkylene group, more preferably a C$_1$-C$_2$ alkylene group, and most preferably a methylene group.

In the general formula (I), the "C$_2$-C$_6$ alkenylene group" is a linear or branched alkenylene group having 2 to 6 carbon atoms and having one or more carbon-carbon double bonds. The group may be a vinylene group [—CH=CH—], a propenylene group (allylene group) [—CH=CH—(CH$_2$)— or —(CH$_2$)—CH=CH—], a 1-methylvinylene group, a 2-methylvinylene group, a butenylene group, a 1-methyl-1-propenylene group, a 2-methyl-1-propenylene group, a 3-methyl-1-propenylene group, a pentenylene group or a hexenylene group, for example, and is preferably a C$_2$-C$_4$ alkenylene group, and more preferably a C$_2$-C$_3$ alkenylene group.

In the general formula (I), the "C$_2$-C$_6$ alkynylene group" is a linear or branched alkynylene group having 2 to 6 carbon atoms and having one or more carbon-carbon triple bonds. The group may be an ethynylene group [—C≡C—], a propynylene group [—C≡C—(CH$_2$)— or —(CH$_2$)—C≡C—], a butynylene group, a 3-methylpropynylene group, a pentynylene group or a hexynylene group, for example, and is preferably a C$_2$-C$_4$ alkynylene group, and more preferably a C$_2$-C$_3$ alkynylene group.

In the general formula (I), the "C$_3$-C$_8$ saturated cyclic hydrocarbon group" is equivalent to the above C$_3$-C$_8$ cycloalkyl group. The group is preferably a C$_3$-C$_6$ cycloalkyl group, and more preferably a C$_3$-C$_5$ cycloalkyl group.

In the general formula (I), the "C$_3$-C$_8$ partially unsaturated cyclic hydrocarbon group" is a C$_3$-C$_{10}$ partially unsaturated cyclic hydrocarbon group included in the above C$_3$-C$_{10}$ cyclic hydrocarbon group, which has 3 to 8 carbon atoms. The group may be a cyclopropenyl group, a cyclobutenyl group, a cyclopentenyl group, a cyclopentanedienyl group, a cyclohexenyl group, a cyclohexanedienyl group, a cycloheptenyl group, a cycloheptanedienyl group, a cyclooctenyl group, a cyclooctanedienyl group or a cyclooctanetrienyl group, for example, and is preferably a C$_3$-C$_6$ partially unsaturated cyclic hydrocarbon group, and more preferably a C$_3$-C$_5$ partially unsaturated cyclic hydrocarbon group.

In the general formula (I), the "3- to 8-membered saturated heterocyclyl group" is a 3- to 10-membered saturated heterocyclyl group included in the above 3- to 10-membered heterocyclyl group, which is a 3- to 8-membered group. The group may be an aziridinyl group, an azetidinyl group, a pyrrolidinyl group, an imidazolidinyl group, a pyrazolidinyl group, an oxazolidinyl group, a thiazolidinyl group, a piperidinyl group, a piperazinyl group, a hexahydropyrimidinyl group, a morpholinyl group, a thiomorpholinyl group, a perhydroazepinyl group, a homopiperazinyl group or a homomorpholinyl group, for example, and is preferably a 3- to 6-membered saturated heterocyclyl group, and more preferably a 3- to 5-membered saturated heterocyclyl group.

In the general formula (I), the "3- to 8-membered partially unsaturated heterocyclyl group" is a 3- to 10-membered partially unsaturated heterocyclyl group included in the above 3- to 10-membered heterocyclyl group, which is a 3- to 8-membered group. The group may be a pyrrolinyl group, an imidazolinyl group, a pyrazolinyl group, an oxazolinyl group, a thiazolinyl group, a dihydropyridyl group or a tetrahydropyridyl group, for example, and is preferably a 3- to 6-membered partially unsaturated heterocyclyl group, and more preferably a 3- to 5-membered partially unsaturated heterocyclyl group.

In the general formula (I), the "halogeno $C_1$-$C_6$ alkyl group" is the above $C_1$-$C_6$ alkyl group substituted with 1 to 7 halogeno groups described below. The group may be a fluoromethyl group, a difluoromethyl group, a dichloromethyl group, a dibromomethyl group, a trifluoromethyl group, a trichloromethyl group, a 2-fluoroethyl group, a 2-bromoethyl group, a 2-chloroethyl group, a 2-iodoethyl group, a 2,2-difluoroethyl group, a 2,2,2-trifluoroethyl group, a trichloroethyl group, a pentafluoroethyl group, a 3-fluoropropyl group, a 3-chloropropyl group, a 4-fluorobutyl group, a 5-fluoropentyl group or a 6-fluorohexyl group, for example. The group is preferably a halogeno $C_1$-$C_4$ alkyl group, and more preferably a halogeno $C_1$-$C_2$ alkyl group (wherein the halogeno group(s) are 1 to 5 groups selected from the group consisting of a fluoro group and a chloro group).

In the general formula (I), the "halogeno ($C_1$-$C_6$ alkoxy) group" is the above $C_1$-$C_6$ alkoxy group substituted with 1 to 7 halogeno groups described below. The group may be a fluoromethoxy group, a difluoromethoxy group, a dichloromethoxy group, a dibromomethoxy group, a trifluoromethoxy group, a trichloromethoxy group, a 2-fluoroethoxy group, a 2-bromoethoxy group, a 2-chloroethoxy group, a 2-iodoethoxy group, a 2,2-difluoroethoxy group, a 2,2,2-trifluoroethoxy group, a trichloroethoxy group, a pentafluoroethoxy group, a 3-fluoropropoxy group, a 3-chloropropoxy group, a 4-fluorobutoxy group, a 5-fluoropentyloxy group or a 6-fluorohexyloxy group, for example, and is preferably a halogeno ($C_1$-$C_4$ alkoxy) group, more preferably a halogeno ($C_1$-$C_2$ alkoxy) group (wherein the halogeno group(s) are 1 to 5 groups selected from the group consisting of a fluoro group and a chloro group), and still more preferably a difluoromethoxy group or a trifluoromethoxy group.

In the general formula (I), the "($C_1$-$C_6$ alkyl)carbonylamino group" is an amino group substituted with one ($C_1$-$C_6$ alkyl)carbonyl group described above. The group may be a methylcarbonylamino group, an ethylcarbonylamino group, a 1-propylcarbonylamino group, a 2-propylcarbonylamino group, a 1-butylcarbonylamino group, a 2-butylcarbonylamino group, a 2-methyl-1-propylcarbonylamino group, a 2-methyl-2-propylcarbonylamino group, a 1-pentylcarbonylamino group, a 2-pentylcarbonylamino group, a 3-pentylcarbonylamino group, a 2-methyl-2-butylcarbonylamino group, a 3-methyl-2-butylcarbonylamino group, a 1-hexylcarbonylamino group, a 2-hexylcarbonylamino group, a 3-hexylcarbonylamino group, a 2-methyl-1-pentylcarbonylamino group, a 3-methyl-1-pentylcarbonylamino group, a 2-ethyl-1-butylcarbonylamino group, a 2,2-dimethyl-1-butylcarbonylamino group or a 2,3-dimethyl-1-butylcarbonylamino group, for example, and is preferably a ($C_1$-$C_4$ alkyl)carbonylamino group, and more preferably a ($C_1$-$C_2$ alkyl)carbonylamino group.

In the general formula (I), the "($C_1$-$C_6$ alkylamino)carbonyl group" is a carbonyl group substituted with one $C_1$-$C_6$ alkylamino group described above. The group may be a methylaminocarbonyl group, an ethylaminocarbonyl group, a 1-propylaminocarbonyl group, a 2-propylaminocarbonyl group, a 1-butylaminocarbonyl group, a 2-butylaminocarbonyl group, a 2-methyl-1-propylaminocarbonyl group, a 2-methyl-2-propylaminocarbonyl group, a 1-pentylaminocarbonyl group, a 2-pentylaminocarbonyl group, a 3-pentylaminocarbonyl group, a 1-hexylaminocarbonyl group, a 2-hexylaminocarbonyl group or a 3-hexylaminocarbonyl group, for example, and is preferably a ($C_1$-$C_4$ alkylamino)carbonyl group, and more preferably a ($C_1$-$C_2$ alkylamino)carbonyl group.

In the general formula (I), the "di($C_1$-$C_6$ alkyl)aminocarbonyl group" is a carbonyl group substituted with one di($C_1$-$C_6$ alkyl)amino group described above. The group may be a dimethylaminocarbonyl group, a methylethylaminocarbonyl group, a methylpropylaminocarbonyl group [such as an N-methyl-N-(1-propyl)aminocarbonyl group], a methylbutylaminocarbonyl group [such as an N-(1-butyl)-N-methylaminocarbonyl group], a methylpentylaminocarbonyl group, a methylhexylaminocarbonyl group, a diethylaminocarbonyl group, an ethylpropylaminocarbonyl group [such as an N-ethyl-N-(1-propyl)aminocarbonyl group], an ethylbutylaminocarbonyl group, a dipropylaminocarbonyl group, a propylbutylaminocarbonyl group, a dibutylaminocarbonyl group, a dipentylaminocarbonyl group or a dihexylaminocarbonyl group, for example, and is preferably a di($C_1$-$C_4$ alkyl)aminocarbonyl group, and more preferably a di($C_1$-$C_2$ alkyl)aminocarbonyl group.

In the general formula (I), the "($C_1$-$C_6$ alkylamino)sulfonyl group" is a sulfonyl group (—$SO_2$—) substituted with one $C_1$-$C_6$ alkylamino group described above. The group may be a (methylamino)sulfonyl group, an (ethylamino)sulfonyl group, a (1-propylamino)sulfonyl group, a (2-propylamino)sulfonyl group, a (1-butylamino)sulfonyl group, a (2-butylamino)sulfonyl group, a (2-methyl-1-propylamino)sulfonyl group, a (2-methyl-2-propylamino)sulfonyl group, a (1-pentylamino)sulfonyl group, a (2-pentylamino)sulfonyl group, a (3-pentylamino)sulfonyl group, a (1-hexylamino)sulfonyl group, a (2-hexylamino)sulfonyl group or a (3-hexylamino)sulfonyl group, for example, and is preferably a ($C_1$-$C_4$ alkylamino)sulfonyl group, and more preferably a ($C_1$-$C_2$ alkylamino)sulfonyl group.

In the general formula (I), the "di($C_1$-$C_6$ alkyl)aminosulfonyl group" is a sulfonyl group (—$SO_2$—) the sulfur atom of which is substituted with one di($C_1$-$C_6$ alkyl)amino group described above. The group may be a (dimethylamino)sulfonyl group, a (methylethylamino)sulfonyl group, a (methylpropylamino)sulfonyl group [such as an [N-methyl-N-(1-propyl)amino]sulfonyl group], a (methylbutylamino)sulfonyl group [such as an [N-(1-butyl)-N-methylamino]sulfonyl group], a (methylpentylamino)sulfonyl group, a (methylhexylamino)sulfonyl group, a (diethylamino)sulfonyl group, an (ethylpropylamino)sulfonyl group [such as an [N-ethyl-N-(1-propyl)amino]sulfonyl group], an (ethylbutylamino)sulfonyl group, a (dipropylamino)sulfonyl group, a (propylbutylamino)sulfonyl group, a (dibutylamino)sulfonyl group, a (dipentylamino)sulfonyl group or a (dihexylamino) sulfonyl group, for example, and is preferably a di($C_1$-$C_4$ alkyl)aminosulfonyl group, and more preferably a di($C_1$-$C_2$ alkyl)aminosulfonyl group.

In the general formula (I), the "halogeno group" may be a fluoro group, a chloro group, a bromo group or an iodo group and is preferably a fluoro group, a chloro group or a bromo group, and more preferably a fluoro group or a chloro group.

In the general formula (I), the "$C_6$-$C_{10}$ aryl group" is a 6- to 10-membered aromatic hydrocarbon group. The group may be a phenyl group or a naphthyl group, for example, and is preferably a phenyl group.

In the general formula (I), the "($C_1$-$C_6$ alkoxy)imino group" is a hydroxyimino group (=N—OH) the oxygen atom of which is substituted with one $C_1$-$C_6$ alkyl group described above. The group may be a methoxyimino group, an ethoxyimino group, a 1-propoxyimino group, a 2-propoxyimino group, a 1-butoxyimino group, a 1-pentyloxyimino group or a 1-hexyloxyimino group, for example, and is preferably a ($C_1$-$C_4$ alkoxy)imino group, and more preferably a ($C_1$-$C_2$ alkoxy)imino group.

In the general formula (I), the "$C_1$-$C_6$ alkylsulfinyl group" is a sulfinyl group (—SO—) substituted with one $C_1$-$C_6$ alkyl group described above. The group may be a methylsulfinyl group, an ethylsulfinyl group, a 1-propylsulfinyl group, a 2-propylsulfinyl group, a 1-butylsulfinyl group, a 2-butylsulfinyl group, a 2-methyl-1-propylsulfinyl group, a 2-methyl-2-propylsulfinyl group, a 1-pentylsulfinyl group, a 2-pentylsulfinyl group, a 3-pentylsulfinyl group, a 2-methyl-2-butylsulfinyl group, a 3-methyl-2-butylsulfinyl group, a 1-hexylsulfinyl group, a 2-hexylsulfinyl group, a 3-hexylsulfinyl group, a 2-methyl-1-pentylsulfinyl group, a 3-methyl-1-pentylsulfinyl group, a 2-ethyl-1-butylsulfinyl group, a 2,2-dimethyl-1-butylsulfinyl group or a 2,3-dimethyl-1-butylsulfinyl group, for example, and is preferably a $C_1$-$C_4$ alkylsulfinyl group, and more preferably a $C_1$-$C_2$ alkylsulfinyl group.

In the general formula (I), the "$C_1$-$C_6$ alkylsulfonyl group" is a sulfonyl group (—$SO_2$—) substituted with one $C_1$-$C_6$ alkyl group described above. The group may be a methanesulfonyl group, an ethanesulfonyl group, a 1-propanesulfonyl group, a 2-propanesulfonyl group, a 1-butanesulfonyl group, a 2-butanesulfonyl group, a 2-methyl-1-propanesulfonyl group, a 2-methyl-2-propanesulfonyl group, a 1-pentanesulfonyl group, a 2-pentanesulfonyl group, a 3-pentanesulfonyl group, a 2-methyl-2-butanesulfonyl group, a 3-methyl-2-butanesulfonyl group, a 1-hexanesulfonyl group, a 2-hexanesulfonyl group, a 3-hexanesulfonyl group, a 2-methyl-1-pentanesulfonyl group, a 3-methyl-1-pentanesulfonyl group, a 2-ethyl-1-butanesulfonyl group, a 2,2-dimethyl-1-butanesulfonyl group or a 2,3-dimethyl-1-butanesulfonyl group, for example, and is preferably a $C_1$-$C_4$ alkylsulfonyl group, and more preferably a $C_1$-$C_2$ alkylsulfonyl group.

In the general formula (I), the "($C_1$-$C_6$ alkyl)sulfonylamino group" is an amino group substituted with one $C_1$-$C_6$ alkylsulfonyl group described above. The group may be a methanesulfonylamino group, an ethanesulfonylamino group, a 1-propanesulfonylamino group, a 2-propanesulfonylamino group, a 1-butanesulfonylamino group, a 2-butanesulfonylamino group, a 2-methyl-1-propanesulfonylamino group, a 2-methyl-2-propanesulfonylamino group, a 1-pentanesulfonylamino group, a 2-pentanesulfonylamino group, a 3-pentanesulfonylamino group, a 2-methyl-2-butanesulfonylamino group, a 3-methyl-2-butanesulfonylamino group, a 1-hexanesulfonylamino group, a 2-hexanesulfonylamino group, a 3-hexanesulfonylamino group, a 2-methyl-1-pentanesulfonylamino group, a 3-methyl-1-pentanesulfonylamino group, a 2-ethyl-1-butanesulfonylamino group, a 2,2-dimethyl-1-butanesulfonylamino group or a 2,3-dimethyl-1-butanesulfonylamino group, for example, and is preferably a ($C_1$-$C_4$ alkyl)sulfonylamino group, and more preferably a ($C_1$-$C_2$ alkyl)sulfonylamino group.

In the general formula (I), the "($C_1$-$C_6$ alkylamino)carbonylamino group" is an amino group substituted with one ($C_1$-$C_6$ alkylamino)carbonyl group described above. The group may be a (methylamino)carbonylamino group, an (ethylamino)carbonylamino group, a (1-propylamino)carbonylamino group, a (2-propylamino)carbonylamino group, a (1-butylamino)carbonylamino group, a (2-butylamino)carbonylamino group, a (2-methyl-1-propylamino)carbonylamino group, a (2-methyl-2-propylamino)carbonylamino group, a (1-pentylamino)carbonylamino group, a (2-pentylamino)carbonylamino group, a (3-pentylamino)carbonylamino group, a (1-hexylamino)carbonylamino group, a (2-hexylamino)carbonylamino group or a (3-hexylamino)carbonylamino group, for example, and is preferably a ($C_1$-$C_4$ alkylamino)carbonylamino group, and more preferably a ($C_1$-$C_2$ alkylamino)carbonylamino group.

In the general formula (I), the "di($C_1$-$C_6$ alkyl)aminocarbonylamino group" is an amino group substituted with one di($C_1$-$C_6$ alkyl)aminocarbonyl group described above. The group may be a (dimethylamino)carbonylamino group, a (methylethylamino)carbonylamino group, a (methylpropylamino)carbonylamino group [such as an [N-methyl-N-(1-propyl)amino]carbonylamino group], a (methylbutylamino)carbonylamino group [such as an [N-(1-butyl)-N-methylamino]carbonylamino group], a (methylpentylamino)carbonylamino group, a (methylhexylamino)carbonylamino group, a (diethylamino)carbonylamino group, an (ethylpropylamino)carbonylamino group [such as an [N-ethyl-N-(1-propyl)amino]carbonylamino group], an (ethylbutylamino)carbonylamino group, a (dipropylamino)carbonylamino group, a (propylbutylamino)carbonylamino group, a (dibutylamino)carbonylamino group, a (dipentylamino)carbonylamino group or a (dihexylamino)carbonylamino group, for example, and is preferably a di($C_1$-$C_4$ alkyl)aminocarbonylamino group, and more preferably a di($C_1$-$C_2$ alkyl)aminocarbonylamino group.

In the general formula (I), the "($C_1$-$C_6$ alkylamino)sulfonylamino group" is a sulfonylamino group (—$SO_2NH$—) the sulfur atom of which is substituted with one $C_1$-$C_6$ alkylamino group described above. The group may be a (methylamino)sulfonylamino group, an (ethylamino)sulfonylamino group, a (1-propylamino)sulfonylamino group, a (2-propylamino)sulfonylamino group, a (1-butylamino)sulfonylamino group, a (2-butylamino)sulfonylamino group, a (2-methyl-1-propylamino)sulfonylamino group, a (2-methyl-2-propylamino)sulfonylamino group, a (1-pentylamino)sulfonylamino group, a (2-pentylamino)sulfonylamino group, a (3-pentylamino)sulfonylamino group, a (1-hexylamino)sulfonylamino group, a (2-hexylamino)sulfonylamino group or a (3-hexylamino)sulfonylamino group, for example, and is preferably a ($C_1$-$C_4$ alkylamino)sulfonylamino group, and more preferably a ($C_1$-$C_2$ alkylamino)sulfonylamino group.

In the general formula (I), the "di($C_1$-$C_6$ alkyl)aminosulfonylamino group" is a sulfonylamino group (—$SO_2NH$—) the sulfur atom of which is substituted with one di($C_1$-$C_6$ alkyl)amino group described above. The group may be a (dimethylamino)sulfonylamino group, a (methylethylamino)sulfonylamino group, a (methylpropylamino)sulfonylamino group [such as an [N-methyl-N-(1-propyl)amino]sulfonylamino group], a (methylbutylamino)sulfonylamino group [such as an [N-(1-butyl)-N-methylamino]sulfonylamino group], a (methylpentylamino)sulfonylamino group, a (methylhexylamino)sulfonylamino group, a (diethylamino)sulfonylamino group, an (ethylpropylamino)sulfonylamino group [such as an [N-ethyl-N-(1-propyl)amino]sulfonylamino group], an (ethylbutylamino)sulfonylamino group, a (dipropylamino)sulfonylamino group, a (propylbutylamino)sulfonylamino group, a (dibutylamino)sulfonylamino group, a (dipentylamino)sulfonylamino group or a (dihexylamino)sulfonylamino group, for example, and is preferably a di($C_1$-$C_4$ alkyl)aminosulfonylamino group, and more preferably a di($C_1$-$C_2$ alkyl)aminosulfonylamino group.

In the general formula (I), a and b independently represent preferably an integer of 0 to 3, more preferably an integer of 0 to 2, and most preferably 0 or 1. In the general formula (I), X forms a part of A, and each cyclic group defined for A contains X as a part thereof. A is preferably a group having the formula $A^a$, $A^b$ or $A^e$ shown below, more preferably a group having the formula $A^a$ or $A^b$, and most preferably a group having the formula $A^b$.

The compound represented by the general formula (I) according to the present invention can form an acid addition salt, and the acid addition salt is included in the present invention. The acid addition salts may be hydrochlorides, hydrobromides, sulfates, nitrates, phosphates, acetates, oxalates, malonates, fumarates, maleates, L-malic acid, D-malic acid, L-tartaric acid, D-tartaric acid, phthalates, trifluoroacetates, methanesulfonates, benzenesulfonates, p-toluenesulfonates, 2,4-dimethylbenzenesulfonates, 2,4,6-trimethylbenzenesulfonates, 4-ethylbenzenesulfonates or naphthalenesulfonates, for example. The compound represented by the general formula (I) according to the present invention can form an acid addition salt with an acid in any ratio. Each of the acid addition salts (such as a monoacid salt, a diacid salt and a hemiacid salt (½ acid salt)) or a mixture thereof is included in the present invention.

The compound represented by the general formula (I) or a pharmacologically acceptable salt thereof according to the present invention can form a hydrate or a solvate. Each of the hydrate and the solvate or a mixture thereof is included in the present invention.

When the compound represented by the general formula (I) or a pharmacologically acceptable salt thereof according to the present invention has at least one asymmetric center, axial asymmetry, carbon-carbon double bond, amidino group or the like, optical isomers (including enantiomers and diastereomers), geometric isomers, tautomers and rotamers may be present. These isomers and mixtures thereof are described by a single formula such as the formula (I). The present invention includes each of these isomers and mixtures thereof in any ratio (including racemates).

In the present invention, hypertension includes commonly known forms of hypertension and includes essential hypertension; and secondary hypertension such as renal hypertension, endocrine hypertension or neurogenic hypertension, for example.

The compound represented by the general formula (I) or a pharmacologically acceptable salt thereof according to the present invention has excellent properties in terms of renin inhibitory activity, solubility, cell membrane permeability, oral absorption, blood concentration, metabolic stability, tissue distribution, bioavailability, in vitro activity, in vivo activity, a rapid onset of drug effect, a lasting drug effect, physical stability, drug interaction, toxicity and the like and is useful as a medicment [in particular, a medicament for the treatment or prevention (preferably treatment) of hypertension].

Preferred compounds represented by the general formula (I) may be compounds shown in the following Tables 1 to 3. However, the compound of the present invention is not limited to these compounds.

The following abbreviations are used in the following Tables 1 to 3.

(S)Bu-Me: (S)-2-Methyl-1-butyl
(S)Bu-OH: (S)-1-Hydroxy-3-methyl-2-butyl
cHx: Cyclohexyl
cPn: Cyclopentyl
cPr: Cyclopropyl
diF-cHx: 4,4-Difluoro-1-cyclohexyl
Et: Ethyl
iBu: 2-Methyl-1-propyl
iPr: 2-Propyl
Me: Methyl
nBu: 1-Butyl
Py: Pyridyl
Thp: Tetrahydropyranyl

TABLE 1

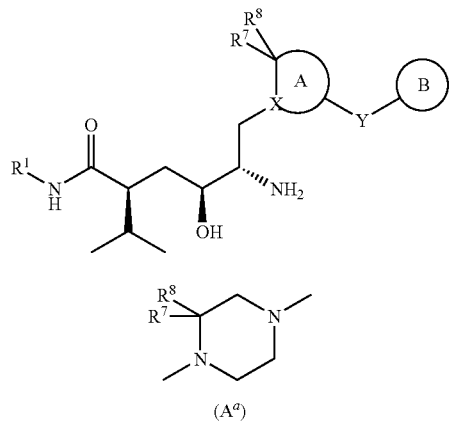

(I-1)

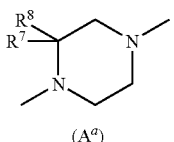

($A^a$)

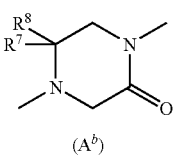

($A^b$)

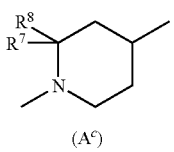

($A^c$)

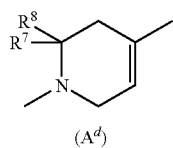

(A$^d$)

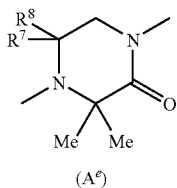

(A$^e$)

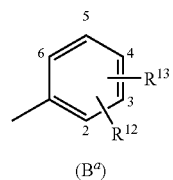

(B$^a$)

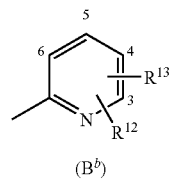

(B$^b$)

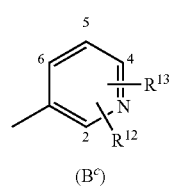

(B$^c$)

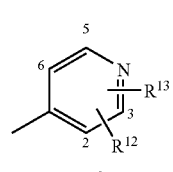

(B$^d$)

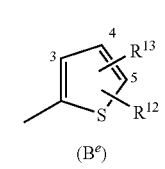

(B$^e$)

| Exemplary Compound No. | R$^1$ | A | R$^7$ | R$^8$ | Y | B | R$^{12}$ | R$^{13}$ |
|---|---|---|---|---|---|---|---|---|
| 1-1 | iPr | A$^b$ | Me | Me | bond | B$^a$ | — | — |
| 1-2 | iPr | A$^b$ | Me | Me | bond | B$^a$ | 2-Cl | — |
| 1-3 | nBu | A$^a$ | Me | Me | bond | B$^a$ | — | — |
| 1-4 | nBu | A$^a$ | Me | Me | bond | B$^a$ | — | 2-OCH$_2$OMe |
| 1-5 | nBu | A$^a$ | Me | Me | bond | B$^a$ | — | 2-O(CH$_2$)$_2$OMe |
| 1-6 | nBu | A$^a$ | Me | Me | bond | B$^a$ | — | 2-O(CH$_2$)$_3$OMe |
| 1-7 | nBu | A$^a$ | Me | Me | bond | B$^a$ | 2-Me | — |
| 1-8 | nBu | A$^a$ | Me | Me | bond | B$^a$ | 2-OMe | — |
| 1-9 | nBu | A$^a$ | Me | Me | bond | B$^a$ | 2-F | — |
| 1-10 | nBu | A$^a$ | Me | Me | bond | B$^a$ | 2-Cl | — |
| 1-11 | nBu | A$^b$ | Me | Me | bond | B$^a$ | — | — |
| 1-12 | nBu | A$^b$ | Me | Me | bond | B$^a$ | — | 2-OCH$_2$OMe |
| 1-13 | nBu | A$^b$ | Me | Me | bond | B$^a$ | — | 3-OCH$_2$OMe |
| 1-14 | nBu | A$^b$ | Me | Me | bond | B$^a$ | — | 2-O(CH$_2$)$_2$OMe |

| No. | | | | | | | | |
|---|---|---|---|---|---|---|---|---|
| 1-15 | nBu | $A^b$ | Me | Me | bond | $B^a$ | — | 3-O(CH$_2$)$_2$OMe |
| 1-16 | nBu | $A^b$ | Me | Me | bond | $B^a$ | — | 2-O(CH$_2$)$_3$OMe |
| 1-17 | nBu | $A^b$ | Me | Me | bond | $B^a$ | — | 3-O(CH$_2$)$_3$OMe |
| 1-18 | nBu | $A^b$ | Me | Me | bond | $B^a$ | 2-Me | — |
| 1-19 | nBu | $A^b$ | Me | Me | bond | $B^a$ | 3-Me | — |
| 1-20 | nBu | $A^b$ | Me | Me | bond | $B^a$ | 2-CF$_3$ | — |
| 1-21 | nBu | $A^b$ | Me | Me | bond | $B^a$ | 3-CF$_3$ | — |
| 1-22 | nBu | $A^b$ | Me | Me | bond | $B^a$ | 2-OH | — |
| 1-23 | nBu | $A^b$ | Me | Me | bond | $B^a$ | 3-OH | — |
| 1-24 | nBu | $A^b$ | Me | Me | bond | $B^a$ | 2-OMe | — |
| 1-25 | nBu | $A^b$ | Me | Me | bond | $B^a$ | 3-OMe | — |
| 1-26 | nBu | $A^b$ | Me | Me | bond | $B^a$ | 2-SH | — |
| 1-27 | nBu | $A^b$ | Me | Me | bond | $B^a$ | 3-SH | — |
| 1-28 | nBu | $A^b$ | Me | Me | bond | $B^a$ | 2-SMe | — |
| 1-29 | nBu | $A^b$ | Me | Me | bond | $B^a$ | 3-SMe | — |
| 1-30 | nBu | $A^b$ | Me | Me | bond | $B^a$ | 2-NH$_2$ | — |
| 1-31 | nBu | $A^b$ | Me | Me | bond | $B^a$ | 2-NHMe | — |
| 1-32 | nBu | $A^b$ | Me | Me | bond | $B^a$ | 2-NMe$_2$ | — |
| 1-33 | nBu | $A^b$ | Me | Me | bond | $B^a$ | 2-NHCHO | — |
| 1-34 | nBu | $A^b$ | Me | Me | bond | $B^a$ | 2-NHCOMe | — |
| 1-35 | nBu | $A^b$ | Me | Me | bond | $B^a$ | 2-CO$_2$H | — |
| 1-36 | nBu | $A^b$ | Me | Me | bond | $B^a$ | 2-CO$_2$Me | — |
| 1-37 | nBu | $A^b$ | Me | Me | bond | $B^a$ | 2-CONH$_2$ | — |
| 1-38 | nBu | $A^b$ | Me | Me | bond | $B^a$ | 2-CONHMe | — |
| 1-39 | nBu | $A^b$ | Me | Me | bond | $B^a$ | 2-CONMe$_2$ | — |
| 1-40 | nBu | $A^b$ | Me | Me | bond | $B^a$ | 2-CN | — |
| 1-41 | nBu | $A^b$ | Me | Me | bond | $B^a$ | 3-CN | — |
| 1-42 | nBu | $A^b$ | Me | Me | bond | $B^a$ | 2-NO$_2$ | — |
| 1-43 | nBu | $A^b$ | Me | Me | bond | $B^a$ | 3-NO$_2$ | — |
| 1-44 | nBu | $A^b$ | Me | Me | bond | $B^a$ | 2-F | — |
| 1-45 | nBu | $A^b$ | Me | Me | bond | $B^a$ | 3-F | — |
| 1-46 | nBu | $A^b$ | Me | Me | bond | $B^a$ | 2-Cl | — |
| 1-47 | nBu | $A^b$ | Me | Me | bond | $B^a$ | 3-Cl | — |
| 1-48 | nBu | $A^b$ | Me | Me | bond | $B^a$ | 2,3-di-Me | — |
| 1-49 | nBu | $A^b$ | Me | Me | bond | $B^a$ | 2,5-di-Me | — |
| 1-50 | nBu | $A^b$ | Me | Me | bond | $B^a$ | 2,6-di-Me | — |
| 1-51 | nBu | $A^b$ | Me | Me | bond | $B^a$ | 2-Me-3-OMe | — |
| 1-52 | nBu | $A^b$ | Me | Me | bond | $B^a$ | 2-Me-5-OMe | — |
| 1-53 | nBu | $A^b$ | Me | Me | bond | $B^a$ | 2-Me-6-OMe | — |
| 1-54 | nBu | $A^b$ | Me | Me | bond | $B^a$ | 2-Me-3-F | — |
| 1-55 | nBu | $A^b$ | Me | Me | bond | $B^a$ | 2-Me-5-F | — |
| 1-56 | nBu | $A^b$ | Me | Me | bond | $B^a$ | 2-Me-6-F | — |
| 1-57 | nBu | $A^b$ | Me | Me | bond | $B^a$ | 2-Me-3-Cl | — |
| 1-58 | nBu | $A^b$ | Me | Me | bond | $B^a$ | 2-Me-5-Cl | — |
| 1-59 | nBu | $A^b$ | Me | Me | bond | $B^a$ | 2-Me-6-Cl | — |
| 1-60 | nBu | $A^b$ | Me | Me | bond | $B^a$ | 2,3-di-OMe | — |
| 1-61 | nBu | $A^b$ | Me | Me | bond | $B^a$ | 2,5-di-OMe | — |
| 1-62 | nBu | $A^b$ | Me | Me | bond | $B^a$ | 2,6-di-OMe | — |
| 1-63 | nBu | $A^b$ | Me | Me | bond | $B^a$ | 2-OMe-3-Me | — |
| 1-64 | nBu | $A^b$ | Me | Me | bond | $B^a$ | 2-OMe-5-Me | — |
| 1-65 | nBu | $A^b$ | Me | Me | bond | $B^a$ | 2-OMe-3-F | — |
| 1-66 | nBu | $A^b$ | Me | Me | bond | $B^a$ | 2-OMe-5-F | — |
| 1-67 | nBu | $A^b$ | Me | Me | bond | $B^a$ | 2-OMe-6-F | — |
| 1-68 | nBu | $A^b$ | Me | Me | bond | $B^a$ | 2-OMe-3-Cl | — |
| 1-69 | nBu | $A^b$ | Me | Me | bond | $B^a$ | 2-OMe-5-Cl | — |
| 1-70 | nBu | $A^b$ | Me | Me | bond | $B^a$ | 2-OMe-6-Cl | — |
| 1-71 | nBu | $A^b$ | Me | Me | bond | $B^a$ | 2,3-di-F | — |
| 1-72 | nBu | $A^b$ | Me | Me | bond | $B^a$ | 2,5-di-F | — |
| 1-73 | nBu | $A^b$ | Me | Me | bond | $B^a$ | 2,6-di-F | — |
| 1-74 | nBu | $A^b$ | Me | Me | bond | $B^a$ | 2-F-3-Me | — |
| 1-75 | nBu | $A^b$ | Me | Me | bond | $B^a$ | 2-F-5-Me | — |
| 1-76 | nBu | $A^b$ | Me | Me | bond | $B^a$ | 2-F-3-OMe | — |
| 1-77 | nBu | $A^b$ | Me | Me | bond | $B^a$ | 2-F-5-OMe | — |
| 1-78 | nBu | $A^b$ | Me | Me | bond | $B^a$ | 2-F-3-Cl | — |
| 1-79 | nBu | $A^b$ | Me | Me | bond | $B^a$ | 2-F-5-Cl | — |
| 1-80 | nBu | $A^b$ | Me | Me | bond | $B^a$ | 2-F-6-Cl | — |
| 1-81 | nBu | $A^b$ | Me | Me | bond | $B^a$ | 2,3-di-Cl | — |
| 1-82 | nBu | $A^b$ | Me | Me | bond | $B^a$ | 2,5-di-Cl | — |
| 1-83 | nBu | $A^b$ | Me | Me | bond | $B^a$ | 2,6-di-Cl | — |
| 1-84 | nBu | $A^b$ | Me | Me | bond | $B^a$ | 2-Cl-3-Me | — |
| 1-85 | nBu | $A^b$ | Me | Me | bond | $B^a$ | 2-Cl-5-Me | — |
| 1-86 | nBu | $A^b$ | Me | Me | bond | $B^a$ | 2-Cl-3-OMe | — |
| 1-87 | nBu | $A^b$ | Me | Me | bond | $B^a$ | 2-Cl-5-OMe | — |
| 1-88 | nBu | $A^b$ | Me | Me | bond | $B^a$ | 2-Cl-3-F | — |
| 1-89 | nBu | $A^b$ | Me | Me | bond | $B^a$ | 2-Cl-5-F | — |
| 1-90 | nBu | $A^b$ | Me | Me | CH$_2$ | $B^a$ | — | — |
| 1-91 | nBu | $A^b$ | Me | Me | CO | $B^a$ | — | — |
| 1-92 | nBu | $A^b$ | —(CH$_2$)$_2$— | | bond | $B^a$ | — | — |
| 1-93 | nBu | $A^b$ | —(CH$_2$)$_2$— | | bond | $B^a$ | 2-Me | — |
| 1-94 | nBu | $A^b$ | —(CH$_2$)$_2$— | | bond | $B^a$ | 2-OMe | — |
| 1-95 | nBu | $A^b$ | —(CH$_2$)$_2$— | | bond | $B^a$ | 2-F | — |
| 1-96 | nBu | $A^b$ | —(CH$_2$)$_2$— | | bond | $B^a$ | 2-Cl | — |

| No. | | | | | | | | |
|---|---|---|---|---|---|---|---|---|
| 1-97 | nBu | $A^b$ | Me | Me | bond | $B^b$ | — | — |
| 1-98 | nBu | $A^b$ | Me | Me | bond | $B^c$ | — | — |
| 1-99 | nBu | $A^b$ | Me | Me | bond | $B^c$ | 6-Me | — |
| 1-100 | nBu | $A^b$ | Me | Me | bond | $B^c$ | 6-OMe | — |
| 1-101 | nBu | $A^b$ | Me | Me | bond | $B^c$ | 6-F | — |
| 1-102 | nBu | $A^b$ | Me | Me | bond | $B^c$ | 6-Cl | — |
| 1-103 | nBu | $A^b$ | Me | Me | bond | $B^d$ | — | — |
| 1-104 | nBu | $A^c$ | Me | Me | bond | $B^a$ | — | — |
| 1-105 | nBu | $A^c$ | Me | Me | bond | $B^a$ | — | 2-OCH$_2$OMe |
| 1-106 | nBu | $A^c$ | Me | Me | bond | $B^a$ | — | 2-O(CH$_2$)$_2$OMe |
| 1-107 | nBu | $A^c$ | Me | Me | bond | $B^a$ | — | 2-O(CH$_2$)$_3$OMe |
| 1-108 | nBu | $A^c$ | Me | Me | bond | $B^a$ | 2-Me | — |
| 1-109 | nBu | $A^c$ | Me | Me | bond | $B^a$ | 2-OMe | — |
| 1-110 | nBu | $A^c$ | Me | Me | bond | $B^a$ | 2-F | — |
| 1-111 | nBu | $A^c$ | Me | Me | bond | $B^a$ | 2-Cl | — |
| 1-112 | nBu | $A^d$ | Me | Me | bond | $B^a$ | — | — |
| 1-113 | nBu | $A^d$ | Me | Me | bond | $B^a$ | — | 2-OCH$_2$OMe |
| 1-114 | nBu | $A^d$ | Me | Me | bond | $B^a$ | — | 2-O(CH$_2$)$_2$OMe |
| 1-115 | nBu | $A^d$ | Me | Me | bond | $B^a$ | — | 2-O(CH$_2$)$_3$OMe |
| 1-116 | nBu | $A^d$ | Me | Me | bond | $B^a$ | 2-Me | — |
| 1-117 | nBu | $A^d$ | Me | Me | bond | $B^a$ | 2-OMe | — |
| 1-118 | nBu | $A^d$ | Me | Me | bond | $B^a$ | 2-F | — |
| 1-119 | nBu | $A^d$ | Me | Me | bond | $B^a$ | 2-Cl | — |
| 1-120 | iBu | $A^a$ | Me | Me | bond | $B^a$ | — | — |
| 1-121 | iBu | $A^b$ | Me | Me | bond | $B^a$ | — | — |
| 1-122 | iBu | $A^b$ | Me | Me | bond | $B^a$ | 2-Me | — |
| 1-123 | iBu | $A^b$ | Me | Me | bond | $B^a$ | 2-OMe | — |
| 1-124 | iBu | $A^b$ | Me | Me | bond | $B^a$ | 2-F | — |
| 1-125 | iBu | $A^b$ | Me | Me | bond | $B^a$ | 2-Cl | — |
| 1-126 | nPn | $A^b$ | Me | Me | bond | $B^a$ | — | — |
| 1-127 | (S)Bu-Me | $A^a$ | Me | Me | bond | $B^a$ | — | — |
| 1-128 | (S)Bu-Me | $A^a$ | Me | Me | bond | $B^a$ | — | 2-OCH$_2$OMe |
| 1-129 | (S)Bu-Me | $A^a$ | Me | Me | bond | $B^a$ | — | 2-O(CH$_2$)$_2$OMe |
| 1-130 | (S)Bu-Me | $A^a$ | Me | Me | bond | $B^a$ | — | 2-O(CH$_2$)$_3$OMe |
| 1-131 | (S)Bu-Me | $A^a$ | Me | Me | bond | $B^a$ | 2-Me | — |
| 1-132 | (S)Bu-Me | $A^a$ | Me | Me | bond | $B^a$ | 2-OMe | — |
| 1-133 | (S)Bu-Me | $A^a$ | Me | Me | bond | $B^a$ | 2-F | — |
| 1-134 | (S)Bu-Me | $A^a$ | Me | Me | bond | $B^a$ | 2-Cl | — |
| 1-135 | (S)Bu-Me | $A^b$ | Me | Me | bond | $B^a$ | — | — |
| 1-136 | (S)Bu-Me | $A^b$ | Me | Me | bond | $B^a$ | — | 2-OCH$_2$OMe |
| 1-137 | (S)Bu-Me | $A^b$ | Me | Me | bond | $B^a$ | — | 3-OCH$_2$OMe |
| 1-138 | (S)Bu-Me | $A^b$ | Me | Me | bond | $B^a$ | — | 2-O(CH$_2$)$_2$OMe |
| 1-139 | (S)Bu-Me | $A^b$ | Me | Me | bond | $B^a$ | — | 3-O(CH$_2$)$_2$OMe |
| 1-140 | (S)Bu-Me | $A^b$ | Me | Me | bond | $B^a$ | — | 2-O(CH$_2$)$_3$OMe |
| 1-141 | (S)Bu-Me | $A^b$ | Me | Me | bond | $B^a$ | — | 3-O(CH$_2$)$_3$OMe |
| 1-142 | (S)Bu-Me | $A^b$ | Me | Me | bond | $B^a$ | 2-Me | — |
| 1-143 | (S)Bu-Me | $A^b$ | Me | Me | bond | $B^a$ | 3-Me | — |
| 1-144 | (S)Bu-Me | $A^b$ | Me | Me | bond | $B^a$ | 2-CF$_3$ | — |
| 1-145 | (S)Bu-Me | $A^b$ | Me | Me | bond | $B^a$ | 3-CF$_3$ | — |
| 1-146 | (S)Bu-Me | $A^b$ | Me | Me | bond | $B^a$ | 2-OH | — |
| 1-147 | (S)Bu-Me | $A^b$ | Me | Me | bond | $B^a$ | 3-OH | — |
| 1-148 | (S)Bu-Me | $A^b$ | Me | Me | bond | $B^a$ | 2-OMe | — |
| 1-149 | (S)Bu-Me | $A^b$ | Me | Me | bond | $B^a$ | 3-OMe | — |
| 1-150 | (S)Bu-Me | $A^b$ | Me | Me | bond | $B^a$ | 2-SH | — |
| 1-151 | (S)Bu-Me | $A^b$ | Me | Me | bond | $B^a$ | 3-SH | — |
| 1-152 | (S)Bu-Me | $A^b$ | Me | Me | bond | $B^a$ | 2-SMe | — |
| 1-153 | (S)Bu-Me | $A^b$ | Me | Me | bond | $B^a$ | 3-SMe | — |
| 1-154 | (S)Bu-Me | $A^b$ | Me | Me | bond | $B^a$ | 2-NH$_2$ | — |
| 1-155 | (S)Bu-Me | $A^b$ | Me | Me | bond | $B^a$ | 2-NHMe | — |
| 1-156 | (S)Bu-Me | $A^b$ | Me | Me | bond | $B^a$ | 2-NMe$_2$ | — |
| 1-157 | (S)Bu-Me | $A^b$ | Me | Me | bond | $B^a$ | 2-NHCHO | — |
| 1-158 | (S)Bu-Me | $A^b$ | Me | Me | bond | $B^a$ | 2-NHCOMe | — |
| 1-159 | (S)Bu-Me | $A^b$ | Me | Me | bond | $B^a$ | 2-CO$_2$H | — |
| 1-160 | (S)Bu-Me | $A^b$ | Me | Me | bond | $B^a$ | 2-CO$_2$Me | — |
| 1-161 | (S)Bu-Me | $A^b$ | Me | Me | bond | $B^a$ | 2-CONH$_2$ | — |
| 1-162 | (S)Bu-Me | $A^b$ | Me | Me | bond | $B^a$ | 2-CONHMe | — |
| 1-163 | (S)Bu-Me | $A^b$ | Me | Me | bond | $B^a$ | 2-CONMe$_2$ | — |
| 1-164 | (S)Bu-Me | $A^b$ | Me | Me | bond | $B^a$ | 2-CN | — |
| 1-165 | (S)Bu-Me | $A^b$ | Me | Me | bond | $B^a$ | 3-CN | — |
| 1-166 | (S)Bu-Me | $A^b$ | Me | Me | bond | $B^a$ | 2-NO$_2$ | — |
| 1-167 | (S)Bu-Me | $A^b$ | Me | Me | bond | $B^a$ | 3-NO$_2$ | — |
| 1-168 | (S)Bu-Me | $A^b$ | Me | Me | bond | $B^a$ | 2-F | — |
| 1-169 | (S)Bu-Me | $A^b$ | Me | Me | bond | $B^a$ | 3-F | — |
| 1-170 | (S)Bu-Me | $A^b$ | Me | Me | bond | $B^a$ | 2-Cl | — |
| 1-171 | (S)Bu-Me | $A^b$ | Me | Me | bond | $B^a$ | 3-Cl | — |
| 1-172 | (S)Bu-Me | $A^b$ | Me | Me | bond | $B^a$ | 2,3-di-Me | — |
| 1-173 | (S)Bu-Me | $A^b$ | Me | Me | bond | $B^a$ | 2,5-di-Me | — |
| 1-174 | (S)Bu-Me | $A^b$ | Me | Me | bond | $B^a$ | 2,6-di-Me | — |
| 1-175 | (S)Bu-Me | $A^b$ | Me | Me | bond | $B^a$ | 2-Me-3-OMe | — |
| 1-176 | (S)Bu-Me | $A^b$ | Me | Me | bond | $B^a$ | 2-Me-5-OMe | — |
| 1-177 | (S)Bu-Me | $A^b$ | Me | Me | bond | $B^a$ | 2-Me-6-OMe | — |
| 1-178 | (S)Bu-Me | $A^b$ | Me | Me | bond | $B^a$ | 2-Me-3-F | — |

| | | | | | | | | |
|---|---|---|---|---|---|---|---|---|
| 1-179 | (S)Bu-Me | A$^b$ | Me | Me | bond | B$^a$ | 2-Me-5-F | — |
| 1-180 | (S)Bu-Me | A$^b$ | Me | Me | bond | B$^a$ | 2-Me-6-F | — |
| 1-181 | (S)Bu-Me | A$^b$ | Me | Me | bond | B$^a$ | 2-Me-3-Cl | — |
| 1-182 | (S)Bu-Me | A$^b$ | Me | Me | bond | B$^a$ | 2-Me-5-Cl | — |
| 1-183 | (S)Bu-Me | A$^b$ | Me | Me | bond | B$^a$ | 2-Me-6-Cl | — |
| 1-184 | (S)Bu-Me | A$^b$ | Me | Me | bond | B$^a$ | 2,3-di-OMe | — |
| 1-185 | (S)Bu-Me | A$^b$ | Me | Me | bond | B$^a$ | 2,5-di-OMe | — |
| 1-186 | (S)Bu-Me | A$^b$ | Me | Me | bond | B$^a$ | 2,6-di-OMe | — |
| 1-187 | (S)Bu-Me | A$^b$ | Me | Me | bond | B$^a$ | 2-OMe-3-Me | — |
| 1-188 | (S)Bu-Me | A$^b$ | Me | Me | bond | B$^a$ | 2-OMe-5-Me | — |
| 1-189 | (S)Bu-Me | A$^b$ | Me | Me | bond | B$^a$ | 2-OMe-3-F | — |
| 1-190 | (S)Bu-Me | A$^b$ | Me | Me | bond | B$^a$ | 2-OMe-5-F | — |
| 1-191 | (S)Bu-Me | A$^b$ | Me | Me | bond | B$^a$ | 2-OMe-6-F | — |
| 1-192 | (S)Bu-Me | A$^b$ | Me | Me | bond | B$^a$ | 2-OMe-3-Cl | — |
| 1-193 | (S)Bu-Me | A$^b$ | Me | Me | bond | B$^a$ | 2-OMe-5-Cl | — |
| 1-194 | (S)Bu-Me | A$^b$ | Me | Me | bond | B$^a$ | 2-OMe-6-Cl | — |
| 1-195 | (S)Bu-Me | A$^b$ | Me | Me | bond | B$^a$ | 2,3-di-F | — |
| 1-196 | (S)Bu-Me | A$^b$ | Me | Me | bond | B$^a$ | 2,5-di-F | — |
| 1-197 | (S)Bu-Me | A$^b$ | Me | Me | bond | B$^a$ | 2,6-di-F | — |
| 1-198 | (S)Bu-Me | A$^b$ | Me | Me | bond | B$^a$ | 2-F-3-Me | — |
| 1-199 | (S)Bu-Me | A$^b$ | Me | Me | bond | B$^a$ | 2-F-5-Me | — |
| 1-200 | (S)Bu-Me | A$^b$ | Me | Me | bond | B$^a$ | 2-F-3-OMe | — |
| 1-201 | (S)Bu-Me | A$^b$ | Me | Me | bond | B$^a$ | 2-F-5-OMe | — |
| 1-202 | (S)Bu-Me | A$^b$ | Me | Me | bond | B$^a$ | 2-F-3-Cl | — |
| 1-203 | (S)Bu-Me | A$^b$ | Me | Me | bond | B$^a$ | 2-F-5-Cl | — |
| 1-204 | (S)Bu-Me | A$^b$ | Me | Me | bond | B$^a$ | 2-F-6-Cl | — |
| 1-205 | (S)Bu-Me | A$^b$ | Me | Me | bond | B$^a$ | 2,3-di-Cl | — |
| 1-206 | (S)Bu-Me | A$^b$ | Me | Me | bond | B$^a$ | 2,5-di-Cl | — |
| 1-207 | (S)Bu-Me | A$^b$ | Me | Me | bond | B$^a$ | 2,6-di-Cl | — |
| 1-208 | (S)Bu-Me | A$^b$ | Me | Me | bond | B$^a$ | 2-Cl-3-Me | — |
| 1-209 | (S)Bu-Me | A$^b$ | Me | Me | bond | B$^a$ | 2-Cl-5-Me | — |
| 1-210 | (S)Bu-Me | A$^b$ | Me | Me | bond | B$^a$ | 2-Cl-3-OMe | — |
| 1-211 | (S)Bu-Me | A$^b$ | Me | Me | bond | B$^a$ | 2-Cl-5-OMe | — |
| 1-212 | (S)Bu-Me | A$^b$ | Me | Me | bond | B$^a$ | 2-Cl-3-F | — |
| 1-213 | (S)Bu-Me | A$^b$ | Me | Me | bond | B$^a$ | 2-Cl-5-F | — |
| 1-214 | (S)Bu-Me | A$^b$ | Me | Me | CH$_2$ | B$^a$ | — | — |
| 1-215 | (S)Bu-Me | A$^b$ | Me | Me | CO | B$^a$ | — | — |
| 1-216 | (S)Bu-Me | A$^b$ | —(CH$_2$)$_2$— | | bond | B$^a$ | — | — |
| 1-217 | (S)Bu-Me | A$^b$ | —(CH$_2$)$_2$— | | bond | B$^a$ | 2-Me | — |
| 1-218 | (S)Bu-Me | A$^b$ | —(CH$_2$)$_2$— | | bond | B$^a$ | 2-OMe | — |
| 1-219 | (S)Bu-Me | A$^b$ | —(CH$_2$)$_2$— | | bond | B$^a$ | 2-F | — |
| 1-220 | (S)Bu-Me | A$^b$ | —(CH$_2$)$_2$— | | bond | B$^a$ | 2-Cl | — |
| 1-221 | (S)Bu-Me | A$^b$ | Me | Me | bond | B$^b$ | — | — |
| 1-222 | (S)Bu-Me | A$^b$ | Me | Me | bond | B$^c$ | — | — |
| 1-223 | (S)Bu-Me | A$^b$ | Me | Me | bond | B$^c$ | 6-Me | — |
| 1-224 | (S)Bu-Me | A$^b$ | Me | Me | bond | B$^c$ | 6-OMe | — |
| 1-225 | (S)Bu-Me | A$^b$ | Me | Me | bond | B$^c$ | 6-F | — |
| 1-226 | (S)Bu-Me | A$^b$ | Me | Me | bond | B$^c$ | 6-Cl | — |
| 1-227 | (S)Bu-Me | A$^b$ | Me | Me | bond | B$^d$ | — | — |
| 1-228 | (S)Bu-Me | A$^c$ | Me | Me | bond | B$^a$ | — | — |
| 1-229 | (S)Bu-Me | A$^c$ | Me | Me | bond | B$^a$ | — | 2-OCH$_2$OMe |
| 1-230 | (S)Bu-Me | A$^c$ | Me | Me | bond | B$^a$ | — | 2-O(CH$_2$)$_2$OMe |
| 1-231 | (S)Bu-Me | A$^c$ | Me | Me | bond | B$^a$ | — | 2-O(CH$_2$)$_3$OMe |
| 1-232 | (S)Bu-Me | A$^c$ | Me | Me | bond | B$^a$ | 2-Me | — |
| 1-233 | (S)Bu-Me | A$^c$ | Me | Me | bond | B$^a$ | 2-OMe | — |
| 1-234 | (S)Bu-Me | A$^c$ | Me | Me | bond | B$^a$ | 2-F | — |
| 1-235 | (S)Bu-Me | A$^c$ | Me | Me | bond | B$^a$ | 2-Cl | — |
| 1-236 | (S)Bu-Me | A$^d$ | Me | Me | bond | B$^a$ | — | — |
| 1-237 | (S)Bu-Me | A$^d$ | Me | Me | bond | B$^a$ | — | 2-OCH$_2$OMe |
| 1-238 | (S)Bu-Me | A$^d$ | Me | Me | bond | B$^a$ | — | 2-O(CH$_2$)$_2$OMe |
| 1-239 | (S)Bu-Me | A$^d$ | Me | Me | bond | B$^a$ | — | 2-O(CH$_2$)$_3$OMe |
| 1-240 | (S)Bu-Me | A$^d$ | Me | Me | bond | B$^a$ | 2-Me | — |
| 1-241 | (S)Bu-Me | A$^d$ | Me | Me | bond | B$^a$ | 2-OMe | — |
| 1-242 | (S)Bu-Me | A$^d$ | Me | Me | bond | B$^a$ | 2-F | — |
| 1-243 | (S)Bu-Me | A$^d$ | Me | Me | bond | B$^a$ | 2-Cl | — |
| 1-244 | (S)Bu-OH | A$^b$ | Me | Me | bond | B$^a$ | 2-Cl | — |
| 1-245 | CH$_2$C(Me)$_2$CH$_2$OH | A$^a$ | Me | Me | bond | B$^a$ | — | — |
| 1-246 | CH$_2$C(Me)$_2$CH$_2$OH | A$^a$ | Me | Me | bond | B$^a$ | — | 2-OCH$_2$OMe |
| 1-247 | CH$_2$C(Me)$_2$CH$_2$OH | A$^a$ | Me | Me | bond | B$^a$ | — | 2-O(CH$_2$)$_2$OMe |
| 1-248 | CH$_2$C(Me)$_2$CH$_2$OH | A$^a$ | Me | Me | bond | B$^a$ | — | 2-O(CH$_2$)$_3$OMe |
| 1-249 | CH$_2$C(Me)$_2$CH$_2$OH | A$^a$ | Me | Me | bond | B$^a$ | 2-Me | — |
| 1-250 | CH$_2$C(Me)$_2$CH$_2$OH | A$^a$ | Me | Me | bond | B$^a$ | 2-OMe | — |
| 1-251 | CH$_2$C(Me)$_2$CH$_2$OH | A$^a$ | Me | Me | bond | B$^a$ | 2-F | — |
| 1-252 | CH$_2$C(Me)$_2$CH$_2$OH | A$^a$ | Me | Me | bond | B$^a$ | 2-Cl | — |
| 1-253 | CH$_2$C(Me)$_2$CH$_2$OH | A$^b$ | Me | Me | bond | B$^a$ | — | — |
| 1-254 | CH$_2$C(Me)$_2$CH$_2$OH | A$^b$ | Me | Me | bond | B$^a$ | — | 2-OCH$_2$OMe |
| 1-255 | CH$_2$C(Me)$_2$CH$_2$OH | A$^b$ | Me | Me | bond | B$^a$ | — | 3-OCH$_2$OMe |
| 1-256 | CH$_2$C(Me)$_2$CH$_2$OH | A$^b$ | Me | Me | bond | B$^a$ | — | 2-O(CH$_2$)$_2$OMe |
| 1-257 | CH$_2$C(Me)$_2$CH$_2$OH | A$^b$ | Me | Me | bond | B$^a$ | — | 3-O(CH$_2$)$_2$OMe |
| 1-258 | CH$_2$C(Me)$_2$CH$_2$OH | A$^b$ | Me | Me | bond | B$^a$ | — | 2-O(CH$_2$)$_3$OMe |
| 1-259 | CH$_2$C(Me)$_2$CH$_2$OH | A$^b$ | Me | Me | bond | B$^a$ | — | 3-O(CH$_2$)$_3$OMe |
| 1-260 | CH$_2$C(Me)$_2$CH$_2$OH | A$^b$ | Me | Me | bond | B$^a$ | 2-Me | — |

| ID | | | | | | | | |
|---|---|---|---|---|---|---|---|---|
| 1-261 | CH$_2$C(Me)$_2$CH$_2$OH | A$^b$ | Me | Me | bond | B$^a$ | 3-Me | — |
| 1-262 | CH$_2$C(Me)$_2$CH$_2$OH | A$^b$ | Me | Me | bond | B$^a$ | 2-CF$_3$ | — |
| 1-263 | CH$_2$C(Me)$_2$CH$_2$OH | A$^b$ | Me | Me | bond | B$^a$ | 3-CF$_3$ | — |
| 1-264 | CH$_2$C(Me)$_2$CH$_2$OH | A$^b$ | Me | Me | bond | B$^a$ | 2-OH | — |
| 1-265 | CH$_2$C(Me)$_2$CH$_2$OH | A$^b$ | Me | Me | bond | B$^a$ | 3-OH | — |
| 1-266 | CH$_2$C(Me)$_2$CH$_2$OH | A$^b$ | Me | Me | bond | B$^a$ | 2-OMe | — |
| 1-267 | CH$_2$C(Me)$_2$CH$_2$OH | A$^b$ | Me | Me | bond | B$^a$ | 3-OMe | — |
| 1-268 | CH$_2$C(Me)$_2$CH$_2$OH | A$^b$ | Me | Me | bond | B$^a$ | 2-SH | — |
| 1-269 | CH$_2$C(Me)$_2$CH$_2$OH | A$^b$ | Me | Me | bond | B$^a$ | 3-SH | — |
| 1-270 | CH$_2$C(Me)$_2$CH$_2$OH | A$^b$ | Me | Me | bond | B$^a$ | 2-SMe | — |
| 1-271 | CH$_2$C(Me)$_2$CH$_2$OH | A$^b$ | Me | Me | bond | B$^a$ | 3-SMe | — |
| 1-272 | CH$_2$C(Me)$_2$CH$_2$OH | A$^b$ | Me | Me | bond | B$^a$ | 2-NH$_2$ | — |
| 1-273 | CH$_2$C(Me)$_2$CH$_2$OH | A$^b$ | Me | Me | bond | B$^a$ | 2-NHMe | — |
| 1-274 | CH$_2$C(Me)$_2$CH$_2$OH | A$^b$ | Me | Me | bond | B$^a$ | 2-NMe$_2$ | — |
| 1-275 | CH$_2$C(Me)$_2$CH$_2$OH | A$^b$ | Me | Me | bond | B$^a$ | 2-NHCHO | — |
| 1-276 | CH$_2$C(Me)$_2$CH$_2$OH | A$^b$ | Me | Me | bond | B$^a$ | 2-NHCOMe | — |
| 1-277 | CH$_2$C(Me)$_2$CH$_2$OH | A$^b$ | Me | Me | bond | B$^a$ | 2-CO$_2$H | — |
| 1-278 | CH$_2$C(Me)$_2$CH$_2$OH | A$^b$ | Me | Me | bond | B$^a$ | 2-CO$_2$Me | — |
| 1-279 | CH$_2$C(Me)$_2$CH$_2$OH | A$^b$ | Me | Me | bond | B$^a$ | 2-CONH$_2$ | — |
| 1-280 | CH$_2$C(Me)$_2$CH$_2$OH | A$^b$ | Me | Me | bond | B$^a$ | 2-CONHMe | — |
| 1-281 | CH$_2$C(Me)$_2$CH$_2$OH | A$^b$ | Me | Me | bond | B$^a$ | 2-CONMe$_2$ | — |
| 1-282 | CH$_2$C(Me)$_2$CH$_2$OH | A$^b$ | Me | Me | bond | B$^a$ | 2-CN | — |
| 1-283 | CH$_2$C(Me)$_2$CH$_2$OH | A$^b$ | Me | Me | bond | B$^a$ | 3-CN | — |
| 1-284 | CH$_2$C(Me)$_2$CH$_2$OH | A$^b$ | Me | Me | bond | B$^a$ | 2-NO$_2$ | — |
| 1-285 | CH$_2$C(Me)$_2$CH$_2$OH | A$^b$ | Me | Me | bond | B$^a$ | 3-NO$_2$ | — |
| 1-286 | CH$_2$C(Me)$_2$CH$_2$OH | A$^b$ | Me | Me | bond | B$^a$ | 2-F | — |
| 1-287 | CH$_2$C(Me)$_2$CH$_2$OH | A$^b$ | Me | Me | bond | B$^a$ | 3-F | — |
| 1-288 | CH$_2$C(Me)$_2$CH$_2$OH | A$^b$ | Me | Me | bond | B$^a$ | 2-Cl | — |
| 1-289 | CH$_2$C(Me)$_2$CH$_2$OH | A$^b$ | Me | Me | bond | B$^a$ | 3-Cl | — |
| 1-290 | CH$_2$C(Me)$_2$CH$_2$OH | A$^b$ | Me | Me | bond | B$^a$ | 2,3-di-Me | — |
| 1-291 | CH$_2$C(Me)$_2$CH$_2$OH | A$^b$ | Me | Me | bond | B$^a$ | 2,5-di-Me | — |
| 1-292 | CH$_2$C(Me)$_2$CH$_2$OH | A$^b$ | Me | Me | bond | B$^a$ | 2,6-di-Me | — |
| 1-293 | CH$_2$C(Me)$_2$CH$_2$OH | A$^b$ | Me | Me | bond | B$^a$ | 2-Me-3-OMe | — |
| 1-294 | CH$_2$C(Me)$_2$CH$_2$OH | A$^b$ | Me | Me | bond | B$^a$ | 2-Me-5-OMe | — |
| 1-295 | CH$_2$C(Me)$_2$CH$_2$OH | A$^b$ | Me | Me | bond | B$^a$ | 2-Me-6-OMe | — |
| 1-296 | CH$_2$C(Me)$_2$CH$_2$OH | A$^b$ | Me | Me | bond | B$^a$ | 2-Me-3-F | — |
| 1-297 | CH$_2$C(Me)$_2$CH$_2$OH | A$^b$ | Me | Me | bond | B$^a$ | 2-Me-5-F | — |
| 1-298 | CH$_2$C(Me)$_2$CH$_2$OH | A$^b$ | Me | Me | bond | B$^a$ | 2-Me-6-F | — |
| 1-299 | CH$_2$C(Me)$_2$CH$_2$OH | A$^b$ | Me | Me | bond | B$^a$ | 2-Me-3-Cl | — |
| 1-300 | CH$_2$C(Me)$_2$CH$_2$OH | A$^b$ | Me | Me | bond | B$^a$ | 2-Me-5-Cl | — |
| 1-301 | CH$_2$C(Me)$_2$CH$_2$OH | A$^b$ | Me | Me | bond | B$^a$ | 2-Me-6-Cl | — |
| 1-302 | CH$_2$C(Me)$_2$CH$_2$OH | A$^b$ | Me | Me | bond | B$^a$ | 2,3-di-OMe | — |
| 1-303 | CH$_2$C(Me)$_2$CH$_2$OH | A$^b$ | Me | Me | bond | B$^a$ | 2,5-di-OMe | — |
| 1-304 | CH$_2$C(Me)$_2$CH$_2$OH | A$^b$ | Me | Me | bond | B$^a$ | 2,6-di-OMe | — |
| 1-305 | CH$_2$C(Me)$_2$CH$_2$OH | A$^b$ | Me | Me | bond | B$^a$ | 2-OMe-3-Me | — |
| 1-306 | CH$_2$C(Me)$_2$CH$_2$OH | A$^b$ | Me | Me | bond | B$^a$ | 2-OMe-5-Me | — |
| 1-307 | CH$_2$C(Me)$_2$CH$_2$OH | A$^b$ | Me | Me | bond | B$^a$ | 2-OMe-3-F | — |
| 1-308 | CH$_2$C(Me)$_2$CH$_2$OH | A$^b$ | Me | Me | bond | B$^a$ | 2-OMe-5-F | — |
| 1-309 | CH$_2$C(Me)$_2$CH$_2$OH | A$^b$ | Me | Me | bond | B$^a$ | 2-OMe-6-F | — |
| 1-310 | CH$_2$C(Me)$_2$CH$_2$OH | A$^b$ | Me | Me | bond | B$^a$ | 2-OMe-3-Cl | — |
| 1-311 | CH$_2$C(Me)$_2$CH$_2$OH | A$^b$ | Me | Me | bond | B$^a$ | 2-OMe-5-Cl | — |
| 1-312 | CH$_2$C(Me)$_2$CH$_2$OH | A$^b$ | Me | Me | bond | B$^a$ | 2-OMe-6-Cl | — |
| 1-313 | CH$_2$C(Me)$_2$CH$_2$OH | A$^b$ | Me | Me | bond | B$^a$ | 2,3-di-F | — |
| 1-314 | CH$_2$C(Me)$_2$CH$_2$OH | A$^b$ | Me | Me | bond | B$^a$ | 2,5-di-F | — |
| 1-315 | CH$_2$C(Me)$_2$CH$_2$OH | A$^b$ | Me | Me | bond | B$^a$ | 2,6-di-F | — |
| 1-316 | CH$_2$C(Me)$_2$CH$_2$OH | A$^b$ | Me | Me | bond | B$^a$ | 2-F-3-Me | — |
| 1-317 | CH$_2$C(Me)$_2$CH$_2$OH | A$^b$ | Me | Me | bond | B$^a$ | 2-F-5-Me | — |
| 1-318 | CH$_2$C(Me)$_2$CH$_2$OH | A$^b$ | Me | Me | bond | B$^a$ | 2-F-3-OMe | — |
| 1-319 | CH$_2$C(Me)$_2$CH$_2$OH | A$^b$ | Me | Me | bond | B$^a$ | 2-F-5-OMe | — |
| 1-320 | CH$_2$C(Me)$_2$CH$_2$OH | A$^b$ | Me | Me | bond | B$^a$ | 2-F-3-Cl | — |
| 1-321 | CH$_2$C(Me)$_2$CH$_2$OH | A$^b$ | Me | Me | bond | B$^a$ | 2-F-5-Cl | — |
| 1-322 | CH$_2$C(Me)$_2$CH$_2$OH | A$^b$ | Me | Me | bond | B$^a$ | 2-F-6-Cl | — |
| 1-323 | CH$_2$C(Me)$_2$CH$_2$OH | A$^b$ | Me | Me | bond | B$^a$ | 2,3-di-Cl | — |
| 1-324 | CH$_2$C(Me)$_2$CH$_2$OH | A$^b$ | Me | Me | bond | B$^a$ | 2,5-di-Cl | — |
| 1-325 | CH$_2$C(Me)$_2$CH$_2$OH | A$^b$ | Me | Me | bond | B$^a$ | 2,6-di-Cl | — |
| 1-326 | CH$_2$C(Me)$_2$CH$_2$OH | A$^b$ | Me | Me | bond | B$^a$ | 2-Cl-3-Me | — |
| 1-327 | CH$_2$C(Me)$_2$CH$_2$OH | A$^b$ | Me | Me | bond | B$^a$ | 2-Cl-5-Me | — |
| 1-328 | CH$_2$C(Me)$_2$CH$_2$OH | A$^b$ | Me | Me | bond | B$^a$ | 2-Cl-3-OMe | — |
| 1-329 | CH$_2$C(Me)$_2$CH$_2$OH | A$^b$ | Me | Me | bond | B$^a$ | 2-Cl-5-OMe | — |
| 1-330 | CH$_2$C(Me)$_2$CH$_2$OH | A$^b$ | Me | Me | bond | B$^a$ | 2-Cl-3-F | — |
| 1-331 | CH$_2$C(Me)$_2$CH$_2$OH | A$^b$ | Me | Me | bond | B$^a$ | 2-Cl-5-F | — |
| 1-332 | CH$_2$C(Me)$_2$CH$_2$OH | A$^b$ | Me | Me | CH$_2$ | B$^a$ | — | — |
| 1-333 | CH$_2$C(Me)$_2$CH$_2$OH | A$^b$ | Me | Me | CO | B$^a$ | — | — |
| 1-334 | CH$_2$C(Me)$_2$CH$_2$OH | A$^b$ | —(CH$_2$)$_2$— | | bond | B$^a$ | — | — |
| 1-335 | CH$_2$C(Me)$_2$CH$_2$OH | A$^b$ | —(CH$_2$)$_2$— | | bond | B$^a$ | 2-Me | — |
| 1-336 | CH$_2$C(Me)$_2$CH$_2$OH | A$^b$ | —(CH$_2$)$_2$— | | bond | B$^a$ | 2-OMe | — |
| 1-337 | CH$_2$C(Me)$_2$CH$_2$OH | A$^b$ | —(CH$_2$)$_2$— | | bond | B$^a$ | 2-F | — |
| 1-338 | CH$_2$C(Me)$_2$CH$_2$OH | A$^b$ | —(CH$_2$)$_2$— | | bond | B$^a$ | 2-Cl | — |
| 1-339 | CH$_2$C(Me)$_2$CH$_2$OH | A$^b$ | Me | Me | bond | B$^b$ | — | — |
| 1-340 | CH$_2$C(Me)$_2$CH$_2$OH | A$^b$ | Me | Me | bond | B$^c$ | — | — |
| 1-341 | CH$_2$C(Me)$_2$CH$_2$OH | A$^b$ | Me | Me | bond | B$^c$ | 2-Me | — |
| 1-342 | CH$_2$C(Me)$_2$CH$_2$OH | A$^b$ | Me | Me | bond | B$^c$ | 2-OMe | — |

| | | | | | | | | |
|---|---|---|---|---|---|---|---|---|
| 1-343 | CH$_2$C(Me)$_2$CH$_2$OH | A$^b$ | Me | Me | bond | B$^c$ | 2-F | — |
| 1-344 | CH$_2$C(Me)$_2$CH$_2$OH | A$^b$ | Me | Me | bond | B$^c$ | 2-Cl | — |
| 1-345 | CH$_2$C(Me)$_2$CH$_2$OH | A$^b$ | Me | Me | bond | B$^d$ | — | — |
| 1-346 | CH$_2$C(Me)$_2$CH$_2$OH | A$^c$ | Me | Me | bond | B$^a$ | — | — |
| 1-347 | CH$_2$C(Me)$_2$CH$_2$OH | A$^c$ | Me | Me | bond | B$^a$ | — | 2-OCH$_2$OMe |
| 1-348 | CH$_2$C(Me)$_2$CH$_2$OH | A$^c$ | Me | Me | bond | B$^a$ | — | 2-O(CH$_2$)$_2$OMe |
| 1-349 | CH$_2$C(Me)$_2$CH$_2$OH | A$^c$ | Me | Me | bond | B$^a$ | — | 2-O(CH$_2$)$_3$OMe |
| 1-350 | CH$_2$C(Me)$_2$CH$_2$OH | A$^c$ | Me | Me | bond | B$^a$ | 2-Me | — |
| 1-351 | CH$_2$C(Me)$_2$CH$_2$OH | A$^c$ | Me | Me | bond | B$^a$ | 2-OMe | — |
| 1-352 | CH$_2$C(Me)$_2$CH$_2$OH | A$^c$ | Me | Me | bond | B$^a$ | 2-F | — |
| 1-353 | CH$_2$C(Me)$_2$CH$_2$OH | A$^c$ | Me | Me | bond | B$^a$ | 2-Cl | — |
| 1-354 | CH$_2$C(Me)$_2$CH$_2$OH | A$^d$ | Me | Me | bond | B$^a$ | — | — |
| 1-355 | CH$_2$C(Me)$_2$CH$_2$OH | A$^d$ | Me | Me | bond | B$^a$ | — | 2-OCH$_2$OMe |
| 1-356 | CH$_2$C(Me)$_2$CH$_2$OH | A$^d$ | Me | Me | bond | B$^a$ | — | 2-O(CH$_2$)$_2$OMe |
| 1-357 | CH$_2$C(Me)$_2$CH$_2$OH | A$^d$ | Me | Me | bond | B$^a$ | — | 2-O(CH$_2$)$_3$OMe |
| 1-358 | CH$_2$C(Me)$_2$CH$_2$OH | A$^d$ | Me | Me | bond | B$^a$ | 2-Me | — |
| 1-359 | CH$_2$C(Me)$_2$CH$_2$OH | A$^d$ | Me | Me | bond | B$^a$ | 2-OMe | — |
| 1-360 | CH$_2$C(Me)$_2$CH$_2$OH | A$^d$ | Me | Me | bond | B$^a$ | 2-F | — |
| 1-361 | CH$_2$C(Me)$_2$CH$_2$OH | A$^d$ | Me | Me | bond | B$^a$ | 2-Cl | — |
| 1-362 | CH$_2$(1-CH$_2$OH-cPr) | A$^a$ | Me | Me | bond | B$^a$ | — | — |
| 1-363 | CH$_2$(1-CH$_2$OH-cPr) | A$^b$ | Me | Me | bond | B$^a$ | — | — |
| 1-364 | CH$_2$(1-CH$_2$OH-cPr) | A$^b$ | Me | Me | bond | B$^a$ | 2-Me | — |
| 1-365 | CH$_2$(1-CH$_2$OH-cPr) | A$^b$ | Me | Me | bond | B$^a$ | 2-OMe | — |
| 1-366 | CH$_2$(1-CH$_2$OH-cPr) | A$^b$ | Me | Me | bond | B$^a$ | 2-F | — |
| 1-367 | CH$_2$(1-CH$_2$OH-cPr) | A$^b$ | Me | Me | bond | B$^a$ | 2-Cl | — |
| 1-368 | CH$_2$C(Me)$_2$CH$_2$OMe | A$^a$ | Me | Me | bond | B$^a$ | — | — |
| 1-369 | CH$_2$C(Me)$_2$CH$_2$OMe | A$^b$ | Me | Me | bond | B$^a$ | — | — |
| 1-370 | CH$_2$C(Me)$_2$CH$_2$OMe | A$^b$ | Me | Me | bond | B$^a$ | 2-Me | — |
| 1-371 | CH$_2$C(Me)$_2$CH$_2$OMe | A$^b$ | Me | Me | bond | B$^a$ | 2-OMe | — |
| 1-372 | CH$_2$C(Me)$_2$CH$_2$OMe | A$^b$ | Me | Me | bond | B$^a$ | 2-F | — |
| 1-373 | CH$_2$C(Me)$_2$CH$_2$OMe | A$^b$ | Me | Me | bond | B$^a$ | 2-Cl | — |
| 1-374 | CH$_2$C(Me)$_2$SOMe | A$^a$ | Me | Me | bond | B$^a$ | — | — |
| 1-375 | CH$_2$C(Me)$_2$SOMe | A$^b$ | Me | Me | bond | B$^a$ | — | — |
| 1-376 | CH$_2$C(Me)$_2$SOMe | A$^b$ | Me | Me | bond | B$^a$ | 2-Me | — |
| 1-377 | CH$_2$C(Me)$_2$SOMe | A$^b$ | Me | Me | bond | B$^a$ | 2-OMe | — |
| 1-378 | CH$_2$C(Me)$_2$SOMe | A$^b$ | Me | Me | bond | B$^a$ | 2-F | — |
| 1-379 | CH$_2$C(Me)$_2$SOMe | A$^b$ | Me | Me | bond | B$^a$ | 2-Cl | — |
| 1-380 | CH$_2$(1-SOMe-cPr) | A$^a$ | Me | Me | bond | B$^a$ | — | — |
| 1-381 | CH$_2$(1-SOMe-cPr) | A$^b$ | Me | Me | bond | B$^a$ | — | — |
| 1-382 | CH$_2$(1-SOMe-cPr) | A$^b$ | Me | Me | bond | B$^a$ | 2-Me | — |
| 1-383 | CH$_2$(1-SOMe-cPr) | A$^b$ | Me | Me | bond | B$^a$ | 2-OMe | — |
| 1-384 | CH$_2$(1-SOMe-cPr) | A$^b$ | Me | Me | bond | B$^a$ | 2-F | — |
| 1-385 | CH$_2$(1-SOMe-cPr) | A$^b$ | Me | Me | bond | B$^a$ | 2-Cl | — |
| 1-386 | CH$_2$C(Me)$_2$SO$_2$Me | A$^a$ | Me | Me | bond | B$^a$ | — | — |
| 1-387 | CH$_2$C(Me)$_2$SO$_2$Me | A$^b$ | Me | Me | bond | B$^a$ | — | — |
| 1-388 | CH$_2$C(Me)$_2$SO$_2$Me | A$^b$ | Me | Me | bond | B$^a$ | 2-Me | — |
| 1-389 | CH$_2$C(Me)$_2$SO$_2$Me | A$^b$ | Me | Me | bond | B$^a$ | 2-OMe | — |
| 1-390 | CH$_2$C(Me)$_2$SO$_2$Me | A$^b$ | Me | Me | bond | B$^a$ | 2-F | — |
| 1-391 | CH$_2$C(Me)$_2$SO$_2$Me | A$^b$ | Me | Me | bond | B$^a$ | 2-Cl | — |
| 1-392 | CH$_2$(1-SO$_2$Me-cPr) | A$^a$ | Me | Me | bond | B$^a$ | — | — |
| 1-393 | CH$_2$(1-SO$_2$Me-cPr) | A$^b$ | Me | Me | bond | B$^a$ | — | — |
| 1-394 | CH$_2$(1-SO$_2$Me-cPr) | A$^b$ | Me | Me | bond | B$^a$ | 2-Me | — |
| 1-395 | CH$_2$(1-SO$_2$Me-cPr) | A$^b$ | Me | Me | bond | B$^a$ | 2-OMe | — |
| 1-396 | CH$_2$(1-SO$_2$Me-cPr) | A$^b$ | Me | Me | bond | B$^a$ | 2-F | — |
| 1-397 | CH$_2$(1-SO$_2$Me-cPr) | A$^b$ | Me | Me | bond | B$^a$ | 2-Cl | — |
| 1-398 | CH$_2$C(Me)$_2$CO$_2$Me | A$^a$ | Me | Me | bond | B$^a$ | — | — |
| 1-399 | CH$_2$C(Me)$_2$CO$_2$Me | A$^b$ | Me | Me | bond | B$^a$ | — | — |
| 1-400 | CH$_2$C(Me)$_2$CO$_2$Me | A$^b$ | Me | Me | bond | B$^a$ | 2-Me | — |
| 1-401 | CH$_2$C(Me)$_2$CO$_2$Me | A$^b$ | Me | Me | bond | B$^a$ | 2-OMe | — |
| 1-402 | CH$_2$C(Me)$_2$CO$_2$Me | A$^b$ | Me | Me | bond | B$^a$ | 2-F | — |
| 1-403 | CH$_2$C(Me)$_2$CO$_2$Me | A$^b$ | Me | Me | bond | B$^a$ | 2-Cl | — |
| 1-404 | CH$_2$(1-CO$_2$Me-cPr) | A$^a$ | Me | Me | bond | B$^a$ | — | — |
| 1-405 | CH$_2$(1-CO$_2$Me-cPr) | A$^b$ | Me | Me | bond | B$^a$ | — | — |
| 1-406 | CH$_2$(1-CO$_2$Me-cPr) | A$^b$ | Me | Me | bond | B$^a$ | 2-Me | — |
| 1-407 | CH$_2$(1-CO$_2$Me-cPr) | A$^b$ | Me | Me | bond | B$^a$ | 2-OMe | — |
| 1-408 | CH$_2$(1-CO$_2$Me-cPr) | A$^b$ | Me | Me | bond | B$^a$ | 2-F | — |
| 1-409 | CH$_2$(1-CO$_2$Me-cPr) | A$^b$ | Me | Me | bond | B$^a$ | 2-Cl | — |
| 1-410 | CH$_2$C(Me)$_2$CONHMe | A$^a$ | Me | Me | bond | B$^a$ | — | — |
| 1-411 | CH$_2$C(Me)$_2$CONHMe | A$^b$ | Me | Me | bond | B$^a$ | — | — |
| 1-412 | CH$_2$C(Me)$_2$CONHMe | A$^b$ | Me | Me | bond | B$^a$ | 2-Me | — |
| 1-413 | CH$_2$C(Me)$_2$CONHMe | A$^b$ | Me | Me | bond | B$^a$ | 2-OMe | — |
| 1-414 | CH$_2$C(Me)$_2$CONHMe | A$^b$ | Me | Me | bond | B$^a$ | 2-F | — |
| 1-415 | CH$_2$C(Me)$_2$CONHMe | A$^b$ | Me | Me | bond | B$^a$ | 2-Cl | — |
| 1-416 | CH$_2$(1-CONHMe-cPr) | A$^a$ | Me | Me | bond | B$^a$ | — | — |
| 1-417 | CH$_2$(1-CONHMe-cPr) | A$^b$ | Me | Me | bond | B$^a$ | — | — |
| 1-418 | CH$_2$(1-CONHMe-cPr) | A$^b$ | Me | Me | bond | B$^a$ | 2-Me | — |
| 1-419 | CH$_2$(1-CONHMe-cPr) | A$^b$ | Me | Me | bond | B$^a$ | 2-OMe | — |
| 1-420 | CH$_2$(1-CONHMe-cPr) | A$^b$ | Me | Me | bond | B$^a$ | 2-F | — |
| 1-421 | CH$_2$(1-CONHMe-cPr) | A$^b$ | Me | Me | bond | B$^a$ | 2-Cl | — |
| 1-422 | CH$_2$C(Me)$_2$CONH$_2$ | A$^a$ | Me | Me | bond | B$^a$ | — | — |
| 1-423 | CH$_2$C(Me)$_2$CONH$_2$ | A$^a$ | Me | Me | bond | B$^a$ | — | 2-OCH$_2$OMe |
| 1-424 | CH$_2$C(Me)$_2$CONH$_2$ | A$^a$ | Me | Me | bond | B$^a$ | — | 2-O(CH$_2$)$_2$OMe |

| | | | | | | | | |
|---|---|---|---|---|---|---|---|---|
| 1-425 | CH$_2$C(Me)$_2$CONH$_2$ | A$^a$ | Me | Me | bond | B$^a$ | — | 2-O(CH$_2$)$_3$OMe |
| 1-426 | CH$_2$C(Me)$_2$CONH$_2$ | A$^a$ | Me | Me | bond | B$^a$ | — | 3-O(CH$_2$)$_3$OMe |
| 1-427 | CH$_2$C(Me)$_2$CONH$_2$ | A$^a$ | Me | Me | bond | B$^a$ | 2-Me | — |
| 1-428 | CH$_2$C(Me)$_2$CONH$_2$ | A$^a$ | Me | Me | bond | B$^a$ | 2-OMe | — |
| 1-429 | CH$_2$C(Me)$_2$CONH$_2$ | A$^a$ | Me | Me | bond | B$^a$ | 3-OMe | — |
| 1-430 | CH$_2$C(Me)$_2$CONH$_2$ | A$^a$ | Me | Me | bond | B$^a$ | 2-F | — |
| 1-431 | CH$_2$C(Me)$_2$CONH$_2$ | A$^a$ | Me | Me | bond | B$^a$ | 2-Cl | — |
| 1-432 | CH$_2$C(Me)$_2$CONH$_2$ | A$^a$ | Me | Me | bond | B$^a$ | 3-Cl | — |
| 1-433 | CH$_2$C(Me)$_2$CONH$_2$ | A$^b$ | Me | Me | bond | B$^a$ | — | — |
| 1-434 | CH$_2$C(Me)$_2$CONH$_2$ | A$^b$ | Me | Me | bond | B$^a$ | — | 2-OCH$_2$OMe |
| 1-435 | CH$_2$C(Me)$_2$CONH$_2$ | A$^b$ | Me | Me | bond | B$^a$ | — | 3-OCH$_2$OMe |
| 1-436 | CH$_2$C(Me)$_2$CONH$_2$ | A$^b$ | Me | Me | bond | B$^a$ | — | 2-O(CH$_2$)$_2$OMe |
| 1-437 | CH$_2$C(Me)$_2$CONH$_2$ | A$^b$ | Me | Me | bond | B$^a$ | — | 3-O(CH$_2$)$_2$OMe |
| 1-438 | CH$_2$C(Me)$_2$CONH$_2$ | A$^b$ | Me | Me | bond | B$^a$ | — | 2-O(CH$_2$)$_3$OMe |
| 1-439 | CH$_2$C(Me)$_2$CONH$_2$ | A$^b$ | Me | Me | bond | B$^a$ | — | 3-O(CH$_2$)$_3$OMe |
| 1-440 | CH$_2$C(Me)$_2$CONH$_2$ | A$^b$ | Me | Me | bond | B$^a$ | 2-Me | — |
| 1-441 | CH$_2$C(Me)$_2$CONH$_2$ | A$^b$ | Me | Me | bond | B$^a$ | 3-Me | — |
| 1-442 | CH$_2$C(Me)$_2$CONH$_2$ | A$^b$ | Me | Me | bond | B$^a$ | 2-CF$_3$ | — |
| 1-443 | CH$_2$C(Me)$_2$CONH$_2$ | A$^b$ | Me | Me | bond | B$^a$ | 3-CF$_3$ | — |
| 1-444 | CH$_2$C(Me)$_2$CONH$_2$ | A$^b$ | Me | Me | bond | B$^a$ | 2-OH | — |
| 1-445 | CH$_2$C(Me)$_2$CONH$_2$ | A$^b$ | Me | Me | bond | B$^a$ | 3-OH | — |
| 1-446 | CH$_2$C(Me)$_2$CONH$_2$ | A$^b$ | Me | Me | bond | B$^a$ | 2-OMe | — |
| 1-447 | CH$_2$C(Me)$_2$CONH$_2$ | A$^b$ | Me | Me | bond | B$^a$ | 3-OMe | — |
| 1-448 | CH$_2$C(Me)$_2$CONH$_2$ | A$^b$ | Me | Me | bond | B$^a$ | 2-SH | — |
| 1-449 | CH$_2$C(Me)$_2$CONH$_2$ | A$^b$ | Me | Me | bond | B$^a$ | 3-SH | — |
| 1-450 | CH$_2$C(Me)$_2$CONH$_2$ | A$^b$ | Me | Me | bond | B$^a$ | 2-SMe | — |
| 1-451 | CH$_2$C(Me)$_2$CONH$_2$ | A$^b$ | Me | Me | bond | B$^a$ | 3-SMe | — |
| 1-452 | CH$_2$C(Me)$_2$CONH$_2$ | A$^b$ | Me | Me | bond | B$^a$ | 2-NH$_2$ | — |
| 1-453 | CH$_2$C(Me)$_2$CONH$_2$ | A$^b$ | Me | Me | bond | B$^a$ | 2-NHMe | — |
| 1-454 | CH$_2$C(Me)$_2$CONH$_2$ | A$^b$ | Me | Me | bond | B$^a$ | 2-NMe$_2$ | — |
| 1-455 | CH$_2$C(Me)$_2$CONH$_2$ | A$^b$ | Me | Me | bond | B$^a$ | 2-NHCHO | — |
| 1-456 | CH$_2$C(Me)$_2$CONH$_2$ | A$^b$ | Me | Me | bond | B$^a$ | 2-NHCOMe | — |
| 1-457 | CH$_2$C(Me)$_2$CONH$_2$ | A$^b$ | Me | Me | bond | B$^a$ | 2-CO$_2$H | — |
| 1-458 | CH$_2$C(Me)$_2$CONH$_2$ | A$^b$ | Me | Me | bond | B$^a$ | 2-CO$_2$Me | — |
| 1-459 | CH$_2$C(Me)$_2$CONH$_2$ | A$^b$ | Me | Me | bond | B$^a$ | 2-CONH$_2$ | — |
| 1-460 | CH$_2$C(Me)$_2$CONH$_2$ | A$^b$ | Me | Me | bond | B$^a$ | 2-CONHMe | — |
| 1-461 | CH$_2$C(Me)$_2$CONH$_2$ | A$^b$ | Me | Me | bond | B$^a$ | 2-CONMe$_2$ | — |
| 1-462 | CH$_2$C(Me)$_2$CONH$_2$ | A$^b$ | Me | Me | bond | B$^a$ | 2-CN | — |
| 1-463 | CH$_2$C(Me)$_2$CONH$_2$ | A$^b$ | Me | Me | bond | B$^a$ | 3-CN | — |
| 1-464 | CH$_2$C(Me)$_2$CONH$_2$ | A$^b$ | Me | Me | bond | B$^a$ | 2-NO$_2$ | — |
| 1-465 | CH$_2$C(Me)$_2$CONH$_2$ | A$^b$ | Me | Me | bond | B$^a$ | 3-NO$_2$ | — |
| 1-466 | CH$_2$C(Me)$_2$CONH$_2$ | A$^b$ | Me | Me | bond | B$^a$ | 2-F | — |
| 1-467 | CH$_2$C(Me)$_2$CONH$_2$ | A$^b$ | Me | Me | bond | B$^a$ | 3-F | — |
| 1-468 | CH$_2$C(Me)$_2$CONH$_2$ | A$^b$ | Me | Me | bond | B$^a$ | 2-Cl | — |
| 1-469 | CH$_2$C(Me)$_2$CONH$_2$ | A$^b$ | Me | Me | bond | B$^a$ | 3-Cl | — |
| 1-470 | CH$_2$C(Me)$_2$CONH$_2$ | A$^b$ | Me | Me | bond | B$^a$ | 2,3-di-Me | — |
| 1-471 | CH$_2$C(Me)$_2$CONH$_2$ | A$^b$ | Me | Me | bond | B$^a$ | 2,5-di-Me | — |
| 1-472 | CH$_2$C(Me)$_2$CONH$_2$ | A$^b$ | Me | Me | bond | B$^a$ | 2,6-di-Me | — |
| 1-473 | CH$_2$C(Me)$_2$CONH$_2$ | A$^b$ | Me | Me | bond | B$^a$ | 2-Me-3-OMe | — |
| 1-474 | CH$_2$C(Me)$_2$CONH$_2$ | A$^b$ | Me | Me | bond | B$^a$ | 2-Me-5-OMe | — |
| 1-475 | CH$_2$C(Me)$_2$CONH$_2$ | A$^b$ | Me | Me | bond | B$^a$ | 2-Me-6-OMe | — |
| 1-476 | CH$_2$C(Me)$_2$CONH$_2$ | A$^b$ | Me | Me | bond | B$^a$ | 2-Me-3-F | — |
| 1-477 | CH$_2$C(Me)$_2$CONH$_2$ | A$^b$ | Me | Me | bond | B$^a$ | 2-Me-5-F | — |
| 1-478 | CH$_2$C(Me)$_2$CONH$_2$ | A$^b$ | Me | Me | bond | B$^a$ | 2-Me-6-F | — |
| 1-479 | CH$_2$C(Me)$_2$CONH$_2$ | A$^b$ | Me | Me | bond | B$^a$ | 2-Me-3-Cl | — |
| 1-480 | CH$_2$C(Me)$_2$CONH$_2$ | A$^b$ | Me | Me | bond | B$^a$ | 2-Me-5-Cl | — |
| 1-481 | CH$_2$C(Me)$_2$CONH$_2$ | A$^b$ | Me | Me | bond | B$^a$ | 2-Me-6-Cl | — |
| 1-482 | CH$_2$C(Me)$_2$CONH$_2$ | A$^b$ | Me | Me | bond | B$^a$ | 2,3-di-OMe | — |
| 1-483 | CH$_2$C(Me)$_2$CONH$_2$ | A$^b$ | Me | Me | bond | B$^a$ | 2,5-di-OMe | — |
| 1-484 | CH$_2$C(Me)$_2$CONH$_2$ | A$^b$ | Me | Me | bond | B$^a$ | 2,6-di-OMe | — |
| 1-485 | CH$_2$C(Me)$_2$CONH$_2$ | A$^b$ | Me | Me | bond | B$^a$ | 2-OMe-3-Me | — |
| 1-486 | CH$_2$C(Me)$_2$CONH$_2$ | A$^b$ | Me | Me | bond | B$^a$ | 2-OMe-5-Me | — |
| 1-487 | CH$_2$C(Me)$_2$CONH$_2$ | A$^b$ | Me | Me | bond | B$^a$ | 2-OMe-3-F | — |
| 1-488 | CH$_2$C(Me)$_2$CONH$_2$ | A$^b$ | Me | Me | bond | B$^a$ | 2-OMe-5-F | — |
| 1-489 | CH$_2$C(Me)$_2$CONH$_2$ | A$^b$ | Me | Me | bond | B$^a$ | 2-OMe-6-F | — |
| 1-490 | CH$_2$C(Me)$_2$CONH$_2$ | A$^b$ | Me | Me | bond | B$^a$ | 2-OMe-3-Cl | — |
| 1-491 | CH$_2$C(Me)$_2$CONH$_2$ | A$^b$ | Me | Me | bond | B$^a$ | 2-OMe-5-Cl | — |
| 1-492 | CH$_2$C(Me)$_2$CONH$_2$ | A$^b$ | Me | Me | bond | B$^a$ | 2-OMe-6-Cl | — |
| 1-493 | CH$_2$C(Me)$_2$CONH$_2$ | A$^b$ | Me | Me | bond | B$^a$ | 2,3-di-F | — |
| 1-494 | CH$_2$C(Me)$_2$CONH$_2$ | A$^b$ | Me | Me | bond | B$^a$ | 2,5-di-F | — |
| 1-495 | CH$_2$C(Me)$_2$CONH$_2$ | A$^b$ | Me | Me | bond | B$^a$ | 2,6-di-F | — |
| 1-496 | CH$_2$C(Me)$_2$CONH$_2$ | A$^b$ | Me | Me | bond | B$^a$ | 3,5-di-F | — |
| 1-497 | CH$_2$C(Me)$_2$CONH$_2$ | A$^b$ | Me | Me | bond | B$^a$ | 2-F-3-Me | — |
| 1-498 | CH$_2$C(Me)$_2$CONH$_2$ | A$^b$ | Me | Me | bond | B$^a$ | 2-F-5-Me | — |
| 1-499 | CH$_2$C(Me)$_2$CONH$_2$ | A$^b$ | Me | Me | bond | B$^a$ | 2-F-3-OMe | — |
| 1-500 | CH$_2$C(Me)$_2$CONH$_2$ | A$^b$ | Me | Me | bond | B$^a$ | 2-F-5-OMe | — |
| 1-501 | CH$_2$C(Me)$_2$CONH$_2$ | A$^b$ | Me | Me | bond | B$^a$ | 2-F-3-Cl | — |
| 1-502 | CH$_2$C(Me)$_2$CONH$_2$ | A$^b$ | Me | Me | bond | B$^a$ | 2-F-5-Cl | — |
| 1-503 | CH$_2$C(Me)$_2$CONH$_2$ | A$^b$ | Me | Me | bond | B$^a$ | 2-F-6-Cl | — |
| 1-504 | CH$_2$C(Me)$_2$CONH$_2$ | A$^b$ | Me | Me | bond | B$^a$ | 2,3-di-Cl | — |
| 1-505 | CH$_2$C(Me)$_2$CONH$_2$ | A$^b$ | Me | Me | bond | B$^a$ | 2,5-di-Cl | — |
| 1-506 | CH$_2$C(Me)$_2$CONH$_2$ | A$^b$ | Me | Me | bond | B$^a$ | 2,6-di-Cl | — |

| | | | | | | | | |
|---|---|---|---|---|---|---|---|---|
| 1-507 | CH$_2$C(Me)$_2$CONH$_2$ | A$^b$ | Me | Me | bond | B$^a$ | 2-Cl-3-Me | — |
| 1-508 | CH$_2$C(Me)$_2$CONH$_2$ | A$^b$ | Me | Me | bond | B$^a$ | 2-Cl-5-Me | — |
| 1-509 | CH$_2$C(Me)$_2$CONH$_2$ | A$^b$ | Me | Me | bond | B$^a$ | 2-Cl-3-OMe | — |
| 1-510 | CH$_2$C(Me)$_2$CONH$_2$ | A$^b$ | Me | Me | bond | B$^a$ | 2-Cl-5-OMe | — |
| 1-511 | CH$_2$C(Me)$_2$CONH$_2$ | A$^b$ | Me | Me | bond | B$^a$ | 2-Cl-3-F | — |
| 1-512 | CH$_2$C(Me)$_2$CONH$_2$ | A$^b$ | Me | Me | bond | B$^a$ | 2-Cl-5-F | — |
| 1-513 | CH$_2$C(Me)$_2$CONH$_2$ | A$^b$ | Me | Me | CH$_2$ | B$^a$ | — | — |
| 1-514 | CH$_2$C(Me)$_2$CONH$_2$ | A$^b$ | Me | Me | CO | B$^a$ | — | — |
| 1-515 | CH$_2$C(Me)$_2$CONH$_2$ | A$^b$ | —(CH$_2$)$_2$— | | bond | B$^a$ | — | — |
| 1-516 | CH$_2$C(Me)$_2$CONH$_2$ | A$^b$ | —(CH$_2$)$_2$— | | bond | B$^a$ | 2-Me | — |
| 1-517 | CH$_2$C(Me)$_2$CONH$_2$ | A$^b$ | —(CH$_2$)$_2$— | | bond | B$^a$ | 2-OMe | — |
| 1-518 | CH$_2$C(Me)$_2$CONH$_2$ | A$^b$ | —(CH$_2$)$_2$— | | bond | B$^a$ | 2-F | — |
| 1-519 | CH$_2$C(Me)$_2$CONH$_2$ | A$^b$ | —(CH$_2$)$_2$— | | bond | B$^a$ | 2-Cl | — |
| 1-520 | CH$_2$C(Me)$_2$CONH$_2$ | A$^b$ | Me | Me | bond | B$^b$ | — | — |
| 1-521 | CH$_2$C(Me)$_2$CONH$_2$ | A$^b$ | Me | Me | bond | B$^c$ | — | — |
| 1-522 | CH$_2$C(Me)$_2$CONH$_2$ | A$^b$ | Me | Me | bond | B$^c$ | 6-Me | — |
| 1-523 | CH$_2$C(Me)$_2$CONH$_2$ | A$^b$ | Me | Me | bond | B$^c$ | 6-OMe | — |
| 1-524 | CH$_2$C(Me)$_2$CONH$_2$ | A$^b$ | Me | Me | bond | B$^c$ | 6-F | — |
| 1-525 | CH$_2$C(Me)$_2$CONH$_2$ | A$^b$ | Me | Me | bond | B$^c$ | 6-Cl | — |
| 1-526 | CH$_2$C(Me)$_2$CONH$_2$ | A$^b$ | Me | Me | bond | B$^d$ | — | — |
| 1-527 | CH$_2$C(Me)$_2$CONH$_2$ | A$^c$ | Me | Me | bond | B$^a$ | — | — |
| 1-528 | CH$_2$C(Me)$_2$CONH$_2$ | A$^c$ | Me | Me | bond | B$^a$ | — | 2-OCH$_2$OMe |
| 1-529 | CH$_2$C(Me)$_2$CONH$_2$ | A$^c$ | Me | Me | bond | B$^a$ | — | 2-O(CH$_2$)$_2$OMe |
| 1-530 | CH$_2$C(Me)$_2$CONH$_2$ | A$^c$ | Me | Me | bond | B$^a$ | — | 2-O(CH$_2$)$_3$OMe |
| 1-531 | CH$_2$C(Me)$_2$CONH$_2$ | A$^c$ | Me | Me | bond | B$^a$ | 2-Me | — |
| 1-532 | CH$_2$C(Me)$_2$CONH$_2$ | A$^c$ | Me | Me | bond | B$^a$ | 2-OMe | — |
| 1-533 | CH$_2$C(Me)$_2$CONH$_2$ | A$^c$ | Me | Me | bond | B$^a$ | 2-F | — |
| 1-534 | CH$_2$C(Me)$_2$CONH$_2$ | A$^c$ | Me | Me | bond | B$^a$ | 2-Cl | — |
| 1-535 | CH$_2$C(Me)$_2$CONH$_2$ | A$^d$ | Me | Me | bond | B$^a$ | — | — |
| 1-536 | CH$_2$C(Me)$_2$CONH$_2$ | A$^d$ | Me | Me | bond | B$^a$ | — | 2-OCH$_2$OMe |
| 1-537 | CH$_2$C(Me)$_2$CONH$_2$ | A$^d$ | Me | Me | bond | B$^a$ | — | 2-O(CH$_2$)$_2$OMe |
| 1-538 | CH$_2$C(Me)$_2$CONH$_2$ | A$^d$ | Me | Me | bond | B$^a$ | — | 2-O(CH$_2$)$_3$OMe |
| 1-539 | CH$_2$C(Me)$_2$CONH$_2$ | A$^d$ | Me | Me | bond | B$^a$ | 2-Me | — |
| 1-540 | CH$_2$C(Me)$_2$CONH$_2$ | A$^d$ | Me | Me | bond | B$^a$ | 2-OMe | — |
| 1-541 | CH$_2$C(Me)$_2$CONH$_2$ | A$^d$ | Me | Me | bond | B$^a$ | 2-F | — |
| 1-542 | CH$_2$C(Me)$_2$CONH$_2$ | A$^d$ | Me | Me | bond | B$^a$ | 2-Cl | — |
| 1-543 | CH$_2$(1-CONH$_2$-cPr) | A$^a$ | Me | Me | bond | B$^a$ | — | — |
| 1-544 | CH$_2$(1-CONH$_2$-cPr) | A$^b$ | Me | Me | bond | B$^a$ | — | — |
| 1-545 | CH$_2$(1-CONH$_2$-cPr) | A$^b$ | Me | Me | bond | B$^a$ | 2-Me | — |
| 1-546 | CH$_2$(1-CONH$_2$-cPr) | A$^b$ | Me | Me | bond | B$^a$ | 2-OMe | — |
| 1-547 | CH$_2$(1-CONH$_2$-cPr) | A$^b$ | Me | Me | bond | B$^a$ | 2-F | — |
| 1-548 | CH$_2$(1-CONH$_2$-cPr) | A$^b$ | Me | Me | bond | B$^a$ | 2-Cl | — |
| 1-549 | CH$_2$C(Me)$_2$SO$_2$NH$_2$ | A$^a$ | Me | Me | bond | B$^a$ | — | — |
| 1-551 | CH$_2$C(Me)$_2$SO$_2$NH$_2$ | A$^b$ | Me | Me | bond | B$^a$ | — | — |
| 1-550 | CH$_2$C(Me)$_2$SO$_2$NH$_2$ | A$^b$ | Me | Me | bond | B$^a$ | 2-Me | — |
| 1-552 | CH$_2$C(Me)$_2$SO$_2$NH$_2$ | A$^b$ | Me | Me | bond | B$^a$ | 2-OMe | — |
| 1-553 | CH$_2$C(Me)$_2$SO$_2$NH$_2$ | A$^b$ | Me | Me | bond | B$^a$ | 2-F | — |
| 1-554 | CH$_2$C(Me)$_2$SO$_2$NH$_2$ | A$^b$ | Me | Me | bond | B$^a$ | 2-Cl | — |
| 1-555 | CH$_2$(1-SO$_2$NH$_2$-cPr) | A$^a$ | Me | Me | bond | B$^a$ | — | — |
| 1-556 | CH$_2$(1-SO$_2$NH$_2$-cPr) | A$^b$ | Me | Me | bond | B$^a$ | — | — |
| 1-557 | CH$_2$(1-SO$_2$NH$_2$-cPr) | A$^b$ | Me | Me | bond | B$^a$ | 2-Me | — |
| 1-558 | CH$_2$(1-SO$_2$NH$_2$-cPr) | A$^b$ | Me | Me | bond | B$^a$ | 2-OMe | — |
| 1-559 | CH$_2$(1-SO$_2$NH$_2$-cPr) | A$^b$ | Me | Me | bond | B$^a$ | 2-F | — |
| 1-560 | CH$_2$(1-SO$_2$NH$_2$-cPr) | A$^b$ | Me | Me | bond | B$^a$ | 2-Cl | — |
| 1-561 | CH$_2$C(Me)$_2$SO$_2$NHMe | A$^a$ | Me | Me | bond | B$^a$ | — | — |
| 1-562 | CH$_2$C(Me)$_2$SO$_2$NHMe | A$^b$ | Me | Me | bond | B$^a$ | — | — |
| 1-563 | CH$_2$C(Me)$_2$SO$_2$NHMe | A$^b$ | Me | Me | bond | B$^a$ | 2-Me | — |
| 1-564 | CH$_2$C(Me)$_2$SO$_2$NHMe | A$^b$ | Me | Me | bond | B$^a$ | 2-OMe | — |
| 1-565 | CH$_2$C(Me)$_2$SO$_2$NHMe | A$^b$ | Me | Me | bond | B$^a$ | 2-F | — |
| 1-566 | CH$_2$C(Me)$_2$SO$_2$NHMe | A$^b$ | Me | Me | bond | B$^a$ | 2-Cl | — |
| 1-567 | CH$_2$(1-SO$_2$NHMe-cPr) | A$^a$ | Me | Me | bond | B$^a$ | — | — |
| 1-568 | CH$_2$(1-SO$_2$NHMe-cPr) | A$^b$ | Me | Me | bond | B$^a$ | — | — |
| 1-569 | CH$_2$(1-SO$_2$NHMe-cPr) | A$^b$ | Me | Me | bond | B$^a$ | 2-Me | — |
| 1-570 | CH$_2$(1-SO$_2$NHMe-cPr) | A$^b$ | Me | Me | bond | B$^a$ | 2-OMe | — |
| 1-571 | CH$_2$(1-SO$_2$NHMe-cPr) | A$^b$ | Me | Me | bond | B$^a$ | 2-F | — |
| 1-572 | CH$_2$(1-SO$_2$NHMe-cPr) | A$^b$ | Me | Me | bond | B$^a$ | 2-Cl | — |
| 1-573 | CH$_2$CF$_3$ | A$^a$ | Me | Me | bond | B$^a$ | — | — |
| 1-574 | CH$_2$CF$_3$ | A$^b$ | Me | Me | bond | B$^a$ | — | — |
| 1-575 | CH$_2$CF$_3$ | A$^b$ | Me | Me | bond | B$^a$ | 2-Me | — |
| 1-576 | CH$_2$CF$_3$ | A$^b$ | Me | Me | bond | B$^a$ | 2-OMe | — |
| 1-577 | CH$_2$CF$_3$ | A$^b$ | Me | Me | bond | B$^a$ | 2-F | — |
| 1-578 | CH$_2$CF$_3$ | A$^b$ | Me | Me | bond | B$^a$ | 2-Cl | — |
| 1-579 | (CH$_2$)$_2$CF$_3$ | A$^a$ | Me | Me | bond | B$^a$ | — | — |
| 1-580 | (CH$_2$)$_2$CF$_3$ | A$^b$ | Me | Me | bond | B$^a$ | — | — |
| 1-581 | (CH$_2$)$_2$CF$_3$ | A$^b$ | Me | Me | bond | B$^a$ | 2-Me | — |
| 1-582 | (CH$_2$)$_2$CF$_3$ | A$^b$ | Me | Me | bond | B$^a$ | 2-OMe | — |
| 1-583 | (CH$_2$)$_2$CF$_3$ | A$^b$ | Me | Me | bond | B$^a$ | 2-F | — |
| 1-584 | (CH$_2$)$_2$CF$_3$ | A$^b$ | Me | Me | bond | B$^a$ | 2-Cl | — |
| 1-585 | (CH$_2$)$_3$CF$_3$ | A$^a$ | Me | Me | bond | B$^a$ | — | — |
| 1-586 | (CH$_2$)$_3$CF$_3$ | A$^b$ | Me | Me | bond | B$^a$ | — | — |
| 1-587 | (CH$_2$)$_3$CF$_3$ | A$^b$ | Me | Me | bond | B$^a$ | 2-Me | — |
| 1-588 | (CH$_2$)$_3$CF$_3$ | A$^b$ | Me | Me | bond | B$^a$ | 2-OMe | — |

| | | | | | | | | |
|---|---|---|---|---|---|---|---|---|
| 1-589 | (CH$_2$)$_3$CF$_3$ | A$^b$ | Me | Me | bond | B$^a$ | 2-F | — |
| 1-590 | (CH$_2$)$_3$CF$_3$ | A$^b$ | Me | Me | bond | B$^a$ | 2-Cl | — |
| 1-591 | (CH$_2$)$_2$CF$_2$CH$_3$ | A$^a$ | Me | Me | bond | B$^a$ | — | — |
| 1-592 | (CH$_2$)$_2$CF$_2$CH$_3$ | A$^b$ | Me | Me | bond | B$^a$ | — | — |
| 1-593 | (CH$_2$)$_2$CF$_2$CH$_3$ | A$^b$ | Me | Me | bond | B$^a$ | 2-Me | — |
| 1-594 | (CH$_2$)$_2$CF$_2$CH$_3$ | A$^b$ | Me | Me | bond | B$^a$ | 2-OMe | — |
| 1-595 | (CH$_2$)$_2$CF$_2$CH$_3$ | A$^b$ | Me | Me | bond | B$^a$ | 2-F | — |
| 1-596 | (CH$_2$)$_2$CF$_2$CH$_3$ | A$^b$ | Me | Me | bond | B$^a$ | 2-Cl | — |
| 1-597 | CH$_2$(CF$_2$)$_2$CH$_3$ | A$^a$ | Me | Me | bond | B$^a$ | — | — |
| 1-598 | CH$_2$(CF$_2$)$_2$CH$_3$ | A$^b$ | Me | Me | bond | B$^a$ | — | — |
| 1-599 | CH$_2$(CF$_2$)$_2$CH$_3$ | A$^b$ | Me | Me | bond | B$^a$ | 2-Me | — |
| 1-600 | CH$_2$(CF$_2$)$_2$CH$_3$ | A$^b$ | Me | Me | bond | B$^a$ | 2-OMe | — |
| 1-601 | CH$_2$(CF$_2$)$_2$CH$_3$ | A$^b$ | Me | Me | bond | B$^a$ | 2-F | — |
| 1-602 | CH$_2$(CF$_2$)$_2$CH$_3$ | A$^b$ | Me | Me | bond | B$^a$ | 2-Cl | — |
| 1-603 | cPr | A$^a$ | Me | Me | bond | B$^a$ | — | — |
| 1-604 | cPn | A$^a$ | Me | Me | bond | B$^a$ | — | — |
| 1-605 | cPn | A$^a$ | Me | Me | bond | B$^a$ | — | 2-OCH$_2$OMe |
| 1-606 | cPn | A$^a$ | Me | Me | bond | B$^a$ | — | 2-O(CH$_2$)$_2$OMe |
| 1-607 | cPn | A$^a$ | Me | Me | bond | B$^a$ | — | 2-O(CH$_2$)$_3$OMe |
| 1-608 | cPn | A$^a$ | Me | Me | bond | B$^a$ | 2-Me | — |
| 1-609 | cPn | A$^a$ | Me | Me | bond | B$^a$ | 2-OMe | — |
| 1-610 | cPn | A$^a$ | Me | Me | bond | B$^a$ | 2-F | — |
| 1-611 | cPn | A$^a$ | Me | Me | bond | B$^a$ | 2-Cl | — |
| 1-612 | cPn | A$^b$ | Me | Me | bond | B$^a$ | — | — |
| 1-613 | cPn | A$^b$ | Me | Me | bond | B$^a$ | — | 2-OCH$_2$OMe |
| 1-614 | cPn | A$^b$ | Me | Me | bond | B$^a$ | — | 3-OCH$_2$OMe |
| 1-615 | cPn | A$^b$ | Me | Me | bond | B$^a$ | — | 2-O(CH$_2$)$_2$OMe |
| 1-616 | cPn | A$^b$ | Me | Me | bond | B$^a$ | — | 3-O(CH$_2$)$_2$OMe |
| 1-617 | cPn | A$^b$ | Me | Me | bond | B$^a$ | — | 2-O(CH$_2$)$_3$OMe |
| 1-618 | cPn | A$^b$ | Me | Me | bond | B$^a$ | — | 3-O(CH$_2$)$_3$OMe |
| 1-619 | cPn | A$^b$ | Me | Me | bond | B$^a$ | 2-Me | — |
| 1-620 | cPn | A$^b$ | Me | Me | bond | B$^a$ | 3-Me | — |
| 1-621 | cPn | A$^b$ | Me | Me | bond | B$^a$ | 2-CF$_3$ | — |
| 1-622 | cPn | A$^b$ | Me | Me | bond | B$^a$ | 3-CF$_3$ | — |
| 1-623 | cPn | A$^b$ | Me | Me | bond | B$^a$ | 2-OH | — |
| 1-624 | cPn | A$^b$ | Me | Me | bond | B$^a$ | 3-OH | — |
| 1-625 | cPn | A$^b$ | Me | Me | bond | B$^a$ | 2-OMe | — |
| 1-626 | cPn | A$^b$ | Me | Me | bond | B$^a$ | 3-OMe | — |
| 1-627 | cPn | A$^b$ | Me | Me | bond | B$^a$ | 2-SH | — |
| 1-628 | cPn | A$^b$ | Me | Me | bond | B$^a$ | 3-SH | — |
| 1-629 | cPn | A$^b$ | Me | Me | bond | B$^a$ | 2-SMe | — |
| 1-630 | cPn | A$^b$ | Me | Me | bond | B$^a$ | 3-SMe | — |
| 1-631 | cPn | A$^b$ | Me | Me | bond | B$^a$ | 2-NH$_2$ | — |
| 1-632 | cPn | A$^b$ | Me | Me | bond | B$^a$ | 2-NHMe | — |
| 1-633 | cPn | A$^b$ | Me | Me | bond | B$^a$ | 2-NMe$_2$ | — |
| 1-634 | cPn | A$^b$ | Me | Me | bond | B$^a$ | 2-NHCHO | — |
| 1-635 | cPn | A$^b$ | Me | Me | bond | B$^a$ | 2-NHCOMe | — |
| 1-636 | cPn | A$^b$ | Me | Me | bond | B$^a$ | 2-CO$_2$H | — |
| 1-637 | cPn | A$^b$ | Me | Me | bond | B$^a$ | 2-CO$_2$Me | — |
| 1-638 | cPn | A$^b$ | Me | Me | bond | B$^a$ | 2-CONH$_2$ | — |
| 1-639 | cPn | A$^b$ | Me | Me | bond | B$^a$ | 2-CONHMe | — |
| 1-640 | cPn | A$^b$ | Me | Me | bond | B$^a$ | 2-CONMe$_2$ | — |
| 1-641 | cPn | A$^b$ | Me | Me | bond | B$^a$ | 2-CN | — |
| 1-642 | cPn | A$^b$ | Me | Me | bond | B$^a$ | 3-CN | — |
| 1-643 | cPn | A$^b$ | Me | Me | bond | B$^a$ | 2-NO$_2$ | — |
| 1-644 | cPn | A$^b$ | Me | Me | bond | B$^a$ | 3-NO$_2$ | — |
| 1-645 | cPn | A$^b$ | Me | Me | bond | B$^a$ | 2-F | — |
| 1-646 | cPn | A$^b$ | Me | Me | bond | B$^a$ | 3-F | — |
| 1-647 | cPn | A$^b$ | Me | Me | bond | B$^a$ | 2-Cl | — |
| 1-648 | cPn | A$^b$ | Me | Me | bond | B$^a$ | 3-Cl | — |
| 1-649 | cPn | A$^b$ | Me | Me | bond | B$^a$ | 2,3-di-Me | — |
| 1-650 | cPn | A$^b$ | Me | Me | bond | B$^a$ | 2,5-di-Me | — |
| 1-651 | cPn | A$^b$ | Me | Me | bond | B$^a$ | 2,6-di-Me | — |
| 1-652 | cPn | A$^b$ | Me | Me | bond | B$^a$ | 2-Me-3-OMe | — |
| 1-653 | cPn | A$^b$ | Me | Me | bond | B$^a$ | 2-Me-5-OMe | — |
| 1-654 | cPn | A$^b$ | Me | Me | bond | B$^a$ | 2-Me-6-OMe | — |
| 1-655 | cPn | A$^b$ | Me | Me | bond | B$^a$ | 2-Me-3-F | — |
| 1-656 | cPn | A$^b$ | Me | Me | bond | B$^a$ | 2-Me-5-F | — |
| 1-657 | cPn | A$^b$ | Me | Me | bond | B$^a$ | 2-Me-6-F | — |
| 1-658 | cPn | A$^b$ | Me | Me | bond | B$^a$ | 2-Me-3-Cl | — |
| 1-659 | cPn | A$^b$ | Me | Me | bond | B$^a$ | 2-Me-5-Cl | — |
| 1-660 | cPn | A$^b$ | Me | Me | bond | B$^a$ | 2-Me-6-Cl | — |
| 1-661 | cPn | A$^b$ | Me | Me | bond | B$^a$ | 2,3-di-OMe | — |
| 1-662 | cPn | A$^b$ | Me | Me | bond | B$^a$ | 2,5-di-OMe | — |
| 1-663 | cPn | A$^b$ | Me | Me | bond | B$^a$ | 2,6-di-OMe | — |
| 1-664 | cPn | A$^b$ | Me | Me | bond | B$^a$ | 2-OMe-3-Me | — |
| 1-665 | cPn | A$^b$ | Me | Me | bond | B$^a$ | 2-OMe-5-Me | — |
| 1-666 | cPn | A$^b$ | Me | Me | bond | B$^a$ | 2-OMe-3-F | — |
| 1-667 | cPn | A$^b$ | Me | Me | bond | B$^a$ | 2-OMe-5-F | — |
| 1-668 | cPn | A$^b$ | Me | Me | bond | B$^a$ | 2-OMe-6-F | — |
| 1-669 | cPn | A$^b$ | Me | Me | bond | B$^a$ | 2-OMe-3-Cl | — |
| 1-670 | cPn | A$^b$ | Me | Me | bond | B$^a$ | 2-OMe-5-Cl | — |

| | | | | | | | | |
|---|---|---|---|---|---|---|---|---|
| 1-671 | cPn | $A^b$ | Me | Me | bond | $B^a$ | 2-OMe-6-Cl | — |
| 1-672 | cPn | $A^b$ | Me | Me | bond | $B^a$ | 2,3-di-F | — |
| 1-673 | cPn | $A^b$ | Me | Me | bond | $B^a$ | 2,5-di-F | — |
| 1-674 | cPn | $A^b$ | Me | Me | bond | $B^a$ | 2,6-di-F | — |
| 1-675 | cPn | $A^b$ | Me | Me | bond | $B^a$ | 2-F-3-Me | — |
| 1-676 | cPn | $A^b$ | Me | Me | bond | $B^a$ | 2-F-5-Me | — |
| 1-677 | cPn | $A^b$ | Me | Me | bond | $B^a$ | 2-F-3-OMe | — |
| 1-678 | cPn | $A^b$ | Me | Me | bond | $B^a$ | 2-F-5-OMe | — |
| 1-679 | cPn | $A^b$ | Me | Me | bond | $B^a$ | 2-F-3-Cl | — |
| 1-680 | cPn | $A^b$ | Me | Me | bond | $B^a$ | 2-F-5-Cl | — |
| 1-681 | cPn | $A^b$ | Me | Me | bond | $B^a$ | 2-F-6-Cl | — |
| 1-682 | cPn | $A^b$ | Me | Me | bond | $B^a$ | 2,3-di-Cl | — |
| 1-683 | cPn | $A^b$ | Me | Me | bond | $B^a$ | 2,5-di-Cl | — |
| 1-684 | cPn | $A^b$ | Me | Me | bond | $B^a$ | 2,6-di-Cl | — |
| 1-685 | cPn | $A^b$ | Me | Me | bond | $B^a$ | 2-Cl-3-Me | — |
| 1-686 | cPn | $A^b$ | Me | Me | bond | $B^a$ | 2-Cl-5-Me | — |
| 1-687 | cPn | $A^b$ | Me | Me | bond | $B^a$ | 2-Cl-3-OMe | — |
| 1-688 | cPn | $A^b$ | Me | Me | bond | $B^a$ | 2-Cl-5-OMe | — |
| 1-689 | cPn | $A^b$ | Me | Me | bond | $B^a$ | 2-Cl-3-F | — |
| 1-690 | cPn | $A^b$ | Me | Me | bond | $B^a$ | 2-Cl-5-F | — |
| 1-691 | cPn | $A^b$ | Me | Me | $CH_2$ | $B^a$ | — | — |
| 1-692 | cPn | $A^b$ | Me | Me | CO | $B^a$ | — | — |
| 1-693 | cPn | $A^b$ | —$(CH_2)_2$— | | bond | $B^a$ | — | — |
| 1-694 | cPn | $A^b$ | —$(CH_2)_2$— | | bond | $B^a$ | 2-Me | — |
| 1-695 | cPn | $A^b$ | —$(CH_2)_2$— | | bond | $B^a$ | 2-OMe | — |
| 1-696 | cPn | $A^b$ | —$(CH_2)_2$— | | bond | $B^a$ | 2-F | — |
| 1-697 | cPn | $A^b$ | —$(CH_2)_2$— | | bond | $B^a$ | 2-Cl | — |
| 1-698 | cPn | $A^b$ | Me | Me | bond | $B^b$ | — | — |
| 1-699 | cPn | $A^b$ | Me | Me | bond | $B^c$ | — | — |
| 1-700 | cPn | $A^b$ | Me | Me | bond | $B^c$ | 6-Me | — |
| 1-701 | cPn | $A^b$ | Me | Me | bond | $B^c$ | 6-OMe | — |
| 1-702 | cPn | $A^b$ | Me | Me | bond | $B^c$ | 6-F | — |
| 1-703 | cPn | $A^b$ | Me | Me | bond | $B^c$ | 6-Cl | — |
| 1-704 | cPn | $A^b$ | Me | Me | bond | $B^d$ | — | — |
| 1-705 | cPn | $A^c$ | Me | Me | bond | $B^a$ | — | — |
| 1-706 | cPn | $A^c$ | Me | Me | bond | $B^a$ | — | 2-OCH$_2$OMe |
| 1-707 | cPn | $A^c$ | Me | Me | bond | $B^a$ | — | 2-O(CH$_2$)$_2$OMe |
| 1-708 | cPn | $A^c$ | Me | Me | bond | $B^a$ | — | 2-O(CH$_2$)$_3$OMe |
| 1-709 | cPn | $A^c$ | Me | Me | bond | $B^a$ | 2-Me | — |
| 1-710 | cPn | $A^c$ | Me | Me | bond | $B^a$ | 2-OMe | — |
| 1-711 | cPn | $A^c$ | Me | Me | bond | $B^a$ | 2-F | — |
| 1-712 | cPn | $A^c$ | Me | Me | bond | $B^a$ | 2-Cl | — |
| 1-713 | cPn | $A^d$ | Me | Me | bond | $B^a$ | — | — |
| 1-714 | cPn | $A^d$ | Me | Me | bond | $B^a$ | — | 2-OCH$_2$OMe |
| 1-715 | cPn | $A^d$ | Me | Me | bond | $B^a$ | — | 2-O(CH$_2$)$_2$OMe |
| 1-716 | cPn | $A^d$ | Me | Me | bond | $B^a$ | — | 2-O(CH$_2$)$_3$OMe |
| 1-717 | cPn | $A^d$ | Me | Me | bond | $B^a$ | 2-Me | — |
| 1-718 | cPn | $A^d$ | Me | Me | bond | $B^a$ | 2-OMe | — |
| 1-719 | cPn | $A^d$ | Me | Me | bond | $B^a$ | 2-F | — |
| 1-720 | cPn | $A^d$ | Me | Me | bond | $B^a$ | 2-Cl | — |
| 1-721 | cHx | $A^a$ | Me | Me | bond | $B^a$ | — | — |
| 1-722 | cHx | $A^b$ | Me | Me | bond | $B^a$ | — | — |
| 1-723 | cHx | $A^b$ | Me | Me | bond | $B^a$ | 2-Me | — |
| 1-724 | cHx | $A^b$ | Me | Me | bond | $B^a$ | 2-OMe | — |
| 1-725 | cHx | $A^b$ | Me | Me | bond | $B^a$ | 2-F | — |
| 1-726 | cHx | $A^b$ | Me | Me | bond | $B^a$ | 2-Cl | — |
| 1-727 | 4-Thp | $A^a$ | Me | Me | bond | $B^a$ | — | — |
| 1-728 | 4-Thp | $A^b$ | Me | Me | bond | $B^a$ | — | — |
| 1-729 | 4-Thp | $A^b$ | Me | Me | bond | $B^a$ | 2-Me | — |
| 1-730 | 4-Thp | $A^b$ | Me | Me | bond | $B^a$ | 2-OMe | — |
| 1-731 | 4-Thp | $A^b$ | Me | Me | bond | $B^a$ | 2-F | — |
| 1-732 | 4-Thp | $A^b$ | Me | Me | bond | $B^a$ | 2-Cl | — |
| 1-733 | iBu | $A^b$ | Me | Me | bond | $B^a$ | 2,3-di-Me | — |
| 1-734 | iBu | $A^b$ | Me | Me | bond | $B^a$ | 2,5-di-Me | — |
| 1-735 | iBu | $A^b$ | Me | Me | bond | $B^a$ | 2,6-di-Me | — |
| 1-736 | iBu | $A^b$ | Me | Me | bond | $B^a$ | 2-Me-3-OMe | — |
| 1-737 | iBu | $A^b$ | Me | Me | bond | $B^a$ | 2-Me-5-OMe | — |
| 1-738 | iBu | $A^b$ | Me | Me | bond | $B^a$ | 2-Me-6-OMe | — |
| 1-739 | iBu | $A^b$ | Me | Me | bond | $B^a$ | 2-Me-3-F | — |
| 1-740 | iBu | $A^b$ | Me | Me | bond | $B^a$ | 2-Me-5-F | — |
| 1-741 | iBu | $A^b$ | Me | Me | bond | $B^a$ | 2-Me-6-F | — |
| 1-742 | iBu | $A^b$ | Me | Me | bond | $B^a$ | 2-Me-3-Cl | — |
| 1-743 | iBu | $A^b$ | Me | Me | bond | $B^a$ | 2-Me-5-Cl | — |
| 1-744 | iBu | $A^b$ | Me | Me | bond | $B^a$ | 2-Me-6-Cl | — |
| 1-745 | iBu | $A^b$ | Me | Me | bond | $B^a$ | 2,3-di-OMe | — |
| 1-746 | iBu | $A^b$ | Me | Me | bond | $B^a$ | 2,5-di-OMe | — |
| 1-747 | iBu | $A^b$ | Me | Me | bond | $B^a$ | 2,6-di-OMe | — |
| 1-748 | iBu | $A^b$ | Me | Me | bond | $B^a$ | 2-OMe-3-Me | — |
| 1-749 | iBu | $A^b$ | Me | Me | bond | $B^a$ | 2-OMe-5-Me | — |
| 1-750 | iBu | $A^b$ | Me | Me | bond | $B^a$ | 2-OMe-3-F | — |
| 1-751 | iBu | $A^b$ | Me | Me | bond | $B^a$ | 2-OMe-5-F | — |
| 1-752 | iBu | $A^b$ | Me | Me | bond | $B^a$ | 2-OMe-6-F | — |

| | | | | | | | | |
|---|---|---|---|---|---|---|---|---|
| 1-753 | iBu | $A^b$ | Me | Me | bond | $B^a$ | 2-OMe-3-Cl | — |
| 1-754 | iBu | $A^b$ | Me | Me | bond | $B^a$ | 2-OMe-5-Cl | — |
| 1-755 | iBu | $A^b$ | Me | Me | bond | $B^a$ | 2-OMe-6-Cl | — |
| 1-756 | iBu | $A^b$ | Me | Me | bond | $B^a$ | 2,3-di-F | — |
| 1-757 | iBu | $A^b$ | Me | Me | bond | $B^a$ | 2,5-di-F | — |
| 1-758 | iBu | $A^b$ | Me | Me | bond | $B^a$ | 2,6-di-F | — |
| 1-759 | iBu | $A^b$ | Me | Me | bond | $B^a$ | 2-F-3-Me | — |
| 1-760 | iBu | $A^b$ | Me | Me | bond | $B^a$ | 2-F-5-Me | — |
| 1-761 | iBu | $A^b$ | Me | Me | bond | $B^a$ | 2-F-3-OMe | — |
| 1-762 | iBu | $A^b$ | Me | Me | bond | $B^a$ | 2-F-5-OMe | — |
| 1-763 | iBu | $A^b$ | Me | Me | bond | $B^a$ | 2-F-3-Cl | — |
| 1-764 | iBu | $A^b$ | Me | Me | bond | $B^a$ | 2-F-5-Cl | — |
| 1-765 | iBu | $A^b$ | Me | Me | bond | $B^a$ | 2-F-6-Cl | — |
| 1-766 | iBu | $A^b$ | Me | Me | bond | $B^a$ | 2,3-di-Cl | — |
| 1-767 | iBu | $A^b$ | Me | Me | bond | $B^a$ | 2,5-di-Cl | — |
| 1-768 | iBu | $A^b$ | Me | Me | bond | $B^a$ | 2,6-di-Cl | — |
| 1-769 | iBu | $A^b$ | Me | Me | bond | $B^a$ | 2-Cl-3-Me | — |
| 1-770 | iBu | $A^b$ | Me | Me | bond | $B^a$ | 2-Cl-5-Me | — |
| 1-771 | iBu | $A^b$ | Me | Me | bond | $B^a$ | 2-Cl-3-OMe | — |
| 1-772 | iBu | $A^b$ | Me | Me | bond | $B^a$ | 2-Cl-5-OMe | — |
| 1-773 | iBu | $A^b$ | Me | Me | bond | $B^a$ | 2-Cl-3-F | — |
| 1-774 | iBu | $A^b$ | Me | Me | bond | $B^a$ | 2-Cl-5-F | — |
| 1-775 | $CH_2CMe_2OH$ | $A^b$ | Me | Me | bond | $B^a$ | — | — |
| 1-776 | $CH_2CMe_2OH$ | $A^b$ | Me | Me | bond | $B^a$ | 2-Me | — |
| 1-777 | $CH_2CMe_2OH$ | $A^b$ | Me | Me | bond | $B^a$ | 3-Me | — |
| 1-778 | $CH_2CMe_2OH$ | $A^b$ | Me | Me | bond | $B^a$ | 2-OMe | — |
| 1-779 | $CH_2CMe_2OH$ | $A^b$ | Me | Me | bond | $B^a$ | 3-OMe | — |
| 1-780 | $CH_2CMe_2OH$ | $A^b$ | Me | Me | bond | $B^a$ | 2-F | — |
| 1-781 | $CH_2CMe_2OH$ | $A^b$ | Me | Me | bond | $B^a$ | 3-F | — |
| 1-782 | $CH_2CMe_2OH$ | $A^b$ | Me | Me | bond | $B^a$ | 2-Cl | — |
| 1-783 | $CH_2CMe_2OH$ | $A^b$ | Me | Me | bond | $B^a$ | 3-Cl | — |
| 1-784 | $CH_2CMe_2OH$ | $A^b$ | Me | Me | bond | $B^a$ | 2,3-di-Me | — |
| 1-785 | $CH_2CMe_2OH$ | $A^b$ | Me | Me | bond | $B^a$ | 2,5-di-Me | — |
| 1-786 | $CH_2CMe_2OH$ | $A^b$ | Me | Me | bond | $B^a$ | 2,6-di-Me | — |
| 1-787 | $CH_2CMe_2OH$ | $A^b$ | Me | Me | bond | $B^a$ | 2-Me-3-OMe | — |
| 1-788 | $CH_2CMe_2OH$ | $A^b$ | Me | Me | bond | $B^a$ | 2-Me-5-OMe | — |
| 1-789 | $CH_2CMe_2OH$ | $A^b$ | Me | Me | bond | $B^a$ | 2-Me-6-OMe | — |
| 1-790 | $CH_2CMe_2OH$ | $A^b$ | Me | Me | bond | $B^a$ | 2-Me-3-F | — |
| 1-791 | $CH_2CMe_2OH$ | $A^b$ | Me | Me | bond | $B^a$ | 2-Me-5-F | — |
| 1-792 | $CH_2CMe_2OH$ | $A^b$ | Me | Me | bond | $B^a$ | 2-Me-6-F | — |
| 1-793 | $CH_2CMe_2OH$ | $A^b$ | Me | Me | bond | $B^a$ | 2-Me-3-Cl | — |
| 1-794 | $CH_2CMe_2OH$ | $A^b$ | Me | Me | bond | $B^a$ | 2-Me-5-Cl | — |
| 1-795 | $CH_2CMe_2OH$ | $A^b$ | Me | Me | bond | $B^a$ | 2-Me-6-Cl | — |
| 1-796 | $CH_2CMe_2OH$ | $A^b$ | Me | Me | bond | $B^a$ | 2,3-di-OMe | — |
| 1-797 | $CH_2CMe_2OH$ | $A^b$ | Me | Me | bond | $B^a$ | 2,5-di-OMe | — |
| 1-798 | $CH_2CMe_2OH$ | $A^b$ | Me | Me | bond | $B^a$ | 2,6-di-OMe | — |
| 1-799 | $CH_2CMe_2OH$ | $A^b$ | Me | Me | bond | $B^a$ | 2-OMe-3-Me | — |
| 1-800 | $CH_2CMe_2OH$ | $A^b$ | Me | Me | bond | $B^a$ | 2-OMe-5-Me | — |
| 1-801 | $CH_2CMe_2OH$ | $A^b$ | Me | Me | bond | $B^a$ | 2-OMe-3-F | — |
| 1-802 | $CH_2CMe_2OH$ | $A^b$ | Me | Me | bond | $B^a$ | 2-OMe-5-F | — |
| 1-803 | $CH_2CMe_2OH$ | $A^b$ | Me | Me | bond | $B^a$ | 2-OMe-6-F | — |
| 1-804 | $CH_2CMe_2OH$ | $A^b$ | Me | Me | bond | $B^a$ | 2-OMe-3-Cl | — |
| 1-805 | $CH_2CMe_2OH$ | $A^b$ | Me | Me | bond | $B^a$ | 2-OMe-5-Cl | — |
| 1-806 | $CH_2CMe_2OH$ | $A^b$ | Me | Me | bond | $B^a$ | 2-OMe-6-Cl | — |
| 1-807 | $CH_2CMe_2OH$ | $A^b$ | Me | Me | bond | $B^a$ | 2,3-di-F | — |
| 1-808 | $CH_2CMe_2OH$ | $A^b$ | Me | Me | bond | $B^a$ | 2,5-di-F | — |
| 1-809 | $CH_2CMe_2OH$ | $A^b$ | Me | Me | bond | $B^a$ | 2,6-di-F | — |
| 1-810 | $CH_2CMe_2OH$ | $A^b$ | Me | Me | bond | $B^a$ | 2-F-3-Me | — |
| 1-811 | $CH_2CMe_2OH$ | $A^b$ | Me | Me | bond | $B^a$ | 2-F-5-Me | — |
| 1-812 | $CH_2CMe_2OH$ | $A^b$ | Me | Me | bond | $B^a$ | 2-F-3-OMe | — |
| 1-813 | $CH_2CMe_2OH$ | $A^b$ | Me | Me | bond | $B^a$ | 2-F-5-OMe | — |
| 1-814 | $CH_2CMe_2OH$ | $A^b$ | Me | Me | bond | $B^a$ | 2-F-3-Cl | — |
| 1-815 | $CH_2CMe_2OH$ | $A^b$ | Me | Me | bond | $B^a$ | 2-F-5-Cl | — |
| 1-816 | $CH_2CMe_2OH$ | $A^b$ | Me | Me | bond | $B^a$ | 2-F-6-Cl | — |
| 1-817 | $CH_2CMe_2OH$ | $A^b$ | Me | Me | bond | $B^a$ | 2,3-di-Cl | — |
| 1-818 | $CH_2CMe_2OH$ | $A^b$ | Me | Me | bond | $B^a$ | 2,5-di-Cl | — |
| 1-819 | $CH_2CMe_2OH$ | $A^b$ | Me | Me | bond | $B^a$ | 2,6-di-Cl | — |
| 1-820 | $CH_2CMe_2OH$ | $A^b$ | Me | Me | bond | $B^a$ | 2-Cl-3-Me | — |
| 1-821 | $CH_2CMe_2OH$ | $A^b$ | Me | Me | bond | $B^a$ | 2-Cl-5-Me | — |
| 1-822 | $CH_2CMe_2OH$ | $A^b$ | Me | Me | bond | $B^a$ | 2-Cl-3-OMe | — |
| 1-823 | $CH_2CMe_2OH$ | $A^b$ | Me | Me | bond | $B^a$ | 2-Cl-5-OMe | — |
| 1-824 | $CH_2CMe_2OH$ | $A^b$ | Me | Me | bond | $B^a$ | 2-Cl-3-F | — |
| 1-825 | $CH_2CMe_2OH$ | $A^b$ | Me | Me | bond | $B^a$ | 2-Cl-5-F | — |
| 1-826 | $CH_2CMe_3$ | $A^b$ | Me | Me | bond | $B^a$ | — | — |
| 1-827 | $CH_2CMe_3$ | $A^b$ | Me | Me | bond | $B^a$ | 2-Me | — |
| 1-828 | $CH_2CMe_3$ | $A^b$ | Me | Me | bond | $B^a$ | 3-Me | — |
| 1-829 | $CH_2CMe_3$ | $A^b$ | Me | Me | bond | $B^a$ | 2-OMe | — |
| 1-830 | $CH_2CMe_3$ | $A^b$ | Me | Me | bond | $B^a$ | 3-OMe | — |
| 1-831 | $CH_2CMe_3$ | $A^b$ | Me | Me | bond | $B^a$ | 2-F | — |
| 1-832 | $CH_2CMe_3$ | $A^b$ | Me | Me | bond | $B^a$ | 3-F | — |
| 1-833 | $CH_2CMe_3$ | $A^b$ | Me | Me | bond | $B^a$ | 2-Cl | — |
| 1-834 | $CH_2CMe_3$ | $A^b$ | Me | Me | bond | $B^a$ | 3-Cl | — |

| | | | | | | | | |
|---|---|---|---|---|---|---|---|---|
| 1-835 | CH$_2$CMe$_3$ | A$^b$ | Me | Me | bond | B$^a$ | 2,3-di-Me | — |
| 1-836 | CH$_2$CMe$_3$ | A$^b$ | Me | Me | bond | B$^a$ | 2,5-di-Me | — |
| 1-837 | CH$_2$CMe$_3$ | A$^b$ | Me | Me | bond | B$^a$ | 2,6-di-Me | — |
| 1-838 | CH$_2$CMe$_3$ | A$^b$ | Me | Me | bond | B$^a$ | 2-Me-3-OMe | — |
| 1-839 | CH$_2$CMe$_3$ | A$^b$ | Me | Me | bond | B$^a$ | 2-Me-5-OMe | — |
| 1-840 | CH$_2$CMe$_3$ | A$^b$ | Me | Me | bond | B$^a$ | 2-Me-6-OMe | — |
| 1-841 | CH$_2$CMe$_3$ | A$^b$ | Me | Me | bond | B$^a$ | 2-Me-3-F | — |
| 1-842 | CH$_2$CMe$_3$ | A$^b$ | Me | Me | bond | B$^a$ | 2-Me-5-F | — |
| 1-843 | CH$_2$CMe$_3$ | A$^b$ | Me | Me | bond | B$^a$ | 2-Me-6-F | — |
| 1-844 | CH$_2$CMe$_3$ | A$^b$ | Me | Me | bond | B$^a$ | 2-Me-3-Cl | — |
| 1-845 | CH$_2$CMe$_3$ | A$^b$ | Me | Me | bond | B$^a$ | 2-Me-5-Cl | — |
| 1-846 | CH$_2$CMe$_3$ | A$^b$ | Me | Me | bond | B$^a$ | 2-Me-6-Cl | — |
| 1-847 | CH$_2$CMe$_3$ | A$^b$ | Me | Me | bond | B$^a$ | 2,3-di-OMe | — |
| 1-848 | CH$_2$CMe$_3$ | A$^b$ | Me | Me | bond | B$^a$ | 2,5-di-OMe | — |
| 1-849 | CH$_2$CMe$_3$ | A$^b$ | Me | Me | bond | B$^a$ | 2,6-di-OMe | — |
| 1-850 | CH$_2$CMe$_3$ | A$^b$ | Me | Me | bond | B$^a$ | 2-OMe-3-Me | — |
| 1-851 | CH$_2$CMe$_3$ | A$^b$ | Me | Me | bond | B$^a$ | 2-OMe-5-Me | — |
| 1-852 | CH$_2$CMe$_3$ | A$^b$ | Me | Me | bond | B$^a$ | 2-OMe-3-F | — |
| 1-853 | CH$_2$CMe$_3$ | A$^b$ | Me | Me | bond | B$^a$ | 2-OMe-5-F | — |
| 1-854 | CH$_2$CMe$_3$ | A$^b$ | Me | Me | bond | B$^a$ | 2-OMe-6-F | — |
| 1-855 | CH$_2$CMe$_3$ | A$^b$ | Me | Me | bond | B$^a$ | 2-OMe-3-Cl | — |
| 1-856 | CH$_2$CMe$_3$ | A$^b$ | Me | Me | bond | B$^a$ | 2-OMe-5-Cl | — |
| 1-857 | CH$_2$CMe$_3$ | A$^b$ | Me | Me | bond | B$^a$ | 2-OMe-6-Cl | — |
| 1-858 | CH$_2$CMe$_3$ | A$^b$ | Me | Me | bond | B$^a$ | 2,3-di-F | — |
| 1-859 | CH$_2$CMe$_3$ | A$^b$ | Me | Me | bond | B$^a$ | 2,5-di-F | — |
| 1-860 | CH$_2$CMe$_3$ | A$^b$ | Me | Me | bond | B$^a$ | 2,6-di-F | — |
| 1-861 | CH$_2$CMe$_3$ | A$^b$ | Me | Me | bond | B$^a$ | 2-F-3-Me | — |
| 1-862 | CH$_2$CMe$_3$ | A$^b$ | Me | Me | bond | B$^a$ | 2-F-5-Me | — |
| 1-863 | CH$_2$CMe$_3$ | A$^b$ | Me | Me | bond | B$^a$ | 2-F-3-OMe | — |
| 1-864 | CH$_2$CMe$_3$ | A$^b$ | Me | Me | bond | B$^a$ | 2-F-5-OMe | — |
| 1-865 | CH$_2$CMe$_3$ | A$^b$ | Me | Me | bond | B$^a$ | 2-F-3-Cl | — |
| 1-866 | CH$_2$CMe$_3$ | A$^b$ | Me | Me | bond | B$^a$ | 2-F-5-Cl | — |
| 1-867 | CH$_2$CMe$_3$ | A$^b$ | Me | Me | bond | B$^a$ | 2-F-6-Cl | — |
| 1-868 | CH$_2$CMe$_3$ | A$^b$ | Me | Me | bond | B$^a$ | 2,3-di-Cl | — |
| 1-869 | CH$_2$CMe$_3$ | A$^b$ | Me | Me | bond | B$^a$ | 2,5-di-Cl | — |
| 1-870 | CH$_2$CMe$_3$ | A$^b$ | Me | Me | bond | B$^a$ | 2,6-di-Cl | — |
| 1-871 | CH$_2$CMe$_3$ | A$^b$ | Me | Me | bond | B$^a$ | 2-Cl-3-Me | — |
| 1-872 | CH$_2$CMe$_3$ | A$^b$ | Me | Me | bond | B$^a$ | 2-Cl-5-Me | — |
| 1-873 | CH$_2$CMe$_3$ | A$^b$ | Me | Me | bond | B$^a$ | 2-Cl-3-OMe | — |
| 1-874 | CH$_2$CMe$_3$ | A$^b$ | Me | Me | bond | B$^a$ | 2-Cl-5-OMe | — |
| 1-875 | CH$_2$CMe$_3$ | A$^b$ | Me | Me | bond | B$^a$ | 2-Cl-3-F | — |
| 1-876 | CH$_2$CMe$_3$ | A$^b$ | Me | Me | bond | B$^a$ | 2-Cl-5-F | — |
| 1-877 | cHx | A$^b$ | Me | Me | bond | B$^a$ | 2,3-di-Me | — |
| 1-878 | cHx | A$^b$ | Me | Me | bond | B$^a$ | 2,5-di-Me | — |
| 1-879 | cHx | A$^b$ | Me | Me | bond | B$^a$ | 2,6-di-Me | — |
| 1-880 | cHx | A$^b$ | Me | Me | bond | B$^a$ | 2-Me-3-OMe | — |
| 1-881 | cHx | A$^b$ | Me | Me | bond | B$^a$ | 2-Me-5-OMe | — |
| 1-882 | cHx | A$^b$ | Me | Me | bond | B$^a$ | 2-Me-6-OMe | — |
| 1-883 | cHx | A$^b$ | Me | Me | bond | B$^a$ | 2-Me-3-F | — |
| 1-884 | cHx | A$^b$ | Me | Me | bond | B$^a$ | 2-Me-5-F | — |
| 1-885 | cHx | A$^b$ | Me | Me | bond | B$^a$ | 2-Me-6-F | — |
| 1-886 | cHx | A$^b$ | Me | Me | bond | B$^a$ | 2-Me-3-Cl | — |
| 1-887 | cHx | A$^b$ | Me | Me | bond | B$^a$ | 2-Me-5-Cl | — |
| 1-888 | cHx | A$^b$ | Me | Me | bond | B$^a$ | 2-Me-6-Cl | — |
| 1-889 | cHx | A$^b$ | Me | Me | bond | B$^a$ | 2,3-di-OMe | — |
| 1-890 | cHx | A$^b$ | Me | Me | bond | B$^a$ | 2,5-di-OMe | — |
| 1-891 | cHx | A$^b$ | Me | Me | bond | B$^a$ | 2,6-di-OMe | — |
| 1-892 | cHx | A$^b$ | Me | Me | bond | B$^a$ | 2-OMe-3-Me | — |
| 1-893 | cHx | A$^b$ | Me | Me | bond | B$^a$ | 2-OMe-5-Me | — |
| 1-894 | cHx | A$^b$ | Me | Me | bond | B$^a$ | 2-OMe-3-F | — |
| 1-895 | cHx | A$^b$ | Me | Me | bond | B$^a$ | 2-OMe-5-F | — |
| 1-896 | cHx | A$^b$ | Me | Me | bond | B$^a$ | 2-OMe-6-F | — |
| 1-897 | cHx | A$^b$ | Me | Me | bond | B$^a$ | 2-OMe-3-Cl | — |
| 1-898 | cHx | A$^b$ | Me | Me | bond | B$^a$ | 2-OMe-5-Cl | — |
| 1-899 | cHx | A$^b$ | Me | Me | bond | B$^a$ | 2-OMe-6-Cl | — |
| 1-900 | cHx | A$^b$ | Me | Me | bond | B$^a$ | 2,3-di-F | — |
| 1-901 | cHx | A$^b$ | Me | Me | bond | B$^a$ | 2,5-di-F | — |
| 1-902 | cHx | A$^b$ | Me | Me | bond | B$^a$ | 2,6-di-F | — |
| 1-903 | cHx | A$^b$ | Me | Me | bond | B$^a$ | 2-F-3-Me | — |
| 1-904 | cHx | A$^b$ | Me | Me | bond | B$^a$ | 2-F-5-Me | — |
| 1-905 | cHx | A$^b$ | Me | Me | bond | B$^a$ | 2-F-3-OMe | — |
| 1-906 | cHx | A$^b$ | Me | Me | bond | B$^a$ | 2-F-5-OMe | — |
| 1-907 | cHx | A$^b$ | Me | Me | bond | B$^a$ | 2-F-3-Cl | — |
| 1-908 | cHx | A$^b$ | Me | Me | bond | B$^a$ | 2-F-5-Cl | — |
| 1-909 | cHx | A$^b$ | Me | Me | bond | B$^a$ | 2-F-6-Cl | — |
| 1-910 | cHx | A$^b$ | Me | Me | bond | B$^a$ | 2,3-di-Cl | — |
| 1-911 | cHx | A$^b$ | Me | Me | bond | B$^a$ | 2,5-di-Cl | — |
| 1-912 | cHx | A$^b$ | Me | Me | bond | B$^a$ | 2,6-di-Cl | — |
| 1-913 | cHx | A$^b$ | Me | Me | bond | B$^a$ | 2-Cl-3-Me | — |
| 1-914 | cHx | A$^b$ | Me | Me | bond | B$^a$ | 2-Cl-5-Me | — |
| 1-915 | cHx | A$^b$ | Me | Me | bond | B$^a$ | 2-Cl-3-OMe | — |
| 1-916 | cHx | A$^b$ | Me | Me | bond | B$^a$ | 2-Cl-5-OMe | — |

| ID | | | | | | | | |
|---|---|---|---|---|---|---|---|---|
| 1-917 | cHx | A[b] | Me | Me | bond | B[a] | 2-Cl-3-F | — |
| 1-918 | cHx | A[b] | Me | Me | bond | B[a] | 2-Cl-5-F | — |
| 1-919 | 4-F-Ph | A[b] | Me | Me | bond | B[a] | — | — |
| 1-920 | 4-F-Ph | A[b] | Me | Me | bond | B[a] | 2-Me | — |
| 1-921 | 4-F-Ph | A[b] | Me | Me | bond | B[a] | 3-Me | — |
| 1-922 | 4-F-Ph | A[b] | Me | Me | bond | B[a] | 2-OMe | — |
| 1-923 | 4-F-Ph | A[b] | Me | Me | bond | B[a] | 3-OMe | — |
| 1-924 | 4-F-Ph | A[b] | Me | Me | bond | B[a] | 2-F | — |
| 1-925 | 4-F-Ph | A[b] | Me | Me | bond | B[a] | 3-F | — |
| 1-926 | 4-F-Ph | A[b] | Me | Me | bond | B[a] | 2-Cl | — |
| 1-927 | 4-F-Ph | A[b] | Me | Me | bond | B[a] | 3-Cl | — |
| 1-928 | 4-F-Ph | A[b] | Me | Me | bond | B[a] | 2,3-di-Me | — |
| 1-929 | 4-F-Ph | A[b] | Me | Me | bond | B[a] | 2,5-di-Me | — |
| 1-930 | 4-F-Ph | A[b] | Me | Me | bond | B[a] | 2,6-di-Me | — |
| 1-931 | 4-F-Ph | A[b] | Me | Me | bond | B[a] | 2-Me-3-OMe | — |
| 1-932 | 4-F-Ph | A[b] | Me | Me | bond | B[a] | 2-Me-5-OMe | — |
| 1-933 | 4-F-Ph | A[b] | Me | Me | bond | B[a] | 2-Me-6-OMe | — |
| 1-934 | 4-F-Ph | A[b] | Me | Me | bond | B[a] | 2-Me-3-F | — |
| 1-935 | 4-F-Ph | A[b] | Me | Me | bond | B[a] | 2-Me-5-F | — |
| 1-936 | 4-F-Ph | A[b] | Me | Me | bond | B[a] | 2-Me-6-F | — |
| 1-937 | 4-F-Ph | A[b] | Me | Me | bond | B[a] | 2-Me-3-Cl | — |
| 1-938 | 4-F-Ph | A[b] | Me | Me | bond | B[a] | 2-Me-5-Cl | — |
| 1-939 | 4-F-Ph | A[b] | Me | Me | bond | B[a] | 2-Me-6-Cl | — |
| 1-940 | 4-F-Ph | A[b] | Me | Me | bond | B[a] | 2,3-di-OMe | — |
| 1-941 | 4-F-Ph | A[b] | Me | Me | bond | B[a] | 2,5-di-OMe | — |
| 1-942 | 4-F-Ph | A[b] | Me | Me | bond | B[a] | 2,6-di-OMe | — |
| 1-943 | 4-F-Ph | A[b] | Me | Me | bond | B[a] | 2-OMe-3-Me | — |
| 1-944 | 4-F-Ph | A[b] | Me | Me | bond | B[a] | 2-OMe-5-Me | — |
| 1-945 | 4-F-Ph | A[b] | Me | Me | bond | B[a] | 2-OMe-3-F | — |
| 1-946 | 4-F-Ph | A[b] | Me | Me | bond | B[a] | 2-OMe-5-F | — |
| 1-947 | 4-F-Ph | A[b] | Me | Me | bond | B[a] | 2-OMe-6-F | — |
| 1-948 | 4-F-Ph | A[b] | Me | Me | bond | B[a] | 2-OMe-3-Cl | — |
| 1-949 | 4-F-Ph | A[b] | Me | Me | bond | B[a] | 2-OMe-5-Cl | — |
| 1-950 | 4-F-Ph | A[b] | Me | Me | bond | B[a] | 2-OMe-6-Cl | — |
| 1-951 | 4-F-Ph | A[b] | Me | Me | bond | B[a] | 2,3-di-F | — |
| 1-952 | 4-F-Ph | A[b] | Me | Me | bond | B[a] | 2,5-di-F | — |
| 1-953 | 4-F-Ph | A[b] | Me | Me | bond | B[a] | 2,6-di-F | — |
| 1-954 | 4-F-Ph | A[b] | Me | Me | bond | B[a] | 2-F-3-Me | — |
| 1-955 | 4-F-Ph | A[b] | Me | Me | bond | B[a] | 2-F-5-Me | — |
| 1-956 | 4-F-Ph | A[b] | Me | Me | bond | B[a] | 2-F-3-OMe | — |
| 1-957 | 4-F-Ph | A[b] | Me | Me | bond | B[a] | 2-F-5-OMe | — |
| 1-958 | 4-F-Ph | A[b] | Me | Me | bond | B[a] | 2-F-3-Cl | — |
| 1-959 | 4-F-Ph | A[b] | Me | Me | bond | B[a] | 2-F-5-Cl | — |
| 1-960 | 4-F-Ph | A[b] | Me | Me | bond | B[a] | 2-F-6-Cl | — |
| 1-961 | 4-F-Ph | A[b] | Me | Me | bond | B[a] | 2,3-di-Cl | — |
| 1-962 | 4-F-Ph | A[b] | Me | Me | bond | B[a] | 2,5-di-Cl | — |
| 1-963 | 4-F-Ph | A[b] | Me | Me | bond | B[a] | 2,6-di-Cl | — |
| 1-964 | 4-F-Ph | A[b] | Me | Me | bond | B[a] | 2-Cl-3-Me | — |
| 1-965 | 4-F-Ph | A[b] | Me | Me | bond | B[a] | 2-Cl-5-Me | — |
| 1-966 | 4-F-Ph | A[b] | Me | Me | bond | B[a] | 2-Cl-3-OMe | — |
| 1-967 | 4-F-Ph | A[b] | Me | Me | bond | B[a] | 2-Cl-5-OMe | — |
| 1-968 | 4-F-Ph | A[b] | Me | Me | bond | B[a] | 2-Cl-3-F | — |
| 1-969 | 4-F-Ph | A[b] | Me | Me | bond | B[a] | 2-Cl-5-F | — |
| 1-970 | nBu | A[b] | Me | Me | bond | B[a] | 4-OMe | — |
| 1-971 | nBu | A[a] | Me | Me | bond | B[a] | 2-Cl-5-OMe | — |
| 1-972 | nBu | A[b] | Me | Me | bond | B[e] | 5-Cl | — |
| 1-973 | nBu | A[b] | Me | Me | bond | B[a] | 2,4-di-F | — |
| 1-974 | nBu | A[b] | Me | Me | bond | B[a] | 4-F | — |
| 1-975 | (CH$_2$)$_3$OMe | A[b] | Me | Me | bond | B[a] | 2-Cl | — |
| 1-976 | nBu | A[b] | Me | Me | bond | B[a] | 2,3,5-tri-F | — |
| 1-977 | iBu | A[b] | Me | Me | bond | B[a] | 2,3,5-tri-F | — |
| 1-978 | iBu | A[b] | Me | Me | bond | B[a] | — | 2-O(CH$_2$)$_3$OMe |
| 1-979 | nBu | A[b] | Me | Me | bond | B[a] | 2-Me-4-F | — |
| 1-980 | nBu | A[b] | Me | Me | bond | B[a] | 2-Cl-4-F | — |
| 1-981 | iBu | A[b] | Me | Me | bond | B[a] | 2,4-di-F | — |
| 1-982 | iBu | A[b] | Me | Me | bond | B[a] | 2-Me-4-F | — |
| 1-983 | iBu | A[b] | Me | Me | bond | B[a] | 2-Cl-4-F | — |
| 1-984 | CH$_2$CF$_3$ | A[b] | Me | Me | bond | B[a] | 2-Me-5-F | — |
| 1-985 | (S)Bu-Me | A[b] | Me | Me | bond | B[a] | 4-F | — |
| 1-986 | nBu | A[b] | Me | Me | bond | B[a] | 4-F | 2-O(CH$_2$)$_3$OMe |
| 1-987 | iBu | A[b] | Me | Me | bond | B[a] | 4-F | 2-O(CH$_2$)$_3$OMe |
| 1-988 | nBu | A[b] | Me | Me | bond | B[a] | 5-F | 2-O(CH$_2$)$_3$OMe |
| 1-989 | iBu | A[b] | Me | Me | bond | B[a] | 5-F | 2-O(CH$_2$)$_3$OMe |
| 1-990 | CH$_2$CF$_3$ | A[b] | Me | Me | bond | B[a] | 2,6-di-F | — |
| 1-991 | CH$_2$CF$_3$ | A[b] | Me | Me | bond | B[a] | 2-Cl-5-F | — |
| 1-992 | CH$_2$CF$_3$ | A[b] | Me | Me | bond | B[a] | 2-Me-4-F | — |
| 1-993 | 4-Thp | A[e] | Me | Me | bond | B[a] | 2-Cl-5-F | — |
| 1-994 | iBu | A[b] | Me | Me | bond | B[a] | — | 2-O(CH$_2$)$_2$OMe |
| 1-995 | Ph | A[b] | Me | Me | bond | B[a] | 2-Cl | — |
| 1-996 | Ph | A[b] | Me | Me | bond | B[a] | 2-Cl-5-F | — |
| 1-997 | cHx | A[b] | Me | Me | bond | B[a] | 2,4-di-F | — |
| 1-998 | cHx | A[b] | Me | Me | bond | B[a] | 2-Cl-4-F | — |

| | | | | | | | | |
|---|---|---|---|---|---|---|---|---|
| 1-999 | 2-Py | $A^b$ | Me | Me | bond | $B^a$ | 2-Cl-5-F | — |
| 1-1000 | 4-F-Ph | $A^b$ | Me | Me | bond | $B^a$ | 2-Cl-4-F | — |
| 1-1001 | diF-cHx | $A^b$ | Me | Me | bond | $B^a$ | 2-Cl-5-F | — |
| 1-1002 | diF-cHx | $A^b$ | Me | Me | bond | $B^a$ | 2-Me-5-F | — |
| 1-1003 | $(CH_2)_2CHMe_2$ | $A^b$ | Me | Me | bond | $B^a$ | 2-Me-5-F | — |
| 1-1004 | $(CH_2)_2CMe_2$ | $A^b$ | Me | Me | bond | $B^a$ | 2-Cl | — |
| 1-1005 | 2-Py | $A^b$ | Me | Me | bond | $B^a$ | 2-Cl | — |
| 1-1006 | $(CH_2)_2CHMe_2$ | $A^b$ | Me | Me | bond | $B^a$ | 2-Cl-5-F | — |
| 1-1007 | 2-Py | $A^b$ | Me | Me | bond | $B^a$ | 2-Me-5-F | — |
| 1-1008 | 2-Py | $A^b$ | Me | Me | bond | $B^a$ | 2-Me | — |
| 1-1009 | 5-Cl-2-Py | $A^b$ | Me | Me | bond | $B^a$ | 2-Cl | — |
| 1-1010 | $(CH_2)_2CMe_3$ | $A^b$ | Me | Me | bond | $B^a$ | 2-Cl-5-F | — |
| 1-1011 | 6-Me-2-Py | $A^b$ | Me | Me | bond | $B^a$ | 2-Cl | — |
| 1-1012 | 5-Me-2-Py | $A^b$ | Me | Me | bond | $B^a$ | 2-Cl | — |
| 1-1013 | 3-Py | $A^b$ | Me | Me | bond | $B^a$ | 2-Cl | — |
| 1-1014 | 4-Py | $A^b$ | Me | Me | bond | $B^a$ | 2-Cl | — |
| 1-1015 | 3-Py | $A^b$ | Me | Me | bond | $B^a$ | 2-Me-5-F | — |
| 1-1016 | iBu | $A^b$ | Me | Me | bond | $B^a$ | 2-$CF_3$ | — |
| 1-1017 | $CH_2CMe_3$ | $A^b$ | Me | Me | bond | $B^a$ | 2-$CF_3$ | — |
| 1-1018 | 3-Me-2-Py | $A^b$ | Me | Me | bond | $B^a$ | 2-Cl | — |
| 1-1019 | 4-Py | $A^b$ | Me | Me | bond | $B^a$ | 2-Me-5-F | — |
| 1-1020 | 6-Me-3-Py | $A^b$ | Me | Me | bond | $B^a$ | 2-Cl | — |
| 1-1021 | iBu | $A^b$ | Me | Me | bond | $B^a$ | 2-Et | — |
| 1-1022 | $CH_2CMe_3$ | $A^b$ | Me | Me | bond | $B^a$ | 2-Et | — |
| 1-1023 | $(CH_2)_2CMe_3$ | $A^b$ | Me | Me | bond | $B^a$ | 2-Cl | — |
| 1-1024 | 5-F-2-Py | $A^b$ | Me | Me | bond | $B^a$ | 2-Cl | — |
| 1-1025 | $CH_2$(1-Me-cPr) | $A^b$ | Me | Me | bond | $B^a$ | 2-Cl | — |
| 1-1026 | $CH_2CMe_2CH_2CH_3$ | $A^b$ | Me | Me | bond | $B^a$ | 2-Cl | — |
| 1-1027 | 2-Me-3-Py | $A^b$ | Me | Me | bond | $B^a$ | 2-Cl | — |
| 1-1028 | $(CH_2)_2(cPr)$ | $A^b$ | Me | Me | bond | $B^a$ | 2-Me-5-F | — |
| 1-1029 | $CH_2CMe_2OH$ | $A^b$ | Me | Me | bond | $B^a$ | 2-Et | — |
| 1-1030 | $CH_2C(CH_2CH_3)_2(OH)$ | $A^b$ | Me | Me | bond | $B^a$ | 2-Cl | — |
| 1-1031 | $(CH_2)_2CMe_2OH$ | $A^b$ | Me | Me | bond | $B^a$ | 2-Cl | — |
| 1-1032 | $(CH_2)_2CMe_2OH$ | $A^b$ | Me | Me | bond | $B^a$ | 2-Me-5-F | — |
| 1-1033 | $(CH_2)_2CMe_2OH$ | $A^b$ | Me | Me | bond | $B^a$ | 2-Cl-5-F | — |
| 1-1034 | $(CH_2)_2CMe_2OH$ | $A^b$ | Me | Me | bond | $B^a$ | 2-Me | — |
| 1-1035 | $(CH_2)_2CMe_2OH$ | $A^b$ | Me | Me | bond | $B^a$ | 2-Et | — |
| 1-1036 | $CH_2C(CH_2CH3)_2(OH)$ | $A^b$ | Me | Me | bond | $B^a$ | 2-Me-5-F | — |
| 1-1037 | $(CH_2)_2CMe_2OH$ | $A^b$ | Me | Me | bond | $B^a$ | 2-$CF_3$ | — |
| 1-1038 | trans-4-HO-cHx | $A^b$ | Me | Me | bond | $B^a$ | 2-Cl | — |
| 1-1039 | trans-4-HO-cHx | $A^b$ | Me | Me | bond | $B^a$ | 2-Me-5-F | — |
| 1-1040 | trans-4-HO-cHx | $A^b$ | Me | Me | bond | $B^a$ | 2-Cl-5-F | — |
| 1-1041 | trans-4-HO-cHx | $A^b$ | Me | Me | bond | $B^a$ | 2-Me-3-F | — |
| 1-1042 | nBu | $A^e$ | Me | Me | bond | $B^a$ | 2-Cl-5-F | — |

TABLE 2

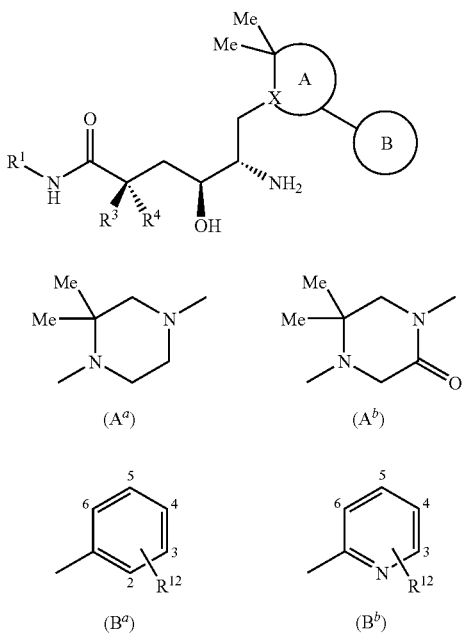

(I-2)

| Exemplary Compound No. | $R^1$ | $R^3$ | $R^4$ | A | B | $R^{12}$ |
|---|---|---|---|---|---|---|
| 2-1 | nBu | Et | H | $A^a$ | $B^a$ | — |
| 2-2 | nBu | Et | H | $A^b$ | $B^a$ | — |
| 2-3 | nBu | Et | H | $A^b$ | $B^a$ | 2-Me |
| 2-4 | nBu | Et | H | $A^b$ | $B^a$ | 2-OMe |
| 2-5 | nBu | Et | H | $A^b$ | $B^a$ | 2-F |
| 2-6 | nBu | Et | H | $A^b$ | $B^a$ | 2-Cl |
| 2-7 | nBu | Et | H | $A^b$ | $B^b$ | — |
| 2-8 | nBu | $CMe_2(OH)$ | H | $A^a$ | $B^a$ | — |
| 2-9 | nBu | $CMe_2(OH)$ | H | $A^b$ | $B^a$ | — |
| 2-10 | nBu | $CMe_2(OH)$ | H | $A^b$ | $B^a$ | 2-Me |
| 2-11 | nBu | $CMe_2(OH)$ | H | $A^b$ | $B^a$ | 2-OMe |
| 2-12 | nBu | $CMe_2(OH)$ | H | $A^b$ | $B^a$ | 2-F |
| 2-13 | nBu | $CMe_2(OH)$ | H | $A^b$ | $B^a$ | 2-Cl |
| 2-14 | nBu | $CMe_2(OH)$ | H | $A^b$ | $B^b$ | — |
| 2-15 | nBu | cPr | H | $A^a$ | $B^a$ | — |
| 2-16 | nBu | cPr | H | $A^b$ | $B^a$ | — |
| 2-17 | nBu | cPr | H | $A^b$ | $B^a$ | 2-Me |
| 2-18 | nBu | cPr | H | $A^b$ | $B^a$ | 2-OMe |
| 2-19 | nBu | cPr | H | $A^b$ | $B^a$ | 2-F |
| 2-20 | nBu | cPr | H | $A^b$ | $B^a$ | 2-Cl |
| 2-21 | nBu | cPr | H | $A^b$ | $B^b$ | — |
| 2-22 | nBu | Me | Me | $A^a$ | $B^a$ | — |
| 2-23 | nBu | Me | Me | $A^b$ | $B^a$ | — |
| 2-24 | nBu | Me | Me | $A^b$ | $B^a$ | 2-Me |
| 2-25 | nBu | Me | Me | $A^b$ | $B^a$ | 2-OMe |
| 2-26 | nBu | Me | Me | $A^b$ | $B^a$ | 2-F |
| 2-27 | nBu | Me | Me | $A^b$ | $B^a$ | 2-Cl |

TABLE 2-continued

| | | | | | | |
|---|---|---|---|---|---|---|
| 2-28 | nBu | Me | Me | $A^b$ | $B^b$ | — |
| 2-29 | (S)Bu-Me | Et | H | $A^a$ | $B^a$ | — |
| 2-30 | (S)Bu-Me | Et | H | $A^b$ | $B^a$ | — |
| 2-31 | (S)Bu-Me | Et | H | $A^b$ | $B^a$ | 2-Me |
| 2-32 | (S)Bu-Me | Et | H | $A^b$ | $B^a$ | 2-OMe |
| 2-33 | (S)Bu-Me | Et | H | $A^b$ | $B^a$ | 2-F |
| 2-34 | (S)Bu-Me | Et | H | $A^b$ | $B^a$ | 2-Cl |
| 2-35 | (S)Bu-Me | Et | H | $A^b$ | $B^b$ | — |
| 2-36 | (S)Bu-Me | CMe$_2$(OH) | H | $A^a$ | $B^a$ | — |
| 2-37 | (S)Bu-Me | CMe$_2$(OH) | H | $A^b$ | $B^a$ | — |
| 2-38 | (S)Bu-Me | CMe$_2$(OH) | H | $A^b$ | $B^a$ | 2-Me |
| 2-39 | (S)Bu-Me | CMe$_2$(OH) | H | $A^b$ | $B^a$ | 2-OMe |
| 2-40 | (S)Bu-Me | CMe$_2$(OH) | H | $A^b$ | $B^a$ | 2-F |
| 2-41 | (S)Bu-Me | CMe$_2$(OH) | H | $A^b$ | $B^a$ | 2-Cl |
| 2-42 | (S)Bu-Me | CMe$_2$(OH) | H | $A^b$ | $B^b$ | — |
| 2-43 | (S)Bu-Me | cPr | H | $A^a$ | $B^a$ | — |
| 2-44 | (S)Bu-Me | cPr | H | $A^b$ | $B^a$ | — |
| 2-45 | (S)Bu-Me | cPr | H | $A^b$ | $B^a$ | 2-Me |
| 2-46 | (S)Bu-Me | cPr | H | $A^b$ | $B^a$ | 2-OMe |
| 2-47 | (S)Bu-Me | cPr | H | $A^b$ | $B^a$ | 2-F |
| 2-48 | (S)Bu-Me | cPr | H | $A^b$ | $B^a$ | 2-Cl |
| 2-49 | (S)Bu-Me | cPr | H | $A^b$ | $B^b$ | — |
| 2-50 | (S)Bu-Me | Me | Me | $A^a$ | $B^a$ | — |
| 2-51 | (S)Bu-Me | Me | Me | $A^b$ | $B^a$ | — |
| 2-52 | (S)Bu-Me | Me | Me | $A^b$ | $B^a$ | 2-Me |
| 2-53 | (S)Bu-Me | Me | Me | $A^b$ | $B^a$ | 2-OMe |
| 2-54 | (S)Bu-Me | Me | Me | $A^b$ | $B^a$ | 2-F |
| 2-55 | (S)Bu-Me | Me | Me | $A^b$ | $B^a$ | 2-Cl |
| 2-56 | (S)Bu-Me | Me | Me | $A^b$ | $B^b$ | — |
| 2-57 | CH$_2$C(Me)$_2$CH$_2$OH | Et | H | $A^a$ | $B^a$ | — |
| 2-58 | CH$_2$C(Me)$_2$CH$_2$OH | Et | H | $A^b$ | $B^a$ | — |
| 2-59 | CH$_2$C(Me)$_2$CH$_2$OH | Et | H | $A^b$ | $B^a$ | 2-Me |
| 2-60 | CH$_2$C(Me)$_2$CH$_2$OH | Et | H | $A^b$ | $B^a$ | 2-OMe |
| 2-61 | CH$_2$C(Me)$_2$CH$_2$OH | Et | H | $A^b$ | $B^a$ | 4-Me |
| 2-62 | CH$_2$C(Me)$_2$CH$_2$OH | Et | H | $A^b$ | $B^a$ | 2-Cl |
| 2-63 | CH$_2$C(Me)$_2$CH$_2$OH | Et | H | $A^b$ | $B^b$ | — |
| 2-64 | CH$_2$C(Me)$_2$CH$_2$OH | CMe$_2$(OH) | H | $A^a$ | $B^a$ | — |
| 2-65 | CH$_2$C(Me)$_2$CH$_2$OH | CMe$_2$(OH) | H | $A^b$ | $B^a$ | — |
| 2-66 | CH$_2$C(Me)$_2$CH$_2$OH | CMe$_2$(OH) | H | $A^b$ | $B^a$ | 2-Me |
| 2-67 | CH$_2$C(Me)$_2$CH$_2$OH | CMe$_2$(OH) | H | $A^b$ | $B^a$ | 2-OMe |
| 2-68 | CH$_2$C(Me)$_2$CH$_2$OH | CMe$_2$(OH) | H | $A^b$ | $B^a$ | 2-F |
| 2-69 | CH$_2$C(Me)$_2$CH$_2$OH | CMe$_2$(OH) | H | $A^b$ | $B^a$ | 2-Cl |
| 2-70 | CH$_2$C(Me)$_2$CH$_2$OH | CMe$_2$(OH) | H | $A^b$ | $B^b$ | — |
| 2-71 | CH$_2$C(Me)$_2$CH$_2$OH | cPr | H | $A^a$ | $B^a$ | — |
| 2-72 | CH$_2$C(Me)$_2$CH$_2$OH | cPr | H | $A^b$ | $B^a$ | — |
| 2-73 | CH$_2$C(Me)$_2$CH$_2$OH | cPr | H | $A^b$ | $B^a$ | 2-Me |
| 2-74 | CH$_2$C(Me)$_2$CH$_2$OH | cPr | H | $A^b$ | $B^a$ | 2-OMe |
| 2-75 | CH$_2$C(Me)$_2$CH$_2$OH | cPr | H | $A^b$ | $B^a$ | 2-F |
| 2-76 | CH$_2$C(Me)$_2$CH$_2$OH | cPr | H | $A^b$ | $B^a$ | 2-Cl |
| 2-77 | CH$_2$C(Me)$_2$CH$_2$OH | cPr | H | $A^b$ | $B^b$ | — |
| 2-78 | CH$_2$C(Me)$_2$CH$_2$OH | Me | Me | $A^a$ | $B^a$ | — |
| 2-79 | CH$_2$C(Me)$_2$CH$_2$OH | Me | Me | $A^b$ | $B^a$ | — |
| 2-80 | CH$_2$C(Me)$_2$CH$_2$OH | Me | Me | $A^b$ | $B^a$ | 2-Me |
| 2-81 | CH$_2$C(Me)$_2$CH$_2$OH | Me | Me | $A^b$ | $B^a$ | 2-OMe |
| 2-82 | CH$_2$C(Me)$_2$CH$_2$OH | Me | Me | $A^b$ | $B^a$ | 2-F |
| 2-83 | CH$_2$C(Me)$_2$CH$_2$OH | Me | Me | $A^b$ | $B^a$ | 2-Cl |
| 2-84 | CH$_2$C(Me)$_2$CH$_2$OH | Me | Me | $A^b$ | $B^b$ | — |
| 2-85 | CH$_2$C(Me)$_2$CONH$_2$ | Et | H | $A^a$ | $B^a$ | — |
| 2-86 | CH$_2$C(Me)$_2$CONH$_2$ | Et | H | $A^b$ | $B^a$ | — |
| 2-87 | CH$_2$C(Me)$_2$CONH$_2$ | Et | H | $A^b$ | $B^a$ | 2-Me |
| 2-88 | CH$_2$C(Me)$_2$CONH$_2$ | Et | H | $A^b$ | $B^a$ | 2-OMe |
| 2-89 | CH$_2$C(Me)$_2$CONH$_2$ | Et | H | $A^b$ | $B^a$ | 2-F |
| 2-90 | CH$_2$C(Me)$_2$CONH$_2$ | Et | H | $A^b$ | $B^a$ | 2-Cl |
| 2-91 | CH$_2$C(Me)$_2$CONH$_2$ | Et | H | $A^b$ | $B^b$ | — |
| 2-92 | CH$_2$C(Me)$_2$CONH$_2$ | CMe$_2$(OH) | H | $A^a$ | $B^a$ | — |
| 2-93 | CH$_2$C(Me)$_2$CONH$_2$ | CMe$_2$(OH) | H | $A^b$ | $B^a$ | — |
| 2-94 | CH$_2$C(Me)$_2$CONH$_2$ | CMe$_2$(OH) | H | $A^b$ | $B^a$ | 2-Me |
| 2-95 | CH$_2$C(Me)$_2$CONH$_2$ | CMe$_2$(OH) | H | $A^b$ | $B^a$ | 2-OMe |
| 2-96 | CH$_2$C(Me)$_2$CONH$_2$ | CMe$_2$(OH) | H | $A^b$ | $B^a$ | 2-F |
| 2-97 | CH$_2$C(Me)$_2$CONH$_2$ | CMe$_2$(OH) | H | $A^b$ | $B^a$ | 2-Cl |
| 2-98 | CH$_2$C(Me)$_2$CONH$_2$ | CMe$_2$(OH) | H | $A^b$ | $B^b$ | — |
| 2-99 | CH$_2$C(Me)$_2$CONH$_2$ | cPr | H | $A^a$ | $B^a$ | — |
| 2-100 | CH$_2$C(Me)$_2$CONH$_2$ | cPr | H | $A^b$ | $B^a$ | — |
| 2-101 | CH$_2$C(Me)$_2$CONH$_2$ | cPr | H | $A^b$ | $B^a$ | 2-Me |
| 2-102 | CH$_2$C(Me)$_2$CONH$_2$ | cPr | H | $A^b$ | $B^a$ | 2-OMe |
| 2-103 | CH$_2$C(Me)$_2$CONH$_2$ | cPr | H | $A^b$ | $B^a$ | 2-F |
| 2-104 | CH$_2$C(Me)$_2$CONH$_2$ | cPr | H | $A^b$ | $B^a$ | 2-Cl |
| 2-105 | CH$_2$C(Me)$_2$CONH$_2$ | cPr | H | $A^b$ | $B^b$ | — |
| 2-106 | CH$_2$C(Me)$_2$CONH$_2$ | Me | Me | $A^a$ | $B^a$ | — |
| 2-107 | CH$_2$C(Me)$_2$CONH$_2$ | Me | Me | $A^b$ | $B^a$ | — |
| 2-108 | CH$_2$C(Me)$_2$CONH$_2$ | Me | Me | $A^b$ | $B^a$ | 2-Me |
| 2-109 | CH$_2$C(Me)$_2$CONH$_2$ | Me | Me | $A^b$ | $B^a$ | 2-OMe |
| 2-110 | CH$_2$C(Me)$_2$CONH$_2$ | Me | Me | $A^b$ | $B^a$ | 2-F |
| 2-111 | CH$_2$C(Me)$_2$CONH$_2$ | Me | Me | $A^b$ | $B^a$ | 2-Cl |
| 2-112 | CH$_2$C(Me)$_2$CONH$_2$ | Me | Me | $A^b$ | $B^b$ | — |
| 2-113 | cPn | Et | H | $A^a$ | $B^a$ | — |
| 2-114 | cPn | Et | H | $A^b$ | $B^a$ | — |
| 2-115 | cPn | Et | H | $A^b$ | $B^a$ | 2-Me |
| 2-116 | cPu | Et | H | $A^b$ | $B^a$ | 2-OMe |
| 2-117 | cPn | Et | H | $A^b$ | $B^a$ | 2-F |
| 2-118 | cPn | Et | H | $A^b$ | $B^a$ | 2-Cl |
| 2-119 | cPn | Et | H | $A^b$ | $B^b$ | — |
| 2-120 | cPn | CMe$_2$(OH) | H | $A^a$ | $B^a$ | — |
| 2-121 | cPn | CMe$_2$(OH) | H | $A^b$ | $B^a$ | — |
| 2-122 | cPn | CMe$_2$(OH) | H | $A^b$ | $B^a$ | 2-Me |
| 2-123 | cPn | CMe$_2$(OH) | H | $A^b$ | $B^a$ | 2-OMe |
| 2-124 | cPn | CMe$_2$(OH) | H | $A^b$ | $B^a$ | 2-F |
| 2-125 | cPn | CMe$_2$(OH) | H | $A^b$ | $B^a$ | 2-Cl |
| 2-126 | cPn | CMe$_2$(OH) | H | $A^b$ | $B^b$ | — |
| 2-127 | cPn | cPr | H | $A^a$ | $B^a$ | — |
| 2-128 | cPn | cPr | H | $A^b$ | $B^a$ | — |
| 2-129 | cPn | cPr | H | $A^b$ | $B^a$ | 2-Me |
| 2-130 | cPn | cPr | H | $A^b$ | $B^a$ | 2-OMe |
| 2-131 | cPn | cPr | H | $A^b$ | $B^a$ | 2-F |
| 2-132 | cPn | cPr | H | $A^b$ | $B^a$ | 2-Cl |
| 2-133 | cPn | cPr | H | $A^b$ | $B^b$ | — |
| 2-134 | cPn | Me | Me | $A^a$ | $B^a$ | — |
| 2-135 | cPn | Me | Me | $A^b$ | $B^a$ | — |
| 2-136 | cPn | Me | Me | $A^b$ | $B^a$ | 2-Me |
| 2-137 | cPn | Me | Me | $A^b$ | $B^a$ | 2-OMe |
| 2-138 | cPn | Me | Me | $A^b$ | $B^a$ | 2-F |
| 2-139 | cPn | Me | Me | $A^b$ | $B^a$ | 2-Cl |
| 2-140 | cPn | Me | Me | $A^b$ | $B^b$ | — |
| 2-141 | nBu | Et | H | $A^b$ | $B^a$ | 2-Me-3-F |
| 2-142 | nBu | Et | H | $A^b$ | $B^a$ | 2-Me-5-F |
| 2-143 | nBu | Et | H | $A^b$ | $B^a$ | 2-Cl-5-F |
| 2-144 | nBu | Me | H | $A^b$ | $B^a$ | — |
| 2-145 | nBu | Me | H | $A^b$ | $B^a$ | 2-Me |
| 2-146 | nBu | Me | H | $A^b$ | $B^a$ | 2-F |
| 2-147 | nBu | Me | H | $A^b$ | $B^a$ | 2-Cl |
| 2-148 | nBu | Me | H | $A^b$ | $B^a$ | 2-Me-3-F |
| 2-149 | nBu | Me | H | $A^b$ | $B^a$ | 2-Me-5-F |
| 2-150 | nBu | Me | H | $A^b$ | $B^a$ | 2-Cl-5-F |
| 2-151 | iBu | Me | H | $A^b$ | $B^a$ | — |
| 2-152 | iBu | Me | H | $A^b$ | $B^a$ | 2-Me |
| 2-153 | iBu | Me | H | $A^b$ | $B^a$ | 2-F |
| 2-154 | iBu | Me | H | $A^b$ | $B^a$ | 2-Cl |
| 2-155 | iBu | Me | H | $A^b$ | $B^a$ | 2-Me-3-F |
| 2-156 | iBu | Me | H | $A^b$ | $B^a$ | 2-Me-5-F |
| 2-157 | iBu | Me | H | $A^b$ | $B^a$ | 2-Cl-5-F |
| 2-158 | iBu | Et | H | $A^b$ | $B^a$ | — |
| 2-159 | iBu | Et | H | $A^b$ | $B^a$ | 2-Me |
| 2-160 | iBu | Et | H | $A^b$ | $B^a$ | 2-F |
| 2-161 | iBu | Et | H | $A^b$ | $B^a$ | 2-Cl |
| 2-162 | iBu | Et | H | $A^b$ | $B^a$ | 2-Me-3-F |
| 2-163 | iBu | Et | H | $A^b$ | $B^a$ | 2-Me-5-F |
| 2-164 | iBu | Et | H | $A^b$ | $B^a$ | 2-Cl-5-F |
| 2-165 | CH$_2$CMe$_2$OH | Me | H | $A^b$ | $B^a$ | — |
| 2-166 | CH$_2$CMe$_2$OH | Me | H | $A^b$ | $B^a$ | 2-Me |
| 2-167 | CH$_2$CMe$_2$OH | Me | H | $A^b$ | $B^a$ | 2-F |
| 2-168 | CH$_2$CMe$_2$OH | Me | H | $A^b$ | $B^a$ | 2-Cl |
| 2-169 | CH$_2$CMe$_2$OH | Me | H | $A^b$ | $B^a$ | 2-Me-3-F |
| 2-170 | CH$_2$CMe$_2$OH | Me | H | $A^b$ | $B^a$ | 2-Me-5-F |
| 2-171 | CH$_2$CMe$_2$OH | Me | H | $A^b$ | $B^a$ | 2-Cl-5-F |
| 2-172 | CH$_2$CMe$_2$OH | Et | H | $A^b$ | $B^a$ | — |
| 2-173 | CH$_2$CMe$_2$OH | Et | H | $A^b$ | $B^a$ | 2-Me |
| 2-174 | CH$_2$CMe$_2$OH | Et | H | $A^b$ | $B^a$ | 2-F |
| 2-175 | CH$_2$CMe$_2$OH | Et | H | $A^b$ | $B^a$ | 2-Cl |
| 2-176 | CH$_2$CMe$_2$OH | Et | H | $A^b$ | $B^a$ | 2-Me-3-F |
| 2-177 | CH$_2$CMe$_2$OH | Et | H | $A^b$ | $B^a$ | 2-Me-5-F |
| 2-178 | CH$_2$CMe$_2$OH | Et | H | $A^b$ | $B^a$ | 2-Cl-5-F |
| 2-179 | CH$_2$CMe$_3$ | Me | H | $A^b$ | $B^a$ | — |
| 2-180 | CH$_2$CMe$_3$ | Me | H | $A^b$ | $B^a$ | 2-Me |
| 2-181 | CH$_2$CMe$_3$ | Me | H | $A^b$ | $B^a$ | 2-F |
| 2-182 | CH$_2$CMe$_3$ | Me | H | $A^b$ | $B^a$ | 2-Cl |
| 2-183 | CH$_2$CMe$_3$ | Me | H | $A^b$ | $B^a$ | 2-Me-3-F |
| 2-184 | CH$_2$CMe$_3$ | Me | H | $A^b$ | $B^a$ | 2-Me-5-F |
| 2-185 | CH$_2$CMe$_3$ | Me | H | $A^b$ | $B^a$ | 2-Cl-5-F |
| 2-186 | CH$_2$CMe$_3$ | Et | H | $A^b$ | $B^a$ | — |
| 2-187 | CH$_2$CMe$_3$ | Et | H | $A^b$ | $B^a$ | 2-Me |

TABLE 2-continued

| | | | | | | |
|---|---|---|---|---|---|---|
| 2-188 | CH$_2$CMe$_3$ | Et | H | A$^b$ | B$^a$ | 2-F |
| 2-189 | CH$_2$CMe$_3$ | Et | H | A$^b$ | B$^a$ | 2-Cl |
| 2-190 | CH$_2$CMe$_3$ | Et | H | A$^b$ | B$^a$ | 2-Me-3-F |
| 2-191 | CH$_2$CMe$_3$ | Et | H | A$^b$ | B$^a$ | 2-Me-5-F |
| 2-192 | CH$_2$CMe$_3$ | Et | H | A$^b$ | B$^a$ | 2-Cl-5-F |
| 2-193 | CH$_2$CMe$_2$OH | Et | H | A$^b$ | B$^a$ | 2-Et |
| 2-194 | CH$_2$CMe$_2$OH | nPr | H | A$^b$ | B$^a$ | 2-Me-5-F |
| 2-195 | CH$_2$CMe$_2$OH | nPr | H | A$^b$ | B$^a$ | 2-Cl |
| 2-196 | CH$_2$CMe$_3$ | nPr | H | A$^b$ | B$^a$ | 2-Me-5-F |
| 2-197 | (CH$_2$)$_2$CMe$_2$OH | Me | H | A$^b$ | B$^a$ | 2-Et |
| 2-198 | (CH$_2$)$_2$CMe$_2$OH | Me | H | A$^b$ | B$^a$ | 2-Et |
| 2-199 | CH$_2$CMe$_3$ | Et | H | A$^b$ | B$^a$ | 2-Et |
| 2-200 | CH$_2$CMe$_3$ | nPr | H | A$^b$ | B$^a$ | 2-Cl |
| 2-201 | (CH$_2$)$_2$CMe$_2$OH | Et | H | A$^b$ | B$^a$ | 2-Cl |
| 2-202 | (CH$_2$)$_2$CMe$_2$OH | Et | H | A$^b$ | B$^a$ | 2-Me-5-F |
| 2-203 | (CH$_2$)$_2$CMe$_2$OH | Me | H | A$^b$ | B$^a$ | 2-Cl |
| 2-204 | (CH$_2$)$_2$CMe$_2$OH | Me | H | A$^b$ | B$^a$ | 2-Me-5-F |
| 2-205 | (CH$_2$)$_2$CMe$_2$OH | Et | H | A$^b$ | B$^a$ | 2-Me |
| 2-206 | (CH$_2$)$_2$CMe$_2$OH | Et | H | A$^b$ | B$^a$ | 2-Cl-5-F |
| 2-207 | (CH$_2$)$_2$CMe$_2$OH | Et | H | A$^b$ | B$^a$ | 2-Et |
| 2-208 | CH$_2$CMe$_3$ | cPr | H | A$^b$ | B$^a$ | 2-Cl |
| 2-209 | CH$_2$CMe$_3$ | cPr | H | A$^b$ | B$^a$ | 2-Cl-5-F |
| 2-210 | (CH$_2$)$_2$CMe$_2$OH | Me | H | A$^b$ | B$^a$ | 2-Cl-5-F |
| 2-211 | iBu | nPr | H | A$^b$ | B$^a$ | 2-Me-5-F |
| 2-212 | iBu | cPr | H | A$^b$ | B$^a$ | 2-Cl-5-F |
| 2-213 | CH$_2$CMe$_3$ | nPr | H | A$^b$ | B$^a$ | 2-Me |
| 2-214 | CH$_2$CMe$_3$ | nPr | H | A$^b$ | B$^a$ | 2-Me-3-F |
| 2-215 | iBu | nPr | H | A$^b$ | B$^a$ | 2-Me-3-F |
| 2-216 | iBu | nPr | H | A$^b$ | B$^a$ | 2-Me |
| 2-217 | CH$_2$CMe$_3$ | nPr | H | A$^b$ | B$^a$ | 2-Cl-5-F |
| 2-218 | iBu | nPr | H | A$^b$ | B$^a$ | 2-Cl |
| 2-219 | CH$_2$CMe$_3$ | cPr | H | A$^b$ | B$^a$ | 2-Me |
| 2-220 | iBu | cPr | H | A$^b$ | B$^a$ | 2-Et |
| 2-221 | iBu | Me | H | A$^b$ | B$^a$ | 2-Et |
| 2-222 | 4-F-Ph | Et | H | A$^b$ | B$^a$ | 2-Cl |
| 2-223 | 4-F-Ph | Et | H | A$^b$ | B$^a$ | 2-Cl-5-F |
| 2-224 | iBu | nPr | H | A$^b$ | B$^a$ | 2-Cl-5-F |
| 2-225 | iBu | cPr | H | A$^b$ | B$^a$ | 2-Cl |
| 2-226 | CH$_2$CMe$_3$ | cPr | H | A$^b$ | B$^a$ | 2-Me-3-F |
| 2-227 | iBu | iBu | H | A$^b$ | B$^a$ | 2-Me-5-F |
| 2-228 | CH$_2$CMe$_3$ | iBu | H | A$^b$ | B$^a$ | 2-Me-5-F |
| 2-229 | CH$_2$CMe$_3$ | iBu | H | A$^b$ | B$^a$ | 2-Cl |
| 2-230 | iBu | iBu | H | A$^b$ | B$^a$ | 2-Cl |
| 2-231 | iBu | cPr | H | A$^b$ | B$^a$ | 2-Me-3-F |
| 2-232 | CH$_2$CMe$_3$ | iBu | H | A$^b$ | B$^a$ | 2-Cl-5-F |
| 2-233 | cHx | Me | H | A$^b$ | B$^a$ | 2-Cl |
| 2-234 | iBu | iBu | H | A$^b$ | B$^a$ | 2-Cl-5-F |
| 2-235 | 4-F-Ph | Me | H | A$^b$ | B$^a$ | 2-Cl |
| 2-236 | CH$_2$CMe$_3$ | Me | H | A$^b$ | B$^a$ | 2,3-di-F |
| 2-237 | CH$_2$CMe$_3$ | Me | H | A$^b$ | B$^a$ | 2,6-di-F |
| 2-238 | cPn | Me | H | A$^b$ | B$^a$ | 2-Cl |
| 2-239 | iBu | CMe$_2$OH | H | A$^b$ | B$^a$ | 2-Cl |
| 2-240 | CH$_2$CMe$_3$ | CMe$_2$OH | H | A$^b$ | B$^a$ | 2-Cl |
| 2-241 | CH$_2$CMe$_3$ | Me | H | A$^b$ | B$^a$ | 2-CF$_3$ |
| 2-242 | CH$_2$CMe$_3$ | Me | H | A$^b$ | B$^a$ | 2-Cl-4-F |
| 2-243 | CH$_2$CMe$_3$ | Me | H | A$^b$ | B$^a$ | 2-Me-4-F |
| 2-244 | CH$_2$CMe$_3$ | Me | H | A$^b$ | B$^a$ | 2,5-di-F |
| 2-245 | cHx | Me | H | A$^b$ | B$^a$ | 2-Me |
| 2-246 | cHx | Me | H | A$^b$ | B$^a$ | 2-Me-5-F |
| 2-247 | (S)Bu-Me | Me | H | A$^b$ | B$^a$ | 2-Cl |
| 2-248 | cHx | Me | H | A$^b$ | B$^a$ | 2,3-di-F |
| 2-249 | cHx | Me | H | A$^b$ | B$^a$ | 2,6-di-F |
| 2-250 | cPn | Me | H | A$^b$ | B$^a$ | 2-Me-5-F |
| 2-251 | (S)Bu-Me | Me | H | A$^b$ | B$^a$ | 2-Me-5-F |
| 2-252 | cPn | Me | H | A$^b$ | B$^a$ | 2,3-di-F |
| 2-253 | cPn | Me | H | A$^b$ | B$^a$ | 2,6-di-F |

TABLE 3

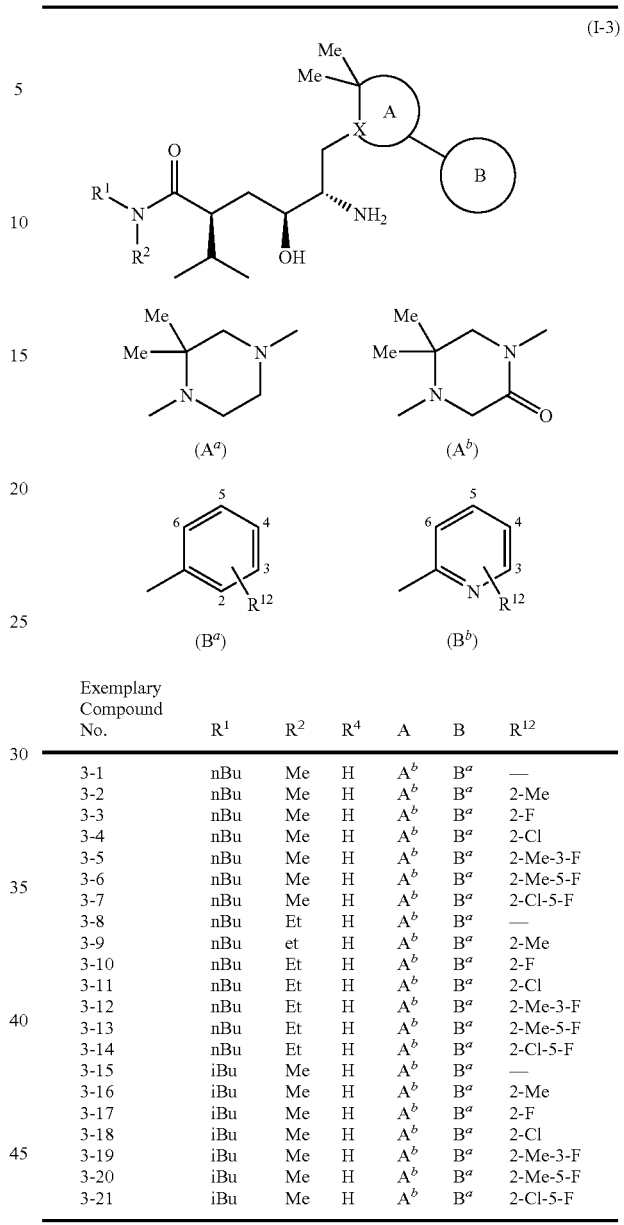

| Exemplary Compound No. | R$^1$ | R$^2$ | R$^4$ | A | B | R$^{12}$ |
|---|---|---|---|---|---|---|
| 3-1 | nBu | Me | H | A$^b$ | B$^a$ | — |
| 3-2 | nBu | Me | H | A$^b$ | B$^a$ | 2-Me |
| 3-3 | nBu | Me | H | A$^b$ | B$^a$ | 2-F |
| 3-4 | nBu | Me | H | A$^b$ | B$^a$ | 2-Cl |
| 3-5 | nBu | Me | H | A$^b$ | B$^a$ | 2-Me-3-F |
| 3-6 | nBu | Me | H | A$^b$ | B$^a$ | 2-Me-5-F |
| 3-7 | nBu | Me | H | A$^b$ | B$^a$ | 2-Cl-5-F |
| 3-8 | nBu | Et | H | A$^b$ | B$^a$ | — |
| 3-9 | nBu | et | H | A$^b$ | B$^a$ | 2-Me |
| 3-10 | nBu | Et | H | A$^b$ | B$^a$ | 2-F |
| 3-11 | nBu | Et | H | A$^b$ | B$^a$ | 2-Cl |
| 3-12 | nBu | Et | H | A$^b$ | B$^a$ | 2-Me-3-F |
| 3-13 | nBu | Et | H | A$^b$ | B$^a$ | 2-Me-5-F |
| 3-14 | nBu | Et | H | A$^b$ | B$^a$ | 2-Cl-5-F |
| 3-15 | iBu | Me | H | A$^b$ | B$^a$ | — |
| 3-16 | iBu | Me | H | A$^b$ | B$^a$ | 2-Me |
| 3-17 | iBu | Me | H | A$^b$ | B$^a$ | 2-F |
| 3-18 | iBu | Me | H | A$^b$ | B$^a$ | 2-Cl |
| 3-19 | iBu | Me | H | A$^b$ | B$^a$ | 2-Me-3-F |
| 3-20 | iBu | Me | H | A$^b$ | B$^a$ | 2-Me-5-F |
| 3-21 | iBu | Me | H | A$^b$ | B$^a$ | 2-Cl-5-F |

Among the compounds shown in the above Tables 1 to 3, a preferred compound is a compound of Exemplary Compound No. 1-2, 1-11, 1-14, 1-16, 1-18, 1-24, 1-44, 1-45, 1-46, 1-47, 1-49, 1-54, 1-55, 1-71, 1-72, 1-73, 1-75, 1-79, 1-82, 1-85, 1-87, 1-89, 1-121, 1-122, 1-135, 1-142, 1-168, 1-170, 1-179, 1-195, 1-197, 1-211, 1-213, 1-244, 1-288, 1-403, 1-423, 1-426, 1-429, 1-432, 1-433, 1-434, 1-436, 1-438, 1-440, 1-446, 1-447, 1-466, 1-467, 1-468, 1-469, 1-491, 1-493, 1-494, 1-495, 1-496, 1-502, 1-505, 1-510, 1-512, 1-578, 1-612, 1-619, 1-645, 1-647, 1-656, 1-672, 1-674, 1-690, 1-726, 1-1041, 1-732, 1-734, 1-739, 1-740, 1-756, 1-757, 1-758, 1-760, 1-770, 1-774, 1-776, 1-782, 1-791, 1-825, 1-826, 1-827, 1-833, 1-841, 1-842, 1-872, 1-876, 1-884, 1-900, 1-918, 1-920, 1-926, 1-935, 1-969, 1-970, 1-971, 1-972, 1-973, 1-974, 1-975, 1-976, 1-977, 1-978, 1-979, 1-980, 1-981, 1-982, 1-983, 1-984, 1-985, 1-986, 1-987, 1-988, 1-989, 1-990, 1-991, 1-992, 1-993, 1-994, 1-995, 1-996, 1-997, 1-998, 1-999, 1-1000, 1-1001, 1-1002, 1-1003, 1-1004, 1-1005, 1-1006, 1-1007, 1-1008, 1-1009, 1-1010, 1-1011, 1-1012, 1-1013, 1-1014, 1-1015, 1-1016, 1-1017, 1-1018, 1-1019, 1-1020, 1-1021, 1-1022, 1-1023, 1-1024, 1-1025, 1-1026, 1-1027, 1-1028, 1-1029, 1-1030, 1-1031, 1-1032, 1-1033, 1-1034, 1-1035, 1-1036, 1-1037, 1-1038, 1-1039, 1-1040, 1-1042, 2-147, 2-154, 2-156, 2-157, 2-161, 2-162, 2-163, 2-164, 2-168, 2-170, 2-171, 2-173, 2-175, 2-177, 2-178, 2-179, 2-180, 2-182, 2-183, 2-184, 2-185, 2-187, 2-189, 2-191, 2-192, 2-193, 2-194, 2-195, 2-196, 2-197, 2-198, 2-199, 2-200, 2-201, 2-202, 2-203, 2-204, 2-205, 2-206, 2-207, 2-208, 2-209, 2-210, 2-211, 2-212, 2-213, 2-214, 2-215, 2-216, 2-217, 2-218, 2-219, 2-220, 2-221, 2-222, 2-223, 2-224, 2-225, 2-226, 2-227, 2-228, 2-229, 2-230, 2-231, 2-232, 2-233, 2-234, 2-235, 2-236, 2-237, 2-238, 2-239, 2-240, 2-241, 2-242, 2-243, 2-244, 2-245, 2-246, 2-247, 2-248, 2-249, 2-250, 2-251, 2-252, 2-253, 3-4, or 3-18, a more preferred compound is a compound of Exemplary Compound No. 1-2, 1-16, 1-44, 1-45, 1-46, 1-89, 1-122, 1-170, 1-244, 1-288, 1-403, 1-423, 1-426, 1-429, 1-433, 1-434, 1-436, 1-438, 1-440, 1-446, 1-447, 1-466, 1-467, 1-468, 1-469, 1-491, 1-493, 1-494, 1-495, 1-496, 1-502, 1-505, 1-510, 1-512, 1-578, 1-647, 1-726, 1-732, 1-734, 1-739, 1-740, 1-756, 1-757, 1-758, 1-774, 1-782, 1-791, 1-826, 1-827, 1-833, 1-841, 1-842, 1-876, 1-884, 1-918, 1-926, 1-969, 1-974, 1-975, 1-977, 1-981, 1-982, 1-983, 1-994, 1-995, 1-1004, 1-1005, 1-1013, 1-1014, 1-1017, 1-1022, 1-1023, 1-1031, 1-1038, 2-147, 2-154, 2-156, 2-157, 2-161, 2-162, 2-163, 2-168, 2-175, 2-179, 2-180, 2-182, 2-183, 2-184, 2-185, 2-187, 2-189, 2-191, 2-192, 2-198, 2-199, 2-200, 2-208, 2-209, 2-211, 2-213, 2-217, 2-218, 2-222, 2-229, 2-230, 2-233, 2-235, 2-236, 2-237, 2-238, 2-241, 2-242, 2-243, 2-244, 2-245, 2-246, 2-247, 2-248, 2-249, 2-250, 2-251, 2-252, or 2-253, a still more preferred compound is a compound of Exemplary Compound No. 1-46, 1-89, 1-170, 1-647, 1-740, 1-826, 1-827, 1-833, 1-841, 1-842, 1-876, 1-1017, 1-1022, 2-161, 2-162, 2-163, 2-179, 2-180, 2-182, 2-183, 2-184, 2-185, 2-187, 2-189, 2-191, 2-192, 2-198, 2-199, 2-200, 2-229, 2-233, 2-236, 2-237, 2-241, 2-242, 2-243, 2-244, 2-245, 2-246, 2-248, 2-249, 2-250, 2-251, 2-252, or 2-253, and a yet more preferred compound is a compound of
Exemplary Compound No. 1-46: (2S,4S,5S)-5-amino-6-[4-(2-chlorophenyl)-2,2-dimethyl-5-oxopiperazin-1-yl]-4-hydroxy-2-isopropylhexanoic acid butylamide,
Exemplary Compound No. 1-89: (2S,4S,5S)-5-amino-6-[4-(2-chloro-5-fluorophenyl)-2,2-dimethyl-5-oxopiperazin-1-yl]-4-hydroxy-2-isopropylhexanoic acid butylamide,
Exemplary Compound No. 1-170: (2S,4S,5S)-5-amino-6-[4-(2-chlorophenyl)-2,2-dimethyl-5-oxopiperazin-1-yl]-4-hydroxy-2-isopropylhexanoic acid [(S)-2-methylbutyl]amide,
Exemplary Compound No. 1-647: (2S,4S,5S)-5-amino-6-[4-(2-chlorophenyl)-2,2-dimethyl-5-oxopiperazin-1-yl]-4-hydroxy-2-isopropylhexanoic acid cyclopentylamide,
Exemplary Compound No. 1-740: (2S,4S,5S)-5-amino-6-[2,2-dimethyl-4-(5-fluoro-2-methylphenyl)-5-oxopiperazin-1-yl]-4-hydroxy-2-isopropylhexanoic acid isobutylamide,
Exemplary Compound No. 1-842: (2S,4S,5S)-5-amino-6-[2,2-dimethyl-4-(5-fluoro-2-methylphenyl)-5-oxopiperazin-1-yl]-4-hydroxy-2-isopropylhexanoic acid (2,2-dimethylpropyl)amide,
Exemplary Compound No. 2-182: (2R,4S,5S)-5-amino-6-[4-(2-chlorophenyl)-2,2-dimethyl-5-oxopiperazin-1-yl]-4-hydroxy-2-methylhexanoic acid (2,2-dimethylpropyl)amide,
Exemplary Compound No. 2-184: (2R,4S,5S)-5-amino-6-[2,2-dimethyl-4-(5-fluoro-2-methylphenyl)-5-oxopiperazin-1-yl]-4-hydroxy-2-methylhexanoic acid (2,2-dimethylpropyl)amide,
Exemplary Compound No. 2-185: (2R,4S,5S)-5-amino-6-[4-(2-chloro-5-fluorophenyl)-2,2-dimethyl-5-oxopiperazin-1-yl]-4-hydroxy-2-methylhexanoic acid (2,2-dimethylpropyl)amide,
Exemplary Compound No. 2-187: (2R,4S,5S)-5-amino-6-[2,2-dimethyl-4-(2-methylphenyl)-5-oxopiperazin-1-yl]-2-ethyl-4-hydroxyhexanoic acid (2,2-dimethylpropyl)amide,
Exemplary Compound No. 2-189: (2R,4S,5S)-5-amino-6-[4-(2-chlorophenyl)-2,2-dimethyl-5-oxopiperazin-1-yl]-2-ethyl-4-hydroxyhexanoic acid (2,2-dimethylpropyl)amide,
Exemplary Compound No. 2-200: (2R,4S,5S)-5-amino-6-[4-(2-chlorophenyl)-2,2-dimethyl-5-oxopiperazin-1-yl]-4-hydroxy-2-propylhexanoic acid (2,2-dimethylpropyl)amide,
Exemplary Compound No. 2-245: (2R,4S,5S)-5-amino-6-[2,2-dimethyl-4-(2-methylphenyl)-5-oxopiperazin-1-yl]-4-hydroxy-2-methylhexanoic acid cyclohexylamide,
Exemplary Compound No. 2-246: (2R,4S,5S)-5-amino-6-[2,2-dimethyl-4-(5-fluoro-2-methylphenyl)-5-oxopiperazin-1-yl]-4-hydroxy-2-methylhexanoic acid cyclohexylamide,
Exemplary Compound No. 2-249: (2R,4S,5S)-5-amino-6-[4-(2,6-difluorophenyl)-2,2-dimethyl-5-oxopiperazin-1-yl]-4-hydroxy-2-methylhexanoic acid cyclohexylamide,
Exemplary Compound No. 2-250: (2R,4S,5S)-5-amino-6-[2,2-dimethyl-4-(5-fluoro-2-methylphenyl)-5-oxopiperazin-1-yl]-4-hydroxy-2-methylhexanoic acid cyclopentylamide,
Exemplary Compound No. 2-251: (2R,4S,5S)-5-amino-6-[2,2-dimethyl-4-(5-fluoro-2-methylphenyl)-5-oxopiperazin-1-yl]-4-hydroxy-2-methylhexanoic acid [(S)-2-methylbutyl]amide,
Exemplary Compound No. 2-252: (2R,4S,5S)-5-amino-6-[4-(2,3-difluorophenyl)-2,2-dimethyl-5-oxopiperazin-1-yl]-4-hydroxy-2-methylhexanoic acid cyclopentylamide or
Exemplary Compound No. 2-253: (2R,4S,5S)-5-amino-6-[4-(2,6-difluorophenyl)-2,2-dimethyl-5-oxopiperazin-1-yl]-4-hydroxy-2-methylhexanoic acid cyclopentylamide.

The compound represented by the general formula (I) according to the present invention can be prepared according to the following Methods A to D.

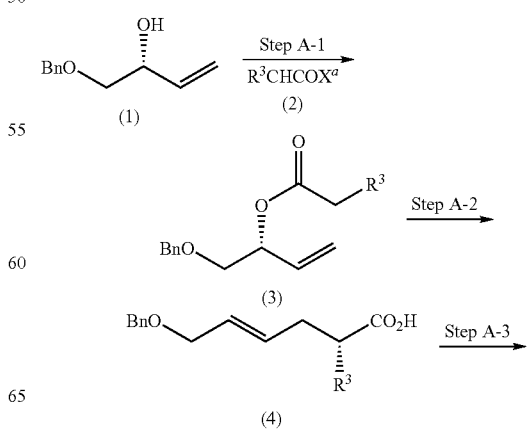

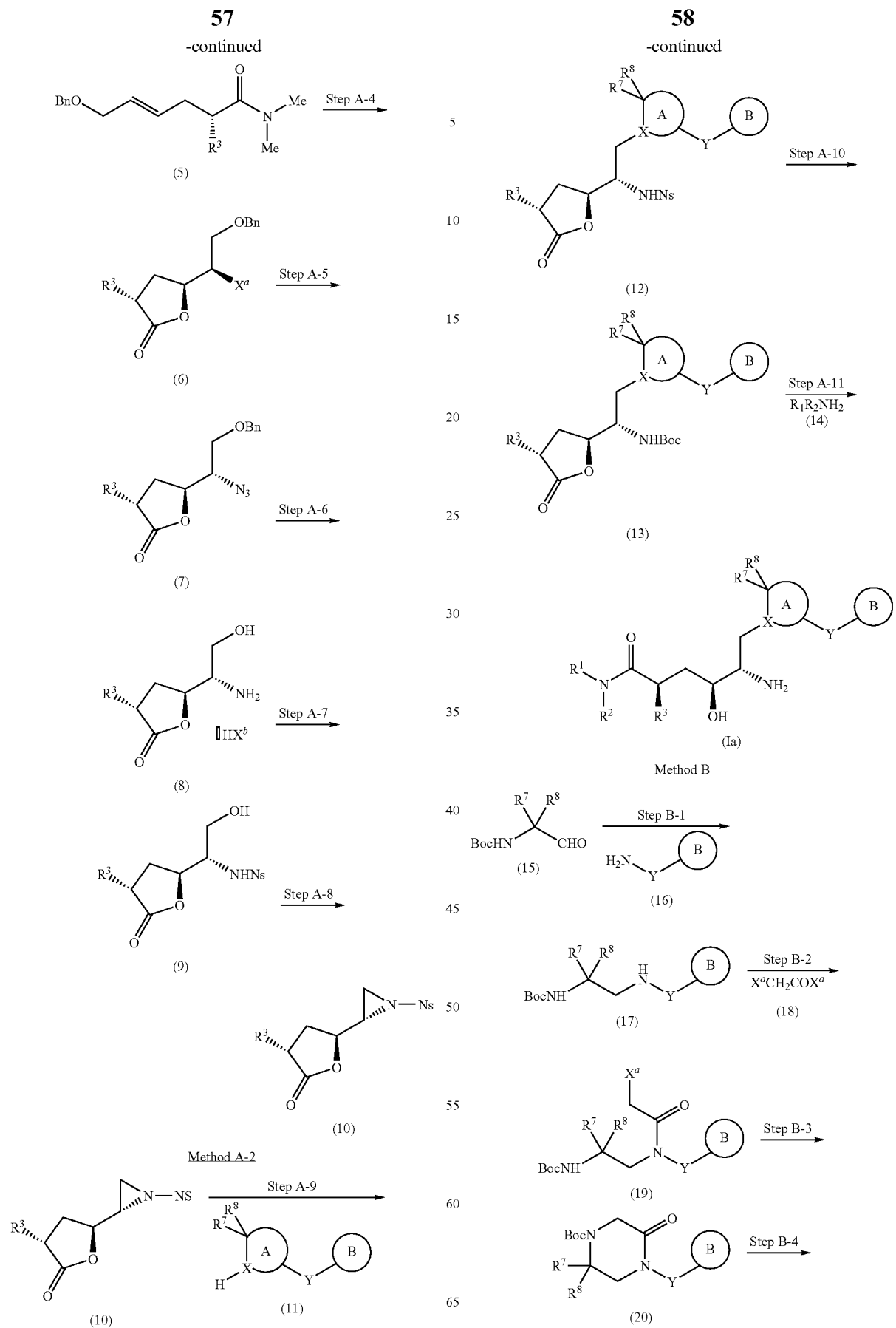

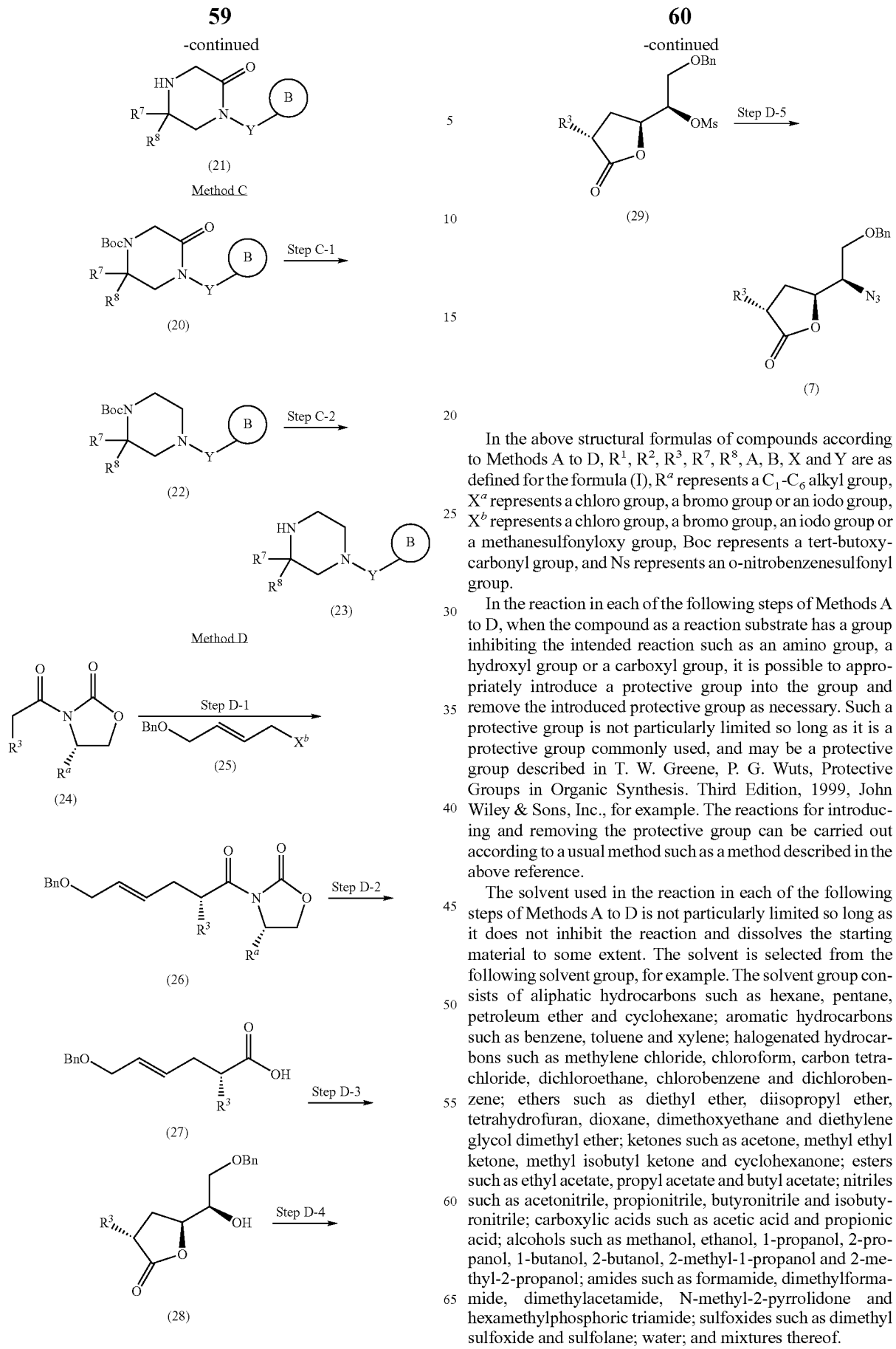

In the above structural formulas of compounds according to Methods A to D, $R^1$, $R^2$, $R^3$, $R^7$, $R^8$, A, B, X and Y are as defined for the formula (I), $R^a$ represents a $C_1$-$C_6$ alkyl group, $X^a$ represents a chloro group, a bromo group or an iodo group, $X^b$ represents a chloro group, a bromo group, an iodo group or a methanesulfonyloxy group, Boc represents a tert-butoxycarbonyl group, and Ns represents an o-nitrobenzenesulfonyl group.

In the reaction in each of the following steps of Methods A to D, when the compound as a reaction substrate has a group inhibiting the intended reaction such as an amino group, a hydroxyl group or a carboxyl group, it is possible to appropriately introduce a protective group into the group and remove the introduced protective group as necessary. Such a protective group is not particularly limited so long as it is a protective group commonly used, and may be a protective group described in T. W. Greene, P. G. Wuts, Protective Groups in Organic Synthesis. Third Edition, 1999, John Wiley & Sons, Inc., for example. The reactions for introducing and removing the protective group can be carried out according to a usual method such as a method described in the above reference.

The solvent used in the reaction in each of the following steps of Methods A to D is not particularly limited so long as it does not inhibit the reaction and dissolves the starting material to some extent. The solvent is selected from the following solvent group, for example. The solvent group consists of aliphatic hydrocarbons such as hexane, pentane, petroleum ether and cyclohexane; aromatic hydrocarbons such as benzene, toluene and xylene; halogenated hydrocarbons such as methylene chloride, chloroform, carbon tetrachloride, dichloroethane, chlorobenzene and dichlorobenzene; ethers such as diethyl ether, diisopropyl ether, tetrahydrofuran, dioxane, dimethoxyethane and diethylene glycol dimethyl ether; ketones such as acetone, methyl ethyl ketone, methyl isobutyl ketone and cyclohexanone; esters such as ethyl acetate, propyl acetate and butyl acetate; nitriles such as acetonitrile, propionitrile, butyronitrile and isobutyronitrile; carboxylic acids such as acetic acid and propionic acid; alcohols such as methanol, ethanol, 1-propanol, 2-propanol, 1-butanol, 2-butanol, 2-methyl-1-propanol and 2-methyl-2-propanol; amides such as formamide, dimethylformamide, dimethylacetamide, N-methyl-2-pyrrolidone and hexamethylphosphoric triamide; sulfoxides such as dimethyl sulfoxide and sulfolane; water; and mixtures thereof.

The acid used in the reaction in each of the following steps of Methods A to D is not particularly limited so long as it does not inhibit the reaction. The acid is selected from the following acid group. The acid group consists of inorganic acids such as hydrochloric acid, hydrobromic acid, hydroiodic acid, phosphoric acid, sulfuric acid and nitric acid; organic acids such as acetic acid, propionic acid, trifluoroacetic acid and pentafluoropropionic acid; and organic sulfonic acids such as methanesulfonic acid, trifluoromethanesulfonic acid, p-toluenesulfonic acid and camphorsulfonic acid.

The base used in the reaction in each of the following steps of Methods A to D is not particularly limited so long as it does not inhibit the reaction. The base is selected from the following base group. The base group consists of alkali metal carbonates such as lithium carbonate, sodium carbonate, potassium carbonate and cesium carbonate; alkali metal bicarbonates such as lithium bicarbonate, sodium bicarbonate and potassium bicarbonate; alkali metal hydroxides such as lithium hydroxide, sodium hydroxide and potassium hydroxide; alkaline earth metal hydroxides such as calcium hydroxide and barium hydroxide; alkali metal hydrides such as lithium hydride, sodium hydride and potassium hydride; alkali metal amides such as lithium amide, sodium amide and potassium amide; alkali metal alkoxides such as lithium methoxide, sodium methoxide, sodium ethoxide, sodium tert-butoxide and potassium tert-butoxide; lithium alkylamides such as lithium diisopropylamide; silylamides such as lithium bistrimethylsilylamide and sodium bistrimethylsilylamide; alkyllithiums such as n-butyllithium, sec-butyllithium and tert-butyllithium; alkylmagnesium halides such as methylmagnesium chloride, methylmagnesium bromide, methylmagnesium iodide, ethylmagnesium chloride, ethylmagnesium bromide, isopropylmagnesium chloride, isopropylmagnesium bromide and isobutylmagnesium chloride; and organic amines such as triethylamine, tributylamine, diisopropylethylamine, N-methylpiperidine, N-methylmorpholine, N-ethylmorpholine, pyridine, picoline, 4-(N,N-dimethylamino)pyridine, 4-pyrrolidinopyridine, 2,6-di(tert-butyl)-4-methylpyridine, quinoline, N,N-dimethylaniline, N,N-diethylaniline, 1,5-diazabicyclo[4,3,0]non-5-ene (DBN), 1,4-diazabicyclo[2,2,2]octane (DABCO) and 1,8-diazabicyclo[5,4,0]undec-7-ene (DBU).

In the reaction in each of the following steps of Methods A to D, the reaction temperature varies depending on the solvent, the starting material, the reagent and the like, and the reaction time varies depending on the solvent, the starting material, the reagent, the reaction temperature and the like.

In the reaction in each of the following steps of Methods A to D, the desired compound in each step is isolated from the reaction mixture according to a usual method after completion of the reaction. The desired compound is obtained by (i) removing the insoluble matter such as a catalyst by filtration as necessary, (ii) adding water and a solvent immiscible with water (such as methylene chloride, diethyl ether or ethyl acetate) to the reaction mixture to extract the desired compound, (iii) washing the organic layer with water and drying the layer over a drying agent such as anhydrous magnesium sulfate, and (iv) evaporating the solvent, for example. The resulting desired compound may be further purified as necessary by a usual method such as recrystallization, reprecipitation or silica gel column chromatography. The desired compound in each step may also be used for the next reaction as is, without purification.

In each step, optical isomers may be separated by fractional crystallization using an optically active amine such as dehydroabietylamine or by separation using an optically active column.

The reaction in each step of Methods A to D is described below.

(Method A)

Method A consists of Method A-1 and Method A-2 and is a method for preparing a compound having the formula (Ia) included in the formula (I).

(Step A-1)

Step A-1 is a step of reacting a compound (1) with a compound (2) in the presence of a base. The compound (1) can be prepared according to the method described in Tetrahedron Lett., 1989, vol. 28, p. 6497. The compound (2) is known or is easily prepared from a known compound.

The base used is preferably an alkali metal bicarbonate, an alkali metal hydroxide, an alkali metal hydride, an alkali metal amide, an alkali metal alkoxide, a lithium alkylamide, a silylamide, an alkyllithium, an alkylmagnesium halide or an organic amine, more preferably an alkylmagnesium halide or an organic amine, and most preferably ethylmagnesium bromide, triethylamine, 4-(N,N-dimethylamino)pyridine or a combination thereof.

The solvent used is preferably an aliphatic hydrocarbon, an aromatic hydrocarbon, a halogenated hydrocarbon, an ether or an ester, more preferably an ether or a halogenated hydrocarbon, and most preferably tetrahydrofuran or methylene chloride.

The reaction temperature is preferably −78 to 150° C., and more preferably −30 to 40° C.

The reaction time is preferably five minutes to 96 hours, and more preferably 15 minutes to 48 hours.

(Step A-2)

Step A-2 is a step of treating a compound (3) obtained in Step A-1 with a silylating reagent and a base.

The silylating reagent used may be a chlorosilane such as chlorotrimethylsilane, chlorotriethylsilane or t-butyldimethylchlorosilane, or a silyl triflate such as trimethylsilyl triflate, triethylsilyl triflate or t-butyldimethylsilyl triflate, for example, and is preferably a chlorosilane, and most preferably chlorotrimethylsilane.

The base used is preferably a lithium alkylamide, a silylamide or an alkyllithium, more preferably a lithium alkylamide, and most preferably lithium diisopropylamide.

The solvent used is preferably an aliphatic hydrocarbon, an aromatic hydrocarbon or an ether, more preferably an ether, and most preferably tetrahydrofuran.

The reaction temperature is preferably −78 to 100° C., and more preferably −78 to 40° C.

The reaction time is preferably 30 minutes to 96 hours, and more preferably 1 to 24 hours.

(Step A-3)

Step A-3 consists of (Step A-3a): a step of reacting a compound (4) obtained in Step A-2 with a halogenating reagent; and (Step A-3b): a step of reacting a compound obtained in Step A-3a with dimethylamine in the presence of a base.

(Step A-3a)

The halogenating agent used may be thionyl chloride; a phosphorus halide such as phosphorus trichloride, phosphorus oxytrichloride, phosphorus pentachloride, phosphorus tribromide or phosphorus pentabromide; oxalyl chloride; or a combination of a reagent selected from the group consisting of carbon tetrachloride, carbon tetrabromide, hexachloroethane, N-chlorosuccinimide and N-bromosuccinic acid and triphenylphosphine, for example, and is preferably thionyl chloride or oxalyl chloride, and most preferably oxalyl chloride. A combination of the halogenating reagent above and N,N-dimethylformamide is still more preferred.

The solvent used is preferably an aliphatic hydrocarbon, an aromatic hydrocarbon, a halogenated hydrocarbon, an ether, an ester or a nitrile, more preferably an aromatic hydrocarbon or a halogenated hydrocarbon, and most preferably methylene chloride. This step may also be carried out in the absence of a solvent.

The reaction temperature is preferably −78 to 150° C., and more preferably 0 to 80° C.

The reaction time is preferably 30 minutes to 96 hours, and more preferably 60 minutes to six hours.

(Step A-3b)

The base used is preferably an alkali metal bicarbonate, an alkali metal hydroxide, an alkali metal hydride, an alkali metal amide, an alkali metal alkoxide, a lithium alkylamide, a silylamide, an alkyllithium or an organic amine, more preferably an organic amine, and most preferably dimethylamine. In this step, a solution of dimethylamine in an alcohol or water is preferably used, and a solution of dimethylamine in water is more preferably used.

The solvent used is the same as in Step A-3a.

The reaction temperature is preferably −78 to 150° C., and more preferably −30 to 40° C.

The reaction time is preferably five minutes to 96 hours, and more preferably five minutes to 24 hours.

In Step A-3, the compound (4) may also be reacted with dimethylamine in the presence of a condensing agent.

The condensing agent used is not particularly limited so long as it is used for an amidation reaction. The condensing agent may be a condensing agent described in R. C. Larock, Comprehensive Organic Transformations. Second Edition, 1999, John Wiley & Sons, Inc. or the like. For example, the condensing agent used may be (i) a combination of a phosphoester such as diethylphosphoryl cyanide and the following base;
(ii) a carbodiimide such as 1,3-dicyclohexylcarbodiimide, 1,3-diisopropylcarbodiimide or 1-ethyl-3-(3-dimethylaminopropyl)carbodiimide (WSC); a combination of the carbodiimide above and the base above; a combination of the carbodiimide above and an N-hydroxy compound such as N-hydroxysuccinimide; or
(iii) an imidazole compound such as N,N'-carbonyldiimidazole (CDI).

(Step A-4)

Step A-4 is a step of treating a compound (5) obtained in Step A-3 with a halogenating reagent.

The halogenating reagent may be a halogen such as chlorine, bromine or iodine; an N-halogenoamide such as N-chlorosuccinimide, N-bromosuccinimide, N-iodosuccinimide or 1,3-dibromo-5,5-dimethylhydantoin; or an α-haloketone such as 5,5-dibromo-Meldrum's acid, and is preferably an N-halogenoamide, and most preferably N-bromosuccinimide. In this step, the halogenating reagent is preferably a brominating reagent. In this step, an additive may be appropriately used as necessary. The additive used is preferably acetic acid or sodium dihydrogenphosphate, and most preferably acetic acid.

The solvent used is preferably an aliphatic hydrocarbon, an aromatic hydrocarbon, a halogenated hydrocarbon, an ether, an ester, a nitrile, an amide, water or a mixture thereof, more preferably a mixture of an ether and water, and most preferably a mixture of tetrahydrofuran and water.

The reaction temperature is preferably −78 to 150° C., and more preferably −30 to 40° C.

The reaction time is preferably five minutes to 96 hours, and more preferably 30 minutes to 24 hours.

(Step A-5)

Step A-5 is a step of treating a compound (6) obtained in Step A-4 with an azidating reagent.

The azidating reagent used may be a metal azide such as lithium azide or sodium azide; an ammonium azide such as tetra-n-butylammonium azide; or a silyl azide such as trimethylsilyl azide, for example, and is preferably a metal azide, and most preferably sodium azide. In this step, the azidating reagent may be appropriately used in combination with an additive as necessary. The additive used is preferably a phase-transfer catalyst such as tetra-n-butylammonium bromide, benzyltriethylammonium chloride, Aliquat 336 (trade mark), 15-crown-5-ether or 18-crown-6-ether.

The solvent used is preferably an aliphatic hydrocarbon, an aromatic hydrocarbon, a halogenated hydrocarbon, an ether, an ester, a nitrile, an amide, a sulfoxide, water or a mixture thereof, more preferably an amide, a sulfoxide or a mixture of an aromatic hydrocarbon and water, and most preferably N,N'-dimethylpropyleneurea.

The reaction temperature is preferably 0 to 150° C., more preferably 20 to 100° C., and most preferably 40 to 60° C.

The reaction time is preferably five minutes to seven days, and more preferably 30 minutes to 96 hours.

(Step A-6)

Step A-6 is a step of reducing a compound (7) obtained in Step A-5.

This step is preferably carried out by catalytic reduction. The catalyst used for catalytic reduction may be a palladium compound such as palladium-carbon, palladium black, palladium hydroxide or palladium-barium sulfate; a platinum compound such as platinum oxide or platinum black; a rhodium compound such as rhodium-aluminum oxide or triphenylphosphine-rhodium chloride; or a nickel compound such as Raney nickel, for example, and is preferably a palladium compound, and most preferably palladium-carbon.

The hydrogen pressure in catalytic reduction is preferably 1 to 10 atm, and more preferably 1 atm.

The solvent used is preferably an aliphatic hydrocarbon, an aromatic hydrocarbon, a halogenated hydrocarbon, an ether, an ester, a nitrile, an alcohol, an amide, water or a mixture thereof, more preferably an ether or an alcohol, and most preferably ethanol. In this step, an acid may be appropriately used as necessary. The acid used may be hydrochloric acid, phosphoric acid, sulfuric acid, methanesulfonic acid or p-toluenesulfonic acid, for example, and is most preferably hydrochloric acid.

The reaction temperature is preferably −20 to 200° C., and more preferably 0 to 100° C.

The reaction time is preferably five minutes to 96 hours, and more preferably 15 minutes to 24 hours.

(Step A-7)

Step A-7 is a step of reacting a compound (8) obtained in Step A-6 with o-nitrobenzenesulfonyl chloride in the presence of a base.

The base used is preferably an alkali metal bicarbonate, an alkali metal hydroxide, a metal alkoxide or an organic amine, more preferably an organic amine, and most preferably triethylamine.

The solvent used is preferably an aliphatic hydrocarbon, an aromatic hydrocarbon, a halogenated hydrocarbon, an ether, an ester, a nitrile, an alcohol, an amide, water or a mixture thereof, more preferably a mixture of an ether and water, and most preferably a mixture of tetrahydrofuran and water.

The reaction temperature is preferably −78 to 150° C., and more preferably −30 to 40° C.

The reaction time is preferably five minutes to 96 hours, and more preferably five minutes to 24 hours.

(Step A-8)

Step A-8 is a step of treating a compound (9) obtained in Step A-7 with a dehydration condensing agent.

The dehydration condensing agent used is preferably a combination of an azodicarboxylic acid compound such as diethyl azodicarboxylate, diisopropyl azodicarboxylate, azodicarboxylic acid dimethylamide or azodicarboxylic acid dipiperidinamide and a phosphine such as triphenylphosphine or a diphenylphosphinopolystyrene carrier, and most preferably a combination of diethyl azodicarboxylate and triphenylphosphine.

The solvent used is preferably an aliphatic hydrocarbon, an aromatic hydrocarbon, a halogenated hydrocarbon, an ether, an ester, a nitrile or an amide, more preferably an aromatic hydrocarbon or an ether, and most preferably tetrahydrofuran.

The reaction temperature is preferably −78 to 150° C., and more preferably 0 to 60° C.

The reaction time is preferably one minute to 24 hours, and more preferably one minute to one hour.

(Step A-9)

Step A-9 is a step of reacting a compound (10) obtained in Step A-8 with a compound (11). The compound (11) is known, is easily prepared from a known compound, or is prepared by Method B or C.

The solvent used is preferably an aliphatic hydrocarbon, an aromatic hydrocarbon, a halogenated hydrocarbon, an ether, an ester, a nitrile or an amide, more preferably an aromatic hydrocarbon or an ether, and most preferably toluene.

The reaction temperature is preferably 0 to 200° C., and more preferably 20 to 150° C.

The reaction time is preferably five minutes to 96 hours, and more preferably 15 minutes to 24 hours.

(Step A-10)

Step A-10 consists of (Step A-10a): a step of treating a compound (12) obtained in Step A-9 with a deprotecting reagent in the presence of a base; and (Step A-10b): a step of reacting a compound obtained in Step A-10a with di-tert-butyl dicarbonate in the presence of a base.

(Step A-10a)

The deprotecting reagent used may be a primary or secondary amine such as methylamine, dimethylamine, ethylamine, diethylamine, n-propylamine, n-butylamine, pyrrole, piperidine, morpholine, piperazine, N-methylpiperazine, hydrazine or N,N-dimethylhydrazine; or a thiol such as methanethiol, ethanethiol, n-propanethiol, n-butanethiol, thiophenol or thioglycolic acid, for example, and is preferably a thiol, and most preferably thiophenol.

The solvent used is preferably an aliphatic hydrocarbon, an aromatic hydrocarbon, a halogenated hydrocarbon, an ester, a nitrile, an amide or a mixture thereof, more preferably a nitrile or an amide, and most preferably N,N-dimethylformamide. In this step, an organic amine may also be used as a solvent.

The base used is preferably an alkali metal carbonate, an alkali metal bicarbonate, an alkali metal hydride, an alkali metal amide, an alkali metal alkoxide, a lithium alkylamide, a silylamide, an alkyllithium or an organic amine, more preferably an alkali metal carbonate, and most preferably cesium carbonate.

The reaction temperature is preferably −78 to 200° C., and more preferably 0 to 100° C.

The reaction time is preferably five minutes to 96 hours, and more preferably 15 minutes to 24 hours.

(Step A-10b)

The base used is preferably an alkali metal carbonate, an alkali metal bicarbonate, an alkali metal hydride, a metal alkoxide or an organic amine, more preferably an organic amine, and most preferably triethylamine.

The solvent used is preferably an aliphatic hydrocarbon, an aromatic hydrocarbon, a halogenated hydrocarbon, an ester, a nitrile, an amide, water or a mixture thereof, more preferably a halogenated hydrocarbon, and most preferably methylene chloride. In this step, an organic amine may also be used as a solvent.

The reaction temperature is preferably −78 to 150° C., and more preferably 0 to 100° C.

The reaction time is preferably five minutes to 96 hours, and more preferably 30 minutes to 48 hours.

In this step, a protective group generally known in the field of organic synthesis chemistry may be used as a protective group for an amino group (T. W. Greene, P. G. Wuts, Protective Groups in Organic Synthesis. Third Edition, 1999, John Wiley & Sons, Inc., for example). Preferred examples of the protective group may include acyl groups such as a formyl group, an acetyl group, a chloroacetyl group, a pivaloyl group and a benzoyl group; alkoxycarbonyl groups such as a methoxycarbonyl group, an ethoxycarbonyl group, a tert-butoxycarbonyl group and a benzyloxycarbonyl group; substituted alkyl groups such as a methoxymethyl group, a 2-(trimethylsilyl)ethoxymethyl group, a benzyloxymethyl group, an allyl group and a benzyl group; and sulfonyl groups such as a methanesulfonyl group, a benzenesulfonyl group, a p-toluenesulfonyl group, an o-nitrobenzenesulfonyl group and an o,p-dinitrobenzenesulfonyl group. The protective group is most preferably a tert-butoxycarbonyl group.

(Step A-11)

Step A-11 consists of (Step A-11a): a step of reacting a compound (13) obtained in Step A-10 with a compound (14) in the presence of a reagent; and (Step A-11b): a step of removing a tert-butoxycarbonyl group of a compound obtained in Step A-11a in the presence of an acid.

The compound (14) is known or is easily prepared from a known compound. Step A-11a may also be carried out according to a method generally known in the field of organic synthesis chemistry (Comprehensive Organic Transformations, Second Edition, 1999, John Wiley & Sons, Inc., p. 1973-1976, for example).

(Step A-11a)

The reagent used may be a cyano compound such as sodium cyanide, potassium cyanide or tetra-n-butylammonium cyanide; an organoaluminum compound such as trimethylaluminum; an organomagnesium halide compound such as methylmagnesium bromide, methylmagnesium iodide, ethylmagnesium bromide or isopropylmagnesium chloride; an organic acid such as acetic acid; or an organic amphoteric compound such as 2-hydroxypyridine, for example, and is preferably an organic amphoteric compound, and most preferably 2-hydroxypyridine.

The solvent used is preferably an aliphatic hydrocarbon, an aromatic hydrocarbon, a halogenated hydrocarbon, an amide or a mixture thereof. The solvent used in this step is more preferably an organic amine, and most preferably triethylamine. This step may also be carried out using an excess of the compound (13) in the absence of a solvent.

The reaction temperature is preferably −78 to 200° C., and more preferably 0 to 150° C.

The reaction time is preferably five minutes to 96 hours, and more preferably 30 minutes to 24 hours.

(Step A-11b)

The acid used may preferably be hydrochloric acid, sulfuric acid, acetic acid, trifluoroacetic acid, methanesulfonic acid, trifluoromethanesulfonic acid or p-toluenesulfonic acid, and is more preferably hydrochloric acid (in particular, hydrochloric acid-1,4-dioxane) or trifluoroacetic acid, and most preferably trifluoroacetic acid.

The solvent used is preferably an aliphatic hydrocarbon, a halogenated hydrocarbon, an ester, an alcohol or an amide, more preferably a halogenated hydrocarbon, and most preferably methylene chloride.

The reaction temperature is preferably −78 to 150° C., more preferably −30 to 80° C., and still more preferably 0 to 50° C.

The reaction time is preferably five minutes to 96 hours, and more preferably five minutes to 12 hours.

When a protective group other than a tert-butoxycarbonyl group is used as a protective group for an amino group in Step A-10, the protective group can be removed in Step A-11b according to a method generally known in the field of organic synthesis chemistry (T. W. Greene, P. G. Wuts, Protective Groups in Organic Synthesis. Third Edition, 1999, John Wiley & Sons, Inc., for example).

In Method A, the racemic compound (1a) can be prepared by using the racemic compound (1) as a starting material. The compound (1) having $R^3$ and $R^4$ can be prepared by using a compound having the formula $R^3R^4CCOX^a$ as the compound (2). $R^5$ and $R^6$ can be introduced into an amino group according to a method generally known in the field of organic synthesis chemistry (Comprehensive Organic Transformations, Second Edition, 1999, John Wiley & Sons, Inc., for example).

(Method B)

Method B is a method for preparing a compound (21) included in the compound (11) used in Step A-9.

(Step B-1)

Step B-1 is a step of reacting a compound (15) with a compound (16) in the presence of a reducing agent. The compounds (15) and (16) are known or are easily prepared from a known compound. This step may also be carried out according to a method generally known in the field of organic synthesis chemistry (Comprehensive Organic Transformations, Second Edition, 1999, John Wiley & Sons, Inc., p. 835-846, for example).

The reducing agent used may be a boron hydride compound such as a borane-tetrahydrofuran complex, a borane-dimethyl sulfide complex, a borane-dimethylamine complex, a borane-pyridine complex, sodium borohydride, sodium cyanoborohydride, tetra-n-butylammonium cyanoborohydride or sodium triacetoxyborohydride; an aluminum hydride compound such as lithium aluminum hydride, aluminum hydride or diisobutylaluminum hydride; or hydrogen, for example, and is preferably a boron hydride compound, and most preferably sodium cyanoborohydride or sodium triacetoxyborohydride. In this step, an acid such as hydrochloric acid, formic acid, acetic acid or trifluoroacetic acid (preferably acetic acid) is preferably used in combination with the reducing agent above.

The solvent used is preferably an aliphatic hydrocarbon, an aromatic hydrocarbon, a halogenated hydrocarbon, an ether, an ester, a nitrile, an alcohol, an amide or water, more preferably a halogenated hydrocarbon or an alcohol, and most preferably dichloromethane or methanol.

The reaction temperature is preferably −78 to 150° C., and more preferably 0 to 100° C.

The reaction time is preferably five minutes to 96 hours, and more preferably 30 minutes to 48 hours.

(Step B-2)

Step B-2 is a step of reacting a compound (17) obtained in Step B-1 with a compound (18) in the presence of a base. The compound (18) is known or is easily prepared from a known compound.

The base used is preferably an alkali metal carbonate, an alkali metal bicarbonate, an alkali metal hydride, an alkali metal alkoxide or an organic amine, more preferably an alkali metal bicarbonate, and most preferably sodium bicarbonate.

The solvent used is preferably an aliphatic hydrocarbon, an aromatic hydrocarbon, a halogenated hydrocarbon, an ester, a nitrile, an amide, water or a mixture thereof, preferably a mixture of an ester and water, or an amide, and most preferably a mixture of ethyl acetate and water, or N,N-dimethylacetamide. In this step, an organic amine may also be used as a solvent.

The reaction temperature is preferably −78 to 150° C., and more preferably 0 to 100° C.

The reaction time is preferably five minutes to 96 hours, and more preferably 10 minutes to 24 hours.

(Step B-3)

Step B-3 is a step of treating a compound (19) obtained in Step B-2 with a base.

The base used is preferably an alkali metal carbonate, an alkali metal bicarbonate, an alkali metal hydride, an alkali metal amide, an alkali metal alkoxide, a lithium alkylamide, a silylamide or an organic amine, more preferably a metal alkoxide or an alkali metal carbonate, and most preferably cesium carbonate or potassium tert-butoxide.

The reaction temperature is preferably −78 to 200° C., more preferably −78 to 80° C., and still more preferably −78 to 20° C.

The reaction time is preferably five minutes to 96 hours, more preferably five minutes to 24 hours, and still more preferably five minutes to six hours.

(Step B-4)

Step B-4 is a step of removing a tert-butoxycarbonyl group of a compound (21) obtained in Step B-3 in the presence of an acid.

Step B-4 can be carried out according to a method similar to Step A-11b.

(Method C)

Method C is a method for preparing a compound (23) included in the compound (11) used in Step A-9.

(Step C-1)

Step C-1 is a step of treating a compound (20) obtained in Step B-3 with a reducing agent. This step may also be carried out according to a method generally known in the field of organic synthesis chemistry (Comprehensive Organic Transformations, Second Edition, 1999, John Wiley & Sons, Inc., p. 869-871, for example).

The reducing agent used may be a boron hydride compound such as a borane-tetrahydrofuran complex, a borane-dimethyl sulfide complex, a borane-dimethylamine complex, a borane-pyridine complex, sodium borohydride, sodium cyanoborohydride, tetra-n-butylammonium cyanoborohydride or sodium triacetoxyborohydride; or an aluminum hydride compound such as lithium aluminum hydride, aluminum hydride or diisobutylaluminum hydride, for example, and is preferably a boron hydride compound, and most preferably a borane-tetrahydrofuran complex.

The solvent used is preferably an aliphatic hydrocarbon, an aromatic hydrocarbon, a halogenated hydrocarbon or an ether, more preferably an ether, and most preferably tetrahydrofuran.

The reaction temperature is preferably −78 to 150° C., and more preferably −30 to 60° C.

The reaction time is preferably five minutes to 96 hours, and more preferably five minutes to 12 hours.
(Step C-2)
Step C-2 is a step of removing a tert-butoxycarbonyl group of a compound (22) obtained in Step C-1 in the presence of an acid.
Step C-2 can be carried out according to a method similar to Step A-11b.
(Method D)
Method D is a method for preparing the compound (7) used in Step A-6.
(Step D-1)
Step D-1 is a step of reacting a compound (24) with a compound (25) in the presence of a base. The compounds (24) and (25) are known or are easily prepared from a known compound.
The base used is preferably a lithium alkylamide, a silylamide, an alkyllithium or an organic amine, more preferably a silylamide, and most preferably sodium bistrimethylsilylamide.
In this step, an additive may be used as necessary. When a lithium alkylamide or a silylamide is used as a base, the additive used may be a phosphoramide such as hexamethylphosphoramide (HMPA); or a cyclic urea such as N,N'-dimethylpropyleneurea, for example. When an organic amine is used as a base, the additive used is a Lewis acid such as dibutylboron triflate or titanium (IV) chloride, for example.
The solvent used is preferably an aliphatic hydrocarbon, an aromatic hydrocarbon, a halogenated hydrocarbon or an ether, more preferably an ether, and most preferably tetrahydrofuran.
The reaction temperature is preferably −78 to 60° C., and more preferably −40 to −20° C.
The reaction time is preferably five minutes to 96 hours, and more preferably 15 minutes to 24 hours.
(Step D-2)
Step D-2 is a step of hydrolyzing a compound (26) obtained in Step D-1 in the presence of a base.
The base used is an alkali metal carbonate, an alkali metal bicarbonate, an alkali metal hydroxide, an alkaline earth metal hydroxide, a combination of an alkali metal hydroxide and a hydrogen peroxide solution, or a combination of an alkaline earth metal hydroxide and a hydrogen peroxide solution, preferably a combination of an alkali metal hydroxide and a hydrogen peroxide solution, and most preferably a combination of lithium hydroxide and a hydrogen peroxide solution.
The solvent used is preferably an aliphatic hydrocarbon, an aromatic hydrocarbon, an ether, an alcohol, water or a mixture thereof, more preferably a mixture of an ether and water, and most preferably a mixture of tetrahydrofuran and water.
The reaction temperature is preferably −78 to 100° C., and more preferably −30 to 40° C.
The reaction time is preferably 30 minutes to 96 hours, and more preferably 60 minutes to 24 hours.
An undesired isomer can be separated from a compound (27) obtained in Step D-2 or a compound obtained in another step by purification by fractional crystallization using an optically active amine such as dehydroabietylamine, for example.
(Step D-3)
Step D-3 is a step of asymmetric oxidation and cyclization of the compound (27) obtained in Step D-2. Asymmetric oxidation in Step D-3 may also be carried out by a method generally known in the field of organic synthesis chemistry (Acc. Chem. Res., 2004, vol. 37, p. 488, for example). A method using a combination of an optically active ketone compound prepared in two steps from D-fructose and an oxidizing agent such as Oxone (trade mark) is preferred.
The oxidizing agent used is Oxone or a hydrogen peroxide solution, for example, and preferably Oxone. The oxidizing agent may be used in combination with an additive such as tetra-n-butylammonium bisulfate. A combination of Oxone and tetra-n-butylammonium bisulfate is preferred.
The solvent used is preferably an ether, a nitrile, water or a mixture thereof, and more preferably a mixture of dimethoxymethane, acetonitrile and water.
The reaction temperature is preferably 0 to 20° C.
The reaction time is preferably 4 to 12 hours.
(Step D-4)
Step D-4 is a step of reacting a compound (28) obtained in Step D-3 with methanesulfonyl chloride in the presence of a base.
The base used is preferably an alkali metal hydride, a lithium alkylamide, a silylamide or an organic amine, more preferably an organic amine, and most preferably triethylamine.
The solvent used is preferably an aliphatic hydrocarbon, an aromatic hydrocarbon, a halogenated hydrocarbon, an ether, an ester, a nitrile or an amide, more preferably a halogenated hydrocarbon, and most preferably methylene chloride.
The reaction temperature is preferably −78 to 150° C., and more preferably −30 to 40° C.
The reaction time is preferably five minutes to 96 hours, and more preferably 10 minutes to 24 hours.
(Step D-5)
Step D-5 is a step of treating a compound (29) obtained in Step D-4 with an azidating reagent.
Step D-5 can be carried out according to a method similar to Step A-5.

When the compound represented by the general formula (I) or a pharmacologically acceptable salt thereof according to the present invention is used as a medicament, it can be administered as is (as bulk), or it can be administered in a mixture with an appropriate pharmacologically acceptable excipient or diluent orally as a formulation such as tablets, capsules, granules, powder or syrup, or parenterally as a formulation such as an injection or suppository (preferably orally).

These formulations are prepared by a generally known method using additives such as an excipient, a binder, a disintegrant, a lubricant, an emulsifier, a stabilizer, a corrigent, a diluent and an injection solvent.

The excipient may be an organic excipient or an inorganic excipient, for example. Examples of organic excipients may include sugar derivatives such as lactose, saccharose, glucose, mannitol and sorbitol; starch derivatives such as corn starch, potato starch, α-starch, dextrin and carboxymethyl starch; cellulose derivatives such as crystalline cellulose, low-substituted hydroxypropylcellulose, hydroxypropylmethylcellulose, carboxymethylcellulose, calcium carboxymethylcellulose and internally crosslinked sodium carboxymethylcellulose; gum arabic; dextran; and pullulan. Examples of inorganic excipients may include silicate derivatives such as light anhydrous silicic acid, synthetic aluminum silicate, calcium silicate and magnesium aluminometasilicate; phosphates such as calcium phosphate; carbonates such as calcium carbonate; and sulfates such as calcium sulfate.

Examples of binders may include the above excipients; gelatin; polyvinylpyrrolidone; and polyethylene glycol.

Examples of disintegrants may include the above excipients; chemically modified starch or cellulose derivatives such as croscarmellose sodium and sodium carboxymethylstarch; and crosslinked polyvinylpyrrolidone.

Examples of lubricants may include talc; stearic acid; metal stearates such as calcium stearate and magnesium stearate; colloidal silica; waxes such as bead wax and spermaceti; boric acid; glycol; D, L-leucine; carboxylic acids such as fumaric acid and adipic acid; sodium carboxylates such as sodium benzoate; sulfates such as sodium sulfate; lauryl sulfates such as sodium lauryl sulfate and magnesium lauryl sulfate; silicic acids such as anhydrous silicic acid and silicic acid hydrate; and the starch derivatives in the above excipients.

Examples of emulsifiers may include colloidal clays such as bentonite and veegum; metal hydroxides such as magnesium hydroxide and aluminum hydroxide; anionic surfactants such as sodium lauryl sulfate and calcium stearate; cationic surfactants such as benzalkonium chloride; and nonionic surfactants such as polyoxyethylene alkyl ether, polyoxyethylene sorbitan fatty acid ester and sucrose fatty acid ester.

Examples of stabilizers may include p-hydroxybenzoic acid esters such as methylparaben and propylparaben; alcohols such as chlorobutanol, benzyl alcohol and phenylethyl alcohol; benzalkonium chloride; phenols such as phenol and cresol; thimerosal; dehydroacetic acid; and sorbic acid.

Examples of the corrigents may include sweeteners, acidulants and flavors usually used.

Examples of diluents may include water, ethanol, propylene glycol, ethoxylated isostearyl alcohol and polyoxyethylene sorbitan fatty acid ester.

Examples of injection solvents may include water, ethanol and glycerol.

The dose of the compound represented by the general formula (I) or a pharmacologically acceptable salt thereof which is the active ingredient of the present invention varies depending on the symptoms, age and the like of the patient. The active ingredient can be orally administered at 0.02 mg/kg (preferably 0.1 mg/kg) per dose as the lower limit to 100 mg/kg (preferably 10 mg/kg) per dose as the upper limit, or parenterally administered at 0.002 mg/kg (preferably 0.01 mg/kg) per dose as the lower limit to 10 mg/kg (preferably 1 mg/kg) per dose as the upper limit to an adult human in one to six doses per day according to symptoms.

The compound represented by the general formula (I) or a pharmacologically acceptable salt thereof according to the present invention has excellent properties in terms of renin inhibitory activity, solubility, cell membrane permeability, oral absorption, blood concentration, metabolic stability, tissue distribution, bioavailability, in vitro activity, in vivo activity, a rapid onset of drug effect, a lasting drug effect, physical stability, drug interaction, toxicity and the like and is useful as a medicament [in particular, a medicament for the treatment or prevention (preferably treatment) of hypertension].

BEST MODE FOR CARRYING OUT THE INVENTION

The present invention is explained in more detail below with reference to Examples, Test Examples and Formulation Examples; however, the scope of the present invention is not limited thereto. Exemplary Compound Nos. in the Examples each represent the structure of the corresponding free form of the compound. For example, it is shown in Example 1 that the corresponding free form of compound is a compound of Exemplary Compound No. 1-468 and the compound prepared in Example 1 is a hemifumarate (½ fumarate) of the compound of Exemplary Compound No. 1-468.

EXAMPLES

Example 1

(2S,4S,5S)-5-Amino-6-[4-(2-chlorophenyl)-2,2-dimethyl-5-oxopiperazin-1-yl]-4-hydroxy-2-isopropylhexanoic acid (2-carbamoyl-2-methylpropyl)amide hemifumarate (½ fumarate) (Exemplary Compound No. 1-468)

(1a) 3-Methylbutanoic acid (1R)-1-[(benzyloxy)methyl]prop-2-en-1-yl ester

A solution of 19.9 ml of isobutyric acid chloride (163 mmol) in methylene chloride (20 ml) was added to a solution of 24.29 g of (2R)-1-(benzyloxy)but-3-en-2-ol obtained in Reference Example (1d) (136 mmol), 28.5 ml of triethylamine (205 mmol) and 1.65 g of N,N-dimethylaminopyridine (13.6 mmol) in methylene chloride (250 ml) under ice-cooling over 10 minutes, and the mixture was stirred at room temperature for four hours. 0.75 ml of water (42 mmol) was added to the reaction mixture, and the mixture was further stirred at room temperature for 15 minutes. The reaction mixture was concentrated under reduced pressure and diluted with 150 ml of water, followed by extraction with ethyl acetate. Then, the organic layer was washed with 1 M hydrochloric acid, a saturated sodium bicarbonate aqueous solution and brine and dried over anhydrous magnesium sulfate. After filtration, the solvent was evaporated under reduced pressure, and the residue was purified by silica gel column chromatography (elution solvent:n-hexane/ethyl acetate=9/1) to obtain 34.96 g of the title compound (total yield over four steps: 95%).

Yellow liquid.

$^1$H NMR spectrum (CDCl$_3$, 400 MHz), δ: 7.36-7.27 (m, 5H), 5.84 (ddd, 1H, J=17.2 Hz, 10.6 Hz, 5.9 Hz), 5.54-5.49 (1H, m), 5.33 (dt, 1H, J=17.2 Hz, 1.2 Hz), 5.24 (dt, 1H, J=10.6 Hz, 1.2 Hz), 4.58 (d, 1H, J=12.5 Hz), 4.54 (d, 1H, J=12.5 Hz), 3.58 (dd, 1H, J=1.0 Hz, 5.9 Hz), 3.56 (dd, 1H, J=1.0 Hz, 4.7 Hz), 2.23 (d, 2H, J=6.6 Hz), 2.17-2.07 (m, 1H), 0.96 (d, 6H, J=6.6 Hz).

mass spectrum (FAB$^+$), m/z: 263 ((M+H)$^+$).

(1b) (2S,4E)-6-(Benzyloxy)-2-isopropylhex-4-enoic acid 94 ml of a solution of n-butyllithium in n-hexane (1.57 mol/l) (148 mmol) was added to a solution of 23 ml of diisopropylamine (163 mmol) in tetrahydrofuran (265 ml) under a nitrogen atmosphere and under ice-cooling over 45 minutes. The mixture was stirred at the same temperature for 20 minutes to prepare a solution of lithium diisopropylamide in tetrahydrofuran. A solution of 34.95 g of 3-methylbutanoic acid (1R)-1-[(benzyloxy)methyl]prop-2-en-1-yl ester obtained in Example (1a) (133 mmol) in tetrahydrofuran (70 ml) was added to the solution above under cooling in a dry ice-acetone bath over 40 minutes, and the mixture was stirred at the same temperature for 20 minutes. Then, 39 ml of trimethylsilyl chloride (307 mmol) was added to the reaction mixture over 20 minutes. The mixture was stirred at the same temperature for 20 minutes and then further stirred at room temperature for three hours. After cooling in an ice bath, 27 ml of methanol (667 mmol) was added to the reaction mixture so that the internal temperature did not exceed 20° C. The mixture was further stirred at room temperature for one hour. The reaction mixture was concentrated under reduced pressure and diluted with 270 ml of a 1 M sodium hydroxide aqueous solution, followed by extraction with t-butyl methyl ether. Then, the organic layer was washed with 68 ml of a 1 M sodium hydroxide aqueous solution. All aqueous layers were combined and made acidic with 78 ml of 6 M hydrochloric acid, followed by extraction with ethyl acetate. Then, the organic layer was washed with water and brine and dried over anhydrous magnesium sulfate. After filtration, the solvent was evaporated under reduced pressure to obtain 19.03 g of the crude title compound.

The resulting (2S,4E)-6-(benzyloxy)-2-isopropylhex-4-enoic acid was converted to a corresponding methyl ester by treatment with trimethylsilyldiazomethane in methanol. Then, the optical purity was determined using an analytical optically active HPLC column [ChiralCel OD-H (0.46 cm×25 cm), manufactured by Daicel Chemical Industries, Ltd., elution solvent:n-hexane/2-propanol=90/10, flow rate: 0.5 ml/min)]. The desired 2S isomer had a retention time of 14.7 minutes and the corresponding 2R isomer had a retention time of 16.2 minutes. The optical purity was 91% ee.

Yellow liquid.

Optical rotation, $[\alpha]^D = -9.9°$ (c=1.07, CHCl$_3$).

$^1$H NMR spectrum (CDCl$_3$, 400 MHz), δ: 7.38-7.27 (m, 5H), 5.72-5.62 (m, 2H), 4.47 (s, 2H), 3.99-3.91 (m, 2H), 2.40-2.20 (m, 3H), 1.96-1.88 (m, 1H), 0.98 (d, 3H, J=6.6 Hz), 0.97 (d, 3H, J=6.6 Hz).

(1c) (2S,4E)-6-(Benzyloxy)-2-isopropylhex-4-enoic acid dimethylamide 7.75 ml of oxalyl chloride (87 mmol) and 0.11 ml of N,N-dimethylformamide (1.4 mmol) were added to a solution of 19.02 g of (2S,4E)-6-(benzyloxy)-2-isopropylhex-4-enoic acid obtained in Example (1b) (72.5 mmol) in methylene chloride (180 ml) at room temperature. The mixture was stirred at the same temperature for one hour to prepare a solution of (2S,4E)-6-(benzyloxy)-2-isopropylhex-4-enoic acid chloride in methylene chloride. The solution of acid chloride in methylene chloride above was added to a solution of 76 ml of a 50% dimethylamine aqueous solution (725 mmol) in a mixed solvent of tetrahydrofuran (180 ml) and t-butanol under ice-cooling over one hour, and the mixture was stirred at the same temperature for 20 minutes. The reaction mixture was concentrated under reduced pressure to about ⅕ of the volume and diluted with 150 ml of water, followed by extraction with ethyl acetate. Then, the organic layer was washed with water, a saturated sodium bicarbonate aqueous solution and brine and dried over anhydrous magnesium sulfate. After filtration, the solvent was evaporated under reduced pressure to obtain 21.20 g of the crude title compound.

Yellow liquid.

$^1$H NMR spectrum (CDCl$_3$, 500 MHz), δ: 7.40-7.27 (m, 5H), 5.86-5.60 (m, 2H), 4.47 (s, 2H), 3.97-3.91 (m, 2H), 3.01 (s, 3H), 2.95 (s, 3H), 2.51-2.47 (m, 1H), 2.43-2.38 (m, 1H), 2.29-2.25 (m, 1H), 1.94-1.87 (m, 1H), 0.95 (d, 3H, J=6.9 Hz), 0.90 (d, 3H, J=6.9 Hz).

(1d) (3S,5S)-5-[(1R)-2-Benzyloxy-1-bromoethyl]-3-isopropyldihydrofuran-2-one 25.81 g of N-bromosuccinimide (145 mmol) was added to a solution of 21.20 g of (2S,4E)-6-(benzyloxy)-2-isopropyl-hex-4-enoic acid dimethylamide obtained in Example (1c) (72.5 mmol) and 8.3 ml of acetic acid (145 mmol) in a mixed solvent of tetrahydrofuran (290 ml) and water (145 ml) under ice-cooling, and the mixture was stirred at the same temperature for three hours. 100 ml of a saturated sodium bicarbonate aqueous solution and 100 ml of a 1.5 M sodium sulfite aqueous solution were added to the reaction mixture, and the mixture was further stirred at room temperature for 30 minutes. The reaction mixture was concentrated under reduced pressure to about ⅔ of the volume, followed by extraction with ethyl acetate. Then, the organic layer was washed with water and brine and dried over anhydrous magnesium sulfate. After filtration, the solvent was evaporated under reduced pressure, and the residue was purified by silica gel column chromatography (elution solvent:n-hexane/ethyl acetate=6/1-5/1) to obtain 22.73 g of the title compound (total yield over three steps: 50%).

Colorless liquid.

$^1$H NMR spectrum (CDCl$_3$, 500 MHz), δ: 7.38-7.30 (m, 5H), 4.75-4.71 (m, 1H), 4.61 (d, 1H, J=12.2 Hz), 4.56 (d, 1H, J=12.2 Hz), 4.22 (q, 1H, J=5.9 Hz), 3.84 (dd, 1H, J=10.7 Hz, 5.4 Hz), 3.78 (dd, 1H, J=10.7 Hz, 6.4 Hz), 2.67-2.63 (m, 1H), 2.27-2.22 (m, 1H), 2.20-2.11 (m, 2H), 1.02 (d, 3H, J=6.8 Hz), 0.94 (d, 3H, J=6.8 Hz).

(1e) (3S,5S)-5-[(S)-1-Azido-2-benzyloxyethyl]-3-isopropyldihydrofuran-2-one 5.10 g of sodium azide (78.5 mmol) was added to a solution of 22.33 g of (3S,5S)-5-[(1R)-2-benzyloxy-1-bromoethyl]-3-isopropyldihydrofuran-2-one obtained in Example (1d) (65.4 mmol) in N,N'-dimethylpropyleneurea (130 ml) at room temperature, and the mixture was stirred at 40° C. for three days. The reaction mixture was cooled and then poured into ice water, followed by extraction with diethyl ether. Then, the organic layer was washed with water and brine and dried over anhydrous magnesium sulfate. After filtration, the solvent was evaporated under reduced pressure, and the residue was purified by silica gel column chromatography (elution solvent:n-hexane/ethyl acetate=6/1) to obtain 10.19 g of the title compound (yield: 51%).

Colorless liquid.

$^1$H NMR spectrum (CDCl$_3$, 500 MHz), δ: 7.38-7.29 (m, 5H), 4.61-4.53 (m, 3H), 3.79-3.73 (m, 2H), 3.66-3.63 (m, 1H), 2.75-2.70 (m, 1H), 2.20-2.10 (m, 3H), 1.02 (d, 3H, J=6.8 Hz), 0.92 (d, 3H, J=6.8 Hz).

(1f) N-{(S)-2-Hydroxy-1-[(2S,4S)-4-isopropyl-5-oxotetrahydrofuran-2-yl]ethyl}-2-nitrobenzenesulfonamide A suspension of 10.12 g of (3S,5S)-5-[(S)-1-azido-2-benzyloxyethyl]-3-isopropyldihydrofuran-2-one obtained in Example (1e) (33.5 mmol), 16.7 ml of a solution of 4 N hydrochloric acid in dioxane (66.8 mmol) and 3.57 g of 10% palladium-carbon (50% wet) in ethanol (170 ml) was stirred under a hydrogen atmosphere at room temperature for six hours. Hydrogen in the reaction vessel was replaced by nitrogen, and then the reaction mixture was diluted with 170 ml of ethanol. Palladium-carbon was separated by filtration and washed with ethanol. The solvent was evaporated from the filtrate under reduced pressure to obtain 8.50 g of crude (3S,5S)-5-[(S)-1-amino-2-hydroxyethyl]-3-isopropyldihydrofuran-2-one hydrochloride.

14 ml of triethylamine (101 mmol) and 11.12 g of O-nitrobenzenesulfonyl chloride (50.1 mmol) were added to a solution of 8.50 g of (3S,5S)-5-[(S)-1-amino-2-hydroxyethyl]-3-isopropyldihydrofuran-2-one hydrochloride obtained in the above reaction (33.5 mmol) in a mixed solvent of tetrahydrofuran (170 ml) and water (17 ml) at room temperature, and the mixture was stirred at the same temperature for 12 hours. The reaction mixture was concentrated under reduced pressure, followed by extraction with ethyl acetate. Then, the organic layer was washed with water, a saturated sodium bicarbonate aqueous solution and brine and dried over anhydrous magnesium sulfate. After filtration, the solvent was evaporated under reduced pressure, and the residue was purified by silica gel column chromatography (elution solvent:ethyl acetate). Further, 110 ml of diisopropyl ether and 11 ml of ethyl acetate were added, and the precipitated solid was collected by filtration to obtain 8.78 g of the title compound (total yield over two steps: 70%).

The optical purity of the resulting N-{(S)-2-hydroxy-1-[(2S,4S)-4-isopropyl-5-oxotetrahydrofuran-2-yl]ethyl}-2-nitrobenzenesulfonamide was determined using an analytical optically active HPLC column [Chiralpak AD-H (0.46 cm×25 cm), manufactured by Daicel Chemical Industries, Ltd., elution solvent:n-hexane/ethanol=30/70, flow rate: 1.0 ml/min)]. The desired [(S), (2S,4S)] isomer had a retention time of 5.7 minutes and the corresponding [(R), (2R,4R)] isomer had a retention time of 9.0 minutes. The optical purity was 90% ee.

Colorless solid.
Optical rotation, $[\alpha]^D$=+26.9° (c=1.00, MeOH).
$^1$H NMR spectrum (CDCl$_3$, 500 MHz), δ: 8.15-8.11 (m, 1H), 7.92-7.88 (m, 1H), 7.77-7.74 (m, 2H), 5.85 (br d, 1H, J=8.3 Hz), 4.64-4.61 (m, 1H), 3.71-3.62 (m, 3H), 2.69 (ddd, 1H, J=10.3 Hz, 6.8 Hz, 5.4 Hz), 2.41 (ddd, 1H, J=13.7 Hz, 10.7 Hz, 5.4 Hz), 2.20-2.10 (m, 2H), 1.99 (t, 1H, J=5.4 Hz), 1.00 (d, 3H, J=6.8 Hz), 0.93 (d, 3H, J=6.8 Hz).
mass spectrum (FAB$^+$), m/z: 373 ((M+H)$^+$).

(1g) (3S,5S)-3-Isopropyl-5-[(S)-1-(2-nitrobenzene-sulfonyl)aziridin-2-yl]dihydrofuran-2-one 5.9 ml of a solution of diethyl azodicarboxylate in toluene (40%) (12.9 mmol) was added to a solution of 4.00 g of N-{(S)-2-hydroxy-1-[(2S,4S)-4-isopropyl-5-oxotetrahydrofuran-2-yl]ethyl}-2-nitrobenzenesulfonamide obtained in Example (1f) (10.7 mmol) and 3.38 g of triphenylphosphine (12.9 mmol) in tetrahydrofuran (100 ml) under ice-cooling over 10 minutes, and the mixture was stirred at the same temperature for 10 minutes. The reaction mixture was concentrated under reduced pressure, and the residue was purified by silica gel column chromatography (elution solvent: toluene/acetone=5/1) to obtain 3.40 g of the title compound (yield: 89%).

Colorless liquid.
$^1$H NMR spectrum (CDCl$_3$, 400 MHz), δ: 8.14 (dd, 1H, J=7.4 Hz, 1.5 Hz), 7.83-7.73 (m, 3H), 4.74-4.70 (m, 1H), 3.26-3.23 (m, 1H), 2.83 (d, 1H, J=7.0 Hz), 2.78 (dt, 1H, J=9.8 Hz, 4.7 Hz), 2.65 (d, 1H, J=4.7 Hz), 2.41-2.35 (m, 1H), 2.29 (dt, 1H, J=12.9 Hz, 9.4 Hz), 2.18-2.10 (m, 1H), 1.00 (d, 3H, J=6.6 Hz), 0.90 (d, 3H, J=7.0 Hz).
mass spectrum (FAB$^+$), m/z: 355 ((M+H)$^+$).

(1h) [2-(2-Chlorophenylamino)-1,1-dimethylethyl] carbamic acid t-butyl ester 4.07 g of sodium triacetoxyborohydride (19.3 mmol) was added to a solution of 3.00 g of (1,1-dimethyl-2-oxoethyl) carbamic acid t-butyl ester obtained in Reference Example 3 (16.0 mmol), 2.04 g of 2-chloroaniline (16.0 mmol) and 0.92 ml of acetic acid (16.0 mmol) in methylene chloride (160 ml) under ice-cooling, and the mixture was stirred at room temperature for 16 hours. A saturated sodium bicarbonate aqueous solution was added to the reaction mixture, followed by extraction with methylene chloride. Then, the organic layer was washed with brine and dried over anhydrous sodium sulfate. After filtration, the solvent was evaporated under reduced pressure, and the residue was purified by silica gel column chromatography (elution solvent:hexane/ethyl acetate=5/1) to obtain 3.49 g of the title compound (yield: 73%).

Colorless solid.
$^1$H NMR spectrum (CDCl$_3$, 400 MHz), δ: 7.23 (dd, 1H, J=8.2 Hz, 1.6 Hz), 7.12-7.07 (m, 1H), 6.72 (dd, 1H, J=8.2 Hz, 1.6 Hz), 6.61-6.57 (m, 1H), 4.59 (br s, 1H), 4.55 (br s, 1H), 3.38 (d, 2H, J=5.9 Hz), 1.43 (s, 9H), 1.36 (s, 6H).

(1i) {2-[(2-Bromoacetyl)-(2-chlorophenyl)amino]-1,1-dimethylethyl}carbamic acid t-butyl ester 1.52 ml of bromoacetyl bromide (17.5 mmol) was added to a solution of 3.49 g of [2-(2-chlorophenylamino)-1,1-dimethylethyl]carbamic acid t-butyl ester obtained in Example (1h) (11.7 mmol) in N,N-dimethylacetamide (58 ml) under ice-cooling, and the mixture was stirred at the same temperature for 10 minutes. A saturated sodium bicarbonate aqueous solution was added to the reaction mixture, followed by extraction with ethyl acetate. Then, the organic layer was washed with water and brine and dried over anhydrous magnesium sulfate. After filtration, the solvent was evaporated under reduced pressure. Hexane was added to the residue, and the solid was collected by filtration to obtain 4.68 g of the title compound (yield: 95%).

Colorless solid.
$^1$H NMR spectrum (CDCl$_3$, 400 MHz), δ: 7.51-7.47 (m, 2H), 7.38-7.29 (m, 2H), 4.63 (br s, 1H), 4.16 (d, 1H, J=14.1 Hz), 3.99 (br d, 1H, J=14.1 Hz), 3.69 (br d, 1H, J=11.7 Hz), 3.53 (d, 1H, J=11.7 Hz), 1.35 (br s, 3H), 1.34 (br s, 3H), 1.18 (s, 9H).

(1j) 4-(2-Chlorophenyl)-2,2-dimethyl-5-oxopiperazine-1-carboxylic acid t-butyl ester A solution of 1.87 g of potassium t-butoxide (16.7 mmol) in tetrahydrofuran (110 ml) was added to a solution of 4.68 g of {2-[(2-bromoacetyl)-(2-chlorophenyl)amino]-1,1-dimethylethyl}carbamic acid t-butyl ester obtained in Example (1i) (11.2 mmol) in tetrahydrofuran (110 ml) under a nitrogen atmosphere and under cooling in a dry ice-acetone bath over 30 minutes, and the mixture was stirred at the same temperature for 10 minutes. A saturated ammonium chloride aqueous solution was added to the reaction mixture. The mixture was returned to room temperature and diluted with water, followed by extraction with ethyl acetate. Then, the organic layer was dried over anhydrous magnesium sulfate. After filtration, the solvent was evaporated under reduced pressure, and the residue was purified by silica gel column chromatography (elution solvent:hexane/ethyl acetate=2/1) to obtain 3.07 g of the title compound (yield: 81%).

Colorless solid.
$^1$H NMR spectrum (CDCl$_3$, 400 MHz), δ: 7.50-7.47 (m, 1H), 7.36-7.27 (m, 3H), 4.41 (br s, 1H), 4.09 (br s, 1H), 3.86 (br s, 1H), 3.28 (br s, 1H), 1.56 (br s, 6H), 1.50 (s, 9H).

(1k)
1-(2-Chlorophenyl)-5,5-dimethylpiperazin-2-one 7.0 ml of trifluoroacetic acid (91 mmol) was added to a solution of 3.07 g of 4-(2-chlorophenyl)-2,2-dimethyl-5-oxopiperazine-1-carboxylic acid t-butyl ester obtained in Example (1j) (9.1 mmol) in methylene chloride (14 ml) at room temperature, and the mixture was stirred at the same temperature for 30 minutes. The reaction mixture was concentrated under reduced pressure. A saturated sodium bicarbonate aqueous solution was added, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol=10/1) to obtain 2.14 g of the title compound (yield: 98%).

Colorless liquid.

$^1$H NMR spectrum (CDCl$_3$, 400 MHz), δ: 7.49-7.46 (m, 1H), 7.35-7.24 (m, 3H), 3.76 (d, 1H, J=18.0 Hz), 3.69 (d, 1H, J=18.0 Hz), 3.47 (d, 1H, J=11.3 Hz), 3.77 (d, 1H, J=11.3 Hz), 1.39 (s, 3H), 1.32 (s, 3H).

mass spectrum (FAB$^+$), m/z: 239 ((M+H)$^+$).

(1l) N-{(S)-2-[4-(2-Chlorophenyl)-2,2-dimethyl-5-oxopiperazin-1-yl]-1-[(2S,4S)-4-isopropyl-5-oxotetrahydrofuran-2-yl]ethyl}-2-nitrobenzenesulfonamide A solution of 192 mg of (3S,5S)-3-isopropyl-5-[(S)-1-(2-nitrobenzenesulfonyl)aziridin-2-yl]dihydrofuran-2-one obtained in Example (1g) (0.54 mmol) and 181 mg of 1-(2-chlorophenyl)-5,5-dimethylpiperazin-2-one obtained in Example (1k) (0.76 mmol) in toluene (7 ml) was stirred at 110° C. for 1.5 hours. After cooling, the reaction mixture was concentrated under reduced pressure, and the residue was purified by silica gel column chromatography (elution solvent: methylene chloride/ethyl acetate=5/1) to obtain 299 mg of the title compound (yield: 93%).

Colorless solid.

$^1$H NMR spectrum (CDCl$_3$, 400 MHz), δ: 8.18-8.16 (m, 1H), 7.93 (br s, 1H), 7.83-7.76 (m, 2H), 7.46 (dd, 1H, J=7.8 Hz, 2.0 Hz), 7.36-7.27 (m, 2H), 7.22-7.11 (m, 1H), 5.93 (br s, 0.5H), 5.53 (br s, 0.5H), 4.88-4.84 (m, 1H), 3.62 (br s, 1H), 3.30-3.10 (m, 3H), 2.92-2.69 (m, 2.5H), 2.56 (br s, 1H), 2.44 (ddd, 1H, J=13.7 Hz, 10.6 Hz, 5.9 Hz), 2.27-2.14 (m, 2.5H), 1.17 (br s, 3H), 1.08 (br s, 3H), 1.04 (d, 3H, J=6.6 Hz), 0.98 (d, 3H, J=6.6 Hz).

(1m) {(S)-2-[4-(2-Chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester 197 mg of cesium carbonate (0.61 mmol) was added to a solution of 299 mg of N-{(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}-2-nitrobenzenesulfonamide obtained in Example (1l) (0.50 mmol) and 0.11 ml of thiophenol (content: 95%) (1.00 mmol) in N,N-dimethylformamide (5 ml) under a nitrogen atmosphere at room temperature, and the mixture was stirred at the same temperature for one hour. Brine was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol=20/1-10/1). 0.21 ml of triethylamine (1.51 mmol) and 132 mg of di-t-butyl dicarbonate (0.61 mmol) were added to a solution of the resulting 4-{(S)-2-amino-2-[(2S,4S)-4-isopropyl-5-oxotetrahydrofuran-2-yl]ethyl}1-(2-chlorophenyl)-5,5-dimethylpiperazin-2-one in methylene chloride (5 ml), and the mixture was stirred at room temperature for 15 hours. Brine was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/ethyl acetate=2/1) to obtain 205 mg of the title compound (yield: 80%).

Colorless solid.

$^1$H NMR spectrum (CDCl$_3$, 400 MHz), δ: 7.47 (dd, 1H, J=7.8 Hz, 2.0 Hz), 7.34-7.20 (m, 3H), 4.86-4.78 (m, 1H), 4.47-4.42 (m, 1H), 3.87-3.81 (m, 1H), 3.58-3.24 (m, 4H), 2.79-2.32 (m, 0.5H), 2.62-2.57 (m, 2H), 2.44-2.39 (m, 0.5H), 2.31-2.24 (m, 1H), 2.21-2.11 (m, 2H), 1.45 (s, 9H), 1.26-1.22 (m, 6H), 1.03 (d, 3H, J=7.0 Hz), 0.97 (d, 3H, J=6.6 Hz).

(1n) {(1S,2S,4S)-4-(2-Carbamoyl-2-methylpropylcarbamoyl)-1-[4-(2-chlorophenyl)-2,2-dimethyl-5-oxopiperazin-1-ylmethyl]-2-hydroxy-5-methylhexyl}carbamic acid t-butyl ester 140 mg of 3-amino-2,2-di(methyl)propionamide obtained in Reference Example 2 (1.21 mmol) and 38 mg of 2-hydroxypyridine (0.40 mmol) were added to a solution of 205 mg of {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) (0.40 mmol) in triethylamine (4 ml), and the mixture was stirred at 80° C. for four hours. The reaction mixture was cooled and then concentrated under reduced pressure and further stirred at 80° C. for 14 hours. The reaction mixture was cooled and then water was added, followed by extraction with methylene chloride. Then, the organic layer was dried over anhydrous magnesium sulfate. After filtration, the solvent was evaporated under reduced pressure, and the residue was purified by silica gel column chromatography (elution solvent: methylene chloride/methanol=40/3) to obtain 167 mg of the title compound (yield: 66%).

Yellow solid.

$^1$H NMR spectrum (CDCl$_3$, 400 MHz), δ: 7.48-7.46 (m, 1H), 7.36-7.14 (m, 3H), 6.31-5.56 (m, 4H), 5.02 (br s, 0.6H), 4.66 (br s, 0.4H), 3.92-3.33 (m, 6H), 3.28-3.14 (m, 2H), 2.76-2.51 (m, 2H), 2.11-2.06 (m, 1H), 1.92-1.76 (m, 2H), 1.67-1.61 (m, 1H), 1.45 (s, 9H), 1.26-1.22 (m, 12H), 0.96-0.92 (m, 6H).

(1o) (2S,4S,5S)-5-Amino-6-[4-(2-chlorophenyl)-2,2-dimethyl-5-oxopiperazin-1-yl]-4-hydroxy-2-isopropylhexanoic acid (2-carbamoyl-2-methylpropyl) amide hemifumarate (½ fumarate)

0.41 ml of trifluoroacetic acid (5.4 mmol) was added to a solution of 167 mg of {(1S,2S,4S)-4-(2-carbamoyl-2-methylpropylcarbamoyl)-1-[4-(2-chlorophenyl)-2,2-dimethyl-5-oxopiperazin-1-ylmethyl]-2-hydroxy-5-methylhexyl}carbamic acid t-butyl ester obtained in Example (1n) (0.28 mmol) in methylene chloride (0.82 ml) at room temperature, and the mixture was stirred at the same temperature for 50 minutes. After concentration under reduced pressure, a saturated sodium bicarbonate solution was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent: methylene chloride/methanol/triethylamine=100/10/1). 10.0 mg of fumaric acid (0.09 mmol) was added to a solution of 90 mg of (2S,4S,5S)-5-amino-6-[4-(2-chlorophenyl)-2,2-dimethyl-5-oxopiperazin-1-yl]-4-hydroxy-2-isopropylhexanoic acid (2-carbamoyl-2-methylpropyl)amide obtained above (0.17 mmol) in methanol (2 ml), and the mixture was stirred at room temperature for five minutes. The reaction mixture was concentrated under reduced pressure, and methylene chloride (0.8 ml) was added to the residue. Diethyl ether (8 ml) was further added and the solid was collected by filtration to obtain 90 mg of the title compound (yield: 58%).

Colorless solid.

$^1$H NMR spectrum (CD$_3$OD, 400 MHz), δ: 7.56-7.53 (m, 1H), 7.44-7.32 (m, 3H), 6.67 (s, 1H), 3.86-3.59 (m, 2H), 3.52-3.12 (m, 6H), 2.95 (br t, 0.6H, J=12.5 Hz), 2.81-2.67 (m, 0.8H), 2.51 (dd, 0.6H, J=13.5 Hz, 4.1 Hz), 2.38-2.33 (m, 1H), 1.88-1.67 (m, 3H), 1.31-1.27 (m, 6H), 1.22 (s, 3H), 1.20 (s, 3H), 0.99-0.96 (m, 6H).

mass spectrum (FAB$^+$), m/z: 525 ((M+H)$^+$).

Example 2

(2S,4S,5S)-5-Amino-6-[4-(2-chlorophenyl)-2,2-dimethyl-5-oxopiperazin-1-yl]-4-hydroxy-2-isopropylhexanoic acid [(S)-2-methylbutyl]amide fumarate (Exemplary Compound No. 1-170)

(2a) {(1S,2S,4S)-1-[4-(2-Chlorophenyl)-2,2-dimethyl-5-oxopiperazin-1-ylmethyl]-2-hydroxy-5-methyl-4-[(S)-2-methylbutylcarbamoyl]hexyl}carbamic acid t-butyl ester 0.24 ml of (S)-2-methylbutylamine (2.0 mmol) and 37 mg of 2-hydroxypyridine (0.39 mmol) were added to 200 mg of {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) (0.39 mmol), and the mixture was stirred at 80° C. for four hours. The reaction mixture was cooled and then water was added, followed by extraction with ethyl acetate. Then, the organic layer was washed with brine and then dried over anhydrous sodium sulfate. After filtration, the solvent was evaporated under reduced pressure, and the residue was purified by silica gel column chromatography (elution solvent: methylene chloride/acetone=3/1) to obtain 184 mg of the title compound (yield: 79%).

Colorless solid.

$^1$H NMR spectrum (CDCl$_3$, 400 MHz), δ: 7.48-7.46 (m, 1H), 7.34-7.21 (m, 3H), 5.70 (br t, 1H, J=5.5 Hz), 5.05 (br s, 1H), 3.89 (br d, 1H, J=9.4 Hz), 3.70 (br s, 0.4H), 3.65 (br s, 0.6H), 3.49-3.10 (m, 6H), 2.81-2.63 (m, 2H), 2.07-2.02 (m, 1H), 1.98-1.89 (m, 1H), 1.79-1.52 (m, 3H), 1.46-1.35 (m, 10H), 1.25-1.11 (m, 7H), 0.97-0.88 (m, 12H).

(2b) (2S,4S,5S)-5-Amino-6-[4-(2-chlorophenyl)-2,2-dimethyl-5-oxopiperazin-1-yl]-4-hydroxy-2-isopropylhexanoic acid [(S)-2-methylbutyl]amide fumarate 2.3 ml of a solution of 4 N hydrochloric acid in dioxane (9.3 mmol) was added to a solution of 184 mg of {(1S,2S,4S)-1-[4-(2-chlorophenyl)-2,2-dimethyl-5-oxopiperazin-1-ylmethyl]-2-hydroxy-5-methyl-4-[(S)-2-methylbutyl]hexyl}carbamic acid t-butyl ester obtained in Example (2a) (0.31 mmol) in dioxane (0.3 ml) at room temperature, and the mixture was stirred at the same temperature for 15 minutes. A saturated sodium bicarbonate aqueous solution was added to the reaction mixture under cooling in an ice bath, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol/triethylamine=100/10/1). 17.6 mg of fumaric acid (0.24 mmol) was added to a solution of 118 mg of (2S,4S,5S)-5-amino-6-[4-(2-chlorophenyl)-2,2-dimethyl-5-oxopiperazin-1-yl]-4-hydroxy-2-isopropylhexanoic acid [(S)-2-methylbutyl]amide obtained above (0.24 mmol) in methanol (2.4 ml), and the mixture was stirred at room temperature for five minutes. The solvent was evaporated under reduced pressure to obtain 111 mg of the title compound (yield: 59%).

Colorless solid.

$^1$H NMR spectrum (CD$_3$OD, 400 MHz), δ: 8.01 (br s, 1H), 7.56-7.54 (m, 1H), 7.44-7.32 (m, 3H), 6.68 (s, 2H), 3.67-3.60 (m, 2H), 3.51-3.45 (m, 1H), 3.37-3.11 (m, 4H), 3.06-2.92 (m, 1.6H), 2.81-2.67 (m, 0.8H), 2.52 (d, 0.6H, J=13.3 Hz, 4.3 Hz), 2.37-2.31 (m, 1H), 1.88-1.80 (m, 2H), 1.74-1.68 (m, 1H), 1.63-1.53 (m, 1H), 1.51-1.41 (m, 1H), 1.31-1.27 (m, 6H), 1.22-1.11 (m, 1H), 1.00-0.91 (m, 12H).

mass spectrum (FAB$^+$), m/z: 496 ((M+H)$^+$).

Example 3

(2S,4S,5S)-5-Amino-6-[4-(2-chlorophenyl)-2,2-dimethyl-5-oxopiperazin-1-yl]-4-hydroxy-2-isopropylhexanoic acid cyclopentylamide hemifumarate (½ fumarate) (Exemplary Compound No. 1-647)

(3a) {(1S,2S,4S)-1-[4-(2-Chlorophenyl)-2,2-dimethyl-5-oxopiperazin-1-ylmethyl]-4-cyclopentylcarbamoyl-2-hydroxy-5-methylhexyl}carbamic acid t-butyl ester 0.17 g of cyclopentylamine (2.0 mmol) and 37 mg of 2-hydroxypyridine (0.39 mmol) were added to 200 mg of {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) (0.39 mmol), and the mixture was stirred at 80° C. for six hours. The reaction mixture was cooled and then water was added, followed by extraction with ethyl acetate. Then, the organic layer was washed with brine and then dried over anhydrous sodium sulfate. After filtration, the solvent was evaporated under reduced pressure, and the residue was purified by silica gel column chromatography (elution solvent: methylene chloride/methanol=20/1) to obtain 193 mg of the title compound (yield: 83%).

Colorless solid.

$^1$H NMR spectrum (CDCl$_3$, 400 MHz), δ: 7.49-7.46 (m, 1H), 7.35-7.21 (m, 3H), 5.68 (br d, 1H, J=7.4 Hz), 5.06 (br s, 1H), 4.27-4.18 (m, 1H), 3.90 (br d, 1H, J=10.2 Hz), 3.70-3.62 (m, 1H), 3.50-3.22 (m, 4H), 2.79-2.64 (m, 2H), 2.01-1.55 (m, 10H), 1.46 (s, 9H), 1.42-1.36 (m, 2H), 1.26-1.23 (m, 6H), 0.96-0.93 (m, 6H).

(3b) (2S,4S,5S)-5-Amino-6-[4-(2-chlorophenyl)-2,2-dimethyl-5-oxopiperazin-1-yl]-4-hydroxy-2-isopropylhexanoic acid cyclopentylamide hemifumarate (½ fumarate)

0.75 ml of trifluoroacetic acid (9.8 mmol) was added to a solution of 193 mg of {(1S,2S,4S)-1-[4-(2-chlorophenyl)-2,2-dimethyl-5-oxopiperazin-1-ylmethyl]-4-cyclopentylcarbamoyl-2-hydroxy-5-methylhexyl}carbamic acid t-butyl ester obtained in Example (3a) (0.33 mmol) in methylene chloride (1.5 ml) at room temperature, and the mixture was stirred at the same temperature for 30 minutes. The reaction mixture was concentrated under reduced pressure and diluted with a saturated sodium bicarbonate aqueous solution, followed by extraction with methylene chloride. Then, the organic layer was dried over anhydrous magnesium sulfate. After filtration, the solvent was evaporated under reduced pressure, and the residue was purified by silica gel column chromatography (elution solvent: methylene chloride/methanol/triethylamine=200/20/1). 33.5 mg of fumaric acid (0.29 mmol) was added to a solution of 144 mg of (2S,4S,5S)-5-amino-6-[4-(2-chlorophenyl)-2,2-dimethyl-5-oxopiperazin-1-yl]-4-hydroxy-2-isopropylhexanoic acid cyclopentylamide obtained above (0.29 mmol) in methanol (3 ml), and the mixture was stirred at room temperature for five minutes. The reaction mixture was concentrated under reduced pressure, and methylene chloride (1.5 ml) and ether (15 ml) were added to the residue. The solid was collected by filtration to obtain 153 mg of the title compound (yield: 86%).

Colorless solid.

$^1$H NMR spectrum (CD$_3$OD, 400 MHz), δ: 8.00 (br d, 1H, J=7.4 Hz), 7.56-7.53 (m, 1H), 7.44-7.32 (m, 3H), 6.69 (s, 1H), 4.17-4.11 (m, 1H), 3.67-3.59 (m, 2H), 3.52-3.46 (m, 1H), 3.37-3.14 (m, 3H), 2.95 (br t, 0.6H, J=12.3 Hz), 2.81-2.69 (m, 0.8H), 2.55-2.50 (m, 0.6H), 2.32-2.27 (m, 1H), 1.96-1.90 (m, 2H), 1.87-1.44 (m, 9H), 1.31-1.26 (m, 6H), 0.99-0.95 (m, 6H).

mass spectrum (FAB$^+$), m/z: 493 ((M+H)$^+$).

Example 4

(2S,4S,5S)-5-Amino-6-[4-(2-chlorophenyl)-2,2-dimethyl-5-oxopiperazin-1-yl]-4-hydroxy-2-isopropylhexanoic acid butylamide fumarate (Exemplary Compound No. 1-46)

(4a) {(1S,2S,4S)-4-Butylcarbamoyl-1-[4-(2-chlorophenyl)-2,2-dimethyl-5-oxopiperazin-1-ylmethyl]-2-hydroxy-5-methylhexyl}carbamic acid t-butyl ester 0.14 g of n-butylamine (2.0 mmol) and 37 mg of 2-hydroxypyridine (0.39 mmol) were added to 200 mg of {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) (0.39 mmol), and the mixture was stirred at 70° C. for one hour. The reaction mixture was cooled and then water was added, followed by extraction with ethyl acetate. Then, the organic layer was washed with brine and then dried over anhydrous sodium sulfate. After filtration, the solvent was evaporated under reduced pressure, and the residue was purified by silica gel column chromatography (elution solvent: methylene chloride/methanol=20/1) to obtain 215 mg of the title compound (yield: 94%).

Colorless solid.

$^1$H NMR spectrum (CDCl$_3$, 400 MHz), δ: 7.48-7.46 (m, 1H), 7.34-7.21 (m, 3H), 5.71 (br s, 1H), 5.04 (br s, 1H), 3.89 (br d, 1H, J=10.2 Hz), 3.70 (br s, 0.4H), 3.65 (br s, 0.6H), 3.48-3.16 (m, 6H), 2.78-2.63 (m, 2H), 2.04-1.88 (m, 2H), 1.79-1.64 (m, 2H), 1.54-1.31 (m, 13H), 1.46-1.23 (m, 6H), 0.97-0.90 (m, 9H).

(4b) (2S,4S,5S)-5-Amino-6-[4-(2-chlorophenyl)-2,2-dimethyl-5-oxopiperazin-1-yl]-4-hydroxy-2-isopropylhexanoic acid butylamide fumarate 0.86 ml of trifluoroacetic acid (11 mmol) was added to a solution of 215 mg of {(1S,2S,4S)-4-butylcarbamoyl-1-[4-(2-chlorophenyl)-2,2-dimethyl-5-oxopiperazin-1-ylmethyl]-2-hydroxy-5-methylhexyl}carbamic acid t-butyl ester obtained in Example (4a) (0.37 mmol) in methylene chloride (1.7 ml) at room temperature, and the mixture was stirred at the same temperature for 30 minutes. The reaction mixture was concentrated under reduced pressure and diluted with a saturated sodium bicarbonate aqueous solution, followed by extraction with methylene chloride. Then, the organic layer was dried over anhydrous magnesium sulfate. After filtration, the solvent was evaporated under reduced pressure, and the residue was purified by silica gel column chromatography (elution solvent: methylene chloride/methanol/triethylamine=200/20/1). 35.2 mg of fumaric acid (0.30 mmol) was added to a solution of 146 mg of (2S,4S,5S)-5-amino-6-[4-(2-chlorophenyl)-2,2-dimethyl-5-oxopiperazin-1-yl]-4-hydroxy-2-isopropylhexanoic acid butylamide obtained above (0.30 mmol) in methanol (3 ml), and the mixture was stirred at room temperature for five minutes. The solvent was evaporated under reduced pressure to obtain 155 mg of the title compound (yield: 71%).

Colorless solid.

$^1$H NMR spectrum (CD$_3$OD, 400 MHz), δ: 8.03 (br s, 1H), 7.56-7.53 (m, 1H), 7.44-7.32 (m, 3H), 6.68 (s, 2H), 3.68-3.60 (m, 2H), 3.51-3.45 (m, 1H), 3.37-3.18 (m, 5H), 2.95 (br t, 0.6H, J=11.0 Hz), 2.82-2.67 (m, 0.8H), 2.52 (dd, 0.6H, J=13.7 Hz, 3.9 Hz), 2.33-2.28 (m, 1H), 1.87-1.78 (m, 2H), 1.75-1.68 (m, 1H), 1.55-1.48 (m, 2H), 1.42-1.33 (m, 2H), 1.31-1.26 (m, 6H), 1.00-0.93 (m, 9H).

mass spectrum (FAB$^+$), m/z: 482 ((M+H)$^+$).

Example 5

(2S,4S,5S)-5-Amino-6-[4-(2-chlorophenyl)-2,2-dimethyl-5-oxopiperazin-1-yl]-4-hydroxy-2-isopropylhexanoic acid isobutylamide hemifumarate (½ fumarate) (Exemplary Compound No. 1-125)

147 mg of the title compound (total yield over two steps: 64%) was obtained in the same manner as in Examples (1n) and (1o) using {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) and isobutylamine.

Colorless solid.

$^1$H NMR spectrum (CD$_3$OD, 400 MHz), δ: 7.56-7.53 (m, 1H), 7.44-7.32 (m, 3H), 6.67 (s, 1H), 3.67-3.60 (m, 2H), 3.52-3.46 (m, 1H), 3.37-3.11 (m, 4H), 2.97-2.89 (m, 1.6H), 2.80-2.67 (m, 0.8H), 2.53-2.49 (m, 0.6H), 2.37-2.32 (m, 1H), 1.88-1.68 (m, 4H), 1.31-1.26 (m, 6H), 1.00-0.93 (m, 12H).

mass spectrum (FAB$^+$), m/z: 481 ((M+H)$^+$).

Example 6

(2S,4S,5S)-5-Amino-6-[4-(2-chlorophenyl)-2,2-dimethyl-5-oxopiperazin-1-yl]-4-hydroxy-2-isopropylhexanoic acid isopropylamide fumarate (Exemplary Compound No. 1-2)

147 mg of the title compound (total yield over two steps: 64%) was obtained in the same manner as in Examples (1n) and (1o) using {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) and isopropylamine.

Colorless solid.

$^1$H NMR spectrum (CD$_3$OD, 500 MHz), δ: 7.90 (br d, J=7.8 Hz, 1H), 7.55-7.54 (m, 1H), 7.43-7.32 (m, 3H), 6.68 (s, 2H), 4.06-3.98 (m, 1H), 3.66-3.60 (m, 2.4H), 3.53-3.46 (m, 1.4H), 3.37-3.35 (m, 0.8H), 3.23-3.19 (m, 0.8H), 3.17-3.13 (m, 0.6H), 2.97-2.92 (m, 0.6H), 2.80-2.69 (m, 0.8H), 2.54-

2.51 (m, 0.6H), 2.29-2.25 (m, 1H), 1.85-1.78 (m, 2H), 1.74-1.68 (m, 1H), 1.31-1.261 (m, 6H), 1.19-1.15 (m, 6H), 1.00-0.96 (m, 6H).

mass spectrum (FAB$^+$), m/z: 467 ((M+H)$^+$).

Example 7

(2S,4S,5S)-5-Amino-6-[4-(2-chlorophenyl)-2,2-dimethyl-5-oxopiperazin-1-yl]-4-hydroxy-2-isopropylhexanoic acid cyclohexylamide fumarate (Exemplary Compound No. 1-726)

133 mg of the title compound (total yield over two steps: 54%) was obtained in the same manner as in Examples (1n) and (1o) using {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) and cyclohexylamine.

Colorless solid.

$^1$H NMR spectrum (CD$_3$OD, 400 MHz), δ: 7.90 (br d, J=7.4 Hz, 1H), 7.56-7.54 (m, 1H), 7.44-7.32 (m, 3H), 6.69 (s, 2H), 3.47-3.59 (m, 4H), 3.54-3.46 (m, 1H), 3.37-3.12 (m, 2H), 2.97-2.91 (m, 0.6H), 2.81-2.68 (m, 0.8H), 2.55-2.50 (m, 0.6H), 2.30-2.24 (m, 1H), 1.90-1.62 (m, 8H), 1.41-1.15 (m, 11H), 1.01-0.95 (m, 6H).

mass spectrum (FAB$^+$), m/z: 507 ((M+H)$^+$).

Example 8

(2S,4S,5S)-5-Amino-6-[4-(2-chlorophenyl)-2,2-dimethyl-5-oxopiperazin-1-yl]-4-hydroxy-2-isopropylhexanoic acid (3-hydroxy-2,2-dimethylpropyl)amide fumarate (Exemplary Compound No. 1-288)

126 mg of the title compound (total yield over two steps: 51%) was obtained in the same manner as in Examples (1n) and (1o) using {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) and 3-amino-2,2-dimethylpropan-1-ol.

Colorless solid.

$^1$H NMR spectrum (CD$_3$OD, 500 MHz), δ: 8.08-8.05 (m, 1H), 7.56-7.55 (m, 1H), 7.44-7.34 (m, 3H), 6.70 (s, 2H), 3.67-3.61 (m, 2H), 3.52-3.45 (m, 1H), 3.39-3.15 (m, 6H), 3.05-3.02 (m, 1H), 2.98-2.93 (m, 0.6H), 2.80-2.70 (m, 0.8H), 2.55-2.52 (m, 0.6H), 2.43-2.39 (m, 1H), 1.89-1.83 (m, 2H), 1.74-1.69 (m, 1H), 1.32-1.27 (m, 6H), 1.02-1.00 (m, 6H), 0.91-0.90 (m, 6H).

mass spectrum (FAB$^+$), m/z: 511 ((M+H)$^+$).

Example 9

(2S,4S,5S)-5-Amino-6-[4-(2-chlorophenyl)-2,2-dimethyl-5-oxopiperazin-1-yl]-4-hydroxy-2-isopropylhexanoic acid [(S)-1-hydroxymethyl-2-methylpropyl]amide fumarate (Exemplary Compound No. 1-244)

188 mg of the title compound (total yield over two steps: 46%) was obtained in the same manner as in Examples (1n) and (1o) using {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) and L-valinol.

Colorless solid.

$^1$H NMR spectrum (CD$_3$OD, 500 MHz), δ: 7.69 (d, 1H, J=8.7 Hz), 7.55-7.54 (m, 1H), 7.43-7.32 (m, 3H), 6.69 (s, 2H), 3.75-3.16 (m, 9H), 2.98-2.94 (m, 0.6H), 2.80-2.69 (m, 0.8H), 2.54-2.51 (m, 0.6H), 2.40-2.36 (m, 1H), 1.95-1.83 (m, 3H), 1.74-1.69 (m, 1H), 1.31-1.27 (m, 6H), 1.01-0.95 (m, 12H).

mass spectrum (FAB$^+$), m/z: 511 ((M+H)$^+$).

Example 10

(2S,4S,5S)-5-Amino-4-hydroxy-2-isopropyl-6-{4-[2-(3-methoxypropoxy)phenyl]-2,2-dimethyl-5-oxopiperazin-1-yl}hexanoic acid (2-carbamoyl-2-methylpropyl)amide hemifumarate (½ fumarate) (Exemplary Compound No. 1-438)

(10a) [2-(2-Benzyloxyphenylamino)-1,1-dimethylethyl]carbamic acid t-butyl ester 6.38 g of sodium triacetoxyborohydride (30.1 mmol) was added to a solution of 4.68 g of (1,1-dimethyl-2-oxoethyl)carbamic acid t-butyl ester obtained in Reference Example 3 (25.0 mmol), 5.0 g of 2-benzyloxyaniline (25.0 mmol) and 1.44 ml of acetic acid (25.0 mmol) in methylene chloride (250 ml) under ice-cooling, and the mixture was stirred at room temperature for 16 hours. A saturated sodium bicarbonate aqueous solution was added to the reaction mixture, followed by extraction with methylene chloride. Then, the organic layer was washed with brine and dried over anhydrous sodium sulfate. After filtration, the solvent was evaporated under reduced pressure, and the residue was purified by silica gel column chromatography (elution solvent:hexane/ethyl acetate=5/1) to obtain 8.50 g of the title compound (yield: 91%).

Colorless solid.

$^1$H NMR spectrum (CDCl$_3$, 400 MHz), δ: 7.45-7.33 (m, 5H), 6.89-6.83 (2H, m), 6.70 (dd, 1H, J=7.8 Hz, 1.5 Hz), 6.64-6.60 (m, 1H), 5.09 (br s, 2H), 4.58 (br s, 1H), 4.51 (br s, 1H), 3.31 (d, 2H, J=5.4 Hz), 1.39 (s, 9H), 1.33 (s, 6H).

(10b) {2-[(2-Benzyloxyphenyl)-(2-bromoacetyl)amino]-1,1-dimethylethyl}carbamic acid t-butyl ester 1.08 g of sodium bicarbonate (12.9 mmol) and 1.0 ml of bromoacetyl bromide (11.3 mmol) were added to a solution of 4.00 g of [2-(2-benzyloxyphenylamino)-1,1-dimethylethyl]carbamic acid t-butyl ester obtained in Example (10a) (10.7 mmol) in a mixed solvent of ethyl acetate (50 ml) and water (50 ml) under ice-cooling, and the mixture was stirred at the same temperature for 10 minutes. After extraction with ethyl acetate, the organic layer was dried over anhydrous magnesium sulfate. After filtration, the solvent was evaporated under reduced pressure, and the residue was purified by silica gel column chromatography (elution solvent:hexane/ethyl acetate=2/1) to obtain 4.86 g of the title compound (yield: 92%).

Colorless solid.

$^1$H NMR spectrum (CDCl$_3$, 400 MHz), δ: 7.41-7.29 (m, 7H), 7.08-7.00 (m, 2H), 5.15 (d, 1H, J=11.3 Hz), 5.08 (d, 1H, J=11.3 Hz), 4.69 (br, 1H), 4.04 (d, 1H, J=14.0 Hz), 3.95 (1H, d, J=14.0 Hz), 3.69 (d, 1H, J=11.3 Hz), 3.62 (d, 1H, J=11.3 Hz), 1.29 (s, 3H), 1.19 (s, 9H), 1.12 (s, 3H).

(10c) 4-(2-Benzyloxyphenyl)-2,2-dimethyl-5-oxopiperazine-1-carboxylic acid t-butyl ester A solution of 1.59 g of potassium t-butoxide (14.2 mmol) in tetrahydrofuran (100 ml) was added to a solution of 4.64 g of {2-[(2-benzyloxyphenyl)-(2-bromoacetyl)amino]-1,1- dimethylethyl}carbamic acid t-butyl ester obtained in Example (10b) (9.64 mmol) in tetrahydrofuran (100 ml) under a nitrogen atmosphere and under cooling in a dry ice-acetone bath over 30 minutes, and the mixture was stirred at the same temperature for 10 minutes. A saturated ammonium chloride aqueous solution was added to the reaction mixture. The mixture was returned to room temperature and then water was added, followed by extraction with ethyl acetate. Then, the organic layer was dried over anhydrous magnesium sulfate. After filtration, the solvent was evaporated under reduced pressure, and the residue was purified by silica gel column chromatography (elution solvent:methylene chloride/ethyl acetate=5/1) to obtain 3.42 g of the title compound (yield: 94%).

Colorless solid.

$^1$H NMR spectrum (CDCl$_3$, 400 MHz), δ: 7.39-7.25 (m, 5H), 7.04-6.99 (m, 4H), 5.10 (s, 2H), 4.19 (br s, 2H), 3.49 (br s, 2H), 1.48 (br s, 15H).

(10d) 4-(2-Hydroxyphenyl)-2,2-dimethyl-5-oxopiperazine-1-carboxylic acid t-butyl ester A suspension of 3.42 g of 4-(2-benzyloxyphenyl)-2,2-dimethyl-5-oxopiperazine-1-carboxylic acid t-butyl ester obtained in Example (10c) (8.94 mmol) and 342 mg of 10% palladium-carbon (50% wet) in methanol (90 ml) was stirred under a hydrogen atmosphere at room temperature for six hours. Hydrogen in the reaction vessel was replaced by nitrogen. Then, palladium-carbon was separated by filtration and washed with methanol. The solvent was evaporated under reduced pressure, and the residue was purified by silica gel column chromatography (elution solvent:hexane/ethyl acetate=1/1) to obtain 2.6 g of the title compound (yield: quant.).

Colorless solid.

$^1$H NMR spectrum (CDCl$_3$, 400 MHz), δ: 7.25-7.22 (m, 1H), 7.11-7.07 (m, 2H), 7.02-6.98 (m, 1H), 4.29 (s, 2H), 3.75 (s, 2H), 1.52 (s, 6H), 1.51 (s, 9H).

(10e) 4-[2-(3-Methoxypropoxy)phenyl]-2,2-dimethyl-5-oxopiperazine-1-carboxylic acid t-butyl ester 450 mg of 3-methoxypropyl bromide (2.94 mmol) and 958 mg of cesium carbonate (2.94 mmol) were added to a solution of 573 mg of 4-(2-hydroxyphenyl)-2,2-dimethyl-5-oxopiperazine-1-carboxylic acid t-butyl ester obtained in Example (10d) (1.96 mmol) in N,N-dimethylformamide (20 ml), and the mixture was stirred at 100° C. for four hours. The reaction mixture was cooled and then water was added, followed by extraction with ethyl acetate. Then, the organic layer was washed with brine and then dried over anhydrous sodium sulfate. After filtration, the solvent was evaporated under reduced pressure, and the residue was purified by silica gel column chromatography (elution solvent:n-hexane/ethyl acetate=1/1) to obtain 540 mg of the title compound (yield: 70%).

Colorless solid.

$^1$H NMR spectrum (CDCl$_3$, 400 MHz), δ: 7.29-7.25 (m, 1H), 7.00-6.95 (m, 3H), 4.22 (br s, 2H), 4.10 (t, 2H, J=6.2 Hz), 3.53-3.50 (m, 4H), 3.34 (s, 3H), 2.04 (quint, 2H, J=6.2 Hz), 1.52 (br s, 6H), 1.50 (s, 9H).

(10f) 1-[2-(3-Methoxypropyloxy)phenyl]-5,5-dimethylpiperazin-2-one 400 mg of the title compound (yield: quant.) was obtained in the same manner as in Example (1k) using 4-[2-(3-methoxypropoxy)phenyl]-2,2-dimethyl-5-oxopiperazine-1-carboxylic acid t-butyl ester obtained in Example (10e).

Colorless liquid.

$^1$H NMR spectrum (CDCl$_3$, 400 MHz), δ: 7.29-7.25 (m, 1H), 7.17-7.15 (m, 1H), 6.99-6.95 (m, 2H), 4.00 (t, 2H, J=6.2 Hz), 3.69 (s, 2H), 3.53 (t, 2H, J=6.2 Hz), 3.40 (br s, 2H), 3.34 (s, 3H), 2.05 (quint, 2H, J=6.2 Hz), 1.32 (6H, s).

(10g) (2S,4S,5S)-5-Amino-4-hydroxy-2-isopropyl-6-{4-[2-(3-methoxypropoxy)phenyl]-2,2-dimethyl-5-oxopiperazin-1-yl}hexanoic acid (2-carbamoyl-2-methylpropyl)amide hemifumarate (½ fumarate)

165 mg of the title compound (total yield over five steps: 28%) was obtained in the same manner as in Examples (11) to (1o) using (3S,5S)-3-isopropyl-5-[(S)-1-(2-nitrobenzenesulfonyl)aziridin-2-yl]dihydrofuran-2-one obtained in Example (1g), 1-[2-(3-methoxypropyloxy)phenyl]-5,5-dimethylpiperazin-2-one obtained in Example (10f) and 3-amino-2,2-di(methyl)propionamide obtained in Reference Example 2.

Colorless solid.

$^1$H NMR spectrum (CD$_3$OD, 400 MHz), δ: 7.35-7.30 (m, 1H), 7.17 (dd, 1H, J=7.8, 1.5 Hz), 7.10-7.08 (m, 1H), 7.01-6.97 (m, 1H), 6.66 (s, 1H), 4.12-4.09 (m, 2H), 3.63-3.45 (m, 5H), 3.41-2.32 (m, 11H), 2.02 (quint, 2H, J=6.2 Hz), 1.86-1.67 (m, 3H), 1.26 (br s, 3H), 1.25 (br s, 3H), 1.21 (s, 3H), 1.20 (s, 3H), 0.99-0.96 (m, 6H).

mass spectrum (FAB$^+$), m/z: 578 ((M+H)$^+$).

Example 11

(2S,4S,5S)-5-Amino-4-hydroxy-2-isopropyl-6-{4-[2-(2-methoxyethoxy)phenyl]-2,2-dimethyl-5-oxopiperazin-1-yl}hexanoic acid (2-carbamoyl-2-methylpropyl)amide hemifumarate (½ fumarate)
(Exemplary Compound No. 1-436)

(11a) 1-[2-(2-Methoxyethoxy)phenyl]-5,5-dimethylpiperazin-2-one 518 mg of 1,1'-(azodicarbonyl)dipiperidine (2.05 mmol), 156 mg of 2-methoxyethanol (2.05 mmol) and 0.42 ml of tributylphosphine (2.05 mmol) were added to a solution of 400 mg of 4-(2-hydroxyphenyl)-2,2-dimethyl-5-oxopiperazine-1-carboxylic acid t-butyl ester obtained in Example (10d) (1.36 mmol) in toluene (14 ml), and the mixture was stirred at 100° C. for three hours. The reaction mixture was cooled and then water was added, followed by extraction with ethyl acetate. Then, the organic layer was washed with brine and then dried over anhydrous sodium sulfate. After filtration, the solvent was evaporated under reduced pressure, and the residue was purified by silica gel column chromatography (elution solvent:n-hexane/ethyl acetate=1/2) to obtain 444 mg of 4-[2-(2-methoxyethoxy)phenyl]-2,2-dimethyl-5-oxopiperazine-1-carboxylic acid t-butyl ester (yield: 86%).

327 mg of the title compound (yield: quant.) was obtained in the same manner as in Example (1k) using 444 mg of 4-[2-(2-methoxyethoxy)phenyl]-2,2-dimethyl-5-oxopiperazine-1-carboxylic acid t-butyl ester obtained in the above reaction (1.17 mmol).

Colorless solid.

$^1$H NMR spectrum (CDCl$_3$, 400 MHz), δ: 7.29-7.17 (m, 1H), 7.18 (dd, 1H, J=7.8 Hz, 1.5 Hz), 7.01-6.96 (m, 2H), 4.14 (t, 2H, J=4.7 Hz), 3.72 (t, 2H, J=4.7 Hz), 3.69 (s, 2H), 3.43 (br s, 2H), 3.40 (s, 3H), 1.32 (s, 6H).

(11b) (2S,4S,5S)-5-Amino-4-hydroxy-2-isopropyl-6-{4-[2-(2-methoxyethoxy)phenyl]-2,2-dimethyl-5-oxopiperazin-1-yl}hexanoic acid (2-carbamoyl-2-methylpropyl)amide hemifumarate (½ fumarate)

136 mg of the title compound (total yield over five steps: 22%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 1-[2-(2-methoxyethoxy)phenyl]-5,5-dimethylpiperazin-2-one obtained in Example (11a) and 3-amino-2,2-di(methyl)propionamide obtained in Reference Example 2.
Colorless solid.
$^1$H NMR spectrum (CD$_3$OD, 400 MHz), δ: 7.36-7.31 (m, 1H), 7.18 (dd, 1H, J=7.8 Hz, 1.5 Hz), 7.13-7.10 (m, 1H), 7.03-6.99 (m, 1H), 6.67 (s, 1H), 4.19-4.16 (m, 2H), 3.72 (t, 2H, J=4.3 Hz), 3.36-3.55 (m, 2H), 3.49-3.45 (m, 1H), 3.38-2.33 (m, 11H), 1.86-1.77 (m, 2H), 1.74-1.67 (m, 1H), 1.27 (br s, 3H), 1.25 (br s, 3H), 1.21 (s, 3H), 1.20 (s, 3H), 1.00-0.96 (m, 6H).
mass spectrum (FAB$^+$), m/z: 564 ((M+H)$^+$).

Example 12

(2S,4S,5S)-5-Amino-4-hydroxy-2-isopropyl-6-[4-(2-methoxymethoxyphenyl)-2,2-dimethyl-5-oxopiperazin-1-yl]hexanoic acid (2-carbamoyl-2-methylpropyl)amide hemifumarate (½ fumarate) (Exemplary Compound No. 1-434)

(12a) 1-(2-Methoxymethoxyphenyl)-5,5-dimethylpiperazin-2-one 0.72 ml of diisopropylethylamine (4.10 mmol) and 0.16 ml of methoxymethyl chloride (2.05 mmol) were added to a solution of 400 mg of 4-(2-hydroxyphenyl)-2,2-dimethyl-5-oxopiperazine-1-carboxylic acid t-butyl ester obtained in Example (10d) (1.36 mmol) in methylene chloride (14 ml), and the mixture was stirred at room temperature overnight. Water was added to the reaction mixture, followed by extraction with methylene chloride. Then, the organic layer was washed with brine and dried over anhydrous sodium sulfate. After filtration, the solvent was evaporated under reduced pressure, and the residue was purified by silica gel column chromatography (elution solvent:n-hexane/ethyl acetate=1/1) to obtain 497 mg of 2,2-dimethyl-4-(2-methoxymethoxyphenyl)-5-oxopiperazine-1-carboxylic acid t-butyl ester (yield: quant.).

0.58 ml of triethylamine (4.10 mmol) and 0.3 ml of iodotrimethylsilane (2.05 mmol) were added to a solution of 497 mg of 4-(2-methoxymethoxyphenyl)-2,2-dimethyl-5-oxopiperazine-1-carboxylic acid t-butyl ester obtained in the above reaction (1.36 mmol) in methylene chloride (14 ml), and the mixture was stirred at 0° C. for 30 minutes. A saturated sodium bicarbonate aqueous solution was added to the reaction mixture, followed by extraction with methylene chloride. Then, the organic layer was washed with brine and dried over anhydrous sodium sulfate. After filtration, the solvent was evaporated under reduced pressure, and the residue was purified by basic silica gel (NH type) column chromatography (elution solvent: methylene chloride/methanol=20/1) to obtain 310 mg of the title compound (yield: 86%).
Colorless liquid.
$^1$H NMR spectrum (CDCl$_3$, 400 MHz), δ: 7.29-7.24 (m, 1H), 7.20-7.16 (m, 2H), 7.05-7.01 (m, 1H), 5.19 (s, 2H), 3.70 (s, 2H), 3.47 (s, 3H), 3.43 (br s, 2H), 1.34 (s, 6H).

(12b) (2S,4S,5S)-5-Amino-4-hydroxy-2-isopropyl-6-[4-(2-methoxymethoxyphenyl)-2,2-dimethyl-5-oxopiperazin-1-yl]hexanoic acid (2-carbamoyl-2-methylpropyl)amide hemifumarate (½ fumarate)

A solution of 214 mg of (3S,5S)-3-isopropyl-5-[(S)-1-(2-nitrobenzenesulfonyl)aziridin-2-yl]dihydrofuran-2-one obtained in Example (1g) (0.60 mmol) and 207 mg of 1-(2-methoxymethoxyphenyl)-5,5-dimethylpiperazin-2-one obtained in Example (12a) (0.78 mmol) in toluene (7 ml) was stirred at 110° C. for 45 minutes. After cooling, the reaction mixture was concentrated under reduced pressure, and the residue was purified by silica gel column chromatography (elution solvent:methylene chloride/methanol=20/1) to obtain 326 mg of N-{(S)-1-[(2S,4S)-4-isopropyl-5-oxotetrahydrofuran-2-yl]-2-[4-(2-methoxymethoxyphenyl)-2,2-dimethyl-5-oxopiperazin-1-yl]ethyl}-2-nitrobenzenesulfonamide (yield: 87%).

206 mg of cesium carbonate (0.63 mmol) was added to a solution of 326 mg of N-{(S)-1-[(2S,4S)-4-isopropyl-5-oxotetrahydrofuran-2-yl]-2-[4-(2-methoxymethoxyphenyl)-2,2-dimethyl-5-oxopiperazin-1-yl]ethyl}-2-nitrobenzenesulfonamide obtained in the above reaction (0.53 mmol) and 0.12 ml of thiophenol (content: 95%) (1.1 mmol) in N,N-dimethylformamide (5 ml) under a nitrogen atmosphere at room temperature, and the mixture was stirred at the same temperature for two hours. Brine was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol=20/1-10/1). 49 mg of sodium bicarbonate (0.57 mmol) and 78 μl of benzyloxycarbonyl chloride (0.53 mmol) were added to a solution of 209 mg of 4-{(S)-2-amino-2-[(2S,4S)-4-isopropyl-5-oxotetrahydrofuran-2-yl]ethyl}-1-(2-methoxymethoxyphenyl)-5,5-dimethylpiperazin-2-one obtained above (0.48 mmol) in a mixed solvent of ethyl acetate (3 ml) and water (3 ml) under ice-cooling, and the mixture was stirred at the same temperature for 30 minutes. Brine was added to the reaction mixture, followed by extraction with ethyl acetate. Then, the organic layer was dried over anhydrous sodium sulfate. After filtration, the solvent was evaporated under reduced pressure. The residue was purified by silica gel column chromatography (elution solvent:methylene chloride/methanol=20/1) to obtain 263 mg of {(S)-1-[(2S,4S)-4-isopropyl-5-oxotetrahydrofuran-2-yl]-2-[4-(2-methoxymethoxyphenyl)-2,2-dimethyl-5-oxopiperazin-1-yl]ethyl}carbamic acid benzyl ester (yield: 87%).

161 mg of 3-amino-2,2-di(methyl)propionamide obtained in Reference Example 2 (1.39 mmol) and 44 mg of 2-hydroxypyridine (0.46 mmol) were added to a solution of 263 mg of {(S)-1-[(2S,4S)-4-isopropyl-5-oxotetrahydrofuran-2-yl]-2-[4-(2-methoxymethoxyphenyl)-2,2-dimethyl-5-oxopiperazin-1-yl]ethyl}carbamic acid benzyl ester obtained in the above reaction (0.46 mmol) in triethylamine (4.6 ml), and the mixture was stirred at 80° C. for two hours. The reaction mixture was cooled and then concentrated under reduced pressure and further stirred at 80° C. for 9 hours. The reaction mixture was cooled and then water was added, followed by extraction with methylene chloride. Then, the organic layer was dried over anhydrous magnesium sulfate. After filtration, the solvent was evaporated under reduced pressure. The residue was purified by silica gel column chromatography (elution solvent:methylene chloride/methanol=40/3) to obtain 166 mg of {(1S,2S,4S)-4-(2-carbamoyl-2-methylpropylcarbamoyl)-2-hydroxy-1-[4-(2-methoxymethoxyphenyl)-2,2- dimethyl-5-oxopiperazin-1-ylmethyl]-5-methylhexyl}carbamic acid benzyl ester (yield: 52%).

A suspension of 166 mg of {(1S,2S,4S)-4-(2-carbamoyl-2-methylpropylcarbamoyl)-2-hydroxy-1-[4-(2-methoxymethoxyphenyl)-2,2-dimethyl-5-oxopiperazin-1-ylmethyl]-5-methylhexyl}carbamic acid benzyl ester obtained in the above reaction (0.24 mmol) and 83 mg of 10% palladium-carbon (50% wet) in ethanol (3 ml) was stirred under a hydrogen atmosphere at room temperature for two hours. Hydrogen in the reaction vessel was replaced by nitrogen. Then, palladium-carbon was separated by filtration and washed with ethanol. The solvent was evaporated from the filtrate under reduced pressure, and the residue was purified by silica gel column chromatography (elution solvent:methylene chloride/methanol/triethylamine=200/20/1). 10.8 mg of fumaric acid (0.093 mmol) was added to a solution of 102 mg of (2S,4S,5S)-5-amino-4-hydroxy-2-isopropyl-6-[4-(2-methoxymethoxyphenyl)-2,2-dimethyl-5-oxopiperazin-1-yl]hexanoic acid (2-carbamoyl-2-methylpropyl)amide obtained above (0.18 mmol) in methanol (3 ml), and the mixture was stirred at room temperature for five minutes. The solvent was evaporated under reduced pressure to obtain 99 mg of the title compound (yield: 66%).

Colorless solid.

$^1$H NMR spectrum (CD$_3$OD, 400 MHz), δ: 7.34-7.30 (m, 1H), 7.26-7.23 (m, 1H), 7.19 (dd, 1H, J=7.8 Hz, 1.5 Hz), 7.08-7.04 (m, 1H), 6.67 (s, 1H), 3.65-3.59 (m, 2H), 3.50-2.33 (m, 14H), 1.88-1.67 (m, 3H), 1.27 (br s, 3H), 1.25 (br s, 3H), 1.21 (s, 3H), 1.20 (s, 3H), 1.00-0.96 (m, 6H).

mass spectrum (FAB$^+$), m/z: 550 ((M+H)$^+$).

Example 13

(2S,4S,5S)-5-Amino-4-hydroxy-2-isopropyl-6-[4-(2-methoxyphenyl)-2,2-dimethyl-5-oxopiperazin-1-yl]hexanoic acid (2-carbamoyl-2-methylpropyl)amide hemifumarate (½ fumarate) (Exemplary Compound No. 1-446)

(13a) 5,5-Dimethyl-1-(2-methoxyphenyl)piperazin-2-one 283 mg of potassium carbonate (2.04 mmol) and 0.13 ml of methyl iodide (2.04 mmol) were added to a solution of 400 mg of the compound obtained in Example (10d) (1.36 mmol) in N,N-dimethylformamide (13 ml), and the mixture was stirred at 50° C. for four hours. The reaction mixture was cooled and then water was added, followed by extraction with ethyl acetate. Then, the organic layer was washed with brine and then dried over anhydrous sodium sulfate. After filtration, the solvent was evaporated under reduced pressure, and the residue was purified by silica gel column chromatography (elution solvent:n-hexane/ethyl acetate=1/1) to obtain 399 mg of 2,2-dimethyl-4-(2-methoxyphenyl)-5-oxopiperazine-1-carboxylic acid t-butyl ester (yield: 95%).

266 mg of the title compound (yield: 87%) was obtained in the same manner as in Example (1k) using 399 mg of 2,2-dimethyl-4-(2-methoxyphenyl)-5-oxopiperazine-1-carboxylic acid t-butyl ester obtained in the above reaction (1.3 mmol).

Colorless liquid.

$^1$H NMR spectrum (CDCl$_3$, 400 MHz), δ: 7.31-7.27 (m, 1H), 7.18-7.15 (m, 1H), 7.00-6.96 (m, 2H), 3.83 (s, 3H), 3.70 (s, 2H), 3.39 (br s, 2H), 1.32 (s, 6H).

(13b) (2S,4S,5S)-5-Amino-4-hydroxy-2-isopropyl-6-[4-(2-methoxyphenyl)-2,2-dimethyl-5-oxopiperazin-1-yl]hexanoic acid (2-carbamoyl-2-methylpropyl)amide hemifumarate (½ fumarate)

81 mg of the title compound (total yield over five steps: 25%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 5,5-dimethyl-1-(2-methoxyphenyl)piperazin-2-one obtained in Example (13a) and 3-amino-2,2-di(methyl)propionamide obtained in Reference Example 2.

Colorless solid.

$^1$H NMR spectrum (CD$_3$OD, 400 MHz), δ: 7.38-7.33 (m, 1H), 7.18-7.15 (m, 1H), 7.12-7.10 (m, 1H), 7.02-6.98 (m, 1H), 6.67 (s, 1H), 3.84 (s, 3H), 3.64-3.57 (m, 2H), 3.51-3.46 (m, 1H), 3.42-2.33 (m, 8H), 1.88-1.67 (m, 3H), 1.26 (br s, 3H), 1.24 (br s, 3H), 1.22 (s, 3H), 1.20 (s, 3H), 1.00-0.96 (m, 6H).

mass spectrum (FAB$^+$), m/z: 520 ((M+H)$^+$).

Example 14

(2S,4S,5S)-5-Amino-6-(2,2-dimethyl-5-oxo-4-phenylpiperazin-1-yl)-4-hydroxy-2-isopropylhexanoic acid (2-carbamoyl-2-methylpropyl)amide fumarate (Exemplary Compound No. 1-433)

(14a) 5,5-Dimethyl-1-phenylpiperazin-2-one 4.41 g of {2-[(2-bromoacetyl)phenylamino]-1,1-dimethylethyl}carbamic acid t-butyl ester (yield: 73%) was obtained in the same manner as in Examples (1h) and (1i) using (1,1-dimethyl-2-oxoethyl)carbamic acid t-butyl ester obtained in Reference Example 3 and aniline.

11.19 g of cesium carbonate (34.4 mmol) was added to a solution of 4.41 g of {2-[(2-bromoacetyl)phenylamino]-1,1-dimethylethyl}carbamic acid t-butyl ester obtained in the above reaction (11.5 mmol) in N,N-dimethylformamide (58 ml) under ice-cooling, and the mixture was stirred at room temperature for 18 hours. Water was added to the reaction mixture, followed by extraction with ethyl acetate. Then, the organic layer was washed with water and brine and dried over anhydrous magnesium sulfate. After filtration, the solvent was evaporated under reduced pressure, and the residue was purified by silica gel column chromatography (elution solvent:hexane/ethyl acetate=10/1-5/1-2/1) to obtain 1.83 g of 2,2-dimethyl-5-oxo-4-phenylpiperazine-1-carboxylic acid t-butyl ester (yield: 53%).

1.0 ml of trifluoroacetic acid (13 mmol) was added to a solution of 0.40 g of 2,2-dimethyl-5-oxo-4-phenylpiperazine-1-carboxylic acid t-butyl ester obtained in the above reaction (1.31 mmol) in methylene chloride (2 ml) at room temperature, and the mixture was stirred at the same temperature for 30 minutes. The reaction mixture was concentrated under reduced pressure. A saturated sodium bicarbonate aqueous solution was added, followed by extraction with methylene chloride. Then, the organic layer was dried over anhydrous sodium sulfate. After filtration, the solvent was evaporated under reduced pressure, and the residue was purified by silica gel column chromatography (elution solvent: methylene chloride/methanol=10/1) to obtain 0.23 g of the title compound (yield: 99%).

$^1$H NMR spectrum (CDCl$_3$, 400 MHz), δ: 7.42-7.38 (m, 2H), 7.28-7.25 (m, 3H), 3.69 (br s, 2H), 3.50 (br s, 2H), 1.31 (br s, 6H).

mass spectrum (FAB$^+$), m/z: 205 ((M+H)$^+$).

(14b) (2S,4S,5S)-5-Amino-6-(2,2-dimethyl-5-oxo-4-phenylpiperazin-1-yl)-4-hydroxy-2-isopropylhexanoic acid (2-carbamoyl-2-methylpropyl)amide fumarate 53 mg of the title compound (total yield over five steps: 19%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 5,5-dimethyl-1-phenylpiperazin-2-one obtained in Example (14a) and 3-amino-2,2-di(methyl)propionamide obtained in Reference Example 2.

Colorless solid.

$^1$H NMR spectrum (CD$_3$OD, 400 MHz), δ: 7.46-7.42 (m, 2H), 7.34-7.28 (m, 3H), 6.68 (s, 2H), 3.73-3.60 (m, 2H), 3.51-3.46 (m, 1H), 3.41-3.17 (m, 5H), 2.91-2.85 (m, 1H), 2.54 (dd, 1H, J=13.5 Hz, 4.1 Hz), 2.37-2.32 (m, 1H), 1.88-1.68 (m, 3H), 1.37-1.16 (m, 12H), 0.99-0.96 (m, 6H).

mass spectrum (FAB$^+$), m/z: 490 ((M+H)$^+$).

Example 15

(2S,4S,5S)-5-Amino-6-[2,2-dimethyl-4-(2-methylphenyl)-5-oxopiperazin-1-yl]-4-hydroxy-2-isopropylhexanoic acid (2-carbamoyl-2-methylpropyl)amide fumarate (Exemplary Compound No. 1-440)

(15a) 5,5-Dimethyl-1-(2-methylphenyl)piperazin-2-one 0.23 g of the title compound (total yield over four steps: 48%) was obtained in the same manner as in Examples (1h) to (1k) using (1,1-dimethyl-2-oxoethyl)carbamic acid t-butyl ester obtained in Reference Example 3 and 2-methylaniline.

Yellow liquid.

$^1$H NMR spectrum (CDCl$_3$, 400 MHz), δ: 7.31-7.21 (m, 3H), 7.12-7.10 (m, 1H), 3.75 (d, 1H, J=18.0 Hz), 3.69 (d, 1H, J=18.0 Hz), 3.46 (d, 1H, J=12.1 Hz), 3.32 (d, 1H, J=12.1 Hz), 2.25 (s, 3H), 1.35 (br s, 3H), 1.33 (br s, 3H).

mass spectrum (FAB$^+$), m/z: 219 ((M+H)$^+$).

(15b) (2S,4S,5S)-5-Amino-6-[2,2-dimethyl-4-(2-methylphenyl)-5-oxopiperazin-1-yl]-4-hydroxy-2-isopropylhexanoic acid (2-carbamoyl-2-methylpropyl)amide fumarate 367 mg of N-{(S)-2-[2,2-dimethyl-4-(2-methylphenyl)-5-oxopiperazin-1-yl]-1-[(2S,4S)-4-isopropyl-5-oxotetrahydrofuran-2-yl]ethyl}-2-nitrobenzenesulfonamide (yield: 89%) was obtained in the same manner as in Example (1l) using (3S,5S)-3-isopropyl-5-[(S)-1-(2-nitrobenzenesulfonyl)aziridin-2-yl]dihydrofuran-2-one obtained in Example (1g) and 5,5-dimethyl-1-(2-methylphenyl)piperazin-2-one obtained in Example (15a).

223 mg of 3-amino-2,2-di(methyl)propionamide obtained in Reference Example 2 (1.92 mmol) and 61 mg of 2-hydroxypyridine (0.64 mmol) were added to a solution of 367 mg of N-{(S)-2-[2,2-dimethyl-4-(2-methylphenyl)-5-oxopiperazin-1-yl]-1-[(2S,4S)-4-isopropyl-5-oxotetrahydrofuran-2-yl]ethyl}-2-nitrobenzenesulfonamide obtained in the above reaction (0.64 mmol) in triethylamine (6 ml), and the mixture was stirred at 80° C. for one hour. The reaction mixture was cooled and then concentrated under reduced pressure and further stirred at 80° C. for 14 hours. The reaction mixture was cooled and then water was added, followed by extraction with methylene chloride. Then, the organic layer was dried over anhydrous sodium sulfate. After filtration, the solvent was evaporated under reduced pressure. The residue was purified by silica gel column chromatography (elution solvent:methylene chloride/methanol=20/1) to obtain 345 mg of (2S,4S,5S)-6-[2,2-dimethyl-4-(2-methylphenyl)-5-oxopiperazin-1-yl]-4-hydroxy-2-isopropyl-5-(2-nitrobenzenesulfonylamino)hexanoic acid (2-carbamoyl-2-methylpropyl)amide (yield: 78%).

196 mg of cesium carbonate (0.6 mmol) was added to a solution of 345 mg of (2S,4S,5S)-6-[2,2-dimethyl-4-(2-methylphenyl)-5-oxopiperazin-1-yl]-4-hydroxy-2-isopropyl-5-(2-nitrobenzenesulfonylamino)hexanoic acid (2-carbamoyl-2-methylpropyl)amide obtained in the above reaction (0.5 mmol) and 0.15 ml of thiophenol (content: 95%) (1.5 mmol) in N,N-dimethylformamide (5 ml) under a nitrogen atmosphere at room temperature, and the mixture was stirred at the same temperature for four hours. Brine was added to the reaction mixture, followed by extraction with methylene chloride. Then, the organic layer was dried over anhydrous sodium sulfate. After filtration, the solvent was evaporated under reduced pressure, and the residue was purified by silica gel column chromatography (elution solvent:methylene chloride/methanol/triethylamine=20/1/0-10/1/0-100/10/1). 38.7 mg of fumaric acid (0.33 mmol) was added to a solution of 168 mg of (2S,4S,5S)-5-amino-6-(2,2-dimethyl-4-(2-methylphenyl)-5-oxopiperazin-1-yl)-4-hydroxy-2-isopropylhexanoic acid (2-carbamoyl-2-methylpropyl)amide obtained above (0.33 mmol) in methanol (3 ml), and the mixture was stirred at room temperature for five minutes. The reaction mixture was concentrated under reduced pressure, and methylene chloride (2 ml) was added to the residue. Diethyl ether (5 ml) was further added and the solid was collected by filtration to obtain 132 mg of the title compound (yield: 67%).

Colorless solid.

$^1$H NMR spectrum (CD$_3$OD, 400 MHz), δ: 7.30-7.24 (m, 3H), 7.18-7.11 (m, 1H), 6.68 (s, 2H), 3.71-3.27 (m, 4H), 3.23-3.15 (m, 4H), 2.97-2.91 (m, 0.6H), 2.86-2.80 (m, 0.4H), 2.64 (dd, 0.4H, J=13.5 Hz, 4.5 Hz), 2.51 (dd, 0.6H, J=13.5 Hz, 3.7 Hz), 2.38-2.34 (m, 1H), 2.24-2.23 (m, 3H), 1.88-1.68 (m, 3H), 1.32-1.16 (m, 12H), 0.99-0.96 (m, 6H).

mass spectrum (FAB$^+$), m/z: 504 ((M+H)$^+$).

Example 16

(2S,4S,5S)-5-Amino-6-[4-(2-fluorophenyl)-2,2-dimethyl-5-oxopiperazin-1-yl]-4-hydroxy-2-isopropylhexanoic acid (2-carbamoyl-2-methylpropyl)amide fumarate (Exemplary Compound No. 1-466)

(16a) 1-(2-Fluorophenyl)-5,5-dimethylpiperazin-2-one 0.25 g of the title compound (total yield over four steps: 30%) was obtained in the same manner as in Examples (1h) to (1k) using (1,1-dimethyl-2-oxoethyl)carbamic acid t-butyl ester obtained in Reference Example 3 and 2-fluoroaniline.

Colorless liquid.

$^1$H NMR spectrum (CDCl$_3$, 400 MHz), δ: 7.32-7.23 (m, 2H), 7.19-7.13 (m, 2H), 3.72 (s, 2H), 3.46 (s, 2H), 1.33 (br s, 6H).

mass spectrum (FAB$^+$), m/z: 223 ((M+H)$^+$).

(16b) (2S,4S,5S)-5-Amino-6-(4-(2-fluorophenyl)-2,2-dimethyl-5-oxopiperazin-1-yl)-4-hydroxy-2-isopropylhexanoic acid (2-carbamoyl-2-methylpropyl)amide fumarate 30 mg of the title compound (total yield over three steps: 14%) was obtained in the same manner as in Example (15b)

using (3S,5S)-3-isopropyl-5-[(S)-1-(2-nitrobenzenesulfonyl)aziridin-2-yl]dihydrofuran-2-one obtained in Example (1g), 1-(2-fluorophenyl)-5,5-dimethylpiperazin-2-one obtained in Example (16a) and 3-amino-2,2-di(methyl)propionamide obtained in Reference Example 2.

Colorless solid.

$^1$H NMR spectrum (CD$_3$OD, 400 MHz), δ: 7.43-7.21 (m, 4H), 6.69 (s, 2H), 3.70-3.63 (m, 2H), 3.51-3.46 (m, 1H), 3.39-3.18 (m, 5H), 2.92-2.86 (m, 1H), 2.59-2.54 (m, 1H), 2.37-2.32 (m, 1H), 1.85-1.67 (m, 3H), 1.33-1.16 (m, 12H), 0.99-0.96 (m, 6H).

mass spectrum (FAB$^+$), m/z: 508 ((M+H)$^+$).

Example 17

(2S,4S,5S)-5-Amino-6-[4-(3-chlorophenyl)-2,2-dimethyl-5-oxopiperazin-1-yl]-4-hydroxy-2-isopropylhexanoic acid (2-carbamoyl-2-methylpropyl)amide hemifumarate (½ fumarate) (Exemplary Compound No. 1-469)

(17a)
1-(3-Chlorophenyl)-5,5-dimethylpiperazin-2-one 0.30 g of the title compound (total yield over four steps: 18%) was obtained in the same manner as in Examples (1h) to (1k) using (1,1-dimethyl-2-oxoethyl)carbamic acid t-butyl ester obtained in Reference Example 3 and 2-fluoroaniline.

Colorless liquid.

$^1$H NMR spectrum (CDCl$_3$, 400 MHz), δ: 7.34-7.24 (m, 3H), 7.20-7.18 (m, 1H), 3.69 (s, 2H), 3.49 (s, 2H), 1.31 (br s, 6H).

mass spectrum (FAB$^+$), m/z: 239 ((M+H)$^+$).

(17b) (2S,4S,5S)-5-Amino-6-[4-(3-chlorophenyl)-2,2-dimethyl-5-oxopiperazin-1-yl]-4-hydroxy-2-isopropylhexanoic acid (2-carbamoyl-2-methylpropyl) amide hemifumarate (½ fumarate)

148 mg of the title compound (total yield over three steps: 63%) was obtained in the same manner as in Example (15b) using (3S,5S)-3-isopropyl-5-[(S)-1-(2-nitrobenzenesulfonyl)aziridin-2-yl]dihydrofuran-2-one obtained in Example (1g), 1-(3-chlorophenyl)-5,5-dimethylpiperazin-2-one obtained in Example (17a) and 3-amino-2,2-di(methyl)propionamide obtained in Reference Example 2.

Colorless solid.

$^1$H NMR spectrum (CD$_3$OD, 400 MHz), δ: 7.44-7.38 (m, 2H), 7.34-7.32 (m, 1H), 7.26-7.24 (m, 1H), 6.66 (s, 1H), 3.72-3.59 (m, 2H), 3.49-3.46 (m, 1H), 3.41-3.26 (m, 5H), 2.92-2.86 (m, 1H), 2.59-2.54 (m, 1H), 2.37-2.32 (m, 1H), 1.85-1.67 (m, 3H), 1.33-1.16 (m, 12H), 0.99-0.96 (m, 6H).

mass spectrum (FAB$^+$), m/z: 524 ((M+H)$^+$).

Example 18

(2S,4S,5S)-5-Amino-6-[4-(3-fluorophenyl)-2,2-dimethyl-5-oxopiperazin-1-yl]-4-hydroxy-2-isopropylhexanoic acid (2-carbamoyl-2-methylpropyl)amide hemifumarate (½ fumarate) (Exemplary Compound No. 1-467)

(18a)
1-(3-Fluorophenyl)-5,5-dimethylpiperazin-2-one 0.26 g of the title compound (total yield over four steps: 42%) was obtained in the same manner as in Example (14a) using (1,1-dimethyl-2-oxoethyl)carbamic acid t-butyl ester obtained in Reference Example 3 and 3-fluoroaniline.

Colorless liquid.

$^1$H NMR spectrum (CDCl$_3$, 400 MHz), δ: 7.40-7.32 (m, 1H), 7.10-7.02 (m, 2H), 7.00-6.94 (m, 1H), 3.71 (s, 2H), 3.51 (s, 2H), 1.32 (s, 6H).

mass spectrum (EI$^+$), m/z: 222 (M$^+$).

(18b) (2S,4S,5S)-5-Amino-6-[4-(3-fluorophenyl)-2,2-dimethyl-5-oxopiperazin-1-yl]-4-hydroxy-2-isopropylhexanoic acid (2-carbamoyl-2-methylpropyl) amide hemifumarate (½ fumarate)

77 mg of the title compound (total yield over three steps: 39%) was obtained in the same manner as in Example (15b) using (3S,5S)-3-isopropyl-5-[(S)-1-(2-nitrobenzenesulfonyl)aziridin-2-yl]dihydrofuran-2-one obtained in Example (1g), 1-(3-fluorophenyl)-5,5-dimethylpiperazin-2-one obtained in Example (18a) and 3-amino-2,2-di(methyl)propionamide obtained in Reference Example 2.

Colorless solid.

$^1$H NMR spectrum (CD$_3$OD, 400 MHz), δ: 7.48-7.42 (m, 2H), 7.17-7.11 (m, 1H), 7.11-7.05 (m, 1H), 6.66 (s, 1H), 3.71 (d, 1H, J=11.7 Hz), 3.62 (d, 1H, J=18.0 Hz), 3.48-3.35 (m, 5H), 3.18-3.12 (m, 1H), 2.85 (dd, 1H, J=13.6 Hz, 10.9 Hz), 2.53 (dd, 1H, J=13.6 Hz, 4.3 Hz), 2.38-2.34 (m, 1H), 1.87-1.66 (m, 3H), 1.25 (s, 3H), 1.23 (s, 3H), 1.21 (s, 3H), 1.20 (s, 3H), 0.98 (d, 3H, J=6.6 Hz), 0.97 (d, 3H, J=6.6 Hz).

mass spectrum (FAB$^+$), m/z: 508 ((M+H)$^+$).

Example 19

(2S,4S,5S)-5-Amino-4-hydroxy-2-isopropyl-6-[4-(3-methoxyphenyl)-2,2-dimethyl-5-oxopiperazin-1-yl]hexanoic acid (2-carbamoyl-2-methylpropyl)amide hemifumarate (½ fumarate) (Exemplary Compound No. 1-447)

(19a)
1-(3-Methoxyphenyl)-5,5-dimethylpiperazin-2-one 0.30 g of the title compound (total yield over four steps: 41%) was obtained in the same manner as in Example (14a) using (1,1-dimethyl-2-oxoethyl)carbamic acid t-butyl ester obtained in Reference Example 3 and 3-methoxyaniline.

Colorless liquid.

$^1$H NMR spectrum (CDCl$_3$, 400 MHz), δ: 7.34-7.28 (m, 1H), 6.84-6.80 (m, 3H), 3.81 (s, 3H), 3.70 (s, 2H), 3.50 (s, 2H), 1.31 (s, 6H).

mass spectrum (EI$^+$), m/z: 234 (M$^+$).

(19b) (2S,4S,5S)-5-Amino-4-hydroxy-2-isopropyl-6-[4-(3-methoxyphenyl)-2,2-dimethyl-5-oxopiperazin-1-yl]hexanoic acid (2-carbamoyl-2-methylpropyl) amide hemifumarate (½ fumarate)

150 mg of the title compound (total yield over three steps: 36%) was obtained in the same manner as in Example (15b) using (3S,5S)-3-isopropyl-5-[(S)-1-(2-nitrobenzenesulfonyl)aziridin-2-yl]dihydrofuran-2-one obtained in Example (1g), 1-(3-methoxyphenyl)-5,5-dimethylpiperazin-2-one obtained in Example (19a) and 3-amino-2,2-di(methyl)propionamide obtained in Reference Example 2.

Colorless solid.

$^1$H NMR spectrum (CD$_3$OD, 400 MHz), δ: 7.34 (t, 1H, J=8.4 Hz), 6.92-6.88 (m, 1H), 6.88-6.84 (m, 2H), 6.66 (s, 1H), 3.80 (s, 3H), 3.70 (d, 1H, J=11.7 Hz), 3.61 (d, 1H, J=17.6 Hz), 3.54-3.24 (m, 5H), 3.18-3.12 (m, 1H), 2.86 (dd, 1H, J=13.5 Hz, 10.9 Hz), 2.53 (dd, 1H, J=13.5 Hz, 4.5 Hz), 2.38-2.33 (m, 1H), 1.88-1.66 (m, 3H), 1.24 (s, 3H), 1.23 (s, 3H), 1.21 (s, 3H), 1.20 (s, 3H), 0.98 (d, 3H, J=6.6 Hz), 0.96 (d, 3H, J=6.3 Hz).
mass spectrum (FAB$^+$), m/z: 520 ((M+H)$^+$).

Example 20

(2S,4S,5S)-5-Amino-6-[4-(2,3-difluorophenyl)-2,2-dimethyl-5-oxopiperazin-1-yl]-4-hydroxy-2-isopropylhexanoic acid (2-carbamoyl-2-methylpropyl) amide hemifumarate (½ fumarate) (Exemplary Compound No. 1-493)

(20a)
1-(2,3-Difluorophenyl)-5,5-dimethylpiperazin-2-one 0.24 g of the title compound (total yield over four steps: 38%) was obtained in the same manner as in Examples (1h) to (1k) using (1,1-dimethyl-2-oxoethyl)carbamic acid t-butyl ester obtained in Reference Example 3 and 2,3-difluoroaniline.
Colorless solid.
$^1$H NMR spectrum (CDCl$_3$, 400 MHz), δ: 7.19-7.07 (m, 2H), 7.06-7.00 (m, 1H), 3.73 (s, 2H), 3.47 (s, 2H), 1.33 (s, 6H).
mass spectrum (EI$^+$), m/z: 240 (M$^+$).

(20b) (2S,4S,5S)-5-Amino-6-[4-(2,3-difluorophenyl)-2,2-dimethyl-5-oxopiperazin-1-yl]-4-hydroxy-2-isopropylhexanoic acid (2-carbamoyl-2-methylpropyl)amide hemifumarate (½ fumarate)

158 mg of the title compound (total yield over three steps: 38%) was obtained in the same manner as in Example (15b) using (3S,5S)-3-isopropyl-5-[(S)-1-(2-nitrobenzenesulfonyl)aziridin-2-yl]dihydrofuran-2-one obtained in Example (1g), 1-(2,3-difluorophenyl)-5,5-dimethylpiperazin-2-one obtained in Example (20a) and 3-amino-2,2-di(methyl)propionamide obtained in Reference Example 2.
Colorless solid.
$^1$H NMR spectrum (CD$_3$OD, 400 MHz), δ: 7.35-7.20 (m, 2H), 7.17-7.12 (m, 1H), 6.66 (s, 1H), 3.69 (d, 1H, J=10.9 Hz), 3.66 (d, 1H, J=17.6 Hz), 3.51-3.44 (m, 2H), 3.39-3.32 (m, 3H), 3.19-3.13 (m, 1H), 2.87 (dd, 1H, J=13.7 Hz, 10.6 Hz), 2.55 (dd, 1H, J=13.7 Hz, 4.3 Hz), 2.40-2.32 (m, 1H), 1.89-1.66 (m, 3H), 1.26 (s, 6H), 1.21 (s, 3H), 1.20 (s, 3H), 0.98 (d, 3H, J=6.6 Hz), 0.97 (d, 3H, J=6.6 Hz).
mass spectrum (FAB$^+$), m/z: 526 ((M+H)$^+$).

Example 21

(2S,4S,5S)-5-Amino-6-[4-(5-chloro-2-fluorophenyl)-2,2-dimethyl-5-oxopiperazin-1-yl]-4-hydroxy-2-isopropylhexanoic acid (2-carbamoyl-2-methylpropyl)amide hemifumarate (½ fumarate) (Exemplary Compound No. 1-502)

(21a) 1-(5-Chloro-2-fluorophenyl)-5,5-dimethylpiperazin-2-one 0.15 g of the title compound (total yield over four steps: 16%) was obtained in the same manner as in Examples (1h) to (1k) using (1,1-dimethyl-2-oxoethyl)carbamic acid t-butyl ester obtained in Reference Example 3 and 5-chloro-2-fluoroaniline.
Colorless liquid.
$^1$H NMR spectrum (CDCl$_3$, 400 MHz), δ: 7.24-7.25 (m, 2H), 7.12-7.08 (m, 1H), 3.71 (br s, 2H), 3.45 (br s, 2H), 1.32 (br s, 6H).
mass spectrum (FAB$^+$), m/z: 257 ((M+H)$^+$).

(21b) (2S,4S,5S)-5-Amino-6-[4-(5-chloro-2-fluorophenyl)-2,2-dimethyl-5-oxopiperazin-1-yl]-4-hydroxy-2-isopropylhexanoic acid (2-carbamoyl-2-methylpropyl)amide hemifumarate (½ fumarate)

91 mg of the title compound (total yield over three steps: 41%) was obtained in the same manner as in Example (15b) using (3S,5S)-3-isopropyl-5-[(S)-1-(2-nitrobenzenesulfonyl)aziridin-2-yl]dihydrofuran-2-one obtained in Example (1g), 1-(5-chloro-2-fluoro-phenyl)-5,5-dimethylpiperazin-2-one obtained in Example (21a) and 3-amino-2,2-di(methyl)propionamide obtained in Reference Example 2.
Colorless solid.
$^1$H NMR spectrum (CD$_3$OD, 400 MHz), δ: 7.43-7.39 (m, 2H), 7.28-7.23 (m, 1H), 6.67 (s, 1H), 3.68-3.62 (m, 2H), 3.49-3.46 (m, 1H), 3.38-3.28 (m, 4H), 3.20-3.16 (m, 1H), 2.91-2.85 (m, 1H), 2.55 (dd, 1H, J=13.3 Hz, 4.3 Hz), 2.37-2.32 (m, 1H), 1.86-1.67 (m, 3H), 1.32-1.14 (m, 12H), 0.99-0.96 (m, 6H).
mass spectrum (FAB$^+$), m/z: 542 ((M+H)$^+$).

Example 22

(2S,4S,5S)-5-Amino-6-[4-(2,6-difluorophenyl)-2,2-dimethyl-5-oxopiperazin-1-yl]-4-hydroxy-2-isopropylhexanoic acid (2-carbamoyl-2-methylpropyl) amide hemifumarate (½ fumarate) (Exemplary Compound No. 1-495)

(22a)
1-(2,6-Difluorophenyl)-5,5-dimethylpiperazin-2-one 0.25 g of the title compound (total yield over four steps: 18%) was obtained in the same manner as in Examples (1h) to (1k) using (1,1-dimethyl-2-oxoethyl)carbamic acid t-butyl ester obtained in Reference Example 3 and 2,6-difluoroaniline.
Colorless solid.
$^1$H NMR spectrum (CDCl$_3$, 400 MHz), δ: 7.30-7.26 (m, 2H), 6.98 (t, 1H, J=8.0 Hz), 3.73 (br s, 2H), 3.46 (br s, 2H), 1.34 (br s, 6H).
mass spectrum (FAB$^+$), m/z: 241 ((M+H)$^+$).

(22b) (2S,4S,5S)-5-Amino-6-[4-(2,6-difluorophenyl)-2,2-dimethyl-5-oxopiperazin-1-yl]-4-hydroxy-2-isopropylhexanoic acid (2-carbamoyl-2-methylpropyl)amide hemifumarate (½ fumarate)

114 mg of the title compound (total yield over three steps: 47%) was obtained in the same manner as in Example (15b) using (3S,5S)-3-isopropyl-5-[(S)-1-(2-nitrobenzenesulfonyl)aziridin-2-yl]dihydrofuran-2-one obtained in Example (1g), 1-(2,6-difluorophenyl)-5,5-dimethylpiperazin-2-one obtained in Example (22a) and 3-amino-2,2-di(methyl)propionamide obtained in Reference Example 2.
Colorless solid.
$^1$H NMR spectrum (CD$_3$OD, 400 MHz), δ: 7.46-7.42 (m, 2H), 7.11 (t, 1H, J=8.5 Hz), 6.67 (s, 1H), 3.72-3.67 (m, 2H), 3.51-3.46 (m, 1H), 3.37-3.30 (m, 4H), 3.19-3.16 (m, 1H), 2.92-2.86 (m, 1H), 2.56 (dd, 1H, J=13.8 Hz, 4.1 Hz), 2.36-2.32 (m, 1H), 1.86-1.67 (m, 3H), 1.32-1.14 (m, 12H), 0.99-0.96 (m, 6H).

mass spectrum (FAB+), m/z: 526 ((M+H)+).

Example 23

(2S,4S,5S)-5-Amino-6-[4-(2-chloro-5-fluorophenyl)-2,2-dimethyl-5-oxopiperazin-1-yl]-4-hydroxy-2-isopropylhexanoic acid (2-carbamoyl-2-methylpropyl)amide hemifumarate (½ fumarate) (Exemplary Compound No. 1-512)

(23a) 1-(2-Chloro-5-fluorophenyl)-5,5-dimethylpiperazin-2-one 0.16 g of the title compound (total yield over four steps: 21%) was obtained in the same manner as in Examples (1h) to (1k) using (1,1-dimethyl-2-oxoethyl)carbamic acid t-butyl ester obtained in Reference Example 3 and 5-chloro-2-fluoroaniline.

Colorless liquid.

¹H NMR spectrum (CDCl₃, 400 MHz), δ: 7.44 (dd, 1H, J=8.6 Hz, 5.5 Hz), 7.05-6.99 (m, 2H), 3.72 (d, 2H, J=13.3 Hz), 3.48-3.38 (m, 2H), 1.38-1.33 (m, 6H).

mass spectrum (FAB+), m/z: 257 ((M+H)+).

(23b) (2S,4S,5S)-5-Amino-6-[4-(2-chloro-5-fluorophenyl)-2,2-dimethyl-5-oxopiperazin-1-yl]-4-hydroxy-2-isopropylhexanoic acid (2-carbamoyl-2-methylpropyl)amide hemifumarate (½ fumarate)

118 mg of the title compound (total yield over three steps: 51%) was obtained in the same manner as in Example (15b) using (3S,5S)-3-isopropyl-5-[(S)-1-(2-nitrobenzenesulfonyl)aziridin-2-yl]dihydrofuran-2-one obtained in Example (1g), 1-(2-chloro-5-fluorophenyl)-5,5-dimethylpiperazin-2-one obtained in Example (23a) and 3-amino-2,2-di(methyl)propionamide obtained in Reference Example 2.

Colorless solid.

¹H NMR spectrum (CD₃OD, 400 MHz), δ: 7.56 (dd, 1H, J=9.8 Hz, 5.1 Hz), 7.21-7.17 (m, 2H), 6.68 (s, 1H), 3.67-3.58 (m, 2H), 3.51-3.46 (m, 1H), 3.41-3.17 (m, 5H), 2.99-2.94 (m, 0.6H), 2.76-2.74 (m, 0.8H), 2.50 (br d, 0.6H, J=14.9 Hz), 2.37-2.32 (m, 1H), 1.87-1.68 (m, 3H), 1.32-1.14 (m, 12H), 0.99-0.96 (m, 6H).

mass spectrum (FAB+), m/z: 542 ((M+H)+).

Example 24

(2S,4S,5S)-5-Amino-6-[4-(2,5-difluorophenyl)-2,2-dimethyl-5-oxopiperazin-1-yl]-4-hydroxy-2-isopropylhexanoic acid (2-carbamoyl-2-methylpropyl)amide hemifumarate (½ fumarate) (Exemplary Compound No. 1-494)

(24a) 1-(2,5-Difluorophenyl)-5,5-dimethylpiperazin-2-one 0.23 g of the title compound (total yield over four steps: 27%) was obtained in the same manner as in Examples (1h) to (1k) using (1,1-dimethyl-2-oxoethyl)carbamic acid t-butyl ester obtained in Reference Example 3 and 2,5-difluoroaniline.

Colorless solid.

¹H NMR spectrum (CDCl₃, 400 MHz), δ: 7.16-7.08 (m, 1H), 7.04-6.97 (m, 2H), 3.72 (s, 2H), 3.46 (s, 2H), 1.33 (s, 6H).

mass spectrum (EI+), m/z: 240 (M+).

(24b) (2S,4S,5S)-5-Amino-6-[4-(2,5-difluorophenyl)-2,2-dimethyl-5-oxopiperazin-1-yl]-4-hydroxy-2-isopropylhexanoic acid (2-carbamoyl-2-methylpropyl)amide hemifumarate (½ fumarate)

116 mg of the title compound (total yield over three steps: 30%) was obtained in the same manner as in Example (15b) using (3S,5S)-3-isopropyl-5-[(S)-1-(2-nitrobenzenesulfonyl)aziridin-2-yl]dihydrofuran-2-one obtained in Example (1g), 1-(2,5-difluorophenyl)-5,5-dimethylpiperazin-2-one obtained in Example (24a) and 3-amino-2,2-di(methyl)propionamide obtained in Reference Example 2.

Colorless solid.

¹H NMR spectrum (CD₃OD, 400 MHz), δ: 7.31-7.22 (m, 1H), 7.19-7.13 (m, 2H), 6.67 (s, 1H), 3.67 (d, 1H, J=11.7 Hz), 3.65 (d, 1H, J=18.0 Hz), 3.50-3.45 (m, 2H), 3.39-3.32 (m, 3H), 3.20-3.14 (m, 1H), 2.88 (dd, 1H, J=13.6 Hz, 10.6 Hz), 2.45 (dd, 1H, J=13.6 Hz, 4.2 Hz), 2.39-2.32 (m, 1H), 1.88-1.66 (m, 3H), 1.25 (s, 6H), 1.21 (s, 3H), 1.20 (s, 3H), 0.98 (d, 3H, J=6.3 Hz), 0.97 (d, 3H, J=6.6 Hz).

mass spectrum (FAB+), m/z: 526 ((M+H)+).

Example 25

(2S,4S,5S)-5-Amino-6-[4-(3,5-difluorophenyl)-2,2-dimethyl-5-oxopiperazin-1-yl]-4-hydroxy-2-isopropylhexanoic acid (2-carbamoyl-2-methylpropyl)amide hemifumarate (½ fumarate) (Exemplary Compound No. 1-496)

(25a) 1-(3,5-Difluorophenyl)-5,5-dimethylpiperazin-2-one 0.25 g of the title compound (total yield over four steps: 13%) was obtained in the same manner as in Example (14a) using (1,1-dimethyl-2-oxoethyl)carbamic acid t-butyl ester obtained in Reference Example 3 and 3,5-difluoroaniline.

Colorless solid.

¹H NMR spectrum (CDCl₃, 400 MHz), δ: 6.92-6.85 (m, 2H), 6.75-6.68 (m, 1H), 3.70 (s, 2H), 3.49 (s, 2H), 1.31 (s, 6H).

mass spectrum (EI+), m/z: 240 (M+).

(25b) (2S,4S,5S)-5-Amino-6-[4-(3,5-difluorophenyl)-2,2-dimethyl-5-oxopiperazin-1-yl]-4-hydroxy-2-isopropylhexanoic acid (2-carbamoyl-2-methylpropyl)amide hemifumarate (½ fumarate)

102 mg of the title compound (total yield over three steps: 26%) was obtained in the same manner as in Example (15b) using (3S,5S)-3-isopropyl-5-[(S)-1-(2-nitrobenzenesulfonyl)aziridin-2-yl]dihydrofuran-2-one obtained in Example (1g), 1-(3,5-difluorophenyl)-5,5-dimethylpiperazin-2-one obtained in Example (25a) and 3-amino-2,2-di(methyl)propionamide obtained in Reference Example 2.

Colorless solid.

¹H NMR spectrum (CD₃OD, 400 MHz), δ: 7.08-7.02 (m, 2H), 6.96-6.89 (m, 1H), 6.66 (s, 1H), 3.71 (d, 1H, J=11.7 Hz), 3.62 (d, 1H, J=18.0 Hz), 3.52-3.34 (m, 5H), 3.18-3.13 (m, 1H), 2.86 (dd, 1H, J=13.6 Hz, 11.3 Hz), 2.53 (dd, 1H, J=13.6

Hz, 3.9 Hz), 2.37-2.34 (m, 1H), 1.88-1.66 (m, 3H), 1.25 (s, 3H), 1.22 (s, 3H), 1.21 (s, 3H), 1.20 (s, 3H), 0.98 (d, 3H, J=6.3 Hz), 0.97 (d, 3H, J=6.6 Hz).

mass spectrum (FAB$^+$), m/z: 526 ((M+H)$^+$).

Example 26

(2S,4S,5S)-5-Amino-6-[4-(2,5-dichlorophenyl)-2,2-dimethyl-5-oxopiperazin-1-yl]-4-hydroxy-2-isopropylhexanoic acid (2-carbamoyl-2-methylpropyl) amide fumarate (Exemplary Compound No. 1-505)

(26a) 1-(2,5-Dichlorophenyl)-5,5-dimethylpiperazin-2-one 0.26 g of the title compound (total yield over four steps: 29%) was obtained in the same manner as in Examples (1h) to (1k) using (1,1-dimethyl-2-oxoethyl)carbamic acid t-butyl ester obtained in Reference Example 3 and 2,5-dichloroaniline.

Colorless liquid.

$^1$H NMR spectrum (CDCl$_3$, 400 MHz), δ: 7.42-7.39 (m, 1H), 7.28-7.25 (m, 2H), 3.78-3.66 (m, 2H), 3.46-3.35 (m, 2H), 1.38 (br s, 3H), 1.32 (br s, 3H).

mass spectrum (FAB$^+$), m/z: 273 ((M+H)$^+$).

(26b) (2S,4S,5S)-5-Amino-6-[4-(2,5-dichlorophenyl)-2,2-dimethyl-5-oxopiperazin-1-yl]-4-hydroxy-2-isopropylhexanoic acid (2-carbamoyl-2-methylpropyl)amide fumarate 95 mg of the title compound (total yield over three steps: 48%) was obtained in the same manner as in Example (15b) using (3S,5S)-3-isopropyl-5-[(S)-1-(2-nitrobenzenesulfonyl)aziridin-2-yl]dihydrofuran-2-one obtained in Example (1g), 1-(2,5-dichlorophenyl)-5,5-dimethylpiperazin-2-one obtained in Example (26a) and 3-amino-2,2-di(methyl)propionamide obtained in Reference Example 2.

Colorless solid.

$^1$H NMR spectrum (CD$_3$OD, 500 MHz), δ: 7.55 (br d, 1H, J=8.3 Hz), 7.45-7.42 (m, 2H), 6.71 (s, 2H), 3.68-3.57 (m, 2H), 3.52-3.19 (m, 6H), 2.98 (br t, 0.6H, J=12.2 Hz), 2.77-2.73 (m, 0.8H), 2.51 (dd, 0.6H, J=13.4 Hz, 4.2 Hz), 2.38-2.33 (m, 1H), 1.88-1.69 (m, 3H), 1.33-1.15 (m, 12H), 0.99-0.96 (m, 6H).

mass spectrum (FAB$^+$), m/z: 558 ((M+H)$^+$).

Example 27

(2S,4S,5S)-5-Amino-6-[4-(2-chloro-5-methoxyphenyl)-2,2-dimethyl-5-oxopiperazin-1-yl]-4-hydroxy-2-isopropylhexanoic acid (2-carbamoyl-2-methylpropyl)amide fumarate (Exemplary Compound No. 1-510)

(27a) 1-(2-Chloro-5-methoxyphenyl)-5,5-dimethylpiperazin-2-one 391 mg of the title compound (total yield over four steps: 43%) was obtained in the same manner as in Examples (1h) to (1k) using (1,1-dimethyl-2-oxoethyl)carbamic acid t-butyl ester obtained in Reference Example 3 and 2-chloro-5-methoxyaniline.

Colorless liquid.

$^1$H NMR spectrum (CDCl$_3$, 400 MHz), δ: 7.35 (d, 1H, J=8.8 Hz), 6.84 (dd, 1H, J=8.8 Hz, 2.9 Hz), 6.87 (d, 1H, J=2.9 Hz), 3.79 (s, 3H), 3.77-3.66 (m, 2H), 3.47-3.36 (m, 2H), 1.39 (s, 3H), 1.32 (s, 3H).

(27b) (2S,4S,5S)-5-Amino-6-[4-(2-chloro-5-methoxyphenyl)-2,2-dimethyl-5-oxopiperazin-1-yl]-4-hydroxy-2-isopropylhexanoic acid (2-carbamoyl-2-methylpropyl)amide fumarate 127 mg of the title compound (total yield over four steps: 35%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 1-(2-chloro-5-methoxyphenyl)-5,5-dimethylpiperazin-2-one obtained in Example (27a) and 3-amino-2,2-di(methyl)propionamide obtained in Reference Example 2.

Colorless liquid.

$^1$H NMR spectrum (CD$_3$OD, 400 MHz), δ: 7.79 (br s, 1H), 7.42 (d, 1H, J=9.0 Hz), 6.97 (dd, 1H, J=9.0 Hz, 2.7 Hz), 6.90-6.88 (m, 1H), 6.68 (s, 2H), 3.81 (s, 3H), 3.66-3.58 (m, 2H), 3.52-3.14 (m, 6H), 2.99-2.94 (m, 0.6H), 2.79-2.71 (m, 0.8H), 2.52-2.49 (m, 0.6H), 2.49-2.33 (m, 1H), 1.87-1.78 (m, 2H), 1.73-1.68 (m, 1H), 1.32-1.16 (m, 12H), 0.99-0.97 (m, 6H).

mass spectrum (FAB$^+$), m/z: 554 ((M+H)$^+$).

Example 28

(2S,4S,5S)-5-Amino-6-[4-(5-chloro-2-methoxyphenyl)-2,2-dimethyl-5-oxopiperazin-1-yl]-4-hydroxy-2-isopropylhexanoic acid (2-carbamoyl-2-methylpropyl)amide fumarate (Exemplary Compound No. 1-491)

(28a) 1-(5-Chloro-2-methoxyphenyl)-5,5-dimethylpiperazin-2-one 259 mg of the title compound (total yield over four steps: 45%) was obtained in the same manner as in Examples (1h) to (1k) using (1,1-dimethyl-2-oxoethyl)carbamic acid t-butyl ester obtained in Reference Example 3 and 3-chloro-5-methoxyaniline.

Colorless liquid.

$^1$H NMR spectrum (CDCl$_3$, 400 MHz), δ: 7.27-7.24 (dd, 1H, J=8.4 Hz, 2.4 Hz), 7.16 (d, 1H, J=2.4 Hz), 6.89 (d, 1H, J=8.4 Hz), 3.82 (s, 3H), 3.69 (s, 2H), 3.37 (s, 2H), 1.31 (s, 6H).

(28b) (2S,4S,5S)-5-Amino-6-[4-(5-chloro-2-methoxyphenyl)-2,2-dimethyl-5-oxopiperazin-1-yl]-4-hydroxy-2-isopropylhexanoic acid (2-carbamoyl-2-methylpropyl)amide fumarate 52 mg of the title compound (total yield over four steps: 14%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 1-(5-chloro-2-methoxyphenyl)-5,5-dimethylpiperazin-2-one obtained in Example (28a) and 3-amino-2,2-di(methyl)propionamide obtained in Reference Example 2.

Colorless liquid.

$^1$H NMR spectrum (CD$_3$OD, 400 MHz), δ: 7.35 (dd, 1H, J=9.0 Hz, 2.7 Hz), 7.22 (d, 1H, J=2.7 Hz), 7.10 (d, 1H, J=9.0 Hz), 6.66 (s, 2H), 3.84 (s, 3H), 3.62-3.35 (m, 2H), 3.49-3.46 (m, 1H), 3.41-3.24 (m, 5H), 3.17-3.12 (m, 0.6H), 2.85 (br s, 0.8H), 2.55 (br s, 0.6H), 2.38-2.33 (m, 1H), 1.86-1.77 (m, 2H), 1.73-1.68 (m, 1H), 1.24-1.20 (m, 12H), 1.00-0.97 (m, 6H).

mass spectrum (FAB$^+$), m/z: 554 ((M+H)$^+$).

Example 29

(2S,4S,5S)-5-Amino-4-hydroxy-2-isopropyl-6-{4-[2-(3-methoxypropoxy)phenyl]-2,2-dimethylpiperazin-1-yl}hexanoic acid (2-carbamoyl-2-methylpropyl)amide fumarate (Exemplary Compound No. 1-425)

(29a) 4-[2-(3-Methoxypropoxy)phenyl]-2,2-dimethylpiperazine-1-carboxylic acid t-butyl ester 2.30 ml of a borane-tetrahydrofuran complex (1.2 mol/l) (2.76 mmol) was added to a solution of 303 mg of 4-[2-(3-methoxypropoxy)phenyl]-2,2-dimethyl-5-oxopiperazine-1-carboxylic acid t-butyl ester obtained in Example (10e) (0.77 mmol) in tetrahydrofuran (2.8 ml) under a nitrogen atmosphere and under ice-cooling over five minutes, and the mixture was stirred at room temperature for 15 minutes. The reaction mixture was cooled in an ice bath. Then, 2.76 ml of a 1 N sodium hydroxide aqueous solution (2.76 mmol) was slowly added and the mixture was further stirred at room temperature for one hour. Water was added to the reaction mixture, followed by extraction with ethyl acetate. Then, the organic layer was washed with water and brine and dried over anhydrous magnesium sulfate. After filtration, the solvent was evaporated under reduced pressure, and the residue was purified by silica gel column chromatography (elution solvent:n-hexane/ethyl acetate=30/1-10/1) to obtain 276 mg of the title compound (yield: 91%).

Colorless liquid.

$^1$H NMR spectrum (CDCl$_3$, 400 MHz), δ: 6.99-6.86 (m, 4H), 4.08 (t, 2H, J=6.3 Hz), 3.62 (m, 2H), 3.58 (t, 2H, J=6.3 Hz), 3.35 (s, 3H), 3.07 (m, 2H), 2.85 (s, 2H), 2.10 (quint., 2H, J=6.3 Hz), 1.49 (s, 9H), 1.48 (s, 6H).

(29b) 1-[2-(3-Methoxypropoxy)phenyl]-5,5-dimethylpiperazine 178 mg of the title compound (yield: 91%) was obtained in the same manner as in Example (1k) using 4-[2-(3-methoxypropoxy)phenyl]-2,2-dimethylpiperazine-1-carboxylic acid t-butyl ester obtained in Example (29a).

Colorless liquid.

$^1$H NMR spectrum (CDCl$_3$, 400 MHz), δ: 6.97-6.85 (m, 4H), 4.08 (t, 2H, J=6.3 Hz), 3.59 (t, 2H, J=6.3 Hz), 3.36 (s, 3H), 3.10-3.05 (m, 4H), 2.97-2.94 (m, 2H), 2.11 (quint., 2H, J=6.3 Hz), 1.47 (br s, 1H), 1.25 (s, 6H).

(29c) (2S,4S,5S)-5-Amino-4-hydroxy-2-isopropyl-6-{4-[2-(3-methoxypropoxy)phenyl]-2,2-dimethylpiperazin-1-yl}hexanoic acid (2-carbamoyl-2-methylpropyl)amide fumarate 61.4 mg of the title compound (total yield over four steps: 56%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 1-[2-(3-methoxypropyloxy)phenyl]-5,5-dimethylpiperazine obtained in Example (29b) and 3-amino-2,2-di(methyl)propionamide obtained in Reference Example 2.

Colorless liquid.

$^1$H NMR spectrum (CD$_3$OD, 400 MHz), δ: 7.77-7.74 (m, 1H), 6.97-6.85 (m, 4H), 6.74 (s, 2H), 4.11-4.02 (m, 2H), 3.60 (t, 2H, J=6.5 Hz), 3.52-3.46 (m, 1H), 3.38-3.35 (m, 8H), 3.30-2.71 (m, 4.6H), 2.62-2.59 (m, 0.8H), 2.45-2.31 (m, 1.6H), 2.07 (quint., 2H, J=6.5 Hz), 1.86-1.76 (m, 2H), 1.71-1.64 (m, 1H), 1.22-1.20 (m, 9H), 1.14 (s, 3H), 0.99-0.96 (m, 6H).

mass spectrum (FAB$^+$), m/z: 578 ((M+H)$^+$).

Example 30

(2S,4S,5S)-5-Amino-4-hydroxy-2-isopropyl-6-{4-[3-(3-methoxypropoxy)phenyl]-2,2-dimethylpiperazin-1-yl}hexanoic acid (2-carbamoyl-2-methylpropyl)amide fumarate (Exemplary Compound No. 1-426)

(30a) 4-[3-(3-Methoxypropoxy)phenyl]-2,2-dimethylpiperazine-1-carboxylic acid t-butyl ester 177 mg of 4-[3-(3-methoxypropoxy)phenyl]-2,2-dimethyl-5-oxopiperazine-1-carboxylic acid t-butyl ester (total yield over five steps: 32%) was obtained in the same manner as in Example (14a) and Examples (10d) to (10f) using (1,1-dimethyl-2-oxoethyl)carbamic acid t-butyl ester obtained in Reference Example 3, 3-benzyloxyaniline and 3-methoxypropyl bromide.

3.47 ml of a borane-tetrahydrofuran complex (1.2 mol/l) (4.16 mmol) was added to a solution of 456 mg of 4-[3-(3-methoxypropoxy)phenyl]-2,2-dimethyl-5-oxopiperazine-1-carboxylic acid t-butyl ester obtained in the above reaction (1.16 mmol) in tetrahydrofuran (4.16 ml) under a nitrogen atmosphere and under ice-cooling over five minutes, and the mixture was stirred at room temperature for 15 minutes. The reaction mixture was cooled in an ice bath. Then, 4.16 ml of a 1 N sodium hydroxide aqueous solution (4.16 mmol) was slowly added and the mixture was further stirred at room temperature for one hour. Water was added to the reaction mixture, followed by extraction with ethyl acetate. Then, the organic layer was washed with water and brine and dried over anhydrous magnesium sulfate. After filtration, the solvent was evaporated under reduced pressure, and the residue was purified by silica gel column chromatography (elution solvent:n-hexane/ethyl acetate=30/1-10/1) to obtain 370 mg of the title compound (yield: 82%).

Colorless liquid.

$^1$H NMR spectrum (CDCl$_3$, 400 MHz), δ: 7.81-7.27 (m, 1H), 6.89-6.78 (m, 3H), 4.22 (s, 2H), 4.05 (t, 2H, J=6.0 Hz), 3.63 (s, 2H), 3.55 (t, 2H, J=6.0 Hz), 2.05 (quint., 2H J=6.0 Hz), 1.52 (s, 6H), 1.50 (s, 9H).

(30b) 1-[3-(3-Methoxypropyloxy)phenyl]-5,5-dimethylpiperazine 258 mg of the title compound (yield: quant.) was obtained in the same manner as in Example (1k) using 4-[3-(3-methoxypropoxy)phenyl]-2,2-dimethylpiperazine-1-carboxylic acid t-butyl ester obtained in Example (30a).

Colorless liquid.

$^1$H NMR spectrum (CDCl$_3$, 400 MHz), δ: 7.15 (t, 1H, J=8.0 Hz), 6.52-6.38 (m, 3H), 4.04 (t, 2H, J=6.0 Hz), 3.56 (t, 2H, J=6.0 Hz), 3.36 (s, 3H), 3.11-3.02 (m, 4H), 2.89 (s, 2H), 2.04 (quint., 2H, J=6.0 Hz), 1.46 (br s, 1H), 1.22 (s, 6H).

mass spectrum (APCI), m/z: 279 ((M+H)$^+$).

(30c) (2S,4S,5S)-5-Amino-4-hydroxy-2-isopropyl-6-{4-[3-(3-methoxypropoxy)phenyl]-2,2-dimethylpiperazin-1-yl}hexanoic acid (2-carbamoyl-2-methylpropyl)amide fumarate 120 mg of the title compound (total yield over four steps: 65%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 1-[3-(3-methoxypropyloxy)phenyl]-5,5-dimethylpiperazine obtained in Example (6b) and 3-amino-2,2-di(methyl)propionamide obtained in Reference Example 2.

Colorless liquid.

$^1$H NMR spectrum (CD$_3$OD, 400 MHz), δ: 7.78 (m, 1H), 7.10 (t, 1H, J=8.0 Hz), 6.71 (s, 2H), 6.53-6.38 (m, 3H), 4.01 (t, 2H, J=6.0 Hz), 3.56 (t, 2H, J=6.0 Hz), 3.51-3.35 (m, 6H), 3.34 (s, 3H), 3.18-3.10 (m, 2H), 2.96-2.89 (m, 1H), 2.84-2.66 (m, 2H), 2.45-2.32 (m, 2H), 1.99 (quint., 2H, J=6.0 Hz), 1.87-1.64 (m, 3H), 1.21-1.19 (m, 6H), 1.15 (m, 6H), 0.99-0.93 (m, 6H).

mass spectrum (FAB$^+$), m/z: 578 ((M+H)$^+$).

Example 31

(2S,4S,5S)-5-Amino-6-[4-(2-chlorophenyl)-2,2-dimethyl-5-oxopiperazin-1-yl]-4-hydroxy-2-isopropyl-hexanoic acid (2,2-dimethylpropyl)amide hemifumarate (½ fumarate) (Exemplary Compound No. 1-833)

89 mg of the title compound (total yield over two steps: 57%) was obtained in the same manner as in Examples (1n) and (1o) using {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) and (2,2-dimethylpropyl)amine.

Colorless solid.

$^1$H NMR spectrum (CD$_3$OD, 400 MHz), δ: 7.92 (br s, 1H), 7.55-7.33 (m, 1H), 7.44-7.31 (m, 3H), 6.67 (s, 1H), 3.67-3.59 (m, 2H), 3.52-3.47 (m, 1H), 3.39-3.11 (m, 4H), 2.97-2.90 (m, 1.6H), 2.80-2.66 (m, 0.8H), 2.51 (dd, 0.6H, J=13.7 Hz, 3.9 Hz), 2.43-2.38 (m, 1H), 1.91-1.80 (m, 2H), 1.74-1.68 (m, 1H), 1.31-1.26 (m, 6H), 1.01-0.99 (m, 6H), 0.94 (s, 9H).

mass spectrum (FAB$^+$), m/z: 495 ((M+H)$^+$).

Example 32

(2S,4S,5S)-5-Amino-6-[4-(2-chlorophenyl)-2,2-dimethyl-5-oxopiperazin-1-yl]-4-hydroxy-2-isopropyl-hexanoic acid (3-methylbutyl)amide hemifumarate (½ fumarate) (Exemplary Compound No. 1-1004)

135 mg of the title compound (total yield over two steps: 83%) was obtained in the same manner as in Examples (1n) and (1o) using {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) and (3-methylbutyl)amine.

Colorless solid.

$^1$H NMR spectrum (CD$_3$OD, 400 MHz), δ: 7.55-7.54 (m, 1H), 7.44-7.32 (m, 3H), 6.68 (s, 1H), 3.68-3.60 (m, 2H), 3.50-3.44 (m, 1H), 3.37-3.10 (m, 5H), 2.98-2.92 (m, 0.6H), 2.79-2.69 (m, 0.8H), 2.51 (dd, 0.6H, J=13.5 Hz, 4.1 Hz), 2.32-2.27 (m, 1H), 1.85-1.79 (m, 2H), 1.75-1.59 (m, 2H), 1.45-1.39 (m, 2H), 1.33-1.26 (m, 6H), 1.00-0.92 (m, 12H).

mass spectrum (FAB$^+$), m/z: 495 ((M+H)$^+$).

Example 33

(2S,4S,5S)-5-Amino-6-[4-(2-chlorophenyl)-2,2-dimethyl-5-oxopiperazin-1-yl]-4-hydroxy-2-isopropyl-hexanoic acid (3,3-dimethylbutyl)amide hemifumarate (½ fumarate) (Exemplary Compound No. 1-1023)

89 mg of the title compound (total yield over two steps: 57%) was obtained in the same manner as in Examples (1n) and (1o) using {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) and (3,3-dimethylbutyl)amine.

Colorless solid.

$^1$H NMR spectrum (CD$_3$OD, 400 MHz), δ: 7.55-7.54 (m, 1H), 7.43-7.33 (m, 3H), 6.67 (s, 1H), 3.67-3.60 (m, 2H), 3.49-3.44 (m, 1H), 3.37-3.26 (m, 3H), 3.20-3.11 (m, 2H), 2.96-2.91 (m, 0.6H), 2.79-2.67 (m, 0.8H), 2.53-2.50 (m, 0.6H), 2.30-2.26 (m, 1H), 1.85-1.80 (m, 2H), 1.74-1.69 (m, 1H), 1.47-1.40 (m, 2H), 1.31-1.27 (m, 6H), 0.99-0.95 (m, 15H).

mass spectrum (FAB$^+$), m/z: 509 ((M+H)$^+$).

Example 34

(2S,4S,5S)-5-Amino-6-[4-(2-chlorophenyl)-2,2-dimethyl-5-oxopiperazin-1-yl]-4-hydroxy-2-isopropyl-hexanoic acid (3-methoxypropyl)amide hemifumarate (½ fumarate) (Exemplary Compound No. 1-975)

128 mg of the title compound (total yield over two steps: 70%) was obtained in the same manner as in Examples (1n) and (1o) using {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) and (3-methoxypropyl)amine.

Colorless solid.

$^1$H NMR spectrum (CD$_3$OD, 400 MHz), δ: 7.55-7.53 (m, 1H), 7.44-7.33 (m, 3H), 6.66 (s, 1H), 3.67-3.59 (m, 2H), 3.50-3.43 (m, 3H), 3.38-3.11 (m, 8H), 2.97-2.91 (m, 0.6H), 2.80-2.67 (m, 0.8H), 2.50 (dd, 0.6H, J=13.5 Hz, 4.1 Hz), 2.33-2.29 (m, 1H), 1.84-1.70 (m, 5H), 1.31-1.26 (m, 6H), 1.00-0.95 (m, 6H).

mass spectrum (FAB$^+$), m/z: 497 ((M+H)$^+$).

Example 35

(2S,4S,5S)-5-Amino-6-[4-(2-chlorophenyl)-2,2-dimethyl-5-oxopiperazin-1-yl]-4-hydroxy-2-isopropyl-hexanoic acid (4H-tetrahydropyran-4-yl)amide fumarate (Exemplary Compound No. 1-732)

42 mg of the title compound (total yield over two steps: 44%) was obtained in the same manner as in Examples (1n) and (1o) using {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) and (4H-tetrahydropyran-4-yl)amine.

Colorless solid.

$^1$H NMR spectrum (CD$_3$OD, 400 MHz), δ: 7.56-7.54 (m, 1H), 7.44-7.38 (m, 2H), 7.35-7.32 (m, 1H), 6.70 (s, 2H), 3.95-3.92 (m, 3H), 3.67-3.59 (m, 2H), 3.51-3.45 (m, 4H), 3.36-3.14 (m, 2H), 2.97-2.93 (m, 0.6H), 2.81-2.68 (m, 0.8H), 2.52 (dd, 0.6H, J=13.4 Hz, 3.7 Hz), 2.32-2.28 (m, 1H), 1.86-1.81 (m, 4H), 1.75-1.70 (m, 1H), 1.60-1.49 (m, 2H), 1.31-1.27 (m, 6H), 1.00-0.97 (m, 6H).

mass spectrum (FAB$^+$), m/z: 509 ((M+H)$^+$).

Example 36

(2S,4S,5S)-5-Amino-6-[4-(2-chlorophenyl)-2,2-dimethyl-5-oxopiperazin-1-yl]-4-hydroxy-2-isopropyl-hexanoic acid (2-methoxycarbonyl-2-methylpropyl)amide hemifumarate (½ fumarate) (Exemplary Compound No. 1-403)

104 mg of the title compound (total yield over two steps: 63%) was obtained in the same manner as in Examples (1n)

and (1o) using {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) and (2-methoxycarbonyl-2-methylpropyl)amine.

Colorless solid.

$^1$H NMR spectrum (CD$_3$OD, 400 MHz), δ: 7.55-7.54 (m, 1H), 7.42-7.32 (m, 3H), 6.67 (s, 1H), 3.68 (s, 3H), 3.63-3.61 (m, 2H), 3.51-3.48 (m, 1H), 3.42-3.12 (m, 5H), 2.96 (br t, 0.6H, J=12.2 Hz), 2.81-2.69 (m, 0.8H), 2.55-2.51 (m, 0.6H), 2.37-2.32 (m, 1H), 1.87-1.78 (m, 2H), 1.72-1.66 (m, 1H), 1.31-1.27 (m, 6H), 1.20-1.18 (m, 6H), 0.99-0.96 (m, 6H).

mass spectrum (FAB$^+$), m/z: 539 ((M+H)$^+$).

Example 37

(2S,4S,5S)-5-Amino-6-[4-(2-chlorophenyl)-2,2-dimethyl-5-oxopiperazin-1-yl]-4-hydroxy-2-isopropylhexanoic acid (2-hydroxy-2-methylpropyl)amide hemifumarate (½ fumarate) (Exemplary Compound No. 1-782)

144 mg of the title compound (total yield over two steps: 66%) was obtained in the same manner as in Examples (1n) and (1o) using {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) and (1,1-dimethylethanol)amine.

Colorless solid.

$^1$H NMR spectrum (CD$_3$OD, 400 MHz), δ: 7.91-7.87 (m, 1H), 7.56-7.53 (m, 1H), 7.44-7.32 (m, 3H), 6.70 (s, 1H), 3.67-3.60 (m, 2H), 3.55-3.48 (m, 1H), 3.38-3.13 (m, 5H), 2.98-2.92 (m, 0.6H), 2.80-2.68 (m, 0.8H), 2.54-2.50 (m, 0.6H), 2.42-2.36 (m, 1H), 1.91-1.69 (m, 3H), 1.31-1.27 (m, 6H), 1.21 (s, 6H), 1.00 (d, 3H, J=4.3 Hz), 0.98 (d, 3H, J=4.3 Hz).

mass spectrum (FAB$^+$), m/z: 497 ((M+H)$^+$).

Example 38

(2S,4S,5S)-5-Amino-6-[4-(2-chlorophenyl)-2,2-dimethyl-5-oxopiperazin-1-yl]-4-hydroxy-2-isopropylhexanoic acid (2-ethyl-2-hydroxybutyl)amide fumarate (Exemplary Compound No. 1-1030)

75 mg of the title compound (total yield over two steps: 36%) was obtained in the same manner as in Examples (1n) and (1o) using {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) and (2,2-diethylethanol)amine.

Colorless solid.

$^1$H NMR spectrum (CD$_3$OD, 500 MHz), δ: 7.77-7.75 (m, 1H), 7.56-7.53 (m, 1H), 7.44-7.32 (m, 3H), 6.69 (s, 2H), 3.68-3.61 (m, 2H), 3.52-3.46 (m, 1H), 3.38-3.15 (m, 5H), 2.98-2.93 (m, 0.6H), 2.81-2.68 (m, 0.8H), 2.50 (dd, 0.6H, J=13.4 Hz, 4.2 Hz), 2.42-2.36 (m, 1H), 1.89-1.70 (m, 3H), 1.55-1.45 (m, 4H), 1.31-1.27 (m, 6H), 0.99 (t, 6H, J=6.8 Hz), 0.92-0.87 (m, 6H).

mass spectrum (FAB$^+$), m/z: 525 ((M+H)$^+$).

Example 39

(2S,4S,5S)-5-Amino-6-[4-(2-chlorophenyl)-2,2-dimethyl-5-oxopiperazin-1-yl]-4-hydroxy-2-isopropylhexanoic acid (3-hydroxy-3-methylbutyl)amide fumarate (Exemplary Compound No. 1-1031)

52 mg of the title compound (total yield over two steps: 22%) was obtained in the same manner as in Examples (1n) and (1o) using {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) and (3,3-dimethylpropanol)amine.

Colorless solid.

$^1$H NMR spectrum (CD$_3$OD, 400 MHz), δ: 7.56-7.53 (m, 1H), 7.44-7.32 (m, 3H), 3.68-3.60 (m, 2H), 3.51-3.12 (m, 6H), 2.99-2.93 (m, 0.6H), 2.82-2.67 (m, 0.8H), 2.53-2.49 (m, 0.6H), 2.31-2.25 (m, 1H), 1.85-1.78 (m, 2H), 1.75-1.66 (m, 3H), 1.32-1.27 (m, 6H), 1.23 (s, 6H), 0.99 (d, 3H, J=6.6 Hz), 0.96 (d, 3H, J=6.6 Hz).

mass spectrum (FAB$^+$), m/z: 511 ((M+H)$^+$).

Example 40

(2S,4S,5S)-5-Amino-6-[4-(2-chlorophenyl)-2,2-dimethyl-5-oxopiperazin-1-yl]-4-hydroxy-2-isopropylhexanoic acid trans-(4-hydroxycyclohexyl)amide fumarate (Exemplary Compound No. 1-1038)

65 mg of the title compound (total yield over two steps: 34%) was obtained in the same manner as in Examples (1n) and (1o) using {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) and trans-(4-hydroxycyclohexyl)amine.

Colorless solid.

$^1$H NMR spectrum (CD$_3$OD, 400 MHz), δ: 7.95-7.93 (m, 1H), 7.56-7.54 (m, 1H), 7.45-7.32 (m, 3H), 6.69 (s, 2H), 3.69-3.59 (m, 3H), 3.55-3.44 (m, 2H), 3.37-3.12 (m, 3H), 2.97-2.91 (m, 0.6H), 2.81-2.67 (m, 0.8H), 2.54-2.50 (m, 0.6H), 2.29-2.23 (m, 1H), 1.98-1.68 (m, 7H), 1.37-1.26 (m, 10H), 0.99-0.95 (m, 6H).

mass spectrum (FAB$^+$), m/z: 522 ((M+H)$^+$).

Example 41

(2S,4S,5S)-5-Amino-6-[4-(2-chlorophenyl)-2,2-dimethyl-5-oxopiperazin-1-yl]-4-hydroxy-2-isopropylhexanoic acid (2,2,2-trifluoroethyl)amide hemifumarate (½ fumarate) (Exemplary Compound No. 1-578)

(41a) {(1S,2S,4S)-1-[4-(2-Chlorophenyl)-2,2-dimethyl-5-oxopiperazin-1-ylmethyl]-2-hydroxy-5-methyl-4-(2,2,2-trifluoroethyl)carbamoylhexyl}carbamic acid t-butyl ester 2 ml of a solution of dimethylaluminum chloride in n-hexane (1.0 mol/l) (2 mmol) was added to a solution of 160 μl of (2,2,2-trifluoroethyl)amine (2 mmol) in methylene chloride under a nitrogen atmosphere at room temperature, and the mixture was stirred at room temperature for one hour. A solution of 200 mg of {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) (0.39 mmol) in methylene chloride (4 ml) was added to the solution obtained above, and the mixture was stirred at room temperature for 26 hours. A 10% potassium sodium tartrate aqueous solution was added to the reaction mixture, followed by dilution with ethyl acetate. Then, the mixture was stirred at room temperature for 0.5 hour. The reaction mixture was extracted with ethyl acetate, and then the organic layer was washed with brine and dried over anhydrous magnesium sulfate. After filtration, the solvent was evaporated under reduced pressure, and the residue was purified by silica gel column chromatography (elution solvent:methylene chloride/methanol=40/1) to obtain 132 mg of the title compound (yield: 55%).

Colorless solid.

¹H NMR spectrum (CDCl₃, 500 MHz), δ: 7.48 (br d, 1H, J=7.8 Hz), 7.35-7.21 (m, 3H), 6.84 (br s, 0.7H), 6.33 (br s, 0.3H), 5.05 (br s, 0.7H), 4.89 (br s, 0.3H), 4.04-3.69 (m, 3H), 3.54 (br d, 1H, J=11.7 Hz), 3.45-5.40 (m, 2H), 3.20-2.63 (m, 3H), 2.36-1.55 (m, 5H), 1.44 (br s, 9H), 1.25-1.22 (m, 6H), 0.96-0.84 (m, 6H).

(41b) (2S,4S,5S)-5-Amino-6-[4-(2-chlorophenyl)-2,2-dimethyl-5-oxopiperazin-1-yl]-4-hydroxy-2-isopropylhexanoic acid (2,2,2-trifluoroethyl)amide hemifumarate (½ fumarate)

88 mg of the title compound (yield: 71%) was obtained in the same manner as in Example (1o) using {(1S,2S,4S)-1-[4-(2-Chlorophenyl)-2,2-dimethyl-5-oxopiperazin-1-ylmethyl]-2-hydroxy-5-methyl-4-(2,2,2-trifluoroethyl)carbamoylhexyl}carbamic acid t-butyl ester obtained in Example (41a).

Colorless solid.

¹H NMR spectrum (CD₃OD, 400 MHz), δ: 7.56-7.53 (m, 1H), 7.44-7.31 (m, 3H), 6.68 (s, 1H), 4.10-3.99 (m, 1H), 3.89-3.77 (m, 1H), 3.67-3.59 (m, 2H), 3.50-3.43 (m, 1H), 3.38-3.13 (m, 3H), 2.98-2.92 (m, 0.6H), 2.80-2.67 (m, 0.8H), 2.52-2.42 (m, 1.6H), 1.90-1.82 (m, 2H), 1.77-1.70 (m, 1H), 1.31-1.26 (m, 6H), 1.00-0.97 (m, 6H).

mass spectrum (FAB⁺), m/z: 507 ((M+H)⁺).

Example 42

(2S,4S,5S)-5-Amino-6-[4-(2-chlorophenyl)-2,2-dimethyl-5-oxopiperazin-1-yl]-4-hydroxy-2-isopropylhexanoic acid phenylamide hemifumarate (½ fumarate) (Exemplary Compound No. 1-995)

99 mg of the title compound (total yield over two steps: 32%) was obtained in the same manner as in Examples (41a) and (1o) using {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) and aniline.

Colorless solid.

¹H NMR spectrum (CD₃OD, 500 MHz), δ: 7.80 (d, 2H, J=8.3 Hz), 7.55-7.53 (m, 1H), 7.43-7.37 (m, 2H), 7.33-7.28 (m, 3H), 7.11 (t, 1H, J=7.3 Hz), 6.69 (s, 1H), 3.66-3.56 (m, 3H), 3.36-3.17 (m, 3H), 2.97-2.92 (m, 0.6 Hz), 2.79-2.70 (m, 0.8H), 2.60-2.50 (m, 1.6H), 1.98-1.89 (m, 2H), 1.83-1.78 (m, 1H), 1.30-1.25 (m, 6H), 1.07-1.05 (m, 6H).

mass spectrum (FAB⁺), m/z: 501 ((M+H)⁺).

Example 43

(2S,4S,5S)-5-Amino-6-[4-(2-chlorophenyl)-2,2-dimethyl-5-oxopiperazin-1-yl]-4-hydroxy-2-isopropylhexanoic acid (4-fluorophenyl)amide hemifumarate (½ fumarate) (Exemplary Compound No. 1-926)

192 mg of the title compound (total yield over two steps: 66%) was obtained in the same manner as in Examples (41a) and (1o) using {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) and 4-fluoroaniline.

Colorless solid.

¹H NMR spectrum (CD₃OD, 400 MHz), δ: 7.61-7.58 (m, 2H), 7.55-7.53 (m, 1H), 7.42-7.37 (m, 2H), 7.34-7.27 (m, 1H), 7.07-7.03 (m, 2H), 6.67 (s, 1H), 3.65-3.52 (m, 3H), 3.34-3.15 (m, 3H), 2.96-2.91 (m, 0.6H), 2.78-2.68 (m, 0.8H), 2.59-2.49 (m, 1.6H), 1.97-1.88 (m, 2H), 1.82-1.78 (m, 1H), 1.30-1.24 (m, 6H), 1.05-1.03 (m, 6H).

mass spectrum (FAB⁺), m/z: 519 ((M+H)⁺).

Example 44

(2S,4S,5S)-5-Amino-6-[4-(2-chlorophenyl)-2,2-dimethyl-5-oxopiperazin-1-yl]-4-hydroxy-2-isopropylhexanoic acid (2-pyridyl)amide fumarate (Exemplary Compound No. 1-1005)

149 mg of the title compound (total yield over two steps: 48%) was obtained in the same manner as in Examples (41a) and (1o) using {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) and 2-aminopyridine.

Colorless solid.

¹H NMR spectrum (CD₃OD, 400 MHz), δ: 8.32-8.30 (m, 1H), 8.12-8.10 (br d, 1H, J=8.6 Hz), 7.81-7.76 (m, 1H), 7.55-7.52 (m, 1H), 7.44-7.27 (m, 3H), 7.14-7.11 (m, 1H), 6.69 (s, 2H), 3.66-3.54 (m, 3H), 3.35-3.18 (m, 3H), 2.97-2.91 (m, 0.6H), 2.76-2.60 (m, 1.8H), 2.55-2.50 (m, 0.6H), 2.00-1.90 (m, 2H), 1.84-1.78 (m, 1H), 1.29-1.24 (m, 6H), 1.05 (d, 6H, J=7.0 Hz).

mass spectrum (FAB⁺), m/z: 502 ((M+H)⁺).

Example 45

(2S,4S,5S)-5-Amino-6-[4-(2-chlorophenyl)-2,2-dimethyl-5-oxopiperazin-1-yl]-4-hydroxy-2-isopropylhexanoic acid (3-pyridyl)amide fumarate (Exemplary Compound No. 1-1013)

125 mg of the title compound (total yield over two steps: 41%) was obtained in the same manner as in Examples (41a) and (1o) using {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) and 3-aminopyridine and using a solution of dimethylaluminum chloride in methylene chloride instead of a solution of trimethylaluminum in hexane.

Colorless solid.

¹H NMR spectrum (CD₃OD, 400 MHz), δ: 8.81 (s, 1H), 8.28-8.27 (m, 1H), 8.15-8.13 (m, 1H), 7.55-7.53 (m, 1H), 7.43-7.29 (m, 4H), 6.68 (s, 2H), 3.66-3.53 (m, 3H), 3.36-3.18 (m, 3H), 2.98-2.91 (m, 0.6H), 2.81-2.62 (m, 1.8H), 2.55-2.51 (m, 0.6H), 2.02-1.91 (m, 2H), 1.84-1.77 (m, 1H), 1.30-1.25 (m, 6H), 1.05 (d, 6H, J=6.6 Hz).

mass spectrum (FAB⁺), m/z: 502 ((M+H)⁺).

Example 46

(2S,4S,5S)-5-Amino-6-[4-(2-chlorophenyl)-2,2-dimethyl-5-oxopiperazin-1-yl]-4-hydroxy-2-isopropylhexanoic acid (4-pyridyl)amide fumarate (Exemplary Compound No. 1-1014)

45 mg of the title compound (total yield over two steps: 14%) was obtained in the same manner as in Examples (41a) and (1o) using {(S)-2-[4-(2-chlorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (1m) and 4-aminopyridine and using a solution of dimethylaluminum chloride in methylene chloride (1.0 mol/l) instead of a solution of trimethylaluminum in hexane (1.0 mlol/l).

Colorless solid.

$^1$H NMR spectrum (CD$_3$OD, 400 MHz), δ: 8.39 (dd, 2H, J=4.6, 1.5 Hz), 7.70 (dd, 2H, J=5.0, 1.5 Hz), 7.56-7.52 (m, 1H), 7.44-7.36 (m, 2H), 7.34-7.28 (m, 1H), 6.68 (s, 2H), 3.67-3.51 (m, 3H), 3.37-3.18 (m, 3H), 2.97-2.91 (m, 0.6H), 2.81-2.64 (m, 1.8H), 2.54-2.50 (m, 0.6H), 2.02-1.92 (m, 2H), 1.83-1.76 (m, 1H), 1.30-1.25 (m, 6H), 1.04 (d, 3H, J=2.3 Hz), 1.03 (d, 3H, J=2.3 Hz).

mass spectrum (FAB$^+$), m/z: 502 ((M+H)$^+$).

Example 47

(2S,4S,5S)-5-Amino-6-(2,2-dimethyl-5-oxo-4-phenylpiperazin-1-yl)-4-hydroxy-2-isopropylhexanoic acid (2,2-dimethylpropyl)amide hemifumarate (½ fumarate) (Exemplary Compound No. 1-826)

181 mg of the title compound (total yield over four steps: 54%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 5,5-dimethyl-1-phenylpiperazin-2-one obtained in Example (14a) and (2,2-dimethylpropyl)amine.

Colorless solid.

$^1$H NMR spectrum (CD$_3$OD, 400 MHz), δ: 7.91 (br t, 1H, J=5.9 Hz), 7.45-7.41 (m, 2H), 7.33-7.27 (m, 3H), 6.66 (1H, s), 3.70 (d, 1H, J=12.1 Hz), 3.60 (d, 1H, J=17.6 Hz), 3.51-3.46 (m, 1H), 3.38 (d, 1H, J=12.1 Hz), 3.27 (d, 1H, J=17.6 Hz), 3.19-3.12 (m, 2H), 2.93 (dd, 1H, J=13.3 Hz, 4.9 Hz), 2.84 (dd, 1H, J=13.3 Hz, 11.0 Hz), 2.53 (dd, 1H, J=13.7 Hz, 4.3 Hz), 2.43-2.37 (m, 1H), 1.89-1.79 (m, 2H), 1.73-1.67 (m, 1H), 1.24 (br s, 6H), 1.01-0.98 (m, 6H), 0.93 (s, 9H).

mass spectrum (FAB$^+$), m/z: 461 ((M+H)$^+$).

Example 48

(2S,4S,5S)-5-Amino-6-[4-(2-fluorophenyl)-2,2-dimethyl-5-oxopiperazin-1-yl]-4-hydroxy-2-isopropylhexanoic acid butylamide fumarate (Exemplary Compound No. 1-44)

289 mg of the title compound (total yield over four steps: 45%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 1-(2-fluorophenyl)-5,5-dimethylpiperazin-2-one obtained in Example (16a) and n-butylamine.

Colorless solid.

$^1$H NMR spectrum (CD$_3$OD, 400 MHz), δ: 8.06 (br t, 1H, J=5.9 Hz), 7.43-7.37 (m, 1H), 7.35-7.30 (m, 1H), 7.28-7.21 (m, 2H), 6.68 (2H, s), 3.70-3.62 (m, 2H), 3.48-3.44 (m, 1H), 3.36-3.25 (m, 3H), 3.21-3.08 (m, 2H), 2.88 (dd, 1H, J=13.5 Hz, 11.4 Hz), 2.55 (dd, 1H, J=13.9 Hz, 4.1 Hz), 2.33-2.27 (m, 1H), 1.86-1.78 (m, 2H), 1.75-1.68 (m, 1H), 1.55-1.48 (m, 2H), 1.42-1.33 (m, 2H), 1.25 (s, 6H), 1.00-0.93 (m, 9H).

mass spectrum (FAB$^+$), m/z: 465 ((M+H)$^+$).

Example 49

(2S,4S,5S)-5-Amino-6-[4-(3-fluorophenyl)-2,2-dimethyl-5-oxopiperazin-1-yl]-4-hydroxy-2-isopropylhexanoic acid butylamide fumarate (Exemplary Compound No. 1-45)

365 mg of the title compound (total yield over four steps: 57%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 1-(3-fluorophenyl)-5,5-dimethylpiperazin-2-one obtained in Example (18a) and butylamine.

Colorless solid.

$^1$H NMR spectrum (CD$_3$OD, 400 MHz), δ: 8.05 (br t, 1H, J=5.9 Hz), 7.47-7.42 (m, 1H), 7.15-7.04 (m, 3H), 6.68 (2H, s), 3.72 (d, 1H, J=11.7 Hz), 3.61 (d, 1H, J=17.6 Hz), 3.48-3.26 (m, 4H), 3.20-3.07 (m, 2H), 2.87 (dd, 1H, J=13.3 Hz, 11.3 Hz), 2.53 (dd, 1H, J=13.7 Hz, 4.3 Hz), 2.33-2.27 (m, 1H), 1.86-1.77 (m, 2H), 1.74-1.67 (m, 1H), 1.55-1.48 (m, 2H), 1.42-1.33 (m, 2H), 1.25 (s, 3H), 1.23 (s, 3H), 1.00-0.93 (m, 9H).

mass spectrum (FAB$^+$), m/z: 465 ((M+H)$^+$).

Example 50

(2S,4S,5S)-5-Amino-6-[4-(4-fluorophenyl)-2,2-dimethyl-5-oxopiperazin-1-yl]-4-hydroxy-2-isopropylhexanoic acid butylamide fumarate (Exemplary Compound No. 1-974)

(50a) 1-(4-Fluorophenyl)-5,5-dimethylpiperazin-2-one 0.30 g of the title compound (total yield over four steps: 14%) was obtained in the same manner as in Examples (1h) to (1k) using (1,1-dimethyl-2-oxoethyl)carbamic acid t-butyl ester obtained in Reference Example 3 and 4-fluoroaniline.

Colorless liquid.

$^1$H NMR spectrum (CDCl$_3$, 400 MHz), δ: 7.25-7.22 (m, 2H), 7.11-7.06 (m, 2H), 3.70 (s, 2H), 3.48 (s, 2H), 1.32 (br s, 6H).

mass spectrum (FAB$^+$), m/z: 223 ((M+H)$^+$).

(50b) (2S,4S,5S)-5-Amino-6-[4-(4-fluorophenyl)-2,2-dimethyl-5-oxopiperazin-1-yl]-4-hydroxy-2-isopropylhexanoic acid butylamide fumarate 220 mg of the title compound (total yield over four steps: 47%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 1-(4-fluorophenyl)-5,5-dimethylpiperazin-2-one obtained in Example (50a) and n-butylamine.

Colorless solid.

$^1$H NMR spectrum (CD$_3$OD, 400 MHz), δ: 8.04 (br s, 1H), 7.32-7.30 (m, 2H), 7.19-7.15 (m, 2H), 6.69 (s, 2H), 3.69 (d, 1H, J=11.7 Hz), 3.62-3.59 (m, 1H), 3.49-3.44 (m, 1H), 3.36 (d, 1H, J=11.7 Hz), 3.31-3.08 (m, 4H), 2.90-2.85 (m, 1H), 2.54 (dd, 1H, J=13.1 Hz, 3.4 Hz), 2.32-2.28 (m, 1H), 1.86-1.78 (m, 2H), 1.73-1.69 (m, 1H), 1.54-1.48 (m, 2H), 1.41-1.34 (m, 2H), 1.25-1.23 (m, 6H), 0.99-0.93 (m, 9H).

mass spectrum (FAB$^+$), m/z: 465 ((M+H)$^+$).

Example 51

(2S,4S,5S)-5-Amino-6-[2,2-dimethyl-4-(2-methylphenyl)-5-oxopiperazin-1-yl]-4-hydroxy-2-isopropylhexanoic acid (2,2-dimethylpropyl)amide hemifumarate (½ fumarate) (Exemplary Compound No. 1-827)

(51a) [1,1-Dimethyl-2-(2-methylphenylamino)ethyl] carbamic acid t-butyl ester 2.5 g of sodium triacetoxyborohydride (12.0 mmol) was added to a solution of 1.87 g of (1,1-dimethyl-2-oxoethyl)

carbamic acid t-butyl ester obtained in Reference Example 3 (10.0 mmol), 10.7 g of 2-methylaniline (10.0 mmol) and 0.57 ml of acetic acid (10.0 mmol) in methylene chloride (100 ml) under ice-cooling, and the mixture was stirred at room temperature for 16 hours. A saturated sodium bicarbonate aqueous solution was added to the reaction mixture, followed by extraction with methylene chloride. Then, the organic layer was washed with brine and dried over anhydrous sodium sulfate. After filtration, the solvent was evaporated under reduced pressure, and the residue was purified by silica gel column chromatography (elution solvent:hexane/ethyl acetate=5/1) to obtain 2.43 g of the title compound (yield: 87%).

Colorless solid.

$^1$H NMR spectrum (CDCl$_3$, 400 MHz), δ: 7.10 (br t, 1H, J=7.8 Hz), 7.05 (br d, 1H, J=7.8 Hz), 6.65-6.60 (m, 2H), 4.60 (br s, 1H), 4.21 (br s, 1H), 3.29 (s, 2H), 2.17 (s, 3H), 1.43 (s, 9H), 1.39 (s, 6H).

(51b) {2-[(2-Bromoacetyl)-(2-methylphenyl)amino]-1,1-dimethylethyl}carbamic acid t-butyl ester 1.12 ml of bromoacetyl bromide (12.9 mmol) was added to a solution of 2.4 g of [1,1-dimethyl-2-(2-methylphenylamino)ethyl]carbamic acid t-butyl ester obtained in Example (51a) (8.62 mmol) in N,N-dimethylacetamide (85 ml) under ice-cooling, and the mixture was stirred at the same temperature for 10 minutes. A saturated sodium bicarbonate aqueous solution was added to the reaction mixture, followed by extraction with ethyl acetate. Then, the organic layer was washed with water and brine and dried over anhydrous magnesium sulfate. After filtration, the solvent was evaporated under reduced pressure. Hexane was added to the residue, and the solid was collected by filtration to obtain 3.21 g of the title compound (yield: 93%).

Colorless solid.

$^1$H NMR spectrum (CDCl$_3$, 400 MHz), δ: 7.34-7.22 (m, 4H), 4.69 (br s, 1H), 4.24 (d, 1H, J=14.1 Hz), 3.74 (br d, 1H, J=14.1 Hz), 3.59 (br d, 1H, J=11.3 Hz), 3.54 (d, 1H, J=11.3 Hz), 1.36 (br s, 3H), 1.32 (br s, 3H), 1.19 (s, 9H).

(51c) 2,2-Dimethyl-4-(2-methylphenyl)-5-oxopiperazine-1-carboxylic acid t-butyl ester A solution of 1.3 g of potassium t-butoxide (12.0 mmol) in tetrahydrofuran (80 ml) was added to a solution of 3.2 g of {2-[(bromoacetyl)-(2-methylphenyl)amino]-1,1-dimethylethyl}carbamic acid t-butyl ester obtained in Example (51b) (8.0 mmol) in tetrahydrofuran (80 ml) under a nitrogen atmosphere and under cooling in a dry ice-acetone bath over 30 minutes, and the mixture was stirred at the same temperature for 10 minutes. A saturated ammonium chloride aqueous solution was added to the reaction mixture. The mixture was returned to room temperature and diluted with water, followed by extraction with ethyl acetate. Then, the organic layer was dried over anhydrous magnesium sulfate. After filtration, the solvent was evaporated under reduced pressure, and the residue was purified by silica gel column chromatography (elution solvent:hexane/ethyl acetate=3/1) to obtain 1.8 g of the title compound (yield: 71%).

Colorless solid.

$^1$H NMR spectrum (CDCl$_3$, 500 MHz), δ: 7.28-7.24 (m, 3H), 7.14-7.15 (m, 1H), 4.33 (br d, 1H, J=17.1 Hz), 4.14 (br d, 1H, J=17.1 Hz), 3.68 (br d, 1H, J=12.7 Hz), 3.41 (br d, 1H, J=12.7 Hz), 2.26 (s, 3H), 1.59 (br s, 3H), 1.54 (br s, 3H), 1.50 (s, 9H).

(51d) 5,5-Dimethyl-1-(2-methylphenyl)piperazin-2-one 0.97 ml of trifluoroacetic acid (12.6 mmol) was added to a solution of 0.4 g of 2,2-dimethyl-4-(2-methylphenyl)-5-oxopiperazine-1-carboxylic acid t-butyl ester obtained in Example (51c) (1.26 mmol) in methylene chloride (1.9 ml) at room temperature, and the mixture was stirred at the same temperature for 30 minutes. The reaction mixture was concentrated under reduced pressure. A saturated sodium bicarbonate aqueous solution was added, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol=10/1) to obtain 230 mg of the title compound (yield: 84%).

Colorless liquid.

$^1$H NMR spectrum (CDCl$_3$, 400 MHz), δ: 7.28-7.23 (m, 3H), 7.12-7.10 (m, 1H), 3.75 (d, 1H, J=18.0 Hz), 3.69 (d, 1H, J=18.0 Hz), 3.46 (d, 1H, J=12.1 Hz), 3.32 (d, 1H, J=12.1 Hz), 2.25 (s, 3H), 1.35 (s, 3H), 1.33 (s, 3H).

mass spectrum (FAB$^+$), m/z: 219 ((M+H)$^+$).

(51e) (2S,4S,5S)-5-Amino-6-[2,2-dimethyl-4-(2-methylphenyl)-5-oxopiperazin-1-yl]-4-hydroxy-2-isopropylhexanoic acid 2,2-dimethylpropylamide hemifumarate (½ fumarate)

112 mg of the title compound (total yield over four steps: 58%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 5,5-dimethyl-1-(2-methylphenyl)piperazin-2-one obtained in Example (51d) and (2,2-dimethylpropyl)amine.

Colorless solid.

$^1$H NMR spectrum (CD$_3$OD, 400 MHz), δ: 7.32-7.25 (m, 3H), 7.18-7.11 (m, 1H), 6.66 (s, 1H), 3.70-3.46 (m, 3H), 3.37-3.13 (m, 4H), 2.93-2.87 (m, 1.6H), 2.82-2.75 (m, 0.4H), 2.65-2.60 (m, 0.4H), 2.49 (dd, 0.6H, J=13.3 Hz, 3.9 Hz), 2.43-2.37 (m, 1H), 2.24-2.23 (m, 3H), 1.88-1.81 (m, 2H), 1.73-1.67 (m, 1H), 1.27-1.25 (m, 6H), 1.01-0.99 (m, 6H), 0.94 (s, 9H).

mass spectrum (FAB$^+$), m/z: 475 ((M+H)$^+$).

Example 52

(2S,4S,5S)-5-Amino-6-[2,2-dimethyl-4-(2-methylphenyl)-5-oxopiperazin-1-yl]-4-hydroxy-2-isopropylhexanoic acid isobutylamide hemifumarate (½ fumarate) (Exemplary Compound No. 1-122)

108 mg of the title compound (total yield over four steps: 66%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 5,5-dimethyl-1-(2-methylphenyl)piperazin-2-one obtained in Example (51d) and isobutylamine.

Colorless solid.

$^1$H NMR spectrum (CD$_3$OD, 400 MHz), δ: 7.32-7.26 (m, 3H), 7.19-7.11 (m, 1H), 6.67 (s, 1H), 3.70-3.45 (m, 3H), 3.37-3.12 (m, 4H), 2.96-2.89 (m, 1.6H), 2.84-2.78 (m, 0.4H), 2.63 (dd, 0.4H, J=13.7 Hz, 4.7 Hz), 2.50 (dd, 0.6H, J=13.5 Hz, 4.1 Hz), 2.37-2.32 (m, 1H), 2.24-2.23 (m, 3H), 1.88-1.68 (m, 4H), 1.28-1.25 (m, 6H), 0.99 (t, 6H, J=7.4 Hz), 0.94 (d, 6H, J=6.7 Hz)

mass spectrum (FAB$^+$), m/z: 461 ((M+H)$^+$). .

Example 53

(2S,4S,5S)-5-Amino-6-[2,2-dimethyl-4-(2-ethylphenyl)-5-oxopiperazin-1-yl]-4-hydroxy-2-isopropylhexanoic acid (2,2-dimethylpropyl)amide hemifumarate (½ fumarate) (Exemplary Compound No. 1-1022)

(53a) 5,5-Dimethyl-1-(2-ethylphenyl)piperazin-2-one 3.43 g of the title compound (total yield over four steps: 42%) was obtained in the same manner as in Examples (1h) to (1k) using (1,1-dimethyl-2-oxoethyl)carbamic acid t-butyl ester obtained in Reference Example 3 and 2-ethylaniline.

Colorless liquid.

$^1$H NMR spectrum (CDCl$_3$, 500 MHz), δ: 7.33-7.24 (m, 3H), 7.10 (d, 1H, J=7.8 Hz), 3.75 (d, 1H, J=18.1 Hz), 3.69 (d, 1H, J=18.1 Hz), 3.44 (d, 1H, J=12.1 Hz), 3.33 (d, 1H, J=12.1 Hz), 2.66-2.53 (m, 2H), 1.36 (s, 3H), 1.33 (s, 3H), 1.24 (t, 3H, J=7.6 Hz).

mass spectrum (FAB$^+$), m/z: 233 ((M+H)$^+$).

(53b) (2S,4S,5S)-5-Amino-6-[2,2-dimethyl-4-(2-ethylphenyl)-5-oxopiperazin-1-yl]-4-hydroxy-2-isopropylhexanoic acid (2,2-dimethylpropyl)amide hemifumarate (½ fumarate)

196 mg of the title compound (total yield over four steps: 68%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 5,5-dimethyl-1-(2-ethylphenyl)piperazin-2-one obtained in Example (53a) and (2,2-dimethylpropyl)amine.

Colorless solid.

$^1$H NMR spectrum (CD$_3$OD, 400 MHz), δ: 7.38-7.25 (m, 3H), 7.17-7.10 (m, 1H), 6.67 (s, 1H), 3.69-3.46 (m, 3H), 3.37-3.13 (m, 4H), 2.94-2.88 (m, 1.6H), 2.81-2.76 (m, 0.4H), 2.66-2.55 (m, 2.4H), 2.49 (dd, 0.6H, J=13.4 Hz, 4.3 Hz), 2.44-2.39 (m, 1H), 1.88-1.80 (m, 2H), 1.75-1.68 (m, 1H), 1.28-1.20 (m, 9H), 1.01-0.93 (m, 15H).

mass spectrum (FAB$^+$), m/z: 489 ((M+H)$^+$).

Example 54

(2S,4S,5S)-5-Amino-6-[2,2-dimethyl-5-oxo-4-(2-trifluoromethylphenyl)piperazin-1-yl]-4-hydroxy-2-isopropylhexanoic acid (2,2-dimethylpropyl)amide hemifumarate (½ fumarate) (Exemplary Compound No. 1-1017)

(54a) 5,5-Dimethyl-1-(2-trifluoromethylphenyl)piperazin-2-one 3.5 g of the title compound (total yield over four steps: 13%) was obtained in the same manner as in Examples (1h) to (1k) using (1,1-dimethyl-2-oxoethyl)carbamic acid t-butyl ester obtained in Reference Example 3 and 2-trifluoromethylaniline.

Colorless liquid.

$^1$H NMR spectrum (CDCl$_3$, 500 MHz), δ: 7.75 (d, 1H, J=7.8 Hz), 7.64 (t, 1H, J=7.8 Hz), 7.48 (t, 1H, J=7.8 Hz), 7.30 (d, 1H, J=7.8 Hz), 3.75 (d, 1H, J=18.1 Hz), 3.65 (d, 1H, J=18.1 Hz), 3.45 (d, 1H, J=11.7 Hz), 3.40 (d, 1H, J=11.7 Hz), 1.35 (s, 3H), 1.31 (s, 3H)

mass spectrum (FAB$^+$), m/z: 273 ((M+H)$^+$).

(54b) (2S,4S,5S)-5-Amino-6-[2,2-dimethyl-5-oxo-4-(2-trifluoromethylphenyl)piperazin-1-yl]-4-hydroxy-2-isopropylhexanoic acid (2,2-dimethylpropyl)amide hemifumarate (½ fumarate)

88 mg of the title compound (total yield over four steps: 55%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 5,5-dimethyl-1-(2-trifluoromethylphenyl)piperazin-2-one obtained in Example (54a) and (2,2-dimethylpropyl)amine.

Colorless solid.

$^1$H NMR spectrum (CD$_3$OD, 400 MHz), δ: 7.92 (br s, 1H), 7.82-7.75 (m, 2H), 7.61-7.58 (m, 1H), 7.45-7.40 (m, 1H), 6.67 (s, 1H), 3.67-3.42 (m, 3H), 3.35-3.13 (m, 4H), 2.98-2.90 (m, 1.6H), 2.78-2.69 (m, 0.8H), 2.49-2.38 (m, 1.6H), 1.89-1.82 (m, 2H), 1.73-1.68 (m, 1H), 1.27-1.25 (m, 6H), 1.01-1.00 (m, 6H), 0.94 (s, 9H).

mass spectrum (FAB$^+$), m/z: 529 ((M+H)$^+$).

Example 55

(2S,4S,5S)-5-Amino-4-hydroxy-2-isopropyl-6-{4-[2-(3-methoxypropoxy)phenyl]-2,2-dimethyl-5-oxopiperazin-1-yl}hexanoic acid butylamide hemifumarate (½ fumarate) (Exemplary Compound No. 1-16)

107 mg of the title compound (total yield over four steps: 35%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 5,1-[2-(3-methoxypropoxy)phenyl]-5,5-dimethylpiperazin-2-one obtained in Example (10f) and n-butylamine.

Colorless solid.

$^1$H NMR spectrum (CD$_3$OD, 400 MHz), δ: 8.03 (br s, 1H), 7.35-7.32 (m, 1H), 7.16 (d, 2H, J=7.8 Hz), 7.09 (d, 1H, J=7.8 Hz), 7.00-6.97 (m, 2H), 6.69 (s, 1H), 4.14-4.07 (m, 2H), 3.65-3.43 (m, 5H), 3.33 (s, 3H), 3.28-3.08 (m, 5.5H), 2.32-2.28 (m, 1.5H), 2.05-2.00 (m, 2H), 1.84-1.80 (m, 3H), 1.74-1.69 (m, 1H), 1.54-1.49 (m, 2H), 1.41-1.34 (m, 2H), 1.29-1.25 (m, 6H), 1.00-0.98 (m, 9H).

mass spectrum (FAB$^+$), m/z: 535 ((M+H)$^+$).

Example 56

(2S,4S,5S)-5-Amino-4-hydroxy-2-isopropyl-6-{4-[2-(3-methoxyethoxy)phenyl]-2,2-dimethyl-5-oxopiperazin-1-yl}hexanoic acid isobutylamide hemifumarate (½ fumarate) (Exemplary Compound No. 1-994)

123 mg of the title compound (total yield over four steps: 59%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 5,1-[2-(3-methoxyethoxy)phenyl]-5,5-dimethylpiperazin-2-one obtained in Example (11a) and isobutylamine.

Colorless solid.

$^1$H NMR spectrum (CD$_3$OD, 400 MHz), δ: 7.35-7.32 (m, 1H), 7.17 (dd, 1H, J=7.8 Hz, 1.5 Hz), 7.12 (br d, 1H, J=7.8 Hz), 7.02-6.99 (m, 1H), 6.67 (s, 1H), 4.18-4.17 (m, 2H), 3.73-3.71 (m, 2H), 3.61-3.45 (m, 3H), 3.37 (s, 3H), 3.33-3.12 (m, 6H), 2.91 (dd, 1H, J=13.2 Hz, 7.3 Hz), 2.36-2.32 (m, 1H), 1.87-1.76 (m, 3H), 1.74-1.69 (m, 1H), 1.27 (br s, 3H), 1.24 (br s, 3H), 1.00-0.97 (m, 6H), 0.94 (d, 6H, J=6.4 Hz).

mass spectrum (FAB$^+$), m/z: 521 ((M+H)$^+$).

Example 57

(2S,4S,5S)-5-Amino-6-[4-(2,3-difluorophenyl)-2,2-dimethyl-5-oxopiperazin-1-yl]-4-hydroxy-2-isopropylhexanoic acid isobutylamide fumarate (Exemplary Compound No. 1-756)

113 mg of the title compound (total yield over four steps: 60%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 1-(2,3-difluorophenyl)-5,5-dimethylpiperazin-2-one obtained in Example (20a) and isobutylamine.

Colorless solid.

$^1$H NMR spectrum (CD$_3$OD, 400 MHz), δ: 8.07 (br s, 1H), 7.33-7.22 (m, 2H), 7.14 (t, 1H, J=7.1 Hz), 6.69 (s, 2H), 3.71-3.64 (m, 2H), 3.51-3.44 (m, 1H), 3.38-3.29 (m, 2H), 3.21-3.12 (m, 2H), 2.94-2.86 (2H, m), 2.56 (dd, 1H, J=4.1, 13.4 Hz), 2.34 (m, 1H), 1.87-1.76 (m, 3H), 1.74-1.69 (m, 1H), 1.28-1.26 (m, 6H), 1.00-0.93 (m, 12H).

mass spectrum (FAB$^+$), m/z: 483 ((M+H)$^+$).

Example 58

(2S,4S,5S)-5-Amino-6-[4-(2,4-difluorophenyl)-2,2-dimethyl-5-oxopiperazin-1-yl]-4-hydroxy-2-isopropylhexanoic acid isobutylamide hemifumarate (½ fumarate) (Exemplary Compound No. 1-981)

(58a)
1-(2,4-Difluorophenyl)5,5-dimethyl-piperazin-2-one 0.61 g of the title compound (total yield over four steps: 43%) was obtained in the same manner as in Examples (1h) to (1k) using (1,1-dimethyl-2-oxoethyl)carbamic acid t-butyl ester obtained in Reference Example 3 and 2,4-difluoroaniline.

Colorless liquid.

$^1$H NMR spectrum (CDCl$_3$, 400 MHz), δ: 7.25-7.19 (m, 1H), 6.93-6.89 (m, 2H), 3.71 (s, 2H), 3.43 (s, 2H), 1.32 (br s, 6H).

mass spectrum (FAB$^+$), m/z: 241 ((M+H)$^+$).

(58b) (2S,4S,5S)-5-Amino-6-[4-(2,4-difluorophenyl)-2,2-dimethyl-5-oxopiperazin-1-yl]-4-hydroxy-2-isopropylhexanoic acid isobutylamide hemifumarate (½ fumarate)

115 mg of the title compound (total yield over four steps: 25%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 1-(2,4-difluorophenyl)-5,5-dimethylpiperazin-2-one obtained in Example (58a) and isobutylamine.

Colorless solid.

$^1$H NMR spectrum (CD$_3$OD, 400 MHz), δ: 8.08 (br s, 1H), 7.38-7.34 (m, 1H), 7.13-7.04 (m, 2H), 6.68 (s, 1H), 3.67-3.62 (m, 2H), 3.48-3.46 (m, 1H), 3.34-3.12 (m, 4H), 2.95-2.85 (m, 2H), 2.55 (dd, 1H, J=13.7 Hz, 3.9 Hz), 2.36-2.31 (m, 1H), 1.85-1.77 (m, 3H), 1.74-1.68 (m, 1H), 1.32-1.25 (m, 6H), 1.00-0.97 (m, 6H), 0.94-0.93 (m, 6H).

mass spectrum (FAB$^+$), m/z: 483 ((M+H)$^+$).

Example 59

(2S,4S,5S)-5-Amino-6-[4-(2,5-difluorophenyl)-2,2-dimethyl-5-oxopiperazin-1-yl]-4-hydroxy-2-isopropylhexanoic acid isobutylamide fumarate (Exemplary Compound No. 1-757)

138 mg of the title compound (total yield over four steps: 33%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 1-(2,5-difluorophenyl)-5,5-dimethylpiperazin-2-one obtained in Example (24a) and isobutylamine.

Colorless solid.

$^1$H NMR spectrum (CD$_3$OD, 400 MHz), δ: 7.29-7.23 (m, 1H), 7.18-7.13 (m, 2H), 6.66 (s, 1H), 3.67 (d, 1H, J=9.4 Hz), 3.63 (d, 1H, J=15.6 Hz), 3.48-3.44 (m, 1H), 3.36-3.27 (m, 2H), 3.17-3.11 (m, 2H), 2.91 (dd, 1H, J=13.1 Hz, 7.2 Hz), 2.85 (dd, 1H, J=13.1 Hz, 11.3 Hz), 2.54 (dd, 1H, J=13.1 Hz, 4.3 Hz), 2.36-2.31 (m, 1H), 1.85-1.68 (m, 4H), 1.25 (br s, 3H), 1.24 (br s, 3H), 0.99 (d, 3H, J=6.7 Hz), 0.97 (d, 3H, J=6.7 Hz), 0.93 (d, 6H, J=7.0 Hz).

mass spectrum (FAB$^+$), m/z: 483 ((M+H)$^+$).

Example 60

(2S,4S,5S)-5-Amino-6-[4-(2,6-difluorophenyl)-2,2-dimethyl-5-oxopiperazin-1-yl]-4-hydroxy-2-isopropylhexanoic acid isobutylamide hemifumarate (½ fumarate) (Exemplary Compound No. 1-758)

(60a) [2-(2,6-Difluorophenylamino)-1,1-dimethylethyl]carbamic acid t-butyl ester 17.0 g of sodium triacetoxyborohydride (80.0 mmol) was added to a solution of 15.0 g of (1,1-dimethyl-2-oxoethyl)carbamic acid t-butyl ester obtained in Reference Example 3 (80.0 mmol), 5.16 g of 2,6-difluoroaniline (40.0 mmol) and 2.09 ml of acetic acid (40.0 mmol) in methylene chloride (400 ml) under ice-cooling, and the mixture was stirred at room temperature for 19 hours. A saturated sodium bicarbonate aqueous solution was added to the reaction mixture, followed by extraction with methylene chloride. Then, the organic layer was washed with brine and dried over anhydrous sodium sulfate. After filtration, the solvent was evaporated under reduced pressure, and the residue was purified by silica gel column chromatography (elution solvent:hexane/ethyl acetate=20/1-10/1) to obtain 3.68 g of the title compound (yield: 31%).

Colorless solid.

$^1$H NMR spectrum (CDCl$_3$, 400 MHz), δ: 6.81-6.77 (m, 2H), 6.67-6.60 (m, 1H), 4.56 (br s, 1H), 3.82 (br s, 1H), 3.47 (br d, 2H, J=6.7 Hz), 1.43 (s, 9H), 1.32 (s, 6H).

(60b) {2-[(2-Bromoacetyl)-(2,6-difluorophenyl)amino]-1,1-dimethylethyl}carbamic acid t-butyl ester 1.17 ml of bromoacetyl bromide (13.4 mmol) was added to a solution of 3.66 g of [2-(2,6-difluorophenylamino)-1,1-dimethylethyl]carbamic acid t-butyl ester obtained in Example (60a) (12.2 mmol) in N,N-dimethylacetamide (61 ml) under ice-cooling, and the mixture was stirred at the same temperature for five minutes. Water was added to the reaction mixture, followed by extraction with diethyl ether. Then, the organic layer was washed with brine and dried over anhydrous sodium sulfate. After filtration, the solvent was evaporated under reduced pressure, and the residue was purified by silica gel column chromatography (elution solvent: hexane/ethyl acetate=10/1) to obtain 5.14 g of the title compound (yield: quant.).

Colorless solid.

$^1$H NMR spectrum (CDCl$_3$, 500 MHz), δ: 7.37-7.32 (m, 1H), 7.02 (br t, 1H, J=8.3 Hz), 4.43 (br s, 1H), 4.09 (br s, 2H), 3.70 (s, 2H), 1.31 (br s, 6H), 1.16 (br s, 9H).

(60c) 4-(2,6-Difluorophenyl)-2,2-dimethyl-5-oxopiperazine-1-carboxylic acid t-butyl ester A solution of 2.05 g of potassium t-butoxide (18.3 mmol) in tetrahydrofuran (120 ml) was added to a solution of 5.14 g of {2-[(2-bromoacetyl)-(2,6-difluorophenyl)amino]-1,1-dimethylethyl}carbamic acid t-butyl ester obtained in Example (60b) (12.2 mmol) in tetrahydrofuran (120 ml) under a nitrogen atmosphere and under cooling in a dry ice-acetone bath over 30 minutes, and the mixture was stirred at the same temperature for 30 minutes. 0.33 ml of acetic acid (6.10 mmol) was added to the reaction mixture. After returning to room temperature, the solvent was evaporated under reduced pressure. The residue was diluted with water, followed by extraction with ethyl acetate. Then, the organic layer was washed with brine and dried over anhydrous sodium sulfate. After filtration, the solvent was evaporated under reduced pressure, and the residue was purified by silica gel column chromatography (elution solvent:hexane/ethyl acetate=3/1) to obtain 3.43 g of the title compound (yield: 83%).

Colorless solid.

$^1$H NMR spectrum (CDCl$_3$, 500 MHz), δ: 7.32-7.26 (m, 1H), 7.00 (t, 2H, J=8.3 Hz), 4.26 (s, 2H), 3.57 (s, 2H), 1.54 (br s, 6H), 1.50 (s, 9H).

(60d) 1-(2,6-Difluorophenyl)-5,5-dimethylpiperazin-2-one 4.2 ml of trifluoroacetic acid (54.7 mmol) was added to a solution of 1.80 g of 4-(2,6-difluorophenyl)-2,2-dimethyl-5-oxopiperazine-1-carboxylic acid t-butyl ester obtained in Example (60c) (5.47 mmol) in methylene chloride (8.4 ml) at room temperature, and the mixture was stirred at the same temperature for 30 minutes. The reaction mixture was concentrated under reduced pressure. A saturated sodium bicarbonate aqueous solution was added, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol=10/1) to obtain 1.25 g of the title compound (yield: quant.).

Colorless liquid.

$^1$H NMR spectrum (CDCl$_3$, 400 MHz), δ: 7.30-7.26 (m, 2H), 6.98 (t, 1H, J=8.0 Hz), 3.73 (br s, 2H), 3.46 (br s, 2H), 1.34 (br s, 6H).

mass spectrum (FAB$^+$), m/z: 241 ((M+H)$^+$).

(60e) (2S,4S,5S)-5-Amino-6-[4-(2,6-difluorophenyl)-2,2-dimethyl-5-oxopiperazin-1-yl]-4-hydroxy-2-isopropylhexanoic acid isobutylamide hemifumarate (½ fumarate)

140 mg of the title compound (total yield over four steps: 52%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 1-(2,6-difluorophenyl)-5,5-dimethylpiperazin-2-one obtained in Example (60d) and isobutylamine.

Colorless solid.

$^1$H NMR spectrum (CD$_3$OD, 400 MHz), δ: 7.48-7.40 (m, 1H), 7.13-7.08 (m, 2H), 6.67 (s, 1H), 3.69-3.65 (m, 2H), 3.49-3.44 (m, 1H), 3.35-3.25 (m, 2H), 3.15-3.06 (m, 2H), 2.92 (dd, 1H, J=12.9 Hz, 7.0 Hz), 2.84 (dd, 1H, J=13.3 Hz, 10.8 Hz), 2.54 (dd, 1H, J=13.3 Hz, 4.3 Hz), 2.35-2.29 (m, 1H), 1.86-1.68 (m, 4H), 1.26 (s, 6H), 0.99 (d, 3H, J=6.7 Hz), 0.97 (d, 3H, J=6.7 Hz), 0.94 (d, 6H, J=6.7 Hz).

mass spectrum (FAB$^+$), m/z: 483 ((M+H)$^+$).

Example 61

(2S,4S,5S)-5-Amino-6-[4-(2-chloro-4-fluorophenyl)-2,2-dimethyl-5-oxopiperazin-1-yl]-4-hydroxy-2-isopropylhexanoic acid isobutylamide hemifumarate (½ fumarate) (Exemplary Compound No. 1-983)

(61a) 1-(2-Chloro-4-fluorophenyl)5,5-dimethyl-piperazin-2-one 0.70 g of the title compound (total yield over four steps: 53%) was obtained in the same manner as in Examples (1h) to (1k) using (1,1-dimethyl-2-oxoethyl)carbamic acid t-butyl ester obtained in Reference Example 3 and 2-chloro-4-fluoroaniline.

Colorless liquid.

$^1$H NMR spectrum (CDCl$_3$, 400 MHz), δ: 7.24-7.21 (m, 2H), 7.06-7.01 (m, 1H), 3.76 (d, 1H, J=18.0 Hz), 3.68 (d, 1H, J=18.0 Hz), 3.44 (d, 1H, J=11.7 Hz), 3.35 (d, 1H, J=11.7 Hz), 1.38 (s, 3H), 1.32 (s, 3H).

mass spectrum (FAB$^+$), m/z: 257 ((M+H)$^+$).

(61b) (2S,4S,5S)-5-Amino-6-[4-(2-chloro-4-fluorophenyl)-2,2-dimethyl-5-oxopiperazin-1-yl]-4-hydroxy-2-isopropylhexanoic acid isobutylamide hemifumarate (½ fumarate)

135 mg of the title compound (total yield over four steps: 45%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 1-(2-chloro-4-fluorophenyl)5,5-dimethyl-piperazin-2-one obtained in Example (61a) and isobutylamine.

Colorless solid.

$^1$H NMR spectrum (CD$_3$OD, 400 MHz), δ: 8.07 (br s, 1H), 7.40-7.35 (m, 2H), 7.21-7.18 (m, 1H), 6.68 (s, 1H), 3.66-3.58 (m, 2H), 3.50-3.45 (m, 1H), 3.35-3.12 (m, 4H), 2.97-2.89 (m, 1.6H), 2.80-2.67 (m, 0.8H), 2.50 (dd, 0.6H, J=13.4 Hz, 3.2 Hz), 2.36-2.32 (m, 1H), 1.87-1.68 (m, 4H), 1.30-1.26 (m, 6H), 1.00-0.97 (m, 6H), 0.94 (d, 6H J=6.8 Hz).

mass spectrum (FAB$^+$), m/z: 499 ((M+H)$^+$).

Example 62

(2S,4S,5S)-5-Amino-6-[4-(2-chloro-5-fluorophenyl)-2,2-dimethyl-5-oxopiperazin-1-yl]-4-hydroxy-2-isopropylhexanoic acid butylamide fumarate (Exemplary Compound No. 1-89)

(62a) [2-(2-Chloro-5-fluorophenylamino)-1,1-dimethylethyl]carbamic acid t-butyl ester 10.0 g of sodium triacetoxyborohydride (47.2 mmol) was added to a solution of 6.0 g of (1,1-dimethyl-2-oxoethyl)carbamic acid t-butyl ester obtained in Reference Example 3 (32.0 mmol), 4.6 g of 2-chloro-5-fluoroaniline (32.0 mmol) and 1.8 ml of acetic acid (32.0 mmol) in methylene chloride (320 ml) under ice-cooling, and the mixture was stirred at room temperature for 16 hours. A saturated sodium bicarbonate aqueous solution was added to the reaction mixture, followed by extraction with methylene chloride. Then, the organic layer was washed with brine and dried over anhydrous sodium sulfate. After filtration, the solvent was evaporated under reduced pressure, and the residue was purified by silica gel column chromatography (elution solvent:hexane/ethyl acetate=5/1) to obtain 5.36 g of the title compound (yield: 53%).

Colorless solid.

$^1$H NMR spectrum (CDCl$_3$, 400 MHz), δ: 7.16-7.13 (m, 1H), 6.48-6.37 (m, 1H), 6.31-6.26 (m, 1H), 4.78 (br s, 1H), 4.52 (br s, 1H), 3.35 (br d, 2H, J=5.9 Hz), 1.43 (s, 9H), 1.35 (s, 6H).

(62b) {2-[(2-Bromoacetyl)-(2-chloro-5-fluorophenyl)amino]-1,1-dimethylethyl}carbamic acid t-butyl ester 2.2 ml of bromoacetyl bromide (25.2 mmol) was added to a solution of 5.3 g of [2-(2-chloro-5-fluorophenylamino)-1,1-dimethylethyl]carbamic acid t-butyl ester obtained in Example (62a) (16.8 mmol) in N,N-dimethylacetamide (170 ml) under ice-cooling, and the mixture was stirred at the same temperature for 15 minutes. A saturated sodium bicarbonate aqueous solution was added to the reaction mixture, followed by extraction with ethyl acetate. Then, the organic layer was washed with water and brine and dried over anhydrous magnesium sulfate. After filtration, the solvent was evaporated under reduced pressure. Hexane was added to the residue, and the solid was collected by filtration to obtain 5.8 g of the title compound (yield: 80%).

Colorless solid.

$^1$H NMR spectrum (CDCl$_3$, 500 MHz), δ: 7.45 (br d, 1H, J=9.0 Hz, 5.6 Hz), 7.29-7.26 (m, 1H), 7.08-7.04 (m, 1H), 4.51 (br s, 1H), 4.15 (br d, 1H, J=13.7 Hz), 3.99 (br d, 1H, J=13.7 Hz), 3.69 (d, 1H, J=11.2 Hz), 3.53 (d, 1H, J=11.2 Hz), 1.34 (s, 3H), 1.32 (s, 3H), 1.21 (s, 9H).

(62c) 4-(2-Chloro-5-fluorophenyl)-2,2-dimethyl-5-oxopiperazine-1-carboxylic acid t-butyl ester A solution of 2.2 g of potassium t-butoxide (19.9 mmol) in tetrahydrofuran (130 ml) was added to a solution of 5.8 g of {2-[(2-bromoacetyl)-(2-chloro-5-fluorophenyl)amino]-1,1-dimethylethyl}carbamic acid t-butyl ester obtained in Example (62b) (13.3 mmol) in tetrahydrofuran (130 ml) under a nitrogen atmosphere and under cooling in a dry ice-acetone bath over 30 minutes, and the mixture was stirred at the same temperature for 10 minutes. A saturated ammonium chloride aqueous solution was added to the reaction mixture. The mixture was returned to room temperature and diluted with water, followed by extraction with ethyl acetate. Then, the organic layer was dried over anhydrous magnesium sulfate. After filtration, the solvent was evaporated under reduced pressure, and the residue was purified by silica gel column chromatography (elution solvent:methylene chloride/ethyl acetate=10/1) to obtain 2.79 g of the title compound (yield: 64%).

Colorless solid.

$^1$H NMR spectrum (CDCl$_3$, 500 MHz), δ: 7.44 (dd, 1H, J=8.8 Hz, 5.4 Hz), 7.07-7.01 (m, 2H), 4.25 (br s, 2H), 3.54 (br s, 2H), 1.55 (br s, 6H), 1.50 (s, 9H).

(62d) 1-(2-Chloro-5-fluorophenyl)-5,5-dimethylpiperazin-2-one 4.2 ml of trifluoroacetic acid (54.7 mmol) was added to a solution of 1.80 g of 4-(2-chloro-5-fluorophenyl)-2,2-dimethyl-5-oxopiperazine-1-carboxylic acid t-butyl ester obtained in Example (62c) (5.47 mmol) in methylene chloride (8.4 ml) at room temperature, and the mixture was stirred at the same temperature for 30 minutes. The reaction mixture was concentrated under reduced pressure. A saturated sodium bicarbonate aqueous solution was added, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol=10/1) to obtain 1.25 g of the title compound (yield: quant.).

Colorless liquid.

$^1$H NMR spectrum (CDCl$_3$, 400 MHz), δ: 7.24-7.25 (m, 2H), 7.12-7.08 (m, 1H), 3.71 (br s, 2H), 3.45 (br s, 2H), 1.32 (br s, 6H).

mass spectrum (FAB$^+$), m/z: 257 ((M+H)$^+$).

(62e) N-{(S)-2-[4-(2-Chloro-5-fluorophenyl)-2,2-dimethyl-5-oxopiperazin-1-yl]-1-[(2S,4S)-4-isopropyl-5-oxotetrahydrofuran-2-yl]ethyl}-2-nitrobenzenesulfonamide A solution of 1.15 g of (3S,5S)-3-isopropyl-5-[(S)-1-(2-nitrobenzenesulfonyl)aziridin-2-yl]dihydrofuran-2-one obtained in Example (1g) (3.25 mmol) and 889 mg of 1-(2-chloro-5-fluorophenyl)-5,5-dimethylpiperazin-2-one obtained in Example (62d) (3.9 mmol) in toluene (32 ml) was stirred at 110° C. for one hour. After cooling, the reaction mixture was concentrated under reduced pressure, and the residue was purified by silica gel column chromatography (elution solvent: toluene/acetone=10/1) to obtain 1.77 g of the title compound (yield: 91%).

Colorless solid.

$^1$H NMR spectrum (CDCl$_3$, 500 MHz), δ: 8.18-8.16 (m, 1H), 7.94 (br s, 1H), 7.83-7.77 (m, 2H), 7.42 (dd, 1H, J=8.8 Hz, 5.4 Hz), 7.05-6.89 (m, 2H), 5.92 (br s, 0.6H), 5.57 (br s, 0.4H), 4.86-4.83 (m, 1H), 3.62 (br s, 1H), 3.30-3.10 (m, 3H), 2.88-2.40 (m, 4.4H), 2.27-2.15 (m, 2.6H), 1.17 (br s, 3H), 1.08 (br s, 3H), 1.03 (d, 3H, J=6.8 Hz), 0.97 (d, 3H, J=6.6 Hz).

(62f) {(S)-2-[4-(2-Chloro-5-fluorophenyl)-2,2-dimethyl-5-oxopiperazin-1-yl]-1-[(2S,4S)-4-isopropyl-5-oxotetrahydrofuran-2-yl]ethyl}carbamic acid t-butyl ester 1.1 g of cesium carbonate (3.42 mmol) was added to a solution of 1.70 g of N-{(S)-2-[4-(2-chloro-5-fluorophenyl)-2,2-dimethyl-5-oxopiperazin-1-yl]-1-[(2S,4S)-4-isopropyl- 5-oxotetrahydrofuran-2-yl]ethyl}-2-nitrobenzenesulfonamide obtained in Example (62e) (2.85 mmol) and 0.87 ml of thiophenol (content: 95%) (8.54 mmol) in N,N-dimethylformamide (15 ml) under a nitrogen atmosphere at room temperature, and the mixture was stirred at the same temperature for one hour. Brine was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol=20/1-10/1). 0.99 ml of triethylamine (7.11 mmol) and 620 mg of di-t-butyl dicarbonate (2.84 mmol) were added to a solution of 4-{(S)-2-amino-2-[(2S,4S)-4-isopropyl-5-oxotetrahydrofuran-2-yl]ethyl}-1-(2-chloro-5-fluorophenyl)-5,5-dimethylpiperazin-2-one obtained above in methylene chloride (24 ml), and the mixture was stirred at room temperature for 15 hours. Brine was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/ethyl acetate=3/1) to obtain 1.05 g of the title compound (yield: 70%).

Colorless solid.

$^1$H NMR spectrum (CDCl$_3$, 400 MHz), δ: 7.43 (dd, 1H, J=8.8 Hz, 5.3 Hz), 7.05-6.99 (m, 2H), 4.82 (br s, 1H), 4.44 (br s, 1H), 3.87-3.81 (m, 1H), 3.59-2.39 (m, 7H), 2.31-2.11 (m, 3H), 1.45 (br s, 9H), 1.25 (br s, 6H), 1.03 (br d, 3H, J=6.7 Hz), 0.97 (br d, 3H, J=7.0 Hz).

(62g) {(1S,2S,4S)-4-Butylcarbamoyl-1-[4-(2-chloro-5-fluorophenyl)-2,2-dimethyl-5-oxopiperazin-1-ylmethyl]-2-hydroxy-5-methylhexyl}carbamic acid t-butyl ester 0.89 ml of n-butylamine (9.5 mmol) and 28 mg of 2-hydroxypyridine (0.48 mmol) were added to 250 mg of {(S)-2-[4-(2-chloro-5-fluorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (62f) (0.48 mmol), and the mixture was stirred at 70° C. for one hour. The reaction mixture was cooled and then water was added, followed by extraction with ethyl acetate. Then, the organic layer was washed with brine and then dried over anhydrous sodium sulfate. After filtration, the solvent was evaporated under reduced pressure, and the residue was purified by silica gel column chromatography (elution solvent: methylene chloride/methanol=20/1) to obtain 254 mg of the title compound (yield: 89%).

Colorless solid.

$^1$H NMR spectrum (CDCl$_3$, 400 MHz), δ: 7.43 (dd, 1H, J=9.0 Hz, 5.5 Hz), 7.05-6.96 (m, 2H), 5.75 (br s, 1H), 5.04 (br s, 1H), 3.89 (br d, 1H, J=10.2 Hz), 3.66 (br d, 1H, J=18.4 Hz), 3.49-3.16 (m, 6H), 2.78-2.65 (m, 2H), 2.05-1.89 (m, 2H), 1.79-1.64 (m, 2H), 1.54-1.24 (m, 19H), 0.97-0.91 (m, 9H).

(62h) (2S,4S,5S)-5-Amino-6-[4-(2-chloro-5-fluorophenyl)-2,2-dimethyl-5-oxopiperazin-1-yl]-4-hydroxy-2-isopropylhexanoic acid butylamide fumarate 0.98 ml of trifluoroacetic acid (12.7 mmol) was added to a solution of 254 mg of {(1S,2S,4S)-4-butylcarbamoyl-1-[4-(2-chloro-5-fluorophenyl)-2,2-dimethyl-5-oxopiperazin-1-ylmethyl]-2-hydroxy-5-methylhexyl}carbamic acid t-butyl ester obtained in Example (62g) (0.42 mmol) in methylene chloride (1.9 ml) at room temperature, and the mixture was stirred at the same temperature for 30 minutes. The reaction mixture was concentrated under reduced pressure and diluted with a saturated sodium bicarbonate aqueous solution, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol/triethylamine=100/10/1). 49 mg of fumaric acid (0.42 mmol) was added to a solution of 207 mg of (2S,4S,5S)-5-amino-6-[4-(2-chloro-5-fluorophenyl)-2,2-dimethyl-5-oxopiperazin-1-yl]-4-hydroxy-2-isopropylhexanoic acid butylamide obtained above (0.42 mmol) in methanol (4 ml), and the mixture was stirred at room temperature for five minutes. The solvent was evaporated under reduced pressure to obtain 220 mg of the title compound (yield: 87%).

Colorless solid.

$^1$H NMR spectrum (CD$_3$OD, 400 MHz), δ: 8.04 (br s, 1H), 7.59-7.56 (m, 1H), 7.22-7.18 (m, 2H), 6.71 (s, 2H), 3.63-3.59 (m, 2H), 3.49-3.44 (m, 1H), 3.36-3.18 (m, 5H), 2.95 (br t, 0.6H, J=13.3 Hz), 2.80-2.69 (m, 0.8H), 2.52-2.48 (m, 0.6H), 2.32-2.28 (m, 1H), 1.85-1.78 (m, 2H), 1.74-1.68 (m, 1H), 1.55-1.48 (m, 2H), 1.41-1.33 (m, 2H), 1.31-1.26 (m, 6H), 1.00-0.93 (m, 9H).

mass spectrum (FAB$^+$), m/z: 499 ((M+H)$^+$).

Example 63

(2S,4S,5S)-5-Amino-6-[4-(2-chloro-5-fluorophenyl)-2,2-dimethyl-5-oxopiperazin-1-yl]-4-hydroxy-2-isopropylhexanoic acid isobutylamide hemifumarate (½ fumarate) (Exemplary Compound No. 1-774)

107 mg of the title compound (total yield over two steps: 65%) was obtained in the same manner as in Examples (1n) and (1o) using {(S)-2-[4-(2-chloro-5-fluorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (62f) and isobutylamine.

Colorless solid.

$^1$H NMR spectrum (CD$_3$OD, 500 MHz), δ: 7.58-7.55 (m, 1H), 7.21-7.18 (m, 2H), 6.67 (s, 1H), 3.66-3.45 (m, 3H), 3.39-3.12 (m, 4H), 2.96-2.89 (m, 1.6H), 2.77-2.69 (m, 0.8H), 2.51-2.48 (m, 0.6H), 2.36-2.32 (m, 1H), 1.87-1.69 (m, 4H), 1.30-1.26 (m, 6H), 1.00-0.97 (m, 6H), 0.93 (d, 6H, J=6.3 Hz).

mass spectrum (FAB$^+$), m/z: 499 ((M+H)$^+$).

Example 64

(2S,4S,5S)-5-Amino-6-[4-(2-chloro-5-fluorophenyl)-2,2-dimethyl-5-oxopiperazin-1-yl]-4-hydroxy-2-isopropylhexanoic acid (2,2-dimethylpropyl)amide hemifumarate (½ fumarate) (Exemplary Compound No. 1-876)

144 mg of the title compound (total yield over two steps: 53%) was obtained in the same manner as in Examples (1n) and (1o) using {(S)-2-[4-(2-chloro-5-fluorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (62f) and (2,2-dimethylpropyl)amine.

Colorless solid.

$^1$H NMR spectrum (CD$_3$OD, 400 MHz), δ: 7.58-7.54 (m, 1H), 7.21-7.16 (m, 2H), 6.66 (s, 1H), 3.64-3.48 (m, 3H), 3.39-3.12 (m, 4H), 2.96-2.90 (m, 1.6H), 2.71 (br s, 0.8H), 2.49 (br d, 0.6H, J=10.2 Hz), 2.42-2.38 (m, 1H), 1.88-1.79

(m, 2H), 1.74-1.67 (m, 1H), 1.30 (br s, 3H), 1.26 (br s, 3H), 1.01-0.98 (m, 6H), 0.93 (s, 9H).

mass spectrum (FAB$^+$), m/z: 513 ((M+H)$^+$).

Example 65

(2S,4S,5S)-5-Amino-6-[4-(2-chloro-5-fluorophenyl)-2,2-dimethyl-5-oxopiperazin-1-yl]-4-hydroxy-2-isopropylhexanoic acid cyclohexylamide hemifumarate (½ fumarate) (Exemplary Compound No. 1-918)

131 mg of the title compound (total yield over two steps: 56%) was obtained in the same manner as in Examples (1n) and (1o) using {(S)-2-[4-(2-chloro-5-fluorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (62f) and cyclohexylamine.

Colorless solid.

$^1$H NMR spectrum (CD$_3$OD, 400 MHz), δ: 7.89 (br d, 1H, J=7.3 Hz), 7.58-7.55 (m, 1H), 7.21-7.18 (m, 2H), 6.68 (s, 1H), 3.71-3.44 (m, 4H), 3.38-3.16 (m, 3H), 2.97-2.91 (m, 0.6H), 2.78-2.70 (m, 0.8H), 2.52-2.50 (m, 0.6H), 2.28-2.24 (m, 1H), 1.90-1.63 (m, 8H), 1.40-1.16 (m, 11H), 0.99-0.96 (m, 6H).

mass spectrum (FAB$^+$), m/z: 525 ((M+H)$^+$).

Example 66

(2S,4S,5S)-5-Amino-6-[4-(2-chloro-5-fluorophenyl)-2,2-dimethyl-5-oxopiperazin-1-yl]-4-hydroxy-2-isopropylhexanoic acid (4-fluorophenyl)amide hemifumarate (½ fumarate) (Exemplary Compound No. 1-969)

122 mg of the title compound (total yield over two steps: 42%) was obtained in the same manner as in Examples (41a) and (1o) using {(S)-2-[4-(2-chloro-5-fluorophenyl)-2,2-dimethyl-5-oxopiperazin-1-yl]-1-[(2S,4S)-4-isopropyl-5-oxotetrahydrofuran-2-yl]ethyl}carbamic acid t-butyl ester obtained in Example (62f) and 4-fluoroaniline.

Colorless solid.

$^1$H NMR spectrum (CD$_3$OD, 400 MHz), δ: 7.62-7.55 (m, 3H), 7.22-7.15 (m, 2H), 7.08-7.04 (m, 2H), 6.68 (s, 1H), 3.65-3.53 (m, 3H), 3.35-3.17 (m, 3H), 2.97-2.92 (m, 0.6H), 2.74-2.72 (m, 0.8H), 2.58-2.49 (m, 1.6H), 1.96-1.88 (m, 2H), 1.83-1.78 (m, 1H), 1.30-1.25 (m, 6H), 1.06-1.04 (m, 6H).

mass spectrum (FAB$^+$), m/z: 537 ((M+H)$^+$).

Example 67

(2S,4S,5S)-5-Amino-6-[2,2-dimethyl-4-(3-fluoro-2-methylphenyl)-5-oxopiperazin-1-yl]-4-hydroxy-2-isopropylhexanoic acid (2,2-dimethylpropyl)amide hemifumarate (½ fumarate) (Exemplary Compound No. 1-841)

(67a) [1,1-Dimethyl-2-(3-fluoro-2-methylphenylamino)ethyl]carbamic acid t-butyl ester 5.8 g of sodium triacetoxyborohydride (27.0 mmol) was added to a solution of 3.5 g of (1,1-dimethyl-2-oxoethyl)carbamic acid t-butyl ester obtained in Reference Example 3 (18.7 mmol), 2.25 g of 3-fluoro-2-methylaniline (18.0 mmol) and 1.0 ml of acetic acid (18.0 mmol) in methylene chloride (190 ml) under ice-cooling, and the mixture was stirred at room temperature for 16 hours. A saturated sodium bicarbonate aqueous solution was added to the reaction mixture, followed by extraction with methylene chloride. Then, the organic layer was washed with brine and dried over anhydrous sodium sulfate. After filtration, the solvent was evaporated under reduced pressure, and the residue was purified by silica gel column chromatography (elution solvent:hexane/ethyl acetate=5/1) to obtain 3.97 g of the title compound (yield: 74%).

Colorless solid.

$^1$H NMR spectrum (CDCl$_3$, 400 MHz), δ: 7.04-6.98 (m, 1H), 6.43-6.36 (m, 2H), 4.57 (br s, 1H), 4.51 (br s, 1H), 3.29 (br s, 2H), 2.06 (br s, 3H), 1.43 (s, 9H), 1.39 (s, 6H).

(67b) {2-[(2-Bromoacetyl)-(3-fluoro-2-methylphenyl)amino]-1,1-dimethylethyl}carbamic acid t-butyl ester 1.4 ml of bromoacetyl bromide (16.1 mmol) was added to a solution of 3.97 g of [1,1-dimethyl-2-(3-fluoro-2-methylphenylamino)ethyl]carbamic acid t-butyl ester obtained in Example (67a) (13.4 mmol) in N,N-dimethylacetamide (67 ml) under ice-cooling, and the mixture was stirred at the same temperature for 10 minutes. A saturated sodium bicarbonate aqueous solution was added to the reaction mixture, followed by extraction with ethyl acetate. Then, the organic layer was washed with water and brine and dried over anhydrous magnesium sulfate. After filtration, the solvent was evaporated under reduced pressure. Hexane was added to the residue, and the solid was collected by filtration to obtain 4.23 g of the title compound (yield: 76%).

Colorless solid.

$^1$H NMR spectrum (CDCl$_3$, 500 MHz), δ: 7.25-7.17 (m, 2H), 7.06 (br t, 1H, J=8.6 Hz), 4.56 (br s, 1H), 4.24 (d, 1H, J=14.2 Hz), 3.84 (br d, 1H, J=14.2 Hz), 3.62 (br d, 1H, J=10.7 Hz), 3.56 (d, 1H, J=10.7 Hz), 2.17 (br s, 3H), 1.35 (br s, 3H), 1.31 (br s, 3H), 1.20 (s, 9H).

(67c) 2,2-Dimethyl-4-(3-fluoro-2-methylphenyl)-5-oxopiperazine-1-carboxylic acid t-butyl ester A solution of 1.7 g of potassium t-butoxide (15.1 mmol) in tetrahydrofuran (100 ml) was added to a solution of 4.2 g of {2-[(2-bromoacetyl)-(3-fluoro-2-methylphenyl)amino]-1,1-dimethylethyl}carbamic acid t-butyl ester obtained in Example (67b) (10.1 mmol) in tetrahydrofuran (100 ml) under a nitrogen atmosphere and under cooling in a dry ice-acetone bath over 30 minutes, and the mixture was stirred at the same temperature for 10 minutes. A saturated ammonium chloride aqueous solution was added to the reaction mixture. The mixture was returned to room temperature and diluted with water, followed by extraction with ethyl acetate. Then, the organic layer was dried over anhydrous magnesium sulfate. After filtration, the solvent was evaporated under reduced pressure, and the residue was purified by silica gel column chromatography (elution solvent:methylene chloride/ethyl acetate=5/1) to obtain 1.6 g of the title compound (yield: 47%).

Colorless solid.

$^1$H NMR spectrum (CDCl$_3$, 500 MHz), δ: 7.23-7.19 (m, 1H), 7.02 (br t, 1H, J=8.8 Hz), 6.96 (br d, 1H, J=7.8H), 4.31 (br d, 1H, J=17.1 Hz), 4.17 (br d, 1H, J=17.1 Hz), 3.65 (br d, 1H, J=13.2 Hz), 3.44 (br d, 1H, J=13.2 Hz), 2.16 (br s, 3H), 1.58 (br s, 3H), 1.54 (br s, 3H), 1.50 (s, 9H).

(67d) 5,5-Dimethyl-1-(3-fluoro-2-methylphenyl)piperazin-2-one 2.8 ml of trifluoroacetic acid (37 mmol) was added to a solution of 1.25 g of 2,2-dimethyl-4-(3-fluoro-2-methylphenyl)-5-oxopiperazine-1-carboxylic acid t-butyl ester obtained in Example (67c) (3.7 mmol) in methylene chloride (5.6 ml) at room temperature, and the mixture was stirred at the same temperature for 30 minutes. The reaction mixture was concentrated under reduced pressure. A saturated sodium bicarbonate aqueous solution was added, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol=10/1) to obtain 0.9 g of the title compound (yield: quant.).

Colorless liquid.

$^1$H NMR spectrum (CDCl$_3$, 400 MHz), δ: 7.23-7.17 (m, 1H), 7.01 (br t, 1H, J=8.8 Hz), 6.92 (br d, 1H, J=7.8 Hz), 3.75 (d, 1H, J=18.4 Hz), 3.68 (d, 1H, J=18.4 Hz), 3.45 (d, 1H, J=11.7 Hz), 3.30 (d, 1H, J=11.7 Hz), 2.15 (br s, 3H), 1.35 (s, 3H), 1.33 (s, 3H).

mass spectrum (FAB$^+$), m/z: 237 ((M+H)$^+$).

(67e) (2S,4S,5S)-5-Amino-6-[2,2-dimethyl-4-(3-fluoro-2-methylphenyl)-5-oxopiperazin-1-yl]-4-hydroxy-2-isopropylhexanoic acid (2,2-dimethylpropyl)amide hemifumarate (½ fumarate)

106 mg of the title compound (total yield over four steps: 47%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 5,5-dimethyl-1-(3-fluoro-2-methylphenyl)piperazin-2-one obtained in Example (67d) and (2,2-dimethylpropyl)amine.

Colorless solid.

$^1$H NMR spectrum (CD$_3$OD, 400 MHz), δ: 7.32-7.26 (m, 1H), 7.13-6.98 (m, 2H), 6.66 (s, 1H), 3.70-3.46 (m, 3H), 3.39-3.13 (m, 4H), 2.93-2.87 (m, 1.6H), 2.83-2.77 (m, 0.4H), 2.61 (dd, 0.4H, J=13.9 Hz, 4.5 Hz), 2.49 (dd, 0.6H, J=13.5 Hz, 4.5 Hz), 2.42-2.38 (m, 1H), 2.14-2.13 (m, 3H), 1.89-1.80 (m, 2H), 1.74-1.67 (m, 1H), 1.28-1.25 (m, 6H), 1.01-0.98 (m, 6H), 0.94 (s, 9H).

mass spectrum (FAB$^+$), m/z: 493 ((M+H)$^+$).

Example 68

(2S,4S,5S)-5-Amino-6-[2,2-dimethyl-4-(3-fluoro-2-methylphenyl)-5-oxopiperazin-1-yl]-4-hydroxy-2-isopropylhexanoic acid isobutylamide hemifumarate (½ fumarate) (Exemplary Compound No. 1-739)

123 mg of the title compound (total yield over four steps: 54%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 5,5-dimethyl-1-(3-fluoro-2-methylphenyl)piperazin-2-one obtained in Example (67d) and isobutylamine.

Colorless solid.

$^1$H NMR spectrum (CD$_3$OD, 400 MHz), δ: 7.32-7.27 (m, 1H), 7.12-7.09 (m, 1H), 7.05-6.99 (m, 1H), 6.68 (s, 1H), 3.71-3.46 (m, 3H), 3.39-3.13 (m, 4H), 2.95-2.90 (m, 1.6H), 2.85-2.80 (m, 0.4H), 2.64-2.61 (m, 0.4H), 2.53-2.49 (m, 0.6H), 2.37-2.33 (m, 1H), 2.15-2.14 (m, 3H), 1.86-1.78 (m, 3H), 1.75-1.70 (m, 1H), 1.29-1.26 (m, 6H), 1.01-0.98 (m, 6H), 0.95 (d, 6H, J=6.4 Hz).

mass spectrum (FAB$^+$), m/z: 479 ((M+H)$^+$).

Example 69

(2S,4S,5S)-5-Amino-6-[2,2-dimethyl-4-(4-fluoro-2-methylphenyl)-5-oxopiperazin-1-yl]-4-hydroxy-2-isopropylhexanoic acid isobutylamide hemifumarate (½ fumarate) (Exemplary Compound No. 1-982)

(69a) 5,5-Dimethyl-1-(4-fluoro-2-methylphenyl)piperazin-2-one 0.62 g of the title compound (total yield over four steps: 34%) was obtained in the same manner as in Examples (1h) to (1k) using (1,1-dimethyl-2-oxoethyl)carbamic acid t-butyl ester obtained in Reference Example 3 and 4-fluoro-2-methylaniline.

Colorless liquid.

$^1$H NMR spectrum (CDCl$_3$, 400 MHz), δ: 7.07 (dd, 1H, J=8.6 Hz, 5.5 Hz), 6.98-6.90 (m, 2H), 3.73 (d, 1H, J=18.4 Hz), 3.69 (d, 1H, J=18.4 Hz), 3.42 (d, 1H, J=12.1 Hz), 3.29 (d, 1H, J=12.1 Hz), 2.23 (s, 3H), 1.35 (br s, 3H), 1.33 (br s, 3H).

mass spectrum (FAB$^+$), m/z: 237 ((M+H)$^+$).

(69b) (2S,4S,5S)-5-Amino-6-[2,2-dimethyl-4-(4-fluoro-2-methylphenyl)-5-oxopiperazin-1-yl]-4-hydroxy-2-isopropylhexanoic acid isobutylamide hemifumarate (½ fumarate)

135 mg of the title compound (total yield over four steps: 42%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 5,5-dimethyl-1-(4-fluoro-2-methylphenyl)piperazin-2-one obtained in Example (69a) and isobutylamine.

Colorless solid.

$^1$H NMR spectrum (CD$_3$OD, 400 MHz), δ: 8.06 (br s, 1H), 7.19-7.13 (m, 1H), 7.08-6.99 (m, 2H), 6.69 (s, 1H), 3.67-3.45 (m, 3H), 3.35-3.12 (m, 4H), 2.95-2.89 (m, 1.6H), 2.83-2.79 (m, 0.4H), 2.64-2.61 (m, 0.4H), 2.51-2.48 (m, 0.6H), 2.35-2.32 (m, 1H), 2.24-2.23 (m, 3H), 1.85-1.78 (m, 3H), 1.73-1.69 (m, 1H), 1.32-1.25 (m, 6H), 0.99. (t, 6H, J=7.6 Hz), 0.94 (d, 6H, J=6.4 Hz).

mass spectrum (FAB$^+$), m/z: 479 ((M+H)$^+$).

Example 70

(2S,4S,5S)-5-Amino-6-[2,2-dimethyl-4-(5-fluoro-2-methylphenyl)-5-oxopiperazin-1-yl]-4-hydroxy-2-isopropylhexanoic acid (2,2-dimethylpropyl)amide hemifumarate (½ fumarate) (Exemplary Compound No. 1-842)

(70a) [1,1-Dimethyl-2-(5-fluoro-2-methylphenylamino)ethyl]carbamic acid t-butyl ester 6.9 g of sodium triacetoxyborohydride (32.5 mmol) was added to a solution of 5.08 g of (1,1-dimethyl-2-oxoethyl)carbamic acid t-butyl ester obtained in Reference Example 3 (27.1 mmol), 5 g of 5-fluoro-2-methylaniline (27.1 mmol) and 1.55 ml of acetic acid (27.1 mmol) in methylene chloride (270 ml) under ice-cooling, and the mixture was stirred at room temperature for 16 hours. A saturated sodium bicarbonate aqueous solution was added to the reaction mixture, followed by extraction with methylene chloride. Then, the organic layer was washed with brine and dried over anhydrous sodium sulfate. After filtration, the solvent was evaporated under reduced pressure, and the residue was purified by silica gel column chromatography (elution solvent:hexane/ethyl acetate=8/1) to obtain 5.68 g of the title compound (yield: 71%).

Colorless solid.

$^1$H NMR spectrum (CDCl$_3$, 400 MHz), δ: 6.96-6.92 (m, 1H), 6.31-6.27 (m, 2H), 4.57 (br s, 2H), 3.25 (d, 2H, J=5.5 Hz), 2.11 (s, 3H), 1.43 (s, 9H), 1.39 (s, 6H).

(70b) {2-[(2-Bromoacetyl)-(5-fluoro-2-methylphenyl)amino]-1,1-dimethylethyl}carbamic acid t-butyl ester 1.67 ml of bromoacetyl bromide (19.1 mmol) was added to a solution of 5.68 g of [1,1-dimethyl-2-(5-fluoro-2-methylphenylamino)ethyl]carbamic acid t-butyl ester obtained in Example (70a) (19.1 mmol) in N,N-dimethylacetamide (95 ml) under ice-cooling, and the mixture was stirred at the same temperature for 10 minutes. A saturated sodium bicarbonate aqueous solution was added to the reaction mixture, followed by extraction with ethyl acetate. Then, the organic layer was washed with water and brine and dried over anhydrous magnesium sulfate. After filtration, the solvent was evaporated under reduced pressure. Hexane was added to the residue, and the solid was collected by filtration to obtain 7.1 g of the title compound (yield: 89%).

Colorless solid.

$^1$H NMR spectrum (CDCl$_3$, 400 MHz), δ: 7.23 (dd, 1H, J=8.2 Hz, 6.3 Hz), 7.11 (dd, 1H, J=9.0 Hz, 2.7 Hz), 7.00 (dt, 1H, J=8.2 Hz, 2.7 Hz), 4.54 (br s, 1H), 4.21 (d, 1H, J=13.7 Hz), 3.80 (br d, 1H, J=13.7 Hz), 3.59 (br d, 1H, J=1.0 Hz), 3.52 (d, 1H, J=11.0 Hz), 2.21 (s, 3H), 1.35 (br s, 3H), 1.31 (br s, 3H), 1.20 (s, 9H).

(70c) 2,2-Dimethyl-4-(5-fluoro-2-methylphenyl)-5-oxopiperazine-1-carboxylic acid t-butyl ester A solution of 2.87 g of potassium t-butoxide (25.6 mmol) in tetrahydrofuran (170 ml) was added to a solution of 7.13 g of {2-[(2-bromoacetyl)-(5-fluoro-2-methylphenyl)amino]-1,1-dimethylethyl}carbamic acid t-butyl ester obtained in Example (70b) (17.0 mmol) in tetrahydrofuran (170 ml) under a nitrogen atmosphere and under cooling in a dry ice-acetone bath over 20 minutes, and the mixture was stirred at the same temperature for 10 minutes. A saturated ammonium chloride aqueous solution was added to the reaction mixture. The mixture was returned to room temperature and diluted with water, followed by extraction with ethyl acetate. Then, the organic layer was dried over anhydrous magnesium sulfate. After filtration, the solvent was evaporated under reduced pressure, and the residue was purified by silica gel column chromatography (elution solvent:hexane/ethyl acetate=2/1) to obtain 4.5 g of the title compound (yield: 78%).

Colorless solid.

$^1$H NMR spectrum (CDCl$_3$, 400 MHz), δ: 7.23 (dd, 1H, J=8.2 Hz, 6.3 Hz), 6.96 (dt, 1H, J=8.2 Hz, 2.7 Hz), 6.88 (dd, 1H, J=9.0 Hz, 2.7 Hz), 4.28 (br s, 1H), 4.18 (br s, 1H), 3.64 (br s, 1H), 3.43 (br s, 1H), 2.21 (s, 3H), 1.56 (br s, 6H), 1.50 (s, 9H).

(70d) 5,5-Dimethyl-1-(5-fluoro-2-methylphenyl)piperazin-2-one 10 ml of trifluoroacetic acid (134 mmol) was added to a solution of 4.5 g of 2,2-dimethyl-4-(5-fluoro-2-methylphenyl)-5-oxopiperazine-1-carboxylic acid t-butyl ester obtained in Example (70c) (13.4 mmol) in methylene chloride (20 ml) at room temperature, and the mixture was stirred at the same temperature for 30 minutes. The reaction mixture was concentrated under reduced pressure. A saturated sodium bicarbonate aqueous solution was added, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol=10/1) to obtain 2.71 g of the title compound (yield: 86%).

Colorless liquid.

$^1$H NMR spectrum (CDCl$_3$, 400 MHz), δ: 7.22 (dd, 1H, J=8.4 Hz, 6.5 Hz), 6.95 (dt, 1H, J=8.4 Hz, 2.7 Hz), 6.84 (dd, 1H, J=9.0 Hz, 2.7 Hz), 3.74 (d, 1H, J=18.0 Hz), 3.68 (d, 1H, J=18.0 Hz), 3.43 (d, 1H, J=11.7 Hz), 3.30 (d, 1H, J=11.7 Hz), 2.20 (s, 3H), 1.35 (s, 3H), 1.33 (s, 3H).

mass spectrum (FAB$^+$), m/z: 237 ((M+H)$^+$).

(70e) N-{(S)-2-[2,2-Dimethyl-4-(5-fluoro-2-methylphenyl)-5-oxopiperazin-1-yl]-1-[(2S,4S)-4-isopropyl-5-oxotetrahydrofuran-2-yl]ethyl}-2-nitrobenzenesulfonamide A solution of 863 mg of (3S,5S)-3-isopropyl-5-[(S)-1-(2-nitrobenzenesulfonyl)aziridin-2-yl]dihydrofuran-2-one obtained in Example (1g) (2.43 mmol) and 805 mg of 5,5-dimethyl-1-(5-fluoro-2-methylphenyl)piperazin-2-one obtained in Example (70d) (3.40 mmol) in toluene (30 ml) was stirred at 110° C. for two hours. After cooling, the reaction mixture was concentrated under reduced pressure, and the residue was purified by silica gel column chromatography (elution solvent:methylene chloride/ethyl acetate=5/1-3/1) to obtain 1.44 g of the title compound (yield: 99%).

Colorless solid.

$^1$H NMR spectrum (CDCl$_3$, 400 MHz), δ: 8.18-8.16 (m, 1H), 7.98-7.90 (m, 1H), 7.85-7.78 (m, 2H), 7.20 (dd, 1H, J=8.2 Hz, 6.7 Hz), 6.96 (dt, 1H, J=8.2 Hz, 2.7 Hz), 6.82-6.67 (m, 1H), 5.89 (br d, 0.6H, J=6.7 Hz), 5.60 (br d, 0.4H, J=7.0 Hz), 4.88-4.79 (m, 1H), 3.68-3.58 (m, 1H), 3.37-3.27 (m, 1H), 3.16-2.17 (m, 9H), 2.11 (s, 3H), 1.16-0.93 (m, 12H).

(70f) {(S)-2-[2,2-Dimethyl-4-(5-fluoro-2-methylphenyl)-5-oxopiperazin-1-yl]-1-[(2S,4S)-4-isopropyl-5-oxotetrahydrofuran-2-yl]ethyl}carbamic acid t-butyl ester 953 mg of cesium carbonate (2.92 mmol) was added to a solution of 1.44 g of N-{(S)-2-[2,2-dimethyl-4-(5-fluoro-2-methylphenyl)-5-oxopiperazin-1-yl]-1-[(2S,4S)-4-isopropyl-5-oxotetrahydrofuran-2-yl]ethyl}-2-nitrobenzenesulfonamide obtained in Example (70e) (2.43 mmol) and 0.52 ml of thiophenol (content: 95%) (4.87 mmol) in acetolitrile (25 ml) under a nitrogen atmosphere at room temperature, and the mixture was stirred at the same temperature for two hours. Brine was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol=20/1-10/1). 211 mg of sodium bicarbonate (2.51 mmol) and 549 mg of di-t-butyl dicarbonate (2.51 mmol) were added to a solution of 4-{(S)-2-amino-2-[(2S,4S)-4-isopropyl-5-oxotetrahydrofuran-2-yl]ethyl}-5,5-dimethyl-1-(5-fluoro-2-methylphenyl)piperazin-2-one obtained above in a mixture of ethyl acetate (11 ml) and water (11 ml), and the mixture was stirred at room temperature for four hours. Brine was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/ethyl acetate=5/1-3/1) to obtain 996 mg of the title compound (yield: 93%).

Colorless solid.

$^1$H NMR spectrum (CDCl$_3$, 500 MHz), δ: 7.21 (dd, 1H, J=8.3 Hz, 6.4 Hz), 6.95 (dt, 1H, J=8.3 Hz, 2.4 Hz), 6.86-6.80 (m, 1H), 4.83-4.76 (m, 1H), 4.47-4.44 (m, 1H), 3.87-3.82 (m, 1H), 3.55-3.16 (m, 4H), 2.75-2.41 (m, 3H), 2.30-2.11 (m, 6H), 1.45 (br s, 9H), 1.22 (br s, 6H), 1.03 (br d, 3H, J=6.8 Hz), 0.98-0.96 (m, 3H).

(70g) {(1S,2S,4S)-4-(2,2-Dimethylpropylcarbamoyl)-1-[2,2-dimethyl-4-(5-fluoro-2-methylphenyl)-5-oxopiperazin-1-ylmethyl]-2-hydroxy-5-methylhexyl}carbamic acid t-butyl ester 0.94 ml of (2,2-dimethylpropyl)amine (8.0 mmol) and 7.6 mg of 2-hydroxypyridine (0.08 mmol) were added to 202 mg of {(S)-2-[2,2-dimethyl-4-(5-fluoro-2-methylphenyl)-5-oxopiperazin-1-yl]-1-[(2S,4S)-4-isopropyl-5-oxotetrahydrofuran-2-yl]ethyl}carbamic acid t-butyl ester obtained in Example (70f) (0.4 mmol), and the mixture was stirred at 70° C. for four hours. The reaction mixture was cooled and then water was added, followed by extraction with ethyl acetate. Then, the organic layer was washed with brine and then dried over anhydrous sodium sulfate. After filtration, the solvent was evaporated under reduced pressure, and the residue was purified by silica gel column chromatography (elution solvent:methylene chloride/methanol=20/1) to obtain 177 mg of the title compound (yield: 75%).

Colorless solid.

$^1$H NMR spectrum (CDCl$_3$, 400 MHz), δ: 7.21 (dd, 1H, J=8.2 Hz, 6.1 Hz), 6.95 (dt, 1H, J=8.2 Hz, 2.7 Hz), 6.83-6.80 (m, 1H), 5.75 (br s, 1H), 5.03 (br s, 1H), 3.92-3.89 (m, 1H), 3.64 (br d, 1H, J=18.0 Hz), 3.49-3.14 (m, 5H), 3.09-2.98 (m, 1H), 2.77-2.61 (m, 2H), 2.17 (br s, 3H), 2.11-2.05 (m, 1H), 1.99-1.90 (m, 1H), 1.79-1.67 (m, 2H), 1.46 (br s, 9H), 1.22 (br s, 6H), 0.97-0.92 (m, 15H).

(70h) (2S,4S,5S)-5-Amino-6-[2,2-dimethyl-4-(5-fluoro-2-methylphenyl)-5-oxopiperazin-1-yl]-4-hydroxy-2-isopropylhexanoic acid (2,2-dimethylpropyl)amide hemifumarate (½ fumarate)

0.69 ml of trifluoroacetic acid (8.96 mmol) was added to a solution of 177 mg of {(1S,2S,4S)-4-(2,2-dimethylpropylcarbamoyl)-1-[2,2-dimethyl-4-(5-fluoro-2-methylphenyl)-5-oxopiperazin-1-ylmethyl]-2-hydroxy-5-methylhexyl}carbamic acid t-butyl ester obtained in Example (70g) (0.30 mmol) in methylene chloride (1.4 ml) at room temperature, and the mixture was stirred at the same temperature for 30 minutes. The reaction mixture was concentrated under reduced pressure and diluted with a saturated sodium bicarbonate aqueous solution, followed by extraction with methylene chloride. Then, the organic layer was dried over anhydrous magnesium sulfate. After filtration, the solvent was evaporated under reduced pressure, and the residue was purified by silica gel column chromatography (elution solvent: methylene chloride/methanol/triethylamine=100/10/1). 14 mg of fumaric acid (0.12 mmol) was added to a solution of 122 mg of the resulting (2S,4S,5S)-5-amino-6-[2,2-dimethyl-4-(5-fluoro-2-methylphenyl)-5-oxopiperazin-1-yl]-4-hydroxy-2-isopropylhexanoic acid (2,2-dimethylpropyl) amide (0.25 mmol) in methanol (2 ml), and the mixture was stirred at room temperature for five minutes. The solvent was evaporated under reduced pressure to obtain 100 mg of the title compound (yield: 74%).

Colorless solid.

$^1$H NMR spectrum (CD$_3$OD, 400 MHz), δ: 7.92 (br s, 1H), 7.33-7.29 (m, 1H), 7.06-6.91 (m, 2H), 6.66 (s, 1H), 3.68-3.45 (m, 3H), 3.39-3.16 (m, 4H), 2.94-2.89 (m, 1.6H), 2.80-2.62 (m, 0.8H), 2.50-2.38 (m, 0.6H), 2.20 (s, 3H), 1.88-1.84 (m, 2H), 1.73-1.67 (m, 1H), 1.27-1.25 (m, 6H), 1.01-0.99 (m, 6H), 0.94 (s, 9H).

mass spectrum (FAB$^+$), m/z: 493 ((M+H)$^+$).

Example 71

(2S,4S,5S)-5-Amino-6-[2,2-dimethyl-4-(5-fluoro-2-methylphenyl)-5-oxopiperazin-1-yl]-4-hydroxy-2-isopropylhexanoic acid isobutylamide hemifumarate (½ fumarate) (Exemplary Compound No. 1-740)

(71a) {(1S,2S,4S)-4-Isobutylcarbamoyl-1-[2,2-dimethyl-4-(5-fluoro-2-methylphenyl)-5-oxopiperazin-1-ylmethyl]-2-hydroxy-5-methylhexyl}carbamic acid t-butyl ester 0.4 ml of isobutylamine (3.96 mmol) and 8 mg of 2-hydroxypyridine (0.079 mmol) were added to 200 mg of {(S)-2-[2,2-dimethyl-4-(5-fluoro-2-methylphenyl)-5-oxopiperazin-1-yl]-1-[(2S,4S)-4-isopropyl-5-oxotetrahydrofuran-2-yl]ethyl}carbamic acid t-butyl ester obtained in Example (70f) (0.39 mmol), and the mixture was stirred at 80° C. for four hours. The reaction mixture was cooled and then water was added, followed by extraction with ethyl acetate. Then, the organic layer was washed with brine and then dried over anhydrous sodium sulfate. After filtration, the solvent was evaporated under reduced pressure, and the residue was purified by silica gel column chromatography (elution solvent: methylene chloride/methanol=20/1) to obtain 226 mg of the title compound (yield: 99%).

Colorless solid.

$^1$H NMR spectrum (CDCl$_3$, 500 MHz), δ: 7.21 (dd, 1H, J=8.3 Hz, 6.1 Hz), 6.95 (dt, 1H, J=8.3 Hz, 2.9 Hz), 6.83-6.80 (m, 1H), 5.77 (br s, 1H), 5.04 (br s, 1H), 3.90-3.80 (m, 1H), 3.64 (br d, 1H, J=17.6 Hz), 3.50-3.15 (m, 5H), 3.05-3.00 (m, 1H), 2.78-2.62 (m, 2H), 2.17 (br s, 3H), 2.07-2.03 (m, 1H), 1.97-1.90 (m, 1H), 1.83-1.67 (m, 3H), 1.46 (br s, 9H), 1.22 (br s, 6H), 0.97-0.92 (m, 12H).

(71b) (2S,4S,5S)-5-Amino-6-[2,2-dimethyl-4-(5-fluoro-2-methylphenyl)-5-oxopiperazin-1-yl]-4-hydroxy-2-isopropylhexanoic acid isobutylamide hemifumarate (½ fumarate)

0.95 ml of trifluoroacetic acid (12.33 mmol) was added to a solution of 238 mg of {(1S,2S,4S)-4-isobutylcarbamoyl-1-[4-(5-fluoro-2-methylphenyl)-2,2-dimethyl-5-oxopiperazin-1-ylmethyl]-2-hydroxy-5-methylhexyl}carbamic acid t-butyl ester obtained in Example (71a) (0.411 mmol) in methylene chloride (2 ml) at room temperature, and the mixture was stirred at the same temperature for 30 minutes. The reaction mixture was concentrated under reduced pressure and diluted with a saturated sodium bicarbonate aqueous solution, followed by extraction with methylene chloride. Then, the organic layer was dried over anhydrous magnesium sulfate. After filtration, the solvent was evaporated under reduced pressure, and the residue was purified by silica gel column chromatography (elution solvent: methylene chloride/methanol=20/1-10/1). 20.8 mg of fumaric acid (0.179 mmol) was added to a solution of 172 mg of (2S,4S,5S)-5-amino-6-[2,2-dimethyl-4-(5-fluoro-2-methylphenyl)-5-oxopiperazin-1-yl]-4-hydroxy-2-isopropylhexanoic acid isobutylamide obtained above (0.35 mmol) in methanol (2 ml), and the mixture was stirred at room temperature for five minutes. The solvent was evaporated under reduced pressure to obtain 152 mg of the title compound (yield: 80%).

Colorless solid.

$^1$H NMR spectrum (CD$_3$OD, 500 MHz), δ: 7.33-7.30 (m, 1H), 7.06-6.93 (m, 2H), 6.66 (s, 1H), 3.68-3.45 (m, 3H), 3.39-3.09 (m, 4H), 2.95-2.89 (m, 1.6H), 2.81-2.76 (m, 0.4H), 2.65 (dd, 0.4H, J=13.4 Hz, 4.2 Hz), 2.48 (dd, 0.6H, J=13.2 Hz, 3.9 Hz), 2.36-2.32 (m, 1H), 2.20 (s, 3H), 1.87-1.69 (m, 4H), 1.27-1.25 (m, 6H), 1.00 (d, 3H, J=6.8 Hz), 0.98 (d, 3H, J=6.8 Hz), 0.94 (d, 6H, J=6.8 Hz).

mass spectrum (FAB$^+$), m/z: 479 ((M+H)$^+$).

Example 72

(2S,4S,5S)-5-Amino-6-[2,2-dimethyl-4-(5-fluoro-2-methylphenyl)-5-oxopiperazin-1-yl]-4-hydroxy-2-isopropylhexanoic acid cyclohexylamide hemifumarate (½ fumarate) (Exemplary Compound No. 1-884)

269 mg of the title compound (total yield over two steps: 48%) was obtained in the same manner as in Examples (1n) and (1o) using {(S)-2-[2,2-dimethyl-4-(5-fluoro-2-methylphenyl)-5-oxopiperazin-1-yl]-1-[(2S,4S)-4-isopropyl-5-oxotetrahydrofuran-2-yl]ethyl}carbamic acid t-butyl ester obtained in Example (70f) and cyclohexylamine.

Colorless solid.

$^1$H NMR spectrum (CD$_3$OD, 400 MHz), δ: 7.33-7.30 (m, 1H), 7.06-7.02 (m, 1H), 6.99-6.93 (m, 1H), 6.67 (s, 1H), 3.71-3.57 (m, 3H), 3.51-3.48 (m, 1H), 3.39-3.12 (m, 3H), 2.94-2.90 (m, 0.6H), 2.80-2.75 (m, 0.4H), 2.68-2.64 (m, 0.4H), 2.49 (m, 0.6H, J=13.4 Hz, 4.1 Hz), 2.29-2.25 (m, 1H), 2.20 (br s, 3H), 1.90-1.63 (m, 8H), 1.40-1.15 (m, 11H), 1.00-0.94 (m, 6H).

mass spectrum (FAB$^+$), m/z: 505 ((M+H)$^+$).

Example 73

(2S,4S,5S)-5-Amino-6-[2,2-dimethyl-4-(5-fluoro-2-methylphenyl)-5-oxopiperazin-1-yl]-4-hydroxy-2-isopropylhexanoic acid (2-hydroxy-2-methylpropyl)amide hemifumarate (½ fumarate) (Exemplary Compound No. 1-791)

120 mg of the title compound (total yield over two steps: 55%) was obtained in the same manner as in Examples (1n) and (1o) using {(S)-2-[2,2-dimethyl-4-(5-fluoro-2-methylphenyl)-5-oxopiperazin-1-yl]-1-[(2S,4S)-4-isopropyl-5-oxotetrahydrofuran-2-yl]ethyl}carbamic acid t-butyl ester obtained in Example (70f) and (1,1-dimethylethanol)amine.

Colorless solid.

$^1$H NMR spectrum (CD$_3$OD, 500 MHz), δ: 7.90-7.88 (m, 1H), 7.33-7.30 (m, 1H), 7.06-7.02 (m, 1H), 6.99-6.94 (m, 1H), 6.71 (s, 1H), 3.68-3.47 (m, 3H), 3.40-3.16 (m, 5H), 2.95-2.91 (m, 0.6H), 2.81-2.76 (m, 0.4H), 2.68-2.65 (m, 0.4H), 2.51-2.47 (m, 0.6H), 2.41-2.37 (m, 1H), 2.20 (s, 3H), 1.90-1.80 (m, 2H), 1.75-1.70 (m, 1H), 1.28-1.25 (m, 6H), 1.21 (s, 6H), 1.01-0.98 (m, 6H).

mass spectrum (FAB$^+$), m/z: 495 ((M+H)$^+$).

Example 74

(2S,4S,5S)-5-Amino-6-[2,2-dimethyl-4-(2,5-dimethylphenyl)-5-oxopiperazin-1-yl]-4-hydroxy-2-isopropylhexanoic acid isobutylamide hemifumarate (½ fumarate) (Exemplary Compound No. 1-734)

(74a)
5,5-Dimethyl-1-(2,5-dimethylphenyl)piperazin-2-one 0.25 g of the title compound (total yield over four steps: 30%) was obtained in the same manner as in Examples (1h) to (1k) using (1,1-dimethyl-2-oxoethyl)carbamic acid t-butyl ester obtained in Reference Example 3 and 2,5-dimethylaniline.

Colorless liquid.

$^1$H NMR spectrum (CDCl$_3$, 400 MHz), δ: 7.82 (d, 1H, J=7.8 Hz), 7.03 (d, 1H, J=7.8 Hz), 6.91 (s, 1H), 3.74 (d, 1H, J=18.1 Hz), 3.67 (d, 1H, J=18.1 Hz), 3.43 (d, 1H, J=12.1 Hz), 3.29 (d, 1H, J=12.1 Hz), 2.31 (s, 3H), 2.20 (s, 3H), 1.34 (s, 3H), 1.33 (s, 3H).

mass spectrum (FAB$^+$), m/z: 233 ((M+H)$^+$).

(74b) (2S,4S,5S)-5-Amino-6-[2,2-dimethyl-4-(2,5-dimethylphenyl)-5-oxopiperazin-1-yl]-4-hydroxy-2-isopropylhexanoic acid isobutylamide hemifumarate (½ fumarate)

153 mg of the title compound (total yield over four steps: 78%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 5,5-dimethyl-1-(2,5-dimethylphenyl)piperazin-2-one obtained in Example (74a) and isobutylamine.

Colorless solid.

$^1$H NMR spectrum (CD$_3$OD, 400 MHz), δ: 8.09 (br s, 1H), 7.18 (d, 1H, J=7.3 Hz), 7.09 (d, 1H, J=7.3 Hz), 6.99 (s, 0.6H), 6.94 (s, 0.4H), 6.68 (s, 1H), 3.68-3.46 (m, 3H), 3.36-3.14 (m, 4H), 2.95-2.90 (m, 1.6H), 2.84-2.79 (m, 0.4H), 2.63 (dd, 0.4H, J=13.4 Hz, 4.1 Hz), 2.50 (dd, 0.6H, J=13.4 Hz, 4.1 Hz), 2.37-2.32 (m, 1H), 2.31 (s, 3H), 2.19 (s, 1.2H), 2.18 (s, 1.8H), 1.88-1.78 (m, 3H), 1.75-1.69 (m, 1H), 1.28-1.26 (m, 6H), 1.01-0.94 (m, 12H).

mass spectrum (FAB$^+$), m/z: 475 ((M+H)$^+$).

Example 75

(2S,4S,5S)-5-Amino-6-[2,2-dimethyl-5-oxo-4-(2,3,5-trifluorophenyl)piperazin-1-yl]-4-hydroxy-2-isopropylhexanoic acid isobutylamide fumarate (Exemplary Compound No. 1-977)

(75a) 5,5-Dimethyl-1-(2,3,5-trifluorophenyl)piperazin-2-one 0.56 g of the title compound (total yield over four steps: 25%) was obtained in the same manner as in Examples (1h) to (1k) using (1,1-dimethyl-2-oxoethyl)carbamic acid t-butyl ester obtained in Reference Example 3 and 2,3,5-trifluoroaniline.

Colorless liquid.

$^1$H NMR spectrum (CDCl$_3$, 400 MHz), δ: 6.94-6.89 (m, 1H), 6.82-6.78 (m, 1H), 3.69 (s, 2H), 3.45 (s, 2H), 1.33 (s, 6H).

mass spectrum (FAB$^+$), m/z: 259 ((M+H)$^+$).

(75b) (2S,4S,5S)-5-Amino-6-[2,2-dimethyl-5-oxo-4-(2,3,5-trifluorophenyl)piperazin-1-yl]-4-hydroxy-2-isopropylhexanoic acid isobutylamide fumarate 120 mg of the title compound (total yield over four steps: 74%) was obtained in the same manner as in Examples (1l) to (1o) using (3S,5S)-3-isopropyl-5-[(S)-1-(2-nitrobenzenesulfonyl)aziridin-2-yl]dihydrofuran-2-one obtained in Example (1g), 5,5-dimethyl-1-(2,3,5-trifluorophenyl)piperazin-2-one obtained in Example (75a) and isobutylamine.

Colorless solid.

$^1$H NMR spectrum (CD$_3$OD, 400 MHz), δ: 8.07 (br t, 1H, J=5.9 Hz), 7.26-7.21 (m, 1H), 7.05-7.01 (m, 1H), 6.69 (s, 2H), 3.68 (d, 1H, J=11.7 Hz), 3.65 (d, 1H, J=17.8 Hz), 3.48-3.45 (m, 1H), 3.38 (d, 1H, J=11.7 Hz), 3.33-3.12 (m, 3H), 2.94-2.85 (m, 2H), 2.55 (dd, 1H, J=13.7 Hz, 4.4 Hz), 2.36-2.32 (m, 1H), 1.87-1.77 (m, 3H), 1.74-1.68 (m, 1H), 1.25 (br s, 3H), 1.25 (br s, 3H), 0.99 (d, 3H, J=6.8 Hz), 0.97 (d, 3H, J=6.8 Hz), 0.94 (d, 6H, J=6.8 Hz).

mass spectrum (FAB$^+$), m/z: 501 ((M+H)$^+$).

Example 76

(2R,4S,5S)-5-Amino-6-[4-(2-chlorophenyl)-2,2-dimethyl-5-oxopiperazin-1-yl]-4-hydroxy-2-methylhexanoic acid (2,2-dimethylpropyl)amide hemifumarate (½ fumarate) (Exemplary Compound No. 2-182)

(76a) (S)-4-Benzyl-3-[(2R,4E)-6-benzyloxy-2-methylhex-4-enoyl]oxazolidin-2-one 164 ml of a solution of sodium bis(trimethylsilyl)amide in n-hexane (1.03 mol/l) (169 mmol) was added to a solution of 32.9 g of (S)-4-benzyl-3-propionyloxazolidin-2-one (141 mmol) in tetrahydrofuran (330 ml) under a nitrogen atmosphere and at −78° C. over 45 minutes, and the mixture was stirred at the same temperature for 30 minutes. Then, a solution of 35.5 g of [(E)-4-bromobut-2-enyloxymethyl]benzene obtained in Reference Example 4 (148 mmol) in tetrahydrofuran (80 ml) was added to the solution over 30 minutes, and the mixture was stirred at the same temperature for 30 minutes. Thereafter, the mixture was raised to −40° C. and further stirred for four hours. 100 ml of a saturated ammonium chloride aqueous solution was added to the reaction mixture, and the mixture was further stirred at room temperature for one hour. The reaction mixture was concentrated under reduced pressure and diluted with 500 ml of water, followed by extraction with ethyl acetate. Then, the organic layer was washed with water and brine and dried over anhydrous magnesium sulfate. After filtration, the solvent was evaporated under reduced pressure, and the residue was purified by silica gel column chromatography (elution solvent:n-hexane/ethyl acetate=7/1-2/1) to obtain 37.9 g of the title compound (yield: 69%).

Colorless liquid.

$^1$H NMR spectrum (CDCl$_3$, 400 MHz), δ: 7.40-7.14 (m, 10H), 5.75 (dt, 1H, J=15.6 Hz, 6.3 Hz), 5.69 (dt, 1H, J=15.6 Hz, 5.4 Hz), 4.71-4.63 (m, 1H), 4.49 (s, 2H), 4.22-4.11 (m, 2H), 3.98 (d, 2H, J=5.5 Hz), 3.92-3.81 (m, 1H), 3.28 (dd, 1H, J=13.3 Hz, 3.1 Hz), 2.67 (dd, 1H, J=13.3 Hz, 10.2 Hz), 2.58-2.49 (m, 1H), 2.30-2.21 (m, 1H) 1.19 (d, 3H, J=6.7 Hz).

(76b) (2R,4E)-6-Benzyloxy-2-methylhex-4-enoic acid

A solution of 18.7 g of (S)-4-benzyl-3-[(2R,4E)-6-benzyloxy-2-methylhex-4-enoyl]oxazolidin-2-one (47.5 mmol) obtained in Example (76a) in a mixed solvent of tetrahydrofuran (700 ml) and water (230 ml) was cooled in an ice bath, and then 30.0 ml of a 30% hydrogen peroxide aqueous solution and 4.15 g of lithium hydroxide monohydrate (95.3 mmol) were added thereto. The mixture was stirred at the same temperature for 30 minutes, and then raised to room temperature and further stirred for 16 hours. After cooling in an ice bath, 250 ml of a 1.5 M sodium thiosulfate aqueous solution was added to the reaction mixture. The mixture was further stirred at room temperature for one hour. The reaction mixture was concentrated under reduced pressure, diluted with 500 ml of water and washed with ethyl acetate. Then, the aqueous layer was made acidic with 30 g of sodium dihydrogenphosphate, followed by extraction with ethyl acetate. The organic layer was washed with brine and dried over anhydrous magnesium sulfate. After filtration, the solvent was evaporated under reduced pressure to obtain 11.0 g of the crude title compound.

Colorless liquid.

$^1$H NMR spectrum (CDCl$_3$, 400 MHz), δ: 7.40-7.25 (m, 5H), 5.73-5.62 (m, 2H), 4.49 (s, 2H), 4.03-3.93 (m, 2H), 2.61-2.51 (m, 1H), 2.50-2.40 (m, 1H), 2.28-2.17 (m, 1H), 1.19 (d, 3H, J=7.0 Hz).

(76c) (3R,5S)-5-[(R)-2-Benzyloxy-1-hydroxyethyl]-3-methyldihydrofuran-2-one 400 ml of a solution of a sodium tetraborate buffer solution (0.05 M) in a 0.4 mM disodium ethylenediaminetetraacetate aqueous solution, 0.648 g of tetrabutylammoniumbisulfate (1.91 mmol) and 11.1 g of 1,2:4,5-di-O-isopropylidene-β-D-erythro-2,3-hexodiuro-2,6-pyranose (43.0 mmol) were added to 10.1 g of (2R,4E)-6-benzyloxy-2-methylhex-4-enoic acid obtained in Example (76b) (43.2 mmol) in a mixed solvent of acetonitrile (167 ml) and dimethoxymethane (333 ml) at room temperature, and the mixture was stirred for 10 minutes. The reaction mixture was cooled in an ice bath. Then, a solution of 36.7 g of Oxone(trade mark) (59.6 mmol) in a 0.4 mM disodium ethylenediaminetetraacetate aqueous solution (200 ml) and a solution of 34.3 g of potassium carbonate (247 mmol) in water (200 ml) were separately added dropwise over eight hours. The mixture was stirred at the same temperature for one hour and then diluted with 100 ml of water, followed by extraction with ethyl acetate. Then, the organic layer was washed with brine and dried over anhydrous magnesium sulfate. After filtration, the solvent was evaporated under reduced pressure, and the residue was purified by silica gel column chromatography (elution solvent:n-hexane/ethyl acetate=6/1-1/1) to obtain 7.82 g of the title compound (total yield over two steps: 72%).

Colorless liquid.

$^1$H NMR spectrum (CDCl$_3$, 400 MHz), δ: 7.42-7.29 (m, 5H), 4.59 (d, 1H, J=11.7 Hz), 4.55 (d, 1H, J=11.7 Hz), 4.48 (ddd, 1H, J=8.2 Hz, 6.3 Hz, 3.9 Hz), 3.91-3.84 (m, 1H), 3.64 (dd, 1H, J=9.8 Hz, 3.9 Hz), 3.56 (dd, 1H, J=9.8, 6.3 Hz), 2.81-2.69 (m, 1H), 2.53 (ddd, 1H, J=13.2 Hz, 9.4 Hz, 3.9 Hz), 2.47 (d, 1H, J=5.1 Hz), 1.93 (dt, 1H, J=13.2 Hz, 8.2 Hz), 1.28 (t, 3H, J=7.0 Hz).

(76d) Methanesulfonic acid (R)-2-benzyloxy-1-[(2S,4R)-4-methyl-5-oxotetrahydrofuran-2-yl]ethyl ester A solution of 7.80 g of (3R,5S)-5-[(R)-2-benzyloxy-1-hydroxyethyl]-3-methyldihydrofuran-2-one obtained in Example (76c) (31.2 mmol) in methylene chloride (200 ml) was cooled in an ice bath. Then, 9.45 g of triethylamine (93.6 mmol) and 5.36 g of methanesulfonyl chloride (47.0 mmol)

were added thereto, and the mixture was stirred at the same temperature for three hours. 500 ml of water was added to the reaction mixture, followed by extraction with methylene chloride. Then, the organic layer was washed with water and brine and dried over anhydrous magnesium sulfate. After filtration, the solvent was evaporated under reduced pressure, and the residue was purified by silica gel column chromatography (elution solvent:n-hexane/ethyl acetate=4/1-1/1) to obtain 9.90 g of the title compound (yield: 97%).

Colorless liquid.

$^1$H NMR spectrum (CDCl$_3$, 400 MHz), δ: 7.41-7.28 (m, 5H), 4.87-4.80 (m, 1H), 4.69-4.63 (m, 1H), 4.56 (s, 2H), 3.80-3.71 (m, 2H), 3.05 (s, 3H), 2.82-2.70 (m, 1H), 2.58 (ddd, 1H, J=13.3 Hz, 9.4 Hz, 3.9 Hz), 1.99 (dt, 1H J=13.3 Hz, 8.2 Hz), 1.29 (d, 3H, J=7.4 Hz).

(76e) (3R,5S)-5-[(S)-1-Azido-2-benzyloxyethyl]-3-methyldihydrofuran-2-one 2.93 g of sodium azide (45.1 mmol) was added to a solution of 9.90 g of methanesulfonic acid (R)-2-benzyloxy-1-[(2S,4R)-4-methyl-5-oxotetrahydrofuran-2-yl]ethyl ester obtained in Example (76d) (30.1 mmol) in N,N'-dimethylpropyleneurea (100 ml) at room temperature, and the mixture was stirred at 60° C. for three days. The reaction mixture was cooled and then poured into ice water, followed by extraction with diethyl ether. Then, the organic layer was washed with water and brine and dried over anhydrous magnesium sulfate. After filtration, the solvent was evaporated under reduced pressure, and the residue was purified by silica gel column chromatography (elution solvent:n-hexane/ethyl acetate=5/1) to obtain 7.56 g of the title compound (yield: 91%).

Colorless liquid.

$^1$H NMR spectrum (CDCl$_3$, 500 MHz), δ: 7.40-7.29 (m, 5H), 4.62-4.54 (m, 3H), 3.78-3.72 (m, 2H), 3.69-3.64 (m, 1H), 2.91-2.82 (m, 1H), 2.38 (ddd, 1H, J=13.2 Hz, 9.8 Hz, 3.9 Hz), 2.00 (dt, 1H, J=13.2 Hz, 8.3 Hz), 1.27 (d, 3H, J=7.3 Hz).

(76f) N-{(S)-2-Hydroxy-1-[(2S,4R)-4-methyl-5-oxotetrahydrofuran-2-yl]ethyl}-2-nitrobenzenesulfonamide A suspension of 7.56 g of (3R,5S)-5-[(S)-1-azido-2-benzyloxyethyl]-3-methyldihydrofuran-2-one obtained in Example (76e) (27.5 mmol), 15.0 ml of a solution of 4 N hydrochloric acid in dioxane (60.0 mmol) and 1.88 g of 10% palladium-carbon (50% wet) in ethanol (150 ml) was stirred under a hydrogen atmosphere at room temperature for six hours. Hydrogen in the reaction vessel was replaced by nitrogen, and then the reaction mixture was diluted with 100 ml of ethanol. Palladium-carbon was separated by filtration washed with ethanol. The solvent was evaporated from the filtrate under reduced pressure to obtain crude (3R,5S)-5-[(S)-1-amino-2-hydroxyethyl]-3-methyldihydrofuran-2-one hydrochloride.

8.66 g of triethylamine (85.7 mmol) and 9.67 g of O-nitrobenzenesulfonyl chloride (41.3 mmol) were added to a solution of (3R,5S)-5-[(S)-1-amino-2-hydroxyethyl]-3-methyldihydrofuran-2-one hydrochloride obtained in the above reaction in a mixed solvent of tetrahydrofuran (120 ml) and water (12.0 ml) at 0° C., and the mixture was stirred at the same temperature for two hours. The reaction mixture was concentrated under reduced pressure and 200 ml of water was added, followed by extraction with ethyl acetate. Then, the organic layer was washed with water, a saturated sodium bicarbonate aqueous solution and brine and dried over anhydrous magnesium sulfate. After filtration, the solvent was evaporated under reduced pressure, and the residue was purified by silica gel column chromatography (elution solvent: ethyl acetate). Further, 10 ml of diisopropyl ether and 20 ml of ethyl acetate were added, and the precipitated solid was collected by filtration to obtain 5.27 g of the title compound (total yield over two steps: 56%).

The optical purity of the resulting N-{(S)-2-hydroxy-1-[(2S,4R)-4-methyl-5-oxotetrahydrofuran-2-yl]ethyl}-2-nitrobenzenesulfonamide was determined using an analytical optically active HPLC column [ChiralPak AD-H (0.46 cm×25 cm), manufactured by Daicel Chemical Industries, Ltd., elution solvent: ethanol, flow rate: 0.8 ml/min)]. The desired [(S), (2S,4R)] isomer had a retention time of 4.9 minutes and the corresponding [(R), (2R,4S)] isomer had a retention time of 6.0 minutes. The optical purity was 99% ee or more.

Colorless solid.

Optical rotation, $[α]_D^{23.8° C.}$=+56.0° (c=1.00, MeOH).

$^1$H NMR spectrum (CDCl$_3$, 500 MHz), δ: 8.16-8.09 (m, 1H), 7.94-7.87 (m, 1H), 7.79-7.71 (m, 2H), 5.89 (br d, 1H, J=6.8 Hz), 4.72-4.64 (m, 1H), 3.74-3.58 (m, 3H), 2.92-2.81 (m, 1H), 2.63 (ddd, 1H, J=13.2 Hz, 9.8 Hz, 4.9 Hz), 2.03 (dt, 1H, J=13.7 Hz, 8.3 Hz), 2.01-1.96 (m, 1H), 1.28 (d, 3H, J=7.3 Hz).

mass spectrum (FAB$^+$), m/z: 345 ((M+H)$^+$).

(76g) (3R,5S)-3-Methyl-5-[(S)-1-(2-nitrobenzenesulfonyl)aziridin-2-yl]dihydrofuran-2-one 1.6 ml of a solution of diethyl azodicarboxylate in toluene (40%) (3.48 mmol) was added to a solution of 1.00 g of N-{(S)-2-hydroxy-1-[(2S,4R)-4-methyl-5-oxotetrahydrofuran-2-yl]ethyl}-2-nitrobenzenesulfonamide obtained in Example (76f) (2.90 mmol) and 0.91 g of triphenylphosphine (3.48 mmol) in tetrahydrofuran (30 ml) under ice-cooling over five minutes, and the mixture was stirred at the same temperature for five minutes. The reaction mixture was concentrated under reduced pressure, and the residue was purified by silica gel column chromatography (elution solvent: toluene/acetone=5/1) to obtain 0.82 g of the title compound (yield: 87%).

Colorless liquid.

$^1$H NMR spectrum (CDCl$_3$, 400 MHz), δ: 8.14 (dd, 1H, J=7.4 Hz, 1.5 Hz), 7.83-7.73 (m, 3H), 4.76 (dt, 1H, J=8.8 Hz, 2.0 Hz), 3.26-3.23 (m, 1H), 2.97-2.88 (m, 1H), 2.83 (d, 1H, J=7.0 Hz), 2.65-2.60 (m, 2H), 2.18-2.10 (m, 1H), 1.26 (d, 3H, J=6.8 Hz).

mass spectrum (FAB$^+$), m/z: 327 ((M+H)$^+$).

(76h) N-{(S)-2-[4-(2-Chlorophenyl)-2,2-dimethyl-5-oxopiperazin-1-yl]-1-[(2S,4R)-4-methyl-5-oxotetrahydrofuran-2-yl]ethyl}-2-nitrobenzenesulfonamide A solution of 822 mg of (3R,5S)-3-methyl-5-[(S)-1-(2-nitrobenzenesulfonyl)aziridin-2-yl]dihydrofuran-2-one obtained in Example (76g) (2.52 mmol) and 722 mg of 1-(2-chlorophenyl)-5,5-dimethylpiperazin-2-one obtained in Example (1k) (3.02 mmol) in toluene (25 ml) was stirred at 110° C. for two hours. After cooling, the reaction mixture was concentrated under reduced pressure, and the residue was purified by silica gel column chromatography (elution solvent:methylene chloride/ethyl acetate=3/1-2/1) to obtain 1.34 g of the title compound (yield: 94%).

Colorless solid.

$^1$H NMR spectrum (CDCl$_3$, 400 MHz), δ: 8.17 (br d, 1H, J=7.0 Hz), 7.93 (br s, 1H), 7.79 (br s, 2H), 7.44 (dd, 1H, J=7.4 Hz, 2.0 Hz), 7.35-7.09 (m, 3H), 5.87 (br s, 0.5H), 5.53 (br s, 0.5H), 4.90 (br s, 1H), 3.63 (br s, 1H), 3.29-3.10 (m, 3H), 2.90-2.56 (m, 4.5H), 2.20-2.05 (m, 1.5H), 1.33 (br d, 3H, J=7.0 Hz), 1.16 (br s, 3H), 1.07 (br s, 3H).

(76i) {(S)-2-[4-(2-Chlorophenyl)-2,2-dimethyl-5-oxopiperazin-1-yl]-1-[(2S,4R)-4-methyl-5-oxotetrahydrofuran-2-yl]ethyl}carbamic acid t-butyl ester 925 mg of cesium carbonate (2.84 mmol) was added to a solution of 1.34 g of N-{(S)-2-[4-(2-chlorophenyl)-2,2-dimethyl-5-oxopiperazin-1-yl]-1-[(2S,4R)-4-methyl-5-oxotetrahydrofuran-2-yl]ethyl}-2-nitrobenzenesulfonamide obtained in Example (76h) (2.37 mmol) and 0.51 ml of thiophenol (content: 95%) (4.74 mmol) in acetonitrile (12 ml) under a nitrogen atmosphere at room temperature, and the mixture was stirred at the same temperature for one hour. Brine was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/ethyl acetate=20/1-10/1). 208 mg of sodium bicarbonate (2.47 mmol) and 538 mg of di-t-butyl dicarbonate (2.47 mmol) were added to a solution of 4-{(S)-2-amino-2-[(2S,4R)-4-methyl-5-oxotetrahydrofuran-2-yl]ethyl}1-(2-chlorophenyl)-5,5-dimethylpiperazin-2-one obtained above in ethyl acetate (10 ml)-water (10 ml), and the mixture was stirred at room temperature for two hours. Brine was added to the reaction mixture, followed by extraction with ethyl acetate. Then, the organic layer was dried over anhydrous magnesium sulfate. After filtration, the solvent was evaporated under reduced pressure, and the residue was purified by silica gel column chromatography (elution solvent:methylene chloride/ethyl acetate=2/1-1/1) to obtain 958 mg of the title compound (yield: 84%).

Colorless solid.

$^1$H NMR spectrum (CDCl$_3$, 400 MHz), δ: 7.49-7.46 (m, 1H), 7.35-7.21 (m, 3H), 4.90 (br s, 1H), 4.43 (br s, 1H), 3.88-3.82 (m, 1H), 3.58-3.24 (m, 4H), 2.80-2.40 (m, 4H), 2.04-1.96 (m, 1H), 1.45 (s, 9H), 1.31 (br d, 3H, J=7.0 Hz), 1.26 (br s, 3H), 1.23 (br s, 3H).

(76j) {(1S,2S,4R)-4-(2,2-Dimethylpropylcarbamoyl)-1-[4-(2-chlorophenyl)-2,2-dimethyl-5-oxopiperazin-1-ylmethyl]-2-hydroxypentyl}carbamic acid t-butyl ester 25 mg of 2-hydroxypyridine (0.26 mmol) was added to a solution of 250 mg of {(S)-2-[4-(2-chlorophenyl)-2,2-dimethyl-5-oxopiperazin-1-yl]-1-[(2S,4R)-4-methyl-5-oxotetrahydrofuran-2-yl]ethyl}carbamic acid t-butyl ester obtained in Example (76i) (0.52 mmol) in (2,2-dimethylpropyl)amine (1.22 ml) (10.4 mmol), and the mixture was stirred at 80° C. for two hours. The reaction mixture was cooled and then water was added, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/acetone=5/2-1/1) to obtain 283 mg of the title compound (yield: 96%).

Colorless solid.

$^1$H NMR spectrum (CDCl$_3$, 400 MHz), δ: 7.47 (dd, 1H, J=7.6 Hz, 1.8 Hz), 7.34-7.22 (m, 3H), 5.82 (br s, 1H), 5.03-4.75 (m, 2H), 3.94 (br s, 1H), 3.69-3.25 (m, 5H), 3.15 (dd, 1H, J=13.3 Hz, 6.7 Hz), 2.98 (dd, 1H, J=13.3 Hz, 5.9 Hz), 2.80-2.57 (m, 3H), 1.74-1.67 (m, 2H), 1.46 (br s, 9H), 1.26-1.23 (m, 9H), 0.91 (br s, 9H).

(76k) (2R,4S,5S)-5-Amino-6-[4-(2-chlorophenyl)-2,2-dimethyl-5-oxopiperazin-1-yl]-4-hydroxy-2-methylhexanoic acid (2,2-dimethylpropyl)amide hemifumarate (½ fumarate)

1.13 ml of trifluoroacetic acid (14.7 mmol) was added to a solution of 280 mg of {(1S,2S,4R)-4-(2,2-dimethylpropylcarbamoyl)-1-[4-(2-chlorophenyl)-2,2-dimethyl-5-oxopiperazin-1-ylmethyl]-2-hydroxypentyl}carbamic acid t-butyl ester obtained in Example (76j) (0.49 mmol) in methylene chloride (2 ml) at room temperature, and the mixture was stirred at the same temperature for 30 minutes. After concentration under reduced pressure, a saturated sodium bicarbonate aqueous solution was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol/triethylamine=100/10/1). 26 mg of fumaric acid (0.22 mmol) was added to a solution of 203 mg of (2R,4S,5S)-5-amino-6-[4-(2-chlorophenyl)-2,2-dimethyl-5-oxopiperazin-1-yl]-4-hydroxy-2-methylhexanoic acid (2,2-dimethylpropyl)amide obtained above (0.43 mmol) in methanol (3 ml), and the mixture was stirred at room temperature for five minutes. The reaction mixture was concentrated under reduced pressure, and methylene chloride (0.5 ml) was added to the residue. Diethyl ether (5 ml) was further added and the solid was collected by filtration to obtain 197 mg of the title compound (yield: 77%).

Colorless solid.

$^1$H NMR spectrum (CD$_3$OD, 400 MHz), δ: 7.99 (br t, 1H, J=5.9 Hz), 7.55-7.53 (m, 1H), 7.44-7.32 (m, 3H), 6.67 (1H, s), 3.67-3.52 (m, 3H), 3.38-3.11 (m, 4H), 2.98-2.91 (m, 1.6H), 2.78-2.68 (m, 1.8H), 2.51 (dd, 0.6H, J=13.3 Hz, 3.9 Hz), 1.94-1.87 (m, 1H), 1.59-1.52 (m, 1H), 1.31-1.26 (m, 6H), 1.21 (d, 3H, J=7.0 Hz), 0.92 (s, 9H).

mass spectrum (FAB$^+$), m/z: 467 ((M+H)$^+$).

Example 77

(2R,4S,5S)-5-Amino-6-[4-(2-chlorophenyl)-2,2-dimethyl-5-oxopiperazin-1-yl]-4-hydroxy-2-methylhexanoic acid isobutylamide hemifumarate (½ fumarate) (Exemplary Compound No. 2-154)

171 mg of the title compound (total yield over two steps: 65%) was obtained in the same manner as in Examples (1n) and (1o) using {(S)-2-[4-(2-chlorophenyl)-2,2-dimethyl-5-oxopiperazin-1-yl]-1-[(2S,4R)-4-methyl-5-oxotetrahydrofuran-2-yl]ethyl}carbamic acid t-butyl ester obtained in Example (76i) and isobutylamine.

Colorless solid.

$^1$H NMR spectrum (CD$_3$OD, 400 MHz), δ: 7.55-7.53 (m, 1H), 7.44-7.32 (m, 3H), 6.67 (1H, s), 3.67-3.51 (m, 3H), 3.37-3.05 (m, 4H), 2.98-2.92 (m, 1.6H), 2.80-2.67 (m, 1.8H), 2.51 (dd, 0.6H, J=13.3 Hz, 3.9 Hz), 1.93-1.86 (m, 1H), 1.84-1.74 (m, 1H), 1.59-1.52 (m, 1H), 1.31-1.26 (m, 6H), 1.20 (d, 3H, J=7.0 Hz), 0.92 (d, 6H, J=6.7 Hz).

mass spectrum (FAB$^+$), m/z: 453 ((M+H)$^+$).

Example 78

(2R,4S,5S)-5-Amino-6-[4-(2-chlorophenyl)-2,2-dimethyl-5-oxopiperazin-1-yl]-4-hydroxy-2-methyl-hexanoic acid (2-hydroxy-2-methylpropyl)amide hemifumarate (½ fumarate) (Exemplary Compound No. 2-168)

50 mg of the title compound (total yield over two steps: 21%) was obtained in the same manner as in Examples (1n) and (1o) using {(S)-2-[4-(2-chlorophenyl)-2,2-dimethyl-5-oxopiperazin-1-yl]-1-[(2S,4R)-4-methyl-5-oxotetrahydrofuran-2-yl]ethyl}carbamic acid t-butyl ester obtained in Example (76i) and (1,1-dimethylethanol)amine.

Colorless solid.

$^1$H NMR spectrum (CD$_3$OD, 400 MHz), δ: 7.55-7.53 (m, 1H), 7.43-7.32 (m, 3H), 6.66 (1H, s), 3.67-3.52 (m, 3H), 3.38-3.12 (m, 5H), 2.95 (t, 0.6H, J=11.0 Hz), 2.81-2.67 (m, 1.8H), 2.50 (dd, 0.6H, J=13.6 Hz, 3.9 Hz), 1.92-1.86 (m, 1H), 1.60-1.53 (m, 1H), 1.31-1.16 (m, 15H).

mass spectrum (FAB$^+$), m/z: 469 ((M+H)$^+$).

Example 79

(2R,4S,5S)-5-Amino-6-[4-(2-chlorophenyl)-2,2-dimethyl-5-oxopiperazin-1-yl]-4-hydroxy-2-methyl-hexanoic acid butylamide hemifumarate (½ fumarate) (Exemplary Compound No. 2-147)

154 mg of the title compound (total yield over two steps: 85%) was obtained in the same manner as in Examples (1n) and (1o) using {(S)-2-[4-(2-chlorophenyl)-2,2-dimethyl-5-oxopiperazin-1-yl]-1-[(2S,4R)-4-methyl-5-oxotetrahydrofuran-2-yl]ethyl}carbamic acid t-butyl ester obtained in Example (76i) and n-butylamine.

Colorless solid.

$^1$H NMR spectrum (CD$_3$OD, 400 MHz), δ: 7.56-7.54 (m, 1H), 7.44-7.32 (m, 3H), 6.68 (s, 1H), 3.67-3.48 (m, 3H), 3.38-3.11 (m, 5H), 2.99-2.93 (m, 0.6H), 2.82-2.65 (m, 1.8H), 2.51 (dd, 0.6H, J=13.5 Hz, 4.1 Hz), 1.92-1.85 (m, 1H), 1.59-1.47 (m, 3H), 1.41-1.34 (m, 2H), 1.31-1.26 (m, 6H), 1.19 (d, 3H, J=7.0 Hz), 0.96-0.93 (m, 3H).

mass spectrum (FAB$^+$), m/z: 453 ((M+H)$^+$).

Example 80

(2R,4S,5S)-5-Amino-6-[4-(2-chlorophenyl)-2,2-dimethyl-5-oxopiperazin-1-yl]-4-hydroxy-2-methyl-hexanoic acid [(S)-2-methylbutyl]amide hemifumarate (½ fumarate) (Exemplary Compound No. 2-247)

113 mg of the title compound (total yield over two steps: 68%) was obtained in the same manner as in Examples (1n) and (1o) using {(S)-2-[4-(2-chlorophenyl)-2,2-dimethyl-5-oxopiperazin-1-yl]-1-[(2S,4R)-4-methyl-5-oxotetrahydrofuran-2-yl]ethyl}carbamic acid t-butyl ester obtained in Example (76i) and [(S)-2-methylbutyl]amine.

Colorless solid.

$^1$H NMR spectrum (CD$_3$OD, 400 MHz), δ: 7.56-7.54 (m, 1H), 7.44-7.33 (m, 3H), 6.68 (s, 1H), 3.67-3.50 (m, 3H), 3.38-3.13 (m, 4H), 3.07 (d, 2H, J=7.0 Hz), 2.99-2.93 (m, 0.6H), 2.82-2.69 (m, 1.8H), 2.51 (dd, 0.6H, J=13.7 Hz, 3.9 Hz), 1.93-1.86 (m, 1H), 1.60-1.52 (m, 2H), 1.46-1.40 (m, 1H), 1.31-1.27 (m, 6H), 1.20 (d, 3H, J=7.0 Hz), 0.95-0.90 (m, 6H).

mass spectrum (FAB$^+$), m/z: 467 ((M+H)$^+$).

Example 81

(2R,4S,5S)-5-Amino-6-[4-(2-chlorophenyl)-2,2-dimethyl-5-oxopiperazin-1-yl]-4-hydroxy-2-methyl-hexanoic acid cyclopentylamide hemifumarate (½ fumarate) (Exemplary Compound No. 2-238)

170 mg of the title compound (total yield over two steps: 86%) was obtained in the same manner as in Examples (1n) and (1o) using {(S)-2-[4-(2-chlorophenyl)-2,2-dimethyl-5-oxopiperazin-1-yl]-1-[(2S,4R)-4-methyl-5-oxotetrahydrofuran-2-yl]ethyl}carbamic acid t-butyl ester obtained in Example (76i) and cyclopentylamine.

Colorless solid.

$^1$H NMR spectrum (CD$_3$OD, 400 MHz), δ: 7.56-7.54 (m, 1H), 7.42-7.32 (m, 3H), 6.69 (s, 1H), 4.13-4.10 (m, 1H), 3.67-3.50 (m, 3H), 3.38-3.13 (m, 4H), 2.99-2.92 (m, 0.6H), 2.78-2.64 (m, 0.8H), 2.52 (dd, 0.6H, J=13.5 Hz, 4.1 Hz), 1.96-1.86 (m, 3H), 1.75-1.71 (m, 2H), 1.62-1.43 (m, 5H), 1.31-1.26 (m, 6H), 1.18 (d, 3H, J=7.0 Hz).

mass spectrum (FAB$^+$), m/z: 465 ((M+H)$^+$).

Example 82

(2R,4S,5S)-5-Amino-6-[4-(2-chlorophenyl)-2,2-dimethyl-5-oxopiperazin-1-yl]-4-hydroxy-2-methyl-hexanoic acid cyclohexylamide fumarate (Exemplary Compound No. 2-233)

154 mg of the title compound (total yield over two steps: 83%) was obtained in the same manner as in Examples (1n) and (1o) using {(S)-2-[4-(2-chlorophenyl)-2,2-dimethyl-5-oxopiperazin-1-yl]-1-[(2S,4R)-4-methyl-5-oxotetrahydrofuran-2-yl]ethyl}carbamic acid t-butyl ester obtained in Example (76i) and cyclohexylamine.

Colorless solid.

$^1$H NMR spectrum (CD$_3$OD, 400 MHz), δ: 7.91-7.89 (m, 1H), 7.56-7.54 (m, 1H), 7.44-7.32 (m, 3H), 6.72 (s, 2H), 3.69-3.51 (m, 4H), 3.37-3.12 (m, 3H), 2.99-2.92 (m, 0.6H), 2.81-2.61 (m, 1.8H), 2.54-2.50 (m, 0.6H), 1.92-1.85 (m, 3H), 1.78-1.75 (m, 2H), 1.67-1.63 (m, 1H), 1.58-1.51 (m, 1H), 1.41-1.15 (m, 14H).

mass spectrum (FAB$^+$), m/z: 479 ((M+H)$^+$).

Example 83

(2R,4S,5S)-5-Amino-6-[4-(2-chlorophenyl)-2,2-dimethyl-5-oxopiperazin-1-yl]-4-hydroxy-2-methyl-hexanoic acid (4-fluorophenyl)amide fumarate (Exemplary Compound No. 2-235)

87 mg of the title compound (total yield over two steps: 45%) was obtained in the same manner as in Examples (41a) and (1o) using {(S)-2-[4-(2-chlorophenyl)-2,2-dimethyl-5-oxopiperazin-1-yl]-1-[(2S,4R)-4-methyl-5-oxotetrahydrofuran-2-yl]ethyl}carbamic acid t-butyl ester obtained in Example (76i) and 4-fluoroaniline.

Colorless solid.

$^1$H NMR spectrum (CD$_3$OD, 400 MHz), δ: 7.61-7.53 (m, 3H), 7.43-7.29 (m, 3H), 7.07-7.03 (m, 2H), 6.69 (s, 2H), 3.64-3.58 (m, 3H), 3.35-3.18 (m, 3H), 2.99-2.87 (m, 1.6H), 2.78-2.73 (m, 0.8H), 2.55-2.51 (m, 0.6H), 2.02-1.95 (m, 1H), 1.66-1.60 (m, 1H), 1.30-1.24 (m, 9H).

mass spectrum (FAB$^+$), m/z: 491 ((M+H)$^+$).

Example 84

(2R,4S,5S)-5-Amino-6-(2,2-dimethyl-5-oxo-4-phenylpiperazin-1-yl)-4-hydroxy-2-methylhexanoic acid (2,2-dimethylpropyl)amide hemifumarate (½ fumarate) (Exemplary Compound No. 2-179)

139 mg of the title compound (total yield over three steps: 67%) was obtained in the same manner as in Example (15b) using (3R,5S)-3-methyl-5-[(S)-1-(2-nitrobenzenesulfonyl) aziridin-2-yl]dihydrofuran-2-one obtained in Example (76g), 5,5-dimethyl-1-phenylpiperazin-2-one obtained in Example (14a) and (2,2-dimethylpropyl)amine.

Colorless solid.

$^1$H NMR spectrum (CD$_3$OD, 400 MHz), δ: 7.46-7.42 (m, 2H), 7.34-7.28 (m, 3H), 6.68 (s, 1H), 3.73-3.52 (m, 3H), 3.40-3.12 (m, 4H), 2.94-2.84 (m, 2H), 2.78-2.74 (m, 1H), 2.55 (dd, 1H, J=13.9 Hz, 4.5 Hz), 1.94-1.87 (m, 1H), 1.58-1.51 (m, 1H), 1.25-1.21 (m, 9H), 0.92 (s, 9H).

mass spectrum (FAB$^+$), m/z: 433 ((M+H)$^+$).

Example 85

(2R,4S,5S)-5-Amino-6-[2,2-dimethyl-4-(2-methylphenyl)-5-oxopiperazin-1-yl]-4-hydroxy-2-methylhexanoic acid (2,2-dimethylpropyl)amide hemifumarate (½ fumarate) (Exemplary Compound No. 2-180)

(85a) N-{(S)-2-[2,2-Dimethyl-4-(2-methylphenyl)-5-oxopiperazin-1-yl]-1-[(2S,4R)-4-methyl-5-oxotetrahydrofuran-2-yl]ethyl}-2-nitrobenzenesulfonamide A solution of 590 mg of (3R,5S)-3-methyl-5-[(S)-1-(2-nitrobenzenesulfonyl)aziridin-2-yl]dihydrofuran-2-one obtained in Example (76g) (1.8 mmol) and 512 mg of 5,5-dimethyl-1-(2-methylphenyl)piperazin-2-one obtained in Example (51d) (2.35 mmol) in toluene (18 ml) was stirred at 110° C. for two hours. After cooling, the reaction mixture was concentrated under reduced pressure, and the residue was purified by silica gel column chromatography (elution solvent: toluene/acetone=4/1-3/1) to obtain 1.01 g of the title compound (yield: quant.).

Colorless solid.

$^1$H NMR spectrum (CDCl$_3$, 400 MHz), δ: 8.18-8.16 (m, 1H), 7.96-7.90 (m, 1H), 7.84-7.74 (m, 2H), 7.28-7.14 (m, 3H), 7.07-7.05 (m, 0.4H), 6.95-6.93 (m, 0.6H), 5.90 (br d, 0.6H, J=6.3 Hz), 5.66 (br d, 0.4H, J=7.4 Hz), 4.96-4.93 (m, 0.4H), 4.88-4.84 (m, 0.6H), 3.68-3.59 (m, 1H), 3.38 (d, 0.4H, J=12.1 Hz), 3.28 (d, 0.4H, J=17.2 Hz), 3.17-3.02 (m, 2.2H), 2.96-2.50 (m, 5H), 2.15-2.03 (m, 4H), 1.34-1.31 (m, 3H), 1.16-1.03 (m, 6H).

(85b) {(S)-2-[2,2-Dimethyl-4-(2-methylphenyl)-5-oxopiperazin-1-yl]-1-[(2S,4R)-4-methyl-5-oxotetrahydrofuran-2-yl]ethyl}carbamic acid t-butyl ester 704 mg of cesium carbonate (2.16 mmol) was added to a solution of 980 mg of N-{(S)-2-[2,2-dimethyl-4-(2-methylphenyl)-5-oxopiperazin-1-yl]-1-[(2S,4R)-4-methyl-5-oxotetrahydrofuran-2-yl]ethyl}-2-nitrobenzenesulfonamide obtained in Example (85a) (1.8 mmol) and 0.55 ml of thiophenol (content: 95%) (5.4 mmol) in acetonitrile (18 ml) under a nitrogen atmosphere at room temperature, and the mixture was stirred at the same temperature for two hours. Brine was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol=20/1-10/1). 160 mg of sodium bicarbonate (1.9 mmol) and 416 mg of di-t-butyl dicarbonate (1.9 mmol) were added to a solution of 4-{(S)-2-amino-2-[(2S,4R)-4-methyl-5-oxotetrahydrofuran-2-yl]ethyl}-5,5-dimethyl-1-(2-methylphenyl)piperazin-2-one obtained above in ethyl acetate (7 ml)-water (7 ml), and the mixture was stirred at room temperature for 2.5 hours. Brine was added to the reaction mixture, followed by extraction with ethyl acetate. Then, the organic layer was dried over anhydrous magnesium sulfate. After filtration, the solvent was evaporated under reduced pressure, and the residue was purified by silica gel column chromatography (elution solvent:methylene chloride/ethyl acetate=2/1) to obtain 506 mg of the title compound (yield: 62%).

Colorless solid.

$^1$H NMR spectrum (CDCl$_3$, 400 MHz), δ: 7.28-7.23 (m, 3H), 7.12-7.06 (m, 1H), 4.92-4.86 (m, 1H), 4.44 (br s, 1H), 3.86 (br s, 1H), 3.56-3.17 (m, 4H), 2.76-2.42 (m, 4H), 2.24 (bs s, 1.5H), 2.23 (br s, 1.5H), 2.05-1.96 (m, 1H), 1.45 (br s, 9H), 1.32 (br d, 3H, J=7.4 Hz), 1.23 (br s, 6H).

(85c) {(1S,2S,4R)-4-(2,2-Dimethylpropylcarbamoyl)-1-[2,2-dimethyl-4-(2-methylphenyl)-5-oxopiperazin-1-ylmethyl]-2-hydroxypentyl}carbamic acid t-butyl ester 6.8 mg of 2-hydroxypyridine (0.072 mmol) was added to a solution of 165 mg of {(S)-2-[2,2-dimethyl-4-(2-methylphenyl)-5-oxopiperazin-1-yl]-1-[(2S,4R)-4-methyl-5-oxotetrahydrofuran-2-yl]ethyl}carbamic acid t-butyl ester obtained in Example (85b) (0.36 mmol) in (2,2-dimethylpropyl)amine (1.5 ml), and the mixture was stirred at 80° C. for 2.5 hours. The reaction mixture was cooled and then water was added, followed by extraction with ethyl acetate. Then, the organic layer was dried over anhydrous magnesium sulfate. After filtration, the solvent was evaporated under reduced pressure, and the residue was purified by silica gel column chromatography (elution solvent:methylene chloride/methanol=20/1) to obtain 167 mg of the title compound (yield: 85%).

Colorless solid.

$^1$H NMR spectrum (CDCl$_3$, 500 MHz), δ: 7.26-7.22 (m, 3H), 7.09-7.07 (m, 1H), 5.84 (br s, 1H), 5.02 (br s, 1H), 4.83 (br s, 1H), 3.95-3.91 (m, 1H), 3.67-3.13 (m, 6H), 2.98 (dd, 1H, J=13.2 Hz, 5.4 Hz), 2.77-2.57 (m, 3H), 2.22 (br s, 3H), 1.75-1.66 (m, 2H), 1.46 (br s, 9H), 1.25-1.22 (m, 9H), 0.91 (br s, 9H).

(85d) (2R,4S,5S)-5-Amino-6-[2,2-dimethyl-4-(2-methylphenyl)-5-oxopiperazin-1-yl]-4-hydroxy-2-methylhexanoic acid (2,2-dimethylpropyl)amide hemifumarate (½ fumarate)

0.71 ml of trifluoroacetic acid (9.16 mmol) was added to a solution of 167 mg of {(1S,2S,4R)-4-(2,2-dimethylpropylcarbamoyl)-1-[2,2-dimethyl-4-(2-methylphenyl)-5-oxopiperazin-1-ylmethyl]-2-hydroxypentyl}carbamic acid t-butyl ester obtained in Example (85c) (0.31 mmol) in methylene chloride (1.4 ml) at room temperature, and the mixture was stirred at the same temperature for 30 minutes. After concentration under reduced pressure, a saturated sodium bicarbonate aqueous solution was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol/triethylamine=100/10/1). 18 mg of fumaric acid (0.15 mmol) was added to a solution of 135 mg of (2R,4S,5S)-5-amino-6-[2,2-dimethyl-4-(2-methylphenyl)-5-oxopiperazin-1-yl]-4-hydroxy-2-methylhexanoic acid (2,2-dimethylpropyl)amide obtained above (0.3 mmol) in methanol (3 ml), and the mixture was stirred at room temperature for five minutes. The reaction mixture was concentrated under reduced pressure, and methylene chloride (0.5 ml) was added to the residue. Diisopropyl ether (5 ml) was further added and the solid was collected by filtration to obtain 145 mg of the title compound (yield: 99%).

Colorless solid.

$^1$H NMR spectrum (CD$_3$OD, 400 MHz), δ: 7.98 (br s, 1H), 7.33-7.25 (m, 3H), 7.18-7.12 (m, 1H), 6.71 (s, 1H), 3.70-3.52 (m, 3H), 3.38-3.12 (m, 4H), 2.97-2.90 (m, 1.6H), 2.85-2.75 (m, 1.4H), 2.67-2.62 (m, 0.4H), 2.51 (dd, 0.6H, J=13.5 Hz, 3.7 Hz), 2.24-2.23 (m, 3H), 1.94-1.88 (m, 1H), 1.58-1.52 (m, 1H), 1.28-1.21 (m, 9H), 0.92 (s, 9H).

mass spectrum (FAB$^+$), m/z: 447 ((M+H)$^+$).

Example 86

(2R,4S,5S)-5-Amino-6-[2,2-dimethyl-4-(2-methylphenyl)-5-oxopiperazin-1-yl]-4-hydroxy-2-methylhexanoic acid cyclohexylamide hemifumarate (½ fumarate) (Exemplary Compound No. 2-245)

(86a) {(1S,2S,4R)-4-(Cyclohexylcarbamoyl)-1-[2,2-dimethyl-4-(2-methylphenyl)-5-oxopiperazin-1-ylmethyl]-2-hydroxypentyl}carbamic acid t-butyl ester 6.8 mg of 2-hydroxypyridine (0.072 mmol) was added to a solution of 165 mg of {(S)-2-[2,2-dimethyl-4-(2-methylphenyl)-5-oxopiperazin-1-yl]-1-[(2S,4R)-4-methyl-5-oxotetrahydrofuran-2-yl]ethyl}carbamic acid t-butyl ester obtained in Example (85b) (0.36 mmol) in cyclohexylamine (1.5 ml), and the mixture was stirred at 80° C. for one hour. The reaction mixture was cooled and then water was added, followed by extraction with ethyl acetate. Then, the organic layer was dried over anhydrous magnesium sulfate. After filtration, the solvent was evaporated under reduced pressure, and the residue was purified by silica gel column chromatography (elution solvent:methylene chloride/methanol=20/1) to obtain 191 mg of the title compound (yield: 95%).

Colorless solid.

$^1$H NMR spectrum (CDCl$_3$, 400 MHz), δ: 7.26-7.22 (m, 3H), 7.09-7.07 (m, 1H), 5.65 (br s, 1H), 5.02 (br s, 1H), 4.94 (br s, 1H), 3.92 (br s, 1H), 3.80-3.71 (m, 1H), 3.68-3.17 (m, 6H), 2.77-2.48 (m, 3H), 2.22 (br s, 3H), 1.92-1.89 (m, 2H), 1.72-1.61 (m, 4H), 1.46-1.08 (m, 23H).

(86b) (2R,4S,5S)-5-Amino-6-[2,2-dimethyl-4-(2-methylphenyl)-5-oxopiperazin-1-yl]-4-hydroxy-2-methylhexanoic acid cyclohexylamide hemifumarate (½ fumarate)

0.79 ml of trifluoroacetic acid (10.26 mmol) was added to a solution of 191 mg of {(1S,2S,4R)-4-(cyclohexylcarbamoyl)-1-[2,2-dimethyl-4-(2-methylphenyl)-5-oxopiperazin-1-ylmethyl]-2-hydroxypentyl}carbamic acid t-butyl ester obtained in Example (86a) (0.34 mmol) in methylene chloride (1.6 ml) at room temperature, and the mixture was stirred at the same temperature for 30 minutes. After concentration under reduced pressure, a saturated sodium bicarbonate aqueous solution was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol/triethylamine=100/10/1). 16 mg of fumaric acid (0.14 mmol) was added to a solution of 125 mg of (2R,4S,5S)-5-amino-6-[2,2-dimethyl-4-(2-methylphenyl)-5-oxopiperazin-1-yl]-4-hydroxy-2-methylhexanoic acid cyclohexylamide obtained above (0.27 mmol) in methanol (3 ml), and the mixture was stirred at room temperature for five minutes. The reaction mixture was concentrated under reduced pressure, and methylene chloride (0.5 ml) was added to the residue. Diisopropyl ether (5 ml) was further added and the solid was collected by filtration to obtain 139 mg of the title compound (yield: 81%).

Colorless solid.

$^1$H NMR spectrum (CD$_3$OD, 400 MHz), δ: 7.32-7.26 (m, 3H), 7.19-7.11 (m, 1H), 6.67 (s, 1H), 3.66-3.51 (m, 4H), 3.37-3.12 (m, 3H), 2.96-2.90 (m, 0.6H), 2.80-2.78 (m, 0.4H), 2.68-2.62 (m, 1.4H), 2.51 (dd, 0.6H, J=13.5 Hz, 4.1 Hz), 2.24-2.23 (m, 3H), 1.91-1.75 (m, 3H), 1.78-1.75 (m, 2H), 1.66-1.63 (m, 1H), 1.58-1.51 (m, 1H), 1.37-1.14 (m, 14H).

mass spectrum (FAB$^+$), m/z: 459 ((M+H)$^+$).

Example 87

(2R,4S,5S)-5-Amino-6-[4-(2-ethylphenyl)-2,2-dimethyl-5-oxopiperazin-1-yl]-4-hydroxy-2-methylhexanoic acid (2,2-dimethylpropyl)amide hemifumarate (½ fumarate) (Exemplary Compound No. 2-198)

76 mg of the title compound (total yield over four steps: 50%) was obtained in the same manner as in Examples (1l) to (1o) using (3R,5S)-3-methyl-5-[(S)-1-(2-nitrobenzenesulfonyl)aziridin-2-yl]dihydrofuran-2-one obtained in Example (76g), 1-(2-ethylphenyl)-5,5-dimethylpiperazin-2-one obtained in Example (53a) and (2,2-dimethylpropyl)amine).

Colorless solid.

$^1$H NMR spectrum (CD$_3$OD, 400 MHz), δ: 7.37-7.25 (m, 4H), 7.16-7.10 (m, 1H), 6.66 (s, 1H), 3.97-3.51 (m, 3H), 3.37-3.11 (m, 4H), 2.95-2.89 (m, 1.6H), 2.82-2.74 (m, 1.4H), 2.67-2.48 (m, 3H), 1.94-1.88 (m, 1H), 1.59-1.52 (m, 1H), 1.28-1.18 (m, 12H), 0.92 (s, 9H).

mass spectrum (FAB$^+$), m/z: 461 ((M+H)$^+$).

Example 88

(2R,4S,5S)-5-Amino-6-[2,2-dimethyl-5-oxo-4-(2-trifluoromethylphenyl)piperazin-1-yl]-4-hydroxy-2-methylhexanoic acid (2,2-dimethylpropyl)amide hemifumarate (½ fumarate) (Exemplary Compound No. 2-241)

112 mg of the title compound (total yield over three steps: 55%) was obtained in the same manner as in Example (19b) using (3R,5S)-3-methyl-5-[(S)-1-(2-nitrobenzenesulfonyl)aziridin-2-yl]dihydrofuran-2-one obtained in Example (76g), 5,5-dimethyl-1-(2-trifluoromethylphenyl)piperazin-2-one obtained in Example (54a) and (2,2-dimethylpropyl)amine.

Colorless solid.

$^1$H NMR spectrum (CD$_3$OD, 400 MHz), δ: 7.97 (br s, 1H), 7.83-7.74 (m, 2H), 7.62-7.58 (m, 1H), 7.45-7.40 (m, 1H), 6.68 (s, 1H), 3.67-3.52 (m, 3H), 3.35-3.12 (m, 4H), 3.00-2.90

(m, 1.6H), 2.79-2.72 (m, 1.8H), 2.48 (dd, 0.6H, J=13.5 Hz, 4.1 Hz), 1.95-1.88 (m, 1H), 1.59-1.52 (m, 1H), 1.27-1.22 (m, 9H), 0.92 (s, 9H).

mass spectrum (FAB+), m/z: 501 ((M+H)+).

Example 89

(2R,4S,5S)-5-Amino-6-[4-(2,3-difluorophenyl)-2,2-dimethyl-5-oxopiperazin-1-yl]-4-hydroxy-2-methyl-hexanoic acid (2,2-dimethylpropyl)amide hemifumarate (½ fumarate) (Exemplary Compound No. 2-236)

116 mg of the title compound (total yield over four steps: 51%) was obtained in the same manner as in Examples (11) to (1o) using (3R,5S)-3-methyl-5-[(S)-1-(2-nitrobenzenesulfonyl)aziridin-2-yl]dihydrofuran-2-one obtained in Example (76g), 1-(2,3-difluorophenyl)-5,5-dimethylpiperazin-2-one obtained in Example (20a) and (2,2-dimethylpropyl)amine.

Colorless solid.

$^1$H NMR spectrum (CD$_3$OD, 400 MHz), δ: 7.34-7.22 (m, 2H), 7.16-7.13 (m, 1H), 6.67 (s, 1H), 3.72-3.63 (m, 2H), 3.57-3.52 (m, 1H), 3.38-3.29 (m, 3H), 3.15-3.11 (m, 1H), 2.95-2.85 (m, 2H), 2.79-2.73 (m, 1H), 2.57 (dd, 1H, J=13.7 Hz, 4.3 Hz), 1.94-1.87 (m, 1H), 1.58-1.51 (m, 1H), 1.26 (s, 6H), 1.22 (d, 6H, J=7.0 Hz), 0.92 (s, 9H).

mass spectrum (FAB+), m/z: 469 ((M+H)+).

Example 90

(2R,4S,5S)-5-Amino-6-[4-(2,3-difluorophenyl)-2,2-dimethyl-5-oxopiperazin-1-yl]-4-hydroxy-2-methyl-hexanoic acid cyclopentylamide hemifumarate (½ fumarate) (Exemplary Compound No. 2-252)

186 mg of the title compound (total yield over four steps: 56%) was obtained in the same manner as in Examples (11) to (1o) using (3R,5S)-3-methyl-5-[(S)-1-(2-nitrobenzenesulfonyl)aziridin-2-yl]dihydrofuran-2-one obtained in Example (76g), 1-(2,3-difluorophenyl)-5,5-dimethylpiperazin-2-one obtained in Example (20a) and cyclopentylamine.

Colorless solid.

$^1$H NMR spectrum (CD$_3$OD, 500 MHz), δ: 7.33-7.22 (m, 2H), 7.14 (br t, 1H, J=6.8 Hz), 6.66 (s, 1H), 4.14-4.08 (m, 1H), 3.70-3.63 (m, 2H), 3.53-3.51 (m, 1H), 3.37-3.30 (m, 2H), 3.17-3.14 (m, 1H), 2.89-2.85 (m, 1H), 2.69-2.65 (m, 1H), 2.57 (dd, 1H, J=13.4 Hz, 3.7 Hz), 1.94-1.85 (m, 3H), 1.74-1.69 (m, 2H), 1.63-1.43 (m, 5H), 1.25 (br s, 6H), 1.17 (br d, 3H, J=7.0 Hz).

mass spectrum (FAB+), m/z: 467 ((M+H)+).

Example 91

(2R,4S,5S)-5-Amino-6-[4-(2,3-difluorophenyl)-2,2-dimethyl-5-oxopiperazin-1-yl]-4-hydroxy-2-methyl-hexanoic acid cyclohexylamide hemifumarate (½ fumarate) (Exemplary Compound No. 2-248)

125 mg of the title compound (total yield over four steps: 48%) was obtained in the same manner as in Examples (11) to (1o) using (3R,5S)-3-methyl-5-[(S)-1-(2-nitrobenzenesulfonyl)aziridin-2-yl]dihydrofuran-2-one obtained in Example (76g), 1-(2,3-difluorophenyl)-5,5-dimethylpiperazin-2-one obtained in Example (20a) and cyclohexylamine.

Colorless solid.

$^1$H NMR spectrum (CD$_3$OD, 400 MHz), δ: 7.34-7.22 (m, 2H), 7.17-7.13 (m, 1H), 6.67 (s, 1H), 3.72-3.62 (m, 3H), 3.55-3.51 (m, 1H), 3.38-3.31 (m, 2H), 3.14 (br s, 1H), 2.89-2.82 (m, 1H), 2.65 (br s, 1H), 2.65 (br dd, 1H, J=13.7 Hz, 4.7 Hz), 1.91-1.85 (m, 3H), 1.78-1.74 (m, 2H), 1.66-1.62 (m, 1H), 1.58-1.52 (m, 1H), 1.40-1.14 (m, 14H).

mass spectrum (FAB+), m/z: 481 ((M+H)+).

Example 92

(2R,4S,5S)-5-Amino-6-[4-(2,5-difluorophenyl)-2,2-dimethyl-5-oxopiperazin-1-yl]-4-hydroxy-2-methyl-hexanoic acid (2,2-dimethylpropyl)amide hemifumarate (½ fumarate) (Exemplary Compound No. 2-244)

128 mg of the title compound (total yield over three steps: 66%) was obtained in the same manner as in Example (15b) using (3R,5S)-3-methyl-5-[(S)-1-(2-nitrobenzenesulfonyl)aziridin-2-yl]dihydrofuran-2-one obtained in Example (76g), 1-(2,5-difluorophenyl)-5,5-dimethyl piperazin-2-one obtained in Example (24a) and (2,2-dimethylpropyl)amine.

Colorless solid.

$^1$H NMR spectrum (CD$_3$OD, 400 MHz), δ: 7.30-7.24 (m, 1H), 7.19-7.14 (m, 2H), 6.68 (s, 1H), 3.69-3.52 (m, 3H), 3.37-3.12 (m, 4H), 2.94-2.85 (m, 2H), 2.79-2.73 (m, 1H), 2.56 (dd, 1H, J=13.9 Hz, 4.1 Hz), 1.94-1.87 (m, 1H), 1.58-1.51 (m, 1H), 1.25-1.21 (m, 9H), 0.92 (s, 9H).

mass spectrum (FAB+), m/z: 469 ((M+H)+).

Example 93

(2R,4S,5S)-5-Amino-6-[4-(2,6-difluorophenyl)-2,2-dimethyl-5-oxopiperazin-1-yl]-4-hydroxy-2-methyl-hexanoic acid (2,2-dimethylpropyl)amide hemifumarate (½ fumarate) (Exemplary Compound No. 2-237)

(93a) N-{(S)-2-[4-(2,6-Difluorophenyl)-2,2-dimethyl-5-oxopiperazin-1-yl]-1-[(2S,4R)-4-methyl-5-oxotetrahydrofuran-2-yl]ethyl}-2-nitrobenzenesulfonamide A solution of 600 mg of (3R,5S)-3-methyl-5-[(S)-1-(2-nitrobenzenesulfonyl)aziridin-2-yl]dihydrofuran-2-one obtained in Example (76g) (1.84 mmol) and 574 mg of 1-(2,6-difluorophenyl)-5,5-dimethylpiperazin-2-one obtained in Example (60d) (2.40 mmol) in toluene (18 ml) was stirred at 110° C. for two hours. After cooling, the reaction mixture was concentrated under reduced pressure, and the residue was purified by silica gel column chromatography (elution solvent: toluene/acetone=5/1) to obtain 1.03 g of the title compound (yield: 99%).

Colorless solid.

$^1$H NMR spectrum (CDCl$_3$, 400 MHz), δ: 8.16 (dd, 1H, J=7.2 Hz, 1.8 Hz), 7.95-7.93 (m, 1H), 7.82-7.75 (m, 2H), 7.33-7.25 (m, 1H), 7.01-6.94 (m, 2H), 5.66 (br d, 1H, J=7.8 Hz), 4.81-4.77 (m, 1H), 3.68-3.62 (m, 1H), 3.14-2.90 (m, 5H), 2.79-2.72 (m, 1H), 2.57-2.56 (m, 2H), 2.13-2.06 (m, 1H), 1.33 (d, 3H, J=7.4 Hz), 1.11 (s, 3H), 1.03 (s, 3H).

(93b) {(S)-2-[4-(2,6-Difluorophenyl)-2,2-dimethyl-5-oxopiperazin-1-yl]-1-[(2S,4R)-4-methyl-5-oxotetrahydrofuran-2-yl]ethyl}carbamic acid t-butyl ester 711 mg of cesium carbonate (2.18 mmol) was added to a solution of 1.03 g of N-{(S)-2-[4-(2,6-difluorophenyl)-2,2-dimethyl-5-oxopiperazin-1-yl]-1-[(2S,4R)-4-methyl-5-oxotetrahydrofuran-2-yl]ethyl}-2-nitrobenzenesulfonamide obtained in Example (93a) (1.82 mmol) and 0.56 ml of thiophenol (content: 95%) (5.45 mmol) in acetonitrile (18 ml) under a nitrogen atmosphere at room temperature, and the mixture was stirred at the same temperature for two hours. Brine was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol=20/1-10/1). 170 mg of sodium bicarbonate (2.02 mmol) and 442 mg of di-t-butyl dicarbonate (2.02 mmol) were added to a solution of the resulting 4-{(S)-2-amino-2-[(2S,4R)-4-methyl-5-oxotetrahydrofuran-2-yl]ethyl}1-(2,6-difluorophenyl)-5,5-dimethylpiperazin-2-one in ethyl acetate (8 ml)-water (8 ml), and the mixture was stirred at room temperature for two hours. Brine was added to the reaction mixture, followed by extraction with ethyl acetate. Then, the organic layer was dried over anhydrous magnesium sulfate. After filtration, the solvent was evaporated under reduced pressure, and the residue was purified by silica gel column chromatography (elution solvent:methylene chloride/ethyl acetate=3/1) to obtain 657 mg of the title compound (yield: 75%). Colorless solid.

$^1$H NMR spectrum (CDCl$_3$, 500 MHz), δ: 7.31-7.25 (m, 1H), 6.98 (br t, 2H, J=8.4 Hz), 4.92-4.89 (m, 1H), 4.42 (br d, 1H, J=9.3 Hz), 3.87-3.82 (m, 1H), 3.56 (br d, 1H, J=18.1 Hz), 3.51 (br d, 1H, J=18.1 Hz), 3.44 (br d, 1H, J=11.2 Hz), 3.31 (br d, 1H, J=11.2 Hz), 2.76-2.67 (m, 2H), 2.52-2.42 (m, 2H), 2.03-1.98 (m, 1H), 1.45 (br s, 9H), 1.32 (br d, 3H, J=7.4 Hz), 1.22 (br s, 6H).

(93c) {(1S,2S,4R)-4-(2,2-Dimethylpropylcarbamoyl)-1-[4-(2,6-difluorophenyl)-2,2-dimethyl-5-oxopiperazin-1-ylmethyl]-2-hydroxypentyl}carbamic acid t-butyl ester 8 mg of 2-hydroxypyridine (0.083 mmol) was added to a solution of 200 mg of {(S)-2-[4-(2,6-difluorophenyl)-2,2-dimethyl-5-oxopiperazin-1-yl]-1-[(2S,4R)-4-methyl-5-oxotetrahydrofuran-2-yl]ethyl}carbamic acid t-butyl ester obtained in Example (93b) (0.42 mmol) in (2,2-dimethylpropyl)amine (1 ml), and the mixture was stirred at 80° C. for six hours. The reaction mixture was cooled and then water was added, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol=40/1-20/1) to obtain 221 mg of the title compound (yield: 94%).

Colorless solid.

$^1$H NMR spectrum (CDCl$_3$, 500 MHz), δ: 7.31-7.25 (m, 1H), 6.97 (br t, 1H, J=8.6 Hz), 5.86 (br s, 1H), 5.01 (br s, 1H), 4.77 (br s, 1H), 3.93 (br d, 1H, J=7.8 Hz), 3.66 (br d, 1H, J=18.1 Hz), 3.53-3.46 (m, 2H), 3.41 (br d, 1H, J=11.7 Hz), 3.32 (br d, 1H, J=11.7 Hz), 3.15 (br dd, 1H, J=12.9 Hz, 6.6 Hz), 2.98 (dd, 1H, J=12.9 Hz, 4.9 Hz), 2.69-2.57 (m, 3H), 1.78-1.61 (m, 2H), 1.45 (br s, 9H), 1.24-1.22 (m, 9H), 0.91 (br s, 9H).

(93d) (2R,4S,5S)-5-Amino-6-[4-(2,6-difluorophenyl)-2,2-dimethyl-5-oxopiperazin-1-yl]-4-hydroxy-2-methylhexanoic acid (2,2-dimethylpropyl)amide hemifumarate (½ fumarate)

0.90 ml of trifluoroacetic acid (11.7 mmol) was added to a solution of 221 mg of {(1S,2S,4R)-4-(2-carbamoyl-2-methylpropylcarbamoyl)-1-[4-(2,6-difluorophenyl)-2,2-dimethyl-5-oxopiperazin-1-ylmethyl]-2-hydroxypentyl}carbamic acid t-butyl ester obtained in Example (93c) (0.39 mmol) in methylene chloride (1.8 ml) at room temperature, and the mixture was stirred at the same temperature for 30 minutes. After concentration under reduced pressure, a saturated sodium bicarbonate aqueous solution was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol/triethylamine 100/10/1). 22 mg of fumaric acid (0.19 mmol) was added to a solution of 169 mg of (2R,4S,5S)-5-amino-6-[4-(2,6-difluorophenyl)-2,2-dimethyl-5-oxopiperazin-1-yl]-4-hydroxy-2-methylhexanoic acid 2,2-dimethylpropylamide obtained above (0.38 mmol) in methanol (4 ml), and the mixture was stirred at room temperature for five minutes. The reaction mixture was concentrated under reduced pressure, and methylene chloride (0.5 ml) was added to the residue. Diisopropyl ether (5 ml) was further added and the solid was collected by filtration to obtain 167 mg of the title compound (yield: 84%).

Colorless solid.

$^1$H NMR spectrum (CD$_3$OD, 400 MHz), δ: 7.98 (br s, 1H), 7.48-7.41 (m, 1H), 7.14-7.09 (m, 2H), 6.69 (s, 1H), 3.74-3.67 (m, 3H), 3.57-3.48 (m, 1H), 3.35-3.11 (m, 3H), 2.95-2.86 (m, 2H), 2.78-2.73 (m, 1H), 2.57 (dd, 1H, J=13.3 Hz, 3.3 Hz), 1.94-1.87 (m, 1H), 1.58-1.51 (m, 1H), 1.26-1.21 (m, 9H), 0.92 (s, 9H).

mass spectrum (FAB$^+$), m/z: 469 ((M+H)$^+$).

Example 94

(2R,4S,5S)-5-Amino-6-[4-(2,6-difluorophenyl)-2,2-dimethyl-5-oxopiperazin-1-yl]-4-hydroxy-2-methylhexanoic acid cyclopentylamide hemifumarate (½ fumarate) (Exemplary Compound No. 2-253)

188 mg of the title compound (total yield over two steps: 73%) was obtained in the same manner as in Examples (1n) and (1o) using {(S)-2-[4-(2,6-difluorophenyl)-2,2-dimethyl-5-oxopiperazin-1-yl]-1-[(2S,4R)-4-methyl-5-oxotetrahydrofuran-2-yl]ethyl}carbamic acid t-butyl ester obtained in Example (93b) and cyclopentylamine.

Colorless solid.

$^1$H NMR spectrum (CD$_3$OD, 500 MHz), δ: 7.47-7.41 (m, 1H), 7.11 (br t, 2H, J=8.6 Hz), 6.67 (s, 1H), 4.14-4.08 (m, 1H), 3.70-3.66 (m, 2H), 3.54-3.51 (m, 1H), 3.35-3.31 (m, 2H), 3.13 (br s, 1H), 2.90-2.85 (m, 1H), 2.66 (br s, 1H), 2.57 (br d, 1H, J=13.1 Hz), 1.95-1.85 (m, 3H), 1.73 (br s, 2H), 1.63-1.43 (m, 5H), 1.26 (br s, 6H), 1.17 (br d, 3H, J=6.8 Hz).

mass spectrum (FAB$^+$), m/z: 467 ((M+H)$^+$).

Example 95

(2R,4S,5S)-5-Amino-6-[4-(2,6-difluorophenyl)-2,2-dimethyl-5-oxopiperazin-1-yl]-4-hydroxy-2-methylhexanoic acid cyclohexylamide hemifumarate (½ fumarate) (Exemplary Compound No. 2-249)

(95a) {(1S,2S,4R)-4-(Cyclohexylcarbamoyl)-1-[4-(2,6-difluorophenyl)-2,2-dimethyl-5-oxopiperazin-1-ylmethyl]-2-hydroxypentyl}carbamic acid t-butyl ester 7.9 mg of 2-hydroxypyridine (0.08 mmol) was added to a solution of 200 mg of {(S)-2-[4-(2,6-difluorophenyl)-2,2- dimethyl-5-oxopiperazin-1-yl]-1-[(2S,4R)-4-methyl-5-oxotetrahydrofuran-2-yl]ethyl}carbamic acid t-butyl ester obtained in Example (93b) (0.41 mmol) in cyclohexylamine (1.0 ml), and the mixture was stirred at 80° C. for three hours. The reaction mixture was cooled and then water was added, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol=20/1) to obtain 218 mg of the title compound (yield: 88%).

Colorless solid.

$^1$H NMR spectrum (CDCl$_3$, 400 MHz), δ: 7.32-7.24 (m, 1H), 6.97 (br t, 1H, J=8.4 Hz), 5.71 (br d, 1H, J=7.8 Hz), 5.02 (br s, 1H), 4.84 (br s, 1H), 3.91 (br d, 1H, J=8.6 Hz), 3.79-3.65 (m, 2H), 3.54-3.36 (m, 3H), 3.32 (br d, 1H, J=11.7 Hz), 2.69-2.48 (m, 3H), 1.92-1.89 (m, 2H), 1.73-1.59 (m, 5H), 1.46-1.09 (m, 23H).

(95b) (2R,4S,5S)-5-Amino-6-[4-(2,6-difluorophenyl)-2,2-dimethyl-5-oxopiperazin-1-yl]-4-hydroxy-2-methylhexanoic acid cyclohexylamide hemifumarate (½ fumarate)

0.88 ml of trifluoroacetic acid (11.3 mmol) was added to a solution of 218 mg of {(1S,2S,4R)-4-(cyclohexylcarbamoyl)-1-[4-(2,6-difluorophenyl)-2,2-dimethyl-5-oxopiperazin-1-ylmethyl]-2-hydroxypentyl}carbamic acid t-butyl ester obtained in Example (95a) (0.38 mmol) in methylene chloride (1.7 ml) at room temperature, and the mixture was stirred at the same temperature for 30 minutes. After concentration under reduced pressure, a saturated sodium bicarbonate aqueous solution was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol/triethylamine=100/10/1). 15 mg of fumaric acid (0.13 mmol) was added to a solution of 126 mg of (2R,4S,5S)-5-amino-6-[4-(2,6-difluorophenyl)-2,2-dimethyl-5-oxopiperazin-1-yl]-4-hydroxy-2-methylhexanoic acid cyclohexylamide obtained above (0.26 mmol) in methanol (3 ml), and the mixture was stirred at room temperature for five minutes. The reaction mixture was concentrated under reduced pressure, and methylene chloride (0.5 ml) was added to the residue. Diisopropyl ether (5 ml) was further added and the solid was collected by filtration to obtain 127 mg of the title compound (yield: 90%).

Colorless solid.

$^1$H NMR spectrum (CD$_3$OD, 400 MHz), δ: 7.47-7.40 (m, 2H), 7.11 (t, 1H, J=8.6 Hz), 6.66 (s, 1H), 3.71-3.62 (m, 3H), 3.56-3.52 (m, 1H), 3.35-3.31 (m, 2H), 3.17-3.12 (m, 1H), 2.90-2.84 (m, 1H), 2.68-2.63 (m, 1H), 2.57 (dd, 1H, J=13.7 Hz, 4.3 Hz), 1.91-1.84 (m, 3H), 1.78-1.74 (m, 2H), 1.64 (br d, 1H, J=12.5 Hz), 1.58-1.51 (m, 1H), 1.40-1.14 (m, 14H).

mass spectrum (FAB$^+$), m/z: 481 ((M+H)$^+$).

Example 96

(2R,4S,5S)-5-Amino-6-[4-(2-chloro-4-fluorophenyl)-2,2-dimethyl-5-oxopiperazin-1-yl]-4-hydroxy-2-methylhexanoic acid (2,2-dimethylpropyl)amide hemifumarate (½ fumarate) (Exemplary Compound No. 2-242)

131 mg of the title compound (total yield over three steps: 81%) was obtained in the same manner as in Example (15b) using (3R,5S)-3-methyl-5-[(S)-1-(2-nitrobenzenesulfonyl)aziridin-2-yl]dihydrofuran-2-one obtained in Example (76g), 1-(2-chloro-4-fluorophenyl)-5,5-dimethylpiperazin-2-one obtained in Example (61a) and (2,2-dimethylpropyl)amine.

Colorless solid.

$^1$H NMR spectrum (CD$_3$OD, 400 MHz), δ: 7.98 (br s, 1H), 7.41-7.36 (m, 2H), 7.22-7.18 (m, 1H), 6.68 (s, 1H), 3.64-3.54 (m, 3H), 3.37-3.12 (m, 4H), 2.99-2.90 (m, 1.6H), 2.80-2.73 (m, 1.8H), 2.53-2.49 (m, 0.6H), 1.94-1.88 (m, 1H), 1.59-1.52 (m, 1H), 1.30-1.26 (m, 6H), 1.22 (d, 3H, J=7.4 Hz), 0.92 (s, 9H).

mass spectrum (FAB$^+$), m/z: 485 ((M+H)$^+$).

Example 97

(2R,4S,5S)-5-Amino-6-[4-(2-chloro-5-fluorophenyl)-2,2-dimethyl-5-oxopiperazin-1-yl]-4-hydroxy-2-methylhexanoic acid (2,2-dimethylpropyl)amide hemifumarate (½ fumarate) (Exemplary Compound No. 2-185)

(97a) N-{(S)-2-[4-(2-Chloro-5-fluorophenyl)-2,2-dimethyl-5-oxopiperazin-1-yl]-1-[(2S,4R)-4-methyl-5-oxotetrahydrofuran-2-yl]ethyl}-2-nitrobenzenesulfonamide A solution of 730 mg of (3R,5S)-3-methyl-5-[(S)-1-(2-nitrobenzenesulfonyl)aziridin-2-yl]dihydrofuran-2-one obtained in Example (76g) (2.24 mmol) and 689 mg of 1-(2-chloro-5-fluorophenyl)-5,5-dimethylpiperazin-2-one obtained in Example (62d) (2.68 mmol) in toluene (22 ml) was stirred at 110° C. for two hours. After cooling, the reaction mixture was concentrated under reduced pressure, and the residue was purified by silica gel column chromatography (elution solvent:methylene chloride/ethyl acetate=3/1-2/1) to obtain 1.23 g of the title compound (yield: 94%).

Colorless solid.

$^1$H NMR spectrum (CDCl$_3$, 400 MHz), δ: 8.18-8.16 (m, 1H), 7.94 (br s, 1H), 7.81-7.77 (m, 2H), 7.41 (dd, 1H, J=9.0 Hz, 5.5 Hz), 7.06-6.83 (m, 2H), 5.85 (br s, 0.5H), 5.52 (br s, 0.5H), 4.89 (br s, 1H), 3.63 (br s, 1H), 3.30-3.06 (m, 3H), 2.91-2.57 (m, 4.5H), 2.13-2.05 (m, 1.5H), 1.33 (br d, 3H, J=7.4 Hz), 1.17 (br s, 3H), 1.07 (br s, 3H).

(97b) {(S)-2-[4-(2-Chloro-5-fluorophenyl)-2,2-dimethyl-5-oxopiperazin-1-yl]-1-[(2S,4R)-4-methyl-5-oxotetrahydrofuran-2-yl]ethyl}carbamic acid t-butyl ester 893 mg of cesium carbonate (2.53 mmol) was added to a solution of 1.23 g of N-{(S)-2-[4-(2-chloro-5-fluorophenyl)-2,2-dimethyl-5-oxopiperazin-1-yl]-1-[(2S,4R)-4-methyl-5-oxotetrahydrofuran-2-yl]ethyl}-2-nitrobenzenesulfonamide obtained in Example (97a) (2.11 mmol) and 0.45 ml of thiophenol (content: 95%) (4.22 mmol) in acetonitrile (10 ml) under a nitrogen atmosphere at room temperature, and the mixture was stirred at the same temperature for two hours. Brine was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol=20/1-10/1). 176 mg of sodium bicarbonate (2.09 mmol) and 456 mg of di-t-butyl dicarbonate (2.09 mmol) were added to a solution of 4-{(S)-2-amino-2-[(2S,4R)-4-methyl-5-oxotetrahydrofuran-2-yl]ethyl}1-(2-chloro-5-fluorophenyl)-5,5-dimethylpiperazin-2-one obtained above in ethyl acetate (10 ml)-water (10 ml), and the mixture was stirred at room temperature for two hours. Brine was added to the reaction mixture, followed by extraction with ethyl acetate. Then, the organic layer was dried over anhydrous magnesium sulfate. After filtration, the solvent was evaporated under reduced pressure, and the residue was purified by silica gel column chromatography (elution solvent:methylene chloride/ethyl acetate=2/1) to obtain 835 mg of the title compound (yield: 80%).

Colorless solid.

$^1$H NMR spectrum (CDCl$_3$, 400 MHz), δ: 7.44 (dd, 1H, J=9.0 Hz, 5.5 Hz), 7.06-6.96 (m, 2H), 4.90 (br s, 1H), 4.43 (br s, 1H), 3.88-3.81 (m, 1H), 3.59-3.24 (m, 4H), 2.81-2.38 (m, 4H), 2.04-1.96 (m, 1H), 1.45 (br s, 9H), 1.32 (br d, 3H, J=7.4 Hz), 1.26 (br s, 3H), 1.23 (br s, 3H).

(97c) {(1S,2S,4R)-4-(2,2-Dimethylpropylcarbamoyl)-1-[4-(2-chloro-5-fluorophenyl)-2,2-dimethyl-5-oxopiperazin-1-ylmethyl]-2-hydroxypentyl}carbamic acid t-butyl ester 20 mg of 2-hydroxypyridine (0.21 mmol) was added to a solution of 210 mg of {(S)-2-[4-(2-chloro-5-fluorophenyl)-2,2-dimethyl-5-oxopiperazin-1-yl]-1-[(2S,4R)-4-methyl-5-oxotetrahydrofuran-2-yl]ethyl}carbamic acid t-butyl ester obtained in Example (97b) (0.42 mmol) in (2,2-dimethylpropyl)amine (0.74 ml) (6.30 mmol), and the mixture was stirred at 80° C. for two hours. The reaction mixture was cooled and then water was added, followed by extraction with methylene chloride. Then, the organic layer was dried over anhydrous magnesium sulfate. After filtration, the solvent was evaporated under reduced pressure, and the residue was purified by silica gel column chromatography (elution solvent: methylene chloride/acetone=5/2-2/1) to obtain 228 mg of the title compound (yield: 93%).

Colorless solid.

$^1$H NMR spectrum (CDCl$_3$, 400 MHz), δ: 7.43 (dd, 1H, J=8.6 Hz, 5.5 Hz), 7.05-6.97 (m, 2H), 5.83 (br s, 1H), 5.01-4.77 (m, 2H), 3.93 (br s, 1H), 3.68-3.24 (m, 5H), 3.16 (dd, 1H, J=12.9 Hz, 6.7 Hz), 2.98 (dd, 1H, J=12.9 Hz, 5.7 Hz), 2.77-2.51 (m, 3H), 1.78-1.61 (m, 2H), 1.45 (br s, 9H), 1.25-1.23 (m, 9H), 0.91 (br s, 9H).

(97d) (2R,4S,5S)-5-Amino-6-[4-(2-chloro-5-fluorophenyl)-2,2-dimethyl-5-oxopiperazin-1-yl]-4-hydroxy-2-methylhexanoic acid (2,2-dimethylpropyl) amide hemifumarate (½ fumarate)

0.88 ml of trifluoroacetic acid (11.4 mmol) was added to a solution of 225 mg of {(1S,2S,4R)-4-(2,2-dimethylpropylcarbamoyl)-1-[4-(2-chloro-5-fluorophenyl)-2,2-dimethyl-5-oxopiperazin-1-ylmethyl]-2-hydroxypentyl}carbamic acid t-butyl ester obtained in Example (97c) (0.38 mmol) in methylene chloride (2 ml) at room temperature, and the mixture was stirred at the same temperature for 30 minutes. After concentration under reduced pressure, a saturated sodium bicarbonate aqueous solution was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol/triethylamine=100/10/1). 20 mg of fumaric acid (0.17 mmol) was added to a solution of 169 mg of (2R,4S,5S)-5-amino-6-[4-(2-chloro-5-fluorophenyl)-2,2-dimethyl-5-oxopiperazin-1-yl]-4-hydroxy-2-methylhexanoic acid (2,2-dimethylpropyl)amide obtained above (0.35 mmol) in methanol (2 ml), and the mixture was stirred at room temperature for five minutes. The reaction mixture was concentrated under reduced pressure, and methylene chloride (0.5 ml) was added to the residue. Diethyl ether (5 ml) was further added and the solid was collected by filtration to obtain 145 mg of the title compound (yield: 70%).

Colorless solid.

$^1$H NMR spectrum (CD$_3$OD, 400 MHz), δ: 7.58-7.54 (m, 1H), 7.21-7.16 (m, 2H), 6.66 (1H, s), 3.66-3.51 (m, 3H), 3.39-3.10 (m, 4H), 2.97-2.90 (m, 1.6H), 2.79-2.71 (m, 1.8H), 2.52-2.46 (m, 0.6H), 1.93-1.87 (m, 1H), 1.58-1.51 (m, 1H), 1.30-1.26 (m, 6H), 1.21 (d, 3H, J=7.0 Hz), 0.92 (s, 9H).

mass spectrum (FAB$^+$), m/z: 485 ((M+H)$^+$).

Example 98

(2R,4S,5S)-5-Amino-6-[4-(2-chloro-5-fluorophenyl)-2,2-dimethyl-5-oxopiperazin-1-yl]-4-hydroxy-2-methylhexanoic acid isobutylamide hemifumarate (½ fumarate) (Exemplary Compound No. 2-157)

145 mg of the title compound (total yield over two steps: 79%) was obtained in the same manner as in Examples (1n) and (1o) using {(S)-2-[4-(2-chloro-5-fluorophenyl)-2,2-dimethyl-5-oxopiperazin-1-yl]-1-[(2S,4R)-4-methyl-5-oxotetrahydrofuran-2-yl]ethyl}carbamic acid t-butyl ester obtained in Example (97b) and isobutylamine.

Colorless solid.

$^1$H NMR spectrum (CD$_3$OD, 400 MHz), δ: 8.08 (br s, 1H), 7.58-7.55 (m, 1H), 7.22-7.12 (m, 2H), 6.69 (s, 1H), 3.66-3.47 (m, 3H), 3.40-3.05 (m, 3H), 3.10-3.05 (m, 1H), 2.99-2.92 (m, 1.6H), 2.76-2.70 (m, 1.8H), 2.50 (dd, 0.6H, J=13.5 Hz, 4.1 Hz), 1.93-1.86 (m, 1H), 1.82-1.74 (m, 1H), 1.59-1.52 (m, 1H), 1.31-1.26 (m, 6H), 1.19 (d, 3H, J=7.04 Hz), 0.93 (d, 6H, J=6.6 Hz).

mass spectrum (FAB$^+$), m/z: 471 ((M+H)$^+$).

Example 99

(2R,4S,5S)-5-Amino-6-[2,2-dimethyl-4-(3-fluoro-2-methylphenyl)-5-oxopiperazin-1-yl]-4-hydroxy-2-methylhexanoic acid (2,2-dimethylpropyl)amide hemifumarate (½ fumarate) (Exemplary Compound No. 2-183)

186 mg of the title compound (total yield over four steps: 77%) was obtained in the same manner as in Examples (1l) to (1o) using (3R,5S)-3-methyl-5-[(S)-1-(2-nitrobenzenesulfonyl)aziridin-2-yl]dihydrofuran-2-one obtained in Example (76g), 5,5-dimethyl-1-(3-fluoro-2-methylphenyl)piperazin-2-one obtained in Example (67d) and (2,2-dimethylpropyl)amine.

Colorless solid.

$^1$H NMR spectrum (CD$_3$OD, 400 MHz), δ: 8.00-7.97 (m, 1H), 7.33-7.27 (m, 1H), 7.13-7.08 (m, 1H), 7.05-6.39 (m, 1H), 6.69 (2H, s), 3.72-3.53 (m, 3H), 3.40-3.12 (m, 4H), 2.97-2.91 (m, 1.6H), 2.86-2.74 (m, 1.4H), 2.66-2.62 (m, 0.4H), 2.60-2.54 (m, 0.6H), 2.15-2.14 (m, 3H), 1.95-1.88 (m, 1H), 1.58-1.52 (m, 1H), 1.29-1.22 (m, 9H), 0.93 (s, 9H).

mass spectrum (FAB$^+$), m/z: 465 ((M+H)$^+$).

Example 100

(2R,4S,5S)-5-Amino-6-[2,2-dimethyl-4-(4-fluoro-2-methylphenyl)-5-oxopiperazin-1-yl]-4-hydroxy-2-methylhexanoic acid (2,2-dimethylpropyl)amide hemifumarate (½ fumarate) (Exemplary Compound No. 2-243)

121 mg of the title compound (total yield over three steps: 67%) was obtained in the same manner as in Example (15b) using (3R,5S)-3-methyl-5-[(S)-1-(2-nitrobenzenesulfonyl)aziridin-2-yl]dihydrofuran-2-one obtained in Example (76g), 5,5-dimethyl-1-(4-fluoro-2-methylphenyl)piperazin-2-one obtained in Example (69a) and (2,2-dimethylpropylamine).

Colorless solid.

$^1$H NMR spectrum (CD$_3$OD, 400 MHz), δ: 7.20-7.13 (m, 1H), 7.09-6.98 (m, 2H), 6.69 (s, 1H), 3.67-3.50 (m, 3H), 3.36-3.12 (m, 4H), 2.96-2.90 (m, 1.6H), 2.84-2.74 (m, 1.4H), 2.66-2.62 (m, 0.4H), 2.50 (dd, 0.6H, J=13.5 Hz, 3.7 Hz), 2.24-2.23 (m, 3H), 1.94-1.83 (m, 1H), 1.59-1.52 (m, 1H), 1.27-1.21 (m, 9H), 0.92 (s, 9H).

mass spectrum (FAB$^+$), m/z: 465 ((M+H)$^+$).

Example 101

(2R,4S,5S)-5-Amino-6-[2,2-dimethyl-4-(5-fluoro-2-methylphenyl)-5-oxopiperazin-1-yl]-4-hydroxy-2-methylhexanoic acid (2,2-dimethylpropyl)amide hemifumarate (½ fumarate) (Exemplary Compound No. 2-184)

(101a) N-{(S)-2-[2,2-Dimethyl-4-(5-fluoro-2-methylphenyl)-5-oxopiperazin-1-yl]-1-[(2S,4R)-4-methyl-5-oxotetrahydrofuran-2-yl]ethyl}-2-nitrobenzenesulfonamide A solution of 844 mg of (3R,5S)-3-methyl-5-[(S)-1-(2-nitrobenzenesulfonyl)aziridin-2-yl]dihydrofuran-2-one obtained in Example (76g) (2.59 mmol) and 733 mg of 5,5-dimethyl-1-(5-fluoro-2-methylphenyl)piperazin-2-one obtained in Example (70d) (3.10 mmol) in toluene (26 ml) was stirred at 110° C. for two hours. After cooling, the reaction mixture was concentrated under reduced pressure, and the residue was purified by silica gel column chromatography (elution solvent:methylene chloride/ethyl acetate=3/1-1/1) to obtain 1.39 g of the title compound (yield: 95%).

Colorless solid.

$^1$H NMR spectrum (CDCl$_3$, 400 MHz), δ: 8.18-8.16 (m, 1H), 7.99-7.78 (m, 3H), 7.22-7.18 (m, 1H), 6.98-6.93 (m, 1H), 6.81 (br d, 0.4H, J=7.0 Hz), 6.66 (br d, 0.6H, J=7.0 Hz), 5.83 (br d, 0.6H, J=7.4 Hz), 5.57 (br d, 0.4H, J=7.8 Hz), 4.94 (br s, 0.4H), 4.85 (br s, 0.6H), 3.70-3.26 (m, 2H), 3.12-2.50 (m, 7H), 2.18-2.05 (m, 4H), 1.34-1.32 (m, 3H), 1.17-1.05 (m, 6H).

(101b) {(S)-2-[2,2-Dimethyl-4-(5-fluoro-2-methylphenyl)-5-oxopiperazin-1-yl]-1-[(2S,4R)-4-methyl-5-oxotetrahydrofuran-2-yl]ethyl}carbamic acid t-butyl ester 966 mg of cesium carbonate (2.96 mmol) was added to a solution of 1.39 g of N-{(S)-2-[2,2-Dimethyl-4-(5-fluoro-2-methylphenyl)-5-oxopiperazin-1-yl]-1-[(2S,4R)-4-methyl-5-oxotetrahydrofuran-2-yl]ethyl}-2-nitrobenzenesulfonamide obtained in Example (101a) (2.47 mmol) and 0.53 ml of thiophenol (content: 95%) (4.94 mmol) in acetonitrile (12 ml) under a nitrogen atmosphere at room temperature, and the mixture was stirred at the same temperature for two hours. Brine was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol=20/1-10/1). 213 mg of sodium bicarbonate (2.53 mmol) and 553 mg of di-t-butyl dicarbonate (2.53 mmol) were added to a solution of the resulting 4-{(S)-2-amino-2-[(2S,4R)-4-methyl-5-oxotetrahydrofuran-2-yl]ethyl}-5,5-dimethyl-1-(5-fluoro-2-methylphenyl)piperazin-2-one in ethyl acetate (10 ml)-water (10 ml), and the mixture was stirred at room temperature for 2.5 hours. Brine was added to the reaction mixture, followed by extraction with ethyl acetate. Then, the organic layer was dried over anhydrous magnesium sulfate. After filtration, the solvent was evaporated under reduced pressure, and the residue was purified by silica gel column chromatography (elution solvent:methylene chloride/ethyl acetate=2/1) to obtain 968 mg of the title compound (yield: 82%).

Colorless solid.

$^1$H NMR spectrum (CDCl$_3$, 400 MHz), δ: 7.22 (dd, 1H, J=8.6 Hz, 6.3 Hz), 6.98-6.93 (m, 1H), 6.87-6.79 (m, 1H), 4.92-4.85 (m, 1H), 4.45-4.41 (m, 1H), 3.88-3.82 (m, 1H), 3.56-3.16 (m, 4H), 2.77-2.41 (m, 4H), 2.19 (bs s, 1.8H), 2.18 (br s, 1.2H), 2.04-1.96 (m, 1H), 1.45 (br s, 9H), 1.32 (br d, 3H, J=7.4 Hz), 1.23 (br s, 6H).

(101c) {(1S,2S,4R)-4-(2,2-Dimethylpropylcarbamoyl)-1-[2,2-dimethyl-4-(5-fluoro-2-methylphenyl)-5-oxopiperazin-1-ylmethyl]-2-hydroxypentyl}carbamic acid t-butyl ester 25 mg of 2-hydroxypyridine (0.26 mmol) was added to a solution of 250 mg of {(S)-2-[2,2-dimethyl-4-(5-fluoro-2-methylphenyl)-5-oxopiperazin-1-yl]-1-[(2S,4R)-4-methyl-5-oxotetrahydrofuran-2-yl]ethyl}carbamic acid t-butyl ester obtained in Example (101b) (0.52 mmol) in 1.22 ml of (2,2-dimethylpropyl)amine (10.4 mmol), and the mixture was stirred at 80° C. for two hours. The reaction mixture was cooled and then water was added, followed by extraction with methylene chloride. Then, the organic layer was dried over anhydrous magnesium sulfate. After filtration, the solvent was evaporated under reduced pressure, and the residue was purified by silica gel column chromatography (elution solvent: methylene chloride/acetone=2/1) to obtain 228 mg of the title compound (yield: 78%).

Colorless solid.

$^1$H NMR spectrum (CDCl$_3$, 400 MHz), δ: 7.21 (dd, 1H, J=8.6 Hz, 6.3 Hz), 6.97-6.92 (m, 1H), 6.83-6.81 (m, 1H), 5.81 (br s, 1H), 5.00 (br s, 1H), 4.83 (br s, 1H), 3.96-3.90 (m, 1H), 3.66-3.13 (m, 6H), 2.98 (dd, 1H, J=13.9 Hz, 6.1 Hz), 2.76-2.57 (m, 3H), 2.17 (br s, 3H), 1.74-1.67 (m, 2H), 1.46 (br s, 9H), 1.26-1.22 (m, 9H), 0.92 (br s, 9H).

(101d) (2R,4S,5S)-5-Amino-6-[2,2-dimethyl-4-(5-fluoro-2-methylphenyl)-5-oxopiperazin-1-yl]-4-hydroxy-2-methylhexanoic acid (2,2-dimethylpropyl) amide hemifumarate (½ fumarate)

0.92 ml of trifluoroacetic acid (12.0 mmol) was added to a solution of 225 mg of {(1S,2S,4R)-4-(2,2-dimethylpropylcarbamoyl)-1-[2,2-dimethyl-4-(5-fluoro-2-methylphenyl)-5-oxopiperazin-1-ylmethyl]-2-hydroxypentyl}carbamic acid t-butyl ester obtained in Example (101c) (0.40 mmol) in methylene chloride (2 ml) at room temperature, and the mixture was stirred at the same temperature for 30 minutes. After concentration under reduced pressure, a saturated sodium bicarbonate aqueous solution was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol/triethylamine=100/10/1). 21 mg of fumaric acid (0.18 mmol) was added to a solution of 165 mg of the resulting (2R,4S,5S)-5-amino-6-[2,2-dimethyl-4-(5-fluoro-2-methylphenyl)-5-oxopiperazin-1-yl]-4-hydroxy-2-methylhexanoic acid (2,2-dimethylpropyl)amide (0.36 mmol) in methanol (3 ml), and the mixture was stirred at room temperature for five minutes. The reaction mixture was concentrated under reduced pressure, and methylene chloride (0.5 ml) was added to the residue. Diethyl ether (5 ml) was further added and the solid was collected by filtration to obtain 148 mg of the title compound (yield: 71%).

Colorless solid.

$^1$H NMR spectrum (CD$_3$OD, 400 MHz), δ: 7.33-7.29 (m, 1H), 7.06-6.93 (m, 2H), 6.66 (1H, s), 3.68-3.48 (m, 3H), 3.39-3.11 (m, 4H), 2.95-2.89 (m, 1.6H), 2.81-2.73 (m, 1.4H), 2.66-2.62 (m, 0.4H), 2.50-2.46 (m, 0.6H), 2.19 (s, 3H), 1.93-1.87 (m, 1H), 1.58-1.51 (m, 1H), 1.27-1.25 (m, 6H), 1.21 (d, 3H, J=7.0 Hz), 0.92 (s, 9H).

mass spectrum (FAB$^+$), m/z: 465 ((M+H)$^+$).

Example 102

(2R,4S,5S)-5-Amino-6-[2,2-dimethyl-4-(5-fluoro-2-methylphenyl)-5-oxopiperazin-1-yl]-4-hydroxy-2-methylhexanoic acid isobutylamide hemifumarate (½ fumarate) (Exemplary Compound No. 2-156)

138 mg of the title compound (total yield over two steps: 87%) was obtained in the same manner as in Examples (1n) and (1o) using {(S)-2-[2,2-dimethyl-4-(5-fluoro-2-methylphenyl)-5-oxopiperazin-1-yl]-1-[(2S,4R)-4-methyl-5-oxotetrahydrofuran-2-yl]ethyl}carbamic acid t-butyl ester obtained in Example (101b) and isobutylamine.

Colorless solid.

$^1$H NMR spectrum (CD$_3$OD, 400 MHz), δ: 7.34-7.30 (m, 1H), 7.07-6.93 (m, 2H), 6.73 (s, 1H), 3.66-3.48 (m, 3H), 3.40-3.06 (m, 4H), 2.99-2.92 (m, 1.6H), 2.80-2.65 (m, 1.8H), 2.50 (dd, 0.6H, J=13.7 Hz, 3.9 Hz), 2.20 (s, 3H), 1.94-1.76 (m, 2H), 1.58-1.52 (m, 1H), 1.29-1.26 (m, 6H), 1.21 (d, 3H, J=7.0 Hz), 0.93 (d, 6H, J=6.7 Hz).

mass spectrum (FAB$^+$), m/z: 451 ((M+H)$^+$).

Example 103

(2R,4S,5S)-5-Amino-6-[2,2-dimethyl-4-(5-fluoro-2-methylphenyl)-5-oxopiperazin-1-yl]-4-hydroxy-2-methylhexanoic acid [(S)-2-methylbutyl]amide fumarate (Exemplary Compound No. 2-251)

129 mg of the title compound (total yield over two steps: 54%) was obtained in the same manner as in Examples (1n) and (1o) using {(S)-2-[2,2-dimethyl-4-(5-fluoro-2-methylphenyl)-5-oxopiperazin-1-yl]-1-[(2S,4R)-4-methyl-5-oxotetrahydrofuran-2-yl]ethyl}carbamic acid t-butyl ester obtained in Example (101b) and [(S)-2-methylbutyl]amine.

Colorless solid.

$^1$H NMR spectrum (CD$_3$OD, 400 MHz), δ: 7.32 (dd, 1H, J=8.2 Hz, 6.3 Hz), 7.04 (dt, 1H, J=8.2 Hz, 2.7 Hz), 6.99-6.93 (m, 1H), 6.69 (s, 2H), 3.69-3.49 (m, 3H), 3.40-3.11 (m, 3H), 3.07 (d, 2H, J=6.7 Hz), 2.98-2.91 (m, 0.6H), 2.83-2.66 (m, 1.8H), 2.50 (dd, 0.6H, J=13.5 Hz, 3.7 Hz), 2.20 (br s, 3H), 1.94-1.87 (m, 1H), 1.62-1.52 (m, 2H), 1.48-1.38 (m, 1H), 1.28-1.25 (m, 6H), 1.21-1.11 (m, 4H), 0.95-0.90 (m, 6H).

mass spectrum (FAB$^+$), m/z: 465 ((M+H)$^+$).

Example 104

(2R,4S,5S)-5-Amino-6-[2,2-dimethyl-4-(5-fluoro-2-methylphenyl)-5-oxopiperazin-1-yl]-4-hydroxy-2-methylhexanoic acid cyclopentylamide hemifumarate (½ fumarate) (Exemplary Compound No. 2-250)

(104a) {(1S,2S,4R)-4-(Cyclopentylcarbamoyl)-1-[2,2-dimethyl-4-(5-fluoro-2-methylphenyl)-5-oxopiperazin-1-ylmethyl]-2-hydroxypentyl}carbamic acid t-butyl ester 7.9 mg of 2-hydroxypyridine (0.08 mmol) was added to a solution of 200 mg of {(S)-2-[2,2-dimethyl-4-(5-fluoro-2-methylphenyl)-5-oxopiperazin-1-yl]-1-[(2S,4R)-4-methyl-5-oxotetrahydrofuran-2-yl]ethyl}carbamic acid t-butyl ester obtained in Example (101b) (0.42 mmol) in cyclopentylamine (1.5 ml), and the mixture was stirred at 85° C. for four hours. The reaction mixture was cooled and then water was added, followed by extraction with ethyl acetate. Then, the organic layer was dried over anhydrous magnesium sulfate. After filtration, the solvent was evaporated under reduced pressure, and the residue was purified by silica gel column chromatography (elution solvent:methylene chloride/methanol=20/1) to obtain 203 mg of the title compound (yield: 86%).

Colorless solid.

$^1$H NMR spectrum (CDCl$_3$, 400 MHz), δ: 7.21 (dd, 1H, J=8.2 Hz, 5.9 Hz), 6.95 (dt, 1H, J=8.2 Hz, 2.7 Hz), 6.84-6.81 (m, 1H), 5.76-72 (m, 1H), 5.01 (br s, 1H), 4.86 (br s, 1H), 4.23-4.14 (m, 1H), 3.94-3.89 (m, 1H), 3.67-3.17 (m, 5H), 2.77-2.44 (m, 3H), 2.17 (br s, 3H), 2.01-1.97 (m, 2H), 1.76-1.56 (m, 6H), 1.46-1.35 (m, 1H), 1.22-1.19 (m, 9H).

(104b) (2R,4S,5S)-5-Amino-6-[2,2-dimethyl-4-(5-fluoro-2-methylphenyl)-5-oxopiperazin-1-yl]-4-hydroxy-2-methylhexanoic acid cyclopentylamide hemifumarate (½ fumarate)

0.83 ml of trifluoroacetic acid (10.8 mmol) was added to a solution of 203 mg of {(1S,2S,4R)-4-(cyclopentylcarbamoyl)-1-[2,2-dimethyl-4-(5-fluoro-2-methylphenyl)-5-oxopiperazin-1-ylmethyl]-2-hydroxypentyl}carbamic acid t-butyl ester obtained in Example (104a) (0.36 mmol) in methylene chloride (1.6 ml) at room temperature, and the mixture was stirred at the same temperature for 30 minutes. After concentration under reduced pressure, a saturated sodium bicarbonate aqueous solution was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol/triethylamine=100/10/1). 15 mg of fumaric acid (0.13 mmol) was added to a solution of 121 mg of (2R,4S,5S)-5-amino-6-[2,2-dimethyl-4-(5-fluoro-2-methylphenyl)-5-oxopiperazin-1-yl]-4-hydroxy-2-methylhexanoic acid cyclopentylamide obtained above (0.26 mmol) in methanol (3 ml), and the mixture was stirred at room temperature for five minutes. The reaction mixture was concentrated under reduced pressure, and methylene chloride (0.5 ml) was added to the residue. Diisopropyl ether (5 ml) was further added and the solid was collected by filtration to obtain 114 mg of the title compound (yield: 84%).

Colorless solid.

$^1$H NMR spectrum (CD$_3$OD, 400 MHz), δ: 7.33-7.29 (m, 1H), 7.06-6.93 (m, 2H), 6.66 (s, 1H), 4.14-4.07 (m, 1H), 3.68-3.48 (m, 3H), 3.39-3.08 (m, 3H), 2.94-2.89 (m, 0.6H), 2.80-2.63 (m, 1.8H), 2.52-2.47 (m, 0.6H), 2.20 (br s, 3H), 1.97-1.85 (m, 3H), 1.77-1.68 (m, 2H), 1.64-1.41 (m, 5H), 1.27-1.25 (m, 6H), 1.17 (br d, 3H, J=7.0 Hz).

mass spectrum (FAB$^+$), m/z: 463 ((M+H)$^+$).

Example 105

(2R,4S,5S)-5-Amino-6-[2,2-dimethyl-4-(5-fluoro-2-methylphenyl)-5-oxopiperazin-1-yl]-4-hydroxy-2-methylhexanoic acid cyclohexylamide hemifumarate (½ fumarate) (Exemplary Compound No. 2-246)

(105a) {(1S,2S,4R)-4-(Cyclohexylcarbamoyl)-1-[2,2-dimethyl-4-(5-fluoro-2-methylphenyl)-5-oxopiperazin-1-ylmethyl]-2-hydroxypentyl}carbamic acid t-butyl ester 7.6 mg of 2-hydroxypyridine (0.08 mmol) was added to a solution of 190 mg of {(S)-2-[2,2-dimethyl-4-(5-fluoro-2-methylphenyl)-5-oxopiperazin-1-yl]-1-[(2S,4R)-4-methyl-5-oxotetrahydrofuran-2-yl]ethyl}carbamic acid t-butyl ester obtained in Example (101b) (0.4 mmol) in cyclohexylamine (1.5 ml), and the mixture was stirred at 80° C. for one hour. The reaction mixture was cooled and then water was added, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol=20/1) to obtain 195 mg of the title compound (yield: 85%).

Colorless solid.

$^1$H NMR spectrum (CDCl$_3$, 400 MHz), δ: 7.21 (dd, 1H, J=8.6 Hz, 6.3 Hz), 6.95 (dt, 1H, J=8.2 Hz, 2.7 Hz), 6.84-6.81 (m, 1H), 5.62 (br s, 1H), 5.00 (br s, 1H), 4.89 (br s, 1H), 3.96-3.90 (m, 1H), 3.80-3.71 (m, 1H), 3.66-3.13 (m, 6H), 2.77-2.49 (m, 3H), 2.18 (br s, 3H), 1.92-1.90 (m, 2H), 1.73-1.61 (m, 4H), 1.46-1.09 (m, 23H).

(105b) (2R,4S,5S)-5-Amino-6-[2,2-dimethyl-4-(5-fluoro-2-methylphenyl)-5-oxopiperazin-1-yl]-4-hydroxy-2-methylhexanoic acid cyclohexylamide hemifumarate (½ fumarate)

0.78 ml of trifluoroacetic acid (10.1 mmol) was added to a solution of 195 mg of {(1S,2S,4R)-4-(cyclohexylcarbamoyl)-1-[2,2-dimethyl-4-(5-fluoro-2-methylphenyl)-5-oxopiperazin-1-ylmethyl]-2-hydroxypentyl}carbamic acid t-butyl ester obtained in Example (105a) (0.34 mmol) in methylene chloride (1.6 ml) at room temperature, and the mixture was stirred at the same temperature for 30 minutes. After concentration under reduced pressure, a saturated sodium bicarbonate aqueous solution was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol/triethylamine=100/10/1). 17 mg of fumaric acid (0.14 mmol) was added to a solution of 136 mg of (2R,4S,5S)-5-amino-6-[2,2-dimethyl-4-(5-fluoro-2-methylphenyl)-5-oxopiperazin-1-yl]-4-hydroxy-2-methylhexanoic acid cyclohexylamide obtained above (0.28 mmol) in methanol (3 ml), and the mixture was stirred at room temperature for five minutes. The reaction mixture was concentrated under reduced pressure, and methylene chloride (0.5 ml) was added to the residue. Diisopropyl ether (5 ml) was further added and the solid was collected by filtration to obtain 137 mg of the title compound (yield: 84%).

Colorless solid.

$^1$H NMR spectrum (CD$_3$OD, 400 MHz), δ: 7.33-7.30 (m, 1H), 7.07-6.93 (m, 2H), 6.67 (s, 1H), 3.66-3.48 (m, 4H), 3.39-3.13 (m, 3H), 2.96-2.90 (m, 0.6H), 2.82-2.75 (m, 0.4H), 2.68-2.64 (m, 1.4H), 2.50 (dd, 0.6H, J=13.3 Hz, 4.3 Hz), 2.20 (s, 3H), 1.91-1.85 (m, 3H), 1.78-1.75 (m, 2H), 1.66-1.63 (m, 1H), 1.58-1.51 (m, 1H), 1.39-1.14 (m, 14H).

mass spectrum (FAB$^+$), m/z: 477 ((M+H)$^+$).

Example 106

(2R,4S,5S)-5-Amino-6-[4-(2-chlorophenyl)-2,2-dimethyl-5-oxopiperazin-1-yl]-2-ethyl-4-hydroxyhexanoic acid (2,2-dimethylpropyl)amide hemifumarate (½ fumarate) (Exemplary Compound No. 2-189)

(106a) (S)-4-Benzyl-3-[(2R,4E)-6-benzyloxy-2-ethylhex-4-enoyl]oxazolidin-2-one 164 ml of a solution of sodium bis(trimethylsilyl)amide in n-hexane (1.03 mol/l) (169 mmol) was added to a solution of 35.3 g of (S)-4-benzyl-3-butyryloxazolidin-2-one obtained in Reference Example 5 (141 mmol) in tetrahydrofuran (330 ml) under a nitrogen atmosphere and at −78° C. over 45 minutes, and the mixture was stirred at the same temperature for 30 minutes. Then, a solution of 35.6 g of [(E)-4-bromobut-2-enyloxymethyl]benzene obtained in Reference Example 4 (148 mmol) in tetrahydrofuran (80 ml) was added to the solution obtained above over 30 minutes, and the mixture was stirred at the same temperature for 30 minutes. Thereafter, the mixture was raised to −40° C. and further stirred for four hours. 100 ml of a saturated ammonium chloride aqueous solution was added to the reaction mixture, and the mixture was further stirred at room temperature for one hour. The reaction mixture was concentrated under reduced pressure and diluted with 500 ml of water, followed by extraction with ethyl acetate. Then, the organic layer was washed with water and brine and dried over anhydrous magnesium sulfate. After filtration, the solvent was evaporated under reduced pressure, and the residue was purified by silica gel column chromatography (elution solvent:n-hexane/ethyl acetate=7/1-2/1) to obtain 46.4 g of the title compound (yield: 81%).

Colorless liquid.

$^1$H NMR spectrum (CDCl$_3$, 500 MHz), δ: 7.33-7.20 (m, 8H), 7.16 (d, 2H, J=6.8 Hz), 5.75 (dt, 1H, J=15.1 Hz, 6.8 Hz), 5.68 (dt, 1H, J=15.1 Hz, 5.4 Hz), 4.71-4.65 (m, 1H), 4.48 (s, 2H), 4.18 (m, 2H), 3.97 (d, 2H, J=5.4 Hz), 3.88-3.82 (m, 1H), 3.29 (dd, 1H, J=13.2 Hz, 3.4 Hz), 2.64 (dd, 1H, J=13.2 Hz 10.3 Hz), 2.52-2.45 (m, 1H), 2.37-2.30 (m, 1H), 1.81-1.70 (m, 1H), 1.62-1.52 (m, 1H), 0.92 (t, 3H, J=7.3 Hz).

(106b) (2R,4E)-6-Benzyloxy-2-ethylhex-4-enoic acid

A solution of 23.4 g of (S)-4-benzyl-3-[(2R,4E)-6-benzyloxy-2-ethylhex-4-enoyl]oxazolidin-2-one (57.5 mmol)

obtained in Example (106a) in a mixed solvent of tetrahydrofuran (800 ml) and water (260 ml) was cooled in an ice bath, and then 35.0 ml of a 30% hydrogen peroxide aqueous solution and 4.83 g of lithium hydroxide monohydrate (115 mmol) were added thereto. The mixture was stirred at the same temperature for one hour, and then raised to room temperature and further stirred for 12 hours. After cooling in an ice bath, 250 ml of a 1.5 M sodium thiosulfate aqueous solution was added to the reaction mixture. The mixture was further stirred at room temperature for one hour. The reaction mixture was concentrated under reduced pressure, diluted with 500 ml of water and washed with ethyl acetate. Then, the aqueous layer was made acidic with 30 g of sodium dihydrogenphosphate, followed by extraction with ethyl acetate. The organic layer was washed with brine and dried over anhydrous magnesium sulfate. After filtration, the solvent was evaporated under reduced pressure to obtain 14.3 g of the crude title compound.

Colorless liquid.

$^1$H NMR spectrum (CDCl$_3$, 400 MHz), δ: 7.37-7.27 (m, 5H), 5.73-5.62 (m, 2H), 4.49 (s, 2H), 4.03-3.91 (m, 2H), 2.45-2.34 (m, 2H), 2.33-2.21 (m, 1H), 1.73-1.52 (m, 2H), 0.95 (t, 3H, J=7.4 Hz).

(106c) (3R,5S)-5-[(R)-2-Benzyloxy-1-hydroxyethyl]-3-ethyldihydrofuran-2-one 335 ml of a solution of a sodium tetraborate buffer solution (0.05 M) in a 0.4 mM disodium ethylenediaminetetraacetate aqueous solution, 0.503 g of tetrabutylammonium bisulfate (1.48 mmol) and 8.63 g of 1,2:4,5-di-O-isopropylidene-β-D-erythro-2,3-hexodiuro-2,6-pyranose (33.4 mmol) were added to 8.30 g of (2R,4E)-6-benzyloxy-2-ethylhex-4-enoic acid obtained in Example (106b) (33.5 mmol) in a mixed solvent of acetonitrile (167 ml) and dimethoxymethane (333 ml) at room temperature, and the mixture was stirred for 10 minutes. The reaction mixture was cooled in an ice bath. Then, a solution of 28.4 g of Oxone (trade mark) (46.1 mmol) in a 0.4 mM disodium ethylenediaminetetraacetate aqueous solution (168 ml) and a solution of 26.7 g of potassium carbonate (193 mmol) in water (168 ml) were separately added dropwise over four hours. The mixture was stirred at the same temperature for one hour and then diluted with 100 ml of water, followed by extraction with ethyl acetate. Then, the organic layer was washed with brine and dried over anhydrous magnesium sulfate. After filtration, the solvent was evaporated under reduced pressure, and the residue was purified by silica gel column chromatography (elution solvent:n-hexane/ethyl acetate=6/1-1/1) to obtain 6.80 g of the title compound (total yield over two steps: 70%).

Colorless liquid.

$^1$H NMR spectrum (CDCl$_3$, 400 MHz), δ: 7.40-7.29 (m, 5H), 4.58 (d, 1H, J=11.9 Hz), 4.54 (d, 1H, J=11.9 Hz), 4.46 (ddd, 1H, J=8.2 Hz, 6.3 Hz, 4.3 Hz), 3.90-3.83 (m, 1H), 3.64 (dd, 1H, J=9.8 Hz, 3.9 Hz), 3.56 (dd, 1H, J=9.8, 6.3 Hz), 2.65-2.56 (m, 1H), 2.51-2.43 (m, 1H), 2.41 (d, 1H, J=5.1 Hz), 2.01-1.93 (m, 1H), 1.92-1.80 (m, 1H), 1.58-1.46 (m, 1H), 1.01 (t, 3H, J=7.4 Hz).

(106d) Methanesulfonic acid (R)-2-benzyloxy-1-[(2S,4R)-4-ethyl-5-oxotetrahydrofuran-2-yl]ethyl ester A solution of 25.0 g of (3R,5S)-5-[(R)-2-benzyloxy-1-hydroxyethyl]-3-ethyldihydrofuran-2-one obtained in Example (106c) (94.7 mmol) in methylene chloride (600 ml) was cooled in an ice bath. Then, 28.7 g of triethylamine (284 mmol) and 15.9 g of methanesulfonyl chloride (139 mmol) were added thereto, and the mixture was stirred at the same temperature for three hours. 500 ml of water was added to the reaction mixture, followed by extraction with methylene chloride. Then, the organic layer was washed with water and brine and dried over anhydrous magnesium sulfate. After filtration, the solvent was evaporated under reduced pressure, and the residue was purified by silica gel column chromatography (elution solvent:n-hexane/ethyl acetate=4/1-1/1) to obtain 31.2 g of the title compound (yield: 96%).

Colorless liquid.

$^1$H NMR spectrum (CDCl$_3$, 400 MHz), δ: 7.43-7.28 (m, 5H), 4.86-4.81 (m, 1H), 4.65 (ddd, 1H, J=8.2 Hz, 5.1 Hz, 4.5 Hz), 4.56 (s, 2H), 3.77 (dd, 1H, J=1.0 Hz, 5.9 Hz), 3.74 (dd, 1H, J=11.0 Hz, 5.5 Hz), 3.04 (s, 3H), 2.66-2.57 (m, 1H), 2.53-2.45 (m, 1H), 2.07-1.98 (m, 1H), 1.91-1.79 (m, 1H), 1.60-1.48 (m, 1H), 1.01 (t, 3H, J=7.4 Hz).

(106e) (3R,5S)-5-[(S)-1-Azido-2-benzyloxyethyl]-3-ethyldihydrofuran-2-one 7.91 g of sodium azide (122 mmol) was added to a solution of 29.5 g of methanesulfonic acid (R)-2-benzyloxy-1-[(2S,4R)-4-ethyl-5-oxotetrahydrofuran-2-yl]ethyl ester obtained in Example (106d) (86.3 mmol) in N,N'-dimethylpropyleneurea (300 ml) at room temperature, and the mixture was stirred at 60° C. for two days. The reaction mixture was cooled and then poured into ice water, followed by extraction with diethyl ether. Then, the organic layer was washed with water and brine and dried over anhydrous magnesium sulfate. After filtration, the solvent was evaporated under reduced pressure, and the residue was purified by silica gel column chromatography (elution solvent:n-hexane/ethyl acetate=6/1) to obtain 23.1 g of the title compound (yield: 93%).

Colorless liquid.

$^1$H NMR spectrum (CDCl$_3$, 400 MHz), δ: 7.40-7.29 (m, 5H), 4.62-4.55 (m, 3H), 3.80-3.73 (m, 2H), 3.66 (ddd, 1H, J=7.0 Hz, 5.5 Hz, 3.1 Hz), 2.77-2.67 (m, 1H), 2.36-2.27 (m, 1H), 2.08-1.99 (m, 1H), 1.92-1.80 (m, 1H), 1.57-1.43 (m, 1H), 1.00 (t, 3H, J=7.4 Hz).

(106f) N-{(S)-1-[(2S,4R)-4-Ethyl-5-oxotetrahydrofuran-2-yl]-2-hydroxyethyl}-2-nitrobenzenesulfonamide A suspension of 23.5 g of (3R,5S)-5-[(S)-1-azido-2-benzyloxyethyl]-3-ethyldihydrofuran-2-one obtained in Example (106e) (81.3 mmol), 40.0 ml of a solution of 4 N hydrochloric acid in dioxane (160 mmol) and 5.21 g of 10% palladium-carbon (50% wet) in ethanol (400 ml) was stirred under a hydrogen atmosphere at room temperature for 12 hours. Hydrogen in the reaction vessel was replaced by nitrogen, and then the reaction mixture was diluted with 300 ml of ethanol. Palladium-carbon was separated by filtration and washed with ethanol. The solvent was evaporated from the filtrate under reduced pressure to obtain crude (3R,5S)-5-[(S)-1-amino-2-hydroxyethyl]-3-ethyldihydrofuran-2-one hydrochloride.

25.6 g of triethylamine (253 mmol) and 28.6 g of O-nitrobenzenesulfonyl chloride (129 mmol) were added to a solution of (3R,5S)-5-[(S)-1-amino-2-hydroxyethyl]-3-ethyldihydrofuran-2-one hydrochloride obtained in the above reaction in a mixed solvent of tetrahydrofuran (350 ml) and water (35.0 ml) at 0° C., and the mixture was stirred at the same temperature for two hours. The reaction mixture was concentrated under reduced pressure and 500 ml of water was added, followed by extraction with ethyl acetate. Then, the organic layer was washed with water, a saturated sodium bicarbonate aqueous solution and brine and dried over anhydrous magnesium sulfate. After filtration, the solvent was evaporated under reduced pressure, and the residue was purified by silica gel column chromatography (elution solvent: ethyl acetate). Further, 20 ml of diisopropyl ether and 40 ml of ethyl acetate were added, and the precipitated solid was collected by filtration to obtain 17.0 g of the title compound (total yield over two steps: 59%).

Colorless solid.

Optical rotation, $[\alpha]_D^{23.5° C.}$=+34.4° (c=1.00, MeOH).

$^1$H NMR spectrum (CDCl$_3$, 500 MHz), δ: 8.15-8.11 (m, 1H), 7.93-7.88 (m, 1H), 7.78-7.73 (m, 2H), 5.85 (br d, 1H, J=7.8 Hz), 4.67 (ddd, 1H, J=8.3 Hz, 5.4 Hz, 2.9 Hz), 3.73-3.61 (m, 3H), 2.73-2.65 (m, 1H), 2.54 (ddd, 1H, J=13.2 Hz, 9.8 Hz, 5.4 Hz), 2.08 (ddd, 1H, J=13.2 Hz, 8.3 Hz, 6.8 Hz), 1.92-1.87 (m, 1H), 1.87-1.77 (m, 1H), 1.59-1.49 (m, 1H), 1.00 (t, 3H, J=7.4 Hz).

(106g) (3R,5S)-3-Ethyl-5-[(S)-1-(2-nitrobenzenesulfonyl)aziridin-2-yl]dihydrofuran-2-one 1.60 ml of a solution of diethyl azodicarboxylate in toluene (40%) (3.52 mmol) was added to a solution of 1.05 g of N-{(S)-2-hydroxy-1-[(2S,4R)-4-methyl-5-oxotetrahydrofuran-2-yl]ethyl}-2-nitrobenzenesulfonamide obtained in Example (106f) (2.93 mmol) and 923 mg of triphenylphosphine (3.52 mmol) in tetrahydrofuran (30 ml) under ice-cooling over five minutes, and the mixture was stirred at the same temperature for five minutes. The reaction mixture was concentrated under reduced pressure, and the residue was purified by silica gel column chromatography (elution solvent: toluene/acetone=5/1) to obtain 916 mg of the title compound (yield: 92%).

Colorless liquid.

$^1$H NMR spectrum (CDCl$_3$, 400 MHz), δ: 8.14 (dd, 1H, J=7.8 Hz, 1.6 Hz), 7.83-7.72 (m, 3H), 4.75 (dt, 1H, J=9.0 Hz, 2.7 Hz), 3.26-3.23 (m, 1H), 2.84 (d, 1H, J=7.4 Hz), 2.81-2.72 (m, 1H), 2.65 (d, 1H, J=4.7 Hz), 2.57-2.51 (m, 1H), 2.18 (dt, 1H, J=12.9 Hz, 9.0 Hz), 1.91-1.80 (m, 1H), 1.53-1.42 (m, 1H), 0.98 (t, 3H, J=7.4 Hz).

mass spectrum (FAB$^+$), m/z: 340 ((M+H)$^+$).

(106h) N-{(S)-2-[4-(2-Chlorophenyl)-2,2-dimethyl-5-oxopiperazin-1-yl]-1-[(2S,4R)-4-ethyl-5-oxotetrahydrofuran-2-yl]ethyl}-2-nitrobenzenesulfonamide A solution of 916 mg of (3R,5S)-3-ethyl-5-[(S)-1-(2-nitrobenzenesulfonyl)aziridin-2-yl]dihydrofuran-2-one obtained in Example (106g) (2.69 mmol) and 771 mg of 1-(2-chlorophenyl)-5,5-dimethylpiperazin-2-one obtained in Example (1k) (3.23 mmol) in toluene (27 ml) was stirred at 110° C. for two hours. After cooling, the reaction mixture was concentrated under reduced pressure, and the residue was purified by silica gel column chromatography (elution solvent:methylene chloride/ethyl acetate=3/1-2/1) to obtain 1.49 g of the title compound (yield: 96%).

Colorless solid.

$^1$H NMR spectrum (CDCl$_3$, 400 MHz), δ: 8.17 (br d, 1H, J=7.8 Hz), 7.93 (br s, 1H), 7.79 (br s, 2H), 7.45 (br d, 1H, J=8.2 Hz), 7.33-7.26 (m, 2H), 7.19-7.10 (m, 1H), 5.90 (br s, 0.5H), 5.51 (br s, 0.5H), 4.89 (br s, 1H), 3.63 (br s, 1H), 3.30-3.10 (m, 3H), 2.91-2.45 (m, 4.5H), 2.15 (br s, 1.5H), 1.92-1.82 (m, 1H), 1.64-1.51 (m, 1H), 1.17 (br s, 3H), 1.07 (br s, 3H), 1.04 (br t, 3H, J=7.4 Hz).

(106i) {(S)-2-[4-(2-Chlorophenyl)-2,2-dimethyl-5-oxopiperazin-1-yl]-1-[(2S,4R)-4-ethyl-5-oxotetrahydrofuran-2-yl]ethyl}carbamic acid t-butyl ester 1.00 g of cesium carbonate (3.08 mmol) was added to a solution of 1.49 g of N—{(S)-2-[4-(2-chlorophenyl)-2,2-dimethyl-5-oxopiperazin-1-yl]-1-[(2S,4R)-4-ethyl-5-oxotetrahydrofuran-2-yl]ethyl}-2-nitrobenzenesulfonamide obtained in Example (106h) (2.57 mmol) and 0.52 ml of thiophenol (content: 95%) (5.14 mmol) in N,N-dimethylformamide (13 ml) under a nitrogen atmosphere at room temperature, and the mixture was stirred at the same temperature for 1.5 hours. Brine was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol=50/1-10/1). 235 mg of sodium bicarbonate (2.80 mmol) and 610 mg of di-t-butyl dicarbonate (2.80 mmol) were added to a solution of 4-{(S)-2-amino-2-[(2S,4R)-4-ethyl-5-oxotetrahydrofuran-2-yl]ethyl}-1-(2-chlorophenyl)-5,5-dimethylpiperazin-2-one obtained above in ethyl acetate (12 ml)-water (12 ml), and the mixture was stirred at room temperature for 2.5 hours. Brine was added to the reaction mixture, followed by extraction with ethyl acetate. Then, the organic layer was dried over anhydrous magnesium sulfate. After filtration, the solvent was evaporated under reduced pressure, and the residue was purified by silica gel column chromatography (elution solvent:methylene chloride/ethyl acetate=2/1-1/1) to obtain 1.11 g of the title compound (yield: 88%).

Colorless solid.

$^1$H NMR spectrum (CDCl$_3$, 400 MHz), δ: 7.47 (br d, 1H, J=7.4 Hz), 7.34-7.20 (m, 3H), 4.91-4.83 (m, 1H), 4.46-4.40 (m, 1H), 3.88-3.81 (m, 1H), 3.58-3.24 (m, 4H), 2.80-2.36 (m, 4H), 2.08-2.01 (m, 1H), 1.91-1.81 (m, 1H), 1.62-1.50 (m, 1H), 1.45 (s, 9H), 1.26 (br s, 3H), 1.22 (br s, 3H) 1.03 (br t, 3H, J=7.4 Hz).

(106j) {(1S,2S,4R)-4-(2,2-Dimethylpropylcarbamoyl)-1-[4-(2-chlorophenyl)-2,2-dimethyl-5-oxopiperazin-1-ylmethyl]-2-hydroxyhexyl}carbamic acid t-butyl ester 24 mg of 2-hydroxypyridine (0.26 mmol) was added to a solution of 250 mg of {(S)-2-[4-(2-chlorophenyl)-2,2-dimethyl-5-oxopiperazin-1-yl]-1-[(2S,4R)-4-ethyl-5-oxotetrahydrofuran-2-yl]ethyl}carbamic acid t-butyl ester obtained in Example (106i) (0.51 mmol) in (2,2-dimethylpropyl)amine (1.20 ml) (10.2 mmol), and the mixture was stirred at 80° C. for two hours. The reaction mixture was cooled and then water was added, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/acetone=3/1-2/1) to obtain 246 mg of the title compound (yield: 83%).

Colorless solid.

$^1$H NMR spectrum (CDCl$_3$, 400 MHz), δ: 7.47 (br d, 1H, J=7.4 Hz), 7.34-7.21 (m, 3H), 5.81 (br s, 1H), 5.03-4.81 (m, 2H), 3.91 (br s, 1H), 3.69-3.62 (m, 1H), 3.51-3.17 (m, 5H), 2.97 (br dd, 1H, J=12.9 Hz, 4.7 Hz), 2.80-2.63 (m, 2H), 2.33

(br s, 1H), 1.80-1.64 (m, 3H), 1.56-1.48 (m, 1H), 1.45 (br s, 9H), 1.26-1.22 (m, 6H), 0.95 (br t, 3H, J=7.6 Hz), 0.92 (br s, 9H).

(106k) (2R,4S,5S)-5-Amino-6-[4-(2-chlorophenyl)-2,2-dimethyl-5-oxopiperazin-1-yl]-2-ethyl-4-hydroxyhexanoic acid (2,2-dimethylpropyl)amide hemifumarate (½ fumarate)

0.97 ml of trifluoroacetic acid (12.6 mmol) was added to a solution of 243 mg of {(1S,2S,4R)-4-(2,2-dimethylpropylcarbamoyl)-1-[4-(2-chlorophenyl)-2,2-dimethyl-5-oxopiperazin-1-ylmethyl]-2-hydroxyhexyl}carbamic acid t-butyl ester obtained in Example (106j) (0.42 mmol) in methylene chloride (2 ml) at room temperature, and the mixture was stirred at the same temperature for 30 minutes. After concentration under reduced pressure, a saturated sodium bicarbonate aqueous solution was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol/triethylamine=100/10/1). 23 mg of fumaric acid (0.20 mmol) was added to a solution of 189 mg of (2R,4S,5S)-5-amino-6-[4-(2-chlorophenyl)-2,2-dimethyl-5-oxopiperazin-1-yl]-2-ethyl-4-hydroxyhexanoic acid (2,2-dimethylpropyl)amide obtained above (0.39 mmol) in methanol (3 ml), and the mixture was stirred at room temperature for five minutes. The reaction mixture was concentrated under reduced pressure, and methylene chloride (0.5 ml) was added to the residue. Diethyl ether (5 ml) was further added and the solid was collected by filtration to obtain 175 mg of the title compound (yield: 77%).

Colorless solid.

$^1$H NMR spectrum (CD$_3$OD, 400 MHz), δ: 7.98 (br t, 1H, J=5.7 Hz), 7.56-7.53 (m, 1H), 7.44-7.32 (m, 3H), 6.67 (1H, s), 3.66-3.50 (m, 3H), 3.37-3.09 (m, 4H), 2.95-2.89 (m, 1.6H), 2.78-2.66 (m, 0.8H), 2.61-2.48 (m, 1.6H), 1.90-1.83 (m, 1H), 1.72-1.48 (m, 3H), 1.30-1.26 (m, 6H), 0.97 (t, 3H, J=7.4 Hz), 0.93 (s, 9H).

mass spectrum (FAB$^+$), m/z: 481 ((M+H)$^+$).

Example 107

(2R,4S,5S)-5-Amino-6-[4-(2-chlorophenyl)-2,2-dimethyl-5-oxopiperazin-1-yl]-2-ethyl-4-hydroxyhexanoic acid isobutylamide hemifumarate (½ fumarate) (Exemplary Compound No. 1-161)

(107a) {(1S,2S,4R)-4-(Isobutylcarbamoyl)-1-[4-(2-chlorophenyl)-2,2-dimethyl-5-oxopiperazin-1-ylmethyl]-2-hydroxyhexyl}carbamic acid t-butyl ester 24 mg of 2-hydroxypyridine (0.26 mmol) was added to a solution of 250 mg of {(S)-2-[4-(2-chlorophenyl)-2,2-dimethyl-5-oxopiperazin-1-yl]-1-[(2S,4R)-4-ethyl-5-oxotetrahydrofuran-2-yl]ethyl}carbamic acid t-butyl ester obtained in Example (106i) (0.51 mmol) in isobutylamine (0.99 ml) (10.2 mmol), and the mixture was stirred at 80° C. for two hours. The reaction mixture was cooled and then water was added, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/acetone=3/1-2/1) to obtain 267 mg of the title compound (yield: 92%).

Colorless solid.

$^1$H NMR spectrum (CDCl$_3$, 400 MHz), δ: 7.47 (dd, 1H, J=7.4 Hz, 2.0 Hz), 7.34-7.21 (m, 3H), 5.82 (br t, 1H, J=5.9 Hz), 5.02 (br s, 1H), 3.90 (br s, 1H), 3.69-3.63 (m, 1H), 3.48-3.13 (m, 5H), 3.08-2.99 (m, 1H), 2.80-2.61 (m, 2H), 2.30 (br s, 1H), 1.80-1.63 (m, 4H), 1.53-1.40 (m, 10H), 1.26 (br s, 3H), 1.22 (br s, 3H), 0.95-0.91 (m, 9H).

(107b) (2R,4S,5S)-5-Amino-6-[4-(2-chlorophenyl)-2,2-dimethyl-5-oxopiperazin-1-yl]-2-ethyl-4-hydroxyhexanoic acid (2,2-dimethylpropyl)amide hemifumarate (½ fumarate)

1.09 ml of trifluoroacetic acid (14.1 mmol) was added to a solution of 264 mg of {(1S,2S,4R)-4-(isobutylcarbamoyl)-1-[4-(2-chlorophenyl)-2,2-dimethyl-5-oxopiperazin-1-ylmethyl]-2-hydroxyhexyl}carbamic acid t-butyl ester obtained in Example (107a) (0.47 mmol) in methylene chloride (2 ml) at room temperature, and the mixture was stirred at the same temperature for 30 minutes. After concentration under reduced pressure, a saturated sodium bicarbonate aqueous solution was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol/triethylamine=100/10/1). 26 mg of fumaric acid (0.22 mmol) was added to a solution of 210 mg of (2R,4S,5S)-5-amino-6-[4-(2-chlorophenyl)-2,2-dimethyl-5-oxopiperazin-1-yl]-2-ethyl-4-hydroxyhexanoic acid isobutylamide obtained above (0.45 mmol) in methanol (3 ml), and the mixture was stirred at room temperature for five minutes. The reaction mixture was concentrated under reduced pressure, and methylene chloride (0.5 ml) was added to the residue. Diethyl ether (5 ml) was further added and the solid was collected by filtration to obtain 192 mg of the title compound (yield: 78%).

Colorless solid.

$^1$H NMR spectrum (CD$_3$OD, 400 MHz), δ: 7.55-7.53 (m, 1H), 7.44-7.32 (m, 3H), 6.66 (1H, s), 3.66-3.48 (m, 3H), 3.37-3.07 (m, 4H), 2.96-2.89 (m, 1.6H), 2.78-2.65 (m, 0.8H), 2.55-2.47 (m, 1.6H), 1.98-1.75 (m, 2H), 1.70-1.47 (m, 3H), 1.30-1.26 (m, 6H), 0.97-0.92 (m, 9H).

mass spectrum (FAB$^+$), m/z: 467 ((M+H)$^+$).

Example 108

(2R,4S,5S)-5-Amino-6-[4-(2-chlorophenyl)-2,2-dimethyl-5-oxopiperazin-1-yl]-2-ethyl-4-hydroxyhexanoic acid (2-hydroxy-2-dimethylpropyl)amide hemifumarate (½ fumarate) (Exemplary Compound No. 2-175)

145 mg of the title compound (total yield over two steps: 60%) was obtained in the same manner as in Examples (1n) and (1o) using {(S)-2-[4-(2-chlorophenyl)-2,2-dimethyl-5-oxopiperazin-1-yl]-1-[(2S,4R)-4-ethyl-5-oxotetrahydrofuran-2-yl]ethyl}carbamic acid t-butyl ester obtained in Example (106i) and (1,1-dimethylethanol)amine.

Colorless solid.

$^1$H NMR spectrum (CD$_3$OD, 400 MHz), δ: 7.55-7.53 (m, 1H), 7.43-7.32 (m, 3H), 6.66 (1H, s), 3.66-3.51 (m, 3H), 3.37-3.10 (m, 5H), 2.92 (t, 0.6H, J=11.3 Hz), 2.77-2.66 (m, 0.8H), 2.61-2.53 (m, 1H), 2.49 (dd, 0.6H, J=12.9 Hz, 3.9 Hz), 1.87-1.81 (m, 1H), 1.72-1.47 (m, 3H), 1.30-1.25 (m, 6H), 1.20 (s, 6H), 0.96 (t, 3H, J=7.4 Hz).

mass spectrum (FAB$^+$), m/z: 483 ((M+H)$^+$)

Example 109

(2R,4S,5S)-5-Amino-6-[4-(2-chlorophenyl)-2,2-dimethyl-5-oxopiperazin-1-yl]-2-ethyl-4-hydroxyhexanoic acid (4-fluorophenyl)amide fumarate (Exemplary Compound No. 2-222)

139 mg of the title compound (total yield over two steps: 42%) was obtained in the same manner as in Examples (41a) and (1o) using {(S)-2-[4-(2-chlorophenyl)-2,2-dimethyl-5-oxopiperazin-1-yl]-1-[(2S,4R)-4-ethyl-5-oxotetrahydrofuran-2-yl]ethyl}carbamic acid t-butyl ester obtained in Example (106i) and 4-fluoroaniline and using a solution of dimethylaluminum chloride in methylene chloride (1.0 mol/l) instead of a solution of trimethylaluminum in hexane (1.0 mlol/l).

Colorless solid.
$^1$H NMR spectrum (CD$_3$OD, 400 MHz), δ: 7.62-7.53 (m, 2H), 7.55-7.53 (m, 1H), 7.43-7.37 (m, 2H), 7.33-7.28 (m, 1H), 7.08-7.03 (m, 2H), 6.69 (2H, s), 3.66-3.56 (m, 3H), 3.34-3.16 (m, 3H), 2.97-2.92 (m, 0.6H), 2.79-2.69 (m, 1.8H), 2.51 (dd, 0.6H, J=13.7 Hz, 3.9 Hz), 1.97-1.92 (m, 1H), 1.79-1.58 (m, 3H), 1.30-1.24 (m, 6H), 1.03 (t, 3H, J=7.3 Hz).

mass spectrum (FAB$^+$), m/z: 505 ((M+H)$^+$)

Example 110

(2R,4S,5S)-5-Amino-6-[2,2-dimethyl-4-(2-methylphenyl)-5-oxopiperazin-1-yl]-2-ethyl-4-hydroxyhexanoic acid (2,2-dimethylpropyl)amide hemifumarate (½ fumarate) (Exemplary Compound No. 2-187)

(110a) N-{(S)-2-[2,2-Dimethyl-4-(2-methylphenyl)-5-oxopiperazin-1-yl]-1-[(2S,4R)-4-ethyl-5-oxotetrahydrofuran-2-yl]ethyl}-2-nitrobenzenesulfonamide A solution of 770 mg of (3R,5S)-3-ethyl-5-[(S)-1-(2-nitrobenzenesulfonyl)aziridin-2-yl]dihydrofuran-2-one obtained in Example (106g) (2.26 mmol) and 593 mg of 5,5-dimethyl-1-(2-methylphenyl)piperazin-2-one obtained in Example (51d) (2.71 mmol) in toluene (23 ml) was stirred at 110° C. for five hours. After cooling, the reaction mixture was concentrated under reduced pressure, and the residue was purified by silica gel column chromatography (elution solvent:methylene chloride/ethyl acetate=4/1) to obtain 1.22 g of the title compound (yield: 97%).

Colorless solid.
$^1$H NMR spectrum (CDCl$_3$, 400 MHz), δ: 8.17 (br d, 1H, J=6.8 Hz), 7.96-7.91 (m, 1H), 7.84-7.75 (m, 2H), 7.26-7.22 (m, 3H), 7.07-7.05 (m, 0.4H), 6.95 (br d, 0.6H, J=6.4 Hz), 5.89 (br d, 0.6H, J=6.4 Hz), 5.59 (br s, 0.4H), 4.94-4.85 (m, 1H), 3.67-3.60 (m, 1H), 3.39-2.50 (m, 8H), 2.20-2.09 (m, 4H), 1.92-1.82 (m, 1H), 1.64-1.53 (m, 1H), 1.16-1.01 (m, 9H).

(110b) {(S)-2-[2,2-Dimethyl-4-(2-methylphenyl)-5-oxopiperazin-1-yl]-1-[(2S,4R)-4-ethyl-5-oxotetrahydrofuran-2-yl]ethyl}carbamic acid t-butyl ester 854 mg of cesium carbonate (2.62 mmol) was added to a solution of 1.22 g of N-{(S)-2-[2,2-dimethyl-4-(2-methylphenyl)-5-oxopiperazin-1-yl]-1-[(2S,4R)-4-ethyl-5-oxotetrahydrofuran-2-yl]ethyl}-2-nitrobenzenesulfonamide obtained in Example (110a) (2.18 mmol) and 0.45 ml of thiophenol (content: 95%) (4.37 mmol) in acetonitrile (22 ml) under a nitrogen atmosphere at room temperature, and the mixture was stirred at the same temperature for one hour. Brine was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol=19/1-9/1). 197 mg of sodium bicarbonate (2.34 mmol) and 510 mg of di-t-butyl dicarbonate (2.34 mmol) were added to a solution of 4-{(S)-2-amino-2-[(2S,4R)-4-ethyl-5-oxotetrahydrofuran-2-yl]ethyl}-5,5-dimethyl-1-(2-methylphenyl)piperazin-2-one obtained above in ethyl acetate (10 ml)-water (10 ml), and the mixture was stirred at room temperature for 15 hours. Brine was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:n-hexane/ethyl acetate=3/7) to obtain 915 mg of the title compound (yield: 88%).

Colorless solid.
$^1$H NMR spectrum (CDCl$_3$, 400 MHz), δ: 7.28-7.22 (m, 3H), 7.13-7.06 (m, 1H), 4.47-4.43 (m, 1H), 3.86 (br s, 1H), 3.56-3.16 (m, 4H), 2.76-2.37 (m, 4H), 2.24 (bs s, 1.8H), 2.23 (br s, 1.2H), 2.08-2.01 (m, 1H), 1.92-1.81 (m, 1H), 1.62-1.51 (m, 1H), 1.46 (br s, 9H), 1.22 (br s, 6H), 1.03 (br t, 3H, J=7.4 Hz).

(110c) {(1S,2S,4R)-4-(2,2-Dimethylpropylcarbamoyl)-1-[2,2-dimethyl-4-(2-methylphenyl)-5-oxopiperazin-1-ylmethyl]-2-hydroxyhexyl}carbamic acid t-butyl ester 10 mg of 2-hydroxypyridine (0.11 mmol) was added to a solution of 100 mg of {(S)-2-[2,2-dimethyl-4-(2-methylphenyl)-5-oxopiperazin-1-yl]-1-[(2S,4R)-4-ethyl-5-oxotetrahydrofuran-2-yl]ethyl}carbamic acid t-butyl ester obtained in Example (110b) (0.21 mmol) in (2,2-dimethylpropyl)amine (0.5 ml), and the mixture was stirred at 80° C. for four hours. The reaction mixture was cooled and then concentrated under reduced pressure and further stirred at 80° C. for 14 hours. The reaction mixture was cooled and then water was added, followed by extraction with ethyl acetate. Then, the organic layer was dried over anhydrous magnesium sulfate. After filtration, the solvent was evaporated under reduced pressure, and the residue was purified by silica gel column chromatography (elution solvent:ethyl acetate) to obtain 105 mg of the title compound (yield: 89%).

Colorless solid.
$^1$H NMR spectrum (CDCl$_3$, 400 MHz), δ: 7.28-7.22 (m, 3H), 7.11-7.07 (m, 1H), 5.05-4.96 (m, 2H), 3.93-3.89 (m, 1H), 3.68-3.15 (m, 6H), 2.99-2.95 (m, 1H), 2.78-2.61 (m, 2H), 2.38-2.29 (m, 1H), 2.22 (br s, 3H), 1.78-1.69 (m, 3H), 1.55-1.39 (m, 1H), 1.46 (br s, 9H), 1.23-1.22 (m, 6H), 0.97-0.91 (m, 12H).

(110d) (2R,4S,5S)-5-Amino-6-[2,2-dimethyl-4-(2-methylphenyl)-5-oxopiperazin-1-yl]-2-ethyl-4-hydroxyhexanoic acid (2,2-dimethylpropyl)amide hemifumarate (½ fumarate)

0.43 ml of trifluoroacetic acid (5.6 mmol) was added to a solution of 105 mg of {(1S,2S,4R)-4-(2,2-dimethylpropylcarbamoyl)-1-[2,2-dimethyl-4-(2-methylphenyl)-5-oxopiperazin-1-ylmethyl]-2-hydroxyhexyl}carbamic acid t-butyl ester obtained in Example (110c) (0.19 mmol) in methylene chloride (1.0 ml) at room temperature, and the mixture was stirred at the same temperature for 30 minutes. After concentration under reduced pressure, a saturated sodium bicarbonate aqueous solution was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol/triethylamine=9/1/0-90/10/1). 9.7 mg of fumaric acid (0.08 mmol) was added to a solution of 77 mg of (2R,4S,5S)-5-amino-6-[4-(2-chlorophenyl)-2,2-dimethyl-5-oxopiperazin-1-yl]-4-hydroxy-2-methylhexanoic acid (2,2-dimethylpropyl)amide obtained above (0.17 mmol) in methanol (2 ml), and the mixture was stirred at room temperature for five minutes. The reaction mixture was concentrated under reduced pressure, and n-hexane (1 ml) was added to the residue. The solid was collected by filtration to obtain 69 mg of the title compound (yield: 71%).

Colorless solid.

$^1$H NMR spectrum (CD$_3$OD, 400 MHz), δ: 7.32-7.24 (m, 3H), 7.19-7.11 (m, 1H), 6.66 (1H, s), 3.69-3.50 (m, 3H), 3.37-3.11 (m, 4H), 2.94-2.82 (m, 1.6H), 2.79-2.76 (m, 0.4H), 2.65-2.54 (m, 1.4H), 2.49 (dd, 0.6H, J=13.4 Hz, 4.3 Hz), 2.24 (s, 1.2H), 2.23 (s, 1.8H), 1.92-1.83 (m, 1H), 1.70-1.49 (m, 3H), 1.27-1.25 (m, 6H), 0.97 (t, 3H, J=7.3 Hz), 0.93 (s, 9H).

mass spectrum (FAB$^+$), m/z: 461 ((M+H)$^+$).

Example 111

(2R,4S,5S)-5-Amino-6-[2,2-dimethyl-4-(2-ethylphenyl)-5-oxopiperazin-1-yl]-2-ethyl-4-hydroxyhexanoic acid (2,2-dimethylpropyl)amide hemifumarate (½ fumarate) (Exemplary Compound No. 2-199)

81 mg of the title compound (total yield over four steps: 57%) was obtained in the same manner as in Examples (1l) to (1o) using (3R,5S)-3-ethyl-5-[(S)-1-(2-nitrobenzenesulfonyl)aziridin-2-yl]dihydrofuran-2-one obtained in Example (106g), 1-(2-ethylphenyl)-5,5-dimethylpiperazin-2-one obtained in Example (53a) and (2,2-dimethylpropyl)amine.

Colorless solid.

$^1$H NMR spectrum (CD$_3$OD, 400 MHz), δ: $^1$H NMR spectrum (CD$_3$OD, 400 MHz), δ: 7.99 (br s, 1H), 7.39-7.26 (m, 3H), 7.16-7.10 (m, 1H), 6.68 (s, 1H), 3.74-3.48 (m, 4H), 3.38-3.13 (m, 2H), 2.95-2.90 (m, 1.6H), 2.67-2.61 (m, 0.4H), 2.52-2.48 (m, 1H), 2.62-2.55 (m, 3H), 1.90-1.84 (m, 1H), 1.69-1.53 (m, 3H), 1.29-1.20 (m, 9H), 0.98 (t, 3H, J=7.6 Hz), 0.94 (s, 9H).

mass spectrum (FAB$^+$), m/z: 475 ((M+H)$^+$).

Example 112

(2R,4S,5S)-5-Amino-6-[4-(2-chloro-5-fluorophenyl)-2,2-dimethyl-5-oxopiperazin-1-yl]-2-ethyl-4-hydroxyhexanoic acid (2,2-dimethylpropyl)amide hemifumarate (½ fumarate) (Exemplary Compound No. 2-192)

179 mg of the title compound (total yield over four steps: 73%) was obtained in the same manner as in Examples (1l) to (1o) using (3R,5S)-3-ethyl-5-[(S)-1-(2-nitrobenzenesulfonyl)aziridin-2-yl]dihydrofuran-2-one obtained in Example (106g), 1-(2-chloro-5-fluorophenyl)-5,5-dimethylpiperazin-2-one obtained in Example (62d) and (2,2-dimethylpropylamine).

Colorless solid.

$^1$H NMR spectrum (CD$_3$OD, 400 MHz), δ: 7.56 (dd, 1H, J=9.7 Hz, 5.2 Hz), 7.21-7.16 (m, 2H), 6.67 (1H, s), 3.63-3.54 (m, 3H), 3.39-3.16 (m, 4H), 2.97-2.90 (m, 1.6H), 2.72 (br s, 0.8H), 2.57-2.48 (m, 1.6H), 1.89-1.82 (m, 1H), 1.70-1.49 (m, 3H), 1.30 (br s, 3H), 1.26 (br s, 6H), 0.97 (t, 3H, J=7.4 Hz), 0.93 (s, 9H).

mass spectrum (FAB$^+$), m/z: 499 ((M+H)$^+$).

Example 113

(2R,4S,5S)-5-Amino-6-[2,2-dimethyl-4-(3-fluoro-2-methylphenyl)-5-oxopiperazin-1-yl]-2-ethyl-4-hydroxyhexanoic acid isobutylamide fumarate (Exemplary Compound No. 2-162)

164 mg of the title compound (total yield over four steps: 46%) was obtained in the same manner as in Examples (1l) to (1o) using (3R,5S)-3-ethyl-5-[(S)-1-(2-nitrobenzenesulfonyl)aziridin-2-yl]dihydrofuran-2-one obtained in Example (106g), 5,5-dimethyl-1-(3-fluoro-2-methylphenyl)piperazin-2-one obtained in Example (67d) and isobutylamine.

Colorless solid.

$^1$H NMR spectrum (CD$_3$OD, 400 MHz), δ: 8.13 (br s, 1H), 7.33-7.26 (m, 1H), 7.10 (br t, 1H, J=8.8 Hz), 7.04-6.99 (m, 1H), 6.70 (s, 2H), 3.71-3.48 (m, 3H), 3.39-3.11 (m, 4H), 2.97-2.89 (m, 1.6H), 2.85-2.79 (m, 0.4H), 2.64-2.60 (m, 0.4H), 2.56-2.48 (m, 1.6H), 2.14 (br s, 3H), 1.89-1.75 (m, 2H), 1.69-1.48 (m, 3H), 1.28-1.25 (m, 6H), 0.98-0.93 (m, 9H).

mass spectrum (FAB$^+$), m/z: 465 ((M+H)$^+$).

Example 114

(2R,4S,5S)-5-Amino-6-[2,2-dimethyl-4-(5-fluoro-2-methylphenyl)-5-oxopiperazin-1-yl]-2-ethyl-4-hydroxyhexanoic acid (2,2-dimethylpropyl)amide hemifumarate (½ fumarate) (Exemplary Compound No. 2-191)

142 mg of the title compound (total yield over four steps: 37%) was obtained in the same manner as in Examples (1l) to (1o) using (3R,5S)-3-ethyl-5-[(S)-1-(2-nitrobenzenesulfonyl)aziridin-2-yl]dihydrofuran-2-one obtained in Example (106g), 5,5-dimethyl-1-(5-fluoro-2-methylphenyl)piperazin-2-one obtained in Example (70d) and (2,2-dimethylpropyl)amine.

Colorless solid.

$^1$H NMR spectrum (CD$_3$OD, 400 MHz), δ: 7.33-7.29 (m, 1H), 7.06-6.92 (m, 2H), 6.66 (1H, s), 3.68-3.47 (m, 3H), 3.38-3.11 (m, 4H), 2.94-2.89 (m, 1.6H), 2.80-2.74 (m, 0.4H), 2.66-2.54 (m, 1.4H), 2.48 (dd, 0.6H, J=12.9 Hz, 3.9 Hz), 2.19 (s, 3H), 1.89-1.82 (m, 1H), 1.72-1.47 (m, 3H), 1.26-1.24 (m, 6H), 0.97 (t, 3H, J=7.4 Hz), 0.93 (s, 9H).

mass spectrum (FAB$^+$), m/z: 479 ((M+H)$^+$).

Example 115

(2R,4S,5S)-5-Amino-6-[2,2-dimethyl-4-(5-fluoro-2-methylphenyl)-5-oxopiperazin-1-yl]-2-ethyl-4-hydroxyhexanoic acid isobutylamide hemifumarate (½ fumarate) (Exemplary Compound No. 2-163)

133 mg of the title compound (total yield over four steps: 35%) was obtained in the same manner as in Examples (1l) to (1o) using (3R,5S)-3-ethyl-5-[(S)-1-(2-nitrobenzenesulfonyl)aziridin-2-yl]dihydrofuran-2-one obtained in Example (106g), 5,5-dimethyl-1-(5-fluoro-2-methylphenyl)piperazin-2-one obtained in Example (70d) and isobutylamine.

Colorless solid.

$^1$H NMR spectrum (CD$_3$OD, 400 MHz), δ: 7.33-7.29 (m, 1H), 7.06-6.92 (m, 2H), 6.66 (s, 1H), 3.68-3.46 (m, 3H), 3.38-3.10 (m, 4H), 2.95-2.89 (m, 1.6H), 2.81-2.75 (m, 0.4H), 2.63 (dd, 0.4H, J=13.7 Hz, 4.3 Hz), 2.57-2.45 (m, 1.6H), 2.20 (s, 3H), 1.88-1.75 (m, 2H), 1.70-1.46 (m, 3H), 1.27-1.25 (m, 6H), 0.97-0.92 (m, 9H).

mass spectrum (FAB$^+$), m/z: 465 ((M+H)$^+$).

Example 116

(2R,4S,5S)-5-Amino-6-[4-(2-chlorophenyl)-2,2-dimethyl-5-oxopiperazin-1-yl]-4-hydroxy-2-propylhexanoic acid (2,2-dimethylpropyl)amide hemifumarate (½ fumarate) (Exemplary Compound No. 2-200)

(116a) (S)-4-Benzyl-3-[(2R,4E)-6-benzyloxy-2-propylhex-4-enoyl]oxazolidin-2-one 165 ml of a solution of sodium bis(trimethylsilyl)amide in n-hexane (1.03 mol/l) (169 mmol) was added to a solution of 37.0 g of (S)-4-benzyl-3-pentanoyloxazolidin-2-one obtained in Reference Example 6 (142 mmol) in tetrahydrofuran (330 ml) under a nitrogen atmosphere and at −78° C. over 45 minutes, and the mixture was stirred at the same temperature for 30 minutes. Then, a solution of 35.8 g of [(E)-4-bromobut-2-enyloxymethyl]benzene obtained in Reference Example 4 (148 mmol) in tetrahydrofuran (80 ml) was added to the solution obtained above over 30 minutes, and the mixture was stirred at the same temperature for 30 minutes. Thereafter, the mixture was raised to −40° C. and further stirred for four hours. 90 ml of an ammonium chloride aqueous solution was added to the reaction mixture, and the mixture was further stirred at room temperature for one hour. The reaction mixture was concentrated under reduced pressure and diluted with 500 ml of water, followed by extraction with ethyl acetate. Then, the organic layer was washed with water and brine and dried over anhydrous magnesium sulfate. After filtration, the solvent was evaporated under reduced pressure, and the residue was purified by silica gel column chromatography (elution solvent:n-hexane/ethyl acetate=7/1-2/1) to obtain 47.3 g of the title compound (yield: 79%).

Colorless liquid.

$^1$H NMR spectrum (CDCl$_3$, 400 MHz), δ: 7.34-7.22 (m, 8H), 7.18-7.13 (m, 2H), 5.75 (dt, 1H, J=15.6 Hz, 6.7 Hz), 5.67 (dt, 1H, J=15.6 Hz, 5.5 Hz), 4.71-4.63 (m, 1H), 4.48 (s, 2H), 4.18-4.13 (m, 1H), 4.11 (dd, 1H, J=9.3 Hz, 2.7 Hz), 3.99-3.89 (m, 3H), 3.29 (dd, 1H, J=13.3 Hz, 3.1 Hz), 2.62 (dd, 1H, J=13.3 Hz, 9.8 Hz), 2.52-2.44 (m, 1H), 2.37-2.29 (m, 1H), 1.77-1.67 (m, 1H), 1.53-1.43 (m, 1H), 1.38-1.27 (m, 2H), 0.91 (t, 3H, J=7.4 Hz).

(116b) (2R,4E)-6-Benzyloxy-2-propylhex-4-enoic acid

A solution of 24.1 g of (S)-4-benzyl-3-[(2R,4E)-6-benzyloxy-2-propylhex-4-enoyl]oxazolidin-2-one (57.2 mmol) obtained in Example (116a) in a mixed solvent of tetrahydrofuran (800 ml) and water (260 ml) was cooled in an ice bath, and then 35.0 ml of a 30% hydrogen peroxide aqueous solution and 4.83 g of lithium hydroxide monohydrate (115 mmol) were added thereto. The mixture was stirred at the same temperature for 30 minutes, and then raised to room temperature and further stirred for 16 hours. After cooling in an ice bath, 250 ml of a 1.5 M sodium thiosulfate aqueous solution was added to the reaction mixture. The mixture was further stirred at room temperature for one hour. The reaction mixture was concentrated under reduced pressure, diluted with 500 ml of water and washed with ethyl acetate. Then, the aqueous layer was made acidic with 30 g of sodium dihydrogenphosphate, followed by extraction with ethyl acetate. The organic layer was washed with brine and dried over anhydrous magnesium sulfate. After filtration, the solvent was evaporated under reduced pressure to obtain 13.6 g of the crude title compound.

Colorless liquid.

$^1$H NMR spectrum (CDCl$_3$, 400 MHz), δ: 7.37-7.25 (m, 5H), 5.73-5.61 (m, 2H), 4.49 (s, 2H), 4.02-3.92 (m, 2H), 2.51-2.34 (m, 2H), 2.31-2.22 (m, 1H), 1.68-1.57 (m, 1H), 1.54-1.23 (m, 3H), 0.91 (t, 3H, J=7.4 Hz).

(116c) (3R,5S)-5-[(R)-2-Benzyloxy-1-hydroxyethyl]-3-propyldihydrofuran-2-one 400 ml of a solution of a sodium tetraborate buffer solution (0.05 M) in a 0.4 mM disodium ethylenediaminetetraacetate aqueous solution, 0.600 g of tetrabutylammonium bisulfate (1.77 mmol) and 10.3 g of 1,2:4,5-di-O-isopropylidene-β-D-erythro-2,3-hexodiuro-2,6-pyranose (39.9 mmol) were added to 10.5 g of (2R,4E)-6-benzyloxy-2-propylhex-4-enoic acid obtained in Example (116b) (40.0 mmol) in a mixed solvent of acetonitrile (150 ml) and dimethoxymethane (300 ml) at room temperature, and the mixture was stirred for 10 minutes. The reaction mixture was cooled in an ice bath. Then, a solution of 34.0 g of Oxone (trade mark) (55.2 mmol) in a 0.4 mM disodium ethylenediaminetetraacetate aqueous solution (200 ml) and a solution of 31.8 g of potassium carbonate (230 mmol) in water (200 ml) were separately added dropwise over seven hours. The mixture was stirred at the same temperature for one hour and then diluted with 200 ml of water, followed by extraction with ethyl acetate. Then, the organic layer was washed with brine and dried over anhydrous magnesium sulfate. After filtration, the solvent was evaporated under reduced pressure, and the residue was purified by silica gel column chromatography (elution solvent:n-hexane/ethyl acetate=6/1-1/1) to obtain 7.30 g of the title compound (total yield over two steps: 66%).

Colorless liquid.

$^1$H NMR spectrum (CDCl$_3$, 400 MHz), δ: 7.40-7.29 (m, 5H), 4.58 (d, 1H, J=11.7 Hz), 4.54 (d, 1H, J=11.7 Hz), 4.46 (ddd, 1H, J=8.2 Hz, 6.3 Hz, 4.3 Hz), 3.90-3.83 (m, 1H), 3.64 (dd, 1H, J=9.8 Hz, 3.7 Hz), 3.56 (dd, 1H, J=9.8 Hz, 5.9 Hz), 2.70-2.61 (m, 1H), 2.50-2.41 (m, 2H), 2.00-1.92 (m, 1H), 1.86-1.75 (m, 1H), 1.49-1.36 (m, 3H), 0.95 (t, 3H, J=7.0 Hz).

(116d) Methanesulfonic acid (R)-2-benzyloxy-1-[(2S,4R)-5-oxo-4-propyltetrahydrofuran-2-yl]ethyl ester A solution of 12.1 g of (3R,5S)-5-[(R)-2-benzyloxy-1-hydroxyethyl]-3-propyldihydrofuran-2-one obtained in Example (116c) (43.5 mmol) in methylene chloride (300 ml) was cooled in an ice bath. Then, 13.2 g of triethylamine (131 mmol) and 7.30 g of methanesulfonyl chloride (63.7 mmol) were added thereto, and the mixture was stirred at the same temperature for one hour. 500 ml of water was added to the reaction mixture, followed by extraction with methylene chloride. Then, the organic layer was washed with water and brine and dried over anhydrous magnesium sulfate. After filtration, the solvent was evaporated under reduced pressure, and the residue was purified by silica gel column chromatography (elution solvent:n-hexane/ethyl acetate=4/1-1/1) to obtain 15.2 g of the title compound (yield: quant.).

Colorless liquid.

$^1$H NMR spectrum (CDCl$_3$, 400 MHz), δ: 7.40-7.28 (m, 5H), 4.86-4.80 (m, 1H), 4.65 (ddd, 1H, J=8.2 Hz, 5.5 Hz, 4.5 Hz), 4.56 (s, 2H), 3.77 (dd, 1H, J=1.0 Hz, 5.9 Hz), 3.74 (dd, 1H, J=11.0 Hz, 5.5 Hz), 3.04 (s, 3H), 2.71-2.62 (m, 1H), 2.54-2.45 (m, 1H), 2.05-1.97 (m, 1H), 1.85-1.76 (m, 1H), 1.51-1.36 (m, 3H), 0.95 (t, 3H, J=7.4 Hz).

(116e) (3R,5S)-5-[(S)-1-Azido-2-benzyloxyethyl]-3-propyldihydrofuran-2-one 7.49 g of sodium azide (115 mmol) was added to a solution of 29.1 g of methanesulfonic acid (R)-2-benzyloxy-1-[(2S,4R)-5-oxo-4-propyltetrahydrofuran-2-yl]ethyl ester obtained in Example (116d) (81.7 mmol) in N,N'-dimethylpropyleneurea (300 ml) at room temperature, and the mixture was stirred at 60° C. for two days. The reaction mixture was cooled and then poured into ice water, followed by extraction with diethyl ether. Then, the organic layer was washed with water and brine and dried over anhydrous magnesium sulfate. After filtration, the solvent was evaporated under reduced pressure, and the residue was purified by silica gel column chromatography (elution solvent:n-hexane/ethyl acetate=6/1) to obtain 23.0 g of the title compound (yield: 93%).

Colorless liquid.

$^1$H NMR spectrum (CDCl$_3$, 400 MHz), δ: 7.40-7.28 (m, 5H), 4.62-4.54 (m, 3H), 3.80-3.73 (m, 2H), 3.66 (ddd, 1H, J=6.6 Hz, 5.5 Hz, 3.1 Hz), 2.81-2.72 (m, 1H), 2.35-2.27 (m, 1H), 2.07-1.97 (m, 1H), 1.87-1.75 (m, 1H), 1.48-1.35 (m, 3H), 0.95 (t, 3H, J=7.0 Hz).

(116f) N-{(S)-2-Hydroxy-1-[(2S,4R)-5-oxo-4-propyltetrahydrofuran-2-yl]ethyl}-2-nitrobenzenesulfonamide A suspension of 23.0 g of (3R,5S)-5-[(S)-1-azido-2-benzyloxyethyl]-3-propyldihydrofuran-2-one obtained in Example (116e) (75.9 mmol), 40.0 ml of a solution of 4 N hydrochloric acid in dioxane (160 mmol) and 5.20 g of 10% palladium-carbon (50% wet) in ethanol (400 ml) was stirred under a hydrogen atmosphere at room temperature for seven hours. Hydrogen in the reaction vessel was replaced by nitrogen, and then the reaction mixture was diluted with 200 ml of ethanol. Palladium-carbon was separated by filtration and washed with ethanol. The solvent was evaporated from the filtrate under reduced pressure to obtain crude (3R,5S)-5-[(S)-1-amino-2-hydroxyethyl]-3-propyldihydrofuran-2-one hydrochloride.

23.9 g of triethylamine (237 mmol) and 26.7 g of O-nitrobenzenesulfonyl chloride (120 mmol) were added to a solution of (3R,5S)-5-[(S)-1-amino-2-hydroxyethyl]-3-propyldihydrofuran-2-one hydrochloride obtained in the above reaction in a mixed solvent of tetrahydrofuran (350 ml) and water (35.0 ml) at 0° C. The mixture was stirred at the same temperature for two hours and further stirred at room temperature for 12 hours. The reaction mixture was concentrated under reduced pressure and 500 ml of water was added, followed by extraction with ethyl acetate. Then, the organic layer was washed with water, a saturated sodium bicarbonate aqueous solution and brine and dried over anhydrous magnesium sulfate. After filtration, the solvent was evaporated under reduced pressure, and the residue was purified by silica gel column chromatography (elution solvent:ethyl acetate).

Further, 30 ml of diisopropyl ether and 30 ml of ethyl acetate were added, and the precipitated solid was collected by filtration to obtain 14.6 g of the title compound (total yield over two steps: 52%).

Colorless solid.

Optical rotation, $[\alpha]_D^{23.6° C.}$=+37.0° (c=1.00, MeOH).

$^1$H NMR spectrum (CDCl$_3$, 400 MHz), δ: 8.16-8.10 (m, 1H), 7.93-7.87 (m, 1H), 7.78-7.72 (m, 2H), 5.85 (br d, 1H, J=7.8 Hz), 4.67 (ddd, 1H, J=8.2 Hz, 5.5 Hz, 3.2 Hz), 3.73-3.61 (m, 3H), 2.80-2.71 (m, 1H), 2.54 (ddd, 1H, J=13.3 Hz, 9.8 Hz, 5.5 Hz), 2.06 (ddd, 1H, J=13.3 Hz, 8.2 Hz, 7.0 Hz), 1.94-1.90 (m, 1H), 1.82-1.70 (m, 1H), 1.51-1.35 (m, 3H), 0.94 (t, 3H, J=7.2 Hz).

(116g) (3R,5S)-5-[(S)-1-(2-Nitrobenzenesulfonyl)aziridin-2-yl]-3-propyldihydrofuran-2-one 2.95 ml of a solution of diethyl azodicarboxylate in toluene (40%) (6.48 mmol) was added to a solution of 2.01 g of N-{(S)-2-hydroxy-1-[(2S,4R)-5-oxo-4-propyltetrahydrofuran-2-yl]ethyl}-2-nitrobenzenesulfonamide obtained in Example (116f) (5.4 mmol) and 1.7 g of triphenylphosphine (6.48 mmol) in tetrahydrofuran (54 ml) under ice-cooling over five minutes, and the mixture was stirred at the same temperature for 10 minutes. The reaction mixture was concentrated under reduced pressure, and the residue was purified by silica gel column chromatography (elution solvent: toluene/acetone=5/1) to obtain 1.4 g of the title compound (yield: 74%).

Colorless liquid.

$^1$H NMR spectrum (CDCl$_3$, 400 MHz), δ: 8.14 (dd, 1H, J=7.4 Hz, 1.6 Hz), 7.83-7.73 (m, 3H), 4.77 (dt, 1H, J=8.6 Hz, 2.4 Hz), 3.26-3.23 (m, 1H), 2.87-2.79 (m, 2H), 2.65 (d, 1H, J=4.7 Hz), 2.59-2.53 (m, 1H), 2.17 (dt, 1H, J=12.5 Hz, 9.4 Hz), 1.87-1.77 (m, 1H), 1.46-1.32 (m, 3H), 0.93 (t, 3H, J=7.6 Hz).

(116h) N—{(S)-2-[4-(2-Chlorophenyl)-2,2-dimethyl-5-oxopiperazin-1-yl]-1-[(2S,4R)-5-oxo-4-propyltetrahydrofuran-2-yl]ethyl}-2-nitrobenzenesulfonamide A solution of 700 mg of (3R,5S)-5-[(S)-1-(2-nitrobenzenesulfonyl)aziridin-2-yl]-3-propyldihydrofuran-2-one obtained in Example (116g) (1.98 mmol) and 611 mg of 1-(2-chlorophenyl)-5,5-dimethylpiperazin-2-one obtained in Example (1k) (2.57 mmol) in toluene (20 ml) was stirred at 110° C. for 1.5 hours. After cooling, the reaction mixture was concentrated under reduced pressure, and the residue was purified by silica gel column chromatography (elution solvent: toluene/acetone 5/1) to obtain 888 mg of the title compound (yield: 76%).

Colorless solid.

$^1$H NMR spectrum (CDCl$_3$, 400 MHz), δ: 8.18-8.10 (m, 1H), 7.95-7.89 (m, 1H), 7.80-7.74 (m, 2H), 7.46-7.11 (m, 4H), 5.91 (br s, 0.5H), 5.52 (br s, 0.5H), 4.89 (br s, 1H), 3.64 (br s, 1H), 3.30-2.50 (m, 7H), 2.17-2.06 (m, 1H), 1.87-1.76 (m, 1H), 1.50-1.39 (m, 2H), 1.17 (br s, 3H), 1.07 (br s, 3H), 0.96 (br t, 3H, J=7.2 Hz).

(116i) {(S)-2-[4-(2-Chlorophenyl)-2,2-dimethyl-5-oxopiperazin-1-yl]-1-[(2S,4R)-5-oxo-4-propyltetrahydrofuran-2-yl]ethyl}carbamic acid t-butyl ester 585 mg of cesium carbonate (1.8 mmol) was added to a solution of 888 mg of N-{(S)-2-[4-(2-chlorophenyl)-2,2-dimethyl-5-oxopiperazin-1-yl]-1-[(2S,4R)-5-oxo-4-propyltetrahydrofuran-2-yl]ethyl}-2-nitrobenzenesulfonamide obtained in Example (116h) (1.50 mmol) and 0.46 ml of thiophenol (content: 95%) (4.5 mmol) in acetonitrile (15 ml) under a nitrogen atmosphere at room temperature, and the mixture was stirred at the same temperature for 2.5 hours. Brine was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol=50/1-10/1). 94 mg of sodium bicarbonate (1.12 mmol) and 245 mg of di-t-butyl dicarbonate (1.12 mmol) were added to a solution of 4-{(S)-2-amino-2-[(2S,4R)-5-oxo-4-propyltetrahydrofuran-2-yl]ethyl}-1-(2-chlorophenyl)-5,5-dimethylpiperazin-2-one obtained above in ethyl acetate (5 ml)-water (5 ml), and the mixture was stirred at room temperature overnight. Brine was added to the reaction mixture, followed by extraction with ethyl acetate. Then, the organic layer was dried over anhydrous magnesium sulfate. After filtration, the solvent was evaporated under reduced pressure, and the residue was purified by silica gel column chromatography (elution solvent:methylene chloride/methanol=40/1-20/1) to obtain 418 mg of the title compound (yield: 55%).

Colorless solid.

$^1$H NMR spectrum (CDCl$_3$, 400 MHz), δ: 7.48 (br d, 1H, J=7.4 Hz), 7.34-7.21 (m, 3H), 4.91-4.85 (m, 1H), 4.49-4.43 (m, 1H), 3.68 (br s, 1H), 3.59-3.24 (m, 5H), 2.80-2.37 (m, 4H), 2.06-2.00 (m, 1H), 1.85-1.78 (m, 1H), 1.45-1.22 (m, 17H), 0.96 (br t, 3H, J=7.0 Hz).

(116j) {(1S,2S,4R)-4-(2,2-Dimethylpropylcarbamoyl)-1-[4-(2-chlorophenyl)-2,2-dimethyl-5-oxopiperazin-1-ylmethyl]-2-hydroxyheptyl}carbamic acid t-butyl ester 3.8 mg of 2-hydroxypyridine (0.04 mmol) was added to a solution of 101 mg of {(S)-2-[4-(2-chlorophenyl)-2,2-dimethyl-5-oxopiperazin-1-yl]-1-[(2S,4R)-5-oxo-4-propyltetrahydrofuran-2-yl]ethyl}carbamic acid t-butyl ester obtained in Example (116i) (0.2 mmol) in (2,2-dimethylpropyl)amine (1 ml), and the mixture was stirred at 80° C. for five hours. The reaction mixture was cooled and then water was added, followed by extraction with ethyl acetate. Then, the organic layer was dried over anhydrous magnesium sulfate. After filtration, the solvent was evaporated under reduced pressure, and the residue was purified by silica gel column chromatography (elution solvent:methylene chloride/methanol=30/1-20/1) to obtain 111 mg of the title compound (yield: 94%).

Colorless solid.

$^1$H NMR spectrum (CDCl$_3$, 400 MHz), δ: 7.47 (br d, 1H, J=7.4 Hz), 7.34-7.21 (m, 3H), 5.84 (br s, 1H), 5.03 (br s, 1H), 3.92 (br s, 1H), 3.70-3.65 (m, 1H), 3.49-3.16 (m, 5H), 2.98-2.95 (m, 1H), 2.80-2.63 (m, 2H), 2.44 (br s, 1H), 1.76-1.65 (m, 4H), 1.46 (br s, 9H), 1.44-1.22 (m, 8H), 0.95-0.91 (m, 12H).

(116k) (2R,4S,5S)-5-Amino-6-[4-(2-chlorophenyl)-2,2-dimethyl-5-oxopiperazin-1-yl]-4-hydroxy-2-propylhexanoic acid (2,2-dimethylpropyl)amide hemifumarate (½ fumarate)

0.43 ml of trifluoroacetic acid (5.6 mmol) was added to a solution of 111 mg of {(1S,2S,4R)-4-(2,2-dimethylpropylcarbamoyl)-1-[4-(2-chlorophenyl)-2,2-dimethyl-5-oxopiperazin-1-ylmethyl]-2-hydroxyheptyl}carbamic acid t-butyl ester obtained in Example (116j) (0.19 mmol) in methylene chloride (0.8 ml) at room temperature, and the mixture was stirred at the same temperature for 30 minutes. After concentration under reduced pressure, a saturated sodium bicarbonate aqueous solution was added to the reaction mixture, followed by extraction with methylene chloride. Then, the organic layer was dried over anhydrous magnesium sulfate. After filtration, the solvent was evaporated under reduced pressure, and the residue was purified by silica gel column chromatography (elution solvent:methylene chloride/methanol/triethylamine=100/10/1). 5.8 mg of fumaric acid (0.05 mmol) was added to a solution of 52 mg of (2R,4S,5S)-5-amino-6-[4-(2-chlorophenyl)-2,2-dimethyl-5-oxopiperazin-1-yl]-4-hydroxy-2-propylhexanoic acid (2,2-dimethylpropyl)amide obtained above (0.1 mmol) in methanol (1 ml), and the mixture was stirred at room temperature for five minutes. The reaction mixture was concentrated under reduced pressure, and methylene chloride (0.5 ml) was added to the residue. Diisopropyl ether (5 ml) was further added and the solid was collected by filtration to obtain 46 mg of the title compound (yield: 84%).

Colorless solid.

$^1$H NMR spectrum (CD$_3$OD, 400 MHz), δ: 7.56-7.54 (m, 1H), 7.42-7.32 (m, 3H), 6.67 (s, 1H), 3.72-3.48 (m, 3H), 3.37-3.13 (m, 4H), 2.92-2.88 (m, 1.6H), 2.67-2.64 (m, 1.8H), 2.52-2.47 (m, 0.6H), 1.89-1.82 (m, 1H), 1.66-1.58 (m, 2H), 1.47-1.36 (m, 3H), 1.30-1.26 (m, 6H), 0.97-0.93 (m, 12H).

mass spectrum (FAB$^+$), m/z: 495 ((M+H)$^+$).

Example 117

(2R,4S,5S)-5-Amino-6-[4-(2-chlorophenyl)-2,2-dimethyl-5-oxopiperazin-1-yl]-4-hydroxy-2-propylhexanoic acid isobutylamide hemifumarate (½ fumarate) (Exemplary Compound No. 2-218)

133 mg of the title compound (total yield over two steps: 80%) was obtained in the same manner as in Examples (1n) and (1o) using {(S)-2-[4-(2-chlorophenyl)-2,2-dimethyl-5-oxopiperazin-1-yl]-1-[(2S,4R)-5-oxo-4-ethyltetrahydrofuran-2-yl]ethyl}carbamic acid t-butyl ester obtained in Example (116i) and isobutylamine.

Colorless solid.

$^1$H NMR spectrum (CD$_3$OD, 400 MHz), δ: 7.55-7.53 (m, 1H), 7.44-7.32 (m, 3H), 6.68 (s, 1H), 3.66-3.50 (m, 4H), 3.38-3.11 (m, 3H), 2.98-2.90 (m, 1.6H), 2.81-2.71 (m, 0.8H), 2.65-2.60 (m, 1H), 2.51 (dd, 0.6H, J=13.5 Hz, 4.5 Hz), 1.89-1.77 (m, 2H), 1.67-1.58 (m, 2H), 1.49-1.34 (m, 3H), 1.29-1.26 (m, 6H), 0.96-0.92 (m, 9H).

mass spectrum (FAB$^+$), m/z: 481 ((M+H)$^+$).

Example 118

(2R,4S,5S)-5-Amino-6-[2,2-dimethyl-4-(2-methylphenyl)-5-oxopiperazin-1-yl]-4-hydroxy-2-propylhexanoic acid (2,2-dimethylpropyl)amide hemifumarate (½ fumarate) (Exemplary Compound No. 2-213)

155 mg of the title compound (total yield over four steps: 74%) was obtained in the same manner as in Examples (1l) to (1o) using (3R,5S)-5-[(S)-1-(2-nitrobenzenesulfonyl)aziridin-2-yl]-3-propyldihydrofuran-2-one obtained in Example (116g), 5,5-dimethyl-1-(2-methylphenyl)piperazin-2-one obtained in Example (51d) and (2,2-dimethylpropyl)amine.

Colorless solid.

$^1$H NMR spectrum (CD$_3$OD, 400 MHz), δ: 7.32-7.24 (m, 3H), 7.19-7.11 (m, 1H), 6.67 (1H, s), 3.69-3.50 (m, 3H), 3.37-3.10 (m, 4H), 2.93-2.87 (m, 1.6H), 2.77 (dd, 0.4H, J=13.2 Hz, 10.2 Hz), 2.69-2.60 (m, 1.4H), 2.47 (dd, 0.6H, J=13.4 Hz, 4.3 Hz), 2.24 (s, 1.2H), 2.23 (s, 1.8H), 1.89-1.82 (m, 1H), 1.68-1.33 (m, 5H), 1.27-1.24 (m, 6H), 0.97-0.90 (m, 12H).

mass spectrum (FAB$^+$), m/z: 475 ((M+H)$^+$).

Example 119

(2R,4S,5S)-5-Amino-6-[4-(2-chloro-5-fluorophenyl)-2,2-dimethyl-5-oxopiperazin-1-yl]-4-hydroxy-2-propylhexanoic acid (2,2-dimethylpropyl)amide hemifumarate (½ fumarate) (Exemplary Compound No. 2-217)

103 mg of the title compound (total yield over two steps: 74%) was obtained in the same manner as in Examples (1l) to (1o) using (3R,5S)-5-[(S)-1-(2-nitrobenzenesulfonyl)aziridin-2-yl]-3-propyldihydrofuran-2-one obtained in Example (116g), 1-(2-chloro-5-fluorophenyl)-5,5-dimethylpiperazin-2-one obtained in Example (62d) and (2,2-dimethylpropyl)amine.

Colorless solid.
$^1$H NMR spectrum (CD$_3$OD, 400 MHz), δ: 7.59-7.55 (m, 1H), 7.22-7.18 (m, 2H), 6.69 (s, 1H), 3.70-3.46 (m, 3H), 3.36-3.13 (m, 4H), 2.90-2.88 (m, 1.6H), 2.72-2.65 (m, 1.8H), 2.52-2.49 (m, 0.6H), 1.89-1.83 (m, 1H), 1.66-1.58 (m, 2H), 1.43-1.35 (m, 3H), 1.30-1.26 (m, 6H), 0.97-0.93 (m, 12H).

mass spectrum (FAB$^+$), m/z: 513 ((M+H)$^+$)

Example 120

(2R,4S,5S)-5-Amino-6-[2,2-dimethyl-4-(5-fluoro-2-methylphenyl)-5-oxopiperazin-1-yl]-4-hydroxy-2-propylhexanoic acid isobutylamide hemifumarate (½ fumarate) (Exemplary Compound No. 2-211)

70 mg of the title compound (total yield over four steps: 73%) was obtained in the same manner as in Examples (1l) to (1o) using (3R,5S)-5-[(S)-1-(2-nitrobenzenesulfonyl)aziridin-2-yl]-3-propyldihydrofuran-2-one obtained in Example (116g), 5,5-dimethyl-1-(5-fluoro-2-methylphenyl)piperazin-2-one obtained in Example (70d) and isobutylamine.

Colorless solid.
$^1$H NMR spectrum (CD$_3$OD, 400 MHz), δ: 7.33-7.30 (m, 1H), 7.06-6.93 (m, 2H), 6.68 (s, 1H), 3.71-3.36 (m, 3H), 3.34-3.11 (m, 4H), 2.95-2.90 (m, 1.6H), 2.80-2.75 (m, 0.4H), 2.66-2.60 (m, 1.4H), 2.49-2.46 (m, 0.6H), 2.20 (s, 3H), 1.87-1.76 (m, 2H), 1.63-1.55 (m, 2H), 1.37-1.34 (m, 3H), 1.26-1.22 (m, 6H), 0.96-0.92 (m, 9H).

mass spectrum (FAB$^+$), m/z: 478 ((M+H)$^+$).

Example 121

(2S,4S,5S)-5-Amino-6-[4-(2-chlorophenyl)-2,2-dimethyl-5-oxopiperazin-1-yl]-2-cyclopropyl-4-hydroxyhexanoic acid (2,2-dimethylpropyl)amide hemifumarate (½ fumarate) (Exemplary Compound No. 2-208)

(121a) (S)-4-Benzyl-3-[(2S,4E)-6-benzyloxy-2-cyclopropylhex-4-enoyl]oxazolidin-2-one 23.0 g of the title compound (yield: 69%) was obtained in the same manner as in Example (76a) using (S)-4-benzyl-3-propionyloxazolidin-2-one obtained in Reference Example 7 and [(E)-4-bromobut-2-enyloxymethyl]benzene obtained in Reference Example 4.

Colorless liquid.
$^1$H NMR spectrum (CDCl$_3$, 400 MHz), δ: 7.34-7.22 (m, 8H), 7.18-7.13 (m, 2H), 5.79 (dt, 1H, J=15.6 Hz, 6.8 Hz), 5.69 (dt, 1H, J=15.6 Hz, 5.8 Hz), 4.74-4.66 (m, 1H), 4.48 (s, 2H), 4.20-4.07 (m, 2H), 3.97 (d, 2H, J=5.9 Hz), 3.34-3.26 (m, 2H), 2.67-2.56 (m, 2H), 2.55-2.46 (m, 1H), 1.16-1.05 (m, 1H), 0.63-0.55 (m, 1H), 0.52-0.44 (m, 1H), 0.32-0.20 (m, 2H).

(121b) (2S,4E)-6-Benzyloxy-2-cyclopropylhex-4-enoic acid 14.3 g of the title compound (yield: quant.) was obtained in the same manner as in Example (76b) using (S)-4-benzyl-3-[(2S,4E)-6-benzyloxy-2-cyclopropylhex-4-enoyl]oxazolidin-2-one obtained in Example (121a).

Colorless liquid.
$^1$H NMR spectrum (CDCl$_3$, 500 MHz), δ: 7.37-7.26 (m, 5H), 5.75 (dt, 1H, J=15.6 Hz, 6.4 Hz), 5.69 (dt, 1H, J=15.6 Hz, 5.4 Hz), 4.49 (s, 2H), 3.98 (d, 2H, J=5.4 Hz), 2.57-2.49 (m, 1H), 2.48-2.40 (m, 1H), 1.73-1.65 (m, 1H), 1.01-0.92 (m, 1H), 0.64-0.51 (m, 2H), 0.39-0.32 (m, 1H), 0.22-0.15 (m, 1H).

(121c) (3S,5S)-5-[(R)-2-Benzyloxy-1-hydroxyethyl]-3-cyclopropyldihydrofuran-2-one 10.3 g of the title compound (yield: 72%) was obtained in the same manner as in Example (76c) using (2S,4E)-6-benzyloxy-2-cyclopropylhex-4-enoic acid obtained in Example (121b).

Colorless liquid.
$^1$H NMR spectrum (CDCl$_3$, 400 MHz), δ: 7.41-7.30 (m, 5H), 4.59 (d, 1H, J=11.7 Hz), 4.55 (d, 1H, J=11.7 Hz), 4.53-4.47 (m, 1H), 3.91-3.85 (m, 1H), 3.63 (dd, 1H, J=9.8 Hz, 4.4 Hz), 3.56 (dd, 1H, J=9.8 Hz, 6.4 Hz), 2.48-2.39 (m, 2H), 2.29-2.22 (m, 1H), 2.11-2.04 (m, 1H), 1.00-0.92 (m, 1H), 0.70-0.62 (m, 1H), 0.57-0.50 (m, 1H), 0.48-0.41 (m, 1H), 0.32-0.25 (m, 1H).

(121d) Methanesulfonic acid (R)-2-benzyloxy-1-[(2S,4S)-4-cyclopropyl-5-oxotetrahydrofuran-2-yl]ethyl ester 16.0 g of the title compound (yield: quant.) was obtained in the same manner as in Example (76d) using (3S,5S)-5-[(R)-2-benzyloxy-1-hydroxyethyl]-3-cyclopropyldihydrofuran-2-one obtained in Example (121c).

Colorless liquid.
$^1$H NMR spectrum (CDCl$_3$, 400 MHz), δ: 7.41-7.28 (m, 5H), 4.86-4.79 (m, 1H), 4.69 (ddd, 1H, J=7.8 Hz, 5.9 Hz, 5.5 Hz), 4.56 (s, 2H), 3.77 (dd, 1H, J=10.6 Hz, 6.7 Hz), 3.73 (dd, 1H, J=10.6 Hz, 5.5 Hz), 3.04 (s, 3H), 2.52-2.43 (m, 1H), 2.28-2.21 (m, 1H), 2.17-2.08 (m, 1H), 1.00-0.90 (m, 1H), 0.70-0.62 (m, 1H), 0.59-0.50 (m, 1H), 0.48-0.40 (m, 1H), 0.33-0.25 (m, 1H).

(121e) (3S,5S)-5-[(S)-1-Azido-2-benzyloxyethyl]-3-cyclopropyldihydrofuran-2-one 10.5 g of the title compound (yield: 77%) was obtained in the same manner as in Example (76e) using methanesulfonic acid (R)-2-benzyloxy-1-[(2S,4S)-4-cyclopropyl-5-oxotetrahydrofuran-2-yl]ethyl ester obtained in Example (121d).

Colorless liquid.

$^1$H NMR spectrum (CDCl$_3$, 400 MHz), δ: 7.41-7.28 (m, 5H), 4.64-4.59 (m, 1H), 4.58 (s, 2H), 3.76 (d, 2H, J=6.3 Hz), 3.65 (ddd, 1H, J=6.3 Hz, 5.5 Hz, 3.1 Hz), 2.38-2.27 (m, 2H), 2.18-2.07 (m, 1H), 0.99-0.88 (m, 1H), 0.70-0.61 (m, 1H), 0.57-0.41 (m, 2H), 0.31-0.23 (m, 1H).

(121f) N-{(S)-1-[(2S,4S)-4-Cyclopropyl-5-oxotetrahydrofuran-2-yl]-2-hydroxyethyl}-2-nitrobenzenesulfonamide 4.00 g of the title compound (total yield over two steps: 38%) was obtained in the same manner as in Example (1f) using (3S,5S)-5-[(S)-1-azido-2-benzyloxyethyl]-3-cyclopropyldihydrofuran-2-one obtained in Example (121e).

Colorless solid.

Optical rotation, $[\alpha]_D^{24.0°\ C.}$=+51.3° (c=1.00, MeOH).

$^1$H NMR spectrum (CDCl$_3$, 400 MHz), δ: 8.16-8.10 (m, 1H), 7.94-7.88 (m, 1H), 7.79-7.73 (m, 2H), 5.81 (br d, 1H, J=7.8 Hz), 4.71 (ddd, 1H, J=7.6 Hz, 6.5 Hz, 2.7 Hz), 3.74-3.61 (m, 3H), 2.54 (ddd, 1H, J=13.1 Hz, 9.6 Hz, 6.3 Hz), 2.34-2.27 (m, 1H), 2.16 (ddd, 1H, J=13.3 Hz, 7.8 Hz, 5.5 Hz), 1.87-1.81 (m, 1H), 1.00-0.90 (m, 1H), 0.68-0.60 (m, 1H), 0.58-0.50 (m, 1H), 0.48-0.41 (m, 1H), 0.33-0.25 (m, 1H).

(121g) (3S,5S)-5-[(S)-1-(2-Nitrobenzenesulfonyl)aziridin-2-yl]-3-cyclopropyldihydrofuran-2-one 1.2 g of the title compound (yield: 63%) was obtained in the same manner as in Example (1g) using N-{(S)-1-[(2S,4S)-4-cyclopropyl-5-oxotetrahydrofuran-2-yl]-2-hydroxyethyl}-2-nitrobenzenesulfonamide obtained in Example (121f).

Colorless liquid.

$^1$H NMR spectrum (CDCl$_3$, 400 MHz), δ: 8.10 (dd, 1H, J=7.4 Hz, 1.6 Hz), 7.84-7.72 (m, 3H), 4.77 (dt, 1H, J=8.2 Hz, 2.7 Hz), 3.25-3.22 (m, 1H), 2.82 (d, 1H, J=7.4 Hz), 2.64 (d, 1H, J=4.7 Hz), 2.56-2.50 (m, 1H), 2.39 (dd, 1H, J=18.0 Hz, 9.0 Hz), 2.28 (dt, 1H, J=12.9 Hz, 9.0 Hz), 0.92-0.84 (m, 1H), 0.70-0.63 (m, 1H), 0.55-0.40 (m, 2H), 0.27-0.21 (m, 1H).

(121h) (2S,4S,5S)-5-Amino-6-[4-(2-chlorophenyl)-2,2-dimethyl-5-oxopiperazin-1-yl]-2-cyclopropyl-4-hydroxyhexanoic acid (2,2-dimethylpropyl)amide hemifumarate (½ fumarate)

63 mg of the title compound (total yield over four steps: 33%) was obtained in the same manner as in Examples (1l) to (1o) using (3S,5S)-5-[(S)-1-(2-nitrobenzenesulfonyl)aziridin-2-yl]-3-cyclopropyldihydrofuran-2-one obtained in Example (121g), 1-(2-chlorophenyl)-5,5-dimethylpiperazin-2-one obtained in Example (1k) and (2,2-dimethylpropyl)amine.

Colorless solid.

$^1$H NMR spectrum (CD$_3$OD, 400 MHz), δ: 7.55-7.54 (m, 1H), 7.42-7.32 (m, 3H), 6.68 (s, 1H), 3.67-3.54 (m, 3H), 3.37-3.15 (m, 4H), 2.98-2.93 (m, 0.6H), 2.84-2.72 (m, 1.8H), 2.53-2.51 (m, 0.6H), 2.07-2.02 (m, 1H), 1.85-1.76 (m, 2H), 1.31-1.26 (m, 6H), 1.01-0.93 (m, 10H), 0.63-0.59 (m, 1H), 0.54-0.50 (m, 1H), 0.46-0.41 (m, 1H), 0.26-0.21 (m, 1H).

mass spectrum (FAB$^+$), m/z: 493 ((M+H)$^+$).

Example 122

(2S,4S,5S)-5-Amino-6-[4-(2-chloro-5-fluorophenyl)-2,2-dimethyl-5-oxopiperazin-1-yl]-2-cyclopropyl-4-hydroxyhexanoic acid (2,2-dimethylpropyl)amide hemifumarate (½ fumarate) (Exemplary Compound No. 2-209)

67 mg of the title compound (total yield over two steps: 83%) was obtained in the same manner as in Examples (1l) to (1o) using (3S,5S)-5-[(S)-1-(2-nitrobenzenesulfonyl)aziridin-2-yl]-3-cyclopropyldihydrofuran-2-one obtained in Example (121g), 1-(2-chloro-5-fluorophenyl)-5,5-dimethylpiperazin-2-one obtained in Example (62d) and (2,2-dimethylpropyl)amine.

Colorless solid.

$^1$H NMR spectrum (CD$_3$OD, 400 MHz), δ: 7.88 (br s, 1H), 7.58-7.56 (m, 1H), 7.21-7.18 (m, 2H), 6.68 (s, 1H), 3.63-3.53 (m, 3H), 3.39-3.16 (m, 4H), 2.98-2.93 (m, 0.6H), 2.84-2.74 (m, 1.8H), 2.53-2.49 (m, 0.6H), 2.06-2.02 (m, 1H), 1.85-1.76 (m, 2H), 1.30-1.26 (m, 6H), 0.99-0.93 (m, 10H), 0.63-0.61 (m, 1H), 0.53-0.51 (m, 1H), 0.45-0.43 (m, 1H), 0.25-0.22 (m, 1H).

mass spectrum (FAB$^+$), m/z: 511 ((M+H)$^+$).

Example 123

(2R,4S,5S)-5-Amino-6-[4-(2-chlorophenyl)-2,2-dimethyl-5-oxopiperazin-1-yl]-2-isobutyl-4-hydroxyhexanoic acid (2,2-dimethylpropyl)amide hemifumarate (½ fumarate) (Exemplary Compound No. 2-229)

(123a) (S)-4-Benzyl-3-[(2R,4E)-6-benzyloxy-2-isobutylhex-4-enoyl]oxazolidin-2-one 26.9 g of the title compound (yield: 71%) was obtained in the same manner as in Example (76a) using (S)-4-benzyl-3-(4-methylpentanoyl)oxazolidin-2-one obtained in Reference Example 8 and [(E)-4-bromobut-2-enyloxymethyl]benzene obtained in Reference Example 4.

Colorless liquid.

$^1$H NMR spectrum (CDCl$_3$, 500 MHz), δ: 7.32-7.24 (m, 8H), 7.15 (d, 2H, J=6.8 Hz), 5.76 (dt, 1H, J=15.6 Hz, 6.8 Hz), 5.67 (dt, 1H, J=15.6 Hz, 5.9 Hz), 4.68-4.64 (m, 1H), 4.48 (s, 2H), 4.17-4.09 (m, 2H), 4.07-4.01 (m, 1H), 3.97 (d, 2H, J=5.9 Hz), 3.29 (dd, 1H, J=13.2 Hz, 3.4 Hz), 2.61 (dd, 1H, J=13.2 Hz, 10.1 Hz), 2.47-2.41 (m, 1H), 2.36-2.31 (m, 1H), 1.76-1.70 (m, 1H), 1.60-1.52 (m, 1H), 1.35-1.29 (m, 1H), 0.91 (d, 3H, J=6.4 Hz), 0.89 (d, 3H, J=6.4 Hz).

(123b) (2R,4E)-6-Benzyloxy-2-isobutylhex-4-enoic acid 21.05 g of the title compound (yield: quant.) was obtained in the same manner as in Example (76b) using (S)-4-benzyl-3-[(2R,4E)-6-benzyloxy-2-isobutylhex-4-enoyl]oxazolidin-2-one obtained in Example (123a).

Colorless liquid.

$^1$H NMR spectrum (CDCl$_3$, 400 MHz), δ: 7.36-7.26 (m, 5H), 5.72-5.62 (m, 2H), 4.49 (s, 2H), 3.98-3.96 (m, 2H), 2.57-2.50 (m, 1H), 2.41-2.34 (m, 1H), 2.28-2.22 (m, 1H), 1.68-1.56 (m, 2H), 1.33-1.27 (m, 1H), 0.91 (d, 3H, J=6.3 Hz), 0.90 (d, 3H, J=6.3 Hz).

(123c) (3R,5S)-5-[(R)-2-Benzyloxy-1-hydroxyethyl]-3-isobutyldihydrofuran-2-one 16.84 g of the title compound (yield: 84%) was obtained in the same manner as in Example (76c) using (2R,4E)-6-benzyloxy-2-isobutylhex-4-enoic acid obtained in Example (123b).

Colorless liquid.

$^1$H NMR spectrum (CDCl$_3$, 400 MHz), δ: 7.38-7.30 (m, 5H), 4.58 (d, 1H, J=11.7 Hz), 4.55 (d, 1H, J=11.7 Hz), 4.49-4.45 (m, 1H), 3.89-3.85 (m, 1H), 3.64 (dd, 1H, J=9.8 Hz, 4.4 Hz), 3.56 (dd, 1H, J=9.8 Hz, 5.9 Hz), 2.72-2.66 (m, 1H), 2.51-2.45 (m, 2H), 1.94 (dt, 1H, J=13.2 Hz, 8.3 Hz), 1.75-1.67 (m, 2H), 1.37-1.30 (m, 1H), 0.95 (d, 3H, J=6.4 Hz), 0.91 (d, 3H, J=6.4 Hz).

(123d) Methanesulfonic acid (R)-2-benzyloxy-1-[(2S,4R)-4-isobutyl-5-oxotetrahydrofuran-2-yl]ethyl ester 18.98 g of the title compound (yield: 93%) was obtained in the same manner as in Example (76d) using (3R,5S)-5-[(R)-2-benzyloxy-1-hydroxyethyl]-3-isobutyldihydrofuran-2-one obtained in Example (123c).
Colorless liquid.
$^1$H NMR spectrum (CDCl$_3$, 500 MHz), δ: 7.38-7.30 (m, 5H), 4.85-4.80 (m, 1H), 4.66-4.62 (m, 1H), 4.56 (s, 2H), 3.76 (d, 2H, J=5.4 Hz), 3.04 (s, 3H), 2.73-2.66 (m, 1H), 2.54-2.49 (m, 1H), 2.02-1.86 (m, 1H), 1.74-1.65 (m, 2H), 1.38-1.31 (m, 1H), 0.95 (d, 3H, J=5.9 Hz), 0.91 (d, 3H, J=5.9 Hz).

(123e) (3R,5S)-5-[(S)-1-Azido-2-benzyloxyethyl]-3-isobutyldihydrofuran-2-one 14.80 g of the title compound (yield: 87%) was obtained in the same manner as in Example (76e) using methanesulfonic acid (R)-2-benzyloxy-1-[(2S,4R)-4-isobutyl-5-oxotetrahydrofuran-2-yl]ethyl ester obtained in Example (123d).
Colorless liquid.
$^1$H NMR spectrum (CDCl$_3$, 500 MHz), δ: 7.38-7.30 (m, 5H), 4.61-4.55 (m, 3H), 3.76 (d, 2H, J=6.4 Hz), 3.68-3.65 (m, 1H), 2.84-2.77 (m, 1H), 2.35-2.30 (m, 1H), 2.00 (dt, 1H, J=13.2 Hz, 8.3 Hz), 1.75-1.64 (m, 2H), 1.34-1.28 (m, 1H), 0.95 (d, 3H, J=5.9 Hz), 0.92 (d, 3H, J=5.9 Hz).

(123f) N-{(S)-1-[(2S,4R)-4-Isobutyl-5-oxotetrahydrofuran-2-yl]-2-hydroxyethyl}-2-nitrobenzenesulfonamide 11.72 g of the title compound (total yield over two steps: 65%) was obtained in the same manner as in Example (1f) using (3R,5S)-5-[(S)-1-azido-2-benzyloxyethyl]-3-isobutyldihydrofuran-2-one obtained in Example (123e).
Colorless solid.
Optical rotation, $[α]_D^{23.9°\,C}$=+37.8° (c=1.00, MeOH).
$^1$H NMR spectrum (CDCl$_3$, 500 MHz), δ: 8.15-8.11 (m, 1H), 7.92-7.88 (m, 1H), 7.77-7.74 (m, 2H), 5.87 (br d, 1H, J=7.8 Hz), 4.69-4.66 (m, 1H), 3.72-3.62 (m, 3H), 2.85-2.79 (m, 1H), 2.57 (ddd, 1H, J=13.2 Hz, 9.8 Hz, 5.4 Hz), 2.05 (dt, 1H, J=13.2 Hz, 5.4 Hz), 1.98 (t, 1H, J=5.4 Hz), 1.72-1.65 (m, 2H), 1.37-1.30 (m, 1H), 0.95 (d, 1H, J=6.4 Hz), 0.91 (d, 1H, J=6.4 Hz).

(123g) (3R,5S)-5-[(S)-1-(2-Nitrobenzenesulfonyl)aziridin-2-yl]-3-isobutyldihydrofuran-2-one 1.76 g of the title compound (yield: 92%) was obtained in the same manner as in Example (1g) using N-{(S)-1-[(2S,4R)-4-isobutyl-5-oxotetrahydrofuran-2-yl]-2-hydroxyethyl}-2-nitrobenzenesulfonamide obtained in Example (123f). Yellow liquid.
$^1$H NMR spectrum (CDCl$_3$, 400 MHz), δ: 8.13 (dd, 1H, J=7.4 Hz, 1.6 Hz), 7.83-7.73 (m, 3H), 4.78 (dt, 1H, J=8.6 Hz, 2.0 Hz), 3.27-3.24 (m, 1H), 2.94-2.85 (m, 1H), 2.83 (d, 1H, J=7.4 Hz), 2.66 (d, 1H, J=4.7 Hz), 2.61 (ddd, 1H, J=12.9 Hz, 9.4 Hz, 2.4 Hz), 2.18-2.10 (m, 1H), 1.77-1.62 (m, 2H), 1.28 (ddd, 1H, J=12.9 Hz, 10.6 Hz, 4.7 Hz), 0.95 (d, 3H, J=6.3 Hz), 0.92 (d, 3H, J=6.3 Hz).

(123h) (2R,4S,5S)-5-Amino-6-[4-(2-chlorophenyl)-2,2-dimethyl-5-oxopiperazin-1-yl]-4-hydroxy-2-isobutylhexanoic acid (2,2-dimethylpropyl)amide hemifumarate (½ fumarate)

122 mg of the title compound (total yield over four steps: 66%) was obtained in the same manner as in Examples (1l) to (1o) using (3R,5S)-5-[(S)-1-(2-nitrobenzenesulfonyl)aziridin-2-yl]-3-isobutyldihydrofuran-2-one obtained in Example (123g), 1-(2-chlorophenyl)-5,5-dimethylpiperazin-2-one obtained in Example (1k) and (2,2-dimethylpropyl)amine.
Colorless solid.
$^1$H NMR spectrum (CD$_3$OD, 400 MHz), δ: 8.01 (br s, 1H), 7.56-7.53 (m, 1H), 7.44-7.32 (m, 3H), 6.70 (s, 1H), 3.73-3.48 (m, 3H), 3.38-3.18 (m, 4H), 2.97-2.82 (m, 1.6H), 2.77-2.68 (m, 1.8H), 2.50 (dd, 0.6H, J=13.3 Hz, 3.9 Hz), 1.84-1.78 (m, 1H), 1.65-1.55 (m, 3H), 1.33-1.22 (m, 7H), 0.97-0.93 (m, 15H).
mass spectrum (FAB$^+$), m/z: 509 ((M+H)$^+$).

Example 124

(2R,4S,5S)-5-Amino-6-[4-(2-chlorophenyl)-2,2-dimethyl-5-oxopiperazin-1-yl]-4-hydroxy-2-isobutylhexanoic acid isobutylamide hemifumarate (½ fumarate) (Exemplary Compound No. 2-230)

160 mg of the title compound (total yield over four steps: 70%) was obtained in the same manner as in Examples (1l) to (1o) using (3R,5S)-5-[(S)-1-(2-nitrobenzenesulfonyl)aziridin-2-yl]-3-isobutyldihydrofuran-2-one obtained in Example (123g), 1-(2-chlorophenyl)-5,5-dimethylpiperazin-2-one obtained in Example (1k) and isobutylamine.
Colorless solid.
$^1$H NMR spectrum (CD$_3$OD, 400 MHz), δ: 8.14 (br s, 1H), 7.56-7.53 (m, 1H), 7.44-7.32 (m, 3H), 6.69 (s, 1H), 3.67-3.47 (m, 3H), 3.37-3.13 (m, 4H), 2.97-2.87 (m, 1.6H), 2.74-2.64 (m, 1.8H), 2.50 (dd, 0.6H, J=13.5 Hz, 3.3 Hz), 1.83-1.77 (m, 2H), 1.64-1.57 (m, 3H), 1.31-1.23 (m, 7H), 0.98-0.92 (m, 12H).
mass spectrum (FAB$^+$), m/z: 495 ((M+H)$^+$).

Reference Example 1

(2R)-1-(Benzyloxy)but-3-en-2-ol (1a) {(4S,5S)-5-[(Benzyloxy)methyl]-2,2-dimethyl-1,3-dioxolan-4-yl}methanol 7.71 g of sodium hydride (content: 60%) (193 mmol) was added portionwise to a solution of 30.92 g of (+)-2,3-O-isopropylidene-L-threitol (191 mmol) in N,N-dimethylformamide (285 ml) under a nitrogen atmosphere and under ice-cooling over 45 minutes, and the mixture was stirred at the same temperature for one hour. 23.8 ml of benzyl bromide (200 mmol) was added to the reaction mixture over 30 minutes, and the mixture was stirred at the same temperature for three hours. 2.2 ml of acetic acid (38 mmol) was added to the reaction mixture, and the mixture was further stirred at room temperature for one hour. The reaction mixture was concentrated under reduced pressure and diluted with water, followed by extraction with ethyl acetate. Then, the organic layer was washed with water and brine and dried over anhydrous magnesium sulfate. After filtration, the solvent was evaporated under reduced pressure, and the residue was purified by silica gel column chromatography (elution solvent:n-hexane/ethyl acetate=2/1-1/1) to obtain 35.27 g of the title compound (yield: 73%).

Yellow liquid.

$^1$H NMR spectrum (CDCl$_3$, 400 MHz), δ: 7.38-7.28 (m, 5H), 4.59 (s, 2H), 4.08-4.03 (m, 1H), 3.97-3.93 (m, 1H), 3.77 (dt, 1H, J=11.7 Hz, 4.3 Hz), 3.71-3.65 (m, 2H), 3.56 (dd, 1H, J=9.8 Hz, 5.9 Hz), 2.17 (dd, 1H, J=8.2 Hz, 4.7 Hz), 1.42 (s, 3H), 1.41 (s, 3H).

(1b) {(4S,5S)-5-[(Benzyloxy)methyl]-2,2-dimethyl-1,3-dioxolan-4-yl}methyl methanesulfonate A solution of 19.21 g of methanesulfonyl chloride (168 mmol) in methylene chloride (90 ml) was added to a solution of 35.27 g of {(4S,5S)-5-[(benzyloxy)methyl]-2,2-dimethyl-1,3-dioxolan-4-yl}methanol obtained in Reference Example (1a) (140 mmol) and 29.2 ml of triethylamine (210 mmol) in methylene chloride (270 ml) under ice-cooling over 30 minutes, and the mixture was stirred at the same temperature for 20 minutes. 0.76 ml of water (42 mmol) was added to the reaction mixture, and the mixture was further stirred at room temperature for 15 minutes. The reaction mixture was concentrated under reduced pressure and diluted with water, followed by extraction with ethyl acetate. Then, the organic layer was washed with water, a saturated sodium bicarbonate aqueous solution and brine and dried over anhydrous magnesium sulfate. After filtration, the solvent was evaporated under reduced pressure to obtain 46.19 g of the crude title compound.

Yellow liquid.

$^1$H NMR spectrum (CDCl$_3$, 500 MHz), δ: 7.37-7.28 (m, 5H), 4.58 (s, 2H), 4.42 (dd, 1H, J=11.2 Hz, 3.4 Hz), 4.27 (dd, 1H, J=11.2 Hz, 5.4 Hz), 4.15-4.11 (m, 1H), 4.07-4.03 (m, 1H), 3.69 (dd, 1H, J=9.8 Hz, 4.9 Hz), 3.58 (dd, 1H, J=9.8 Hz, 5.4 Hz), 3.02 (s, 3H), 1.43 (s, 3H), 1.42 (s, 3H).

(1c) (4S,5S)-4-[(Benzyloxy)methyl]-5-(iodomethyl)-2,2-dimethyl-1,3-dioxolane

A solution of 46.19 g of the crude {(4S,5S)-5-[(benzyloxy)methyl]-2,2-dimethyl-1,3-dioxolan-4-yl}methyl methanesulfonate obtained in Reference Example (1b) (140 mmol) and 62.87 g of sodium iodide (419 mmol) in acetonitrile (420 ml) was stirred at 80° C. for 22 hours. The reaction mixture was cooled and then concentrated under reduced pressure and diluted with water, followed by extraction with ethyl acetate. Then, the organic layer was washed with a 1.5 M sodium sulfite aqueous solution, water and brine and dried over anhydrous magnesium sulfate. After filtration, the solvent was evaporated under reduced pressure to obtain 49.20 g of the crude title compound.

Yellow liquid.

$^1$H NMR spectrum (CDCl$_3$, 400 MHz), δ: 7.38-7.27 (m, 5H), 4.59 (s, 2H), 3.99-3.95 (m, 1H), 3.9-3.84 (m, 1H), 3.67 (dd, 1H, J=10.2 Hz, 5.1 Hz), 3.64 (dd, 1H, J=10.2 Hz, 5.1 Hz), 3.35 (dd, 1H, J=10.6 Hz, 5.1 Hz), 3.28 (dd, 1H, J=10.6 Hz, 5.1 Hz), 1.47 (s, 3H), 1.42 (s, 3H).

(1d) (2R)-1-(Benzyloxy)but-3-en-2-ol

A mixture of 49.20 g of the crude (4S,5S)-4-[(benzyloxy)methyl]-5-(iodomethyl)-2,2-dimethyl-1,3-dioxolane obtained in Reference Example (1c) (136 mmol) and 26.66 g of zinc powder (408 mmol) in ethanol (420 ml) was stirred at 80° C. for three hours. After cooling the reaction mixture, the unreacted zinc powder was separated by filtration using Celite 545 and washed with ethanol. The filtrate was concentrated under reduced pressure and diluted with 1 M hydrochloric acid, followed by extraction with ethyl acetate. Then, the organic layer was washed with water, a 1.5 M sodium sulfite aqueous solution and brine and dried over anhydrous magnesium sulfate. After filtration, the solvent was evaporated under reduced pressure to obtain 24.29 g of the crude title compound.

Yellow liquid.

$^1$H NMR spectrum (CDCl$_3$, 500 MHz), δ: 7.38-7.29 (m, 5H), 5.84 (ddd, 1H, J=17.1 Hz, 10.3 Hz, 5.4 Hz), 5.37 (dt, 1H, J=17.1 Hz, 1.5 Hz), 5.20 (dt, 1H, J=10.3 Hz, 1.5 Hz), 4.58 (s, 2H), 4.38-4.33 (m, 1H), 3.55 (dd, 1H, J=9.8 Hz, 3.4 Hz), 3.38 (dd, 1H, J=9.8 Hz, 7.8 Hz), 2.41 (d, 1H, J=3.4 Hz).

Reference Example 2

3-Amino-2,2-di(methyl)propionamide (2a)
3-Benzyloxycarbonylamino-2,2-di(methyl)propanol 50.0 g of N-(benzyloxycarbonyloxy)succinimide (200 mmol) was added to a solution of 13.8 g of 3-amino-2,2-dimethylpropanol (134 mmol) in tetrahydrofuran (140 ml), and the mixture was stirred at room temperature for 18 hours. The reaction mixture was concentrated under reduced pressure and diluted with water, followed by extraction with ethyl acetate. Then, the organic layer was dried over anhydrous magnesium sulfate. After filtration, the solvent was evaporated under reduced pressure, and the residue was purified by silica gel column chromatography (elution solvent: toluene/ethyl acetate=9/1-3/1) to obtain 29.52 g of the title compound (yield: 93%).

Colorless liquid.

$^1$H NMR spectrum (CDCl$_3$, 400 MHz), δ: 7.39-7.31 (m, 5H), 5.16 (br s, 1H), 5.11 (s, 2H), 3.42 (t, 1H, J=7.0 Hz), 3.22 (d, 2H, J=7.0 Hz), 3.04 (d, 2H, J=7.0 Hz), 0.86 (s, 6H).

(2b) 3-Benzyloxycarbonylamino-2,2-di(methyl)propionamide 11.6 g of sodium periodate (54.2 mmol) and 0.2 g of ruthenium trichloride (0.96 mmol) were added to a solution of 4.6 g of 3-benzyloxycarbonylamino-2,2-di(methyl)propanol obtained in Reference Example (2a) (19.4 mmol) in a mixed solvent of carbon tetrachloride (40 ml), acetonitrile and water (40 ml), and the mixture was stirred at room temperature for 16 hours. 11.6 g of sodium periodate (54.2 mmol) and 0.2 g of ruthenium trichloride (0.96 mmol) were added to the reaction mixture, and the mixture was further stirred at room temperature for three days. The reaction mixture was diluted with water, followed by extraction with ethyl acetate. Then, the organic layer was dried over magnesium sulfate. After filtration, 300 ml of a saturated potassium carbonate aqueous solution was added to the residue, followed by washing with ethyl acetate. The aqueous layer was adjusted to pH 1 with concentrated hydrochloric acid, followed by extraction with ethyl acetate. Then, the organic layer was washed with brine and dried over anhydrous magnesium sulfate. After filtration, the solvent was evaporated under reduced pressure to obtain 3.16 g of crude 3-benzyloxycarbonylamino-2,2-di(methyl) propionic acid. 3.0 g of 1,1'-carbonylbis-1H-imidazole (18.5 mmol) was added to a solution of 3.1 g of the crude 3-benzyloxycarbonylamino-2,2-di(methyl)propionic acid obtained above (12.3 mmol) in tetrahydrofuran (20 ml), and the mixture was stirred at room temperature for one hour. 20 ml of a 28% ammonia aqueous solution (914 mmol) was added to the reaction mixture, and the mixture was further stirred at room temperature for one hour. The reaction mixture was diluted with water, followed by extraction with ethyl acetate. Then, the organic layer was washed with a 1 M hydrochloric acid aqueous solution and brine and dried over magnesium sulfate. After filtration, 300 ml of a saturated potassium carbonate aqueous solution was added to the residue, followed by washing with ethyl acetate. The aqueous layer was adjusted to pH 1 with concentrated hydrochloric acid, followed by extraction with ethyl acetate. Then, the organic layer was washed with brine and dried over anhydrous magnesium sulfate. After filtration, the solvent was evaporated under reduced pressure, and the residue was purified by silica gel column chromatography (elution solvent:ethyl acetate/n-hexane=2/1-3/1) to obtain 2.54 g of the title compound (yield: 54%).

Colorless liquid.

$^1$H NMR spectrum (CDCl$_3$, 400 MHz), δ: 7.36-7.28 (m, 5H), 5.82 (br s, 1H), 5.71 (br s, 1H), 5.48 (br s, 1H), 5.09 (s, 2H), 3.31 (d, 2H, J=6.7 Hz), 1.21 (s, 6H).

(2c) 3-Amino-2,2-di(methyl)propionamide

A suspension of 2.5 g of 3-benzyloxycarbonylamino-2,2-di(methyl)propionamide obtained in Reference Example (2b) (10 mmol) and 1.2 g of 7.5% palladium-carbon (50% wet) in ethanol (50 ml) was stirred under a hydrogen atmosphere at room temperature for two hours. Hydrogen in the reaction vessel was replaced by nitrogen. Then, palladium-carbon was separated by filtration and washed with ethanol. The solvent was evaporated under reduced pressure, and methylene chloride was added. Then, the organic layer was dried over anhydrous magnesium sulfate. After filtration, the solvent was evaporated under reduced pressure. n-Hexane was added to the residue, and the precipitated solid was collected by filtration to obtain 0.99 g of the title compound (yield: 85%).

Colorless solid.

$^1$H NMR spectrum (CDCl$_3$, 400 MHz), δ: 7.73 (br s, 1H), 5.68 (br s, 1H), 2.78 (s, 2H), 1.16 (s, 6H).

Reference Example 3

(1,1-Dimethyl-2-oxoethyl)carbamic acid t-butyl ester (3a) (2-Hydroxy-1,1-dimethylethyl)carbamic acid t-butyl ester 230.4 ml of di-t-butyl dicarbonate (1.00 mol) was added to a solution of 98.05 g of 2-amino-2-methyl-1-propanol (1.10 mol) and 154 ml of triethylamine (1.10 mol) in methylene chloride (500 ml) at room temperature over 20 minutes, and the mixture was stirred at room temperature for 2.5 hours. The reaction mixture was concentrated under reduced pressure and diluted with a 10% citric acid aqueous solution, followed by extraction with ethyl acetate. Then, the organic layer was washed with water and brine and dried over anhydrous magnesium sulfate. After filtration, the solvent was evaporated under reduced pressure to obtain 189.25 g of the crude title compound (yield: quant.).

Colorless solid.

$^1$H NMR spectrum (CDCl$_3$, 400 MHz), δ: 4.64 (br s, 1H), 4.01 (br s, 1H), 3.59 (d, 2H, J=6.3 Hz), 1.43 (s, 9H), 1.25 (s, 6H).

(3b) (1,1-Dimethyl-2-oxoethyl)carbamic acid t-butyl ester 0.94 g of tetramethylpiperidine N-oxide (6.0 mmol) and 3.57 g of potassium bromide (30 mmol) were added to a solution of 56.78 g of (2-hydroxy-1,1-dimethylethyl)carbamic acid t-butyl ester obtained in Reference Example (3a) (300 mmol) in a mixture of methylene chloride (500 ml) and a saturated sodium bicarbonate aqueous solution (525 ml) under ice-cooling, and the mixture was stirred at the same temperature for 30 minutes. 534 ml of a 5% sodium hypochlorite aqueous solution (360 mmol) was added to the reaction mixture under ice-cooling over 1.5 hours, and the mixture was stirred at the same temperature for 20 minutes. A saturated sodium thiosulfate aqueous solution was added to the reaction mixture, and the reaction mixture was returned to room temperature, followed by extraction with methylene chloride. Then, the organic layer was washed with brine and then dried over anhydrous magnesium sulfate. After filtration, the solvent was evaporated under reduced pressure. Hexane was added to the residue, and the solid was collected by filtration to obtain 42.32 g of the title compound (yield: 79%).

Colorless solid.

$^1$H NMR spectrum (CDCl$_3$, 400 MHz), δ: 9.43 (s, 1H), 4.97 (br s, 1H), 1.44 (s, 9H), 1.33 (s, 6H).

Reference Example 4

[(E)-4-Bromobut-2-enyloxymethyl]benzene

A solution of 10.8 ml of benzyl alcohol (103 mmol), 3.16 g of tetrabutylammonium bisulfate (58.5 mmol) and 8.63 g of sodium hydroxide (840 mmol) in water (45.6 ml) was added to a solution of 20.0 g of trans-1,4-dibromo-2-butene (94.7 mmol) in methylene chloride (80 ml) at room temperature, and the mixture was stirred for two days. The reaction mixture was diluted with 300 ml of water, followed by extraction with methylene chloride. Then, the organic layer was washed with water and brine and dried over anhydrous magnesium sulfate. After filtration, the solvent was evaporated under reduced pressure, and the residue was purified by silica gel column chromatography (elution solvent:n-hexane/ethyl acetate=20/1) to obtain 10.9 g of the title compound (yield: 48%).

Yellow liquid.

$^1$H NMR spectrum (CDCl$_3$, 400 MHz), δ: 7.40-7.25 (m, 5H), 6.03-5.94 (m, 1H), 5.93-5.84 (m, 1H), 4.52 (s, 2H), 4.05 (dd, 1H, J=5.4 Hz, 1.0 Hz), 3.97 (dd, 1H, J=7.4. 0.8 Hz).

Reference Example 5

(S)-4-Benzyl-3-butylryloxazolidin-2-one 90 ml of a solution of n-butyllithium in n-hexane (1.60 mol/l) (144 mmol) was added to a solution of 25.0 g of (S)-4-benzyl-2-oxazolidinone (141 mmol) in tetrahydrofuran (600 ml) under a nitrogen atmosphere and at −78° C. over 10 minutes, and the mixture was stirred at the same temperature for 20 minutes. Then, 16.5 ml of n-butyryl chloride (156 mmol) was added over 10 minutes. The mixture was stirred at the same temperature for 20 minutes and then further stirred at room temperature for three hours. 90 ml of a saturated ammonium chloride aqueous solution was added to the reaction mixture, and the mixture was further stirred at room temperature for 15 minutes. The reaction mixture was concentrated under reduced pressure and diluted with 300 ml of water, followed by extraction with methylene chloride. Then, the organic layer was washed with a saturated sodium bicarbonate aqueous solution and brine and dried over anhydrous magnesium sulfate. After filtration, the solvent was evaporated under reduced pressure to obtain 35.3 g of the crude title compound.

Yellow liquid.

$^1$H NMR spectrum (CDCl$_3$, 400 MHz), δ: 7.37-7.19 (m, 5H), 4.71-4.64 (m, 1H), 4.23-4.14 (m, 2H), 3.30 (dd, 1H, J=13.3 Hz, 3.5 Hz), 3.01-2.83 (m, 2H), 2.77 (dd, 1H, J=13.3 Hz, 9.4 Hz), 1.79-1.68 (m, 2H), 1.01 (t, 3H, J=7.4 Hz).

Reference Example 6

(S)-4-Benzyl-3-pentanoyloxazolidin-2-one 90 ml of a solution of n-butyllithium in n-hexane (1.60 mol/l) (144 mmol) was added to a solution of 25.0 g of (S)-4-benzyl-2-oxazolidinone (141 mmol) in tetrahydrofuran (600 ml) under a nitrogen atmosphere and at −78° C. over 10 minutes, and the mixture was stirred at the same temperature for 20 minutes. Then, 19.0 ml of n-valeryl chloride (159 mmol) was added over 10 minutes. The mixture was stirred at the same temperature for 20 minutes and then further stirred at room temperature for three hours. 90 ml of a saturated ammonium chloride aqueous solution was added to the reaction mixture, and the mixture was further stirred at room temperature for 15 minutes. The reaction mixture was concentrated under reduced pressure and diluted with 300 ml of water, followed by extraction with methylene chloride. Then, the organic layer was washed with a saturated sodium bicarbonate aqueous solution and brine and dried over anhydrous magnesium sulfate. After filtration, the solvent was evaporated under reduced pressure to obtain 37.3 g of the crude title compound.

Yellow liquid.

$^1$H NMR spectrum (CDCl$_3$, 400 MHz), δ: 7.36-7.19 (m, 5H), 4.71-4.64 (m, 1H), 4.23-4.14 (m, 2H), 3.30 (dd, 1H, J=13.3 Hz, 3.5 Hz), 3.02-2.86 (m, 2H), 2.77 (dd, 1H, J=13.5 Hz, 9.8 Hz), 1.73-1.64 (m, 2H), 1.47-1.37 (m, 2H), 0.96 (t, 3H, J=7.1 Hz).

Reference Example 7

(S)-4-Benzyl-3-(2-cyclopropylacetyl)oxazolidin-2-one 21.0 g of the title compound (yield: 90%) was obtained in the same manner as in Reference Example 5 using (S)-4-benzyl-2-oxazolidinone and pivaloyl chloride.

Colorless liquid.

$^1$H NMR spectrum (CDCl$_3$, 400 MHz), δ: 7.37-7.19 (m, 5H), 4.74-4.66 (m, 1H), 4.24-4.15 (m, 2H), 3.32 (dd, 1H, J=13.7 Hz, 3.1 Hz), 2.94 (dd, 1H, J=17.2 Hz, 7.0 Hz), 2.84-2.76 (m, 2H), 1.21-1.10 (m, 1H), 0.65-0.55 (m, 2H), 0.28-0.18 (m, 2H).

Reference Example 8

(S)-4-Benzyl-3-(4-methylpentanoyl)oxazolidin-2-one 27.1 g of the crude title compound (yield: quant.) was obtained in the same manner as in Reference Example 5 using (S)-4-benzyl-2-oxazolidinone and 4-methylpentanoyl chloride.

Yellow liquid.

$^1$H NMR spectrum (CDCl$_3$, 400 MHz), δ: 7.36-7.20 (m, 5H), 4.70-4.64 (m, 1H), 4.22-4.15 (m, 2H), 3.30 (dd, 1H, J=13.5 Hz, 3.3 Hz), 3.02-2.87 (m, 2H), 2.76 (dd, 1H, J=13.3 Hz, 9.8 Hz), 1.70-1.54 (m, 3H), 0.95 (d, 6H, J=6.3 Hz).

The compound of Exemplary Compound No. 1-11, 1-14, 1-18, 1-24, 1-47, 1-49, 1-54, 1-55, 1-71, 1-72, 1-73, 1-75, 1-79, 1-82, 1-85, 1-87, 1-121, 1-135, 1-142, 1-168, 1-179, 1-195, 1-197, 1-211, 1-213, 1-432, 1-612, 1-619, 1-645, 1-656, 1-672, 1-674, 1-690, 1-1041, 1-760, 1-770, 1-776, 1-825, 1-872, 1-900, 1-920, 1-935, 1-970, 1-971, 1-972, 1-973, 1-976, 1-978, 1-979, 1-980, 1-984, 1-985, 1-986, 1-987, 1-988, 1-989, 1-990, 1-991, 1-992, 1-993, 1-996, 1-997, 1-998, 1-999, 1-1000, 1-1001, 1-1002, 1-1003, 1-1006, 1-1007, 1-1008, 1-1009, 1-1010, 1-1011, 1-1012, 1-1015, 1-1016, 1-1018, 1-1019, 1-1020, 1-1021, 1-1024, 1-1025, 1-1026, 1-1027, 1-1028, 1-1029, 1-1030, 1-1032, 1-1033, 1-1034, 1-1035, 1-1036, 1-1037, 1-1039, 1-1040, 1-1042, 2-164, 2-170, 2-171, 2-173, 2-177, 2-178, 2-193, 2-194, 2-195, 2-196, 2-197, 2-201, 2-202, 2-203, 2-204, 2-205, 2-206, 2-207, 2-210, 2-212, 2-214, 2-215, 2-216, 2-219, 2-220, 2-221, 2-223, 2-224, 2-225, 2-226, 2-227, 2-228, 2-231, 2-232, 2-234, 2-239, 2-240, 3-4, or 3-18 was obtained according to a method similar to those described above.

Test Example 1

Renin Inhibitory Activity Test (1) Method 1

Renin activity was measured as the ratio of angiotensin I generated after addition of both human renin and a synthetic renin substrate and its reaction at 37° C.

Human renin was transiently expressed in 293T cells, and the conditioned medium was used for an enzyme source. The prepared conditioned medium was treated with trypsin to activate human renin. Then, 2 μl of a solution of the test compound in a solvent (such as DMSO etc.) or a solvent was added to a final concentration of 1 vol %. Further, a buffer (1 mM EDTA, 100 mM Tris-HCl, pH 7.4) containing a synthetic renin substrate (NH$_2$-Asp-Arg-Val-Tyr-Ile-His-Pro-Phe-His-Leu-Val-Ile-His-Thr-Glu-COOH) was added, followed by incubation at 37° C. for one hour. The concentration of generated angiotensin I was measured by radioimmunoassay [Renin RIA beads (trade mark), Yamasa Corporation] according to the attached instructions. Renin inhibitory activity was evaluated from IC$_{50}$ which is the concentration of each test compound inhibiting 50% of angiotensin I generation.

(2) Method 2

Renin activity was measured as the ratio of angiotensin I generated after addition of both human renin and a fluorescence-labeled synthetic renin substrate and its reaction at 37° C. by the fluorescence method.

Human renin was transiently expressed in 293T cells, and the conditioned medium was used for an enzyme source. The prepared conditioned medium was treated with trypsin to activate human renin. Then, a solution of the test compound in a solvent (such as DMSO etc.) or a solvent was added to a final concentration of 1 vol %. Further, a buffer (1 mM EDTA, 100 mM Tris-HCl, pH 7.4) containing a fluorescence-labeled synthetic renin substrate [Arg-Glu(EDANS)-Ile-His-Pro-Phe-His-Leu-Val-Ile-His-Thr-Lys(dabcyl)-Arg] was added, followed by incubation at 37° C. for 90 minutes. After completion of the incubation, the concentration of angiotensin I generated by fluorescence (Ex: 340 nm, Em: 492 nm) was measured. Renin inhibitory activity was evaluated from IC$_{50}$ which is the concentration of each test compound inhibiting 50% of angiotensin I generation.

The compounds of Examples 1 to 120 each had an IC$_{50}$ of 100 nM or less in the test according to Method 2. The compound of the present invention has excellent renin inhibitory activity and is useful as a medicament for treating or preventing hypertension.

Test Example 2

Plasma Renin Activity (PRA) Test

Plasma renin activity was measured as the amount of angiotensin I generated per unit time from endogenous angiotensinogen and endogenous renin by incubation of plasma at 37° C.

The test compound or a solvent (such as DMSO etc.) was added to pooled cynomolgus monkey plasma. A buffer was added according to the attached instructions, followed by incubation at 37° C. for one hour. The concentration of angiotensin I generated per unit time was measured by radioimmunoassay (see Test Example 1). Plasma renin inhibitory activity was evaluated from $IC_{50}$ which is the concentration of each test compound inhibiting 50% of PRA.

The compound of the present invention has excellent plasma renin inhibitory activity and is useful as a medicament for treating or preventing hypertension.

Test Example 3

Ex Vivo Test

Plasma samples were collected before administration of the test compound and 1, 2, 4, 8 and 24 hours after the administration in normal animals or marmosets or cynomolgus monkeys in which the renin-angiotensin system was enhanced by ingestion of a low-sodium diet (one week) and intramuscular administration of furosemide (3 or 10 mg/kg). The test compound was suspended in 1% methylcellulose and forcibly orally administered. The obtained plasma was incubated at 4° C. or 37° C., and the concentration of angiotensin I existing in each reaction solution was measured by radioimmunoassay (see Test Example 1).

PRA was calculated as the concentration of angiotensin I generated per unit time from the value obtained by subtracting the angiotensin I concentration in the reaction solution incubated at 4° C. from the angiotensin I concentration in the reaction solution incubated at 37° C. PRA inhibitory activity of the test compound was evaluated from the PRA inhibition rate after each administration time against PRA before administration of the test compound.

The compound of the present invention has excellent PRA inhibitory activity and plasma angiotensin I concentration lowering effect and is useful as a medicament for treating or preventing hypertension.

Test Example 4

Blood Pressure Lowering Effect Test

The test was carried out using renin-dependent hypertensive mice (Tsukuba hypertensive mice) obtained by mating human renin transgenic mice with human angiotensinogen transgenic mice (Igaku no Ayumi (Journal of Clinical and Experimental Medicine), 1994, vol. 169, No. 5, p. 422). Blood pressure was noninvasively measured before administration of the test compound and 1, 2, 4, 8 and 24 hours after the administration under conscious condition. The test compound was suspended in 1% methylcellulose and forcibly orally administered.

The compound of the present invention has an excellent blood pressure lowering effect and is useful as a medicament for treating or preventing hypertension.

Test Example 5

Solubility Test (1) Stock Solution

The test compound was dissolved in dimethyl sulfoxide (DMSO) to a concentration of 10 mM. The resulting solution was used as stock solution (10 mM).

(2) Standard Solution

25 µl of the stock solution (10 mM) was added to an HPLC sample bottle (made of glass, volume: 1.5 ml). 475 µl of acetonitrile was added to the HPLC sample bottle, and the resulting solution was mixed well. Further, 500 µl of distilled water was added, the bottle was tightly stoppered, and the resulting solution was mixed well. The resulting solution was used as standard solution (St, 250 µl).

(3) Test Solution

Japanese Pharmacopoeia first solution (JP1) or second solution (JP2), an acetic acid-sodium acetate buffer (pH 4.0) or phosphate buffered saline (PBS, pH 7.4) was used as test solution.

(4) Test Compound Solution

990 µl of the test solution was dispensed to a microtube, and 10 µl of the stock solution (10 mM) was further added. Then, the resulting solution was stirred in a mixer (1000 revolutions) for 10 minutes. Further, the solution was shaken in a constant temperature bath at 25° C. for 10 minutes and equilibrated.

The solution obtained above was filtered using a filter (Ekicrodisc CR3, pore size: 0.45 mm) attached to a disposable syringe. 500 µl of the resulting filtrate was added to an HPLC sample bottle (made of glass, volume: 1.5 ml). Further, 500 µl of acetonitrile was added, the bottle was tightly stoppered, and the resulting solution was mixed well. The resulting solution was used as test compound solution.

(5) Quantitative Determination of Test Compound

The test compound solution obtained in (4) above was quantitatively analyzed by high-performance liquid chromatography from a calibration curve prepared from the standard solution to measure the concentration of the test compound in the test compound solution. Solubility of the test compound was evaluated from the concentration of the test compound measured.

The compound of the present invention has excellent solubility and is useful as a medicament (in particular, a medicament for treating or preventing hypertension).

Test Example 6

Pharmacokinetic Study

The pharmacokinetic study can be carried out according to a generally known method in the field of pharmacokinetics.

The test compound was dissolved in a 1% methylcellulose aqueous solution. The resulting solution was orally administered to animals generally used in pharmacokinetic studies (such as mice, rats, marmosets and cynomolgus monkeys) at a dose within a suitable range (3 mg/kg to 100 mg/kg, for example). The test compound was dissolved in physiological saline. The resulting solution was administered into a vein (such as the tail vein, cephalic vein or saphenous vein) of animals generally used in pharmacokinetic studies (such as mice, rats, marmosets and cynomolgus monkeys) at a dose within a suitable range (1 mg/kg to 10 mg/kg, for example). Blood was collected from a suitable blood collection site (such as the jugular vein, orbital venous plexus or cephalic vein) at a certain time (0.08, 0.25, 0.5, 1, 2, 4, 6, 8 or 24 hours, for example) after the administration. The resulting blood was centrifuged to prepare a plasma sample. The concentration of the test compound contained in the plasma sample was measured by quantitative analysis using a liquid chromatography mass spectrometer (LC/MS/MS).

Pharmacokinetics of the test compound were evaluated from the maximum plasma test compound concentration ($C_{max}$), the area under the plasma test compound concentration-time curve (AUC) and absolute bioavailability. $C_{max}$ indicates the maximum plasma test compound concentration measured after the oral administration. AUC was calculated by the trapezoidal rule from the time of administration of the test compound to the time of final blood collection. Absolute bioavailability was calculated by the following formula.

(AUC/dose after oral administration)/(AUC/dose after intravenous administration)

The compound of the present invention has excellent pharmacokinetics ($C_{max}$, AUC or absolute bioavailability) and is useful as a medicament (in particular, a medicament for treating or preventing hypertension).

Formulation Example 1

Tablets

A tablet is prepared using example compound (10 mg), colloidal silicon dioxide (0.2 mg), magnesium stearate (5 mg), microcrystalline cellulose (175 mg), starch (10 mg) and lactose (98.8 mg) according to a usual method. The resulting tablet may be coated as necessary.

Formulation Example 2

Hard Capsules

A standard bipartite hard gelatin capsule is filled with powdery example compound (10 mg), lactose (150 mg), cellulose (50 mg) and magnesium stearate (6 mg) to prepare a hard capsule. The capsule is washed and then dried.

Formulation Example 3

Soft Capsules

A mixture of a digestive oil such as soybean oil or olive oil and example compound is poured into a gelatin to prepare a soft capsule containing 10 mg of an active ingredient. The capsule is washed and then dried.

Formulation Example 4

Suspension

A suspension is prepared so that 5 ml of the suspension contains micronized example compound (10 mg), sodium carboxymethylcellulose (100 mg), sodium benzoate (5 mg), a sorbitol solution (Japanese Pharmacopoeia, 1.0 g) and vanillin (0.025 ml).

Formulation Example 5

Cream

Micronized example compound (10 mg) is blended into 5 g of cream consisting of white petrolatum (40 wt %), microcrystalline wax (3 wt %), lanolin (10 wt %), sorbitan monolaurate (5 wt %), 0.3% polyoxyethylene (20) sorbitan monolaurate (0.3 wt %) and water (41.7 wt %) to prepare a cream.

INDUSTRIAL APPLICABILITY

The compound represented by the general formula (I) or a pharmacologically acceptable salt thereof according to the present invention has excellent properties in terms of renin inhibitory activity, solubility, cell membrane permeability, oral absorption, blood concentration, metabolic stability, tissue distribution, bioavailability, in vitro activity, in vivo activity, a rapid onset of drug effect, a lasting drug effect, physical stability, drug interaction, toxicity and the like and is useful as a medicament [in particular, a medicament for the treatment or prevention (preferably treatment) of hypertension].

The invention claimed is:
1. A compound having the general formula (I) or a pharmacologically acceptable salt thereof:

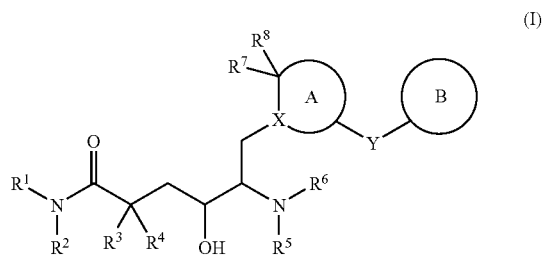

(I)

wherein $R^1$ represents a hydrogen atom, a $C_1$-$C_8$ alkyl group, a substituted $C_1$-$C_8$ alkyl group, a $C_2$-$C_6$ alkenyl group, a substituted $C_2$-$C_6$ alkenyl group, a $C_2$-$C_6$ alkynyl group, a substituted $C_2$-$C_6$ alkynyl group, a hydroxyl group, a $C_1$-$C_6$ alkoxy group, a substituted $C_1$-$C_6$ alkoxy group, a $C_1$-$C_6$ alkylthio group, a substituted $C_1$-$C_6$ alkylthio group, an amino group, a $C_1$-$C_6$ alkylamino group, a substituted $C_1$-$C_6$ alkylamino group, a di($C_1$-$C_6$ alkyl) amino group (wherein the alkyl groups are the same or different), a substituted di($C_1$-$C_6$ alkyl)amino group (wherein the alkyl groups are the same or different), a formyl group, a ($C_1$-$C_6$ alkyl)carbonyl group, a substituted ($C_1$-$C_6$ alkyl)carbonyl group, a ($C_1$-$C_6$ alkoxy)carbonyl group, a substituted ($C_1$-$C_6$ alkoxy)carbonyl group, a $C_3$-$C_{10}$ cyclic hydrocarbon group, a substituted $C_3$-$C_{10}$ cyclic hydrocarbon group, a 3- to 10-membered heterocyclyl group or a substituted 3- to 10-membered heterocyclyl group, the substituent(s) of each group other than the cyclic hydrocarbon group and the heterocyclyl group in $R^1$ represent 1 to 3 groups which are the same or different and are selected from Substituent Group α or β, two substituents together may form a $C_1$-$C_5$ alkylene group, and the substituent(s) of the cyclic hydrocarbon group and the heterocyclyl group in $R^1$ represent 1 to 3 groups which are the same or different and are selected from Substituent Group α; and $R^2$ represents a hydrogen atom, a $C_1$-$C_6$ alkyl group, a substituted $C_1$-$C_6$ alkyl group, a $C_2$-$C_6$ alkenyl group, a substituted $C_2$-$C_6$ alkenyl group, a $C_2$-$C_6$ alkynyl group, a substituted $C_2$-$C_6$ alkynyl group, a $C_3$-$C_8$ cycloalkyl group or a substituted $C_3$-$C_8$ cycloalkyl group, and the substituent(s) of each group in $R^2$ represent 1 to 3 groups which are the same or different and are selected from Substituent Group α or β, or $R^1$ and $R^2$ together with the nitrogen atom to which they are bonded form a 3- to 10-membered nitrogen-containing heterocyclyl group or a substituted 3- to 10-membered nitrogen-containing heterocyclyl group, and the substituent(s) of the nitrogen-containing heterocyclyl group represent 1 to 3 groups which are the same or different and are selected from Substituent Group α;

$R^3$ represents a hydrogen atom, a $C_1$-$C_6$ alkyl group, a substituted $C_1$-$C_6$ alkyl group, a $C_2$-$C_6$ alkenyl group, a substituted $C_2$-$C_6$ alkenyl group, a $C_2$-$C_6$ alkynyl group, a substituted $C_2$-$C_6$ alkynyl group, a $C_3$-$C_8$ cycloalkyl group, a substituted $C_3$-$C_8$ cycloalkyl group, a hydroxyl group, a $C_1$-$C_6$ alkoxy group, a substituted $C_1$-$C_6$ alkoxy group, a $C_1$-$C_6$ alkylthio group or a substituted $C_1$-$C_6$ alkylthio group, and the substituent(s) of each group in $R^3$ represent 1 to 3 groups which are the same or different and are selected from Substituent Group α; and $R^4$ represents a hydrogen atom, a $C_1$-$C_6$ alkyl group, a substituted $C_1$-$C_6$ alkyl group, a $C_2$-$C_6$ alkenyl group, a substituted $C_2$-$C_6$ alkenyl group, a $C_2$-$C_6$ alkynyl group, a substituted $C_2$-$C_6$ alkynyl group, a $C_3$-$C_8$ cycloalkyl group, a substituted $C_3$-$C_8$ cycloalkyl group, a hydroxyl group, a $C_1$-$C_6$ alkoxy group, a substituted $C_1$-$C_6$ alkoxy group, a $C_1$-$C_6$ alkylthio group or a substituted $C_1$-$C_6$ alkylthio group, and the substituent(s) of each group in $R^4$ represent 1 to 3 groups which are the same or different and are selected from Substituent Group α, or $R^3$ and $R^4$ together form a $C_1$-$C_5$ alkylene group or a substituted $C_1$-$C_5$ alkylene group, and the substituent(s) of the alkylene group represent 1 to 3 groups which are the same or different and are selected from Substituent Group α;

$R^5$ represents a hydrogen atom, a $C_1$-$C_6$ alkyl group, a substituted $C_1$-$C_6$ alkyl group, a $C_3$-$C_8$ cycloalkyl group, a substituted $C_3$-$C_8$ cycloalkyl group, a hydroxyl group, a $C_1$-$C_6$ alkoxy group, a substituted $C_1$-$C_6$ alkoxy group, an amino group, a $C_1$-$C_6$ alkylamino group, a substituted $C_1$-$C_6$ alkylamino group, a di($C_1$-$C_6$ alkyl)amino group (wherein the alkyl groups are the same or different) or a substituted di($C_1$-$C_6$ alkyl)amino group (wherein the alkyl groups are the same or different), and the substituent(s) of each group in $R^5$ represent 1 to 3 groups which are the same or different and are selected from Substituent Group α;

$R^6$ represents a hydrogen atom, a $C_1$-$C_6$ alkyl group, a substituted $C_1$-$C_6$ alkyl group, a $C_3$-$C_8$ cycloalkyl group, a substituted $C_3$-$C_8$ cycloalkyl group, a hydroxyl group, a $C_1$-$C_6$ alkoxy group, a substituted $C_1$-$C_6$ alkoxy group, an amino group, a $C_1$-$C_6$ alkylamino group, a substituted $C_1$-$C_6$ alkylamino group, a di($C_1$-$C_6$ alkyl)amino group (wherein the alkyl groups are the same or different) or a substituted di($C_1$-$C_6$ alkyl)amino group (wherein the alkyl groups are the same or different), and the substituent(s) of each group in $R^6$ represent 1 to 3 groups which are the same or different and are selected from Substituent Group α;

$R^7$ represents a hydrogen atom, a $C_1$-$C_6$ alkyl group, a substituted $C_1$-$C_6$ alkyl group, a $C_2$-$C_6$ alkenyl group, a substituted $C_2$-$C_6$ alkenyl group, a $C_2$-$C_6$ alkynyl group, a substituted $C_2$-$C_6$ alkynyl group, a $C_3$-$C_8$ cycloalkyl group, a substituted $C_3$-$C_8$ cycloalkyl group, a hydroxyl group, a $C_1$-$C_6$ alkoxy group, a substituted $C_1$-$C_6$ alkoxy group, a $C_1$-$C_6$ alkylthio group or a substituted $C_1$-$C_6$ alkylthio group, and the substituent(s) of each group in $R^7$ represent 1 to 3 groups which are the same or different and are selected from Substituent Group α; and $R^8$ represents a hydrogen atom, a $C_1$-$C_6$ alkyl group, a substituted $C_1$-$C_6$ alkyl group, a $C_2$-$C_6$ alkenyl group, a substituted $C_2$-$C_6$ alkenyl group, a $C_2$-$C_6$ alkynyl group, a substituted $C_2$-$C_6$ alkynyl group, a $C_3$-$C_8$ cycloalkyl group, a substituted $C_3$-$C_8$ cycloalkyl group, a hydroxyl group, a $C_1$-$C_6$ alkoxy group, a substituted $C_1$-$C_6$ alkoxy group, a $C_1$-$C_6$ alkylthio group or a substituted $C_1$-$C_6$ alkylthio group, and the substituent(s) of each group in $R^8$ represent 1 to 3 groups which are the same or different and are selected from Substituent Group α, or $R^7$ and $R^8$ together form a $C_1$-$C_5$ alkylene group or a substituted $C_1$-$C_5$ alkylene group, and the substituent(s) of the alkylene group represent 1 to 3 groups which are the same or different and are selected from Substituent Group α;

X represents a group having the formula (II):

(II)

A represents a 3- to 10-membered nitrogen-containing saturated heterocyclyl group, a substituted 3- to 10-membered nitrogen-containing saturated heterocyclyl group, a 3- to 10-membered nitrogen-containing partially unsaturated heterocyclyl group or a substituted 3- to 10-membered nitrogen-containing partially unsaturated heterocyclyl group, and the substituent(s) of each group in A represent 1 to 3 groups which are the same or different and are selected from Substituent Group α;

Y represents a single bond, a $C_1$-$C_6$ alkylene group, a substituted $C_1$-$C_6$ alkylene group, a $C_2$-$C_6$ alkenylene group, a substituted $C_2$-$C_6$ alkenylene group, a $C_2$-$C_6$ alkynylene group, a substituted $C_2$-$C_6$ alkynylene group or a group having the formula —$(CH_2)_a$—$X^1$—$(CH_2)_b$— [wherein $X^1$ represents a group having the formula —NH—, —$NR^9$— (wherein $R^9$ represents a $C_1$-$C_6$ alkyl group), —O—, —S—, —SO— or —$SO_2$—, a and b independently represent an integer of 0 to 5, and the sum of a and b is 0 to 5], and the substituent(s) of each group in Y represent 1 to 3 groups which are the same or different and are selected from Substituent Group γ; and B represents a $C_3$-$C_{10}$ cyclic hydrocarbon group, a substituted $C_3$-$C_{10}$ cyclic hydrocarbon group, a 3- to 10-membered heterocyclyl group, a substituted 3- to 10-membered heterocyclyl group or a group having the formula (V):

(V)

wherein D represents a $C_3$-$C_{10}$ cyclic hydrocarbon group, a substituted $C_3$-$C_{10}$ cyclic hydrocarbon group, a 3- to 10-membered heterocyclyl group or a substituted 3- to 10-membered heterocyclyl group, and the substituent(s) of each group in D represent 1 to 3 groups which are the same or different and are selected from Substituent Group α, $X^2$ represents a group having the formula —NH—, —$NR^{11}$— (wherein $R^{11}$ represents a $C_1$-$C_6$ alkyl group), —O—, —S—, —SO— or —$SO_2$—, and $R^{10}$ represents a $C_1$-$C_6$ alkyl group, a substituted $C_1$-$C_6$ alkyl group, a $C_2$-$C_6$ alkenyl group, a substituted $C_2$-$C_6$ alkenyl group, a $C_2$-$C_6$ alkynyl group, a substituted $C_2$-$C_6$ alkynyl group, a $C_3$-$C_8$ cycloalkyl group or a substituted $C_3$-$C_8$ cycloalkyl group, and the substituent(s) of each group in $R^{10}$ represent 1 to 3 groups which are the same or different and are selected from Substituent Group δ, and the substituent(s) of each group in B represent 1 to 3 groups which are the same or different and are selected from Substituent Group α, or the carbon atom $C_A$ of the ring A to which Y is bonded, Y and B together represent a group having the formula (VI):

wherein E is bonded to A in spiro form and fused with B, E represents a $C_3$-$C_8$ saturated cyclic hydrocarbon group, a substituted $C_3$-$C_8$ saturated cyclic hydrocarbon group, a $C_3$-$C_8$ partially unsaturated cyclic hydrocarbon group, a substituted $C_3$-$C_8$ partially unsaturated cyclic hydrocarbon group, a 3- to 8-membered saturated heterocyclyl group, a substituted 3- to 8-membered saturated heterocyclyl group, a 3- to 8-membered partially unsaturated heterocyclyl group or a substituted 3- to 8-membered partially unsaturated heterocyclyl group, and the substituent(s) of each group in E represent 1 to 3 groups which are the same or different and are selected from Substituent Group α;

Substituent Group α represents the group consisting of a $C_1$-$C_6$ alkyl group, a halogeno $C_1$-$C_6$ alkyl group, a hydroxyl group, a $C_1$-$C_6$ alkoxy group, a halogeno $C_1$-$C_6$ alkoxy group, a mercapto group, a $C_1$-$C_6$ alkylthio group, a $C_1$-$C_6$ alkylsulfinyl group, a $C_1$-$C_6$ alkylsulfonyl group, an amino group, a $C_1$-$C_6$ alkylamino group, a di($C_1$-$C_6$ alkyl)amino group (wherein the alkyl groups are the same or different), a formylamino group, a ($C_1$-$C_6$ alkyl)carbonylamino group, a formyl group, a ($C_1$-$C_6$ alkyl)carbonyl group, a carboxyl group, a ($C_1$-$C_6$ alkoxy)carbonyl group, a carbamoyl group, a ($C_1$-$C_6$ alkylamino)carbonyl group, a di($C_1$-$C_6$ alkyl)aminocarbonyl group (wherein the alkyl groups are the same or different), an aminosulfonyl group, a ($C_1$-$C_6$ alkylamino)sulfonyl group, a di($C_1$-$C_6$ alkyl)aminosulfonyl group (wherein the alkyl groups are the same or different), a cyano group, a nitro group, a halogeno group and an oxo group;

Substituent Group β represents the group consisting of a $C_3$-$C_8$ cycloalkyl group, a substituted $C_3$-$C_8$ cycloalkyl group, a $C_6$-$C_{10}$ aryl group, a substituted $C_6$-$C_{10}$ aryl group, a 3- to 10-membered heterocyclyl group and a substituted 3- to 10-membered heterocyclyl group, and the substituent(s) of each group in Substituent Group β represent 1 to 3 groups which are the same or different and are selected from Substituent Group α;

Substituent Group γ represents the group consisting of a $C_1$-$C_6$ alkyl group, a hydroxyl group, a halogeno group, an oxo group, a hydroxyimino group and a ($C_1$-$C_6$ alkoxy)imino group; and Substituent Group δ represents the group consisting of a hydroxyl group, a $C_1$-$C_6$ alkoxy group, a mercapto group, a $C_1$-$C_6$ alkylthio group, a $C_1$-$C_6$ alkylsulfinyl group, a $C_1$-$C_6$ alkylsulfonyl group, an amino group, a $C_1$-$C_6$ alkylamino group, a di($C_1$-$C_6$ alkyl)amino group (wherein the alkyl groups are the same or different), a ($C_1$-$C_6$ alkyl)carbonylamino group, a ($C_1$-$C_6$ alkyl)sulfonylamino group, an aminocarbonylamino group, a ($C_1$-$C_6$ alkylamino)carbonylamino group, a di($C_1$-$C_6$ alkyl)aminocarbonylamino group (wherein the alkyl groups are the same or different), an aminosulfonylamino group, a ($C_1$-$C_6$ alkylamino)sulfonylamino group and a di($C_1$-$C_6$ alkyl)aminosulfonylamino group (wherein the alkyl groups are the same or different).

2. The compound according to claim 1 or a pharmacologically acceptable salt thereof, wherein $R^1$ is a $C_1$-$C_8$ alkyl group, a substituted $C_1$-$C_8$ alkyl group, a $C_2$-$C_6$ alkenyl group, a substituted $C_2$-$C_6$ alkenyl group, a $C_2$-$C_6$ alkynyl group, a substituted $C_2$-$C_6$ alkynyl group, a $C_3$-$C_{10}$ cyclic hydrocarbon group, a substituted $C_3$-$C_{10}$ cyclic hydrocarbon group, a 3- to 10-membered heterocyclyl group or a substituted 3- to 10-membered heterocyclyl group, the substituent(s) of each group other than the cyclic hydrocarbon group and the heterocyclyl group in $R^1$ represent 1 to 3 groups which are the same or different and are selected from Substituent Group α1 or β1, and the substituent(s) of the cyclic hydrocarbon group and the heterocyclyl group in $R^1$ represent 1 to 3 groups which are the same or different and are selected from Substituent Group α1, Substituent Group α1 represents the group consisting of a $C_1$-$C_6$ alkyl group, a halogeno $C_1$-$C_6$ alkyl group, a hydroxyl group, a $C_1$-$C_6$ alkoxy group, a halogeno $C_1$-$C_6$ alkoxy group, a mercapto group, a $C_1$-$C_6$ alkylthio group, a $C_1$-$C_6$ alkylsulfinyl group, a $C_1$-$C_6$ alkylsulfonyl group, an amino group, a $C_1$-$C_6$ alkylamino group, a di($C_1$-$C_6$ alkyl)amino group (wherein the alkyl groups are the same or different), a carbamoyl group, a ($C_1$-$C_6$ alkylamino)carbonyl group, a di($C_1$-$C_6$ alkyl)aminocarbonyl group (wherein the alkyl groups are the same or different) and a halogeno group, and Substituent Group β1 represents the group consisting of a $C_3$-$C_8$ cycloalkyl group, a $C_6$-$C_{10}$ aryl group and a 3- to 10-membered heterocyclyl group.

3. The compound according to claim 1 or a pharmacologically acceptable salt thereof, wherein $R^1$ is a $C_1$-$C_6$ alkyl group, a substituted $C_1$-$C_6$ alkyl group (wherein the substituent(s) represent 1 to 3 groups which are the same or different and are selected from Substituent Group α2 or β2), a $C_3$-$C_8$ cyclic hydrocarbon group or a substituted $C_3$-$C_8$ cyclic hydrocarbon group (wherein the substituent(s) represent 1 to 3 groups which are the same or different and are selected from Substituent Group α2), Substituent Group α2 represents the group consisting of a $C_1$-$C_6$ alkyl group, a hydroxyl group, a $C_1$-$C_6$ alkoxy group, a carbamoyl group, a ($C_1$-$C_6$ alkylamino)carbonyl group and a di($C_1$-$C_6$ alkyl)aminocarbonyl group (wherein the alkyl groups are the same or different), and Substituent Group β2 represents the group consisting of a $C_3$-$C_8$ cycloalkyl group and a $C_6$-$C_{10}$ aryl group.

4. The compound according to claim 1 or a pharmacologically acceptable salt thereof, wherein $R^1$ is a $C_2$-$C_7$ alkyl group or a $C_4$-$C_7$ cycloalkyl group.

5. The compound of claim 1 or a pharmacologically acceptable salt thereof, wherein $R^2$ is a hydrogen atom, a $C_1$-$C_6$ alkyl group or a $C_3$-$C_8$ cycloalkyl group, or $R^1$ and $R^2$ together with the nitrogen atom to which they are bonded form a 3- to 10-membered nitrogen-containing heterocyclyl group.

6. The compound of claim 1 or a pharmacologically acceptable salt thereof, wherein $R^2$ is a hydrogen atom.

7. The compound of claim 1 or a pharmacologically acceptable salt thereof, wherein $R^3$ is a $C_1$-$C_6$ alkyl group, a $C_3$-$C_8$ cycloalkyl group or a $C_1$-$C_6$ alkoxy group, and $R^4$ is a hydrogen atom, a $C_1$-$C_6$ alkyl group or a $C_3$-$C_8$ cycloalkyl group, or $R^3$ and $R^4$ together form a $C_1$-$C_5$ alkylene group.

8. The compound of claim 1 or a pharmacologically acceptable salt thereof, wherein $R^3$ is a $C_1$-$C_6$ alkyl group, and $R^4$ is a hydrogen atom.

9. The compound of claim 1 or a pharmacologically acceptable salt thereof, wherein $R^5$ is a hydrogen atom, a $C_1$-$C_6$ alkyl group or a $C_3$-$C_8$ cycloalkyl group, and $R^6$ is a hydrogen atom, a $C_1$-$C_6$ alkyl group or a $C_3$-$C_8$ cycloalkyl group.

10. The compound of claim 1 or a pharmacologically acceptable salt thereof, wherein $R^5$ and $R^6$ are hydrogen atoms.

11. The compound of claim 1 or a pharmacologically acceptable salt thereof, wherein $R^7$ is a hydrogen atom, a $C_1$-$C_6$ alkyl group or a $C_3$-$C_8$ cycloalkyl group, and $R^8$ is a hydrogen atom, a $C_1$-$C_6$ alkyl group or a $C_3$-$C_8$ cycloalkyl group, or $R^7$ and $R^8$ together form a $C_2$-$C_4$ alkylene group.

12. The compound of claim 1 or a pharmacologically acceptable salt thereof, wherein $R^7$ is a $C_1$-$C_4$ alkyl group, and $R^8$ is a $C_1$-$C_4$ alkyl group.

13. The compound of claim 1 or a pharmacologically acceptable salt thereof, wherein A is a 4- to 8-membered nitrogen-containing saturated heterocyclyl group, a substituted 4- to 8-membered nitrogen-containing saturated heterocyclyl group, a 4- to 8-membered nitrogen-containing partially unsaturated heterocyclyl group or a substituted 4- to 8-membered nitrogen-containing partially unsaturated heterocyclyl group, and the substituent(s) of each group in A represent 1 to 3 groups which are the same or different and are selected from Substituent Group α3, and Substituent Group α3 represents the group consisting of a $C_1$-$C_6$ alkyl group, a hydroxyl group, a $C_1$-$C_6$ alkoxy group, an amino group, a $C_1$-$C_6$ alkylamino group, a di($C_1$-$C_6$ alkyl)amino group (wherein the alkyl groups are the same or different), a halogeno group and an oxo group.

14. The compound of claim 1 or a pharmacologically acceptable salt thereof, wherein A is a 5- or 6-membered nitrogen-containing saturated heterocyclyl group or a substituted 5- or 6-membered nitrogen-containing saturated heterocyclyl group (wherein the substituent(s) represent 1 to 3 groups which are the same or different and are selected from Substituent Group α4), and Substituent Group α4 represents the group consisting of a $C_1$-$C_6$ alkyl group, a hydroxyl group, a $C_1$-$C_6$ alkoxy group and an oxo group.

15. The compound of claim 1 or a pharmacologically acceptable salt thereof, wherein A is a piperazinyl group or a substituted piperazinyl group (wherein the substituent(s) represent 1 to 3 groups which are the same or different and are selected from Substituent Group α4), wherein Substituent Group α4 represents the group consisting of a $C_1$-$C_6$ alkyl group, a hydroxyl group, a $C_1$-$C_6$ alkoxy group and an oxo group.

16. The compound of claim 1 or a pharmacologically acceptable salt thereof, wherein Y is a single bond, a $C_1$-$C_6$ alkylene group or a substituted $C_1$-$C_6$ alkylene group (wherein the substituent(s) represent 1 to 3 groups which are the same or different and are selected from Substituent Group γ), wherein Substituent Group γ represents the group consisting of a $C_1$-$C_6$ alkyl group, a hydroxyl group, a halogeno group, an oxo group, a hydroxyimino group and a ($C_1$-$C_6$ alkoxy)imino group.

17. The compound of claim 1 or a pharmacologically acceptable salt thereof, wherein Y is a single bond.

18. The compound of claim 1 or a pharmacologically acceptable salt thereof, wherein B is a $C_3$-$C_{10}$ cycloalkyl group, a substituted $C_3$-$C_{10}$ cycloalkyl group, a $C_6$-$C_{10}$ aryl group, a substituted $C_6$-$C_{10}$ aryl group, a 5- to 10-membered aromatic heterocyclyl group, a substituted 5- to 10-membered heterocyclyl group or a group having the formula (Va):

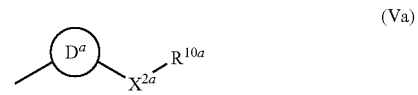

(Va)

wherein $D^a$ represents a $C_3$-$C_{10}$ cycloalkyl group, a substituted $C_3$-$C_{10}$ cycloalkyl group, a $C_6$-$C_{10}$ aryl group, a substituted $C_6$-$C_{10}$ aryl group, a 5- to 10-membered aromatic heterocyclyl group or a substituted 5- to 10-membered heterocyclyl group, and the substituent(s) of each group in $D^a$ represent 1 to 3 groups which are the same or different and are selected from Substituent Group α1, $X^{2a}$ represents a group having the formula —NH—, —O— or —S—, and $R^{10a}$ represents a $C_1$-$C_6$ alkyl group, a substituted $C_1$-$C_6$ alkyl group, a $C_2$-$C_6$ alkenyl group, a substituted $C_2$-$C_6$ alkenyl group, a $C_2$-$C_6$ alkynyl group or a substituted $C_2$-$C_6$ alkynyl group, and the substituent(s) of each group in $R^{ma}$ represent 1 to 3 groups which are the same or different and are selected from Substituent Group δ1, and the substituent(s) of each group in B represent 1 to 3 groups which are the same or different and are selected from Substituent Group α1, wherein Substituent Group α1 represents the group consisting of a $C_1$-$C_6$ alkyl group, a halogeno $C_1$-$C_6$ alkyl group, a hydroxyl group, a $C_1$-$C_6$ alkoxy group, a halogeno $C_1$-$C_6$ alkoxy group, a mercapto group, a $C_1$-$C_6$ alkylthio group, a $C_1$-$C_6$ alkylsulfinyl group, a $C_1$-$C_6$ alkylsulfonyl group, an amino group, a $C_1$-$C_6$ alkylamino group, a di($C_1$-$C_6$ alkyl)amino group (wherein the alkyl groups are the same or different), a carbamoyl group, a ($C_1$-$C_6$ alkylamino)carbonyl group, a di($C_1$-$C_6$ alkyl)aminocarbonyl group (wherein the alkyl groups are the same or different) and a halogeno group, and Substituent Group δ1 represents the group consisting of a hydroxyl group, a $C_1$-$C_6$ alkoxy group, a $C_1$-$C_6$ alkylthio group, a $C_1$-$C_6$ alkylsulfinyl group, a $C_1$-$C_6$ alkylsulfonyl group, a $C_1$-$C_6$ alkylamino group and a di($C_1$-$C_6$ alkyl)amino group (wherein the alkyl groups are the same or different).

19. The compound of claim 1 or a pharmacologically acceptable salt thereof, wherein B is a $C_6$-$C_{10}$ aryl group, a substituted $C_6$-$C_{10}$ aryl group, a 5- or 6-membered aromatic heterocyclyl group, a substituted 5- or 6-membered aromatic heterocyclyl group or a group having the formula (Vb):

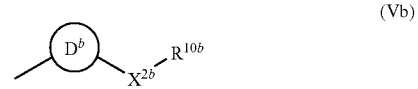

(Vb)

wherein $D^b$ represents a $C_6$-$C_{10}$ aryl group, a substituted $C_6$-$C_{10}$ aryl group, a 5- or 6-membered aromatic heterocyclyl group or a substituted 5- or 6-membered aromatic heterocyclyl group, and the substituent(s) of each group in $D^b$ represent 1 to 3 groups which are the same or different and are selected from Substituent Group α1, $X^{2b}$ represents a group having the formula —O—, and $R^{10b}$ represents a $C_1$-$C_6$ alkyl group, a substituted $C_1$-$C_6$ alkyl group, a substituted $C_2$-$C_6$ alkenyl group or a substituted $C_2$-$C_6$ alkynyl group, and the substituent(s) of each group in $R^{10b}$ represent 1 to 3 groups which are the same or different and are selected from Substituent Group δ2, and the substituent(s) of each group in B represent 1 to 3 groups which are the same or different and are selected from Substituent Group α1, wherein Substituent Group α1 represents the group consisting of a $C_1$-$C_6$ alkyl group, a halogeno $C_1$-$C_6$ alkyl group, a hydroxyl group, a $C_1$-$C_6$ alkoxy group, a halogeno $C_1$-$C_6$ alkoxy group, a mercapto group, a $C_1$-$C_6$ alkylthio group, a $C_1$-$C_6$ alkylsulfinyl group, a $C_1$-$C_6$ alkylsulfonyl group, an amino group, a $C_1$-$C_6$ alkylamino group, a di($C_1$-$C_6$ alkyl)amino group (wherein the alkyl groups are the same or different), a carbamoyl group, a ($C_1$-$C_6$ alkylamino)carbonyl group, a di($C_1$-$C_6$ alkyl)aminocarbonyl group (wherein the alkyl groups are the same or different) and a halogeno group, and Substituent Group δ2 represents the group consisting of a hydroxyl group, a $C_1$-$C_6$ alkoxy group, a $C_1$-$C_6$ alkylthio group, a $C_1$-$C_6$ alkylamino group and a di($C_1$-$C_6$ alkyl)amino group (wherein the alkyl groups are the same or different).

20. The compound of claim 1 or a pharmacologically acceptable salt thereof, wherein B is a phenyl group, a substituted phenyl group (wherein the substituent(s) represent 1 to 3 groups which are the same or different and are selected from Substituent Group α5) or a group having the formula (Vc):

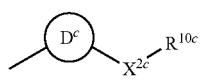

(Vc)

wherein $D^c$ represents a phenyl group or a substituted phenyl group (wherein the substituent(s) represent 1 to 3 groups which are the same or different and are selected from Substituent Group α5), $X^{2c}$ represents a group having the formula —O—, and $R^{10c}$ represents a substituted $C_1$-$C_6$ alkyl group (wherein the substituent(s) represent 1 to 3 groups which are the same or different and are selected from Substituent Group δ3), Substituent Group α5 represents the group consisting of a $C_1$-$C_6$ alkyl group, a halogeno $C_1$-$C_6$ alkyl group, a $C_1$-$C_6$ alkoxy group, a halogeno $C_1$-$C_6$ alkoxy group, an amino group, a $C_1$-$C_6$ alkylamino group, a di($C_1$-$C_6$ alkyl)amino group (wherein the alkyl groups are the same or different) and a halogeno group, and Substituent Group δ3 represents the group consisting of a hydroxyl group, a $C_1$-$C_6$ alkoxy group and a $C_1$-$C_6$ alkylthio group.

21. The compound according to claim 1 or a pharmacologically acceptable salt thereof, wherein $R^1$ is a $C_1$-$C_8$ alkyl group, a substituted $C_1$-$C_8$ alkyl group, a $C_2$-$C_6$ alkenyl group, a substituted $C_2$-$C_6$ alkenyl group, a $C_2$-$C_6$ alkynyl group, a substituted $C_2$-$C_6$ alkynyl group, a $C_3$-$C_{10}$ cyclic hydrocarbon group, a substituted $C_3$-$C_{10}$ cyclic hydrocarbon group, a 3- to 10-membered heterocyclyl group or a substituted 3- to 10-membered heterocyclyl group, the substituent(s) of each group other than the cyclic hydrocarbon group and the heterocyclyl group in $R^1$ represent 1 to 3 groups which are the same or different and are selected from Substituent Group α1 or β1, and the substituent(s) of the cyclic hydrocarbon group and the heterocyclyl group in $R^1$ represent 1 to 3 groups which are the same or different and are selected from Substituent Group α1, and $R^2$ is a hydrogen atom, a $C_1$-$C_6$ alkyl group or a $C_3$-$C_8$ cycloalkyl group, or $R^1$ and $R^2$ together with the nitrogen atom to which they are bonded form a 3- to 10-membered nitrogen-containing heterocyclyl group, $R^3$ is a $C_1$-$C_6$ alkyl group, a $C_3$-$C_8$ cycloalkyl group or a $C_1$-$C_6$ alkoxy group, and $R^4$ is a hydrogen atom, a $C_1$-$C_6$ alkyl group or a $C_3$-$C_8$ cycloalkyl group, or $R^3$ and $R^4$ together form a $C_1$-$C_5$ alkylene group, $R^5$ is a hydrogen atom, a $C_1$-$C_6$ alkyl group or a $C_3$-$C_8$ cycloalkyl group, $R^6$ is a hydrogen atom, a $C_1$-$C_6$ alkyl group or a $C_3$-$C_8$ cycloalkyl group, $R^7$ is a hydrogen atom, a $C_1$-$C_6$ alkyl group or a $C_3$-$C_8$ cycloalkyl group, and $R^8$ is a hydrogen atom, a $C_1$-$C_6$ alkyl group or a $C_3$-$C_8$ cycloalkyl group, or $R^7$ and $R^8$ together form a $C_2$-$C_4$ alkylene group, Y is a single bond, a $C_1$-$C_6$ alkylene group or a substituted $C_1$-$C_6$ alkylene group (wherein the substituent(s) represent 1 to 3 groups which are the same or different and are selected from Substituent Group γ), and B is a $C_3$-$C_{10}$ cycloalkyl group, a substituted $C_3$-$C_{10}$ cycloalkyl group, a $C_6$-$C_{10}$ aryl group, a substituted $C_6$-$C_{10}$ aryl group, a 5- to 10-membered aromatic heterocyclyl group, a substituted 5- to 10-membered heterocyclyl group or a group having the formula (Va):

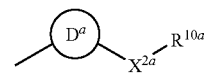

(Va)

wherein $D^a$ represents a $C_3$-$C_{10}$ cycloalkyl group, a substituted $C_3$-$C_{10}$ cycloalkyl group, a $C_6$-$C_{10}$ aryl group, a substituted $C_6$-$C_{10}$ aryl group, a 5- to 10-membered aromatic heterocyclyl group or a substituted 5- to 10-membered heterocyclyl group, and the substituent(s) of each group in $D^a$ represent 1 to 3 groups which are the same or different and are selected from Substituent Group α1, $X^{2a}$ represents a group having the formula —NH—, —O— or —S—, and $R^{10a}$ represents a $C_1$-$C_6$ alkyl group, a substituted $C_1$-$C_6$ alkyl group, a $C_2$-$C_6$ alkenyl group, a substituted $C_2$-$C_6$ alkenyl group, a $C_2$-$C_6$ alkynyl group or a substituted $C_2$-$C_6$ alkynyl group, and the substituent(s) of each group in $R^{10a}$ represent 1 to 3 groups which are the same or different and are selected from Substituent Group δ1, and the substituent(s) of each group in B represent 1 to 3 groups which are the same or different and are selected from Substituent Group α1, wherein Substituent Group α1 represents the group consisting of a $C_1$-$C_6$ alkyl group, a halogeno $C_1$-$C_6$ alkyl group, a hydroxyl group, a $C_1$-$C_6$ alkoxy group, a halogeno $C_1$-$C_6$ alkoxy group, a mercapto group, a $C_1$-$C_6$ alkylthio group, a $C_1$-$C_6$ alkylsulfinyl group, a $C_1$-$C_6$ alkylsulfonyl group, an amino group, a $C_1$-$C_6$ alkylamino group, a di($C_1$-$C_6$ alkyl)amino group (wherein the alkyl groups are the same or different), a carbamoyl group, a ($C_1$-$C_6$ alkylamino)carbonyl group, a di($C_1$-$C_6$ alkyl)aminocarbonyl group (wherein the alkyl groups are the same or different) and a halogeno group, Substituent Group β1 represents the group consisting of a $C_3$-$C_8$ cycloalkyl group, a $C_6$-$C_{10}$ aryl group and a 3- to 10-membered heterocyclyl group, Substituent Group γ represents the group consisting of a $C_1$-$C_6$ alkyl group, a hydroxyl group, a halogeno group, an oxo group, a hydroxyimino group and a ($C_1$-$C_6$ alkoxy)imino group, and Substituent Group δ1 represents the group consisting of a hydroxyl group, a $C_1$-$C_6$ alkoxy group, a $C_1$-$C_6$ alkylthio group, a $C_1$-$C_6$ alkylsulfinyl group, a $C_1$-$C_6$ alkylsulfonyl group, a $C_1$-$C_6$ alkylamino group and a di($C_1$-$C_6$ alkyl)amino group (wherein the alkyl groups are the same or different).

22. The compound according to claim 1 or a pharmacologically acceptable salt thereof, wherein $R^1$ is a $C_1$-$C_6$ alkyl group, a substituted $C_1$-$C_6$ alkyl group (wherein the substituent(s) represent 1 to 3 groups which are the same or different and are selected from Substituent Group α2 or β2), a $C_3$-$C_8$ cyclic hydrocarbon group or a substituted $C_3$-$C_8$ cyclic hydrocarbon group (wherein the substituent(s) represent 1 to 3 groups which are the same or different and are selected from Substituent Group α2), $R^2$ is a hydrogen atom,
$R^3$ is a $C_1$-$C_6$ alkyl group,
$R^4$ is a hydrogen atom,
$R^5$ and $R^6$ are hydrogen atoms,
$R^7$ is a $C_1$-$C_4$ alkyl group,
$R^8$ is a $C_1$-$C_4$ alkyl group,
Y is a single bond, and
B is a $C_6$-$C_{10}$ aryl group, a substituted $C_6$-$C_{10}$ aryl group, a 5- or 6-membered aromatic heterocyclyl group, a substituted 5- or 6-membered aromatic heterocyclyl group or a group having the formula (Vb):

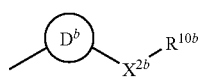

(Vb)

wherein $D^b$ represents a $C_6$-$C_{10}$ aryl group, a substituted $C_6$-$C_{10}$ aryl group, a 5- or 6-membered aromatic heterocyclyl group or a substituted 5- or 6-membered aromatic heterocyclyl group, and the substituent(s) of each group in $D^b$ represent 1 to 3 groups which are the same or different and are selected from Substituent Group α1, $X^{2b}$ represents a group having the formula —O—, and $R^{10b}$ represents a $C_1$-$C_6$ alkyl group, a substituted $C_1$-$C_6$ alkyl group, a substituted $C_2$-$C_6$ alkenyl group or a substituted $C_2$-$C_6$ alkynyl group, and the substituent(s) of each group in $R^{10b}$ represent 1 to 3 groups which are the same or different and are selected from Substituent Group δ2, and the substituent(s) of each group in B represent 1 to 3 groups which are the same or different and are selected from Substituent Group α1, wherein Substituent Group α1 represents the group consisting of a $C_1$-$C_6$ alkyl group, a halogeno $C_1$-$C_6$ alkyl group, a hydroxyl group, a $C_1$-$C_6$ alkoxy group, a halogeno $C_1$-$C_6$ alkoxy group, a mercapto group, a $C_1$-$C_6$ alkylthio group, a $C_1$-$C_6$ alkylsulfinyl group, a $C_1$-$C_6$ alkylsulfonyl group, an amino group, a $C_1$-$C_6$ alkylamino group, a di($C_1$-$C_6$ alkyl)amino group (wherein the alkyl groups are the same or different), a carbamoyl group, a ($C_1$-$C_6$ alkylamino)carbonyl group, a di($C_1$-$C_6$ alkyl)aminocarbonyl group (wherein the alkyl groups are the same or different) and a halogeno group, Substituent Group α2 represents the group consisting of a $C_1$-$C_6$ alkyl group, a hydroxyl group, a $C_1$-$C_6$ alkoxy group, a carbamoyl group, a ($C_1$-$C_6$ alkylamino)carbonyl group and a di($C_1$-$C_6$ alkyl)aminocarbonyl group (wherein the alkyl groups are the same or different), Substituent Group β2 represents the group consisting of a $C_3$-$C_8$ cycloalkyl group and a $C_6$-$C_{10}$ aryl group, and Substituent Group δ2 represents the group consisting of a hydroxyl group, a $C_1$-$C_6$ alkoxy group, a $C_1$-$C_6$ alkylthio group, a $C_1$-$C_6$ alkylamino group and a di($C_1$-$C_6$ alkyl)amino group (wherein the alkyl groups are the same or different).

23. The compound according to claim 1 or a pharmacologically acceptable salt thereof, wherein $R^1$ is a $C_2$-$C_7$ alkyl group or a $C_4$-$C_7$ cycloalkyl group, $R^2$ is a hydrogen atom,
$R^3$ is a $C_1$-$C_6$ alkyl group,
$R^4$ is a hydrogen atom,
$R^5$ and $R^6$ are hydrogen atoms,
$R^7$ is a $C_1$-$C_4$ alkyl group,
$R^8$ is a $C_1$-$C_4$ alkyl group,
Y is a single bond, and
B is a phenyl group, a substituted phenyl group (wherein the substituent(s) represent 1 to 3 groups which are the same or different and are selected from Substituent Group α5) or a group having the formula (Vc):

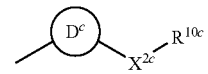

(Vc)

wherein $D^c$ represents a phenyl group or a substituted phenyl group (wherein the substituent(s) represent 1 to 3 groups which are the same or different and are selected from Substituent Group α5), $X^{2c}$ represents a group having the formula —O—, and $R^{10c}$ represents a substituted $C_1$-$C_6$ alkyl group (wherein the substituent(s) represent 1 to 3 groups which are the same or different and are selected from Substituent Group δ3), wherein Substituent Group α5 represents the group consisting of a $C_1$-$C_6$ alkyl group, a halogeno $C_1$-$C_6$ alkyl group, a $C_1$-$C_6$ alkoxy group, a halogeno $C_1$-$C_6$ alkoxy group, an amino group, a $C_1$-$C_6$ alkylamino group, a di($C_1$-$C_6$ alkyl)amino group (wherein the alkyl groups are the same or different) and a halogeno group, and Substituent Group δ3 represents the group consisting of a hydroxyl group, a $C_1$-$C_6$ alkoxy group and a $C_1$-$C_6$ alkylthio group.

24. The compound according to claim 1 or a pharmacologically acceptable salt thereof, which is selected from the group consisting of:

(2S,4S,5S)-5-amino-6-[4-(2-chlorophenyl)-2,2-dimethyl-5-oxopiperazin-1-yl]-4-hydroxy-2-isopropylhexanoic acid butylamide, (2S,4S,5S)-5-amino-6-[4-(2-chloro-5-fluorophenyl)-2,2-dimethyl-5-oxopiperazin-1-yl]-4-hydroxy-2-isopropylhexanoic acid butylamide, (2S,4S,5S)-5-amino-6-[4-(2-chlorophenyl)-2,2-dimethyl-5-oxopiperazin-1-yl]-4-hydroxy-2-isopropylhexanoic acid [(S)-2-methylbutyl]amide, (2S,4S,5S)-5-amino-6-[4-(2-chlorophenyl)-2,2-dimethyl-5-oxopiperazin-1-yl]-4-hydroxy-2-isopropylhexanoic acid cyclopentylamide, (2S,4S,5S)-5-amino-6-[2,2-dimethyl-4-(5-fluoro-2-methylphenyl)-5-oxopiperazin-1-yl]-4-hydroxy-2-isopropylhexanoic acid isobutylamide, (2S,4S,5S)-5-amino-6-[2,2-dimethyl-4-(5-fluoro-2-methylphenyl)-5-oxopiperazin-1-yl]-4-hydroxy-2-isopropylhexanoic acid (2,2-dimethylpropyl)amide, (2R,4S,5S)-5-amino-6-[4-(2-chlorophenyl)-2,2-dimethyl-5-oxopiperazin-1-yl]-4-hydroxy-2-methylhexanoic acid (2,2-dimethylpropyl)amide, (2R,4S,5S)-5-amino-6-[2,2-dimethyl-4-(5-fluoro-2-methylphenyl)-5-oxopiperazin-1-yl]-4-hydroxy-2-methylhexanoic acid (2,2-dimethylpropyl)amide, (2R,4S,5S)-5-amino-6-[4-(2-chloro-5-fluorophenyl)-2,2-dimethyl-5-oxopiperazin-1-yl]-4-hydroxy-2-methylhexanoic acid (2,2-dimethylpropyl)amide, (2R,4S,5S)-5-amino-6-[2,2-dimethyl-4-(2-methylphenyl)-5-oxopiperazin-1-yl]-2-ethyl-4-hydroxyhexanoic acid (2,2-dimethylpropyl)amide, (2R,4S,5S)-5-amino-6-[4-(2-chlorophenyl)-2,2-dimethyl-5-oxopiperazin-1-yl]-2-ethyl-4-hydroxyhexanoic acid (2,2-dimethylpropyl)amide, (2R,4S,5S)-5-amino-6-[4-(2-chlorophenyl)-2,2-dimethyl-5-oxopiperazin-1-yl]-4-hydroxy-2-propylhexanoic acid (2,2-dimethylpropyl)amide, (2R,4S,5S)-5-amino-6-[2,2-dimethyl-4-(2-methylphenyl)-5-oxopiperazin-1-yl]-4-hydroxy-2-methylhexanoic acid cyclohexylamide, (2R,4S,5S)-5-amino-6-[2,2-dimethyl-4-(5-fluoro-2-methylphenyl)-5-oxopiperazin-1-yl]-4-hydroxy-2-methylhexanoic acid cyclohexylamide, (2R,4S,5S)-5-amino-6-[4-(2,6-difluorophenyl)-2,2-dimethyl-5-oxopiperazin-1-yl]-4-hydroxy-2-methylhexanoic acid cyclohexylamide, (2R,4S,5S)-5-amino-6-[2,2-dimethyl-4-(5-fluoro-2-methylphenyl)-5-oxopiperazin-1-yl]-4-hydroxy-2-methylhexanoic acid cyclopentylamide, (2R,4S,5S)-5-amino-6-[2,2-dimethyl-4-(5-fluoro-2-methylphenyl)-5-oxopiperazin-1-yl]-4-hydroxy-2-methylhexanoic acid [(S)-2-methylbutyl]amide, (2R,4S,5S)-5-amino-6-[4-(2,3-difluorophenyl)-2,2-dimethyl-5-oxopiperazin-1-yl]-4-hydroxy-2-methylhexanoic acid cyclopentylamide, and (2R,4S,5S)-5-amino-6-[4-(2,6-difluorophenyl)-2,2-dimethyl-5-oxopiperazin-1-yl]-4-hydroxy-2-methylhexanoic acid cyclopentylamide.

25. A pharmaceutical composition comprising a compound according to any one of claim 1 or 24 or a pharmacologically acceptable salt thereof as an active ingredient.

26. A method for treating or preventing a disease which can be treated or prevented by inhibiting renin, comprising administering a pharmacologically effective amount of a compound according to any one of claim 1 or 24 or a pharmacologically acceptable salt thereof to a warm-blooded animal.

27. The method according to claim 26, wherein the disease is hypertension.

28. The method of claim 26, wherein the warm-blooded animal is a human.

* * * * *

UNITED STATES PATENT AND TRADEMARK OFFICE
CERTIFICATE OF CORRECTION

PATENT NO. : 8,158,790 B2
APPLICATION NO. : 12/306281
DATED : April 17, 2012
INVENTOR(S) : S. Miyazaki et al.

Page 1 of 1

It is certified that error appears in the above-identified patent and that said Letters Patent is hereby corrected as shown below:

In the Claims

| COLUMN | LINE | | |
|---|---|---|---|
| 196 (Claim 18) | 27 | "$R^{ma}$" should read --$R^{10a}$-- | |
| 202 (Claim 25, | 17 line 2) | "claim 1 or 24" should read --claims 1 or 24-- | |
| 202 (Claim 26, | 22 line 4) | "claim 1 or 24" should read --claims 1 or 24-- | |

Signed and Sealed this
Tenth Day of June, 2014

Michelle K. Lee
*Deputy Director of the United States Patent and Trademark Office*